United States Patent
Scobie et al.

(10) Patent No.: US 10,632,125 B2
(45) Date of Patent: *Apr. 28, 2020

(54) MTH1 INHIBITORS FOR TREATMENT OF INFLAMMATORY AND AUTOIMMUNE CONDITIONS

(71) Applicant: THOMAS HELLEDAYS STIFTELSE FÖR MEDICINSK FORSKNING, Stocksund (SE)

(72) Inventors: Martin Scobie, Uppsala (SE); Olov Wallner, Solna (SE); Tobias Koolmeister, Stockholm (SE); Karl Sven Axel Vallin, Stockholm (SE); Carl Martin Henriksson, Bromma (SE); Evert Homan, Sollentuna (SE); Thomas Helleday, Stocksund (SE); Sylvain Jacques, Lyons (FR); Roland Julius Yu Fiskesund, Arsta (SE)

(73) Assignee: THOMAS HELLEDAYS STIFTELSE FOR MEDICINSK FORSKNING, Stocksund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/120,170

(22) Filed: Aug. 31, 2018

(65) Prior Publication Data
US 2019/0000856 A1    Jan. 3, 2019

Related U.S. Application Data

(63) Continuation of application No. 15/315,478, filed as application No. PCT/SE2015/050654 on Jun. 4, 2015, now Pat. No. 10,064,869.

(30) Foreign Application Priority Data

Jun. 4, 2014 (SE) ...................................... 1450681

(51) Int. Cl.
| | | |
|---|---|---|
| A61K 31/538 | (2006.01) | |
| A61K 31/505 | (2006.01) | |
| A61K 31/519 | (2006.01) | |
| A61K 31/506 | (2006.01) | |
| A61K 31/52 | (2006.01) | |
| A61K 45/06 | (2006.01) | |
| A61K 31/53 | (2006.01) | |
| A61K 31/5377 | (2006.01) | |
| C07D 491/048 | (2006.01) | |
| C07D 487/04 | (2006.01) | |
| C07D 417/12 | (2006.01) | |
| C07D 413/12 | (2006.01) | |
| C07D 409/12 | (2006.01) | |
| C07D 409/04 | (2006.01) | |
| C07D 405/12 | (2006.01) | |
| C07D 405/04 | (2006.01) | |
| C07D 403/12 | (2006.01) | |
| C07D 401/12 | (2006.01) | |

(Continued)

(52) U.S. Cl.
CPC .......... *A61K 31/538* (2013.01); *A61K 31/505* (2013.01); *A61K 31/506* (2013.01); *A61K 31/519* (2013.01); *A61K 31/52* (2013.01); *A61K 31/53* (2013.01); *A61K 31/5377* (2013.01); *A61K 45/06* (2013.01); *C07D 239/48* (2013.01); *C07D 401/12* (2013.01); *C07D 403/04* (2013.01); *C07D 403/12* (2013.01); *C07D 405/04* (2013.01); *C07D 405/12* (2013.01); *C07D 409/04* (2013.01); *C07D 409/12* (2013.01); *C07D 413/12* (2013.01); *C07D 413/14* (2013.01); *C07D 417/12* (2013.01); *C07D 487/04* (2013.01); *C07D 491/048* (2013.01); *Y02A 50/465* (2018.01)

(58) Field of Classification Search
CPC .............. C07D 403/04; A61K 31/5513; A61K 31/497; A61K 31/4985
See application file for complete search history.

(56) References Cited

U.S. PATENT DOCUMENTS

| | | |
|---|---|---|
| 6,169,086 B1 | 1/2001 | Ejima et al. |
| 8,268,846 B2 | 9/2012 | Wakefield et al. |

(Continued)

FOREIGN PATENT DOCUMENTS

| | | |
|---|---|---|
| CN | 104288170 A | 1/2015 |
| GB | 0 681 712 A | 10/1952 |

(Continued)

OTHER PUBLICATIONS

Database CAPLUS in STN Acc. No. 1955:60839, Hitchings et al., U.S. Pat. No. 2,691,655 (Oct. 12, 1954) (abstract).

(Continued)

*Primary Examiner* — Alexander R Pagano
*Assistant Examiner* — Ebenezer O Sackey
(74) *Attorney, Agent, or Firm* — Foley & Lardner LLP

(57) ABSTRACT

A compound of formula (I), or a pharmaceutically acceptable salt thereof, for use in the treatment of autoimmune diseases and inflammatory conditions.

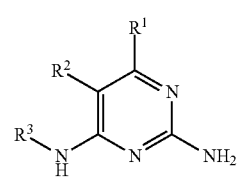

(I)

23 Claims, 1 Drawing Sheet

(51) Int. Cl.
  *C07D 413/14*  (2006.01)
  *C07D 239/48*  (2006.01)
  *C07D 403/04*  (2006.01)

(56) References Cited

U.S. PATENT DOCUMENTS

| | | | | |
|---|---|---|---|---|
| 10,064,869 | B2* | 9/2018 | Scobie | A61K 31/519 |
| 2004/0204386 | A1 | 10/2004 | Bhatt et al. | |
| 2008/0194577 | A1 | 8/2008 | Cai et al. | |
| 2010/0016344 | A1 | 1/2010 | Wakefield et al. | |
| 2010/0035863 | A1* | 2/2010 | Raphy | C07D 401/14 |
| | | | | 514/218 |
| 2011/0275611 | A1 | 11/2011 | Axten et al. | |
| 2017/0217961 | A1 | 8/2017 | Scobie et al. | |

FOREIGN PATENT DOCUMENTS

| | | |
|---|---|---|
| JP | 49-021147 B | 5/1974 |
| JP | 49-021148 B | 5/1974 |
| WO | WO-86/04583 A1 | 8/1986 |
| WO | WO-00/05230 A1 | 2/2000 |
| WO | WO02/0202093 | 1/2002 |
| WO | WO-02/096867 A2 | 12/2002 |
| WO | WO-03/015776 A1 | 2/2003 |
| WO | WO-2004/080979 A1 | 9/2004 |
| WO | WO-2005/026129 A1 | 3/2005 |
| WO | WO-2005/092899 A1 | 10/2005 |
| WO | WO-2006/078886 A2 | 7/2006 |
| WO | WO-2009/105220 A1 | 8/2009 |
| WO | WO-2011/056916 A1 | 5/2011 |
| WO | WO-2011/100285 A1 | 8/2011 |
| WO | WO-2012/080729 A3 | 6/2012 |
| WO | WO-2013/066839 A2 | 5/2013 |
| WO | WO-2014/033480 | 3/2014 |

OTHER PUBLICATIONS

Database CAPLUS in STN, Acc. No. 2010:84378, Wakefield et al., U.S. Pat. No. 8,268,846 B2 (Sep. 18, 2012) (abstract).
Database Registry Extract, American Chemical Society [database online], Jul. 22, 2016 [retrieved on Aug. 1, 2016] (856972-52-6/RN, 856972-54-8/RN, 856972-56-0/RN, 856972-52-6/RN).
Engelhardt, et al., "Bispyrimidines as Potent Histamine H4 Receptor Ligands: Delineation of Structure—Activity Relationships and Detailed H4 Receptor Binding Mode," Journal of Medicinal Chemistry, 2013, pp. 4264-4276, vol. 56, No. 11.
Extract from STN Registry—database, STN International, File Registry—RN: 634582-11-9 Entered STN: Jan. 6, 2004; RN: 634195-10-1 Entered STN: Jan. 5, 2004; RN: 634195-07-6 Entered STN: Jan. 5, 2004, 1 page.
Gad et al., "MTH1 inhibition eradicates cancer by preventing sanitation of the dNTP pool." Nature 508: 215-221 (2014).
Gong, et al., "Synthesis, SAR, and Antitumor Properties of Diamino-C, N-Diarylpyrimidine Positional Isomers: Inhibitors of Lysophosphatidic Acid Acyltransferase-beta," Bioorganic & Medicinal Chemistry Letters, 2004, pp. 2303-2308, vol. 14.
Huber et al., "Stereospecific targeting of MTH1 by (S)-crizotinib as an anticancer strategy," Nature 508: 222-227 (2014).
Kambe et al., "Mapping the Protein Interaction Landscape for Fully Functionalized Small-Molecule Probes in Human Cells," J Am Chem Soc 136(30): 10777-10782 (2014).
Katiyar, et al., "Syntheses of 2,4,6-trisubstituted pyrimidine derivatives as a new class of antifilarial topoisomerase II inhibitors," Bioorganic & Medicinal Chemistry Letters 15, Jan. 3, 2005, pp. 47-50, vol. 15, Issue 1.
Kumar et al., "A novel and convenient synthesis of 2-amino-4-(N-alkyl-N-arylamino)-pyrimidines using polarized ketene S,S- and S,N-acetals." Synthesis 1980(9): 748-751 (1980).
Lee, et al., "Discovery of a novel class of 2-aminopyrimidines as CDK1 and CDK2 inhibitors," Bioorganic & Medicinal Chemistry Letters, 2011, pp. 4203-4205, vol. 21.
Medina, et al., "Structure-Based Design of Potent and Selective 3-Phosphoinositide-Depdendent Kinase-1 (PDK1) Inhibitors," Journal of Medicinal Chemistry, 2011, pp. 1871-1895, vol. 54, No. 6.
Mizar, et al., "Three-component synthesis of 5:6 and 6:6 fused pyrimidines using KF-alumina as a catalyst," Tetrahedron Letters, 2008, pp. 5283-5285, vol. 49.
Pedersen M, et al. Successful treatment with Ipilimumab and Interleukin-2 in two patients with metastatic melanoma and systemic autoimmune disease. Cancer Immunol Immunother. 2014 63:1341-6.
Rabbani et al., International Journal of Cancer (1995), 63, pp. 840-845.
Rai, et al., "Human Mut T homolog 1 (MTH1): A roadblock for the tumor-suppressive effects of oncogenic RAS-induced ROS," Small GTPASES, 2012, pp. 120-125, vol. 3, No. 2.
Saleh et al., "Development and validation of method for TH588 and TH287, potent MTH1 inhibitors and new anti-cancer agents, for pharmacokinetic studies in mice plasma," J Pharm Biomed Analysis 104: 1-11 (2015).
Sander, et al., "2, 4-Diaminopyrimidines as Histamine H4 Receptor Ligands-Scaffold Optimization and Pharmacological Characterization," Bioorganic & Medicinal Chemistry, 2009, pp. 7186-7196, vol. 17.
Schreeb, et al., "Piperazine Modification in 2, 4, 6-Triaminopyrimidine Derivatives as Histamine H4, Receptor Ligands," Pharmazine, 2013, pp. 521-525, vol. 68.
Shi, et al., "Modulation of Peripheral Serotonin Levels by Novel Tryptophan Hydroxylase Inhibitors for the Potential Treatment of Functional Gastrointestinal Disorders," Journal of Medicinal Chemistry, 2008, pp. 3684-3687, vol. 51, No. 13.
Streib et al., "An Organometallic Inhibitor for the Human Repair Enzyme 7,8-Dihydro-8-oxoguanosine Triphosphatase," Angewandte Chemie 53(1): 305-309 (Jan. 2014).
Sunduru, et al., "Discovery of new 1,3,5-triazine scaffolds with potent activity against *Mycobacterium tuberculosis* H37Rv," European Journal of Medicinal Chemistry, Aug. 2010, pp. 3335-3345, vol. 45, Issue 8.
Svennson, et al., "Crystal structure of human MTH1 and the 8-oxo-dGMP product complex," FEBS Letters, Aug. 19, 2011, pp. 2617-2621, vol. 585, Issue 16.
Tani, Database CAPLUS 1975:140168, JP 4921147B, abstract, 1974.
Tani, Database CAPLUS 1975:140173, JP 4921147B, abstract, 1974.
Vishwakarma et al., "Reactions of Polarized Keten S,N-Acetals with Guanidine: A Facile General Route to Novel 5,6-Substituted 2-Amino-4-N-alkyl/aryl/N-azacycloalkylaminopyrimidines." Indian J Chem 24B: 466-471 (1985).
Vishwakarma, et al., "Reactions of Polarized Keten S, N-Acetals with Guanidine: A Facile General Route to Novel 5, 6-Substituted 2-Amino-4-N-alkyl/aryl/N-azacycloalkylaminopyrimidines," Indian Journal of Chemistry, May 1985, pp. 466-471, vol. 24B.

* cited by examiner

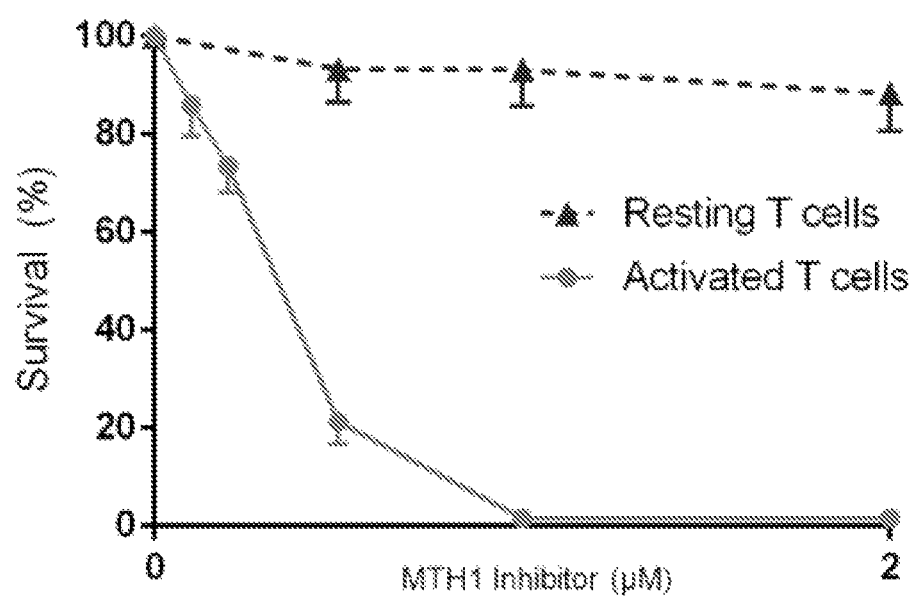

MTH1 INHIBITORS FOR TREATMENT OF INFLAMMATORY AND AUTOIMMUNE CONDITIONS

CROSS REFERENCE TO RELATED APPLICATIONS

This application is a continuation of U.S. patent application Ser. No. 15/315,478, filed Dec. 1, 2016, which is a U.S. National Stage Application under 35 U.S.C. § 371 of International Application of PCT/SE2015/050654, filed Jun. 4, 2015, which claims the benefit of and priority to SE Application 1450681-0, filed Jun. 4, 2014, the contents of which are incorporated herein by reference in their entireties.

FIELD OF THE INVENTION

The invention relates to compositions and methods for treatment, prevention and/or prophylaxis of autoimmune diseases and inflammatory (e.g. chronic inflammatory) conditions. In particular, the invention relates to compositions and methods for the treatment and/or prophylaxis of common autoimmune diseases including rheumatoid arthritis, multiple sclerosis and psoriasis through inhibition of MTH1.

BACKGROUND OF THE INVENTION

The listing or discussion of an apparently prior-published document in this specification should not necessarily be taken as an acknowledgement that the document is part of the state of the art or is common general knowledge.
Autoimmune and Inflammatory Disorders Autoimmune diseases and hyperinflammatory disorders are conditions where a mammal's immune system starts reacting against its own tissues. Such conditions include, without limitation, arthritis, e.g. rheumatoid arthritis, systemic lupus erythematosus, Crohn's disease, ulcerous colitis, multiple sclerosis, lymphoproliferative diseases (e.g. those caused by Epstein Barr virus and cytomegalovirus), rejection after organ transplantation, Wegener' granulomatosus, psoriasis, Mb Bechterews, Behcets disease, Guillain Barre, dermatomyositis, myositis, polymyositis, primary biliary cirrhosis, anti-phospholipid syndrome, autoimmune hepatitis, autoimmune cardiomyopathy, alopecia areata, atherosclerosis, type 1 diabetes, autoimmune uveitis, Goodpasteure's syndrome, Graves' disease, Hashimotos disease, mixed connective tissue disease, myasthenia gravis, pemphigus vulgaris, pernicious anemia, Sjögren's syndrome, giant cell arteritis, ulcerative colitis, vasculitis, Churg-Strauss syndrome, postpolio syndrome, idiopathic thrombocytopenic purpura, Peyronie disease and Dupuytren's contracture.
Shortcomings and Complications with Current Treatment Today's treatment of inflammatory and autoimmune diseases and disorders is not effective for all patients with diagnosed disease also including a large proportion of patients that experience adverse effects from treatments with existing therapies.

Today's treatment of autoimmune conditions like RA is not effective for all patients with diagnosed disease also including a large proportion of patients that experience adverse effects from treatments with biological agents, as represented by the therapy with TNF-α inhibitors, or from treatment with Methotrexate and COX-2 inhibitors. In similarity to RA, the cause and pathology of autoimmune and (hyper) inflammatory conditions including MS, IBD and the majority of less prevalent autoimmune conditions, is far from understood and many patients suffer from a disease that current treatments do not have the capacity to treat or ameliorate, hence there is a great need to understand the mechanisms driving these diseases which will enable novel ways for treatments.

The present invention aims at providing new treatments for inflammatory and autoimmune diseases based on immunomodulatory effects that can be achieved by inhibition of the MTH1 enzyme.

PRIOR ART

Engelhardt, H. et al. *Journal of Medicinal Chemistry* (2013), 56(11), 4264-4276 discloses certain 6-aryl-2,4-diaminopyrimidines having an additional pyrimidine appendage as histamine H4 receptor modulators. The paper suggests that the compounds are useful for the treatment of e.g. immune and inflammatory conditions, but there are no data that supports such statements. The only 6-aryl compounds that are exemplified or mentioned are phenyl or 3-chlorophenyl and there is nothing that suggests that any particular substitution pattern, e.g. 2,3-disubstituted phenyls, or heteroaryls, would be particularly advantageous.

US patent application US 2010/0016344 disclose certain 6-aryl-2,4-diamino-pyrimidines having an additional pyrimidine appendage as histamine H4 receptor modulators. The compounds are claimed to be useful for the treatment of e.g. autoimmune and inflammatory disorders. Data supporting the usefullness in the treatment of inflammatory pain is presented. There is no support that the compounds would be effective in the treatment of autoimmune diseases in general. The preferred 6-aryl is stated to be phenyl or 3-chlorophenyl although also 3,5-dichlorophenyl and 5-chloro-5-methoxyphenyl are exemplified. However, there is nothing that suggests that 2,3-disubstituted phenyls would be particularly advantageous.

International patent application WO 2013/066839 discloses three 6-(3-pyridyl)-(2,4-diaminopyrimidines as HDAC inhibitors. However, the 3-pyridyl is unsubstituted and there is nothing that suggests that replacing them with other heteroaryls or substituted phenyls would be advantageous. Moreover, the substituent on the 4-amino group contains an essential 5-trifluoromethyl-1,2,4-oxadiazol-3-yl group.

International patent application WO 2005/066839 discloses benzamides which are necessarily substituted in the 2-position by hydroxy or amino. In one case this moiety is linked to the 4-amino group of a 2,4-diamino-6-(3-pyridyl) pyrimidine. The compounds are stated to be useful in the treatment of cell prolifeartive diseases and conditions. Autoimmune or inflammatory disorders are not mentioned or suggested.

International patent application WO 2010/059658 describes 2,4-diamino-pyrimidines substituted in the 6-position with 6-indazolyl or 3-cyano-2-fluorophenyl, where the latter is just a synthetic precursor to the former. In addition, the relevant indazoles all carry a 3-amino substituent. Although immune diseases are mentioned in the text, there are no data to support the usefulness of the compounds for such diseases; the only claimed use is for cancer. The same compounds are also discussed in and J. R. Medina *Journal of Medicinal Chemistry* (2011), 54, 1871-1895, where it is stated that the compounds only modestly inhibits tumor growth in vivo.

International patent application WO 2006/078886 describes 2,4-diamino-pyrimidines substituted in the 6-position by phenyl and where the 4-amine is substituted by an arylalkyl or heteroarylalkyl group. The phenyl must be unsubstituted or have one or more alkoxy substituents. The arylalkyl and heteroarylalkyl must be unsubstituted or have one or more halogens, cyano and/or hydroxy. The compounds are claimed to be useful to treat disorders where wnt-signalling is involved, but inflammatory or auto-immune disorders are not mentioned.

International patent application WO 2005/026129 discloses 4,6-disubstituted aminopyrimidines as protein kinase modulators useful in the treatment of e.g. inflammation an autoimmune diseases. Of the 385 examples only two are 2,4-diaminopyrimidines and both these have a phenyl attached directly to the 4-amino group of the pyrimidine. These phenyls also carry an additional 4-aminosubstituent.

Two publications from the group of H. Junjappa (*Indian Journal Chemistry* (1985), 24B 466; *Synthesis* (1980), 748) describes the synthesis of certain 2-amino-4-(N-alkylamino)-6-arylpyrimidines. The publications do not mention or suggest the use of the synthesized compounds in the treatment of autoimmune and inflammatory disorders.

Japanese patents JP49021147 and JP49021148 disclose certain 2-amino-4-(N-alkylamino)-6-(pyridyl)pyrimidines claimed to be anti-inflammatory. There is however no data to support this claim. Also, all pyridines are unsubstituted and there is nothing that indicates that substituents on the pyridines would be beneficial.

There are numerous 2-amino-4-(N-alkylamino)-6-arylpyrimidines that are, or that at some point have been stated to be, commercially available but that do not have any ascribed pharmaceutical use ascribed to them.

MTH1 inhibitors have been described in Streib, M. et al. *Angewandte Chemie, Int*, Ed. (2014), 52, 305-309. The compounds are organometallic and are not substituted 2,4-diaminopyrimidines.

Huber, K. V. M. et al. *Nature* (2014), 508, 222-227 describe certain compounds, i.e. (S)-crizotinib, as MTH1 inhibitors. However, the compounds are not substituted 2,4-diaminopyrimidines.

Gad, H. et al. *Nature* (2014), 508, 215-221 and Saleh, A. et al. *Journal of Pharmaceutical and Biomedical Analysis* (2015), 104, 1, describe certain 2,4-diaminopyrimidines as MTH1 inhibitors. However, there is nothing that suggests that the compounds are useful for treatment of inflammatory or auto-immune diseases.

International patent application WO 2013/066839 discloses certain 6-aryl-2,4-diaminopyrimidines, which may be useful in the treatment of cancer.

Chinese patent application CN104288170 describes the natural product echinacoside as an inhibitor of MTH1. However this compound is a sugar derivative and not a pyrimidine Kambe, T. et al. *Journal of the American Chemical Society* (2014), 136, 10777 demonstrate a tetrazole-based MTH1 ligand.

SUMMARY OF THE INVENTION

In autoimmune conditions and after organ transplantation, it is vital to eliminate the activated auto-reactive lymphocytes while preferably preserving their normal counterparts. Inhibiting MTH1 activity will kill the activated lymphocytes and thus reduce destructive inflammation. It should therefore be a promising novel therapy for autoimmunity and organ rejection, either as monotherapy or in combination with other drugs (e.g. cortisone) that are currently on the market.

We have observed that silencing the enzymatic activity of MTH1 in human lymphocytes results in selective killing of activated lymphocytes. Resting lymphocytes are not affected by the treatment. The present invention aims at providing a new treatment option for autoimmune conditions and transplantation patients through pharmacologic inhibition of MTH1. Diseases which may benefit from this treatment include rheumatoid arthritis, systemic lupus erythematosus, Crohn's disease, ulcerous colitis, multiple sclerosis, lymphoproliferative diseases (e.g. those caused by Epstein Barr virus and cytomegalovirus), rejection after organ transplantation, Wegener' granulomatosus, psoriasis, Mb Bechterews, Behcets disease, Guillain Barre, dermatomyositis, myositis, polymyositis, primary biliary cirrhosis, anti-phospholipid syndrome, autoimmune hepatitis, autoimmune cardiomyopathy, alopecia areata, atherosclerosis, type 1 diabetes, autoimmune uveitis, Goodpasteure's syndrome, Graves' disease, Hashimotos disease, mixed connective tissue disease, myasthenia gravis, pemphigus vulgaris, pernicious anemia, Sjögren's syndrome, giant cell arteritis, ulcerative colitis, vasculitis, Churg-Strauss syndrome, postpolio syndrome, idiopathic thrombocytopenic purpura, Peyronie disease and Dupuytren's contracture.

BRIEF DESCRIPTION OF THE DRAWINGS

FIG. 1. An MTH1 inhibitor (example 297) selectively kills activated T-lymphocytes while unactivated T-lymphocytes are unaffected.

DETAILED DESCRIPTION OF THE INVENTION

There is provided a compound of formula I,

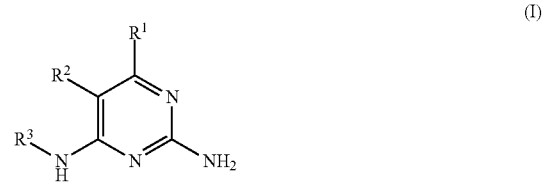

or a pharmaceutically acceptable salt thereof,
for use in the treatment of autoimmune diseases and inflammatory conditions, wherein:
$R^1$ represents
(i)

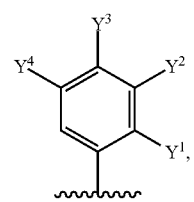

or
(ii) a 6-membered heteroaryl substituted by one or more groups selected from $Y^5$, or
(iii) a 5- to 10-membered monocyclic or bicyclic heteroaryl connected to the pyrimidine ring of the compound of formula I via a carbon atom of the heteroaryl, which heteroaryl is optionally substituted by one or more groups selected from $Y^5$, or
(iv) -ethynyl-$Y^6$;

$R^2$ represents hydrogen, halogen, —CN or $C_{1-3}$alkyl optionally substituted by one or more fluoro; and $R^3$ represents —X-L-J, —$C_{1-12}$alkyl optionally substituted by one or more $Z^1$ or heterocycloalkyl optionally substituted by one or more groups selected from $Z^2$; or $R^1$ represents (v) a 3- to 8-membered nonaromatic ring, which ring optionally contains one or two heteroatoms and/or one or two double bonds, and which ring is optionally substituted by one or more groups selected from $Y^7$;

$R^2$ represents hydrogen, halogen, —CN or $C_{1-3}$alkyl optionally substituted by one or more fluoro; and $R^3$ represents —X-L-J; or $R^1$ is as defined herein above; and $R^2$ and $R^3$ are linked together to form, along with the atoms to which they are attached, a 5- to 8-membered non-aromatic ring, wherein the link formed by $R^2$ and $R^3$ is optionally substituted by one or more groups selected from $Z^3$ and optionally substituted by —X-L-J;

X represents —$C_{1-6}$alkylene-, optionally substituted by one or more $T^1$, or —$(C(R^A)_2)_p$—$C_{2-5}$heterocycloalkylene-$(C(R^A)_2)_q$—, where the heterocycloalkylene is optionally substituted by one or more $T^2$;

L represents a single bond or -$L^1$-$L^2$-;

$L^1$ represents —N($R^B$)—, —O—, —S(O)$_m$—, —C(O)N($R^C$)—, —N($R^D$)C(O)—, —S(O)$_n$N($R^E$)—, —N($R^F$)S(O)$_n$— or —N($R^G$)C(O)N($R^H$)—;

$L^2$ represents a single bond or —$C_{1-6}$alkylene-;

J represents (i) a 6- to 10-membered aryl optionally substituted by $D^1$ and optionally substituted by one or more groups selected from $R^x$, or (ii) a 5- to 11-membered monocyclic or bicyclic heteroaryl ring, which heteroaryl contains 1 to 3 nitrogen atoms, and/or one oxygen atom and/or one or two sulfur atoms and which heteroaryl is optionally substituted by $D^2$ and optionally substituted by one or more groups selected from $R^Y$;

$Y^1$ represents hydrogen, halogen, —CN, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —$N_3$, —$NO_2$, —O$R^m$—S$R^n$;

$Y^2$, $Y^3$ and $Y^4$ each independently represents hydrogen, halogen, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —$N_3$, —$NO_2$, —OH, —O$R^m$ or —S$R^n$;

$Y^5$ represents halogen, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —$N_3$, —$NO_2$, —OH, —O$R^m$ or —S$R^n$;

$Y^6$ represents aryl or heteroaryl, both optionally substituted by one or more groups selected from halogen, —CN, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —$N_3$, —$NO_2$, —OH, —O$R^m$ and —S$R^n$;

$Y^7$ represents halogen, $R^a$, -A-C(Q)$R^b$, -A-C(Q)N($R^c$)$R^d$, -A-C(Q)O$R^e$, -A-S(O)$_n$$R^f$, -A-S(O)$_n$N($R^i$)$R^j$, -A-S(O)$_n$O$R^k$, —OH, —O$R^m$, or Q;

Q represents =O, =S, =N$R^o$, =NN($R^p$)$R^q$, =N(O$R^r$), =NS(O)$_2$N($R^s$)$R^t$ or =C(H)NO$_2$;

A represents a single bond, —N($R^I$)—, —C(Q)N($R^j$)— or —O—;

each $R^a$, $R^f$, $R^h$ and $R^m$ independently represents $C_{1-6}$ alkyl optionally substituted by one or more groups selected from $W^1$, heterocycloalkyl optionally substituted by one or more groups selected from $W^2$ or aryl or heteroaryl both optionally substituted by one or more groups selected from $W^3$;

each $R^b$, $R^c$, $R^d$, $R^e$, $R^g$, $R^i$, $R^j$, $R^k$, $R^l$, $R^o$, $R^p$, $R^q$, $R^r$, $R^s$ and $R^t$ independently represents hydrogen, $C_{1-6}$ alkyl optionally substituted by one or more groups selected from $W^1$, heterocycloalkyl optionally substituted by one or more groups selected from $W^2$ or aryl or heteroaryl both optionally substituted by one or more groups selected from $W^3$; or any two $R^c$ and $R^d$, $R^i$ and $R^j$, $R^p$ and $R^q$ and/or $R^s$ and $R^t$ are linked together to form, along with the nitrogen atom to which they are attached, a 3- to 8-membered monocyclic or bicyclic ring, which ring optionally contains one or two further heteroatoms and which ring optionally is substituted by one or more groups selected from $W^2$, $C_{1-3}$alkyl optionally substituted by one or more groups selected from $W^1$, and =O; or two $R^l$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, $C_{1-3}$alkyl optionally substituted by one or more halogens, and =O;

$W^1$ represents halogen, —CN, -$A^1$-C(O)$R^{b1}$, -$A^1$-C(O)N($R^{c1}$)$R^{d1}$, -$A^1$-C(O)O$R^{e1}$, -$A^1$-S(O)$_n$$R^{f1}$, -$A^1$-S(O)$_n$O$R^{g1}$, —N($R^{h1}$)$R^{i1}$, —O$R^{j1}$ or =O;

$W^2$ represents halogen, —CN, $R^{a1}$, -$A^1$-C(O)$R^{b1}$, -$A^1$-C(O)N($R^{c1}$)$R^{d1}$, -$A^1$-C(O)O$R^{e1}$, -$A^1$-S(O)$_n$$R^{f1}$, -$A^1$-S(O)$_n$O$R^{g1}$, —N($R^{h1}$)$R^{i1}$, —O$R^{j1}$ or =O;

$W^3$ represents halogen, —CN, $R^{a1}$, -$A^1$-C(O)$R^{b1}$, -$A^1$-C(O)N($R^{c1}$)$R^{d1}$, -$A^1$-C(O)O$R^{e1}$, -$A^1$-S(O)$_n$$R^{f1}$, -$A^1$-S(O)$_n$O$R^{g1}$, —O$R^{j1}$, -$A^1$-S(N$R^{k1}$)(O)$R^{l1}$, -$A^1$-S(O)$_n$N($R^{m1}$)$R^{n1}$, —$N_3$, —$NO_2$, —S$R^{o1}$ or =O;

$A^1$ represents a single bond, —N($R^K$)— or —O—;

each $R^{a1}$, $R^{f1}$ and $R^{l1}$ independently represents $C_{1-6}$ alkyl optionally substituted by one or more fluoro;

each $R^{b1}$, $R^{c1}$, $R^{d1}$, $R^{e1}$, $R^{g1}$, $R^{h1}$, $R^{i1}$, $R^{j1}$, $R^{k1}$, $R^{m1}$, $R^{n1}$ and $R^{o1}$ independently represents hydrogen or $C_{1-6}$ alkyl optionally substituted by one or more fluoro; or any two $R^{c1}$ and $R^{d1}$, $R^{h1}$ and $R^{i1}$ and/or $R^{m1}$ and $R^{n1}$ are linked together to form, along with the nitrogen atom to which they are attached, a 3- to 6-membered ring, which ring optionally contains one further heteroatom and which ring optionally is substituted by one or more groups selected from fluoro, $C_{1-3}$alkyl optionally substituted by one or more fluoro, and =O;

$Z^1$ represents halogen, —CN, -$A^2$-C($Q^1$)$R^{b2}$, -$A^2$-C($Q^1$)N($R^{c2}$)$R^{d2}$, -$A^2$-C($Q^1$)O$R^{e2}$, -$A^2$-S(O)$_n$$R^{f2}$, -$A^2$-S(O)$_n$O$R^{g2}$, -$A^2$-S(N$R^{h2}$)(O)$R^{i2}$, -$A^2$-S(O)$_n$N($R^{j2}$)$R^{k2}$, —N($R^{l2}$)$R^{m2}$, —O$R^{n2}$, —S$R^{o2}$ or heterocycloalkyl optionally substituted by one or more groups selected from $W^5$;

$Z^2$ represents halogen, —CN, $R^{a2}$, -$A^2$-C($Q^1$)$R^{b2}$, -$A^2$-C($Q^1$)N($R^{c2}$)$R^{d2}$, -$A^2$-C($Q^1$)O$R^{e2}$, -$A^2$-S(O)$_n$$R^{f2}$, -$A^2$-S(O)$_n$O$R^{g2}$, -$A^2$-S(N$R^{h2}$)(O)$R^{i2}$, -$A^2$-S(O)$_n$N($R^{j2}$)$R^{k2}$, —N($R^{l2}$)$R^{m2}$, —O$R^{n2}$ or =$Q^1$;

$Z^3$ represents $R^{a2}$ or =$Q^1$;

$Q^1$ represents =O, =S, =N$R^{p2}$, =NN($R^{q2}$)$R^{r2}$, =N(O$R^{s2}$), =NS(O)$_2$N($R^{t2}$)$R^{u2}$ or =C(H)NO$_2$;

$A^2$ represents a single bond, —N($R^L$)—, —C($Q^1$)N($R^M$)— or —O—;

each $R^{a2}$, $R^{f2}$, $R^{i2}$, $R^{n2}$ and $R^{o2}$ independently represents $C_{1-6}$alkyl optionally substituted by one or more groups selected from $W^4$ or heterocycloalkyl optionally substituted by one or more groups selected from $W^5$;

$R^{m2}$ represents $C_{2-6}$alkyl optionally substituted by one or more groups selected from $W^4$;

each $R^{b2}$, $R^{c2}$, $R^{d2}$, $R^{e2}$, $R^{g2}$, $R^{h2}$, $R^{j2}$, $R^{k2}$, $R^{l2}$, $R^{p2}$, $R^{q2}$, $R^{r2}$, $R^{s2}$, $R^{t2}$ and $R^{u2}$ independently represents hydrogen, $C_{1-6}$alkyl optionally substituted by one or more groups selected from $W^4$, heterocycloalkyl optionally substituted by one or more groups selected from $W^5$; or any two $R^{c2}$ and $R^{d2}$, $R^{j2}$ and $R^{k2}$, $R^{l2}$ and $R^{m2}$, $R^{q2}$ and $R^{r2}$ and/or $R^{t2}$ and $R^{u2}$ are linked together to form, along with the nitrogen atom to which they are attached, a 3- to 8-membered monocyclic or bicyclic ring, which ring optionally contains one or two further heteroatoms and which ring optionally is substituted by one or more groups selected from $W^5$, $C_{1-3}$alkyl optionally substituted by one or more groups selected from $W^4$, and =O;

$W^4$ represents halogen, —CN, -$A^3$-C(O)$R^{b3}$, -$A^3$-C(O)N($R^{c3}$)$R^{d3}$, -$A^3$-C(O)O$R^{e3}$, -$A^3$-S(O)$_n$$R^{f3}$, -$A^3$-S(O)$_n$O$R^{g3}$, —O$R^{h3}$, =O or $W^6$;

$W^5$ represents halogen, —CN, $R^{a3}$, -$A^3$-C(O)$R^{b3}$, -$A^3$-C(O)N($R^{c3}$)$R^{d3}$, -$A^3$-C(O)O$R^{e3}$, -$A^3$-S(O)$_n$$R^{f3}$, -$A^3$-S(O)$_n$O$R^{g3}$, —O$R^{h3}$, =O or $W^6$;

$W^6$ represents phenyl or heteroaryl, both optionally substituted by one or more groups selected from halogen and $R^{a3}$;

$A^3$ represents a single bond, —N($R^L$)— or —O—;

each $R^{a3}$ and $R^{f3}$ independently represents $C_{1-6}$ alkyl optionally substituted by one or more fluoro;

each $R^{b3}$, $R^{c3}$, $R^{d3}$, $R^{e3}$, $R^{g3}$ and $R^{h3}$ independently represents hydrogen or $C_{1-6}$alkyl optionally substituted by one or more fluoro; or $R^{c3}$ and $R^{d3}$ are linked together to form, along with the nitrogen atom to which they are attached, a 3- to 6-membered ring, which ring optionally contains one further heteroatoms and which ring optionally is substituted by one or more groups selected from fluoro, $C_{1-3}$alkyl optionally substituted by one or more fluoro, and =O;

$D^1$ and $D^2$ represent $R^{a4}$, -$A^4$-C(Q$^2$)$R^{b4}$, -$A^4$-C(Q$^2$)N($R^{c4}$)$R^{d4}$, -$A^4$-C(Q$^2$)O$R^{e4}$, -$A^4$-S(O)$_n$$R^{f4}$, -$A^4$-S(O)$_n$C(O)$R^{g4}$, -$A^4$-S(N$R^{h4}$)(O)$R^{i4}$, -$A^4$-S(O)$_n$N($R^{j4}$)$R^{k4}$, -$A^4$-S(O)$_n$O$R^{l4}$, —B(O$R^{m4}$)$_2$, —N$_3$, —N($R^{n4}$)$R^{o4}$, —N(H)CN, —NO$_2$, —ONO$_2$, —O$R^{p4}$, —S$R^{q4}$ or, when J is partly aromatic, =Q$^2$;

$Q^2$ represents =O, =S, =N$R^{r4}$, =NN($R^{s4}$)$R^{t4}$, =N(O$R^{u4}$), =NS(O)$_2$N($R^{v4}$)$R^{w4}$ or =C(H)NO$_2$;

$A^4$ represents a single bond, —N($R^M$)—, —C(Q)N($R^N$)— or —O—;

each $R^X$ and $R^Y$ independently represent halogen, —CN, $R^{a4}$, —N($R^{n4}$)$R^{o4}$, —NO$_2$, —O$R^{p4}$ or =O;

$R^{c4}$ represents hydrogen, $R^{a4}$, —C(O)O$R^{e4}$, —S(O)$_n$$R^{f4}$, —S(O)$_n$N($R^{j4}$)$R^{k4}$, —N($R^{n4}$)$R^{o4}$ or —O$R^{p4}$;

each $R^{a4}$, $R^{f4}$ and $R^{i4}$ independently represent $C_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$;

each $R^{b4}$, $R^{d4}$, $R^{e4}$, $R^{g4}$, $R^{h4}$, $R^{j4}$, $R^{k4}$, $R^{l4}$, $R^{m4}$, $R^{n4}$, $R^{o4}$, $R^{p4}$, $R^{q4}$, $R^{r4}$, $R^{s4}$, $R^{t4}$, $R^{u4}$, $R^{v4}$ and $R^{w4}$ independently represent hydrogen, $C_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$; or any two $R^{c4}$ and $R^{d4}$, $R^{j4}$ and $R^{k4}$, $R^{n4}$ and $R^{o4}$, $R^{s4}$ and $R^{t4}$ and/or $R^{v4}$ and $R^{w4}$ are linked together to form, along with the nitrogen atom to which they are attached, a 3- to 6-membered ring, which ring optionally contains one heteroatom and which ring optionally is substituted by one or more groups selected from fluoro, $C_{1-3}$alkyl optionally substituted by one or more fluoro, and =O; or two $R^{m4}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, $C_{1-3}$alkyl optionally substituted by one or more halogens, and =O;

each $G^1$ is independently selected from halogen, —CN, —N($R^{b5}$)$R^{c5}$, —N(H)C(O)$R^{d5}$, —N(H)S(O)$_n$$R^{h5}$, —O$R^{k5}$, —S(O)$_m$$R^{l2}$ or =O;

each $G^2$ is independently selected from halogen, $R^{a5}$, —CN, —N($R^{b5}$)$R^{c5}$, —N(H)C(O)$R^{d5}$, —N(H)S(O)$_n$$R^{h5}$, —O$R^{k5}$, —S(O)$_m$$R^{l2}$ or =O;

each $G^3$ and $G^4$ are independently selected from halogen, —CN, $R^{a5}$, —N($R^{b5}$)$R^{c5}$, -$A^5$-C(O)$R^{d5}$, -$A^5$-C(O)N($R^{e5}$)$R^{f5}$, -$A^5$-C(O)O$R^{g5}$, -$A^5$-S(O)$_n$$R^{h5}$, -$A^5$-S(O)$_n$N($R^{i5}$)$R^{j5}$, —O$R^{k5}$ or =O;

$A^5$ represents a single bond or —N(H)—;

$R^{a5}$ represents $C_{1-6}$ alkyl optionally substituted by one or more halogens;

each $R^{b5}$, $R^{c5}$, $R^{d5}$, $R^{e5}$, $R^{f5}$, $R^{g5}$, $R^{h5}$, $R^{i5}$, $R^{j5}$, $R^{k5}$ and $R^{l5}$ independently represents hydrogen or $C_{1-6}$ alkyl optionally substituted by one or more halogens; or any two $R^{b5}$ and $R^{c5}$, $R^{e5}$ and $R^{f5}$ and/or $R^{i5}$ and $R^{j5}$ are linked together to form, along with the nitrogen atom to which they are attached, a 3- to 6-membered ring, which ring optionally contains one further heteroatom and which ring optionally is substituted by one or more groups selected from halogen, $C_{1-3}$alkyl optionally substituted by one or more halogens, and =O;

each $R^A$, $R^B$, $R^C$, $R^D$, $R^E$, $R^F$, $R^G$, $R^H$, $R^I$, $R^J$, $R^K$, $R^L$, $R^M$ and $R^N$ independently represents hydrogen or $C_{1-3}$ alkyl optionally substituted by one or more fluoro;

$T^1$ represents halogen, —CN, —N($R^{b6}$)$R^{c6}$ or —O$R^{d6}$;

$T^2$ represents halogen, —CN, $R^{a6}$, —O$R^{d6}$ or =O;

each $R^{a6}$ independently represents $C_{1-6}$alkyl optionally substituted by one or more halogens;

each $R^{b6}$, $R^{c6}$ and $R^{d6}$ independently represents hydrogen or $C_{1-6}$alkyl optionally substituted by one or more halogens; or $R^{b6}$ and $R^{c6}$ are linked together to form, along with the nitrogen atom to which they are attached, a 3- to 6-membered ring;

each p and q independently represents 0, 1 or 2, provided that the sum of p and q is 0, 1 or 2;

each m independently represents 0, 1 or 2;

each n independently represents 1 or 2;

provided that when X represents —CH$_2$CH$_2$—, L represents -L$^1$-L$^2$-, L$^1$ represents —N(H)— or —N(Me)-, L$^2$ represents a single bond and J represents 4-pyrimidinyl, and said 4-pyrimidinyl is unsubstituted or substituted with —CH$_3$, —NH$_2$ or —N(H)CH$_2$CH(CH$_3$)$_2$, then $R^1$ does not represent phenyl, 3-chlorophenyl, 3,5-dichlorophenyl or 5-chloro-2-methoxyphenyl, and provided that formula I does not represent
(S)-N$^4$-(1-(2,4-difluorophenyl)ethyl)-6-(pyrazolo[1,5-a]pyrimidin-3-yl)pyrimidine-2,4-diamine.

The compounds of formula (I) as defined herein above may be referred to herein as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin. For the avoidance of doubt, solvates are also included within the scope of the invention.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

The terms "halo" or "halogen", when used herein, includes fluoro, chloro, bromo and iodo (for example, fluoro and chloro).

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise specified, $C_{1-q}$ alkylene groups (where q is the upper limit of the range) defined herein may (in a similar manner to the definition of $C_{1-q}$ alkyl) be straight-chain or, when there is a sufficient number (i.e. a minimum of two or three, as appropriate) of carbon atoms, be branched-chain, and/or cyclic (so forming a $C_{3-q}$-cycloalkylene group). When there is a sufficient number (i.e. a minimum of four) of carbon atoms, such groups may also be part cyclic. Such alkylene groups may also be saturated or, when there is a sufficient number (i.e. a minimum of two) of carbon atoms, be unsaturated (forming, for example, a $C_{2-q}$ alkenylene or a $C_{2-q}$ alkynylene group). Particular alkylene groups that may be mentioned include those that are straight-chained or cyclic and saturated.

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-q}$ (e.g. $C_{4-q}$) heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1]heptanyl, 6-azabicyclo[3.1.1]heptanyl, 6-azabicyclo-[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), 1,3,2-dioxaborinane, 1,3,6,2-dioxazaborocane, 1,3,2☐dioxaborolane, dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo [3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, tetrahydrothiopyranyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. At each occurrence when mentioned herein, a heterocycloalkyl group is preferably a 3- to 8-membered heterocycloalkyl group (e.g. a 5- or 6-membered heterocycloalkyl group).

The term "aryl", when used herein, includes $C_{6-10}$ aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like). For the avoidance of doubt, the point of attachment of substituents on aryl groups may be via any carbon atom of the ring system.

The term "heteroaryl" (or heteroaromatic), when used herein, includes 5- to 11-membered heteroaromatic groups containing one or more heteroatoms selected from oxygen, nitrogen and/or sulfur. Such heteroaryl group may comprise one, or two rings, of which at least one is aromatic. Substituents on heteroaryl/hetero-aromatic groups may, where appropriate, be located on any atom in the ring system including a heteroatom. The point of attachment of heteroaryl/hetero-aromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycloalkyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl. The oxides of heteroaryl/heteroaromatic groups are also embraced within the scope of the invention (e.g. the N-oxide). As stated above, heteroaryl includes polycyclic (e.g. bicyclic) groups where all rings are aromatic, and partly aromatic groups where at least one ring is aromatic and at least one other ring is not aromatic. Hence, other heteroaryl groups that may be mentioned include e.g. benzo[1,3]dioxolyl, benzo[1,4]dioxinyl, dihydrobenzo[d]isothiazolyl, 1,2-dihydrobenzo[d][1,2,3]diazaborininyl, 3,4-dihydro-1H-benzo[c][1,2]oxaborininyl, 1,3-dihydrobenzo[c][1,2]oxaborolyl, 3,4-dihydrobenz[1,4]oxazinyl, dihydrobenzothiophene, indolinyl, 5H,6H,7H-pyrrolo[1,2-b]pyrimidinyl, 1,2,3,4-tetrahydroquinolinyl, thiochromane and the like.

Heteroatoms that may be mentioned include phosphorus, silicon, preferably boron and, more preferably, oxygen, nitrogen and sulfur.

For the avoidance of doubt, in cases in which the identity of two or more substituents in a compound of the invention may be the same, the actual identities of the respective substituents are not in any way interdependent.

For the avoidance of doubt, when $R^1$ is defined as

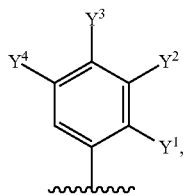

it is connected to the rest of formula I by the bond interrupted by the wiggly line, and formula I can thus be represented by

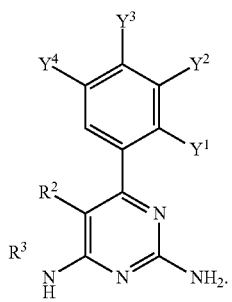

For the avoidance of doubt, when $R^3$ represents —X-L-J, X represents —(C($R^4$)$_2$)$_p$—C$_{2-5}$heterocycloalkylene-(C($R^4$)$_2$)$_q$—, $R^A$ represents hydrogen, p represents 1 and q represents 0, then —(C($R^4$)$_2$)$_p$—C$_{2-5}$heterocycloalkylene-(C($R^4$)$_2$)$_q$— may represent e.g.

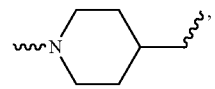

and formula I can then be represented by

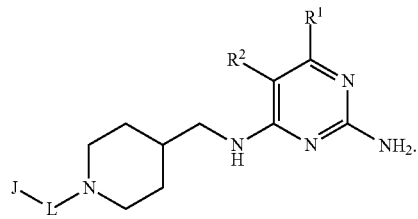

Likewise, when $R^3$ represents —X-L-J, L represents -$L^1$-$L^2$-, $L^1$ represents —C(O)N($R^C$)— and $L^2$ represents a single bond, then formula I can be represented by

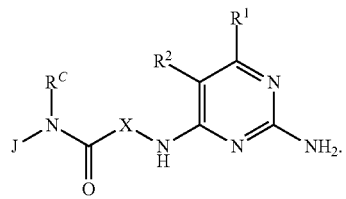

Likewise, when J is phenyl substituted in the 4-position by $D^1$, $D^1$ is -$A^4$-S(O)$_n R^{fA}$ and $A^4$ represents —C(Q)N($R^N$)—, then formula I can be represented by

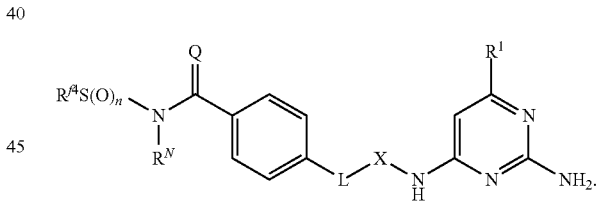

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

All individual features (e.g. preferred features) mentioned herein may be taken in isolation or in combination with any other feature (including preferred features) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

In some embodiments of the invention, $R^1$ represents (i)

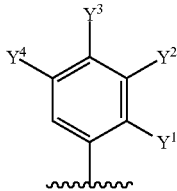

wherein $Y^1$, $Y^2$, $Y^3$ and $Y^4$ are as defined herein above.

Particular compounds of formula I that may be mentioned include those in which $R^1$ represents

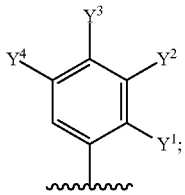

$Y^1$ in particular may represent hydrogen, halogen, —CN, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —N$_3$, —NO$_2$, —O$R^m$, —S$R^n$; and $Y^2$, $Y^3$ and $Y^4$ in particular may each independently represent hydrogen, halogen, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —N$_3$, —NO$_2$, —OH, —O$R^m$ or —S$R^n$.

When $R^1$ represents

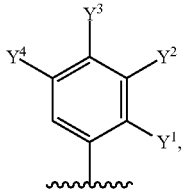

one of $Y^1$, $Y^2$, $Y^3$ and $Y^4$ is preferably other than hydrogen, or more preferably, two or three of $Y^1$, $Y^2$, $Y^3$ and $Y^4$ is other than hydrogen;

$R^2$ represents methyl, or preferably, hydrogen;

$R^3$ represents —X-L-J or —C$_{1-6}$alkyl optionally substituted by one or more $Z^1$ or heterocycloalkyl optionally substituted by one or more $Z^2$;

$Y^1$ represents halogen, —CN, $R^a$ or —O$R^m$; and $Y^2$, $Y^3$ and $Y^4$ each independently represent hydrogen, halogen, $R^a$, -A-C(Q)$R^b$, —C(Q)N($R^c$)$R^d$, —C(Q)O$R^e$, -A-S(O)$_n$$R^f$, —S(O)$_n$N($R^i$)$R^j$, —OH or —O$R^m$.

Preferred compounds of formula I that may be mentioned include those in which $R^1$ represents

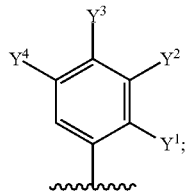

$Y^2$, $Y^3$ and $Y^4$ represent hydrogen; and
$Y^1$ represents fluoro, chloro, —CH$_3$, —CF$_3$, —CN, CH$_2$OH or —OCH$_3$; or
$Y^1$, $Y^3$ and $Y^4$ represent hydrogen; and
$Y^2$ represents fluoro, chloro, —CH$_3$, —CF$_3$, —CH=CHC(O)OCH$_3$, —CH$_2$NH$_2$, —CN, —CH$_2$N(H)C (O)CH=CH$_2$, —CH$_2$OH, —C(O)N(H)(4-methylphenyl), —N(H)C(O)CH$_3$, —N(H)C(O)CH=CH$_2$, —N(H)C(O) CH=CHCH$_2$NMe$_2$, —N(H)C(O)CH=CHPh, —N(H)C (O)C≡CH, —N(H)C(O)(2-hydroxyphenyl), —N(H)C(O)(6-hydroxypyrid-2-yl), —N(H)C(O)(5-chloro-2-hydroxyphenyl), —N(H)C(O)CH$_2$CH$_2$C(O)(1-pyrrolidinyl), —N(H)C(O)CH$_2$(OH), —N(H)C(O)CH(OH) Ph, —N(H)C(O)C(O)CH$_3$, —N(H)C(O)C(O)Ph, —N(H)S (O)$_2$CH=CH$_2$, —OH, —OCH$_3$, —OCH$_2$C(O)NH$_2$ or —OSO$_2$CF$_3$; or
$Y^1$, $Y^2$ and $Y^4$ represent hydrogen; and
$Y^3$ represent fluoro, chloro, —CH$_3$, —CF$_3$, —C(CH$_3$)$_3$, —CH=CH$_2$, —CH=CHC(O)OH, —CH=CHC(O)OCH$_3$, —CH$_2$NH$_2$, —CN, —CH$_2$N(H)C(O)CH=CH$_2$, —CH$_2$OH, —C(O)H, —C(O)CH$_3$, —C(O)CF$_3$, —C(O)N(H)CH$_3$, —C(O)N(H)CH$_2$(2-furanyl), —C(O)(4-morpholinyl), —C(O)OH, —C(O)OCH$_3$, —N(H)C(O)CH$_3$, —N(H)C(O) CH=CH$_2$, —N(H)S(O)$_2$CH$_3$, —OCH(CH$_3$)$_2$, —OCH$_3$, —OCF$_3$, —S(O)$_2$CH$_3$, or —S(O)$_2$(4-morpholinyl); and $R^2$ represents methyl, or preferably, hydrogen;

$R^3$ represents —X-L-J or —C$_{1-6}$alkyl optionally substituted by one or more, preferably one to three, groups selected from $Z^1$, or heterocycloalkyl optionally substituted by one or more, preferably one to three, groups selected from $Z^2$;

X represents —C$_{1-6}$alkylene-optionally substituted by $T^1$, or —(C($R^A$)$_2$)$_p$—C$_{2-5}$heterocycloalkylene-(C($R^A$)$_2$)$_q$—;

L represents a single bond or -$L^1$-$L^2$-;

$L^1$ represents —N(H)—, —O—, —SO$_2$—, —C(O)N (H)—, —S(O)$_n$N(H)— or —N(H)C(O)N(H)—;

$L^2$ represents a single bond or —C$_{1-6}$alkylene-;

J represents phenyl optionally substituted by $D^1$ and optionally substituted by one or more groups selected from $R^X$, or a 5- to 10-membered monocyclic or bicyclic heteroaryl containing 1 to 3 nitrogen atoms, and/or one oxygen atom and/or one sulfur atom and which ring is optionally substituted by $D^2$ and optionally substituted by one or more groups selected from $R^Y$;

$Z^1$ represents halogen, —CN, -$A^2$-C(O)$R^{b2}$, -$A^2$-C(O)N ($R^{c2}$)$R^{d2}$, -$A^2$-C(O)O$R^{e2}$, —N($R^{l2}$)$R^{m2}$, —O$R^{n2}$ or heterocycloalkyl optionally substituted by =O;

$Z^2$ represents $R^{a2}$, —C(O)O$R^{e2}$ or =O;

$T^1$ represents —N($R^{l2}$)$R^m$;

$A^2$ represents a single bond or —N(H)—;

$D^1$ represents $R^{a4}$, -$A^4$-C(Q$^2$)$R^{b4}$, -$A^4$-C(Q$^2$)N($R^{c4}$)$R^{d4}$, -$A^4$-C(O)O$R^{e4}$, -$A^4$-S(O)$_n$$R^{f4}$, -$A^4$-SO$_2$N($R^{j4}$)$R^{k4}$, —SO$_2$O$R^{l4}$, —N($R^{m4}$)$R^{o4}$, —N(H)CN, —NO$_2$, —O$R^{p4}$ or —S$R^{q4}$;

$D^2$ represents $R^{a4}$, -$A^4$-C(O)$R^{b4}$, —C(O)N($R^{c4}$)$R^{d4}$, —C(O)O$R^{e4}$, -$A^4$-S(O)$_n$$R^{f4}$, —S(O)$_n$N($R^{j4}$)$R^{k4}$, —N($R^{m4}$) $R^{o4}$, —NO$_2$, or —O$R^{p4}$;

$Q^2$ represents =O, =S, =NR$^{r4}$ or =N(OR$^{u4}$);

$A^4$ represents a single bond or —N(H)—;

each $R^X$ and $R^Y$ independently represent halogen, —CN, $R^{a4}$ or —OR$^{p4}$;

$R^{a4}$ represents $C_{1-6}$alkyl optionally substituted by one or more groups selected from $G^1$, phenyl optionally substituted by one or more groups selected from $G^3$ or heteroaryl optionally substituted by one or more groups selected from $G^4$;

$R^{c4}$ represents hydrogen, $R^{a4}$ or —O(O)OR$^{e4}$;

$R^{b4}$ and $R^{f4}$ represent $C_{1-6}$alkyl optionally substituted by one or more fluoro;

each, $R^{d4}$, $R^{e4}$, $R^{j4}$, $R^{k4}$, $R^{l4}$, $R^{n4}$, $R^{o4}$, $R^{p4}$, $R^{q4}$, $R^{r4}$ and $R^{u4}$ independently represent hydrogen or $C_{1-6}$alkyl optionally substituted by one or more fluoro; or any two $R^{c4}$ and $R^{d4}$, $R^{j4}$ and $R^{k4}$, and/or $R^{n4}$ and $R^{o4}$ are linked together to form, along with the nitrogen atom to which they are attached, a 4- to 6-membered ring;

each $G^1$ independently represent one or more halogens;

each $G^3$ and $G^4$ independently represent one or more groups selected from halogen, $R^{a5}$ or —OR$^{k5}$;

$R^{a5}$ represents $C_{1-6}$ alkyl optionally substituted by one or more fluoro;

$R^{k5}$ represents hydrogen or $C_{1-6}$ alkyl optionally substituted by one or more fluoro; each p and q independently represents 0 or 1, provided that the sum of p and q is 0 or 1; and each n independently represents 1 or 2.

Other preferred compounds of formula I that may be mentioned include those in which $R^1$ represents

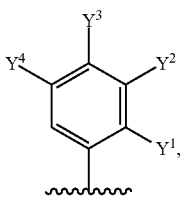

$Y^3$ and $Y^4$ represent hydrogen; and $Y^1$ represents fluoro and $Y^2$ represent fluoro, chloro, —CH$_3$ or —CF$_3$; or $Y^1$ represents chloro and $Y^2$ represents fluoro, chloro, —CH$_3$ or —CF$_3$; or $Y^1$ represents —CH$_3$ and $Y^2$ represents fluoro, chloro, —CH$_3$, —CF$_3$, —CN —N(H)C(O)CH=CH$_2$ or —N(H)C(O)(4-chloro-2-hydroxyphenyl); or $Y^2$ and $Y^4$ represent hydrogen; and $Y^1$ represents fluoro and $Y^3$ represents fluoro or phenyl; or $Y^1$ represents chloro and $Y^3$ represents fluoro, chloro; or $Y^1$ represents —CH$_3$ and $Y^3$ represents chloro or —OCH$_2$phenyl; or $Y^1$ represents —OCH$_3$ and $Y^3$ represents fluoro; or $Y^2$ and $Y^3$ represent hydrogen; and $Y^1$ represents fluoro and $Y^4$ represents chloro, —CH$_3$ or —CN; or $Y^1$ represents chloro and $Y^4$ represent fluoro, chloro, —CH$_3$, —CF$_3$ or —OCH$_3$; or $Y^1$ represents —CH$_3$ and $Y^4$ represent fluoro, chloro, —CH$_3$, —CF$_3$, —CN, —N(H)C(O)CH=CH$_2$ or —S(O)$_2$(4-morpholinyl); or $Y^1$ represents —CF$_3$ and $Y^4$ represents fluoro or —CF$_3$; or $Y^1$ represents —CN and $Y^4$ represents chloro; or $Y^1$ represents —OCH$_3$ and $Y^4$ represents fluoro, chloro, bromo, —CH$_3$, —CH(CH$_3$)$_2$, —C(CH$_3$)$_3$, —CN or —OCH$_3$; or $Y^1$ and $Y^4$ represent hydrogen; and $Y^2$ represents fluoro and $Y^3$ represents fluoro, chloro, —OH or —OCH$_3$; or $Y^2$ represents chloro and $Y^3$ represents fluoro or —C(O)(4-morpholinyl); or $Y^2$ represents —CH$_3$ and $Y^3$ represents fluoro or —OCH$_3$; or $Y^1$ represents —OCH$_3$ and $Y^3$ represents —OH; or $Y^1$ represents-CH$_2$OCH$_3$ and $Y^3$ represents (piperidin-4-yl)methoxy or ((1-tertbutoxycarbonyl)piperidin-4-yl)methoxy; or $Y^1$ and $Y^3$ represent hydrogen; and $Y^2$ and $Y^4$ represent fluoro; or $Y^2$ and $Y^4$ represent —CF$_3$; or $Y^4$ represents hydrogen; and $Y^1$, $Y^2$ and $Y^3$ represent fluoro or chloro; or $Y^1$ and $Y^2$ represent chloro and $Y^3$ represents chloro, —OH or —OCH$_3$; or $Y^1$ and $Y^2$ represent —CH$_3$ and $Y^3$ represents fluoro or —OCH$_3$; or $Y^1$ and $Y^3$ represent chloro and $Y^2$ represents —OCH$_3$; or $Y^2$ and $Y^3$ represent chloro and $Y^1$ represents —CH$_3$; or $Y^2$ represents hydrogen; and $Y^1$, $Y^3$ and $Y^4$ represent fluoro; or $Y^3$ and $Y^4$ represent chloro and $Y^1$ represents —CH$_3$; or $Y^1$ and $Y^4$ represent chloro and $Y^1$ represents —OCH$_3$; or $Y^1$ and $Y^4$ represent —CH$_3$ and $Y^3$ represents fluoro, —CH$_3$ or —OCH$_3$; or $Y^1$ represents fluoro, $Y^3$ represents —CH$_3$ and $Y^4$ represents chloro; or $Y^1$ represents chloro, $Y^3$ represents fluoro and $Y^4$ represents —CH$_3$; or $Y^1$ represents chloro, $Y^3$ represents —CH$_3$ and $Y^4$ represents fluoro; or $Y^1$ and $Y^4$ represent —CH$_3$ and $Y^3$ represents fluoro; or $Y^1$ represents —CH$_3$, $Y^4$ represents chloro and $Y^3$ represents —CF$_3$ or —OCH$_3$; or $Y^1$ represents hydrogen; and $Y^2$ and $Y^4$ represent —CH$_3$ and $Y^3$ represents —OH; or $Y^3$ represents hydrogen; and $Y^1$ and $E^2$ represent chloro and $Y^4$ represents —CH$_3$;

$R^2$ represents methyl, or preferably, hydrogen;

$R^3$ represents —X-L-J or $C_{1-6}$alkyl optionally substituted by one or more, preferably one to three groups selected from $Z^1$, or heterocycloalkyl optionally substituted by one or more, preferably one to three, groups selected from $Z^2$;

X represents $C_{1-6}$alkylene-optionally substituted by $T^1$, or —(C(R$^A$)$_2$)$_p$—C$_{2-5}$heterocycloalkylene-(C(R$^A$)$_2$)$_q$—;

L represents -L$^1$-L$^2$-;

L$^1$ represents —N(H)—, —O—, —SO$_2$—, —C(O)N(H)—, —S(O)$_n$N(H)— or —N(H)C(O)N(H)—;

L$^2$ represents a single bond or —C$_{1-6}$alkylene-;

J represents phenyl optionally substituted by D$^1$ and optionally substituted by one or more groups selected from R$^x$, or a 5- to 10-membered monocyclic or bicyclic heteroaryl having 1 to 3 nitrogen atoms, and/or one oxygen atom and/or one sulfur atom and which ring is optionally substituted by D$^2$ and optionally substituted by one or more groups selected from R$^Y$;

$Z^1$ represents halogen, —CN, -A$^2$-C(O)R$^{b2}$, -A$^2$-C(O)N(R$^{c2}$)R$^{d2}$, -A$^2$-C(O)OR$^{e2}$, —N(R$^{l2}$)R$^{m2}$, —OR$^{n2}$ or heterocycloalkyl optionally substituted by =O;

$A^2$ represents a single bond or —N(H)—;

$Z^2$ represents $R^{a2}$, —C(Q$^1$)OR$^{e2}$ or =O;

D$^1$ represents R$^{a4}$, -A$^4$-C(Q$^2$)R$^{b4}$, -A$^4$-C(Q$^2$)N(R$^{c4}$)R$^{d4}$, -A$^4$-C(O)OR$^{e4}$, -A$^4$-S(O)$_n$R$^{f4}$, -A$^4$-SO$_2$N(R$^{j4}$)R$^{k4}$, —SO$_2$OR$^{l4}$, —N(R$^{n4}$)R$^{o4}$, —N(H)CN, —NO$_2$, —OR$^{p4}$ or —SR$^{q4}$;

D$^2$ represents R$^{a4}$, -A$^4$-C(O)R$^{b4}$, —C(O)N(R$^{c4}$)R$^{d4}$, —C(O)OR$^{e4}$, -A$^4$-S(O)$_n$R$^{f4}$, —S(O)$_n$N(R$^{j4}$)R$^{k4}$, —N(R$^{n4}$)R$^{o4}$, —NO$_2$, or —OR$^{p4}$;

Q$^2$ represents =O, =S, =NR$^{r4}$ or =N(OR$^{u4}$);

A$^4$ represents a single bond or —N(H)—;

each R$^X$ and R$^Y$ independently represent halogen, —CN, R$^{a4}$ or —OR$^{p4}$;

R$^{a4}$ represents C$_{1-6}$alkyl optionally substituted by one or more groups selected from G$^1$, phenyl optionally substituted by one or more groups selected from G$^3$ or heteroaryl optionally substituted by one or more groups selected from G$^4$;

R$^{c4}$ represents hydrogen, R$^{a4}$ or —C(O)OR$^{e4}$;

R$^{b4}$ and R$^{f4}$ represent C$_{1-6}$alkyl optionally substituted by one or more fluoro;

each R$^{d4}$, R$^{e4}$, R$^{j4}$, R$^{k4}$, R$^{l4}$, R$^{n4}$, R$^{o4}$, R$^{p4}$, R$^{q4}$, R$^{r4}$ and R$^{u4}$ independently represent hydrogen or C$_{1-6}$alkyl optionally substituted by one or more fluoro; or any two R$^{c4}$ and R$^{d4}$, R$^{j4}$ and R$^{k4}$, and/or R$^{n4}$ and R$^{o4}$ are linked together to form, along with the nitrogen atom to which they are attached, a 4- to 6-membered ring;

each G$^1$ independently represent one or more halogens;

each G$^3$ and G$^4$ independently represent one or more groups selected from halogen, R$^{a5}$ or —OR$^{k5}$;

R$^{a5}$ represents C$_{1-6}$ alkyl optionally substituted by one or more fluoro;

R$^{k5}$ represents hydrogen or C$_{1-6}$ alkyl optionally substituted by one or more fluoro;

T$^1$ represents —N(R$^{b6}$)R$^{c6}$ or —OR$^{d6}$;

each R$^{b6}$, R$^{c6}$ and R$^{d6}$ independently represents hydrogen or —C$_{1-6}$alkyl;

each p and q independently represents 0 or 1, provided that the sum of p and q is 0 or 1; and each n independently represents 1 or 2.

Particularly preferred compounds of formula I that may be mentioned include those in which R$^1$ represents

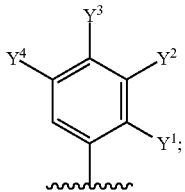

Y$^1$, Y$^3$ and Y$^4$ represent hydrogen; and
Y$^2$ represents —CH=CHC(O)OCH$_3$, —CH$_2$NH$_2$, —CH$_2$N(H)C(O)CH=CH$_2$, —CH$_2$OH, —N(H)C(O)CH=CH$_2$, —N(H)C(O)CH=CHCH$_2$NMe$_2$, —N(H)C(O)CH=CHPh, —N(H)C(O)C≡CH, —N(H)C(O)CH$_2$(OH), —N(H)C(O)CH(OH)Ph, —N(H)C(O)C(O)CH$_3$, —N(H)C(O)C(O)Ph or —N(H)S(O)$_2$CH=CH$_2$; or Y$^1$, Y$^2$ and Y$^4$ represent hydrogen and
Y$^3$ represents —CH=CH$_2$, —CH=CHC(O)OH, —CH=CHC(O)OCH$_3$, —CH$_2$NH$_2$, —CH$_2$N(H)C(O)CH=CH$_2$, —CH$_2$OH, —C(O)H, —C(O)CH$_3$, —C(O)CF$_3$, —N(H)C(O)CH=CH$_2$; or Y$^3$ and Y$^4$ represent hydrogen; and
Y$^1$ represents fluoro and Y$^2$ represents fluoro, chloro, or —CF$_3$; or Y$^1$ represents —Cl and Y$^2$ represents v, —CH$_3$ or —CF$_3$; or Y$^1$ represents —CH$_3$ and Y$^2$ represents chloro, —CH$_3$, —CF$_3$, —CN or —N(H)C(O)CH=CH$_2$; or Y$^2$ and Y$^4$ represent hydrogen; and
Y$^1$ and Y$^3$ represent fluoro; or
Y$^1$ represents chloro and Y$^3$ represents fluoro or chloro; or
Y$^1$ represents —CH$_3$ and Y$^3$ represents chloro; or Y$^2$ and Y$^3$ represent hydrogen; and
Y$^1$ represents fluoro and Y$^4$ represents chloro, —CH$_3$ or —CN; or
Y$^1$ represents chloro and Y$^4$ represents fluoro, chloro, —CH$_3$ or —CF$_3$; or
Y$^1$ represents —CH$_3$ and Y$^4$ represent, chloro, —CH$_3$, —CF$_3$, —CN or —N(H)C(O)CH=CH; or
Y$^1$ represents —CF$_3$ and Y$^4$ represents fluoro or —CF$_3$; or
Y$^1$ represents —CN and Y$^4$ represents chloro; or Y$^4$ represents hydrogen; and
Y$^1$, Y$^2$ and Y$^3$ represent fluoro; or
Y$^1$ and Y$^2$ represent —CH$_3$ and Y$^3$ represents fluoro; or
Y$^2$ and Y$^3$ represent chloro and Y$^1$ represents —CH$_3$; or Y$^2$ represents hydrogen; and
Y$^1$, Y$^3$ and Y$^4$ represent fluoro; or
Y$^3$ and Y$^4$ represent chloro and Y$^1$ represents —CH$_3$; or
Y$^1$ and Y$^4$ represent —CH$_3$ and Y$^3$ represents fluoro or —CH$_3$; or
Y$^1$ represents fluoro, Y$^3$ represents —CH$_3$ and Y$^4$ represents chloro; or
Y$^1$ represents chloro, Y$^3$ represents —F and Y$^4$ represents —CH$_3$; or
Y$^1$ represents chloro, Y$^3$ represents —CH$_3$ and Y$^4$ represents fluoro; or
Y$^1$ and Y$^4$ represent —CH$_3$ and Y$^3$ represents fluoro; or
Y$^1$ represents —CH$_3$, Y$^3$ represents —CF$_3$ and Y$^4$ represents chloro; or Y$^1$ represents hydrogen; and
Y$^2$ and Y$^4$ represent —CH$_3$ and Y$^3$ represents —OH; or
Y$^3$ represents hydrogen; and
Y$^1$, Y$^2$ and Y$^4$ represent chloro; or
Y$^1$ and Y$^2$ represent chloro and Y$^4$ represents —CH$_3$;

In some embodiments of the invention R$^2$ represents methyl, or preferably, hydrogen;

R$^3$ represents —X-L-J or —C$_{1-6}$alkyl optionally substituted by one to three groups selected from Z$^1$, or heterocycloalkyl optionally substituted by Z$^2$;

X represents —C$_{1-6}$alkylene-;
L represents -L$^1$-L$^2$-;
L$^1$ represents —N(H)—, —O—, —C(O)N(H)—, —S(O)$_n$N(H)— or —N(H)C(O)N(H)—;
L$^2$ represents a single bond;

J represents phenyl optionally substituted by D$^1$ and optionally substituted by one or more groups selected from R$^X$, or a 5- to 10-membered monocyclic or bicyclic heteroaryl having 1 to 3 nitrogen atoms and/or one oxygen atom and/or one sulfur atom and which ring is optionally substituted by D$^2$ and optionally substituted by one or more groups selected from R$^Y$;

Z$^1$ represents halogen, —CN, -A$^2$-C(O)R$^{b2}$, -A$^2$-C(O)N(R$^{c2}$)R$^{d2}$, -A$^2$-C(O)OR$^{e2}$, —N(R$^{l2}$)R$^{m2}$, —OR$^{n2}$ or heterocycloalkyl optionally substituted by =O;

Z$^2$ represents R$^{a2}$, —C(O)OR$^{e2}$ or =O;

A$^2$ represents a single bond or —N(H)—;

D$^1$ represents R$^{a4}$, -A$^4$-C(Q$^2$)R$^{b4}$, -A$^4$-C(Q$^2$)N(R$^{c4}$)R$^{d4}$, -A$^4$-C(O)OR$^{e4}$, -A$^4$-S(O)$_n$R$^{f4}$, -A$^4$-SO$_2$N(R$^{j4}$)R$^{k4}$, —SO$_2$OR$^{l4}$, —N(R$^{n4}$)R$^{o4}$, —N(H)CN, —NO$_2$, —OR$^{p4}$ or —SR$^{q4}$;

$D^2$ represents $R^{a4}$, -$A^4$-C(O)$R^{b4}$, —C(O)N($R^{c4}$)$R^{d4}$, —C(O)O$R^{e4}$, -$A^4$-S(O)$_n R^{f4}$, —S(O)$_n$N($R^{j4}$)$R^{k4}$, —N($R^{n4}$)$R^{o4}$, —NO$_2$, or —OR$^{p4}$;

$Q^2$ represents =O, =S, =N$R^{r4}$ or =N(O$R^{u4}$);

$A^4$ represents a single bond or —N(H)—;

each $R^X$ and $R^Y$ independently represent halogen, —CN, —$R^{a4}$ or —OR$^{p4}$;

$R^{a4}$ represents $C_{1-6}$alkyl optionally substituted by one or more groups selected from $G^1$, phenyl optionally substituted by one or more groups selected from $G^3$ or heteroaryl optionally substituted by one or more groups selected from $G^4$;

$R^{c4}$ represents hydrogen, $R^{a4}$ or —C(O)OR$^{e4}$;

each $R^{b4}$ and $R^{f4}$ independently represent $C_{1-6}$alkyl optionally substituted by one or more fluoro;

each, $R^{d4}$, $R^{e4}$, $R^{j4}$, $R^{k4}$, $R^{l4}$, $R^{n4}$, $R^{o4}$, $R^{p4}$, $R^{q4}$, $R^{r4}$ and $R^{u4}$ independently represent hydrogen or $C_{1-6}$alkyl optionally substituted by one or more fluoro; or any two $R^{c4}$ and $R^{d4}$, $R^{j4}$ and $R^{k4}$, and/or $R^{n4}$ and $R^{o4}$ are linked together to form, along with the nitrogen atom to which they are attached, a 4- to 6-membered ring;

each $G^1$ independently represent one or more halogens;

each $G^3$ and $G^4$ independently represent one or more groups selected from halogen, $R^{a5}$ or —OR$^{k5}$;

$R^{a5}$ represents $C_{1-6}$ alkyl optionally substituted by one or more fluoro;

$R^{k5}$ represents hydrogen or $C_{1-6}$alkyl optionally substituted by one or more fluoro; and each n independently represents 1 or 2;

More particularly preferred compounds of formula I that may be mentioned include those in which $R^1$ represents

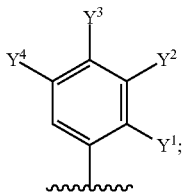

$Y^3$ and $Y^4$ represent hydrogen and $Y^1$ and $Y^2$ are selected from fluoro, chloro, -Me or —CF$_3$;

$R^2$ represents hydrogen;

$R^3$ represents —X-L-J or —C$_{1-6}$alkyl optionally substituted by one or more, preferably one to three, $Z^1$.

Examples of more particularly preferred compounds of formula I that may be mentioned are those where $R^1$ is 3-chloro-2-fluorophenyl, 2-chloro-3-methyl-phenyl, 3-chloro-2-methylphenyl, 2,3-dichlorophenyl, 2,3-dimethylphenyl or 2-methyl-3-trifluoromethyl;

$R^2$ represents hydrogen; and $R^3$ represents —X-L-J or $C_{1-6}$alkyl optionally substituted by one to three, $Z^1$.

In some embodiments of the invention $R^1$ represents

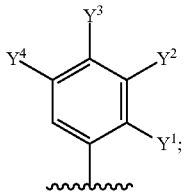

at least one, preferably two, of $Y^1$, $Y^2$, $Y^3$ and $Y^4$ is other than hydrogen;

$R^2$ represents hydrogen;

$R^3$ represents —X-L-J;

X represents —CH$_2$—, —CH$_2$CH$_2$—, —CH$_2$CH$_2$CH$_2$—, —CH$_2$CH$_2$CH$_2$CH$_2$—, —CH$_2$C(CH$_3$)$_2$CH$_2$—, -cyclopropylene- or —CH$_2$=CH$_2$—;

L represents -$L^1$-$L^2$-;

$L^1$ represents —N(H)—, —O—, —C(O)N(H)—, —SO$_2$N(H)— or —N(H)C(O)N(H)—;

$L^2$ represents a single bond;

J represents phenyl optionally substituted by $D^1$ and optionally substituted by one or more groups selected from $R^x$, or a 5- to 10-membered monocyclic or bicyclic heteroaryl having 1 to 3 nitrogen atoms, and/or one oxygen atom and/or one or two sulfur atoms and which ring is optionally substituted by $D^2$ and optionally substituted by $R^Y$;

In some embodiments of the invention $R^1$ represents

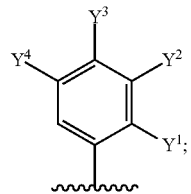

at least one, preferably two, of $Y^1$, $Y^2$, $Y^3$ and $Y^4$ is other than hydrogen;

$R^2$ represents hydrogen;

$R^3$ represents —X-L-J;

X represents —CH$_2$CH$_2$—, —CH$_2$CH$_2$CH$_2$—, —CH$_2$CH$_2$CH$_2$CH$_2$— or -cyclopropylene-;

L represents -$L^1$-$L^2$-;

$L^1$ represents —N(H)—, —O—, —C(O)N(H)—, —SO$_2$N(H)— or —N(H)C(O)N(H)—;

$L^2$ represents a single bond;

J represents phenyl optionally substituted by $D^1$ and optionally substituted by $R^X$, or a 5- to 10-membered monocyclic or bicyclic heteroaryl having either 1 to 3 nitrogen atoms, one oxygen atom and/or one or two sulfur atoms and which ring is optionally substituted by $D^2$ and optionally substituted by $R^Y$;

In some embodiments of the invention $R^1$ represents

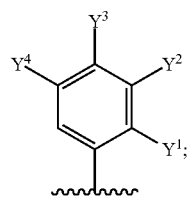

at least one, preferably two, of $Y^1$, $Y^2$, $Y^3$ and $Y^4$ is other than hydrogen;

$R^2$ represents hydrogen;

$R^3$ represents $C_{1-6}$alkyl optionally substituted by one, two or three $Z^1$;

Preferred compounds that may be mentioned when $R^1$ represents

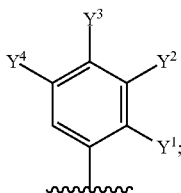

$R^2$ represents hydrogen; and $R^3$ represents $C_{1-6}$alkyl substituted by one, two or three groups selected from $Z^1$ include those where $Z^1$ represents fluoro, bromo, —CN, —C(O)NH$_2$, —C(O)NH$_2$, —C(O)-(4-morpholinyl), —C(O)OMe, —C(O)OEt, —N(H)C(O)Me, —N(H)C(O)CH$_2$NMe$_2$, —N(H)C(O)OCMe$_3$, —N(H)C(O)OCH$_2$Ph, —N(Me)C(O)OCMe$_3$, —N(H)C(O)N(H)Me, —N(H)C(O)N(H)CHMe$_2$, —N(H)C(O)N(H)(4-morpholinyl), —N(H)S(O)$_2$Me, —OMe, —OCF$_3$, —OEt, —OCH$_2$CH=CH$_2$, —OCH$_2$cyclopropyl, 2-oxopyrrolidin-1-yl, 2-oxoimidazolidin-1-yl, 2-tetrahydrofuryl or 4-tetrahydropyranyl.

Preferred compounds that may be mentioned when $R^1$ represents

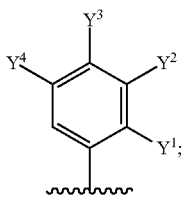

$R^2$ represents hydrogen;

$R^3$ represents $C_{1-6}$alkyl substituted by $Z^1$; and $Z^1$ represents heterocycloalkyl, include those where $Z^1$ represents dihydropyridinyl, imidazolinyl, morpholinyl, piperidinyl, pyrrolidinyl, 2-tetrahydrofuryl or 4-tetrahydropyranyl, wherein the heterocycloalkyl is optionally substituted by —C(O)OC$_{1-6}$alkyl or =O.

In some embodiments of the invention $R^1$ represents

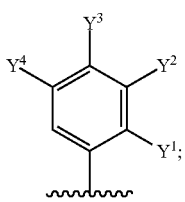

at least one, preferably two, of $Y^1$, $Y^2$, $Y^3$ and $Y^4$ is other than hydrogen;

$R^2$ represents hydrogen or methyl; and $R^3$ represents $C_{1-10}$alkyl.

Preferred compounds that may be mentioned when $R^1$ represents

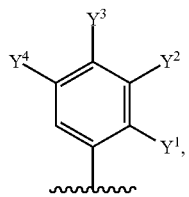

$R^2$ represents hydrogen and $R^3$ represents $C_{1-10}$alkyl, include those where $R^3$ represents —CH$_3$, —CD$_3$, ethyl, 1-propyl, 2-propyl, 1-butyl, tert-butyl, 3-pentyl, neopentyl, allyl, methallyl, 1-buten-4-yl, geranyl, propargyl, cyclopropyl, cyclobutyl, cyclopentyl, cyclohexyl, cyclopropylmethyl, 2-cyclopropyl-2-ethyl, methylcyclopropyl, 2-(cyclohexen-1-yl)ethyl, bicyclo[2.2.1]hept-2-yl, 1-noradamantyl, 1-adamantyl or 3-pinanyl.

Preferred compounds that may be mentioned when $R^1$ represents

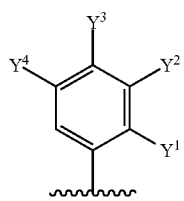

and $R^2$ represents methyl include those where $R^3$ represents cyclopropyl.

In some embodiments of the invention $R^1$ represents

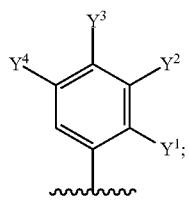

at least two of $Y^1$, $Y^2$, $Y^3$ and $Y^4$ is other than hydrogen;

$R^2$ represents hydrogen; and $R^3$ represents $C_{2-10}$alkyl.

Preferred compounds that may be mentioned when $R^1$ represents

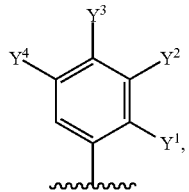

$R^2$ represents hydrogen and $R^3$ represents $C_{2-10}$alkyl, include those where $R^3$ represents ethyl, 1-propyl, 2-propyl, 1-butyl, tert-butyl, 3-pentyl, neopentyl, allyl, propargyl, cyclopropyl, cyclobutyl, cyclopentyl, cyclohexyl, cyclopropylmethyl, 2-cyclopropyl-2-ethyl, methylcyclopropyl, bicyclo[2.2.1]hept-2-yl, 1-noradamantyl, 1-adamantyl or 3-pinanyl.

In some embodiments of the invention $R^1$ represents

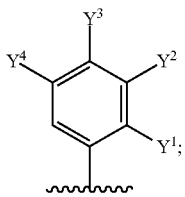

at least two of $Y^1$, $Y^2$, $Y^3$ and $Y^4$ is other than hydrogen;
$R^2$ represents hydrogen; and
$R^3$ represents $C_{3-10}$alkyl, where the alkyl is cyclic or part cyclic.

Preferred compounds that may be mentioned when $R^1$ represents

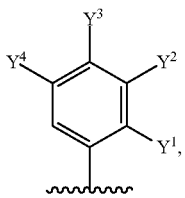

$R^2$ represents hydrogen and $R^3$ represents $C_{3-10}$alkyl, where the alkyl is cyclic or part cyclic include those where $R^3$ represents cyclopropyl, cyclobutyl, cyclopentyl, cyclohexyl, cyclopropylmethyl, 2-cyclopropyl-2-ethyl, methylcyclopropyl, 2-(cyclohexen-1-yl)ethyl, bicyclo[2.2.1]hept-2-yl, 1-noradamantyl, 1-adamantyl or 3-pinanyl.

In some embodiments of the invention $R^1$ represents

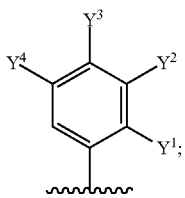

at least one, preferably two, of $Y^1$, $Y^2$, $Y^3$ and $Y^4$ is other than hydrogen;
$R^2$ represents hydrogen;
$R^3$ represents heterocycloalkyl optionally substituted by one or two groups selected from $Z^3$;
$Z^3$ represents $R^{a2}$ or —C(O)OR$^{e2}$; and
$R^{a2}$ and $R^{e2}$ represents $C_{1-4}$alkyl.

Preferred compounds that may be mentioned when $R^1$ represents

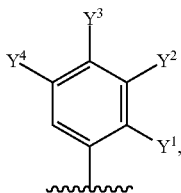

$R^2$ represents hydrogen and $R^3$ represents heterocycloalkyl optionally substituted by one or two groups selected from $Z^3$, include those where $R^3$ represents tetrahydrofuranyl, tetrahydropyranyl, azetidinyl, pyrrolidinyl, piperidinyl or quinuclidinyl.

Particularly preferred compounds that may be mentioned when $R^1$ represents

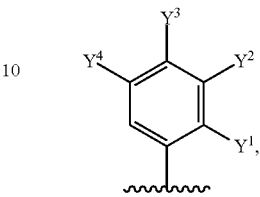

$R^2$ represents hydrogen and $R^3$ represents heterocycloalkyl optionally substituted by one or two groups selected from $Z^3$, include those where $R^3$ represents tetrahydrofuran-3-yl, tetrahydropyran-4-yl, 2,2-dimethyltetrahydropyran-4-yl, 1-(tert-butoxycarbonyl)azetidin-3-yl, 1-(tert-butoxycarbonyl)-piperidin-4-yl, 1-(ethoxycarbonyl)-piperidin-4-yl or quinuclidin-3-yl.

In some embodiments $R^1$ is a 6-membered heteroaryl substituted by one or more groups selected from $Y^5$. Such a 6-membered heteroaryl e.g. may be pyridyl, pyrimidinyl or pyrazinyl.

In some embodiments of the invention, $R^1$ represents (ii) a 6-membered heteroaryl substituted by one or more groups $Y^5$, wherein each $Y^5$ is as defined herein above.

In some particular embodiments, when $R^1$ represents a 6-membered heteroaryl, it is substituted by one or more $Y^5$;
$R^2$ represents hydrogen; and
$R^3$ represents $C_{1-6}$alkyl optionally substituted by one or more groups selected from $Z^1$.

Preferred compounds of formula I that may be mentioned when $R^1$ represents a 6-membered heteroaryl include those in which $R^1$ represents pyridyl, preferably 3- or 4-pyridinyl, substituted by one or more $Y^5$;
$R^2$ represents hydrogen;
$R^3$ represents $C_{1-6}$alkyl;
$Y^5$ represents halogen, $R^a$, —OH or —OR$^m$; and
$R^a$ and $R^m$ represents $C_{1-6}$alkyl optionally substituted by —OH or one or more fluoro.

Particularly preferred compounds of formula I that may be mentioned when $R^1$ represents a 6-membered heteroaryl include those in which $R^1$ represents 3-pyridinyl substituted in the 6-position by —CH$_2$OH or —OH, or in the 2-position by —CF$_3$, or 4-pyridinyl substituted in the 3-position by chloro and optionally in the 2-position by —OCH$_3$;
$R^2$ represents hydrogen; and
$R^3$ represents $C_{1-6}$alkyl.

In some embodiments of the invention $R^1$ represents a 6-membered heteroaryl substituted by one or more $Y^5$;
$R^2$ represents hydrogen; and
$R^3$ represents $C_{1-6}$alkyl optionally substituted by one or more $Z^1$.

In some embodiments, $R^1$ represents a 5- to 10-membered monocyclic or bicyclic heteroaryl connected to the pyrimidine of formula I via a carbon atom of the heteroaryl ring, which heteroaryl ring is optionally substituted by one or more groups selected from $Y^5$, wherein each $Y^5$ is as defined herein above.

In some embodiments, $R^1$ represents a 5- to 7-membered monocyclic heteroaryl, e.g. a 5- or 6-membered heteroaryl, in particular a 5-membered heteroaryl, connected to the pyrimidine ring of the compound of formula I via a carbon atom of the heteroaryl, which heteroaryl is optionally substituted by one or more groups selected from $Y^5$, wherein each $Y^5$ is as defined herein above.

In some particular embodiments, when $R^1$ represents a 5-membered heteroaryl connected to the pyrimidine ring of the compound of formula I via a carbon atom of the heteroaryl, said heteroaryl optionally being substituted by one or more $Y^5$;

$R^2$ represents hydrogen; and
$R^3$ represents —X-L-J or —$C_{1-6}$alkyl optionally substituted by $Z^1$;

Preferred compounds of formula I that may be mentioned when $R^1$ represents a 5-membered heteroaryl connected to the ring of the compound pyrimidine of formula I via a carbon atom of the heteroaryl ring, include those in which $R^1$ represents oxazolyl, pyrazolyl, thiazolyl, or preferably, furanyl, isoxazyl, pyrrolyl or thiophenyl, which heteroaryl rings are optionally substituted by one or more groups selected from $Y^5$;

$R^2$ represents hydrogen;
$R^3$ represents —X-L-J;
$Y^5$ represents $R^a$, —C(O)$R^b$, —$SO_2R^f$ or —$SO_2N(R^i)R^j$;
X represents $C_{1-6}$alkylene-, e.g. —$CH_2CH_2$—;
L represents -$L^1$-$L^2$-, or preferably, a single bond;
$L^1$ represents —N(H)—;
$L^2$ represents a single bond;
J represents phenyl optionally substituted in the 3-position, but preferably in the 4-position, by $D^1$ and optionally substituted by one or more groups selected from $R^x$;
$D^1$ represents —C(O)N($R^{c4}$)$R^{d4}$, or preferably, —$SO_2R^{f4}$, or —$SO_2N(R^{j4})R^{k4}$;
each $R^x$ independently represent $R^{a4}$, or preferably, halogen;
$R^a$ represents $C_{1-6}$alkyl, preferably $C_1$alkyl optionally substituted by one or more fluoro, but preferably $C_{1-6}$alkyl substituted by —N(H)C(O)O$R^{e1}$;
each $R^b$ and $R^f$ independently represent $C_{1-6}$alkyl;
each $R^i$ and $R^j$ independently represent hydrogen or $C_{1-4}$alkyl;
$R^{e1}$ represents $C_{1-6}$alkyl;
each $R^{a4}$ and $R^{f4}$ represents $C_{1-4}$alkyl optionally substituted by one or more fluoro (but are preferably unsubstituted); and
each $R^{c4}$, $R^{d4}$, $R^{j4}$, and $R^{k4}$ independently represents hydrogen or $C_{1-4}$alkyl optionally substituted by one or more fluoro (but preferably unsubstituted).

Particularly preferred compounds of formula I that may be mentioned when $R^1$ represents a 5-membered heteroaryl connected to the pyrimidine ring of the compound of formula I via a carbon atom of the heteroaryl, include those in which $R^1$ represents furanyl, isoxazyl, pyrrolyl or thiophenyl which heteroaryls are optionally substituted by one or more groups selected from halogen, —$CH_3$, —C(O)$CH_3$, —$CH_2N(H)C(O)OC(CH_3)_3$ or —$SO_2N(H)C(CH_3)_3$;

$R^2$ represents hydrogen;
$R^3$ represents —$CH_2CH_2$-J; and
J represents phenyl substituted in the 4-position by chloro, —$SO_2CH_3$ or —$SO_2NH_2$.

In some embodiments of the invention $R^1$ represents a 5-membered heteroaryl connected to the pyrimidine ring of the compound of formula I via a carbon atom of the heteroaryl, which heteroaryl is optionally substituted by one or more $Y^5$;

$R^2$ represents hydrogen;
$R^3$ represents —X-L-J.

Other preferred compounds of formula I that may be mentioned when $R^1$ represents a 5-membered heteroaryl connected to the pyrimidine ring of the compound of formula I via a carbon atom of the heteroaryl, include those in which $R^1$ represents isoxazyl, oxazolyl, thiazolyl, or preferably, furanyl, pyrazolyl, pyrrolyl or thiophenyl, which heteroaryl rings are optionally substituted by one or more groups selected from $Y^5$;

$R^2$ represents hydrogen;
$R^3$ represents $C_{1-6}$alkyl optionally substituted by one or more groups selected from $Z^1$;
$Y^5$ represents halogen, or preferably $R^a$;
$Z^1$ represents heterocycloalkyl, optionally substituted by =O;
$R^a$ represents $C_{1-6}$alkyl optionally substituted by one or more fluoro, but preferably $C_{1-6}$alkyl substituted by —C(O)N($R^{c1}$)$R^{d1}$ or —N($R^{h1}$)$R^{i1}$;
each $R^{c1}$, $R^{d1}$, $R^{h1}$ and $R^{i1}$ independently represents hydrogen or $C_{1-4}$alkyl, but preferably all represent hydrogen; or $R^{h1}$ and $R^{i1}$ are linked together to form, along with the nitrogen atom to which they are attached, a 6-, or preferably, a 5-membered ring.

Particularly preferred compounds of formula I that may be mentioned when $R^1$ represents a 5-membered heteroaryl connected to the pyrimidine ring of the compound of formula I via a carbon atom of the heteroaryl, include those in which $R^1$ represents furanyl, pyrazolyl, pyrrolyl or thiophenyl, which heteroaryl rings are optionally substituted by —$CH_3$, —$CH_2CH_2C(O)NH_2$ or —$CH_2$-(1-pyrrolidinyl);
$R^2$ represents hydrogen;
$R^3$ represents $C_{2-4}$alkyl optionally substituted by $Z^1$;
$Z^1$ represents pyrrolidinyl substituted by =O, preferably 2-oxopyrrolidin-1-yl.

In some embodiments of the invention $R^1$ represents a 5-membered heteroaryl connected to the pyrimidine ring of the compound of formula I via a carbon atom of the heteroaryl, which heteroaryl is optionally substituted by one or more one or more groups selected from $Y^5$;

$R^2$ represents hydrogen; and
$R^3$ represents $C_{1-6}$alkyl optionally substituted by one or more groups selected from $Z^1$.

In some embodiments, $R^1$ represents a 8- to 10-membered bicyclic heteroaryl, e.g. a 9- to 10-membered heteroaryl, connected to the pyrimidine ring of the compound of formula I via a carbon atom of the heteroaryl, which heteroaryl is optionally substituted by one or more groups selected from $Y^5$, wherein each $Y^5$ is as defined herein above.

In some particular embodiments, when $R^1$ represents such a bicyclic heteroaryl connected to the pyrimidine ring of the compound of formula I via a carbon atom of the heteroaryl, said heteroaryl is optionally substituted by one or more groups selected from $Y^5$;

$R^2$ represents hydrogen; and
$R^3$ represents —X-L-J or $C_{1-6}$alkyl optionally substituted by one or more groups selected from $Z^1$.

Preferred compounds of formula I that may be mentioned when $R^1$ represents a bicyclic heteroaryl connected to the pyrimidine ring of the compound of formula I via a carbon atom of the heteroaryl ring, include those in which $R^1$ represents benzofuranyl, indazolyl, or preferably, benzothiophenyl, indolyl and quinolinyl which heteroaryls are optionally substituted by one or more groups selected from $Y^5$;

$R^2$ represents hydrogen;
$R^3$ represents —X-L-J;
each $Y^5$ independently represent halogen, or preferably, $R^a$;
X represents —$C_{1-6}$alkylene-, e.g. —$CH_2CH_2$—;
L represents -$L^1$-$L^2$- or preferably, a single bond;
$L^1$ represents —O—, —N(H)—;

$L^2$ represents a single bond;

J represents phenyl optionally substituted in the 3-position, but preferably in the 4-position, by $D^1$ and optionally substituted by one group selected from $R^x$;

$D^1$ represents —C(O)N($R^{c4}$)$R^{d4}$ or —$SO_2R^{f4}$, or preferably, —$SO_2$N($R^{j4}$)$R^{k4}$;

$R^x$ represents $R^{a4}$, or preferably, halogen;

each $R^{a4}$ and $R^{f4}$ represents $C_{1-4}$alkyl optionally substituted by one or more fluoro (but preferably unsubstituted); and each $R^{c4}$, $R^{d4}$, $R^{j4}$, and $R^{k4}$ independently represents hydrogen or $C_{1-4}$alkyl optionally substituted by one or more fluoro (but preferably unsubstituted).

Particularly preferred compounds of formula I that may be mentioned when $R^1$ represents a bicyclic heteroaryl connected to the pyrimidine ring of the compound of formula I via a carbon atom of the heteroaryl, include those in which $R^1$ represents 3-benzothiophenyl, 4-indolyl or 5-quinolinyl, all optionally substituted by one or more chloro, fluoro, —$CH_3$ or —$CF_3$, but preferably unsubstituted;

$R^2$ represents hydrogen;

$R^3$ represents —$CH_2CH_2$-J; and

J represents phenyl optionally substituted in the 4-position by fluoro or —$SO_2CH_3$, or preferably by, chloro or —$SO_2NH_2$.

In some embodiments of the invention $R^1$ represents a bicyclic heteroaryl connected to the pyrimidine ring of the compound of formula I via a carbon atom of the heteroaryl, which heteroaryl is optionally substituted by one or more $Y^5$;

$R^2$ represents hydrogen; and $R^3$ represents —X-L-J.

Other preferred compounds of formula I that may be mentioned when $R^1$ represents a bicyclic heteroaryl connected to the pyrimidine ring of the compound of formula I via a carbon atom of the heteroaryl, include those in which $R^1$ represents 7-azaindolyl, benzofuranyl, benzothiophenyl, 2,3-dihydrobenzofuranyl, indazolyl, indolyl, isoquinolinyl, quinolinyl, and which heteroaryls are optionally substituted by one or more groups selected from $Y^5$;

$R^2$ represents hydrogen;

$R^3$ represents $C_{1-6}$alkyl optionally substituted by one or more groups selected from $Z^1$;

each $Y^5$ independently represent halogen, or preferably, $R^a$ or —$SO_2R^f$;

$Z^1$ represents heterocycloalkyl, optionally substituted by =O;

$R^a$ represents $C_{1-6}$alkyl optionally substituted by one or more fluoro; and $R^f$ represents phenyl optionally substituted by halogen or $C_{1-4}$alkyl optionally substituted by one or more fluoro;

Particularly preferred compounds of formula I that may be mentioned when $R^1$ represents a bicyclic heteroaryl connected to the pyrimidine ring of the compound of formula I via a carbon atom of the heteroaryl, include those in which $R^1$ represents 7-azaindol-3-yl, benzofuran-3-yl, benzothiophen-3-yl, 2,3-dihydrobenzofuran-7-yl, indazol-5-yl, indazol-6-yl, indol-3-yl, indol-4-yl, indol-5-yl, isoquinolin-4-yl, quinolin-5-yl, and which heteroaryls are optionally substituted by one or more groups selected from $Y^5$;

$R^2$ represents hydrogen;

$R^3$ represents $C_{1-6}$alkyl optionally substituted by one or more groups selected from $Z^1$;

each $Y^5$ independently represent fluoro, chloro, or preferably, $R^a$ or —$SO_2R^f$;

$Z^1$ represents pyrrolidinyl substituted by =O, preferably 2-oxopyrrolidin-1-yl;

$R^a$ represents —$CF_3$, or preferably, —$CH_3$;

$R^f$ represents phenyl optionally substituted in the 4-position by fluoro, or preferably by, chloro, —$CH_3$ or —$CF_3$; and each $Z^1$ independently represents pyrrolidinyl substituted by =O, preferably 2-oxopyrrolidin-1-yl.

In some embodiments of the invention $R^1$ represents a bicyclic heteroaryl connected to the pyrimidine ring of the compound of formula I via a carbon atom of the heteroaryl ring, which ring is optionally substituted by one or more $Y^5$;

$R^2$ represents hydrogen; and $R^3$ represents $C_{1-6}$alkyl optionally substituted by $Z^1$.

In certain embodiments of the invention $R^1$ represents indolyl, e.g. indol-3-yl, indol-4-yl or indol-5-yl, where the indolyls are optionally substituted in the 1-position by $Y^5$;

$R^2$ represents hydrogen;

$R^3$ represents $C_{1-6}$alkyl;

$Y^5$ represents —$SO_2R^f$; and $R^f$ represents phenyl optionally substituted in the 4-position by chloro, —$CH_3$ or —$CF_3$.

In some embodiments of the invention, $R^1$ represents (iv) -ethynyl-$Y^6$, wherein $Y^6$ is as defined herein above.

In some particular embodiments, when $R^1$ represents -ethynyl-$Y^6$, $Y^6$ in particular may represent phenyl optionally substituted by halogen or $C_{1-6}$alkyl optionally substituted by one or more halogens;

$R^2$ represents hydrogen; and $R^3$ represents $C_{1-6}$alkyl optionally substituted by $Z^1$.

Preferred compounds of formula I that may be mentioned when $R^1$ represents ethynyl-$Y^6$ include those where $Y^6$ represents phenyl optionally substituted by one or more halogens and/or $C_{1-6}$alkyl optionally substituted by one or mote halogens;

$R^2$ represents hydrogen; and $R^3$ represents-$C_{1-6}$alkyl.

In some embodiments of the invention $R^1$ represents ethynyl-$Y^6$;

$R^2$ represents hydrogen; and $R^3$ represents —X-L-J, or preferably, $C_{1-6}$alkyl optionally substituted by one or more groups selected from $Z^1$;

In some embodiments, $R^1$ represents a 3- to 8-membered nonaromatic ring, in particular a 5- to 7-membered nonaromatic ring, which ring optionally contains one or two heteroatoms and/or one or two double bonds, and which ring is optionally substituted by one or more groups selected from $Y^7$.

In some particular embodiments, when $R^1$ represents a 3- to 8-membered nonaromatic ring, $R^1$ optionally contains one or two heteroatoms, optionally contains one or two double bonds and is optionally substituted by one or more groups selected from $Y^7$;

$R^2$ represents hydrogen; and $R^3$ represents —X-L-J.

Preferred compounds of formula I that may be mentioned when $R^1$ represents a nonaromatic ring include those where $R^1$ is 5-7 membered nonaromatic ring optionally containing one heteroatom and/or one double bond and is optionally substituted by one or more groups selected from $Y^7$;

$R^2$ represents hydrogen;

$R^3$ represents —X-L-J;

each $Y^7$ independently represents $R^a$, —C(O)$R^b$, —C(O)$OR^e$ or —$SO_2R^f$; X represents —$C_{1-6}$alkylene-, e.g. —$CH_2CH_2$—;

L represents -$L^1$-$L^2$-, or preferably, a single bond;

$L^1$ represents —N(H)— or —O—;

$L^2$ represents a single bond;

J represents phenyl optionally substituted in the 3-position, but preferably in the 4-position, by $D^1$;

D¹ represents —C(O)N(R^{c4})R^{d4}, or preferably, —SO₂R^{f4} or —SO₂N(R^{j4})R^{k4};

each R^a and R^e independently represent C_{1-6}alkyl optionally substituted by one or more fluoro;

each R^b and R^f independently represent C_{1-6}alkyl optionally substituted by one or more fluoro, phenyl optionally substituted by one or more halogens and/or by one or more R^{a1}, or heteroaryl optionally substituted by one or more halogens and/or by one or more Rat;

each R^{a1} independently represent C_{1-6}alkyl optionally substituted by one or more fluoro;

each R^{c4}, R^{d4}, R^{j4}, and R^{k4} independently represent hydrogen or C_{1-4}alkyl optionally substituted by one or more fluoro (but preferably unsubstituted); and R^{f4} represents C_{1-4}alkyl optionally substituted by one or more fluoro (but preferably unsubstituted).

Particularly preferred compounds of formula I that may be mentioned when R¹ represents a nonaromatic ring include those where R¹ is 5-7 membered and optionally contains one heteroatom and/or one double bond and is optionally substituted by one or more groups selected from Y⁷;

R² represents hydrogen;

R³ represents —CH₂CH₂-J;

Y⁷ represents —C(O)R^b, —C(O)OR^e or —SO₂R^f;

J represents phenyl substituted in the 4-position by —SO₂Me or —SO₂NH₂;

each R^e independently represent C_{1-6}alkyl;

each R^b and R^f independently represent C_{1-6}alkyl, phenyl optionally substituted by R^{a1} or heteroaryl optionally substituted by R^{a1}; and each R^{a1} independently represent C_{1-6}alkyl.

More particularly preferred compounds of formula I that may be mentioned when R¹ represents a nonaromatic ring include those where R¹ represents cycloheptanyl, cyclohexanyl, cyclopentanyl, piperidin-3-yl, pyrrolidin-3-yl, or preferably, cyclohepten-1-yl, piperidin-4-yl or 1,2,3,6-tetrahydropiperidin-4-yl and where the piperidine, pyrrolidine and the 1,2,3,6-tetrahydropiperidin-4-yl are preferably substituted in the 1-position by —C(O)Me, —C(O)CH(CH₃)₂, —C(O)cyclopentyl, —C(O)methylcyclopentyl, —C(O)(4-methylphenyl), —C(O)(5-isoxazolyl), —C(O)OC(CH₃)₃, —SO₂Me or —SO₂(4-methylphenyl).

In some embodiments of the invention R¹ represents a 3-8 membered nonaromatic ring optionally substituted by one or more groups selected from Y⁷;

R² represents hydrogen; and

R³ represents —X-L-J;

When R² and R³ are linked together to form, along with the atoms to which they are attached, a 5- to 8-membered non-aromatic ring, the link formed by R² and R³ is optionally substituted by one or more Z³ and optionally substituted by —X-L-J.

Preferred compounds of formula I that may be mentioned when R² and R³ are linked together to form, along with the atoms to which they are attached, a 5- to 6-membered non-aromatic ring are those wherein the link formed by R² and R³ is optionally substituted by one or more C_{1-6}alkyl or =O, but wherein the link is preferably unsubstituted or substituted by methyl.

In some embodiments of the invention R² and R³ are linked together to form, along with the atoms to which they are attached, a 5- to 8-membered non-aromatic ring, wherein the link formed by R² and R³ is optionally substituted by one or more Z³ and optionally substituted by —X-L-J;

In a compound of formula I, the moiety X represents —C_{1-6}alkylene-, optionally substituted by one or more T¹, or —(C(R^A)₂)_p—C_{2-5}heterocycloalkylene-(C(R^A)₂)_q—, where the heterocycloalkylene is optionally substituted by one or more T².

In some embodiments, X represents —C_{1-6}alkylene-, optionally substituted by one or more T¹.

In some embodiments, X represents —C_{2-4}alkylene-substituted by T¹;

T¹ represents —OR^{d3}, and

R^{d3} represents C_{1-4}alkyl, or preferably, hydrogen.

Particular compounds of formula I that may be mentioned include those in which X represents —CH₂CH(OH)—.

In some other embodiments, X represents —(C(R^A)₂)_p—C_{2-5}heterocycloalkylene-(C(R^A)₂)_q—, where the heterocycloalkylene is optionally substituted by one or more T².

When R¹ is phenyl, heteroaryl, -ethynyl-Y⁶ or a 3- to 8-membered nonaromatic ring and R² is hydrogen and R³ represents —X-L-J; or when R² and R³ are linked together, and the link formed between R² and R³ is substituted by —X-L-J, then X preferably represents

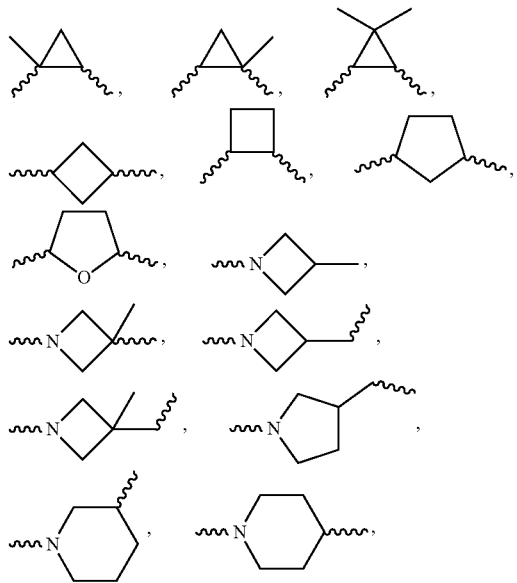

or more preferably, —CH₂—, —CH₂CH₂—, —CH(Me)-, —C(Me)₂-, —CH₂CH(Me)-, —CH(Me)CH₂—, —CH₂CH₂CH₂—, —CH(Me)CH₂CH₂—, —CH₂CH₂CH₂CH₂—, —CH₂C(CH₃)₂CH₂—, -cyclopropylene-, —CH₂—≡—CH₂—,

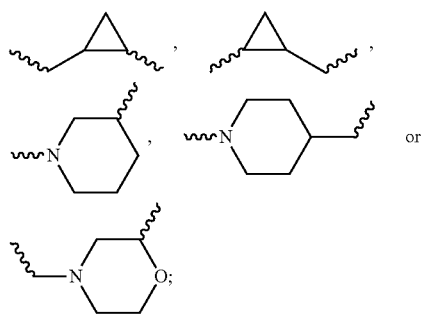

Preferred compounds of formula I that may be mentioned include those where X represents —CH(Me)-, —C(Me)₂-, —CH₂CH(Me)-, —CH(Me)CH₂—, —CH(Me)CH₂CH₂—,

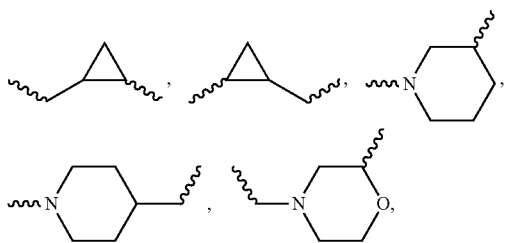

or preferably —CH$_2$CH$_2$CH$_2$—, —CH$_2$CH$_2$CH$_2$CH$_2$—, —CH$_2$C(CH$_3$)$_2$CH$_2$—, -cyclopropylene-, —CH$_2$—=—CH$_2$—, or more preferably, —CH$_2$CH$_2$—.

In some embodiments L represents a single bond.

In some embodiments L represents -L$^1$-L$^2$-.

Compounds of formula I that may be mentioned include those where L$^1$ represents —N(R$^B$)—, —O—, —S(O)$_m$—, —C(O)N(R$^C$)—, —N(R$^D$)C(O)—, —S(O)$_n$N(R$^E$)—, —N(R$^F$)S(O)$_n$— or —N(R$^G$)C(O)N(R$^H$)—.

Preferred compounds of formula I that may be mentioned include those where L$^1$ represents —N(R$^B$)—, —O—, —S(O)$_m$—, —C(O)N(R$^D$)—, —S(O)$_n$N(R$^E$)—, or —N(R$^G$)C(O)N(R$^H$)—.

Particularly preferred compounds of formula I that may be mentioned include those where L$^1$ represents —N(H)—, —O—, —S—, —S(O)—, —S(O)$_2$—, —C(O)N(H)—, —S(O)$_n$N(H)— or —N(H)C(O)N(H)—;

Compounds of formula I that may be mentioned include those in which L$^2$ represents a single bond or —C$_{1-2}$alkylene-.

In some embodiments, L$^2$ represents a single bond.

In some embodiments, L$^2$ represents —C$_{1-2}$alkylene-, i.e. —CH$_2$— and —CH$_2$CH$_2$—.

In a compound of formula (I), J represents
(i) a 6- to 10-membered aryl optionally substituted by D$^1$ and optionally substituted by one or more groups selected from R$^x$, or
(ii) a 5- to 11-membered monocyclic or bicyclic heteroaryl ring, which heteroaryl contains 1 to 3 nitrogen atoms, and/or one oxygen atom and/or one or two sulfur atoms and which heteroaryl is optionally substituted by D$^2$ and optionally substituted by one or more groups selected from R$^Y$.

In some embodiments, J represents (i) a 6- to 10-membered aryl, e.g. phenyl, said aryl optionally being substituted by D$^1$ and optionally being substituted by one or more groups selected from R$^X$.

In some other embodiments, J represents (ii) a 5- to 11-membered monocyclic or bicyclic heteroaryl, which heteroaryl contains 1 to 3 nitrogen atoms, and/or one oxygen atom and/or one or two sulfur atoms and which ring is optionally substituted by D$^2$ and optionally substituted by one or more groups selected from R$^Y$.

In some particular embodiments, J represents (ii) a 5- to 7-membered, e.g. 5- or 6-membered, monocyclic heteroaryl, which heteroaryl contains 1 to 3 nitrogen atoms, and/or one oxygen atom and/or one or two sulfur atoms and which ring is optionally substituted by D$^2$ and optionally substituted by one or more groups selected from R$^Y$.

In some other particular embodiments, J represents (ii) a 8- to 11-membered, in particular 9- or 10-membered, bicyclic heteroaryl, which heteroaryl contains 1 to 3 nitrogen atoms, and/or one oxygen atom and/or one or two sulfur atoms and which ring is optionally substituted by D$^2$ and optionally substituted by one or more groups selected from R$^Y$.

Compounds of formula I that may be mentioned include those in which J represents phenyl substituted by halogen, —B(OH)$_2$, —CN, R$^{a4}$, —C(Q$^2$)R$^{b4}$, —N(H)C(O)R$^{b4}$, —C(Q$^2$)N(H)R$^{d4}$, —N(H)C(O)N(H)R$^{d4}$, —N(H)C(NR$^w$)N(H)R$^{d4}$, —C(O)OR$^{e4}$, —N(H)C(O)OR$^{e4}$, —C(O)N(H)S(O)$_2$ R$^{f4}$, —N(H)S(O)$_n$e, —S(O)$_n$R$^{f4}$, —S(NR$^{h4}$)(O)R$^{i4}$, —S(O)$_n$N(R$^{j4}$)R$^{k4}$, —N(R$^{n4}$)R$^{o4}$, —NO$_2$, —OR$^{p4}$, —S(O)$_2$OH, —SR$^t$ or a 5-membered heteroaryl.

Preferred compounds of formula I that may be mentioned include those in which J represents phenyl substituted, preferably in the 3- or 4-position, by fluoro, chloro, bromo, —B(OH)$_2$, methyl, ethyl, ethynyl, —CF$_3$, —CN, —C(O)Me, —C(O)NH$_2$, —C(NH)NH$_2$, —C(NOH)NH$_2$, —C(S)NH$_2$, —C(O)N(H)Me, —C(O)NHCH(CH$_3$)CH$_2$OH, —C(O)N(CH$_3$)propargyl, —C(O)N(H)NH$_2$, —C(O)N(H)OH, —C(O)N(H)S(O)$_2$Me, —C(O)OH, —CO(O)Me, —C(O)OEt, —C(O)OCH$_2$CH$_2$CH$_3$, —C(O)OCH$_2$CH(CH$_3$)$_2$, —C(O)OCH$_2$CH$_2$OH, —C(O)OCH$_2$CH$_2$SO$_2$Me, —C(O)OCH$_2$CH(OH)CH$_2$OH, —NH$_2$, —NMe$_2$, —N(H)CN, —N(H)C(NH)NH$_2$, —NHC(O)Me, —NH(CO)cyclopropyl, —NH(CO)C(Me)$_3$, —NHC(O)OEt, —NHC(O)OCH(Me)$_2$, —NHC(O)OC(Me)$_3$, —NHC(O)OCH$_2$CH(Me)$_2$, —NHC(O)OCH$_2$C(Me)$_3$, —NHC(O)OCH$_2$CH$_2$OMe, —N(H)C(O)N(H)Et, —N(H)C(O)N(H)CH(Me)$_2$, —N(H)C(O)N(H)C(Me)$_3$, —N(H)C(O)N(H)CH(Me)CH$_2$CH$_3$, —N(H)C(O)N(H)CH$_2$CH=CH$_2$, —N(H)C(O)N(CH$_3$)$_2$, —N(H)C(O)N(H)C(O)OEt, —N(H)C(S)N(H)Et, —NO$_2$, —NHS(O)$_2$Me, —NHS(O)$_2$Et, —NHS(O)$_2$CH(Me)$_2$, —NHS(O)$_2$CH$_2$CH(Me)$_2$, —NHS(O)$_2$CH$_2$CF$_3$, —OH, —OMe, —SMe, —S(O)Me, —S(NH)(O)Me, —S(O)$_2$Me, —S(O)$_2$CF$_3$, —S(O)$_2$CH(CH$_3$)$_2$, —S(O)$_2$CH$_2$CH$_2$N(Me)$_2$, —S(O)$_2$CH$_2$CH$_2$CH$_2$NMe$_2$, —S(O)NH$_2$, —S(O)$_2$NH$_2$, —S(O)$_2$NHMe, —S(O)$_2$NHCH$_2$CH$_2$OMe, —S(O)$_2$OH,

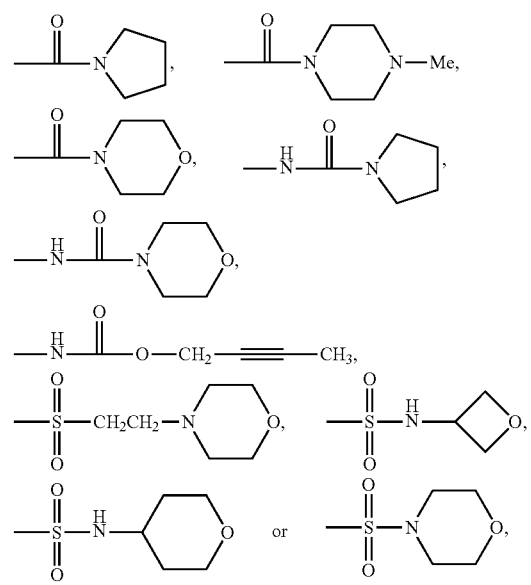

2-imidazolyl, 1,3,4-oxadiazol-2-yl, 2-oxazolyl, 5-tetrazolyl, 2-thiazolyl and optionally substituted by one or more (e.g. two, or more preferably one) fluoro, chloro, -Me, —OH, —OMe or —CF$_3$.

Examples of particularly preferred compounds of formula I that may be mentioned include those in which J represents phenyl substituted in the 3- or 4-position by —C(O)NH$_2$, —C(O)N(H)Me, —C(O)OEt, —NHC(O)Me, —NH(CO)cyclopropyl, —NH(CO)C(Me)$_3$, —NHS(O)$_2$Me, —NHS(O)$_2$Et, —NHS(O)$_2$CH(Me)$_2$, —NHS(O)$_2$CH$_2$CF$_3$, —S(O)$_2$Me, —S(O)$_2$NH$_2$ or —S(O)$_2$NHMe.

Examples of particularly preferred compounds of formula I that may be mentioned include those in which J represents phenyl substituted, preferably in the 4-position, by —C(O)OCH$_3$, —C(O)OCH$_2$CH$_3$, —C(O)OCH$_2$CH$_2$CH$_3$, —C(O)OCH$_2$CH(CH$_3$)$_2$, —C(O)OCH$_2$CH$_2$OH, —C(O)OCH$_2$CH$_2$SO$_2$Me and —C(O)OCH$_2$CH(OH)CH$_2$OH.

Examples of particularly preferred compounds of formula I that may be mentioned include those in which J represents phenyl substituted, preferably in the 4-position, by —SO$_2$CH(CH$_3$)$_2$, —SO$_2$NHCH$_2$CH$_2$OMe,

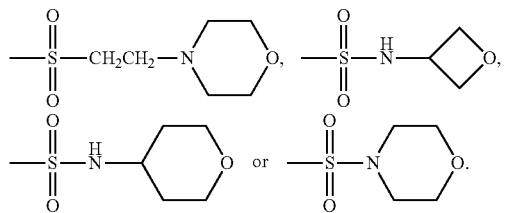

Compounds of formula I that may be mentioned include those in which J represents heteroaryl optionally substituted by halogen, —B(OR$^{m4}$)$_2$, —CN, R$^{a4}$, —C(Q$^2$)R$^{b4}$, —N(H)C(O)R$^{b4}$, —C(Q$^2$)N(H)R$^{d4}$, —N(H)C(O)N(H)R$^{d4}$, —N(H)C(NR$^w$)N(H)R$^{d4}$, —C(O)OR$^{e4}$, —N(H)C(O)OR$^{e4}$, —C(O)N(H)S(O)$_2$R$^{f4}$, —N(H)S(O)$_n$R$^{f4}$, —S(O)$_n$R$^{f4}$, —S(NR$^{h4}$)(O)R$^{i4}$, —S(O)$_n$N(R$^{j4}$)R$^{k4}$, —N(R$^{n4}$)R$^{o4}$, —NO$_2$, —OR$^{p4}$, —S(O)$_2$OH, —SR$^t$, phenyl optionally substituted by halogen, or pyridinyl optionally substituted by halogen.

In some embodiments, when J is a heteroaryl as defined herein above, said heteroaryl is 6-membered. Particular compounds of formula I that may be mentioned when J represents a 6-membered heteroaryl include those in which J represents pyridinyl optionally substituted by D$^2$ and optionally substituted by one or more groups selected from R$^Y$;

D$^2$ represents halogen, R$^{a4}$, -A$^4$-C(Q$^2$)R$^{b4}$, -A$^4$-C(Q$^2$)N(R$^{c4}$)R$^{d4}$, -A$^4$-C(Q$^2$)OR$^{e4}$, -A$^4$-S(O)$_n$R$^{f4}$, -A$^4$-S(O)$_n$C(O)R$^{g4}$, -A$^4$-S(NR$^{h4}$)(O)R$^{i4}$, -A$^4$-S(O)$_n$N(R$^{j4}$)R$^{k4}$, -A$^4$-S(O)$_n$OR$^{i4}$, —B(OR$^{m4}$)$_2$, —N(R$^{n4}$)R$^{o4}$, —NO$_2$ or —OR$^{p4}$;

Q$^2$ represents =O, =S, =NR$^{r4}$ or =N(OR$^{u4}$); and

R$^Y$ represents halogen or C$_{1-3}$ alkyl optionally substituted by one or more fluoro.

Preferred compounds of formula I that may be mentioned when J represents a 6-membered heteroaryl include those in which J represents 4-pyridinyl, or preferably, 2-pyridinyl or 3-pyridinyl optionally substituted by R$^{a4}$, —C(Q$^2$)N(H)R$^{d4}$, —C(O)O R$^{e4}$, —N(H)C(O)R$^{b4}$, —B(OR$^{m4}$)$_2$, —NO$_2$, —N(H)S(O)$_n$R$^{f4}$, —S(O)$_n$R$^{f4}$, —N(R$^{n4}$)R$^{o4}$ or —OR$^{p4}$.

Particular compounds of formula I that may be mentioned when J represents a 6-membered heteroaryl include those in which J represents 2-pyridinyl substituted in the 4-position by —C(O)NH$_2$, —C(O)OMe or in the 5-position by —CF$_3$, —C(O)NH$_2$, —C(O)OH, —C(O)OEt, —N(H)C(O)Me, —N(H)C(O)N(H)C(CH$_3$)$_3$, —N(H)C(O)OC(CH$_3$)$_3$, —N(H)SO$_2$Me, —NO$_2$, —SO$_2$Me, —SO$_2$NH$_2$ or —SO$_2$N(H)Me, 3-pyridinyl substituted in the 4-position by —NH$_2$ or —SO$_2$Me, or pyridinyl substituted in the 4-position by —OMe and in the 5-position by Me, or substituted in the 5-position by —SO$_2$NH$_2$.

Particular compounds of formula I that may be mentioned when J represents a 6-membered heteroaryl include those in which J represents pyrimidinyl optionally substituted by D$^2$ and optionally substituted by one or more groups selected from R$^Y$;

D$^2$ represents -A$^4$-C(Q$^2$)R$^{b4}$, -A$^4$-C(Q$^2$)N(R$^{c4}$)R$^{d4}$, -A$^4$-C(Q$^2$)OR$^{e4}$, -A$^4$-S(O)$_n$R$^{f4}$, -A$^4$-S(O)$_n$N(R$^{j4}$)R$^{k4}$, -A$^4$-S(O)$_n$OR$^{i4}$, —B(OR$^{m4}$)$_2$, or —N(R$^{n4}$)R$^{o4}$;

Q$^2$ represents =O, =S, =NR$^{r4}$ or =N(OR$^{u4}$); and

R$^Y$ represents halogen or C$_{1-3}$ alkyl optionally substituted by one or more fluoro.

Preferred compounds of formula I that may be mentioned when J represents a 6-membered heteroaryl include those in which J represents 2-pyrimidinyl or 4-pyrimidinyl substituted by —N(H)C(O)R$^{b4}$, —C(O)N(H)R$^{d4}$, —C(O)OR$^{e4}$, —N(H)S(O)$_n$R$^{f4}$, —S(O)$_n$R$^{f4}$, or —N(R$^{n4}$)R$^{o4}$.

Particularly preferred compounds of formula I that may be mentioned when J represents a 6-membered heteroaryl include those in which J represents 2-pyrimidinyl substituted in the 4-position by —C(O)NH$_2$, —C(O)OH, —C(O)OMe, —NH$_2$, —S(O)$_2$Me or —S(O)$_2$NH$_2$, substituted in the 5-position by —C(O)NH$_2$, or 4-pyrimidinyl substituted in the 2-position by —C(O)NH$_2$, —NH$_2$, —S(O)$_2$Me or —S(O)$_2$NH$_2$; and R$^2$ represents halogen (e.g. fluoro or chloro), or preferably, —CF$_3$.

For example, particularly preferred compounds of formula I that may be mentioned when J represents a 6-membered heteroaryl include those in which J represents 2-pyrimidinyl substituted in the 4-position by —S(O)$_2$Me or —S(O)$_2$NH$_2$, or preferably by —C(O)NH$_2$ or —C(O)OMe.

Particular compounds of formula I that may be mentioned when J represents a 6-membered heteroaryl include those in which J represents pyrazinyl optionally substituted by D$^2$;

D$^2$ represents -A$^4$-C(Q$^2$)R$^{b4}$, -A$^4$-C(Q$^2$)N(R$^{c4}$)R$^{d4}$, -A$^4$-C(Q$^2$)OR$^{e4}$, -A$^4$-S(O)$_n$R$^{f4}$, -A$^4$-S(O)$_n$N(R$^{j4}$)R$^{k4}$, -A$^4$-S(O)$_n$OR$^{i4}$, —B(OR$^{m4}$)$_2$, or —N(R$^{n4}$)R$^{o4}$; and Q$^2$ represents =O, =S, =NR$^{r4}$ or =N(OR$^{u4}$).

Preferred compounds of formula I that may be mentioned when J represents a 6-membered heteroaryl include those in which J represents 2-pyrazinyl substituted in the 6-position, or preferably in the 3- or 5-position by —S(O)$_2$Me or —S(O)$_2$NH$_2$, or preferably, by —C(O)NH$_2$ or —C(O)OMe.

In some embodiments of the invention J represents 1,3,5-triazinyl substituted by D$^2$ and optionally substituted by one or more groups selected from R$^Y$.

In some embodiments, when J represents a 6-membered heteroaryl, in particular 1,3,5-triazinyl, substituted by D$^2$ and optionally substituted by one or more groups selected from R$^2$, D$^2$ in particular may represent -A-C(O)R$^c$, -A-C(O)N(R$^d$)R$^e$, -A-C(O)OR$^f$, -A-S(O)$_n$R$^g$, -A-S(O)$_n$N(R$^k$)R$^l$, or —N(R$^o$)R$^p$.

Particularly preferred compounds of formula I that may be mentioned include those in which J represents 1,3,5-triazinyl substituted by —C(O)NH$_2$, —C(O)OR$^f$, —S(O)$_2$R$^g$, —S(O)$_2$NH$_2$, or in particular one or two —NH$_2$.

In some embodiments, when J is a heteroaryl as defined herein above, said heteroaryl is 5-membered. Particular compounds of formula I that may be mentioned when J represents heteroaryl include those in which J represents a 5-membered heteroaryl optionally substituted by D$^2$;

$D^2$ represents $-A^4-C(Q^2)R^{b4}$, $-A^4-C(Q^2)N(R^{c4})R^{d4}$, $-A^4-C(Q^2)OR^{e4}$, $-A^4-S(O)_nR^{f4}$, $-A^4-S(O)_nN(R^{j4})R^{k4}$, $-A^4-S(O)_nOR^{j4}$, $-B(OR^{m4})_2$, or $-N(R^{n4})R^{o4}$;

$Q^2$ represents $=O$, $=S$, $=NR^{r4}$ or $=N(OR^{u4})$.

Preferred compounds of formula I that may be mentioned when J represents a 5-membered heteroaryl include those in which J represents furanyl, imidazolyl, isoxazolyl, oxazolyl, 1,2,4-oxadiazolyl, 1,3,4-oxadiazolyl, pyrazolyl, 1,3,4-thiadiazolyl, thiazolyl, 1,2,3-triazolyl or thiophenyl, optionally substituted by halogen, $-CH_3$, cyclopropyl, $-C(O)NH_2$, $-C(O)OMe$, $-NH_2$, $-S(O)_2Me$ or $-S(O)_2NH_2$.

Particular compounds of formula I that may be mentioned include those in which J represents a bicyclic heteroaryl optionally substituted by $D^2$, and optionally substituted by one or more groups selected from $R^Y$;

$D_2$ represents $R^{a4}$, $-A^4-C(Q^2)R^{b4}$, $-A^4-C(Q^2)N(R^{c4})R^{d4}$, $-A^4-C(Q^2)OR^{e4}$, $-A^4-S(O)_nR^{f4}$, $-A^4-S(O)_nN(R^{j4})R^{k4}$), or $-N(R^{n4})R^{o4}$;

each $R^Y$ independently represent halogen, $-CN$, $C_{1-3}$ alkyl optionally substituted by F or $-OC_{1-3}$ alkyl optionally substituted by fluoro, or, when Y is partly aromatic, $=O$.

Certain compounds of formula I where J represents a bicyclic heteroaryl that may be mentioned include those where the bicyclic heteroaryl is connected to L via a 5-membered ring and where the bicyclic heteroaryl is optionally substituted by $D^2$ and optionally substituted by one or more substituents independently selected from $R^Y$.

Certain compounds of formula I where J represents a bicyclic heteroaryl that may be mentioned include those where the bicyclic heteroaryl is connected to L via a 6-membered ring and where the bicyclic heteroaryl is optionally substituted by $D^2$ and optionally substituted by one or more substituents independently selected from $R^Y$.

Preferred compounds of formula I that may be mentioned when J represents a bicyclic heteroaryl include those where J represents benzimidazolyl, benzoxazolyl, benzothiazolyl, benzothiophenyl, 2,3-dihydrobenz[1,3]oxazin-6-yl, 3,4-dihydrobenz[1,4]oxazinyl, dihydrobenzothiophenyl, furo[2,3-c]pyridin-5-yl, imidazo[1,2-a]pyridinyl, indolyl, isoindolinyl, isoquinolinyl, tetrahydroquinolinyl, tetrahydroisoquinolinyl, tetrahydroquinazolinyl, thieno[3,2-b]thiophenyl, thiochromanyl, quinolinyl, quinazolinyl, or purin-6-yl, all optionally substituted by one or more groups selected from fluoro, chloro, -Me, $-CHF_2$, $-CF_3$, $-NH_2$, $-NHMe$, $-NMe_2$, $-OH$, $-OMe$, $=NH$ or $=O$.

Particularly preferred compounds of formula I that may be mentioned when J represents a bicyclic heteroaryl, $L^2$ is a single bond and $L^1$ is $-N(H)-$ include those where J represents imidazo[2,1-b]thiazol-6-yl, 1,1-dioxobenzothiophen-6-yl, 1-oxo-1-iminobenzothiophen-6-yl, thieno[3,2-b]thiophen-2-yl or more preferably, 2-methyl-1,3-benzothiazol-5-yl, 2-methyl-1,3-benzothiazol-6-yl, 4-oxoquinazolin-7-yl, 3,4-dihydro-3-oxo-1,4-benzoxazin-6-yl, 3,4-dihydro-4-methyl-3-oxo-1,4-benzoxazin-6-yl, 3,4-dihydro-2,2-dimethyl-3-oxo-1,4-benzoxazin-6-yl, purin-6-yl, 2-aminopurin-6-yl.

In one embodiment, the compound according to the invention is selected from the compounds of Examples 1-761.

As discussed hereinbefore, compounds of the invention are indicated as pharmaceuticals. According to a further aspect of the invention there is provided a compound of the invention, as hereinbefore defined, for use as a pharmaceutical.

In another aspect of the invention the use of a compound of the invention, as hereinbefore defined, is provided for the manufacture of a medicament for the treatment of autoimmune or inflammatory conditions.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

By "prodrug of a compound of the invention", we include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds, which possess pharmacological activity.

It is stated herein that the compounds of the invention may be useful in the treatment of autoimmune or inflammatory conditions. For the purposes of this specification, and for the avoidance of doubt, the term "treatment" includes treatment per se, prevention and prophylaxis.

Preferably the autoimmune or inflammatory conditions are selected from the group comprising: rheumatoid arthritis, systemic lupus erythematosus, Crohn's disease, ulcerous colitis, multiple sclerosis, lymphoproliferative diseases (e.g. those caused by Epstein Barr virus and cytomegalovirus), rejection after organ transplantation, Wegener' granulomatosus, psoriasis, Mb Bechterews, Behcets disease, Guillain Barre, dermatomyositis, myositis, polymyositis, primary biliary cirrhosis, anti-phospholipid syndrome, autoimmune hepatitis, autoimmune cardiomyopathy, alopecia areata, atherosclerosis, type 1 diabetes, autoimmune uveitis, Goodpasteure's syndrome, Graves' disease, Hashimotos disease, mixed connective tissue disease, myasthenia gravis, pemphigus vulgaris, pernicious anemia, Sjögren's syndrome, giant cell arteritis, ulcerative colitis, vasculitis, Churg-Strauss syndrome, postpolio syndrome, idiopathic thrombocytopenic purpura, Peyronie disease and Dupuytren's contracture.

In certain embodiments of the present invention, the autoimmune or inflammatory conditions are selected from rheumatoid arthritis, systemic lupus erythematosus, Crohn's disease, multiple sclerosis, rejection after organ transplantation, psoriasis and atherosclerosis.

In certain embodiments of the present invention, the autoimmune or inflammatory conditions are selected from rheumatoid arthritis, systemic lupus erythematosus, Crohn's disease, multiple sclerosis, rejection after organ transplantation, and atherosclerosis.

In certain embodiments of the present invention, the autoimmune or inflammatory condition is not psoriasis.

Compounds of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Compounds of the invention may be administered alone, but are preferably administered by way of known pharmaceutical compositions/formulations, including tablets, capsules or elixirs for oral administration, suppositories for rectal administration, sterile solutions or suspensions for parenteral or intramuscular administration, and the like.

Compounds of the invention (i.e. compounds that inhibit MTH1) may be administered in the form of tablets or capsules, e.g., time-release capsules that are taken orally. Alternatively, the compounds of the invention may be in a liquid form and may be taken orally or by injection. The compounds of the invention may also be in the form of suppositories, or, creams, gels, and foams e.g. that can be applied to the skin. In addition, they may be in the form of an inhalant that is applied nasally.

Such compositions/formulations may be prepared in accordance with standard and/or accepted pharmaceutical practice.

According to a further aspect of the invention there is thus provided a pharmaceutical composition/formulation including a compound of the invention, as hereinbefore defined, optionally in admixture with a pharmaceutically acceptable adjuvant, diluent and/or carrier. Such compositions/formulations may be of use in the treatment, prevention and/or prophylaxis of autoimmune and inflammatory conditions which benefit by inhibition of MTH1.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The invention further provides a process for the preparation of a pharmaceutical formulation, as hereinbefore defined, which process comprises bringing into association a compound of the invention, as hereinbefore defined, or a pharmaceutically acceptable salt thereof with a pharmaceutically-acceptable adjuvant, diluent or carrier.

In yet another aspect the present invention provides methods for the treatment of autoimmune and inflammatory conditions comprising administering a therapeutically effective amount of a compound of the invention to a subject (e.g. patient) in need of such treatment.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention may also be combined with other therapeutic agents that are useful in the treatment of autoimmune and inflammatory conditions.

Examples of therapeutic agents that may be useful in combination with compounds of this invention are glucocorticoids (e.g. cortisone or prednisolone, TNF-alpha inhibitors (e.g. infliximab), anti-CD20 (e.g. rituximab), immunosupressants (e.g. mycophenolate mofetil or azathioprine) or antimetabolites (e.g. methotrexate).

According to a further aspect of the invention, there is provided a combination product comprising:
(A) a compound of the invention, as hereinbefore defined; and
(B) another therapeutic agent that is useful in the treatment of an autoimmune or inflammatory condition,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of autoimmune diseases and inflammatory conditions, and a pharmaceutically-acceptable adjuvant, diluent or carrier; and
(2) a kit of parts comprising components:
  (a) a pharmaceutical formulation including a compound of the invention, as hereinbefore defined, in admixture with a pharmaceutically-acceptable adjuvant, diluent or carrier; and
  (b) a pharmaceutical formulation including another therapeutic agent that is useful in the treatment of autoimmune and inflammatory conditions in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, or a pharmaceutically acceptable salt thereof with the other therapeutic agent that is useful in the treatment of autoimmune or inflammatory conditions, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention may be administered at varying doses. Oral, pulmonary and topical dosages (and subcutaneous dosages, although these dosages may be relatively lower) may range from between about 0.01 mg/kg of body weight per day (mg/kg/day) to about 100 mg/kg/day, preferably about 0.01 to about 10 mg/kg/day, and more preferably about 0.1 to about 5.0 mg/kg/day. For e.g. oral administration, the compositions typically contain between about 0.01 mg to about 2000 mg, for example between about 0.1 mg to about 500 mg, or between 1 mg to about 100 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

It is contemplated that any method or composition described herein can be implemented with respect to any other method or composition described herein.

Unless otherwise defined, all technical and scientific terms used herein have the same meaning as commonly understood by one of ordinary skill in the art to which this invention pertains.

EXAMPLES

The invention is illustrated by way of the following examples, in which the following abbreviations may be employed.
aq aqueous
DMF dimethylformamide
DMSO dimethylsulfoxide
EtOAc ethyl acetate
EtOH ethanol
MeOH methanol
MeCN acetonitrile
Pd—C palladium on carbon
sat. saturated
TFA trifluoroacetic acid
THF tetrahydrofuran
min. minutes
h. hours
Hunigs base N,N-diisopropylethylamine
DCM dichloromethane
n-BuOH butan-1-ol
iPrOH propan-2-ol
NEt$_3$ triethylamine
Boc tert-butoxycarbonyl
HATU (1-[bis(dimethylamino)methylene]-1H-1,2,3-triazolo-[4,5-b]pyridinium 3-oxid hexafluorophosphate
NMP N-methylpyrrolidine
LCMS liquid-chromatography electrospray mass spectroscopy
NMR nuclear magnetic resonance
NCS N-chlorosuccinimide
Pd(PPh$_3$)$_4$ tetrakis(triphenylphosphine)palladium (0)
RuPhos 2-Dicyclohexylphosphino-2',6'-diisopropoxybiphenyl
SPhos 2-Dicyclohexylphosphino-2',6'-dimethoxybiphenyl
B(OMe)$_3$ trimethylborate
n-BuLi n-butyl lithium
MeI iodomethane
NaOMe sodium methoxide
CHCl$_3$ chloroform
MgSO$_4$ anhydrous magnesium sulphate
K$_2$CO$_3$ anhydrous potassium carbonate
NH$_4$OH ammonium hydroxide
Ac$_2$O acetic anhydride
POCl$_3$ phosphorus oxychloride
TBTU O-(benzotriazol-1-yl)-N,N,N',N'-tetramethyluronium tetrafluoroborate
CuCl copper(I) chloride
NaHCO$_3$ sodium bicarbonate
KOH potassium hydroxide
PdCl$_2$dppf.DCM 1,1'-Bis(diphenylphosphino)ferrocene-palladium(II)dichloride dichloromethane complex
TMPMgCl.LiCl 2,2,6,6-Tetramethylpiperidinylmagnesium chloride lithium chloride complex
Oxone Potassium peroxymonosulfate Starting materials and chemical reagents specified in the syntheses described below are commercially available, e.g. from Sigma-Aldrich, Fine Chemicals Combi-Blocks and other vendors.

In the event that there is a discrepancy between nomenclature and any compounds depicted graphically, then it is the latter that presides (unless contradicted by any experimental details that may be given or unless it is clear from the context). Final compounds were named using Marvin software versions 6.1. and 6.2. or ChemBioDraw Ultra 13.

Purification of compounds may be carried out using silica-gel column chromatography or preparative reverse phase HPLC (ACE column, acidic gradients with MeCN—H$_2$O containing 0.1% TFA or XBridge column, basic gradients using MeCN—H$_2$O containing ammonium bicarbonate) to give the products as their free bases or trifluoroacetic acid salts.

Intermediate 1

(7-chloro-2H-1,3-benzodioxol-5-yl)boronic Acid

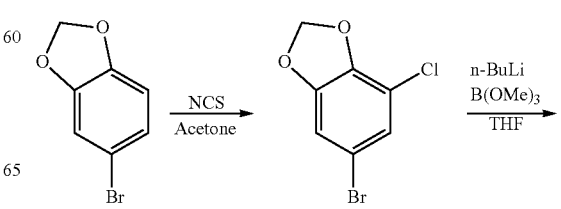

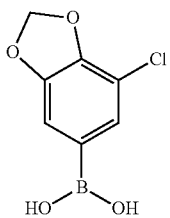

Step 1: 6-bromo-4-chloro-2H-1,3-benzodioxole

To a solution of 5-bromo-2H-1,3-benzodioxole (60 µL, 0.50 mmol, 1 equiv.) in acetonitrile (1 mL) was added 1-chloropyrrolidine-2,5-dione (73 mg, 0.55 mmol, 1.1 equiv.). The reaction was stirred overnight at room temperature. After completion of the reaction, the reaction mixture was concentrated and purified by column chromatography (Heptane/EtOAc 100%→5:1) to afford the desired product as a colourless solid (104 mg, 89%). LCMS [M+H]$^+$ 234; $^1$H NMR (400 MHz, CD$_3$OD) δ 7.05 (1H, s), 6.93 (1H, s), 2.78 (2H, s).

Step 2: (7-chloro-2H-1,3-benzodioxol-5-yl)boronic Acid

To a solution of 6-bromo-4-chloro-2H-1,3-benzodioxole (104 mg, 0.44 mmol, 1 equiv.) in THF (5.8 mL) was added, at −78° C., n-BuLi (2.5 M in hexanes, 265 µL, 0.66 mmol, 1.5 equiv.). The reaction mixture was stirred at this temperature for 30 min, before addition of B(OMe)$_3$ (248 µL, 2.21 mmol, 5 equiv.). The reaction was slowly allowed to warm up to rt, 2N HCl was added, and stirring was continued for 1 h. The reaction mixture was extracted with EtOAc, and the organic layer was dried over MgSO$_4$ and evaporated under reduced pressure. The crude product was purified by column chromatography (Pentane/EtOAc 100%→3:1) to afford the desired product as a white solid (22 mg, 25%). LCMS [M+H]$^+$ 201; $^1$H NMR (400 MHz, DMSO-d$_6$) δ 7.34 (1H, s), 6.81 (1H, s), 5.99 (2H, s).

Intermediate 2

2,3-dichloro-4-(tetramethyl-1,3,2-dioxaborolan-2-yl)phenol

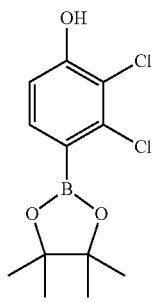 [SMILES: CC1(C)OB(c2ccc(O)c(Cl)c2Cl)OC1(C)C]

To a solution of 4-bromo-2,3-dichlorophenol (250 mg, 1.03 mmol, 1 equiv.) in THF (10 mL) was added, at −78° C., n-BuLi (2.5 M in hexanes, 1.25 mL, 3.10 mmol, 3 equiv.). The reaction mixture was stirred at this temperature for 30 min, before addition of 2-isopropoxy-4,4,5,5-tetramethyl-1,3,2-dioxaborolane (316 µL, 1.55 mmol, 1.5 equiv.). The reaction was slowly allowed to warm up to rt, 2N HCl was added, and stirring was continued for 1 h. The reaction mixture was extracted with EtOAc, and the organic layer was dried over MgSO$_4$ and evaporated under reduced pressure. The crude product was purified by column chromatography (Pentane/EtOAc 100%→4:1) to afford the desired product as a white solid (102 mg, 34%). LCMS [M+H]$^+$ 289; $^1$H NMR (400 MHz, CD$_3$OD) δ 7.47 (1H, d, J=8.1 Hz), 6.85 (1H, d, J=8.1 Hz), 1.36 (12H, s).

Intermediate 3

(2,3-dichloro-4-methoxyphenyl)boronic Acid

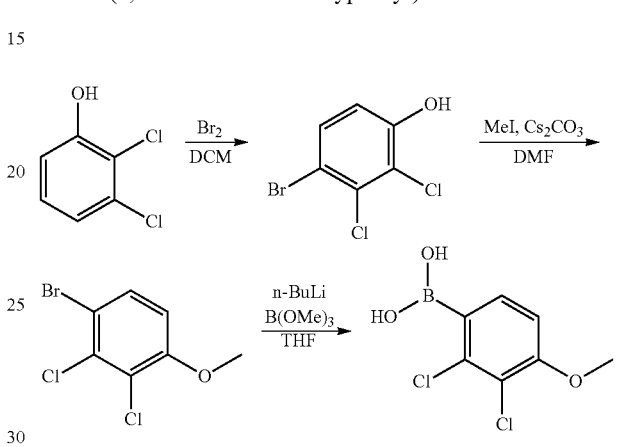

Step 1: 4-Bromo-2,3-dichlorophenol

To a solution of 2,3-dichlorophenol (1.0 g, 6.13 mmol, 1 equiv.) in DCM (4 mL) was added, at 0° C., bromine (348 µL, 6.75 mmol, 1.1 equiv.) over 15 min. The reaction was allowed to warm up to rt over 12 hours. NMR showed unreacted starting material, bromine (0.33 equiv.) was added at 0° C. and the reaction was allowed to warm up to rt over 12 hours. The reaction was stopped by addition of Na$_2$S$_2$O$_3$, the organic layer was washed with brine, dried with MgSO$_4$ and concentrated under reduced pressure. The crude product was purified by column chromatography (Pentane/EtOAc 100%→25:1) to afford the desired product as a white solid (685 mg, 46%). LCMS [M+H]$^+$ 239; $^1$H NMR (400 MHz, DMSO-d$_6$) δ 10.98 (1H, s), 7.54 (1H, d, J=8.8 Hz), 6.91 (1H, d, J=8.8 Hz).

Step 2: 1-Bromo-2,3-dichloro-4-methoxybenzene

To a solution of 4-bromo-2,3-dichlorophenol (200 mg, 0.83 mmol, 1 equiv.) in DMF (3 mL) was added Cs$_2$CO$_3$ (538 mg, 1.65 mmol, 2 equiv.) followed by iodomethane (208 µL, 3.3 mmol, 4 equiv.). The reaction mixture was stirred at 70° C. for 3 h. The reaction was stopped by addition of H$_2$O, extracted with DCM, dried with MgSO$_4$ and concentrated under reduced pressure. The crude product was purified by column chromatography (Pentane/EtOAc 100%→20:1) to afford the desired product as a white solid (190 mg, 89%). LCMS [M+H]$^+$ 256; $^1$H NMR (400 MHz, CDCl$_3$) δ 7.47 (1H, d, J=9.0 Hz), 6.73 (1H, d, J=8.8 Hz), 3.88 (3H, s).

Step 3: (2,3-dichloro-4-methoxyphenyl)boronic Acid

To a solution of 1-bromo-2,3-dichloro-4-methoxybenzene (100 mg, 0.39 mmol, 1 equiv.) in THF (5 mL) was added, at −78° C., n-BuLi (2.5 M in hexanes, 234 µL, 0.59 mmol, 1.5 equiv.). The reaction mixture was stirred at this temperature for 30 min, before addition of B(OMe)₃ (218 µL, 1.95 mmol, 5 equiv.). The reaction was slowly allowed to warm up to rt, 2N HCl was added, and stirring was continued for 1 h. The reaction mixture was extracted with EtOAc, and the organic layer was dried over MgSO₄ and evaporated under reduced pressure. The crude product was purified by column chromatography (Pentane/EtOAc 100%→3:1) to afford the desired product as a white solid (52 mg, 59%). LCMS [M+H]⁺ 221; ¹H NMR (400 MHz, DMSO-d₆) δ 8.25 (1H, s), 7.35 (1H, d, J=8.1 Hz), 7.10 (1H, d, J=8.1 Hz), 3.87 (3H, s).

Intermediate 4

(2,3-dichloro-5-methoxyphenyl)boronic Acid

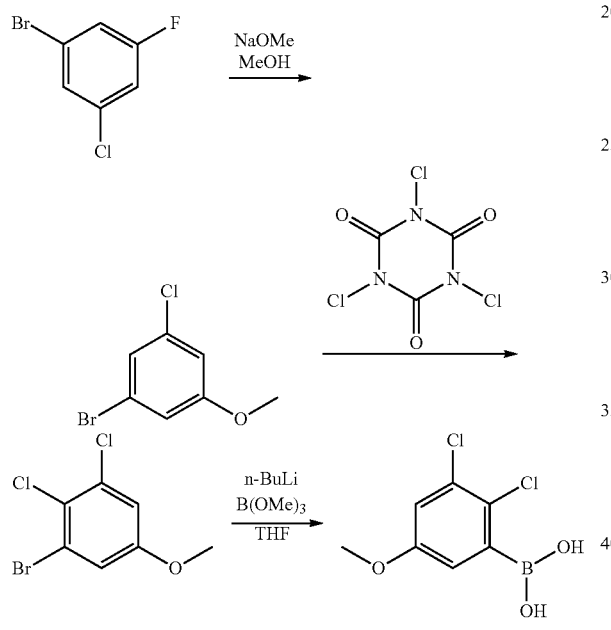

Step 1: 1-Bromo-3-chloro-5-methoxybenzene

1-Bromo-3-chloro-5-fluorobenzene (1 g, 4.77 mmol, 1 equiv.) was treated at 0° C. with sodium methoxide (25% in MeOH, 1.2 mL, 5.71 mmol, 1.2 equiv.). The reaction mixture was stirred at 100° C. for 3 h. The solution was concentrated under reduced pressure, the crude product was extracted with DCM, washed with H₂O, brine, dried over MgSO₄ and concentrated. The product was obtained as a white solid (747 mg, 71%). LCMS [M+H]⁺ 220; ¹H NMR (400 MHz, CD₃Cl) δ 7.09 (1H, t, J=1.7 Hz), 6.94-6.92 (1H, m), 6.83-6.80 (1H, m), 3.77 (3H, s).

Step 2: 1-Bromo-2,3-dichloro-5-methoxybenzene

To a solution of 1-bromo-3-chloro-5-methoxybenzene (300 mg, 1.35 mmol, 1 equiv.) in DMF (5 mL) was added trichloro-1,3,5-triazinane-2,4,6-trione (115 mg, 0.49 mmol, 0.36 equiv.) and the reaction was stirred at 50° C. for 3 h. The reaction mixture was concentrated and the crude product was purified by column chromatography (Heptane/EtOAc 100%→20:1) to afford the desired product as a white solid (253 mg, 73%). LCMS [M+H]⁺ 254; ¹H NMR (400 MHz, CD₃Cl) δ 7.09 (1H, d, J=3.0 Hz), 6.97 (1H, d, J=3.0 Hz), 3.77 (3H, s).

Step 3: (2,3-dichloro-5-methoxyphenyl)boronic Acid

To a solution of 1-bromo-2,3-dichloro-5-methoxybenzene (87 mg, 0.34 mmol, 1 equiv.) in THF (4.5 mL) was added, at −78° C., n-BuLi (2.5 M in hexanes, 205 µL, 0.51 mmol, 1.5 equiv.). The reaction mixture was stirred at this temperature for 30 min, before addition of B(OMe)₃ (191 µL, 1.70 mmol, 5 equiv.). The reaction was slowly allowed to warm up to rt, 2N HCl was added, and stirring was continued for 1 h. The reaction mixture was extracted with EtOAc, and the organic layer was dried over MgSO₄ and evaporated under reduced pressure to afford the desired product as a white solid (75 mg, 100%). LCMS [M+H]⁺ 221.

Intermediate 5

4-chloro-5H,6H,7H,8H-pyrido[2,3-d]pyrimidin-2-amine

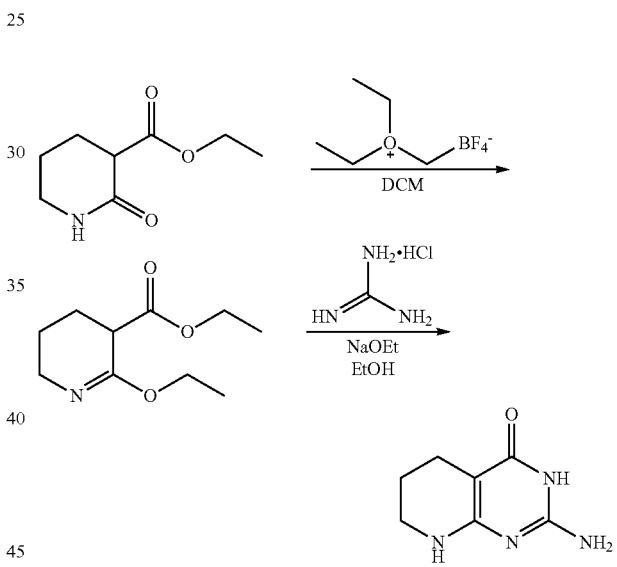

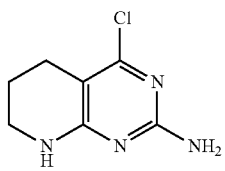

Step 1: ethyl 2-ethoxy-3,4,5,6-tetrahydropyridine-3-carboxylate

To a solution of ethyl 2-oxopiperidine-3-carboxylate (1.5 g, 8.76 mmol, 1 equiv.) in DCM (6.5 mL) under N₂ was added a solution of triethyloxonium tetrafluoroborate (2.0 g, 10.51 mmol, 1.2 equiv.) in DCM (6.5 mL). The reaction mixture was stirred at room temperature overnight. The solution was poured in water (5 mL) and allowed to stand for 30 min. The organic layer was washed with NaHCO₃, H₂O, dried over Na₂SO₄ and concentrated under reduced pressure to afford the desired product as a colourless oil (1.2 g, 66%). ¹H NMR (400 MHz, CDCl₃) δ 4.15 (2H, q, J=7.2 Hz), 4.00-3.98 (2H, m), 3.46-3.44 (2H, m), 3.18-3.16 (1H, m), 1.97-1.95 (2H, m), 1.68-1.66 (1H, m), 1.49-1.47 (1H, m), 1.25 (3H, t, J=7.1 Hz), 1.20 (3H, t, J=7.0 Hz).

Step 2: 2-amino-3H,4H,5H,6H,7H,8H-pyrido[2,3-d]pyrimidin-4-one

A solution of sodium ethoxide (21% in EtOH, 197 μL, 2.51 mmol, 2.5 equiv.) was added to the mixture of ethyl 2-ethoxy-3,4,5,6-tetrahydropyridine-3-carboxylate (200 mg, 1 mmol, 1 equiv.) and guanidine hydrochloride (96 mg, 1 mmol, 1 equiv.) in EtOH (2 mL). The reaction mixture was stirred a reflux overnight. The solvent were removed under vacuum and the obtained solid was dried to afford the desired product as a light yellow solid (116 mg, 70% yield). ¹H NMR (400 MHz, CDCl₃) δ 9.89 (1H, br s), 6.18 (1H, br s), 6.10 (2H, br s), 3.10-3.08 (2H, m), 2.20-2.18 (2H, m), 1.61-1.59 (2H, m).

Step 3: 4-chloro-5H,6H,7H,8H-pyrido[2,3-d]pyrimidin-2-amine

A mixture of 2-amino-5,6,7,8-tetrahydropyrido[2,3-d]pyrimidin-4(3H)-one and acetic anhydride was heated at reflux for 1 h until completion of the reaction as monitored by LCMS. The solvent was removed under reduced pressure and the obtained residue was treated with benzyltriethylammonium chloride (547 mg, 2.4 mmol, 2 equiv.) and POCl₃ (671 μL, 7.2 mmol, 6 equiv.) and heated at reflux for 1 h. After evaporation of the solvents, ice water was added to the residue and HCl (6N, 5.5 mL) was added. The reaction mixture was heated at 50° C. overnight. After evaporation of the solvents, the residue is diluted in EtOAc and washed with NaHCO₃, brine and dried over Na₂SO₄. The combined organic layers were then evaporated, and the crude product was purified by column chromatography (DCM/MeOH 98/2 200 mL, 95/5 100 mL). The pure product was obtained as a yellow powder (45 mg, 20%). LCMS [M+H]⁺ 185. ¹H NMR (400 MHz, CDCl₃) δ 8.09-8.03 (1H, br s), 3.28-3.26 (2H, m), 2.53-2.51 (2H, m), 1.81-1.79 (2H, m).

Intermediate 6

4-chloro-6-phenylpyrimidin-2-amine

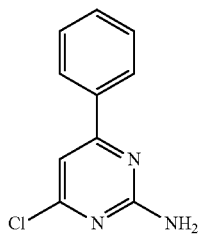 [SMILES: Nc1nc(Cl)cc(-c2ccccc2)n1]

A mixture of 2-amino-4,6-dichloropyrimidine (3 g, 18.29 mmol, 1 equiv.), phenylboronic acid (2.45 g, 20.12 mmol, 1.1 equiv.), K₂CO₃ (5.06 g, 36.6 mmol, 2 equiv.) and Pd(PPh₃)₄ (700 mg, 0.6 mmol, 0.03 equiv.) in 1,4-dioxane (15 mL) and water (1 mL) was heated in a sealed tube at 95° C. for 12 h. The mixture was run through a plug of silica using EtOAc as eluent, concentrated and purified by column chromatography (1:4 EtOAc/pentane) to give the desired product as a white solid (2.2 g, 60%). LCMS [M+H]⁺ 206; ¹H NMR (400 MHz, CDCl₃) δ 8.27-8.20 (2H, m), 8.16-8.05 (3H, m), 7.19 (2H, s), 6.76 (1H, s).

Intermediate 7

6-chloro-4-N-propylpyrimidine-2,4-diamine

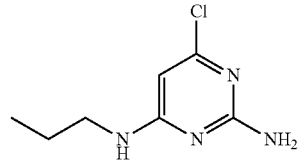

A solution of 4,6-dichloropyrimidin-2-amine (820 mg, 5.0 mmol, 1 equiv.) in EtOH (40 mL) was treated with propan-1-amine (5.0 ml). The reaction mixture was stirred at 85° C. for 48 h. The mixture was cooled, concentrated by evaporation then flash-chromatographed over silica to afford the product as a colorless solid (705 mg; 76%). LCMS [M+H]⁺ 187.

Intermediate 8

4-N-tert-butyl-6-chloropyrimidine-2,4-diamine

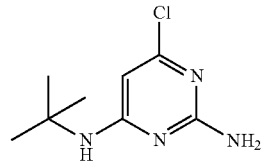

To a solution of 4,6-dichloropyrimidin-2-amine (820 mg, 5.0 mmol, 1 equiv.) in n-BuOH (20 mL) was added tert-butylamine (365 mg, 5.0 mmol, 1 equiv.) and Hünig's base (645 mg, 5.0 mmol, 1 equiv.). The reaction mixture was stirred overnight at 95° C. The mixture was cooled and some unreacted starting material removed by filtration. The filtrate was concentrated and the residue flash-chromatographed over silica to afford the product (0.27 g; 27%). LCMS [M+H]⁺ 201.

Intermediate 9

6-chloro-4-N-(oxan-4-yl)pyrimidine-2,4-diamine

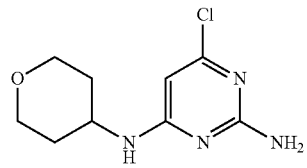 [SMILES: Nc1nc(Cl)cc(NC2CCOCC2)n1]

To a solution of 4,6-dichloropyrimidin-2-amine (492 mg, 3.0 mmol, 1 equiv.) in n-BuOH (20 mL) was added tetrahydro-2H-pyran-4-amine (303 mg, 3.0 mmol, 1 equiv.) and Hünig's base (387 mg, 3.0 mmol, 1 equiv.). The reaction mixture was stirred overnight at 95° C. The mixture was cooled and the precipitated solid was collected and washed with water to give the product (0.42 g; 37%). LCMS [M+H]+ 229.

Intermediate 10

6-chloro-4-N-cyclopropylpyrimidine-2,4-diamine

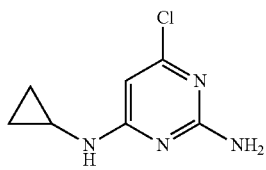 [SMILES: Nc1nc(Cl)cc(NC2CC2)n1]

To a solution of 4,6-dichloropyrimidin-2-amine (164 mg, 1.0 mmol, 1 equiv.) in n-BuOH (5 mL) were added cyclopropanamine (80 µL, 1.1 mmol, 1.1 equiv.) and Hünig's base (260 µL, 1.5 mmol, 1.5 equiv.). The reaction mixture was stirred overnight at 95° C. The solvent was removed in vacuo. The crude product was diluted in EtOAc and washed with H₂O, brine, dried over MgSO₄ and concentrated to afford the desired product as an off-white solid (152 mg, 82%). LCMS [M+H]+ 185; ¹H NMR (400 MHz, DMSO-d₆) δ 7.29 (1H, s), 6.38 (2H, s), 5.85 (1H, s), 3.52 (1H, s), 0.73-0.64 (2H, m), 0.53-0.35 (2H, m).

Intermediate 11

6-chloro-4-N-(1-methoxybutan-2-yl)pyrimidine-2,4-diamine

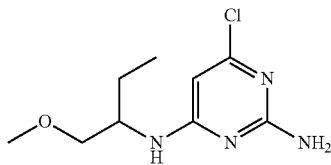

To a solution of 4,6-dichloropyrimidin-2-amine (500 mg, 3.1 mmol, 1 equiv.) in n-BuOH (10 mL) were added 1-methoxybutan-2-amine (315 mg, 3.1 mmol, 1 equiv.) and Hünig's base (531 µL, 3.1 mmol, 1 equiv.). The reaction mixture was stirred overnight at 95° C. The solvent was removed in vacuo. The crude product was diluted in EtOAc and washed with H₂O, brine, dried over MgSO₄ and concentrated to afford the desired product as an off-white solid (592 mg, 84%). LCMS [M+H]+ 231.

Intermediate 12

6-chloro-4-N-(2,2,2-trifluoroethyl)pyrimidine-2,4-diamine

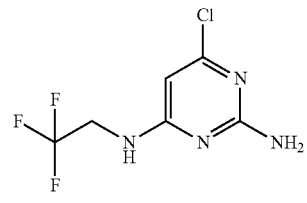 [SMILES: Nc1nc(Cl)cc(NCC(F)(F)F)n1]

To a solution of 4,6-dichloropyrimidin-2-amine (164 mg, 1.00 mmol, 1 equiv.) in n-BuOH (5 mL) were added 2,2,2-trifluoroethanamine hydrochloride (149 mg, 1.1 mmol, 1.1 equiv.) and NEt₃ (202 mg, 2.0 mmol, 2 equiv.). The reaction mixture was stirred overnight at 90° C. The solvent was removed in vacuo. The crude product was diluted in EtOAc and washed with H₂O, brine, dried over MgSO₄ and concentrated to afford the desired product as a yellow solid (59 mg, 26%). LCMS [M+H]+ 227.

Intermediate 13

6-chloro-4-N-(2,2-difluoroethyl)pyrimidine-2,4-diamine

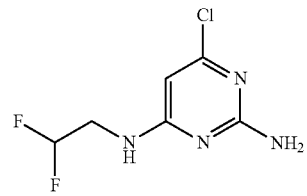 [SMILES: Nc1nc(Cl)cc(NCC(F)F)n1]

To a solution of 4,6-dichloropyrimidin-2-amine (164 mg, 1.00 mmol, 1 equiv.) in n-BuOH (5 mL) were added 2,2-difluoroethanamine hydrochloride (129 mg, 1.1 mmol, 1.1 equiv.) and triethylamine (202 mg, 2.0 mmol, 2 equiv.). The reaction mixture was stirred overnight at 90° C. The solvent was removed in vacuo. The crude product was diluted in EtOAc and washed with H₂O, brine, dried over MgSO₄ and concentrated to afford the desired product as a yellow solid (80 mg, 38%). LCMS [M+H]+ 209.

Intermediate 14

6-chloro-4-N-(prop-2-en-1-yl)pyrimidine-2,4-diamine

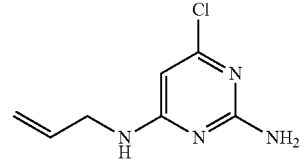

To a solution of 4,6-dichloropyrimidin-2-amine (500 mg, 3.04 mmol, 1 equiv.) in n-BuOH (10 mL) were added 2,2-difluoroethanamine hydrochloride (229 µL, 3.04 mmol, 1 equiv.) and Hünig's base (584 µL, 3.35 mmol, 1.1 equiv.). The reaction mixture was stirred overnight at 95° C. The solvent was removed in vacuo. The crude product was diluted in EtOAc and washed with H$_2$O, brine, dried over MgSO$_4$ and concentrated to afford the desired product as a yellow solid (471 mg, 84%). LCMS [M+H]$^+$ 185.

Intermediate 15

6-chloro-4-N-cyclopentylpyrimidine-2,4-diamine

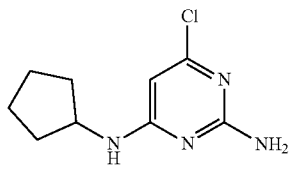 [SMILES: Nc1nc(Cl)cc(NC2CCCC2)n1]

To a solution of 4,6-dichloropyrimidin-2-amine (500 mg, 3.04 mmol, 1 equiv.) in n-BuOH (10 mL) were added cyclopentanamine (301 µL, 3.04 mmol, 1 equiv.) and Hünig's base (584 µL, 3.35 mmol, 1.1 equiv.). The reaction mixture was stirred overnight at 95° C. The solvent was removed in vacuo. The crude product was diluted in EtOAc and washed with H$_2$O, brine, dried over MgSO$_4$ and concentrated to afford the desired product as a brown foam (620 mg, quantitative). LCMS [M+H]$^+$ 213.

Intermediate 16

6-chloro-4-N-cyclobutylpyrimidine-2,4-diamine

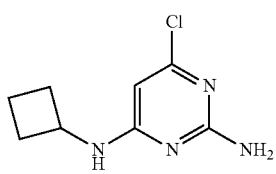 [SMILES: Nc1nc(Cl)cc(NC2CCC2)n1]

To a solution of 4,6-dichloropyrimidin-2-amine (250 mg, 1.52 mmol, 1 equiv.) in n-BuOH (5 mL) were added cyclobutanamine (130 µL, 1.52 mmol, 1 equiv.) and Hünig's base (292 µL, 1.72 mmol, 1.1 equiv.). The reaction mixture was stirred overnight at 95° C. The solvent was removed in vacuo. The crude product was diluted in EtOAc and washed with H$_2$O, brine, dried over MgSO$_4$ and concentrated to afford the desired product as a white solid (248 mg, 80%). LCMS [M+H]$^+$ 199.

Intermediate 17

6-iodo-4-N-methylpyrimidine-2,4-diamine

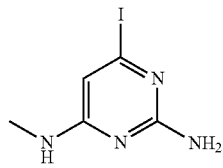

To a suspension of 6-Chloro-4-N-methylpyrimidine-2,4-diamine (1.5 g, 9.43 mmol, 1 equiv.) in acetone (6.2 mL) was added sodium iodide (7.9 g, 52.8 mmol, 5.6 equiv.) and hydrogen iodide (15 mL). The reaction mixture was stirred at 60° C. for 12 h. The solid was filtered off, dissolved in EtOAc, washed with NaHCO$_3$, brine, dried over MgSO$_4$ and concentrated under reduced pressure to afford the desired compound as an orange solid (1.7 g, 73%). LCMS [M+H]$^+$ 251; $^1$H NMR (400 MHz, CDCl$_3$) δ 6.27 (1H, s), 2.80 (3H, s).

Intermediate 18

6-chloro-4-N-(2-phenylethyl)pyrimidine-2,4-diamine

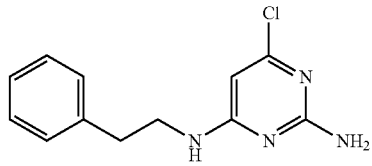 [SMILES: Nc1nc(Cl)cc(NCCc2ccccc2)n1]

To a solution of 4,6-dichloropyrimidin-2-amine (66 mg, 0.40 mmol, 1 equiv.) in n-BuOH (2.5 mL) were added 2-phenylethanamine (75 µL, 0.60 mmol, 1.1 equiv.) and Hünig's base (100 µg, 0.60 mmol, 1.1 equiv.). The reaction mixture was stirred at 95° C. for 3 h. The solvent was removed in vacuo. The crude product was diluted in EtOAc and washed with H$_2$O, brine, dried over MgSO$_4$ and concentrated to afford the desired product as a yellow solid (88 mg, 88%). LCMS [M+H]$^+$ 249.

Intermediate 19

4-chloro-6-(2,3-dimethylphenyl)pyrimidin-2-amine

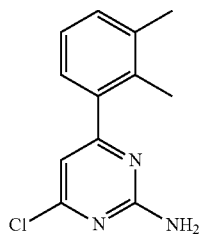 [SMILES: Cc1cccc(-c2cc(Cl)nc(N)n2)c1C]

A mixture of 2-amino-4,6-dichloropyrimidine (0.82 g, 5.0 mmol, 1 equiv.), 2,3-dimethylphenylboronic acid (0.75 g, 5.0 mmol, 1 equiv.), K$_2$CO$_3$ (1.38 g, 10.0 mmol, 2 equiv.)

and palladium tetrakis(triphenylphosphine)palladium (0) (0.12 g, 0.10 mmol, 0.1 equiv.) in 1,4-dioxane (20 mL) and water (5 mL) was heated in a sealed tube at 90° C. for 2.5 hours. The mixture was run through a plug of silica using EtOAc as eluent, concentrated and purified by column chromatography (1:4 EtOAc/pentane) to give the desired product as a white solid (0.76 g, 65%). LCMS [M+H]+ 234; 1H NMR (400 MHz, CD3OD) δ 7.21-7.29 (1H, m), 7.20-7.09 (2H, m), 6.70 (1H, s), 2.34 (3H, s), 2.23 (3H, s).

Intermediate 20

4-chloro-6-(2,3-dichlorophenyl)pyrimidin-2-amine

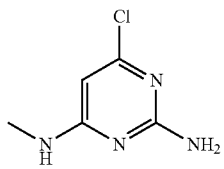

A mixture of 4,6-dichloropyrimidin-2-amine (3.28 g, 20.0 mmol), methanamine (12.0 mL, 24.0 mmol; as a 2 M solution in methanol) and Hünig's base in n-butanol (20 mL) was heated at 95° C. overnight. The mixture was concentrated and the crude was taken up in EtOAc (300 mL) and washed with water (3×150 mL). The organic layer was dried over MgSO4, filtered and concentrated to give the desired product as a buff solid (2.90 g, 91%). LCMS [M+H]+ 159.

Intermediate 21

6-chloro-4-N-methylpyrimidine-2,4-diamine

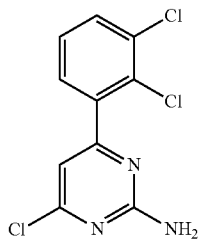 [SMILES: Nc1nc(Cl)cc(-c2cccc(Cl)c2Cl)n1]

A mixture of 4,6-dichloropyrimidin-2-amine (0.50 g, 3.05 mmol), (2,3-dichlorophenyl)boronic acid (0.64 g, 3.35 mmol), sodium carbonate (0.65 g, 6.10 mmol) and palladium tetrakis(triphenylphosphine)palladium (0) (0.088 g, 0.076 mmol) in 1,4-dioxane/water (30 mL; 4:1) was heated in a sealed tube at 95° C. for 2 h. The reaction mixture was run through a plug of silica (EtOAc) and then concentrated. Purification by column chromatography (1:4→1:3 EtOAc/hexane) afforded the desired product as a white solid (0.26 g, 31%). LCMS [M+H]+ 274; 1H NMR (400 MHz, DMSO-d6) δ 6.89 (1H, s) 7.33 (2H, br s) 7.44-7.52 (2H, m) 7.71-7.81 (1H, m).

Intermediate 22

6-Chloro-4-N-[2-(4-chlorophenyl)ethyl]pyrimidine-2,4-diamine

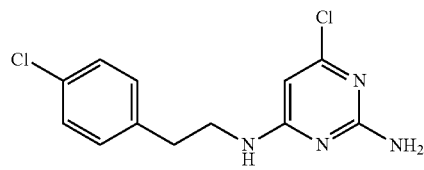 [SMILES: Nc1nc(Cl)cc(NCCc2ccc(Cl)cc2)n1]

A mixture of 4,6-dichloropyrimidin-2-amine (0.50 g, 3.05 mmol), 2-(4-chlorophenyl)ethan-1-amine (0.56 mL, 3.96 mmol) and Hünig's base (0.80 mL, 4.57 mmol) in n-butanol (5 mL) was heated in a sealed tube at 95° C. overnight. The mixture was concentrated and the crude was taken up in EtOAc (50 mL) and washed with water (3×40 mL). The organic layer was dried over MgSO4, filtered and concentrated to give the desired product as a buff solid (0.61 g, 71%). LCMS [M+H]+ 283.

Intermediate 23

1-{3-[(2-amino-6-chloropyrimidin-4-yl)amino]propyl}pyrrolidin-2-one

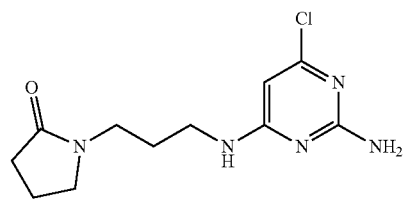 [SMILES: Nc1nc(Cl)cc(NCCCN2CCCC2=O)n1]

A mixture of 4,6-dichloropyrimidin-2-amine (1.64 g, 10.0 mmol), 1-(3-aminopropyl)pyrrolidin-2-one (1.96 mL, 14.0 mmol) and Hünig's base (2.61 mL, 15.0 mmol) in n-butanol (20 mL) was heated in a sealed tube at 110° C. overnight. The mixture was concentrated and the crude was taken up in EtOAc (300 mL) and washed with water (3×150 mL). The aqueous layers were combined and extracted with EtOAc (2×200 mL). The combined organic layers were dried over MgSO4, filtered and concentrated to give the desired product as a buff solid (1.63 g, 60%). LCMS [M+H]+ 270.

Intermediate 24

4-chloro-6-(3-chloro-2-methylphenyl)pyrimidin-2-amine

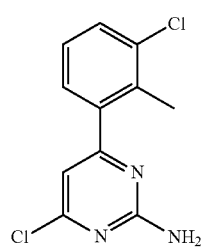 [SMILES: Cc1c(Cl)cccc1-c1cc(Cl)nc(N)n1]

A stirred mixture of 2-amino-4,6-dichloropyrimidine (0.50 g, 3.1 mmol), 3-chloro-2-methylphenylboronic acid (0.57 g, 3.4 mmol), Na$_2$CO$_3$ (1.0 g, 9.8 mmol), palladium tetrakis(triphenylphosphine)palladium (0) (88 mg, 0.076 mmol), dioxane (22 mL) and water (8 mL) were heated in a sealed tube at 90° C. for 2 hours. The solvents were removed in vacuo and the remaining solid was added EtOAc (20 mL) and washed with water. The organic phase was dried over MgSO$_4$ and removed in vacuo. The crude material was purified by flash chromatography (1:4 EtOAc/petroleum ether) to give the desired product as a white solid (365 mg, 47%). LCMS [M+H]$^+$ 254; $^1$H NMR (400 MHz, DMSO-d$_6$) δ ppm 7.52-7.56 (1H, dd, J$_1$=6.5 Hz, J$_2$=2.5 Hz) 7.30-7.33 (2H, m) 7.26 (2H, s) 6.79 (1H, s) 2.32 (3H, s).

Intermediate 25

4-{2-[(2-amino-6-chloropyrimidin-4-yl)amino]ethyl}benzene-1-sulfonamide

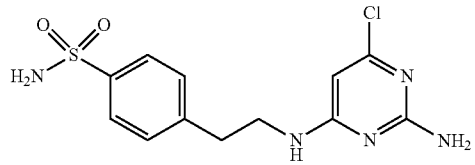 [SMILES: Nc1nc(Cl)cc(NCCc2ccc(S(N)(=O)=O)cc2)n1]

To a suspension of 4,6-dichloropyrimidin-2-amine (800 mg, 4.9 mmol) and 4-(2-aminoethyl)benzenesulfonamide (980 mg, 4.9 mmol) in 2-propanol (10 mL), was added Hünig's base (1.0 mL, 5.7 mmol) and the resulting mixture was heated at reflux for 15 h. The mixture was then poured into NaHCO$_3$ (aq) and extracted three times with DCM. The combined organic layers were dried and concentrated and the crude mixture was purified by column chromatography to afford the title compound. LCMS [M+H]$^+$ 328; $^1$H NMR (400 MHz, CD$_3$OD) δ ppm 7.80-7.85 (m, 2 H), 7.41 (d, J=8.6 Hz, 2 H), 5.76-5.81 (m, 1 H), 3.54-3.64 (m, 2 H), 2.95 (t, J=7.1 Hz, 2 H).

Intermediate 26

4-chloro-6-(2,3,4-trichlorophenyl)pyrimidin-2-amine

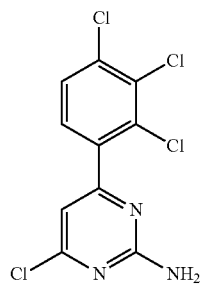 [SMILES: Nc1nc(Cl)cc(-c2ccc(Cl)c(Cl)c2Cl)n1]

A mixture of 4,6-dichloropyrimidin-2-amine (82 mg, 0.50 mmol), (2,3,4-trichlorophenyl)-boronic acid (113 mg, 0.50 mmol), potassium carbonate (138 mg, 1.0 mmol) and palladium tetrakis(triphenylphosphine)palladium (0) (14 mg, 0.013 mmol) in 1,4-dioxane/water (8 mL; 4:1) was heated in a sealed tube at 90° C. for 2 h. The reaction mixture was run through a plug of silica (EtOAc) and then concentrated and purified by preparative HPLC. LCMS [M+H]$^+$ 308.

Intermediate 27

6-chloro-4-N-ethylpyrimidine-2,4-diamine

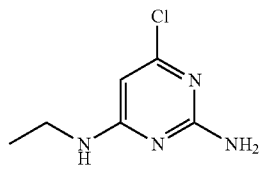

To a solution of 4,6-dichloropyrimidin-2-amine (1 g, 6.09 mmol, 1 equiv.) in n-BuOH (18 mL) were added ethaneamine (2M, 3.0 mL, 6.09 mmol, 1 equiv.) and Hünig's base (1.17 mL, 6.70 mmol, 1.1 equiv.). The reaction mixture was stirred overnight at 95° C. Ethaneamine (1 eq) was added and the reaction was stirred overnight at 95° C. until complete consumption of starting material (2 additions). The solvent was removed in vacuo. The crude product was taken up in EtOAc and H$_2$O. The aqueous layer was extracted twice with EtOAc and once with CHCl$_3$/$^i$PrOH (3:1). The combined organic layers were washed with brine, dried over MgSO$_4$ and concentrated to afford the desired product as a white solid. LCMS [M+H]$^+$ 173; $^1$H NMR (400 MHz, CDCl$_3$) δ ppm 5.76 (1H, s), 4.79 (3H, br s), 3.26 (2H, br s), 1.20 (3H, t, J=7.2 Hz).

Intermediate 28

6-chloro-4-N-cyclohexylpyrimidine-2,4-diamine

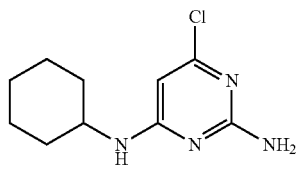 [SMILES: Nc1nc(Cl)cc(NC2CCCCC2)n1]

To a solution of 4,6-dichloropyrimidin-2-amine (1 g, 6.09 mmol, 1 equiv.) in n-BuOH (18 mL) were added cyclohexanamine (698 µL, 6.09 mmol, 1 equiv.) and Hünig's base (1.17 mL, 6.70 mmol, 1.1 equiv.). The reaction mixture was stirred overnight at 95° C. Cyclohexanamine (1 eq) was added and the reaction was stirred overnight at 95° C. until complete consumption of starting material (2 additions). The solvent was removed in vacuo. The crude product was taken up in EtOAc and H$_2$O. The aqueous layer was extracted twice with EtOAc and once with CHCl$_3$/$^i$PrOH (3:1). The combined organic layers were washed with brine, dried over MgSO$_4$ and concentrated to afford the desired product as a white solid. LCMS [M+H]$^+$ 227; $^1$H NMR (400 MHz, CDCl$_3$) δ ppm 5.73 (1H, s), 4.97 (2H, s), 4.79 (1H, br s), 3.45 (1H, br s), 1.97-1.92 (2H, m), 1.74-1.69 (2H, m), 1.63-1.58 (1H, m), 1.39-1.32 (2H, m), 1.22-1.10 (2H, m).

Intermediate 29

6-chloro-4-N-(cyclopropylmethyl)pyrimidine-2,4-diamine

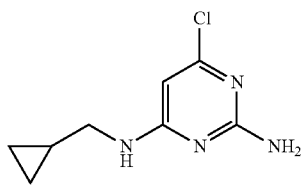 [SMILES: Nc1nc(Cl)cc(NCC2CC2)n1]

To a solution of 4,6-dichloropyrimidin-2-amine (250 mg, 1.52 mmol, 1 equiv.) in n-BuOH (4.5 mL) were added cyclopropylmethanamine (131 µL, 6.09 mmol, 1 equiv.) and Hünig's base (292 µL, 6.70 mmol, 1.1 equiv.). The reaction mixture was stirred overnight at 95° C. The solvent was removed in vacuo. The crude product was taken up in EtOAc and H$_2$O. The aqueous layer was extracted twice with EtOAc and once with CHCl$_3$/$^i$PrOH (3:1). The combined organic layers were washed with brine, dried over MgSO$_4$ and concentrated to afford the desired product as a white solid. LCMS [M+H]$^+$ 199; $^1$H NMR (400 MHz, CDCl$_3$) δ ppm 5.75 (1H, s), 4.92 (3H, br s), 3.07 (2H, s), 1.04-0.96 (1H, m), 0.55-0.49 (2H, m), 0.23-0.19 (2H, m).

Intermediate 30

6-chloro-4-N-[(1R)-1-cyclopropylethyl]pyrimidine-2,4-diamine

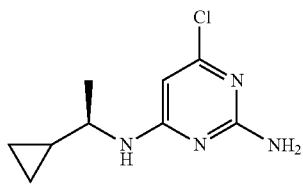

To a solution of 4,6-dichloropyrimidin-2-amine (250 mg, 1.52 mmol, 1 equiv.) in n-BuOH (4.5 mL) were added (1R)-1-cyclopropylethan-1-amine (141 µL, 6.09 mmol, 1 equiv.) and Hünig's base (292 µL, 6.70 mmol, 1.1 equiv.). The reaction mixture was stirred overnight at 95° C. The solvent was removed in vacuo. The crude product was taken up in EtOAc and H$_2$O. The aqueous layer was extracted twice with EtOAc and once with CHCl$_3$/$^i$PrOH (3:1). The combined organic layers were washed with brine, dried over MgSO$_4$ and concentrated to afford the desired product as a colourless oil (321 mg, 99%). LCMS [M+H]$^+$ 213; $^1$H NMR (400 MHz, CDCl$_3$) δ ppm 5.71 (1H, s), 4.97 (2H, s), 4.86 (1H, br s), 3.23 (1H, s), 1.19 (3H, d, J=6.4 Hz), 0.89-0.81 (1H, m), 0.52-0.41 (2H, m), 0.31-0.25 (1H, m), 0.23-0.18 (1H, m).

Intermediate 31

6-chloro-4-N-(propan-2-yl)pyrimidine-2,4-diamine

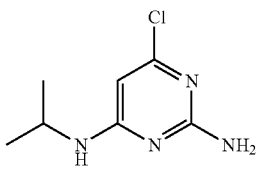

To a solution of 4,6-dichloropyrimidin-2-amine (500 mg, 3.05 mmol, 1 equiv.) in n-BuOH (9 mL) were added propan-2-amine (262 µL, 6.09 mmol, 1 equiv.) and Hünig's base (584 µL, 6.70 mmol, 1.1 equiv.). The reaction mixture was stirred overnight at 95° C. The solvent was removed in vacuo. The crude product was taken up in EtOAc and H$_2$O. The aqueous layer was extracted twice with EtOAc and once with CHCl$_3$/$^i$PrOH (3:1). The combined organic layers were washed with brine, dried over MgSO$_4$ and concentrated to afford the desired product as a white solid (569 mg, 99%). LCMS [M+H]$^+$ 187; $^1$H NMR (400 MHz, CDCl$_3$) δ ppm 5.74 (1H, s), 4.76 (2H, s), 4.60 (1H, br s), 3.85 (1H, br s), 1.19 (3H, s), 1.18 (3H, s).

Intermediate 32

6-chloro-4-N-[(1S)-1-cyclopropylethyl]pyrimidine-2,4-diamine

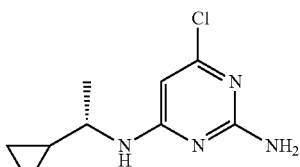

To a solution of 4,6-dichloropyrimidin-2-amine (250 mg, 1.52 mmol, 1 equiv.) in n-BuOH (4.5 mL) were added (1S)-1-cyclopropylethan-1-amine (141 µL, 6.09 mmol, 1 equiv.) and Hünig's base (292 µL, 6.70 mmol, 1.1 equiv.). The reaction mixture was stirred overnight at 95° C. The solvent was removed in vacuo. The crude product was taken up in EtOAc and H$_2$O. The aqueous layer was extracted twice with EtOAc and once with CHCl$_3$/$^i$PrOH (3:1). The combined organic layers were washed with brine, dried over MgSO$_4$ and concentrated to afford the desired product as a colourless oil (296 mg, 91%). LCMS [M+H]$^+$ 213; $^1$H NMR (400 MHz, CDCl$_3$) δ ppm 5.71 (1H, s), 4.99 (2H, s), 4.89 (1H, br s), 3.23 (1H, s), 1.19 (3H, d, J=6.4 Hz), 0.88-0.81 (1H, m), 0.50-0.40 (2H, m), 0.31-0.25 (1H, m), 0.23-0.17 (1H, m).

Intermediate 33

6-chloro-4-N-[2-(4-methanesulfonylphenyl)ethyl]pyrimidine-2,4-diamine

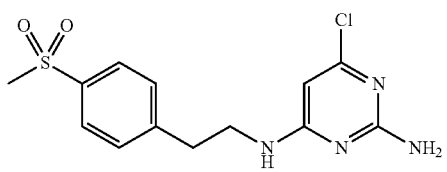 [SMILES: CS(=O)(=O)c1ccc(CCNc2cc(Cl)nc(N)n2)cc1]

A mixture of 4,6-dichloropyrimidin-2-amine (500 mg, 3.0 mmol), 2-(4-methylsulfonylphenyl)ethanamine (600 mg, 3.0 mmol) and Hünig's base (0.63 mL, 3.6 mmol) in 2-propanol (10 mL) was heated at reflux for 15 h. The reaction mixture was poured into NaHCO$_3$ (aq) and extracted three times with DCM. The combined organic layers were dried and concentrated. The crude mixture was purified by column chromatography which afforded the title compound. LCMS [M+H]+ 327; $^1$H NMR (400 MHz, CDCl3) δ ppm 7.90 (d, J=8.3 Hz, 2 H), 7.41 (d, J=8.3 Hz, 2 H), 5.77 (s, 1 H), 4.80-4.89 (m, 2 H), 4.69-4.79 (m, 1 H), 3.56-3.67 (m, 2 H), 3.07 (s, 3 H), 3.00 (t, J=6.8 Hz, 2 H).

Intermediate 34

6-chloro-4-N-(2,2-dimethylpropyl)pyrimidine-2,4-diamine

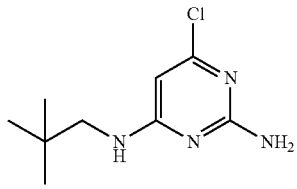

To a solution of 4,6-dichloropyrimidin-2-amine (250 mg, 1.52 mmol, 1 equiv.) in n-BuOH (9 mL) were added 2,2-dimethylpropan-1-amine (6.09 mmol, 1 equiv.) and Hünig's base (292 μL, 6.70 mmol, 1.1 equiv.). The reaction mixture was stirred overnight at 95° C. The solvent was removed in vacuo. The crude product was taken up in EtOAc and H$_2$O. The aqueous layer was extracted twice with EtOAc and once with CHCl$_3$/$^i$PrOH (3:1). The combined organic layers were washed with brine, dried over MgSO$_4$ and concentrated to afford the desired product as a white solid. LCMS [M+H]$^+$ 215; $^1$H NMR (400 MHz, CDCl$_3$) δ ppm 5.94 (1H, s), 3.24 (2H, br s), 0.98 (9H, s).

Intermediate 35

4-N-(2-aminoethyl)-6-(2,3-dimethylphenyl)pyrimidine-2,4-diamine

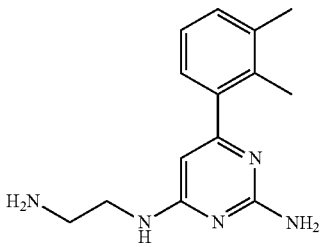 [SMILES: Cc1cccc(-c2cc(NCCN)nc(N)n2)c1C]

Step 1: To a suspension of 4,6-dichloropyrimidin-2-amine (500 mg, 3.05 mmol) and Hünig's base (0.80 mL) in 2-propanol (3.0 mL) was added tert-butyl N-(2-aminoethyl)carbamate (586 mg, 3.66 mmol) and the mixture was stirred at 150° C. for 15 min. The crude mixture was poured into NaHCO$_3$ (aq) and extracted three times with DCM. The combined organic layers were dried and concentrated. Purification by column chromatography (0→10% MeOH in DCM) afforded tert-butyl N-[2-[(2-amino-6-chloro-pyrimidin-4-yl)amino]ethyl]carbamate (850 mg, 2.95 mmol).

Step 2: tert-Butyl N-[2-[(2-amino-6-chloro-pyrimidin-4-yl)amino]ethyl]carbamate (850 mg, 2.95 mmol), (2,3-dimethylphenyl)boronic acid (532 mg, 3.55 mmol), palladium tetrakis(triphenylphosphine)palladium (0) (34 mg, 0.030 mmol), and K$_2$CO$_3$ (1020 mg, 7.39 mmol) were suspended in 1,4-dioxane (10 ml) and H$_2$O (2.0 ml). The vial was flushed with nitrogen and the resulting mixture was stirred at 90° C. for 16 h. The crude mixture was poured into NaHCO$_3$ (aq) and extracted three times with DCM. The combined organic layers were dried and concentrated. Purification by column chromatography (0→10% MeOH in DCM) afforded tert-butyl N-[2-[[2-amino-6-(2,3-dimethylphenyl)pyrimidin-4-yl]amino]ethyl]carbamate (770 mg, 2.15 mmol).

Step 3: tert-Butyl N-[2-[[2-amino-6-(2,3-dimethylphenyl)pyrimidin-4-yl]amino]ethyl]carbamate (770 mg, 2.15 mmol) was dissolved in TFA (6 mL) and the resulting mixture was stirred for 1 h at rt, after which the TFA was distilled off. Purification by column chromatography (5→30% MeOH [containing 1 v/v % NH$_4$OH] in DCM) afforded 4-N-(2-aminoethyl)-6-(2,3-dimethylphenyl)pyrimidine-2,4-diamine (500 mg, 1.94 mmol). LCMS [M+H]$^+$ 258.

Intermediate 36

4-N-(3-aminopropyl)-6-(2,3-dimethylphenyl)pyrimidine-2,4-diamine

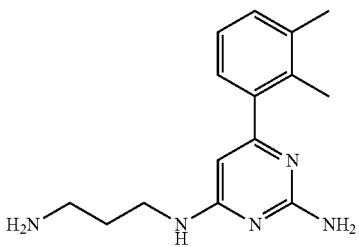 [SMILES: Cc1cccc(-c2cc(NCCCN)nc(N)n2)c1C]

Step 1: A vial was charged with 4,6-dichloropyrimidin-2-amine (500 mg, 3.0 mmol) and tert-butyl N-(2-aminopropyl)carbamate (640 mg, 3.7 mmol). Then 2-propanol (3.0 ml) and Hünig's base (0.80 ml) were added and the resulting mixture was heated at 150° C. using microwave irradiation for 15 min. The mixture was then concentrated and purified by column chromatography (2→10% MeOH in DCM) to afford tert-butyl N-[3-[(2-amino-6-chloro-pyrimidin-4-yl)amino]propyl]-carbamate (788 mg, 2.61 mmol).

Step 2: tert-Butyl N-[3-[(2-amino-6-chloro-pyrimidin-4-yl)amino]propyl]carbamate (790 mg, 2.6 mmol), (2,3-dimethylphenyl)boronic acid (470 mg, 3.1 mmol), palladium tetrakis(triphenylphosphine)palladium (0) (60 mg, 0.050 mmol), and K$_2$CO$_3$ (720 mg 5.2 mmol) were suspended in 1,4-dioxane (6.0 ml) and H$_2$O (1.5 ml). The resulting mixture was heated at 90° C. for 16 h and then poured into H$_2$O and extracted three times with DCM. The combined organic layers were dried and concentrated. Purification by column chromatography (1→10% MeOH in DCM) afforded tert-butyl N-[3-[[2-amino-6-(2,3-dimethylphenyl)pyrimidin-4-yl]amino]propyl]carbamate (800 mg, 2.1 mmol).

Step 3: tert-Butyl N-[3-[[2-amino-6-(2,3-dimethylphenyl)pyrimidin-4-yl]amino]propyl]carbamate (800 mg, 2.1 mmol) was dissolved in TFA and heated at reflux for 1 h. The TFA was evaporated and the crude residue was purified by column chromatography (2→30% MeOH [containing 1 v/v % NH$_4$OH] in DCM) to afford 4-N-(3-aminopropyl)-6-(2,3-dimethylphenyl)pyrimidine-2,4-diamine (540 mg, 2.0 mmol). LCMS [M+H]$^+$ 272.

Intermediate 37

4-chloro-6-(2-chloro-3-methylphenyl)pyrimidin-2-amine

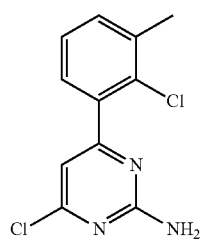 [SMILES: Cc1cccc(-c2cc(Cl)nc(N)n2)c1Cl]

To a suspension of 4,6-dichloropyrimidin-2-amine (250 mg, 1.52 mmol, 1 eq) in dioxane/H$_2$O (5 mL, 4:1) was added (2-chloro-3-methylphenyl)boronic acid (260 mg, 1.52 mmol, 1 eq) followed by potassium carbonate (421 mg, 3.05 mmol, 2 eq) and Pd(PPh$_3$)$_4$ (44 mg, 0.04 mmol, 0.025 eq). The resulting mixture was stirred at 90° C. for 12 hrs. The solvent was removed in vacuo. The residue was taken up in DMF and purified by preparative to afford the desired product as an off-white solid (166 mg, 43%). LCMS [M+H]$^+$ 254; $^1$H NMR (400 MHz, CDCl$_3$) δ ppm 7.32-7.28 (2H, m), 7.25-7.21 (1H, m), 6.92 (1H, s), 5.31 (2H, br s), 2.42 (3H, s).

Intermediate 38

4-chloro-6-(quinolin-5-yl)pyrimidin-2-amine

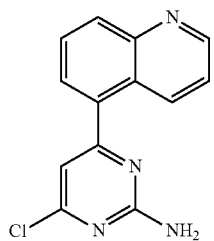 [SMILES: Nc1nc(Cl)cc(-c2cccc3ncccc23)n1]

To a suspension of 4,6-dichloropyrimidin-2-amine (150 mg, 0.91 mmol, 1 eq) in dioxane/H$_2$O (5 mL, 4:1) was added (quinolin-5-yl)boronic acid (158 mg, 0.91 mmol, 1 eq) followed by potassium carbonate (253 mg, 1.83 mmol, 2 eq) and Pd(PPh$_3$)$_4$ (26 mg, 0.020 mmol, 0.025 eq). The resulting mixture was stirred at 90° C. for 12 hrs. The solvent was removed in vacuo and the residue was purified by preparative HPLC to afford the desired product as a yellow solid (63 mg, 27%). LCMS [M+H]$^+$ 257; $^1$H NMR (400 MHz, CDCl$_3$) δ ppm 9.21-9.19 (2H, m), 8.62 (1H, d, J=8.8 Hz), 8.30-7.99 (1H, m), 7.92 (1H, dd, J=7.2 and 0.8 Hz), 7.81-7.77 (1H, m), 6.98 (1H, s), 5.40 (2H, br s).

Intermediate 39

4-chloro-6-(1H-indol-4-yl)pyrimidin-2-amine

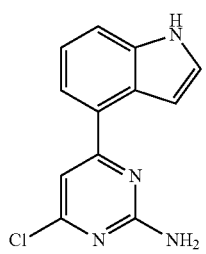 [SMILES: Nc1nc(Cl)cc(-c2cccc3[nH]ccc23)n1]

To a suspension of 4,6-dichloropyrimidin-2-amine (150 mg, 0.91 mmol, 1 eq) in dioxane/H$_2$O (5 mL, 4:1) was added (1H-indol-4-yl)boronic acid (147 mg, 0.91 mmol, 1 eq) followed by potassium carbonate (253 mg, 1.83 mmol, 2 eq) and Pd(PPh$_3$)$_4$ (26 mg, 0.02 mmol, 0.025 eq). The resulting mixture was stirred at 90° C. for 12 hrs. The solvent was removed in vacuo and the residue was purified by preparative HPLC to afford the desired product as a yellow solid (111 mg, 50%). LCMS [M+H]$^+$ 245; $^1$H NMR (400 MHz, CDCl$_3$) δ ppm 8.45 (1H, br s), 7.57 (1H, d, J=7.2 Hz), 7.51 (1H, d, J=8.0 Hz), 7.35 (1H, t, J=4.0 Hz), 7.27 (1H, d, J=7.6 Hz), 7.18 (1H, s), 7.00-6.99 (1H, m), 5.90 (2H, br s).

Intermediate 40

4-chloro-6-(5-chloro-2-methylphenyl)pyrimidin-2-amine

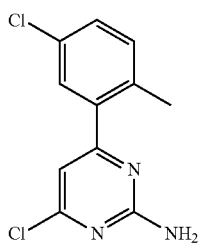 [SMILES: Cc1ccc(Cl)cc1-c1cc(Cl)nc(N)n1]

To a suspension of 4,6-dichloropyrimidin-2-amine (150 mg, 0.91 mmol, 1 eq) in dioxane/H$_2$O (5 mL, 4:1) was added (5-chloro-2-methylphenyl)boronic acid (155 mg, 0.91 mmol, 1 eq) followed by potassium carbonate (253 mg, 1.83 mmol, 2 eq) and Pd(PPh$_3$)$_4$ (26 mg, 0.02 mmol, 0.025 eq). The resulting mixture was stirred at 90° C. for 12 hrs. The solvent was removed in vacuo and the residue was purified by preparative HPLC to afford the desired product as an off-white solid (98 mg, 42%). LCMS [M+H]$^+$ 254; $^1$H NMR (400 MHz, CDCl$_3$) δ ppm 7.35 (1H, d, J=2.0 Hz), 7.28 (1H, dd, J=8.4 and 2.4 Hz), 7.18 (1H, d, J=8.4 Hz), 6.72 (1H, s), 5.30 (2H, br s), 2.34 (3H, s).

Intermediate 41

6-(3-aminophenyl)-4-N-methylpyrimidine-2,4-diamine

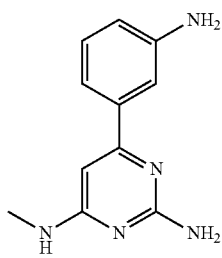 [SMILES: CNc1cc(-c2cccc(N)c2)nc(N)n1]

Tetrakis(triphenylphosphine)palladium (0) (5 mol %) was added to a stirred mixture of 6-chloro-4-N-methylpyrimidine-2,4-diamine (1.00 mmol), (3-aminophenyl)boronic acid (1.3 equiv.), sodium carbonate (3.2 equiv.), 1,4-dioxane (4 mL) and water (1 mL) in a tube. The tube was sealed and the reaction was heated at 90° C. for 5 h and then concentrated. The crude material was taken up in ethyl acetate and washed with water. The organic phase was dried over magnesium sulfate, concentrated and purified by flash chromatography (0→15% MeOH in DCM) to give the title compound. LCMS [M+H]$^+$ 216.

Intermediate 42

6-(3-amino-2-methylphenyl)-4-N-methylpyrimidine-2,4-diamine

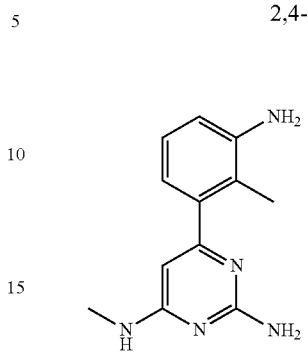

Tetrakis(triphenylphosphine)palladium (0) (5 mol %) was added to a stirred mixture of 6-chloro-4-N-methylpyrimidine-2,4-diamine (3.00 mmol), (3-amino-2-methylphenyl)boronic acid (1.3 equiv.), sodium carbonate (3.2 equiv.), 1,4-dioxane (4 mL) and water (1 mL). The tube was sealed and the reaction was heated at 90° C. for 5 h. The mixture was concentrated and purified by column chromatography (13% MeOH in DCM) to give the title compound. LCMS [M+H]$^+$ 230; $^1$H NMR (400 MHz, DMSO-d$_6$) δ ppm 6.88 (1 H, t, J=7.71 Hz), 6.71-6.81 (1 H, m), 6.61 (1 H, dd, J=7.96, 1.14 Hz), 6.44 (1 H, dd, J=7.58, 1.01 Hz), 5.90 (2 H, br. s.), 5.64 (1 H, s), 4.83 (2 H, s), 2.75 (3 H, d, J=4.55 Hz), 1.98 (3 H, s).

Intermediate 43

6-(5-amino-2-methylphenyl)-4-N-methylpyrimidine-2,4-diamine

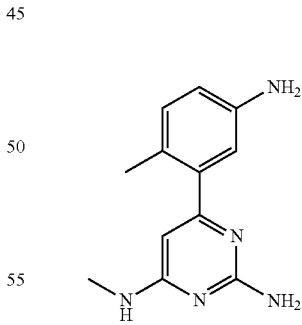

Tetrakis(triphenylphosphine)palladium (0) (5 mol %) was added to a stirred mixture of 6-chloro-4-N-methylpyrimidine-2,4-diamine (3.0 mmol), (5-amino-2-methylphenyl)boronic acid (1.3 equiv.), sodium carbonate (3.2 equiv.), 1,4-dioxane (4 mL) and water (1 mL) in a tube. The tube was sealed and the reaction was heated at 90° C. for 5 h. The mixture was concentrated and purified by column chromatography (13% MeOH in DCM) to give the title compound. LCMS [M+H]$^+$ 230.

Intermediate 44

6-(4-aminophenyl)-4-N-methylpyrimidine-2,4-diamine

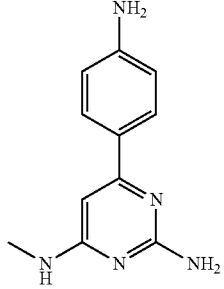 [SMILES: CNc1cc(-c2ccc(N)cc2)nc(N)n1]

Tetrakis(triphenylphosphine)palladium (0) (5 mol %) was added to a stirred mixture of 6-chloro-4-N-methylpyrimidine-2,4-diamine (1.0 mmol), 4-(tetramethyl-1,3,2-dioxaborolan-2-yl)aniline (1.3 equiv.), sodium carbonate (3.2 equiv.), 1,4-dioxane (4 mL) and water (1 mL) in a tube. The tube was sealed and the reaction was heated at 90° C. for 5 h and then concentrated. The crude material was taken up in ethyl acetate and washed with water. The organic phase was dried over magnesium sulfate, concentrated and purified by flash chromatography (0→15% MeOH/DCM) to give the title compound. LCMS [M+H]+ 216; 1H NMR (400 MHz, CDCl3) δ ppm 7.64 (2 H, d, J=8.53 Hz), 6.50-6.62 (3 H, m), 6.03 (1 H, s), 5.74 (2 H, s), 5.37 (2 H, s), 2.76 (3 H, d, J=4.77 Hz).

Intermediate 45

4-[2-[(2-amino-6-chloro-pyrimidin-4-yl)amino]ethyl]benzamide

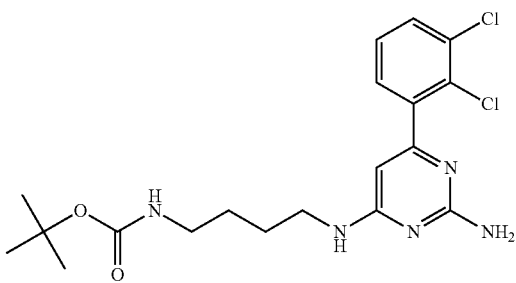

Step 1. A mixture of 2-(4-carboxyphenyl)ethylammonium chloride (1.0 equiv.), 4,6-dichloropyrimidin-2-amine (1.0 equiv.), diisopropylethylamine (3.2 equiv.), and 2-propanol was heated to 110° C. in a sealed vial for 16 h.

The mixture was concentrated and purified by silica gel chromatography which afforded 4-[2-[(2-amino-6-chloro-pyrimidin-4-yl)amino]ethyl]benzoic acid. LCMS [M+H]+ 293.

Step 2. A mixture of 4-[2-[(2-amino-6-chloro-pyrimidin-4-yl)amino]ethyl]benzoic acid (1.0 equiv.), HATU (1.1 equiv.), and DMF was stirred at 20° C. for 5 min, thereafter ammonium hydroxide (3 equiv.) was added. The mixture was stirred at 20° C. for 16 h and then the mixture was diluted with NaHCO3 and extracted with DCM ×3. The combined organics were dried and purified by silica gel chromatography. [M+H]+ 292.

Intermediate 46

4-N-M-aminobutyl)-6-(2,3-dimethylphenyl)pyrimidine-2,4-diamine

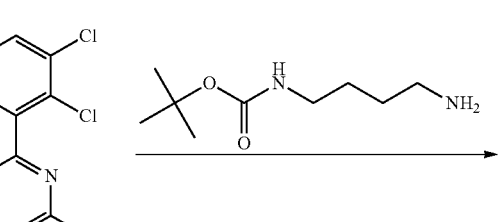

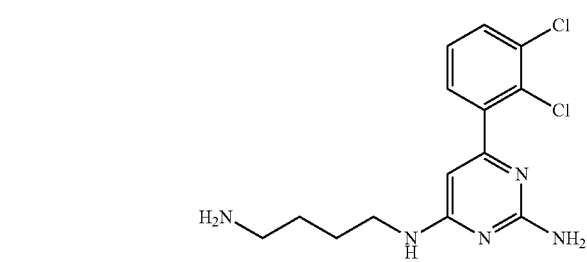

Step 1: A mixture of intermediate 21 (1 equiv.), tert-butyl N-(4-aminobutyl)carbamate (1.9 equiv.), and diisopropylethylamine (2.1 equiv.) in dioxane was stirred at 150° C. in a microwave reactor for 30 min. The crude reaction mixture was then purified by preparative LC.

LCMS [M+H]+ 426.

Step 2: tert-butyl N-[4-[[2-amino-6-(2,3-dichlorophenyl)pyrimidin-4-yl]amino]butyl]carbamate was stirred in TFA at 20° C. for 1 h. The TFA was then removed and the crude residue was purified by silica gel chromatography.

LCMS [M+H]+ 326.

Intermediate 47

4-N-[2-(3-aminophenyl)ethyl]-6-(3-chloro-2-methyl-phenyl)pyrimidine-2,4-diamine

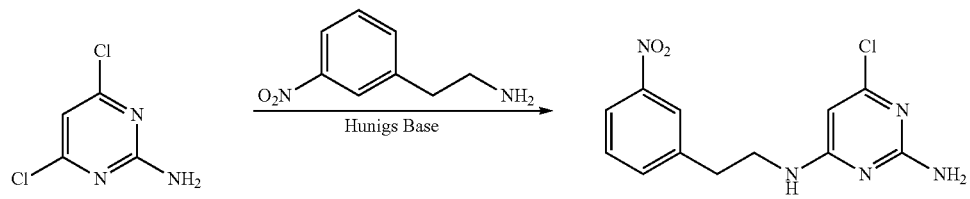

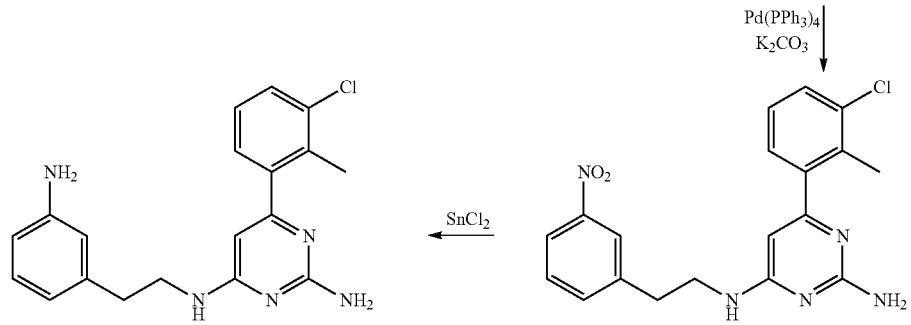

Step 1: A mixture of 2-amino-4,6-dichloropyrimidine (1.0 equiv.), 2-(3-nitrophenyl)ethylammonium chloride (1.3 equiv.), and diisopropylethylamine (2.5 equiv.) in 2-propanol was stirred at 100° C. in a sealed vial for 16 h. The reaction mixture was then diluted with NaHCO₃ (aq) and extracted with DCM. The crude material was then purified by silica gel chromatography.

Step 2: A mixture of 6-(3-chloro-2-methyl-phenyl)-N4-[2-(3-nitrophenyl)ethyl]pyrimidine-2,4-diamine (1.0 equiv.), (3-chloro-2-methyl-phenyl)boronic acid (1.2 equiv.), K₂CO₃ (3.0 equiv.) and Pd(PPh₃)₄ (0.05 equiv.) in 1,4-dioxane and water was stirred at 90° C. for 16 h. Thereafter water was added and the mixture was extracted with DCM ×3. The combined organic phases were concentrated and purified by silica gel chromatography. LCMS [M+H]+ 384.

Step 3: A mixture of 6-(3-chloro-2-methyl-phenyl)-N4-[2-(3-nitrophenyl)ethyl]pyrimidine-2,4-diamine (1.0 equiv.) and SnCl₂.H₂O (5.0 equiv.) was stirred in ethanol at reflux for 16 h. Then KOH (1 M) was added and the mixture was extracted with DCM ×5. The organics were dried, concentrated and purified by silica gel chromatography. LCMS [M+H]+ 354. 1H NMR (400 MHz, CHLOROFORM-d) δ ppm 7.37 (d, J=1.6 Hz, 1 H), 7.19 (d, J=1.6 Hz, 1 H), 7.14-7.18 (m, 1 H), 7.09-7.14 (m, 1 H), 6.61-6.64 (m, 1 H), 6.54-6.60 (m, 2 H), 5.77 (s, 1 H), 4.77 (br. s., 3 H), 3.66 (br. s., 2 H), 3.51-3.62 (m, 2 H), 2.83 (t, J=7.0 Hz, 2 H), 2.37 (s, 3 H).

Intermediate 48

4-N-[2-(4-aminophenyl)ethyl]-6-(3-chloro-2-methyl-phenyl)pyrimidine-2,4-diamine


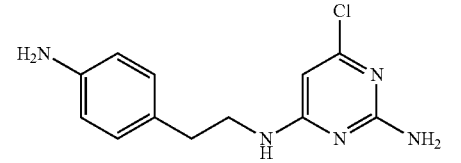

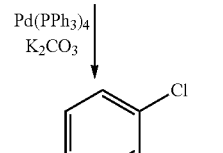

Step 1: A mixture of 2-amino-4,6-dichloropyrimidine (1.0 equiv.), 4-(2-aminoethyl)aniline (1.3 equiv.), and diisopropylethylamine (2.0 equiv.) in 2-propanol was stirred at 90° C. in a sealed vial for 16 h. The reaction mixture was then diluted with NaHCO₃ (aq) and extracted with DCM. The crude material was then purified by silica gel chromatography. [M+H]⁺ 264.

Step 2: A mixture of N4-[2-(4-aminophenyl)ethyl]-6-chloro-pyrimidine-2,4-diamine (1.0 equiv.), (3-chloro-2-methylphenyl)boronic acid (1.2 equiv.), K₂CO₃ (3.0 equiv.) and Pd(PPh₃)₄ (0.05 equiv.) in 1,4-dioxane and water was stirred at 90° C. for 16 h. Thereafter water was added and the mixture was extracted with DCM ×3. The combined organic phases were concentrated and purified by silica gel chromatography. LCMS [M+H]⁺ 354.

Intermediate 49

4-chloro-6-(4-fluoro-2,5-dimethylphenyl)pyrimidin-2-amine

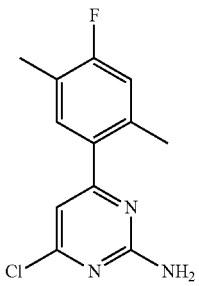 [SMILES: Cc1cc(-c2cc(Cl)nc(N)n2)c(C)cc1F]

A mixture of 2-amino-4,6-dichloropyrimidine (0.72 g, 4.4 mmol, 1 equiv.), 4-fluoro-2,5-dimethylphenylboronic acid (0.78 g, 4.6 mmol, 1 equiv.), K₂CO₃ (1.2 g, 8.8 mmol, 2 equiv.) and tetrakis(triphenylphosphine)palladium (0.17 g, 0.15 mmol, 0.033 equiv.) in 1,4-dioxane (10 mL) and water (2 mL) was heated in a sealed tube at 60° C. for 23 hours. The mixture was diluted with NaHCO₃ and extracted with DCM ×3. The combined organics were concentrated and purified by column chromatography. LCMS [M+H]⁺ 252. ¹H NMR (400 MHz, CHLOROFORM-d) δ ppm 7.23 (d, J=7.83 Hz, 1 H), 6.92 (d, J=10.61 Hz, 1 H), 6.73 (s, 1 H), 5.37 (br. s., 2 H), 2.37 (s, 3 H), 2.27 (d, J=0.76 Hz, 3 H).

Intermediate 50

4-N-[2-(4-aminophenyl)ethyl]-6-(2,3-dimethylphenyl)pyrimidine-2,4-diamine

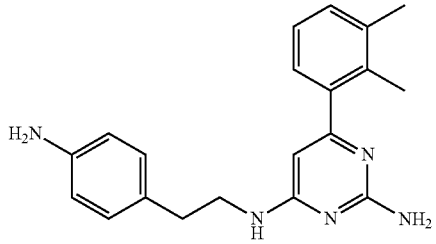 [SMILES: Cc1cccc(-c2cc(NCCc3ccc(N)cc3)nc(N)n2)c1C]

This compound was produced according to general procedure 9 from intermediate 19 and 4-(2-aminoethyl)aniline. LCMS [M+H]⁺ 334. 1H NMR (400 MHz, CHLOROFORM-d) δ ppm 7.19 (br. s., 1 H), 7.13 (s, 1 H), 7.08 (s, 1 H), 7.00 (d, J=8.34 Hz, 2 H), 6.68 (d, J=8.34 Hz, 2 H), 0.80 (s, 1 H), 3.48-3.60 (m, 2 H), 2.77 (t, J=7.45 Hz, 2 H), 2.32 (s, 3 H), 2.20 (s, 3 H).

Intermediate 51

[3-(carbamoylmethoxy)phenyl]boronic Acid

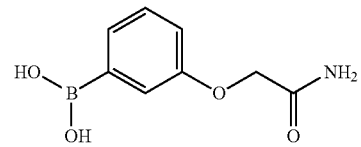 [SMILES: NC(=O)COc1cccc(B(O)O)c1]

Step 1: 3-(tetramethyl-1,3,2-dioxaborolan-2-yl)phenol (300 mg, 1.4 mmol), 2-bromoacetamide (210 mg, 1.5 mmol), K₂CO₃ (570 mg, 4.1 mmol) and MeCN (15 mL) were heated in a sealed tube at 65° C. overnight. The reaction was cooled and filtered. The solvent was removed in vacuo to afford 2-[3-(tetramethyl-1,3,2-dioxaborolan-2-yl)phenoxy]acetamide LCMS [M+H]⁺ 278

Step 2: 2-[3-(tetramethyl-1,3,2-dioxaborolan-2-yl)phenoxy]acetamide (370 mg, 1.4 mmol), NaIO4 (870 mg, 4.1 mmol), THF (12 ml) and water (3 ml) was stirred at r.t. for 30 min. 1M HCl (1 mL) was added and the reaction was stirred at r.t. for 3 hours. Water (~15 mL) was added and the organic solvent was removed in vacuo. [3-(carbamoylmethoxy)phenyl]boronic acid was collected by filtration. LCMS [M+H]⁺ 196.

Intermediate 52

[4-[2-[(2-amino-6-chloro-pyrimidin-4-yl)amino]ethyl]phenyl]-morpholino-methanone

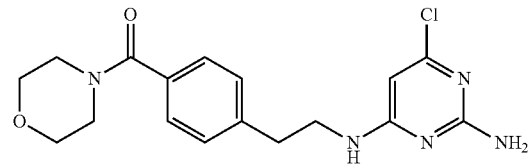 [SMILES: Nc1nc(Cl)cc(NCCc2ccc(C(=O)N3CCOCC3)cc2)n1]

A mixture of 4-[2-[(2-amino-6-chloro-pyrimidin-4-yl)amino]ethyl]benzoic acid (from step 1 of the synthesis of intermediate 45 and TBTU in DMF was stirred at 20° C. for 10 min, then morpholine was added and the resulting mixture was stirred at 20° C. for 20 h. The mixture was then diluted with NaHCO₃ (aq) and extracted with DCM ×3. The combined organics were dried, concentrated, and purified by silica gel chromatography. [M+H]⁺ 362.

Intermediate 53

4-(2-{[2-amino-6-(3-chloro-2-methylphenyl)pyrimidin-4-yl]amino}ethyl)benzonitrile

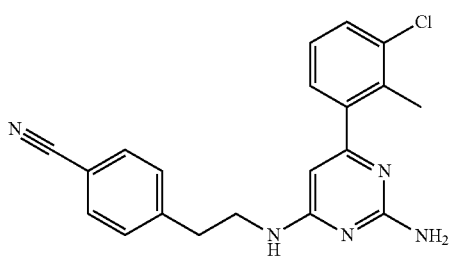 [SMILES: Cc1c(Cl)cccc1-c1cc(NCCc2ccc(C#N)cc2)nc(N)n1]

A mixture of 4-chloro-6-(3-chloro-2-methylphenyl)pyrimidin-2-amine (150 mg, 0.59 mmol), 4-(2-aminoethyl)benzonitrile hydrochloride (110 mg, 0.59 mmol), $K_2CO_3$ (240 mg, 1.8 mmol) and MeCN (5 mL) was heated for 1 hour at 170° C. in a sealed vial. Thereafter the mixture was diluted with MeOH and purified by preparative LC to afford 4-(2-{[2-amino-6-(3-chloro-2-methylphenyl)pyrimidin-4-yl]amino}ethyl)benzonitrile. LCMS [M+H]$^+$ 364.

Intermediate 54

2-{[2-amino-6-(2,3-dimethylphenyl)pyrimidin-4-yl]amino}ethan-1-ol

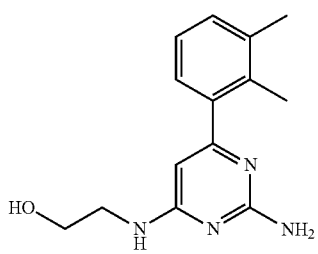 [SMILES: Cc1cccc(-c2cc(NCCO)nc(N)n2)c1C]

A mixture of Intermediate 19 (1.0 equiv.) and 2-aminoethanol (2.2 equiv.) in ethanol was heated in a sealed tube at 130° C. for 4 h. After cooling a precipitate formed which was filtered and washed with cold ethanol and dried to furnish the title compound. LCMS [M+H]$^+$ 259. $^1$H NMR (400 MHz, DMSO-d6) δ ppm 7.12-7.17 (m, 1 H), 7.08 (t, J=7.5 Hz, 1 H), 7.00-7.05 (m, 1 H), 6.88 (br. s., 1 H), 5.93 (s, 2 H), 5.73 (s, 1 H), 4.74 (t, J=5.3 Hz, 1 H), 3.51 (q, J=5.8 Hz, 2 H), 3.28-3.33 (m, 2 H), 2.26 (s, 3 H), 2.15 (s, 3 H).

Intermediate 55

2-[[2-amino-6-(3-chloro-2-methyl-phenyl)pyrimidin-4-yl]amino]ethanol

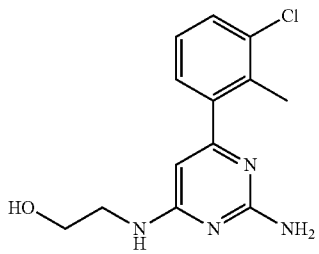 [SMILES: Cc1c(Cl)cccc1-c1cc(NCCO)nc(N)n1]

A mixture of Intermediate 24 (1.0 equiv.) and 2-aminoethanol (2.2 equiv.) in isopropanol was heated in a sealed tube at 130° C. for 1 h. After cooling a precipitate formed which was filtered and washed with cold isopropanol and dried to furnish the title compound. LCMS [M+H]$^+$ 279.

Intermediate 56

4-[2-[[2-amino-6-(1,2,3,6-tetrahydropyridin-4-yl)pyrimidin-4-yl]amino]ethyl]-benzenesulfonamide

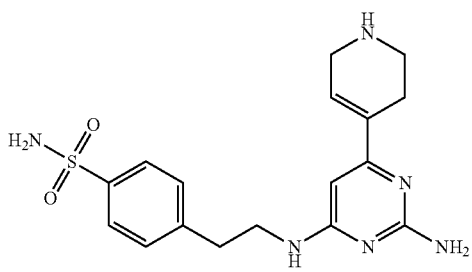 [SMILES: Nc1nc(NCCc2ccc(S(N)(=O)=O)cc2)cc(C2=CCNCC2)n1]

To tert-butyl 4-[2-amino-6-[2-(4-sulfamoylphenyl)ethylamino]pyrimidin-4-yl]-3,6-dihydro-2H-pyridine-1-carboxylate was added 5 M HCl in dioxane and methanol and the mixture was stirred at rt for 40 min. The solvent was removed to obtain the title compound. LCMS [M+H]$^+$ 375.

Intermediate 57

4-N-[2-(4-methanesulfonylphenyl)ethyl]-6-(1,2,3,6-tetrahydropyridin-4-yl)pyrimidine-2,4-diamine

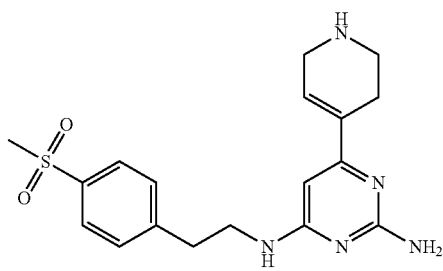 [SMILES: CS(=O)(=O)c1ccc(CCNc2cc(C3=CCNCC3)nc(N)n2)cc1]

To tert-butyl 4-(2-amino-6-{[2-(4-methanesulfonylphenyl)ethyl]amino}pyrimidin-4-yl)-1,2,3,6-tetrahydropyridine-1-carboxylate was added HCl (5 M) in 1,4-dioxane), then the mixture was stirred at 20° C. for 20 min. The solvent was removed to obtain the title compound. LCMS [M+H]⁺ 374.

Intermediate 58

N4-(2-aminoethyl)-6-(3-chloro-2-methyl-phenyl)pyrimidine-2,4-diamine

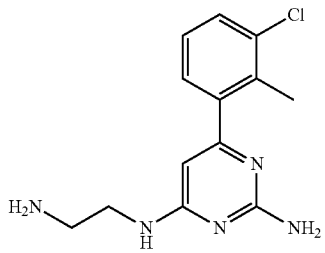 [SMILES: Cc1c(Cl)cccc1-c1cc(NCCN)nc(N)n1]

Step 1. A mixture of 4,6-dichloropyrimidin-2-amine (1 equiv.), tert-butyl N-(2-aminoethyl)carbamate (1.2 equiv.), and diisopropylethylamine (3 equiv.) in 2-propanol was stirred at 90° C. for 16 h. The reaction mixture was then poured into water and extracted with DCM ×3. The combined organics were dried (MgSO₄) and concentrated. The crude material was used in step 2 without further purification.
Step 2. The crude material from step 1 was dissolved in dioxane, then K₂CO₃ (2 equiv.), Pd(PPh₃)₄ (0.05 equiv.), and (3-chloro-2-methyl-phenyl)boronic acid (1.2 equiv.) were added. The flask was flushed with N2 and the mixture was stirred at reflux for 16 h. The reaction mixture was then poured into water and extracted with DCM ×3. The combined organics were dried (MgSO₄) and concentrated. The crude material was purified by silica gel chromatography using MeOH (0-9%) in DCM.
Step 3. The material from step 2 was dissolved in TFA and stirred at 20° C. for 2 h. The solvent was removed and the crude residue was purified by silica gel chromatography using 5-30% MeOH (containing 1% v/v NH₄OH) in DCM. LCMS [M+H]⁺ 278. ¹H NMR (400 MHz, DMSO-d₆) δ ppm 7.97 (br. s., 2 H), 7.62-7.70 (m, 1 H), 7.38-7.44 (m, 1 H), 7.33-7.37 (m, 1 H), 7.27 (br. s., 1 H), 7.14 (br. s., 1 H), 7.01 (br. s., 1 H), 6.08 (s, 1 H), 3.61 (d, J=4.7 Hz, 2 H), 3.10 (br. s., 2H), 2.31 (s, 3 H).

Intermediate 59

N4-(3-aminopropyl)-6-(3-chloro-2-methylphenyl)pyrimidine-2,4-diamine

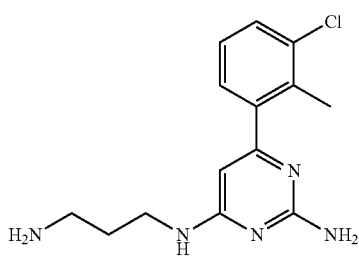 [SMILES: Cc1c(Cl)cccc1-c1cc(NCCCN)nc(N)n1]

A mixture of tert-butyl N-[3-[[2-amino-6-(3-chloro-2-methyl-phenyl)pyrimidin-4-yl]amino]propyl]carbamate (prepared in example 668) and TFA was stirred at 20° C. for 2 h, thereafter the solvent was removed by co-evaporation with 2-propanol. The crude residue was purified by silica gel chromatography. LCMS [M+H]⁺ 292.

Intermediate 60

3-{[2-amino-6-(3-chloro-2-methylphenyl)pyrimidin-4-yl]amino}propan-1-ol

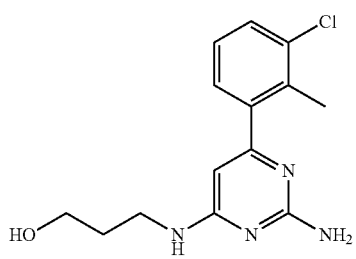 [SMILES: Cc1c(Cl)cccc1-c1cc(NCCCO)nc(N)n1]

A mixture of 4-chloro-6-(3-chloro-2-methylphenyl)pyrimidin-2-amine (intermediate 24), 3-aminopropan-1-ol (2.2 equiv.) in 2-propanol was microwave heated in a sealed tube at 130° C. for 30 min. Purification by column chromatography afforded the title compound (10% MeOH in DCM). LCMS [M+H]⁺ 293.

Intermediate 61

4-(2-{[2-amino-6-(3-chloro-2-methylphenyl)pyrimidin-4-yl]amino}ethoxy)benzonitrile

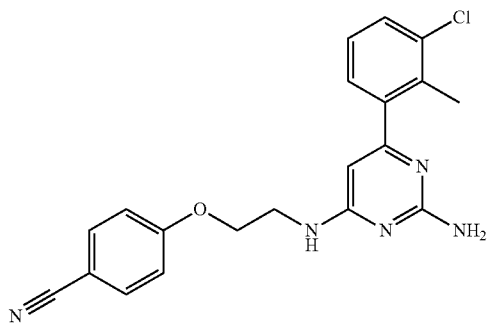 [SMILES: Cc1c(Cl)cccc1-c1cc(NCCOc2ccc(C#N)cc2)nc(N)n1]

A mixture of 4-chloro-6-(3-chloro-2-methylphenyl)pyrimidin-2-amine (intermediate 24), 4-(2-aminoethoxy)benzonitrile (1.5 equiv.) and N,N-Diisopropylethylamine (2 equiv.) in 2-propanol (0.3 mL) was heated in a sealed tube at 100° C. for 30 h. Purification by column chromatography afforded the title compound (70% EtOAc in iso-Hexane). LCMS [M+H]⁺ 380. ¹H NMR (400 MHz, DMSO-d₆) δ ppm 7.75-7.82 (m, 2 H), 7.44 (dd, J=7.7, 1.4 Hz, 1 H), 7.17-7.28 (m, 3 H), 7.15 (d, J=8.8 Hz, 2 H), 6.10 (br. s., 2 H), 5.79 (s, 1 H), 4.20 (t, J=5.7 Hz, 2 H), 3.60-3.76 (m, 2 H), 2.29 (s, 3 H),

Intermediate 62

4-(2-acetamidoethyl)benzene-1-sulfonyl Chloride

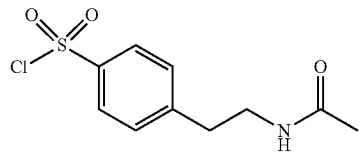 [SMILES: CC(=O)NCCc1ccc(S(=O)(=O)Cl)cc1]

Chlorosulfuric acid (5 equiv.) was slowly added to N-(2-phenylethyl)acetamide (1 equiv.). The mixture was stirred for 2 hours at r.t. and dropped on a mixture of water and ice. The title compound was collected by filtration and washed with water. LCMS [M+H]$^+$ 262.

General Procedures

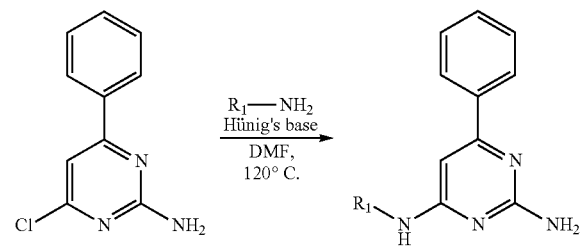

General Procedure 1: To a mixture of 4-chloro-6-phenylpyrimidin-2-amine (1 equiv.) is added Hünig's base (3.4 equiv.) and an appropriate amine (1.6 equiv.) in DMF (500 μL). The mixture is heated at 120° C. overnight. The crude mixture is purified by preparative HPLC to afford the desired product.

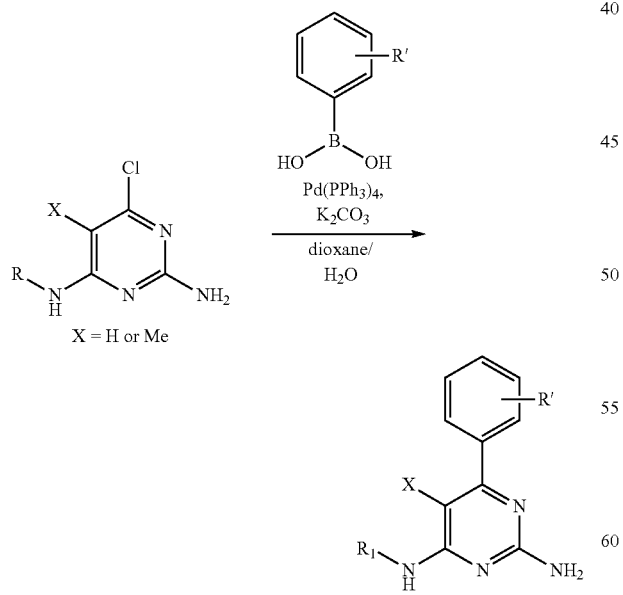

General Procedure 2: To a mixture of a suitable chloropyrimidine derivative (1 equiv.) in 1,4-dioxane/water (4:1) is added the appropriate boronic acid (or boronic ester) derivative (1.3 equiv.), K$_2$CO$_3$ (2 equiv.) and Pd(PPh$_3$)$_4$ (0.1 equiv.). The mixture is heated at 95° C. overnight or in a microwave reactor until the reaction is complete as shown by LCMS. The crude mixture is purified by preparative HPLC to afford the desired product.

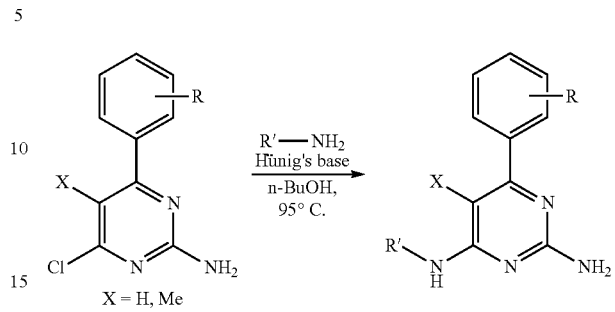

General Procedure 3: To a mixture of a suitable chloropyrimidine derivative (1 equiv.) is added Hünig's base (3.4 equiv.) and an appropriate amine (1.6 equiv.) in n-BuOH (500 μL). The mixture is heated at 95° C. overnight. The crude mixture was purified by preparative HPLC to afford the desired product.

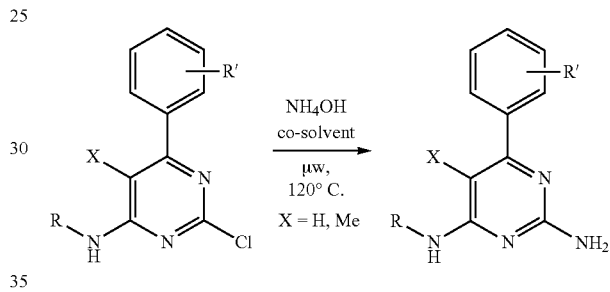

General Procedure 4: A solution of an appropriate chloropyrimidine derivative (1 equiv.) in ammonium hydroxide (25% aq) is heated in the microwave at 120° C. until completion of the reaction as monitored by LCMS. The solvent is then evaporated and the product is dried under vacuum. Further purification by preparative HPLC is performed when required.

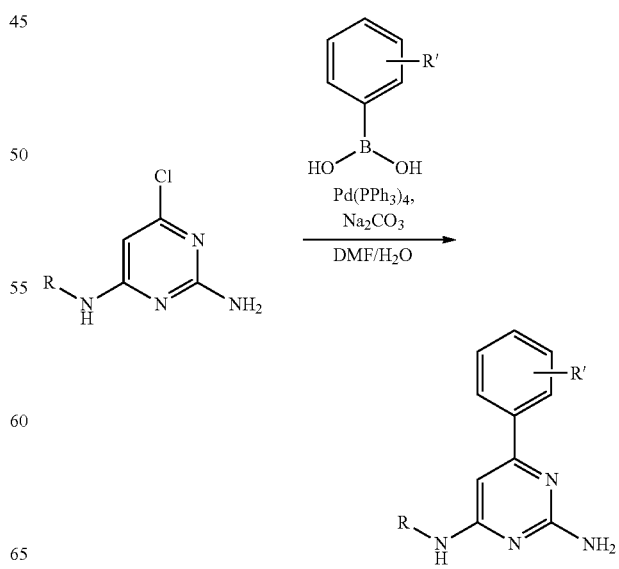

General Procedure 5: To a mixture of a suitable chloropyrimidine derivative (1 equiv.) in DMF/water (9:1) is added the appropriate boronic acid (or boronic ester) derivative (1.1 equiv.), Na₂CO₃ (2 equiv.) and Pd(PPh₃)₄ (0.1 equiv.). The mixture is heated at 120° C. overnight or in the microwave until the reaction is complete as shown by LCMS. The crude mixture is then purified by preparative HPLC to afford the desired product.

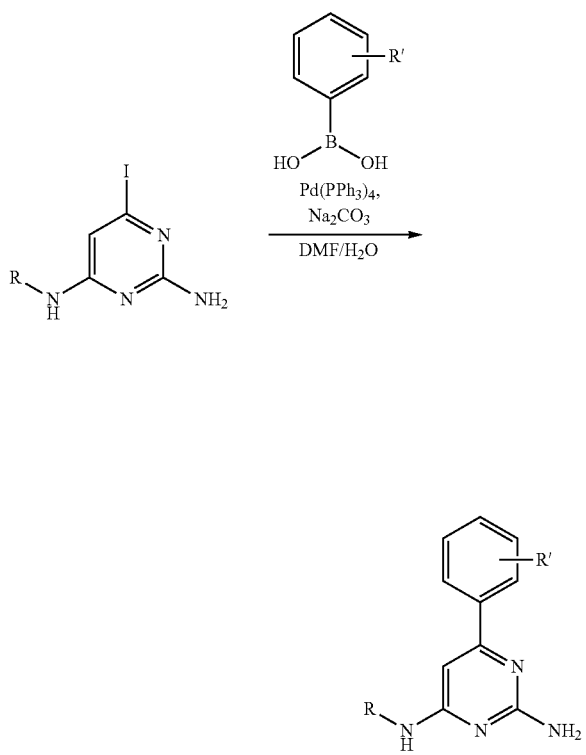

General Procedure 6: To a mixture of a suitable iodopyrimidine derivative (1 equiv.) in DMF/water (20:1) is added the appropriate boronic acid (or boronic ester) derivative (1.3 equiv.), Na₂CO₃ (2 equiv.) and Pd(PPh₃)₄ (0.1 equiv.). The mixture is heated at 120° C. overnight or in a microwave reactor until the reaction is complete as shown by LCMS. The crude mixture is then purified by HPLC to afford the desired product.

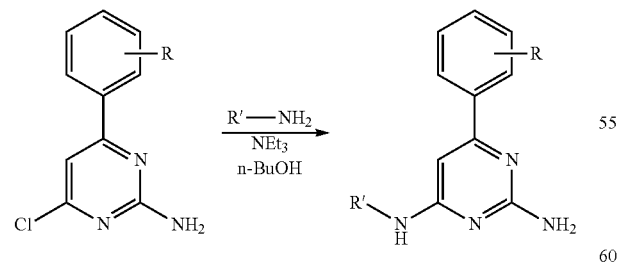

General procedure 7: A mixture of a suitable 6-aryl-4-chloropyrimidin-2-amine (1 equiv.), a suitable amine (1.5 equiv.) and triethylamine (2 equiv.) in n-butanol (1.5 mL) is heated in a sealed tube at 95° C. overnight. Concentrated and purified by preparative HPLC to give the desired product.

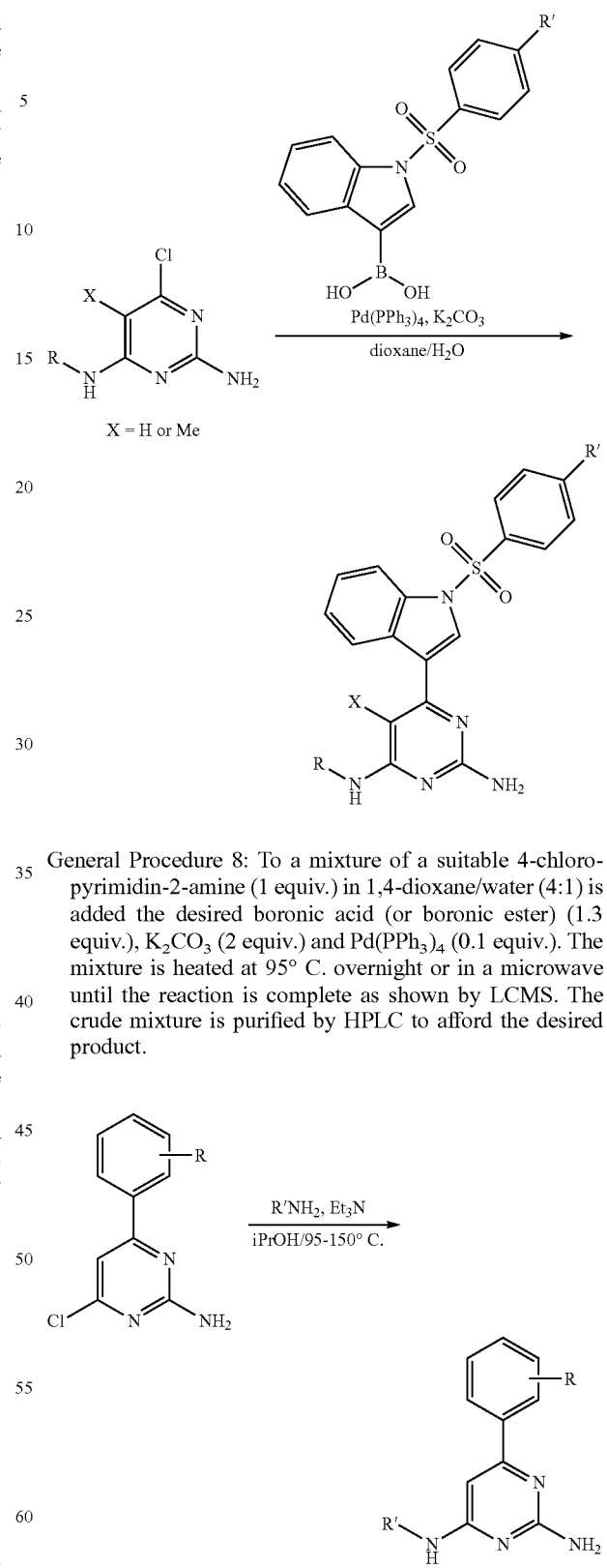

General Procedure 8: To a mixture of a suitable 4-chloropyrimidin-2-amine (1 equiv.) in 1,4-dioxane/water (4:1) is added the desired boronic acid (or boronic ester) (1.3 equiv.), K₂CO₃ (2 equiv.) and Pd(PPh₃)₄ (0.1 equiv.). The mixture is heated at 95° C. overnight or in a microwave until the reaction is complete as shown by LCMS. The crude mixture is purified by HPLC to afford the desired product.

General Procedure 9: A mixture of a suitable amine (1 equiv.), and a suitable chloropyrimidine derivative (1.2 equiv.) and triethylamine (1.5 equiv.) in 2-propanol (1.0 mL) is heated in a sealed tube at 95° C. overnight or at 150° C. for 15 min in a microwave reactor. The reaction mixture is then concentrated and purified by preparative HPLC or by silica gel chromatography.

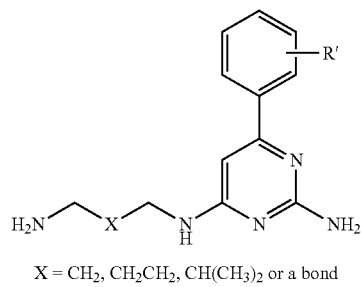

General Procedure 10: A mixture of an 4-N-(aminoalkyl)-6-(aryl)pyrimidine-2,4-diamine (1.0 equiv.), a suitable sulfonyl chloride (1.2 equiv.), and triethylamine (1.5 equiv.) in DCM or MeCN (1.0 mL) is stirred in a sealed tube at rt or 50° C. After completion the crude mixture is concentrated and purified by preparative HPLC or by silica gel chromatography.

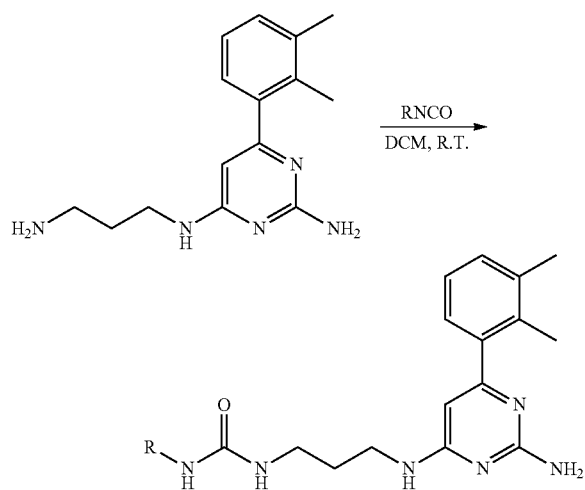

General Procedure 11: A mixture of 4-N-(3-aminopropyl)-6-(2,3-dimethylphenyl)pyrimidine-2,4-diamine (1.0 equiv.) and the corresponding isocyanate (1.05 equiv.) is dissolved in DCM. The resulting reaction mixture is stirred at room temperature until completion according to LCMS. The mixture is then concentrated and purified by preparative HPLC or by silica gel chromatography.

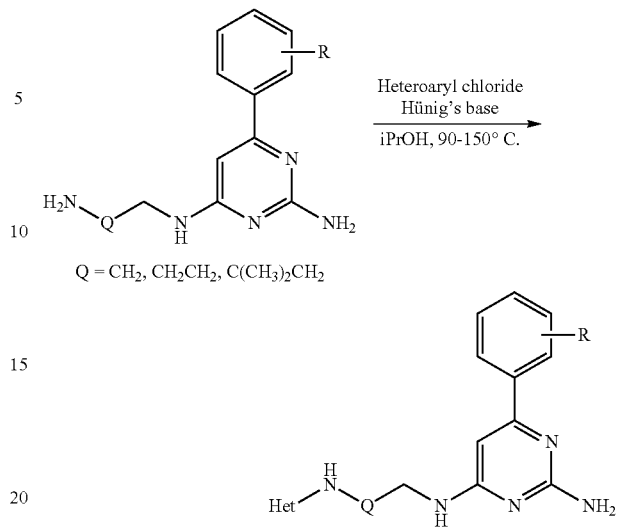

General Procedure 12: A mixture of the corresponding 4-N-(aminoalkyl)-6-(aryl)pyrimidine-2,4-diamine (1.0 equiv.) and the corresponding heteroaryl chloride (1.5 equiv.), and Hünig's base (1.5 equiv.) in 2-propanol was stirred in a sealed tube at 90-150° C. until the reaction was complete. The crude mixture was then concentrated and purified by preparative LC or by silica gel chromatography.

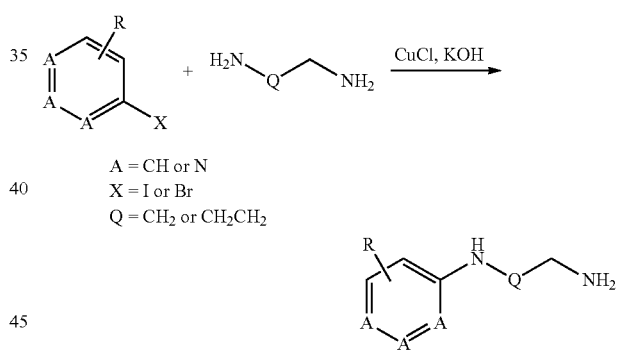

General Procedure 13: A mixture of the corresponding aryl halide or heteroaryl halide (1.0 equiv.), CuCl (0.10 equiv.), KOH (2.0 equiv.), and ethylenediamine or propane-1,3-diamine (4.5 equiv.) was stirred at 20 □C (for aryl iodides) or 90 □C (for aryl bromides) for 12-24 h in a sealed vial. The mixture was allowed to cool and was then extracted with hot EtOAc (×5). The combined organics were concentrated and the excess of diamine was removed by co-evaporation with toluene. The crude material was used without further purification.

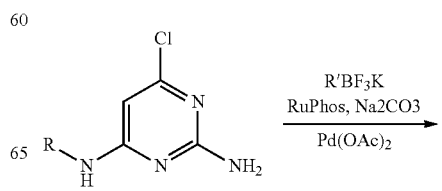

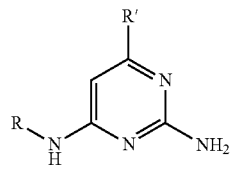

General Procedure 14: A mixture of the corresponding 6-chloro-4-N-(alkyl)-pyrimidine-2,4-diamine compound (1.0 equiv.), the appropriate potassium (aryl)trifluoroborate (2.0 equiv.), Pd(OAc)$_2$ (0.10 equiv.), RuPhos (0.20 equiv), and Na$_2$CO$_3$ (3.0 equiv.) was stirred in ethanol at reflux for 16 h. The crude mixture was then diluted with NaHCO$_3$ (aq) and extracted with DCM ×3. The crude material was purified by preparative LC or by silica gel chromatography.

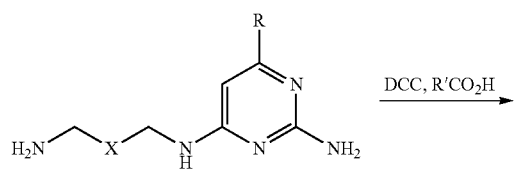

X = CH$_2$, CH$_2$CH$_2$, C(CH$_3$)$_2$ or a bond

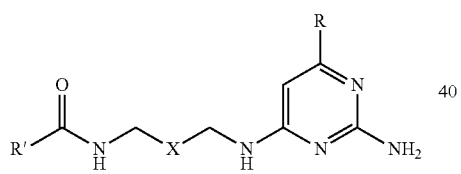

General Procedure 15: A mixture of the corresponding 4-N-(aminoalkyl)-6-(aryl)pyrimidine-2,4-diamine (1 equiv.), a suitable carboxylic acid (2.0 equiv.), and dicyclohexylcarbodiimide (1.0 equiv) were stirred in acetonitrile at 20° C. for 12-24 h. The crude mixture was then purified by preparative LC or by silica gel chromatography.

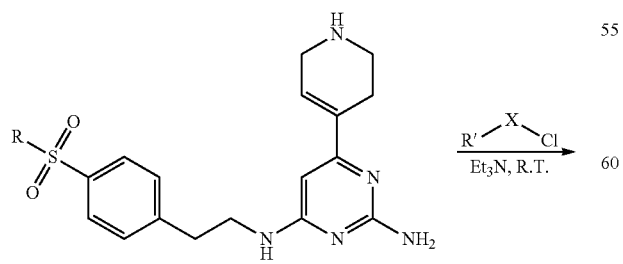

R = Me or NH$_2$
X = CO or SO$_2$

General Procedure 16: A mixture of an N4-[2-(4-methylsulfonylphenyl)ethyl]-6-(1,2,3,6-tetrahydropyridin-4-yl)pyrimidine-2,4-diamine hydrochloride or 4-[2-[[2-amino-6-(1,2,3,6-tetrahydropyridin-4-yl)pyrimidin-4-yl]amino]ethyl]benzenesulfonamide hydrochloride, a suitable sulfonyl chloride or acid chloride (1.2 equiv.), and triethylamine (3.0 equiv.) in DCM was stirred in a sealed tube at rt. After completion the crude mixture was purified by preparative HPLC.

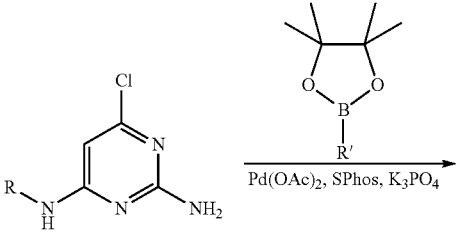

General Procedure 17: A mixture of the corresponding 6-chloro-4-N-(alkyl)-pyrimidine-2,4-diamine compound (1.0 equiv.), the appropriate arylboronic ester (1.5 equiv.), Pd(OAc)$_2$ (0.10 equiv.), SPhos (0.20 equiv) and K$_3$PO$_3$ (3.0 equiv.) was stirred in a suitable solvent (ethanol or a 5:2 mixture of 1-butanol and water) at 80-100° C. until LCMS indicated full conversion. The crude mixture was then diluted with NaHCO$_3$ (aq) and extracted with DCM ×3. The crude material was purified by preparative LC or by silica gel chromatography.

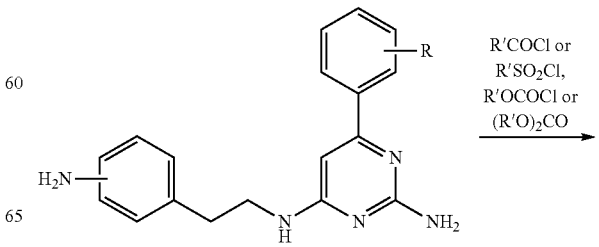

-continued

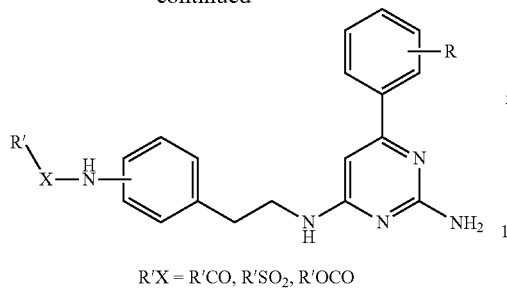

R'X = R'CO, R'SO₂, R'OCO

General Procedure 18: A mixture of the corresponding 4-N-(aminophenethyl) 6-(aryl)pyrimidine-2,4-diamine (1.0 equiv.), a suitable electrophile (acid chloride, sulfonyl chloride, chloroformate, or carbonate) (1.3 equiv.), and triethylamine or diisopropylethylamine (5 equiv.) in DCM or acetonitrile was stirred at 20-50° C. for 12-24 h. After completion the mixture was concentrated and purified by preparative LC or by silica gel chromatography.

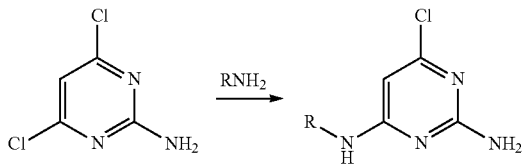

General Procedure 20: A mixture of 2-amino-4,6-dichloropyrimidine (1.0 equiv.), the corresponding amine (0.8-2.0 equiv.), and a base ($K_2CO_3$, $Cs_2CO_3$, triethylamine or diisopropylethylamine) (1.2-3.0 equiv.) in a suitable solvent (acetonitrile, methanol, 2-propanol, 1-butanol, DMF or DMSO) was stirred at 60-150° C. in a sealed vial until LCMS indicated that the reaction was complete. The reaction mixture was then diluted with $NaHCO_3$ (aq) and extracted with DCM or EtOAc. The crude material was then purified by preparative LC or by silica gel chromatography.

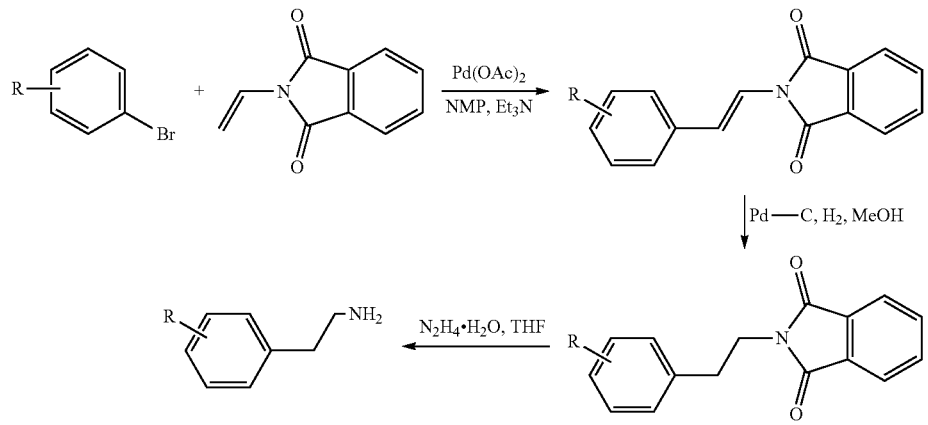

General Procedure 19: Step 1: A mixture of the corresponding aryl halide (1.0 equiv.), N-vinylphthalimide (1.1 equiv.), Pd(OAc)₂ (0.0005 equiv.), and Et₃N (1.2 equiv.) were dissolved in NMP and stirred at 135° C. for 16 h. The reaction mixture was cooled to room temperature and then water was added which precipitated a solid. The solid was filtered off and washed with water.

Step 2: In a flask, the solid from step 1 was dissolved in MeOH and then Pd/C (0.10 eqiv.) was added. The atmosphere in the flask was changed to H₂ and the resulting mixture was stirred at 60° C. for 16-24 h. The solution was then passed through a syringe filter and concentrated.

Step 3: The crude material from step 2 was dissolved in THF, and then hydrazine hydrate (1.25 equiv.) was added. The resulting mixture was stirred at reflux for 16-24 h. The reaction mixture was concentrated and purified by preparative LC.

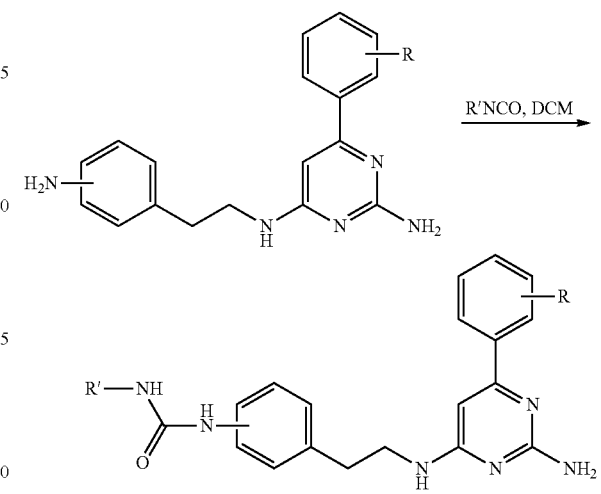

General Procedure 21: A mixture of the corresponding amine, a suitable isocyanate, and DCM was stirred at 20-60° C. for 1-48 hours. Thereafter the mixture was concentrated and purified by preparative LC or by silica gel chromatography.

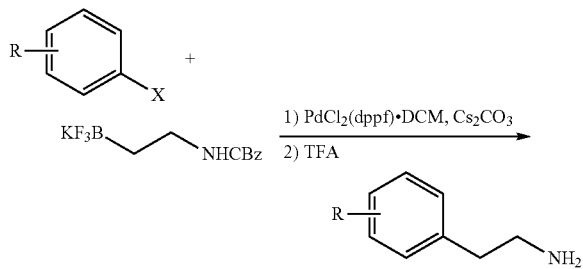

General Procedure 22: Step 1. A mixture of the corresponding aryl halide (1.0 equiv.), potassium 2-(benzyloxycarbonylamino)ethyl-trifluoro-boranuide (1.0 equiv.), PdCl$_2$(dppf).DCM (0.05 equiv.), and Cs$_2$CO$_3$ (3.0 equiv.) in toluene and water was stirred at 90° C. under N$_2$ for 16 h. The reaction mixture was then poured into water and extracted with DCM. The combined organics were dried (MgSO$_4$) and concentrated. The crude material was purified by silica gel chromatography.

Step 2. The material from step 1 was stirred in refluxing TFA until the reaction was complete. The solvent was removed by co-evaporation with 2-propanol. The crude material was used without further purification.

EXAMPLES

Example 1

4-N-cyclohexyl-6-phenylpyrimidine-2,4-diamine

Prepared according to general procedure 1 from cyclohexanamine and 4-chloro-6-phenylpyrimidin-2-amine. LCMS [M+H]$^+$ 269; $^1$H NMR (400 MHz, DMSO-d$_6$) δ 8.79-8.61 (1H, m), 7.78-7.67 (2H, m), 7.66-7.55 (3H, m), 6.33 (1H, s), 4.05-3.85 (1H, m), 2.00-1.83 (2H, m), 1.80-1.70 (2H, m), 1.41-1.10 (6H, m).

Example 2

4-N-ethyl-6-phenylpyrimidine-2,4-diamine

Prepared according to general procedure 1 from ethanamine and 4-chloro-6-phenylpyrimidin-2-amine. LCMS [M+H]$^+$ 215; $^1$H NMR (400 MHz, DMSO-d$_6$) δ ppm 8.82 (1H, s), 7.74-7.71 (2H, m), 7.67-7.57 (3H, m), 6.33 (1H, s), 3.53-3.41 (2H, m), 1.18 (3H, t, J=7.1 Hz).

Example 3

4-N-(3-ethoxypropyl)-6-phenylpyrimidine-2,4-diamine

Prepared according to general procedure 1 from 3-ethoxypropan-1-amine and 4-chloro-6-phenylpyrimidin-2-amine. LCMS [M+H]$^+$ 273; $^1$H NMR (400 MHz, DMSO-d$_6$) δ ppm 8.82 (1H, s), 7.74-7.71 (2H, m), 7.63-7.59 (3H, m), 6.37 (1H, s), 3.45-3.41 (6H, m), 1.80 (2H, q, J=6.5 Hz), 1.11 (3H, t, J=6.5 Hz).

Example 4

6-phenyl-4-N-propylpyrimidine-2,4-diamine

Prepared according to general procedure 2 from phenylboronic acid and 6-chloro-4-N-propylpyrimidine-2,4-diamine. LCMS [M+H]$^+$ 229.

Example 5

6-(4-methanesulfonylphenyl)-4-N-propylpyrimidine-2,4-diamine

Prepared according to general procedure 2 from (4-methane-sulfonylphenyl)boronic acid and 6-chloro-4-N-propylpyrimidine-2,4-diamine. LCMS [M+H]$^+$ 307; $^1$H NMR (400 MHz, DMSO-d$_6$) δ ppm 8.21-8.11 (2H, m), 8.05-7.92 (2H, m), 6.42 (1H, s), 3.50-3.40 (2H, m), 3.31 (3H, s), 1.68-1.51 (2H, m), 0.94 (3H, t, J=7.1 Hz).

Example 6

4-N-(cyclopropylmethyl)-6-phenylpyrimidine-2,4-diamine

Prepared according to general procedure 1 from cyclopropylmethanamine and 4-chloro-6-phenylpyrimidin-2-amine. LCMS [M+H]$^+$ 241; $^1$H NMR (400 MHz, DMSO-d$_6$) δ ppm 8.92 (1H, s), 7.83-7.50 (5H, m), 6.39 (1H, s), 3.33-3.20 (2H, m), 1.15-0.95 (1H, m), 0.51 (1H, d, J=5.8 Hz), 0.27 (1H, d, J=5.8 Hz).

Example 7

4-N-(oxan-4-yl)-6-phenylpyrimidine-2,4-diamine

Prepared according to general procedure 1 from oxan-4-amine and 4-chloro-6-phenylpyrimidin-2-amine. LCMS [M+H]$^+$ 271.

Example 8

4-N-(furan-2-ylmethyl)-6-phenylpyrimidine-2,4-diamine

Prepared according to general procedure 1 from furan-2-ylmethanamine and 4-chloro-6-phenylpyrimidin-2-amine. LCMS [M+H]$^+$ 267.

Example 9

4-N-(pentan-3-yl)-6-phenylpyrimidine-2,4-diamine

Prepared according to general procedure 1 from pentan-3-amine and 4-chloro-6-phenylpyrimidin-2-amine. LCMS [M+H]$^+$ 257.

Example 10

6-phenyl-4-N-(propan-2-yl)pyrimidine-2,4-diamine

Prepared according to general procedure 1 from propan-2-amine and 4-chloro-6-phenylpyrimidin-2-amine. LCMS [M+H]$^+$ 229.

Example 11

4-N-benzyl-6-phenylpyrimidine-2,4-diamine

Prepared according to general procedure 1 from phenylmethanamine and 4-chloro-6-phenylpyrimidin-2-amine. LCMS [M+H]$^+$ 277; $^1$H NMR (400 MHz, DMSO-d$_6$) δ ppm 7.92-7.84 (2H, m), 7.48-7.40 (4H, m), 7.37-7.27 (4H, m), 7.27-7.20 (1H, m), 6.29 (1H, s), 6.06 (2H, s), 4.54 (2H, d, J=5.9 Hz).

Example 12

4-N-[2-(morpholin-4-yl)ethyl]-6-phenylpyrimidine-2,4-diamine

Prepared according to general procedure 1 from 2-(morpholin-4-yl)ethan-1-amine and 4-chloro-6-phenylpyrimidin-2-amine. LCMS [M+H]$^+$ 300.

Example 13

6-(4-chlorophenyl)-4-N-cyclopropylpyrimidine-2,4-diamine

Prepared according to general procedure 1 from cyclopropanamine and 4-chloro-6-phenylpyrimidin-2-amine. LCMS [M+H]$^+$ 261.

Example 14

4-N-tert-butyl-6-(4-chlorophenyl)pyrimidine-2,4-diamine

Prepared according to general procedure 2 from (4-chlorophenyl)boronic acid and 4-N-tert-butyl-6-chloropyrimidine-2,4-diamine. LCMS [M+H]$^+$ 277; $^1$H NMR (400 MHz, DMSO-d$_6$) δ ppm 8.38 (1H, s), 7.75-7.66 (4H, m), 6.38 (1H, s), 1.46 (9H, s).

Example 15

6-(4-chlorophenyl)-4-N-(oxan-4-yl)pyrimidine-2,4-diamine

Prepared according to general procedure 2 from (4-chlorophenyl)boronic acid and 6-chloro-4-N-(oxan-4-yl)pyrimidine-2,4-diamine. LCMS [M+H]$^+$ 305.

Example 16

4-N-cyclopropyl-6-[3-(trifluoromethyl)phenyl]pyrimidine-2,4-diamine

Prepared according to general procedure 2 from [3-(trifluoromethyl)phenyl]-boronic acid and 6-chloro-4-N-cyclopropylpyrimidine-2,4-diamine. LCMS [M+H]$^+$ 295.

Example 17

4-N-tert-butyl-6-(4-methoxyphenyl)pyrimidine-2,4-diamine

Prepared according to general procedure 2 from (4-methoxyphenyl)boronic acid and 4-N-tert-butyl-6-chloropyrimidine-2,4-diamine. LCMS [M+H]$^+$ 273; $^1$H NMR (400 MHz, DMSO-d$_6$) δ ppm 7.65 (2H, d, J=9.4 Hz), 7.15 (2H, d, J=9.4 Hz), 6.35 (1H, s), 3.85 (3H, s), 1.45 (9H, s).

Example 18

4-N-cyclopropyl-6-(4-methoxyphenyl)pyrimidine-2,4-diamine

Prepared according to general procedure 2 from (4-methoxyphenyl)boronic acid and 6-chloro-4-N-cyclopropylpyrimidine-2,4-diamine. LCMS [M+H]$^+$ 257; $^1$H NMR (400 MHz, DMSO-d$_6$) δ ppm 7.79-7.72 (2H, m), 7.17-7.15 (2H, m), 6.24 (1H, s), 3.85 (4H, s), 0.83-0.81 (2H, m), 0.62-0.60 (2H, m).

Example 19

6-(3-chlorophenyl)-4-N-cyclopropylpyrimidine-2,4-diamine

Prepared according to general procedure 2 from (3-chlorophenyl)boronic acid and 6-chloro-4-N-cyclopropylpyrimidine-2,4-diamine. LCMS [M+H]$^+$ 261; $^1$H NMR (400 MHz, CD$_3$OD) δ ppm 7.78-7.76 (1H, m), 7.64-7.57 (3H, m), 6.27 (1H, s), 0.89-0.87 (2H, m), 0.70-0.63 (3H, m).

Example 20

4-N-tert-butyl-6-[3-(trifluoromethyl)phenyl]pyrimidine-2,4-diamine

Prepared according to general procedure 2 from [3-(trifluoromethyl)phenyl]boronic acid and 4-N-tert-butyl-6-chloropyrimidine-2,4-diamine. LCMS [M+H]$^+$ 311.

Example 21

6-(3-chlorophenyl)-4-N-(oxan-4-yl)pyrimidine-2,4-diamine

Prepared according to general procedure 2 from (3-chlorophenyl)boronic acid and 6-chloro-4-N-(oxan-4-yl)pyrimidine-2,4-diamine. LCMS [M+H]$^+$ 305; $^1$H NMR (400 MHz, CD$_3$OD) δ ppm 7.78-7.76 (1H, m), 7.65-7.63 (2H, m), 7.59-7.57 (1H, m), 6.30 (1H, s), 4.30-4.28 (1H, m), 4.02-3.98 (2H, m), 3.53-3.51 (2H, m), 2.01-2.00 (2H, m), 1.65-1.63 (2H, m).

Example 22

4-N-tert-butyl-6-(3-chlorophenyl)pyrimidine-2,4-diamine

Prepared according to general procedure 2 from (3-chlorophenyl)boronic acid and 4-N-tert-butyl-6-chloropyrimidine-2,4-diamine. LCMS [M+H]$^+$ 277; $^1$H NMR (400 MHz, CD$_3$OD) δ ppm 7.75-7.73 (1H, m), 7.65-7.62 (2H, m), 7.59-7.55 (2H, m), 1.52 (9H, s).

Example 23

4-N-methyl-6-[1-(4-methylbenzenesulfonyl)-1H-indol-3-yl]pyrimidine-2,4-diamine

Prepared according to general procedure 8 from [1-(4-methylbenzenesulfonyl)-1H-indol-3-yl]boronic acid and 6-chloro-4-N-methylpyrimidine-2,4-diamine. LCMS [M+H]$^+$ 394; $^1$H NMR (400 MHz, CD$_3$OD) δ ppm 8.36 (1H, s), 8.07 (1H, d, J=8.3 Hz), 7.93 (2H, d, J=8.3 Hz), 7.83 (1H, d, J=7.9 Hz), 7.51-7.44 (1H, m), 7.43-7.31 (3H, m), 6.46 (1H, s), 3.04 (3H, s), 2.37 (3H, s).

Example 24

6-(2,3-dichlorophenyl)-4-N-(2,2,2-trifluoroethyl) pyrimidine-2,4-diamine

Prepared according to general procedure 2 from (2,3-dichlorophenyl)boronic acid and 6-chloro-4-N-(2,2,2-trifluoroethyl)pyrimidine-2,4-diamine. LCMS [M+H]$^+$ 337.

Example 25

6-(3-chlorophenyl)-4-N-(2,2,2-trifluoroethyl)pyrimidine-2,4-diamine

Prepared according to general procedure 2 from (3-chlorophenyl)boronic acid and 6-chloro-4-N-(2,2,2-trifluoroethyl)pyrimidine-2,4-diamine. LCMS [M+H]$^+$ 303.

Example 26

6-[1-(benzenesulfonyl)-1H-indol-3-yl]-4-N-methylpyrimidine-2,4-diamine

Prepared according to general procedure 8 from [1-(benzenesulfonyl)-1H-indol-3-yl]boronic acid and 6-chloro-4-N-methylpyrimidine-2,4-diamine. LCMS [M+H]$^+$ 380; $^1$H NMR (400 MHz, DMSO-d$_6$) δ ppm 8.43-8.25 (2H, m), 8.10-8.03 (2H, m), 8.01-7.95 (1H, m), 7.77-7.68 (1H, m), 7.66-7.56 (2H, m), 7.46-7.26 (2H, m), 6.74 (1H, br s), 6.32 (1H, s), 6.02 (2H, s), 2.81 (3H, d, J=5.0 Hz).

Example 27

4-N-cyclopropyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclopropylpyrimidine-2,4-diamine. LCMS [M+H]$^+$ 420; $^1$H NMR (400 MHz, CD$_3$OD) δ ppm 8.14 (1H, s), 8.07 (1H, d, J=7.9 Hz), 8.01 (1H, d, J=8.2 Hz), 7.86 (2H, d, J=8.2 Hz), 7.43-7.23 (4H, m), 6.43 (1H, s), 2.65 (1H, s), 2.34 (3H, s), 0.88-0.74 (2H, m), 0.65-0.48 (2H, m).

Example 28

6-[1-(benzenesulfonyl)-1H-indol-3-yl]-4-N-cyclopropylpyrimidine-2,4-diamine

Prepared according to general procedure 8 from [1-(benzenesulfonyl)-1H-indol-3-yl]boronic acid and 6-chloro-4-N-cyclopropylpyrimidine-2,4-diamine. LCMS [M+H]$^+$ 406; $^1$H NMR (400 MHz, CD$_3$OD) δ ppm 8.16 (1H, s), 8.10-7.98 (4H, m), 7.66-7.58 (1H, m), 7.56-7.46 (2H, m), 7.43-7.25 (2H, m), 6.43 (1H, s), 2.66 (1H, s), 0.84-0.81 (2H, m), 0.58-0.55 (2H, m).

Example 29

6-[1-(benzenesulfonyl)-1H-pyrrolo[2,3-b]pyridin-3-yl]-4-N-methylpyrimidine-2,4-diamine Prepared according to general procedure 8 from [1-(benzenesulfonyl)-1H-pyrrolo[2,3-b]pyridin-3-yl]boronic acid and 6-chloro-4-N-methylpyrimidine-2,4-diamine. LCMS [M+H]$^+$ 381; $^1$H NMR (400 MHz, CD$_3$OD) δ ppm 8.55 (1H, d, J=8.2 Hz), 8.41-8.30 (2H, m), 8.22-8.11 (2H, m), 7.71-7.61 (1H, m), 7.57-7.50 (2H, m), 7.37-7.28 (1H, m), 6.27 (1H, s), 2.92 (3H, s).

Example 30

6-[1-(benzenesulfonyl)-1H-indol-4-yl]-4-N-methylpyrimidine-2,4-diamine

Prepared according to general procedure 8 from [1-(benzenesulfonyl)-1H-indol-4-yl]boronic acid and 6-chloro-4-N-methylpyrimidine-2,4-diamine and 6-chloro-4-N-methylpyrimidine-2,4-diamine. LCMS [M+H]$^+$ 380; $^1$H NMR (400 MHz, CD$_3$OD) δ ppm 8.08 (1H, d, J=8.2 Hz), 7.97-7.89 (2H, m), 7.73 (1H, d, J=3.8 Hz), 7.65-7.56 (1H, m), 7.53-7.45 (3H, m), 7.39 (1H, t, J=8.2 Hz), 7.10 (1H, d, J=3.8 Hz), 6.10 (1H, s), 2.89 (3H, s).

Example 31

6-[1-(benzenesulfonyl)-1H-indol-5-yl]-4-N-methylpyrimidine-2,4-diamine.

Prepared according to general procedure 8 from [1-(benzenesulfonyl)-1H-indol-5-yl]boronic acid and 6-chloro-4-N-methylpyrimidine-2,4-diamine. LCMS [M+H]$^+$ 380; $^1$H NMR (400 MHz, CD$_3$OD) δ ppm 8.07-7.99 (2H, m), 7.98-7.89 (2H, m), 7.83-7.74 (1H, m), 7.71 (1H, d, J=4.0 Hz), 7.64-7.55 (1H, m), 7.54-7.45 (2H, m), 6.80 (1H, d, J=4.0 Hz), 6.21 (1H, s), 2.90 (3H, s).

Example 32

6-(2-methoxyphenyl)-4-N-methylpyrimidine-2,4-diamine

Prepared according to general procedure 2 from (2-methoxyphenyl)boronic acid and 6-chloro-4-N-methylpyrimidine-2,4-diamine. LCMS [M+H]$^+$ 231; $^1$H NMR (400 MHz, CD$_3$OD) δ ppm 7.50 (1H, dd, J=7.5 and 1.7 Hz), 7.41-7.36 (1H, m), 7.08 (1H, d, J=8.3 Hz), 7.01 (1H, td, J=7.5 and 1.0 Hz), 6.17 (1H, s), 3.84 (3H, s), 2.89 (3H, s).

Example 33

6-(4-methoxyphenyl)-4-N-methylpyrimidine-2,4-diamine

Prepared according to general procedure 2 from (4-methoxyphenyl)boronic acid and 6-chloro-4-N-methylpyrimidine-2,4-diamine. LCMS [M+H]$^+$ 231.

Example 34

6-[3,5-bis(trifluoromethyl)phenyl]-4-N-methylpyrimidine-2,4-diamine

Prepared according to general procedure 2 from [3,5-bis(trifluoromethyl)phenyl]boronic acid and 6-chloro-4-N-methylpyrimidine-2,4-diamine. LCMS [M+H]$^+$ 337; $^1$H NMR (400 MHz, CD$_3$OD) δ ppm 8.31 (2H, s), 8.17 (1H, s), 7.55-7.20 (3H, br s), 6.45 (1H, s), 3.02 (3H, s).

Example 35

6-(isoquinolin-4-yl)-4-N-methylpyrimidine-2,4-diamine

Prepared according to general procedure 2 from (isoquinolin-4-yl)boronic acid and 6-chloro-4-N-methylpyrimidine-2,4-diamine. LCMS [M+H]+ 252; ¹H NMR (400 MHz, CD₃OD) δ ppm 9.17 (1H, s), 8.78 (1H, s), 8.17 (1H, d, J=8.4 Hz), 8.12 (1H, d, J=8.1 Hz), 7.98-7.94 (1H, m), 7.80-7.77 (1H, m), 6.54 (1H, s), 3.10 (3H, s).

Example 36

4-N-methyl-6-[4-(trifluoromethyl)phenyl]pyrimidine-2,4-diamine

Prepared according to general procedure 2 from [4-(trifluoromethyl)phenyl]boronic acid and 6-chloro-4-N-methylpyrimidine-2,4-diamine. LCMS [M+H]+ 269; ¹H NMR (400 MHz, CD₃OD) δ ppm 7.93-7.87 (4H, m), 6.38 (1H, s), 3.04 (3H, s).

Example 37

4-N-methyl-6-[3-(trifluoromethyl)phenyl]pyrimidine-2,4-diamine

Prepared according to general procedure 2 from [3-(trifluoromethyl)phenyl]boronic acid and 6-chloro-4-N-methylpyrimidine-2,4-diamine. LCMS [M+H]+ 269; ¹H NMR (400 MHz, CD₃OD) δ ppm 8.05 (1H, s), 7.99 (1H, d, J=8.0 Hz), 7.92 (1H, d, J=8.0 Hz), 7.79 (1H, t, J=8.0 Hz), 6.38 (1H, s), 3.05 (3H, s).

Example 38

6-(2,3-dichlorophenyl)-4-N-methylpyrimidine-2,4-diamine

Prepared according to general procedure 3 from methanamine and 4-chloro-6-(2,3-dichlorophenyl)pyrimidin-2-amine. LCMS [M+H]+ 269; ¹H NMR (400 MHz, CD₃OD) δ ppm 7.79-7.77 (1H, m), 7.50-7.49 (2H, m), 6.12 (1H, s), 3.04 (3H, s).

Example 39

6-(2H-1,3-benzodioxol-5-yl)-4-N-methylpyrimidine-2,4-diamine

Prepared according to general procedure 2 from (2H-1,3-benzodioxol-5-yl)boronic acid and 6-chloro-4-N-methylpyrimidine-2,4-diamine. LCMS [M+H]+ 245; ¹H NMR (400 MHz, CD₃OD) δ ppm 7.42-7.39 (1H, m), 7.36-7.35 (1H, m), 6.89 (1H, d, J=8.0 Hz), 6.15 (1H, s), 6.02 (1H, s), 2.92 (3H, s).

Example 40

3-[2-amino-6-(methylamino)pyrimidin-4-yl]benzonitrile

Prepared according to general procedure 2 from (3-cyanophenyl)boronic acid and 6-chloro-4-N-methylpyrimidine-2,4-diamine. LCMS [M+H]+ 226; ¹H NMR (400 MHz, CD₃OD) δ ppm 8.15 (1H, s), 8.05-8.03 (1H, m), 7.95-7.92 (1H, m), 7.74 (1H, t, J=8.5 Hz), 6.35 (1H, s), 3.02 (3H, s).

Example 41

N-{3-[2-amino-6-(methylamino)pyrimidin-4-yl]phenyl}acetamide

Prepared according to general procedure 2 from (3-acetamidophenyl)boronic acid and 6-chloro-4-N-methylpyrimidine-2,4-diamine. LCMS [M+H]+ 258; ¹H NMR (400 MHz, CD₃OD) δ ppm 8.20 (1H, s), 7.56-7.52 (2H, m), 7.45-7.43 (1H, m), 6.31 (1H, s), 3.06 (3H, s), 2.19 (3H, s).

Example 42

4-N-methyl-6-[4-(morpholine-4-sulfonyl)phenyl]pyrimidine-2,4-diamine

Prepared according to general procedure 2 from [4-(morpholine-4-sulfonyl)phenyl]boronic acid and 6-chloro-4-N-methylpyrimidine-2,4-diamine. LCMS [M+H]+ 350; ¹H NMR (400 MHz, CD₃OD) δ ppm 7.99 (4H, s), 6.42 (1H, s), 3.76-3.72 (4H, m), 3.07 (3H, s), 3.06-3.03 (4H, m).

Example 43

6-(4-methanesulfonylphenyl)-4-N-methylpyrimidine-2,4-diamine

Prepared according to general procedure 2 from (4-methanesulfonyl-phenyl) boronic acid and 6-chloro-4-N-methylpyrimidine-2,4-diamine. LCMS [M+H]+ 279; ¹H NMR (400 MHz, CD₃OD) δ ppm 8.20-8.17 (2H, m), 8.00-7.97 (2H, m), 6.41 (1H, s), 3.22 (3H, s), 3.08 (3H, s).

Example 44

4-N-methyl-6-[3-(morpholine-4-carbonyl)phenyl]pyrimidine-2,4-diamine

Prepared according to general procedure 2 from [3-(morpholine-4-carbonyl)phenyl]boronic acid and 6-chloro-4-N-methylpyrimidine-2,4-diamine. LCMS [M+H]+ 314; ¹H NMR (400 MHz, CD₃OD) δ ppm 8.00-7.96 (1H, m), 7.92 (1H, s), 7.57 (1H, t, J=7.8 Hz), 7.52 (1H, dt, J=7.8 and 1.4 Hz), 6.27 (1H, s), 3.79-3.50 (8H, m), 2.94 (3H, s).

Example 45

4-[2-amino-6-(methylamino)pyrimidin-4-yl]-N-(furan-2-ylmethyl)benzamide

Prepared according to general procedure 2 from {4-[(furan-2-ylmethyl)carbamoyl]phenyl}boronic acid and 6-chloro-4-N-methylpyrimidine-2,4-diamine. LCMS [M+H]+ 324; ¹H NMR (400 MHz, CD₃OD) δ ppm 7.93-7.90 (4H, m), 7.46-7.44 (1H, m), 6.39-6.37 (1H, m), 6.34-6.32 (1H, m), 6.28 (1H, s), 4.60 (2H, s), 2.94 (3H, s).

Example 46

N-{4-[2-amino-6-(methylamino)pyrimidin-4-yl]phenyl}methanesulfonamide

Prepared according to general procedure 2 from (4-methanesulfon-amidophenyl)boronic acid and 6-chloro-4-N-methylpyrimidine-2,4-diamine. LCMS [M+H]+ 294; ¹H NMR (400 MHz, CD₃OD) δ ppm 7.72-7.70 (2H, m), 7.43-7.40 (2H, m), 6.29 (1H, s), 3.06 (3H, s), 3.03 (3H, s).

Example 47

N-{4-[2-amino-6-(methylamino)pyrimidin-4-yl]phenyl}acetamide

Prepared according to general procedure 2 from (4-acetamidophenyl)boronic acid and 6-chloro-4-N-methylpyrimidine-2,4-diamine. LCMS [M+H]⁺ 258; ¹H NMR (400 MHz, CD₃OD) δ ppm 7.82-7.80 (2H, m), 7.75-7.73 (2H, m), 6.31 (1H, s), 3.03 (3H, s), 2.18 (3H, d, J=2.5 Hz).

Example 48

4-[2-[[2-amino-6-(3-chloro-2-methyl-phenyl)pyrimidin-4-yl]amino]ethyl]-N'-hydroxy-benzamidine A mixture of 4-[2-[[2-amino-6-(3-chloro-2-methyl-phenyl)pyrimidin-4-yl]amino]ethyl]benzonitrile (intermediate 53) (1.0 equiv.) and hydroxylamine (2.0 equiv.) was stirred at reflux in ethanol for 3 h. The mixture was then purified by preparative LC. LCMS [M+H]⁺ 397. ¹H NMR (400 MHz, METHANOL-d₄) δ ppm 7.66-7.70 (m, 2 H), 7.58-7.62 (m, 1 H), 7.53-7.58 (m, 2 H), 7.30-7.38 (m, 2H), 6.02 (s, 1 H), 3.82 (t, J=7.3 Hz, 2 H), 3.09 (t, J=7.4 Hz, 2 H), 2.37 (s, 3 H).

Example 49

6-(6-methoxypyridin-3-yl)-4-N-methylpyrimidine-2,4-diamine.

Prepared according to general procedure 2 from (6-methoxypyridin-3-yl)boronic acid and 6-chloro-4-N-methylpyrimidine-2,4-diamine. LCMS [M+H]⁺ 232; ¹H NMR (400 MHz, CD₃OD) δ ppm 8.57 (1H, s), 8.03 (1H, d, J=7.3 Hz), 6.98 (1H, d, J=7.3 Hz), 6.30 (1H, s), 4.02 (3H, s), 3.07 (3H, s).

Example 50

6-(2-fluoro-4-phenylphenyl)-4-N-methylpyrimidine-2,4-diamine.

Prepared according to general procedure 2 from (2-fluoro-4-phenylphenyl)boronic acid and 6-chloro-4-N-methylpyrimidine-2,4-diamine. LCMS [M+H]⁺ 295; ¹H NMR (400 MHz, CD₃OD) δ ppm 7.75-7.61 (5H, m), 7.54-7.44 (3H, m), 6.41 (1H, s), 6.30 (1H, s), 3.06 (3H, s).

Example 51

4-[2-amino-6-(methylamino)pyrimidin-4-yl]benzonitrile.

Prepared according to general procedure 2 from (4-cyanophenyl)boronic acid and 6-chloro-4-N-methylpyrimidine-2,4-diamine. LCMS [M+H]⁺ 226; ¹H NMR (400 MHz, CD₃OD) δ ppm 8.03 (2H, d, J=8.2 Hz), 7.84-7.80 (2H, m), 6.29 (1H, s), 2.93 (3H, s).

Example 52

4-N-methyl-6-(quinolin-5-yl)pyrimidine-2,4-diamine.

Prepared according to general procedure 2 from (quinolin-5-yl)boronic acid and 6-chloro-4-N-methylpyrimidine-2,4-diamine. LCMS [M+H]⁺ 252; ¹H NMR (400 MHz, CD₃OD) δ ppm 8.98 (1H, dd, J=4.2 and 1.9 Hz), 8.49 (1H, d, J=8.6 Hz), 8.26 (1H, d, J=8.6 Hz), 7.95-7.91 (1H, m), 7.82 (1H, d, J=7.2 Hz), 7.67 (1H, dd, J=8.6 and 4.2 Hz), 6.23 (1H, s), 3.08 (3H, s).

Example 53

6-(4-chlorophenyl)-4-N-(prop-2-en-1-yl)pyrimidine-2,4-diamine

Prepared according to general procedure 2 from (4-chlorophenyl)boronic acid and 6-chloro-4-N-(prop-2-en-1-yl)pyrimidine-2,4-diamine. LCMS [M+H]⁺ 261; ¹H NMR (400 MHz, CD₃OD) δ ppm 7.75-7.73 (2H, m), 7.64-7.62 (2H, m), 6.36 (1H, s), 6.02-5.92 (1H, m), 5.33-5.31 (1H, m), 5.23-5.20 (1H, m), 4.18-4.16 (2H, m).

Example 54

6-(4-methoxyphenyl)-4-N-(prop-2-en-1-yl)pyrimidine-2,4-diamine

Prepared according to general procedure 2 from (4-methoxyphenyl)boronic acid and 6-chloro-4-N-(prop-2-en-1-yl)pyrimidine-2,4-diamine. LCMS [M+H]⁺ 257.

Example 55

6-(4-chlorophenyl)-4-N-cyclopentylpyrimidine-2,4-diamine

Prepared according to general procedure 2 from (4-chlorophenyl)boronic acid and 6-chloro-4-N-cyclopentylpyrimidine-2,4-diamine. LCMS [M+H]⁺ 289; ¹H NMR (400 MHz, CD₃OD) δ ppm 7.60 (2H, d, J=8.8 Hz), 7.51-7.49 (2H, m), 6.17 (1H, s), 4.36 (1H, s), 2.00-1.93 (2H, m), 1.73-1.65 (2H, m), 1.61-1.53 (2H, m), 1.50-1.43 (2H, m).

Example 56

4-N-cyclopentyl-6-(4-methoxyphenyl)pyrimidine-2,4-diamine

Prepared according to general procedure 2 from 6-chloro-4-N-cyclopentylpyrimidine-2,4-diamine and (4-methoxyphenyl)boronic acid. LCMS [M+H]⁺ 285; ¹H NMR (400 MHz, CD₃OD) δ ppm 7.68 (2H, d, J=9.2 Hz), 7.12 (2H, d, J=9.2 Hz), 6.27 (1H, s), 4.47 (1H, q, J=6.7 Hz), 3.89 (3H, s), 2.10-2.03 (2H, m), 1.82-1.79 (2H, m), 1.72-1.63 (2H, m), 1.62-1.53 (2H, m).

Example 57

4-N-cyclopentyl-6-[3-(trifluoromethyl)phenyl]pyrimidine-2,4-diamine

Prepared according to general procedure 2 from [3-(trifluoromethyl)-phenyl]boronic acid and 6-chloro-4-N-cyclopentylpyrimidine-2,4-diamine. LCMS [M+H]⁺ 323; ¹H NMR (400 MHz, CD₃OD) δ ppm 8.17 (1H, s), 8.08 (1H, d, J=7.9 Hz), 7.74 (1H, d, J=7.9 Hz), 7.65 (1H, t, J=7.9 Hz), 6.28 (1H, s), 4.29 (1H, s), 2.09-1.99 (2H, m), 1.75-1.74 (2H, m), 1.71-1.62 (2H, m), 1.60-1.49 (2H, m).

Example 58

6-(4-chlorophenyl)-4-N-cyclobutylpyrimidine-2,4-diamine

Prepared according to general procedure 2 from (4-chlorophenyl)boronic acid and 6-chloro-4-N-cyclobutylpyrimidine-2,4-diamine. LCMS [M+H]⁺ 275; ¹H NMR (400 MHz, CD₃OD) δ ppm 7.83 (2H, d, J=8.4 Hz), 7.45 (2H, d, J=8.4 Hz), 6.17 (1H, s), 4.42 (1H, s), 2.44-2.38 (2H, m), 2.02-1.94 (2H, m), 1.83-1.76 (2H, m).

Example 59

4-N-cyclobutyl-6-(4-methoxyphenyl)pyrimidine-2,4-diamine

Prepared according to general procedure 2 from (4-methoxyphenyl)boronic acid and 6-chloro-4-N-cyclobutylpyrimidine-2,4-diamine. LCMS [M+H]⁺ 271; ¹H NMR (400 MHz, CD₃OD) δ ppm 7.68 (2H, d, J=8.5 Hz), 7.14 (2H, d, J=8.5 Hz), 6.22 (1H, s), 4.64 (1H, q, J=7.9 Hz), 3.90 (3H, s), 2.46-2.38 (2H, m), 2.12-2.01 (2H, m), 1.87-1.78 (2H, m).

Example 60

4-N-cyclobutyl-6-[3-(trifluoromethyl)phenyl]pyrimidine-2,4-diamine

Prepared according to general procedure 2 from [3-(trifluoromethyl)phenyl]boronic acid and 6-chloro-4-N-cyclobutylpyrimidine-2,4-diamine. LCMS [M+H]⁺ 309; ¹H NMR (400 MHz, CD₃OD) δ ppm 7.68 (2H, d, J=8.5 Hz), 7.14 (2H, d, J=8.5 Hz), 6.22 (1H, s), 4.64 (1H, q, J=7.9 Hz), 3.90 (3H, s), 2.46-2.38 (2H, m), 2.12-2.01 (2H, m), 1.87-1.78 (2H, m).

Example 61

6-(2,3-dichlorophenyl)-4-N-pentylpyrimidine-2,4-diamine

Prepared according to general procedure 3 from pentan-1-amine and 4-chloro-6-(2,3-dichlorophenyl)pyrimidin-2-amine. LCMS [M+H]⁺ 325; ¹H NMR (400 MHz, CD₃OD) δ ppm 7.80-7.78 (1H, m), 7.52-7.50 (2H, m), 6.12 (1H, s), 3.54-3.50 (2H, m), 1.69-1.65 (2H, m), 1.42-1.39 (4H, m), 0.98-0.95 (3H, m).

Example 62

4-N-cyclopropyl-6-(2,3-dichlorophenyl)pyrimidine-2,4-diamine

Prepared according to general procedure 3 from cyclopropanamine and 4-chloro-6-(2,3-dichlorophenyl)pyrimidin-2-amine. LCMS [M+H]⁺ 295; ¹H NMR (400 MHz, CDCl₃) δ ppm 7.51 (1H, dd, J=7.9 and 1.6 Hz), 7.41 (1H, dd, J=7.9 and 1.6 Hz), 7.28 (1H, t, J=7.9 Hz), 6.35 (1H, s), 5.21 (1H, s), 4.78 (2H, s), 2.63-2.47 (1H, m), 0.86-0.78 (2H, m), 0.64-0.57 (2H, m).

Example 63

4-N-tert-butyl-6-(2,3-dichlorophenyl)pyrimidine-2,4-diamine

Prepared according to general procedure 3 from 2-methylpropan-2-amine and 4-chloro-6-(2,3-dichlorophenyl)pyrimidin-2-amine. LCMS [M+H]⁺ 311.

Example 64

4-N-cyclobutyl-6-(2,3-dichlorophenyl)pyrimidine-2,4-diamine

Prepared according to general procedure 3 from cyclobutanamine and 4-chloro-6-(2,3-dichlorophenyl)pyrimidin-2-amine. LCMS [M+H]⁺ 309; ¹H NMR (400 MHz, CD₃OD) δ ppm 7.60-7.58 (1H, m), 7.37-7.34 (2H, m), 5.89 (1H, s), 4.46 (1H, s), 3.37 (2H, s), 2.43-2.35 (2H, m), 2.01-1.94 (2H, m), 1.80-1.72 (2H, m).

Example 65

4-N-cyclopentyl-6-(2,3-dichlorophenyl)pyrimidine-2,4-diamine

Prepared according to general procedure 3 from cyclopentanamine and 4-chloro-6-(2,3-dichlorophenyl)pyrimidin-2-amine. LCMS [M+H]⁺ 323; ¹H NMR (400 MHz, CD₃OD) δ ppm 7.62-7.56 (1H, m), 7.40-7.34 (2H, m), 5.93 (1H, s), 3.37 (1H, s), 2.09-1.98 (2H, m), 1.82-1.72 (2H, m), 1.71-1.61 (2H, m), 1.58-1.48 (2H, m).

Example 66

6-(2,3-dichlorophenyl)-4-N-ethylpyrimidine-2,4-diamine

Prepared according to general procedure 3 from ethanamine and 4-chloro-6-(2,3-dichlorophenyl)pyrimidin-2-amine. LCMS [M+H]⁺ 283; ¹H NMR (400 MHz, CD₃OD) δ ppm 7.62-7.57 (1H, m), 7.40-7.35 (2H, m), 5.92 (1H, s), 3.44-3.36 (2H, m), 1.24 (3H, t, J=7.1 Hz).

Example 67

6-(2,3-dichlorophenyl)-4-N-(oxolan-3-yl)pyrimidine-2,4-diamine

Prepared according to general procedure 3 from oxolan-3-amine and 4-chloro-6-(2,3-dichlorophenyl)pyrimidin-2-amine. LCMS [M+H]⁺ 325; ¹H NMR (400 MHz, CD₃OD) δ ppm 7.63-7.58 (1H, m), 7.39-7.35 (2H, m), 5.98 (1H, s), 4.59 (1H, s), 4.02-3.94 (2H, m), 3.90-3.82 (1H, m), 3.73-3.67 (1H, m), 2.36-2.26 (1H, m), 1.99-1.89 (1H, m).

Example 68

6-(3,4-dichlorophenyl)-4-N-methylpyrimidine-2,4-diamine

Prepared according to general procedure 2 from (3,4-dichlorophenyl)boronic acid and 6-chloro-4-N-methylpyrimidine-2,4-diamine. LCMS [M+H]⁺ 269; ¹H NMR (400 MHz, CD₃OD) δ ppm 7.96 (1H, d, J=2.0 Hz), 7.77 (1H, d, J=8.5 Hz), 7.70-7.55 (2H, m), 6.35 (1H, s), 3.06 (3H, s).

Example 69

6-(4-tert-butylphenyl)-4-N-methylpyrimidine-2,4-diamine

Prepared according to general procedure 5 from (4-tert-butylphenyl)boronic acid and 6-chloro-4-N-methylpyrimidine-2,4-diamine. LCMS [M+H]⁺ 257; ¹H NMR (400 MHz, CD$_3$OD) δ ppm 7.77 (2H, d, J=8.7 Hz), 7.53-7.48 (2H, m), 6.22 (1H, s), 2.93 (3H, s), 1.38 (9H, s).

Example 70

4-N-methyl-6-(4-methylphenyl)pyrimidine-2,4-diamine

Prepared according to general procedure 5 from (4-methylphenyl)boronic acid and 6-chloro-4-N-methylpyrimidine-2,4-diamine. LCMS [M+H]$^+$ 215; $^1$H NMR (400 MHz, CD$_3$OD) δ ppm 7.73 (2H, d, J=8.9 Hz), 7.28 (2H, d, J=8.9 Hz), 6.20 (1H, s), 2.93 (3H, s), 2.41 (3H, s).

Example 71

6-(2,4-dichlorophenyl)-4-N-methylpyrimidine-2,4-diamine

Prepared according to general procedure 5 from (2,4-dichlorophenyl)boronic acid and 6-chloro-4-N-methylpyrimidine-2,4-diamine. LCMS [M+H]$^+$ 269; $^1$H NMR (400 MHz, CD$_3$OD) δ 7.57 (1H, d, J=1.9 Hz), 7.48-7.41 (2H, m), 5.98 (1H, s), 2.92 (3H, s).

Example 72

4-N-methyl-6-(2,4,5-trifluorophenyl)pyrimidine-2,4-diamine

Prepared according to general procedure 5 from (2,4,5-trifluorophenyl)boronic acid and 6-chloro-4-N-methylpyrimidine-2,4-diamine. LCMS [M+H]$^+$ 255; $^1$H NMR (400 MHz, CD$_3$OD) δ ppm 7.86-7.75 (1H, m), 7.31-7.24 (1H, m), 6.25 (1H, s), 2.91 (3H, s).

Example 73

6-(4-fluoro-2-methoxyphenyl)-4-N-methylpyrimidine-2,4-diamine

Prepared according to general procedure 5 from (4-fluoro-2-methoxyphenyl)-boronic acid and 6-chloro-4-N-methylpyrimidine-2,4-diamine. LCMS [M+H]$^+$ 249; $^1$H NMR (400 MHz, CD$_3$OD) δ ppm 7.57 (1H, dd, J=8.5 and 6.3 Hz), 6.89 (1H, dd, J=11.4 and 2.5 Hz), 6.76 (1H, td, J=8.5 and 2.5 Hz), 6.19 (1H, s), 3.87 (3H, s), 2.90 (3H, s).

Example 74

6-(5-chloro-2-methylphenyl)-4-N-methylpyrimidine-2,4-diamine

Prepared according to general procedure 5 from (5-chloro-2-methylphenyl)-boronic acid and 6-chloro-4-N-methylpyrimidine-2,4-diamine. LCMS [M+H]$^+$ 249; $^1$H NMR (400 MHz, CD$_3$OD) δ ppm 7.33-7.23 (3H, m), 5.85 (1H, s), 2.92 (3H, s), 2.32 (3H, s).

Example 75

6-(2,4-difluorophenyl)-4-N-methylpyrimidine-2,4-diamine

Prepared according to general procedure 5 from (2,4-difluorophenyl)boronic acid and 6-chloro-4-N-methylpyrimidine-2,4-diamine. LCMS [M+H]$^+$ 237; $^1$H NMR (400 MHz, CD$_3$OD) δ ppm 7.88-7.79 (1H, m), 7.10-7.00 (2H, m), 6.19 (1H, d, J=2.0 Hz), 2.92 (3H, s).

Example 76

6-(5-fluoro-2-methoxyphenyl)-4-N-methylpyrimidine-2,4-diamine

Prepared according to general procedure 5 from (5-fluoro-2-methoxyphenyl)-boronic acid and 6-chloro-4-N-methylpyrimidine-2,4-diamine. LCMS [M+H]$^+$ 249; $^1$H NMR (400 MHz, CD$_3$OD) δ ppm 7.36 (1H, dd, J=9.4 and 3.1 Hz), 7.15-7.04 (2H, m), 6.28 (1H, s), 3.85 (3H, s), 2.91 (3H, s).

Example 77

6-(2-chlorophenyl)-4-N-methylpyrimidine-2,4-diamine

Prepared according to general procedure 5 from (2-chlorophenyl)boronic acid and 6-chloro-4-N-methylpyrimidine-2,4-diamine. LCMS [M+H]$^+$ 235; $^1$H NMR (400 MHz, CD$_3$OD) δ ppm 7.51-7.44 (1H, m), 7.42-7.36 (2H, m), 5.98 (1H, s), 2.92 (3H, s).

Example 78

6-(2,3-dichlorophenyl)-N4-[2-(3-methylsulfonylanilino)ethyl]pyrimidine-2,4-diamine Step 1. N'-(3-methylsulfonylphenyl)ethane-1,2-diamine was prepared according to general procedure 13 from 1-bromo-3-methylsulfonyl-benzene.

Step 2. The title compound was prepared according to general procedure 9 from intermediate 21 and N'-(3-methylsulfonylphenyl)ethane-1,2-diamine. [M+H]$^+$ 452.

$^1$H NMR (400 MHz, CHLOROFORM-d) δ ppm 7.50 (dd, J=8.1, 1.7 Hz, 1 H), 7.36-7.40 (m, 1 H), 7.28-7.35 (m, 3 H), 7.25 (t, J=1.4 Hz, 1 H), 6.85 (d, J=0.9 Hz, 1H), 5.97 (s, 1 H), 5.03-5.26 (m, 3 H), 4.70 (br. s., 1 H), 3.65 (q, J=6.1 Hz, 2 H), 3.44 (q, J=6.4 Hz, 2 H), 3.08 (s, 3 H).

Example 79

6-(4-methoxy-3-methylphenyl)-4-N-methylpyrimidine-2,4-diamine

Prepared according to general procedure 6 from (4-methoxy-3-methylphenyl)-boronic acid and 6-iodo-4-N-methylpyrimidine-2,4-diamine. LCMS [M+H]$^+$ 245; $^1$H NMR (400 MHz, CD$_3$OD) δ ppm 7.72-7.62 (2H, m), 6.99 (1H, d, J=8.3 Hz), 6.18 (1H, s), 3.91 (3H, s), 2.94 (3H, s), 2.28 (3H, s).

Example 80

6-(3-chloro-4-fluorophenyl)-4-N-methylpyrimidine-2,4-diamine

Prepared according to general procedure 6 from (3-chloro-4-fluorophenyl)boronic acid and 6-iodo-4-N-methylpyrimidine-2,4-diamine. LCMS [M+H]$^+$ 253; $^1$H NMR (400 MHz, CD$_3$OD) δ ppm 8.05-7.99 (1H, m), 7.87-7.79 (1H, m), 7.33 (1H, t, J=8.2 Hz), 6.23 (1H, s), 2.94 (3H, s).

Example 81

4-N-methyl-6-[4-(trifluoromethoxy)phenyl]pyrimidine-2,4-diamine

Prepared according to general procedure 6 from [4-(trifluoromethoxy)phenyl]boronic acid and 6-iodo-4-N-methylpyrimidine-2,4-diamine. LCMS [M+H]$^+$ 285; $^1$H NMR (400 MHz, CD$_3$OD) δ ppm 7.98-7.92 (2H, m), 7.38-7.32 (2H, m), 6.23 (1H, s), 2.93 (3H, s).

Example 82

6-(3-fluoro-4-methoxyphenyl)-4-N-methylpyrimidine-2,4-diamine

Prepared according to general procedure 6 from (3-fluoro-4-methoxyphenyl)-boronic acid and 6-iodo-4-N-methylpyrimidine-2,4-diamine. LCMS [M+H]$^+$ 249; $^1$H NMR (400 MHz, CD$_3$OD) δ ppm 7.97-7.60 (2H, m), 7.21-7.12 (1H, m), 6.20 (1H, s), 3.95 (3H, s), 2.94 (3H, s).

Example 83

6-(3,4-difluorophenyl)-4-N-methylpyrimidine-2,4-diamine

Prepared according to general procedure 6 from (3,4-difluorophenyl)boronic acid and 6-iodo-4-N-methylpyrimidine-2,4-diamine. LCMS [M+H]$^+$ 237; $^1$H NMR (400 MHz, CD$_3$OD) δ ppm 7.86-7.77 (1H, m), 7.74-7.66 (1H, m), 7.40-7.30 (1H, m), 6.23 (1H, s), 2.94 (3H, s).

Example 84

4-N-methyl-6-[4-(propan-2-yloxy)phenyl]pyrimidine-2,4-diamine

Prepared according to general procedure 6 from [4-(propan-2-yloxy)phenyl]boronic acid and 6-iodo-4-N-methylpyrimidine-2,4-diamine. LCMS [M+H]$^+$ 259.

Example 85

6-[2-fluoro-3-(trifluoromethyl)phenyl]-4-N-methylpyrimidine-2,4-diamine

Prepared according to general procedure 6 from [2-fluoro-3-(trifluoromethyl)phenyl]boronic acid and 6-iodo-4-N-methylpyrimidine-2,4-diamine. LCMS [M+H]$^+$ 287; $^1$H NMR (400 MHz, CD$_3$OD) δ ppm 7.98 (1H, t, J=7.0 Hz), 7.87 (1H, t, J=7.0 Hz), 7.52 (1H, t, J=8.0 Hz), 6.27 (1H, d, J=1.5 Hz), 3.00 (3H, s).

Example 86

6-(2,3-dimethylphenyl)-4-N-methylpyrimidine-2,4-diamine

Prepared according to general procedure 6 from (2,3-dimethylphenyl)boronic acid and 6-iodo-4-N-methylpyrimidine-2,4-diamine. LCMS [M+H]$^+$ 229; $^1$H NMR (400 MHz, CD$_3$OD) δ ppm 7.24-7.18 (1H, m), 7.17-7.05 (2H, m), 5.82 (1H, s), 2.92 (3H, s), 2.35 (3H, s), 2.22 (3H, s).

Example 87

6-(3-chloro-2-fluorophenyl)-4-N-methylpyrimidine-2,4-diamine

Prepared according to general procedure 6 from (3-chloro-2-fluorophenyl)boronic acid and 6-iodo-4-N-methylpyrimidine-2,4-diamine. LCMS [M+H]$^+$ 253; $^1$H NMR (400 MHz, CD$_3$OD) δ ppm 7.71-7.65 (1H, m), 7.58-7.53 (1H, m), 7.30-7.22 (1H, m), 6.18 (1H, d, J=2.1 Hz), 2.93 (3H, s).

Example 88

6-(4-chloro-3-fluorophenyl)-4-N-methylpyrimidine-2,4-diamine

Prepared according to general procedure 6 from (4-chloro-3-fluorophenyl)boronic acid and 6-iodo-4-N-methylpyrimidine-2,4-diamine. LCMS [M+H]$^+$ 253; $^1$H NMR (400 MHz, CD$_3$OD) δ ppm 7.73-7.65 (2H, m), 7.62-7.55 (1H, m), 6.34 (1H, s), 3.03 (3H, s).

Example 89

4-N-methyl-6-[2-(trifluoromethyl)phenyl]pyrimidine-2,4-diamine

Prepared according to general procedure 6 from [2-(trifluoromethyl)-phenyl]boronic acid and 6-iodo-4-N-methylpyrimidine-2,4-diamine. LCMS [M+H]$^+$ 269; $^1$H NMR (400 MHz, CD$_3$OD) δ ppm 7.80 (1H, d, J=8.1 Hz), 7.70 (1H, t, J=7.7 Hz), 7.61 (1H, t, J=7.7 Hz), 7.48 (1H, d, J=8.1 Hz), 5.88 (1H, s), 2.92 (3H, s).

Example 90

4-N-methyl-6-(1-methyl-1H-indazol-4-yl)pyrimidine-2,4-diamine

Prepared according to general procedure 6 from (1-methyl-1H-indazol-4-yl)boronic acid and 6-iodo-4-N-methylpyrimidine-2,4-diamine. LCMS [M+H]$^+$ 255; $^1$H NMR (400 MHz, CD$_3$OD) δ ppm 8.42 (1H, s), 7.69-7.63 (1H, m), 7.60-7.50 (2H, m), 6.33 (1H, s), 4.14 (3H, s), 2.97 (3H, s).

Example 91

6-[2-chloro-3-(trifluoromethyl)phenyl]-4-N-methylpyrimidine-2,4-diamine

Prepared according to general procedure 6 from [2-chloro-3-(trifluoromethyl)phenyl]boronic acid and 6-iodo-4-N-methylpyrimidine-2,4-diamine. LCMS [M+H]$^+$ 303; $^1$H NMR (400 MHz, CD$_3$OD) δ ppm 7.90-7.85 (1H, m), 7.71-7.66 (1H, m), 7.62-7.55 (1H, m), 5.95 (1H, s), 2.94 (3H, s).

Example 92

6-(2-chloro-3-fluorophenyl)-4-N-methylpyrimidine-2,4-diamine

Prepared according to general procedure 6 from (2-chloro-3-fluorophenyl)boronic acid and 6-iodo-4-N- methylpyrimidine-2,4-diamine. LCMS [M+H]⁺ 253; ¹H NMR (400 MHz, CD₃OD) δ ppm 7.46-7.38 (1H, m), 7.35-7.28 (2H, m), 5.98 (1H, s), 2.93 (3H, s).

Example 93

6-(2,3-difluorophenyl)-4-N-methylpyrimidine-2,4-diamine

Prepared according to general procedure 6 from (2,3-difluorophenyl)boronic acid and 6-iodo-4-N-methylpyrimidine-2,4-diamine. LCMS [M+H]⁺ 237; ¹H NMR (400 MHz, CD₃OD) δ ppm 7.58-7.51 (1H, m), 7.34-7.31 (1H, m), 7.29-7.22 (1H, m), 6.20 (1H, s), 2.93 (3H, s).

Example 94

6-(3-chloro-2-methylphenyl)-4-N-methylpyrimidine-2,4-diamine

Prepared according to general procedure 6 from (3-chloro-2-methylphenyl)boronic acid and 6-iodo-4-N-methylpyrimidine-2,4-diamine. LCMS [M+H]⁺ 249; ¹H NMR (400 MHz, CD₃OD) δ ppm 7.47-7.41 (1H, m), 7.27-7.21 (2H, m), 5.85 (1H, s), 2.93 (3H, s), 2.36 (3H, s).

Example 95

6-(2,3-dichlorophenyl)-4-N,5-dimethylpyrimidine-2,4-diamine

Step 1: 4-chloro-6-(2,3-dichlorophenyl)-5-methylpyrimidin-2-amine was prepared according to general procedure 2 from 4,6-dichloro-5-methylpyrimidin-2-amine and (2,3-dichlorophenyl)boronic acid (and using DMF instead of dioxane).
Step 2: 6-(2,3-dichlorophenyl)-4-N,5-dimethylpyrimidine-2,4-diamine was prepared according to general procedure 3 from methanamine and 4-chloro-6-(2,3-dichlorophenyl)-5-methylpyrimidin-2-amine (prepared in step 1 above). LCMS [M+H]⁺ 283; ¹H NMR (400 MHz, CD₃OD) δ ppm 7.62 (1H, dd, J=7.9 and 1.9 Hz), 7.41 (1H, t, J=7.9 Hz), 7.27 (1H, dd, J=7.9 and 1.9 Hz), 3.01 (3H, s), 1.71 (3H, s).

Example 96

4-N-cyclopropyl-6-(2,3-dichlorophenyl)-5-methylpyrimidine-2,4-diamine

Was prepared according to general procedure 3 from cyclopropanamine and 4-chloro-6-(2,3-dichlorophenyl)-5-methylpyrimidin-2-amine (prepared in example 95, step 1 above). LCMS [M+H]⁺ 309; ¹H NMR (400 MHz, CD₃OD) δ ppm 7.83 (1H, dd, J=7.7 and 1.2 Hz), 7.56 (1H, t, J=7.8 Hz), 7.48 (1H, dd, J=7.8 and 1.2 Hz), 3.17-3.09 (1H, m), 1.79 (3H, s), 0.96-0.90 (2H, m), 0.82-0.75 (2H, m).

Example 97

6-(7-chloro-2H-1,3-benzodioxol-5-yl)-4-N-methylpyrimidine-2,4-diamine

Prepared according to general procedure 6 from (7-chloro-2H-1,3-benzodioxol-5-yl)boronic acid and 6-iodo-4-N-methylpyrimidine-2,4-diamine. LCMS [M+H]⁺ 279; ¹H NMR (400 MHz, CD₃OD) δ ppm 7.11 (1H, s), 7.04 (1H, s), 6.13 (2H, s), 6.10 (1H, s), 3.04 (3H, s).

Example 98

6-(2,3-dichloro-4-methoxyphenyl)-4-N-methylpyrimidine-2,4-diamine

Step 1: 4-chloro-6-(2,3-dichloro-5-methoxyphenyl)pyrimidin-2-amine was prepared according to general procedure 2 from 4,6-dichloropyrimidin-2-amine and 2,3-dichloro-4-methoxyphenyl)boronic acid.
Step 2: Prepared according to general procedure 3 from methanamine and 4-chloro-6-(2,3-dichloro-5-methoxyphenyl)pyrimidin-2-amine (prepared in step 1 above). LCMS [M+H]⁺ 299; ¹H NMR (400 MHz, CD₃OD) δ 7.49 (1H, d, J=8.6 Hz), 7.24 (1H, d, J=8.6 Hz), 6.11 (1H, s), 4.01 (3H, s), 3.09 (3H, s).

Example 99

6-(2,3-dichloro-5-methoxyphenyl)-4-N-methylpyrimidine-2,4-diamine

Prepared according to general procedure 6 from (2,3-dichloro-5-methoxyphenyl)boronic acid and 6-iodo-4-N-methylpyrimidine-2,4-diamine. LCMS [M+H]⁺ 299; ¹H NMR (400 MHz, CD₃OD) δ ppm 7.38 (1H, d, J=2.9 Hz), 7.12 (1H, d, J=2.9 Hz), 6.13 (1H, s), 3.88 (3H, s), 3.05 (3H, s).

Example 100

4-[2-amino-6-(methylamino)pyrimidin-4-yl]phenol

Prepared according to general procedure 6 from (4-hydroxyphenyl)boronic acid and 6-iodo-4-N-methylpyrimidine-2,4-diamine. LCMS [M+H]⁺ 217; ¹H NMR (400 MHz, CD₃OD) δ ppm 7.69 (2H, d, J=8.5 Hz), 6.85 (2H, d, J=8.5 Hz), 6.15 (1H, s), 4.59 (1H, s), 2.93 (3H, s).

Example 101

{3-[2-amino-6-(methylamino)pyrimidin-4-yl]phenyl}methanol

Prepared according to general procedure 6 from [3-(hydroxymethyl)phenyl]boronic acid and 6-iodo-4-N-methylpyrimidine-2,4-diamine. LCMS [M+H]⁺ 231; ¹H NMR (400 MHz, CD₃OD) δ ppm 7.83 (1H, s), 7.76-7.70 (1H, m), 7.45-7.41 (2H, m), 6.22 (1H, s), 4.68 (2H, s), 2.92 (3H, s).

Example 102

4-[2-amino-6-(methylamino)pyrimidin-4-yl]benzoic acid

Prepared according to general procedure 6 from 4-(dihydroxyboranyl)benzoic acid and 6-iodo-4-N-methylpyrimidine-2,4-diamine. LCMS [M+H]⁺ 245.

Example 103 methyl 4-[2-amino-6-(methylamino)pyrimidin-4-yl]benzoate

Prepared according to general procedure 6 from [4-(methoxycarbonyl)-phenyl]boronic acid and 6-iodo-4-N- methylpyrimidine-2,4-diamine. LCMS [M+H]⁺ 259; ¹H NMR (400 MHz, CD₃OD) δ ppm 8.12-8.06 (2H, m), 7.95 (2H, d, J=8.2 Hz), 6.28 (1H, s), 3.94 (3H, s), 2.93 (3H, s).

Example 104

6-[3-chloro-4-(morpholine-4-carbonyl)phenyl]-4-N-methylpyrimidine-2,4-diamine

Prepared according to general procedure 6 from [3-chloro-4-(morpholine-4-carbonyl)phenyl]boronic acid and 6-iodo-4-N-methylpyrimidine-2,4-diamine. LCMS [M+H]⁺ 348; ¹H NMR (400 MHz, CD₃OD) δ ppm 7.90 (1H, d, J=1.8 Hz), 7.75 (1H, dd, J=7.9 and 1.8 Hz), 7.59 (1H, d, J=7.9 Hz), 6.35 (1H, s), 3.85-3.74 (6H, m), 3.69-3.60 (2H, m), 3.04 (3H, s).

Example 105

4-[2-amino-6-(methylamino)pyrimidin-4-yl]-2,3-dichlorophenol

Prepared according to general procedure 6 from 2,3-dichloro-4-(tetramethyl-1,3,2-dioxaborolan-2-yl)phenol and 6-iodo-4-N-methylpyrimidine-2,4-diamine. LCMS [M+H]⁺ 285; ¹H NMR (400 MHz, CD₃OD) δ ppm 7.32 (1H, d, J=8.7 Hz), 7.04 (1H, d, J=8.7 Hz), 6.09 (1H, s), 3.04 (3H, s).

Example 106 methyl (2E)-3-{4-[2-amino-6-(methylamino)pyrimidin-4-yl]phenyl}prop-2-enoate

Prepared according to general procedure 6 from {4-[(1E)-3-methoxy-3-oxoprop-1-en-1-yl]phenyl}boronic acid and 6-iodo-4-N-methylpyrimidine-2,4-diamine. LCMS [M+H]⁺ 285; ¹H NMR (400 MHz, CD₃OD) δ ppm 7.82 (4H, s), 7.76 (1H, d, J=16.0 Hz), 6.69 (1H, d, J=16.0 Hz), 6.36 (1H, s), 3.83 (3H, s), 3.04 (3H, s).

Example 107 methyl (2E)-3-{3-[2-amino-6-(methylamino)pyrimidin-4-yl]phenyl}prop-2-enoate

Prepared according to general procedure 6 from {3-[(1E)-3-methoxy-3-oxoprop-1-en-1-yl]phenyl}boronic acid and 6-iodo-4-N-methylpyrimidine-2,4-diamine. LCMS [M+H]⁺ 285; ¹H NMR (400 MHz, CD₃OD) δ ppm 7.99-7.95 (1H, m), 7.92-7.86 (1H, m), 7.83-7.73 (2H, m), 7.69-7.63 (1H, m), 6.72 (1H, d, J=16.0 Hz), 6.37 (1H, s), 3.83 (3H, s), 3.07 (3H, s).

Example 108

4-[2-amino-6-(methylamino)pyrimidin-4-yl]benzaldehyde

Prepared according to general procedure 6 from (4-formylphenyl)boronic acid and 6-iodo-4-N-methylpyrimidine-2,4-diamine. LCMS [M+H]⁺ 229.

Example 109

1-(4-(2-Amino-6-(methylamino)pyrimidin-4-yl)phenyl)ethanone

Prepared according to general procedure 6 from (4-acetylphenyl)boronic acid and 6-iodo-4-N-methylpyrimidine-2,4-diamine. LCMS [M+H]⁺ 243; ¹H NMR (400 MHz, CD₃OD) δ ppm 8.22-8.15 (2H, m), 7.88-7.82 (2H, m), 6.38 (1H, s), 3.05 (3H, s), 2.67 (3H, s).

Example 110

4-[2-amino-6-(methylamino)pyrimidin-4-yl]-N-methylbenzamide

Prepared according to general procedure 6 from [4-(methylcarbamoyl)phenyl]boronic acid and 6-iodo-4-N-methylpyrimidine-2,4-diamine. LCMS [M+H]⁺ 258; ¹H NMR (400 MHz, CD₃OD) δ ppm 8.02 (2H, d, J=8.5 Hz), 7.83 (2H, d, J=8.5 Hz), 6.38 (1H, s), 3.06 (3H, s), 2.97 (3H, s).

Example 111

6-(4-ethenylphenyl)-4-N-methylpyrimidine-2,4-diamine

Prepared according to general procedure 6 from (4-ethenylphenyl)boronic acid and 6-iodo-4-N-methylpyrimidine-2,4-diamine. LCMS [M+H]⁺ 227; ¹H NMR (400 MHz, CD₃OD) δ ppm 7.75-7.63 (4H, m), 6.84 (1H, dd, J=17.5 and 10.7 Hz), 6.34 (1H, s), 5.98 (1H, d, J=17.5 Hz), 5.43 (1H, d, J=10.7 Hz), 3.06 (3H, s).

Example 112

6-(2,3-dimethylphenyl)-4-N-[2-(piperidin-1-yl)ethyl]pyrimidine-2,4-diamine

Prepared according to general procedure 7 from 2-(piperidin-1-yl)ethan-1-amine and 4-chloro-6-(2,3-dimethylphenyl)pyrimidin-2-amine. LCMS [M+H]⁺ 326.

Example 113

6-(2,3-dimethylphenyl)-4-N-[2-(morpholin-4-yl)ethyl]pyrimidine-2,4-diamine

Prepared according to general procedure 7 from 2-(morpholin-4-yl)ethan-1-amine and 4-chloro-6-(2,3-dimethylphenyl)pyrimidin-2-amine. LCMS [M+H]⁺ 328.

Example 114

4-N-cyclopropyl-6-(2,3-dimethylphenyl)pyrimidine-2,4-diamine

Prepared according to general procedure 2 from (2,3-dimethylphenyl)boronic acid and 6-chloro-4-N-cyclopropylpyrimidine-2,4-diamine. LCMS [M+H]⁺ 255; ¹H NMR (400 MHz, CD₃OD) δ ppm 7.42-7.31 (1H, m), 7.29-7.12 (2H, m), 6.44 (0.3 H, s), 5.95 (0.7 H, s), 3.13. (0.7H, s), 2.68 (0.3H, s), 2.36 (3H, s), 2.25 (3H, s), 0.95-0.79 (2H, m), 0.72-0.55 (2H, m).

Example 115

3-[2-amino-6-(methylamino)pyrimidin-4-yl]-N-(4-methylphenyl)benzamide

Step 1: A mixture of 6-chloro-4-N-methylpyrimidine-2,4-diamine (48 mg, 0.30 mmol), 3-(dihydroxyboranyl)benzoic acid (60 mg, 0.36 mmol), K₂CO₃ (104 mg, 0.75 mmol) and palladium tetrakis(triphenylphosphine)palladium (0) (17 mg, 0.015 mmol) in 1,4-dioxane (3 mL) and water (1 mL) was heated in a sealed tube at 90° C. for 15 h. Concentrated and purified by preparative HPLC. LCMS [M+H]$^+$ 245.

Step 2: To a mixture of 3-(2-amino-6-(methylamino)pyrimidin-4-yl)benzoic acid (50 mg, 0.47 mmol) and p-toluidine (150 mg, 1.4 mmol) in DMF (2.5 mL) were added HATU (266 mg, 0.70 mmol) and NEt$_3$ (200 μL, 1.4 mmol). The mixture was stirred at rt overnight. The crude reaction mixture was purified by HPLC. LCMS [M+H]$^+$ 334.

Example 116

6-(1H-indol-3-yl)-4-N-methylpyrimidine-2,4-diamine

To a solution of 4-N-methyl-6-[1-(4-methylbenzenesulfonyl)-1H-indol-3-yl]pyrimidine-2,4-diamine (1 equiv.; prepared in example 23) in MeOH (2 mL) was added 10% NaOH (1 mL). The reaction mixture was heated at 50° C. overnight and the crude product was purified by HPLC. LCMS [M+H]$^+$ 240; $^1$H NMR (400 MHz, CD$_3$OD) δ ppm 8.04 (1H, d, J=7.7 Hz), 7.82 (1H, s), 7.46-7.36 (1H, m), 7.21-7.09 (2H, m), 6.29 (1H, s), 2.92 (3H, s).

Example 117

6-phenyl-4-N-(2-phenylethyl)pyrimidine-2,4-diamine

Prepared according to general procedure 2 from phenylboronic acid and 6-chloro-4-N-(2-phenylethyl)pyrimidine-2,4-diamine. LCMS [M+H]$^+$ 291; $^1$H NMR (400 MHz, CD$_3$OD) δ ppm 7.83-7.73 (2H, m), 7.47-7.37 (3H, m), 7.31-7.22 (4H, m), 7.21-7.15 (1H, m), 6.17 (1H, s), 3.60 (2H, t, J=7.3 Hz), 2.91 (2H, t, J=7.3 Hz).

Example 118

6-(2,3-dimethylphenyl)-4-N-(2-phenylethyl)pyrimidine-2,4-diamine

Prepared according to general procedure 2 from (2,3-dimethylphenyl)boronic acid and 6-chloro-4-N-(2-phenylethyl)pyrimidine-2,4-diamine. LCMS [M+H]$^+$ 319; $^1$H NMR (400 MHz, CD$_3$OD) δ ppm 7.31-7.23 (4H, m), 7.21-7.15 (2H, m), 7.10 (1H, t, J=7.0 Hz), 7.05 (1H, d, J=7.0 Hz), 5.77 (1H, s), 3.64-3.50 (2H, m), 2.90 (2H, t, J=7.6 Hz), 2.31 (3H, s), 2.19 (3H, s).

Example 119

6-(3-chlorophenyl)-4-N-(2,2-difluoroethyl)pyrimidine-2,4-diamine

Prepared according to general procedure 2 from (3-chlorophenyl)boronic acid and 6-chloro-4-N-(2,2-difluoroethyl)pyrimidine-2,4-diamine. LCMS [M+H]$^+$ 285.

Example 120

6-(3-chloro-2-methoxypyridin-4-yl)-4-N-methylpyrimidine-2,4-diamine

Prepared according to general procedure 2 from (3-chloro-2-methoxypyridin-4-yl)boronic acid and 6-chloro-4-N-methylpyrimidine-2,4-diamine. LCMS [M+H]$^+$ 266.

Example 121

4-(2,3-dimethylphenyl)-5H,6H,7H,8H-pyrido[2,3-d]pyrimidin-2-amine

To a solution of 4-chloro-5,6,7,8-tetrahydropyrido[2,3-d]pyrimidin-2-amine (10 mg, 0.054 mmol, 1 equiv.) in DMF/water (9:1) is added 2,3-dimethylphenylboronic acid (8.9 mg, 0.060 mmol, 1.1 equiv.), Na$_2$CO$_3$ (11.5 mg, 0.11 mmol, 2 equiv.) and Pd(PPh$_3$)$_4$ (3.1 mg, 0.002 mmol, 0.05 equiv.). The mixture is heated at 120° C. in a microwave reactor until the reaction is complete as shown by LCMS. The crude mixture is then purified by HPLC to afford the desired product. LCMS [M+H]$^+$255; $^1$H NMR (400 MHz, DMSO-d$_6$) δ ppm 12.05 (1H, br s), 8.88 (1H, br s), 7.37 (1H, d, J=6.9 Hz), 7.29 (1H, t, J=7.6 Hz), 7.17 (1H, d, J=6.3 Hz), 3.34-3.32 (2H, m), 2.32 (3H, s), 2.28-2.26 (2H, m), 2.09 (3H, s), 1.76-1.74 (2H, m).

Example 122

4-(2,3-dichlorophenyl)-5H,6H,7H,8H-pyrido[2,3-d]pyrimidin-2-amine

To a solution of 4-chloro-5,6,7,8-tetrahydropyrido[2,3-d]pyrimidin-2-amine (10 mg, 0.054 mmol, 1 equiv.) in DMF/water (9:1) is added 2,3-dichlorophenylboronic acid (11.3 mg, 0.060 mmol, 1.1 equiv.), Na$_2$CO$_3$ (11.5 mg, 0.11 mmol, 2 equiv.) and Pd(PPh$_3$)$_4$ (3.1 mg, 0.002 mmol, 0.05 equiv.). The mixture is heated at 120° C. in a microwave reactor until the reaction is complete as shown by LCMS. The crude mixture is then purified by HPLC to afford the desired product. LCMS [M+H]$^+$ 295.

Example 123

4-[1-(benzenesulfonyl)-1H-indol-3-yl]-5H,6H,7H,8H-pyrido[2,3-d]pyrimidin-2-amine To a solution of 4-chloro-5,6,7,8-tetrahydropyrido[2,3-d]pyrimidin-2-amine (10 mg, 0.054 mmol, 1 equiv.) in DMF/water (9:1) is added (1-(phenylsulfonyl)-1H-indol-3-yl)boronic acid (18.0 mg, 0.060 mmol, 1.1 equiv.), Na$_2$CO$_3$ (11.5 mg, 0.11 mmol, 2 equiv.) and Pd(PPh$_3$)$_4$ (3.1 mg, 0.002 mmol, 0.05 equiv.). The mixture is heated at 120° C. in a microwave reactor until the reaction is complete as shown by LCMS. The crude mixture is then purified by HPLC to afford the desired product. LCMS [M+H]$^+$ 406; $^1$H NMR (400 MHz, DMSO-d$_6$) δ ppm 12.03 (1H, br s), 8.03 (1H, br s), 8.36 (1H, s), 8.09 (2H, dd, J=8.6 Hz and 1.2 Hz), 8.04 (1H, d, J=8.3 Hz), 7.78-7.76 (1H, m), 7.68-7.66 (2H, m), 7.61 (1H, d, J=7.8 Hz), 7.48 (1H, ddd, J=8.4 Hz, 7.3 Hz and 1.1 Hz), 7.38 (1H, ddd, J=8.0 Hz, 7.2 Hz and 1.0 Hz), 3.38-3.36 (2H, m), 2.48-2.46 (2H, m), 1.76-1.74 (2H, m).

Example 124

6-(3,5-difluorophenyl)-4-N-methylpyrimidine-2,4-diamine

Prepared according to general procedure 2 from (3,5-difluorophenyl)boronic acid and 6-chloro-4-N-methylpyrimidine-2,4-diamine. LCMS [M+H]$^+$ 237.

Example 125

6-(2,3-dimethylphenyl)-4-N-[2-(4-methoxyphenyl)ethyl]pyrimidine-2,4-diamine

Prepared according to general procedure 7 from 2-(4-methoxyphenyl)ethan-1-amine and 4-chloro-6-(2,3-dimethylphenyl)pyrimidin-2-amine. LCMS [M+H]$^+$ 349.

Example 126

6-(2,3-dimethylphenyl)-4-N-[2-(2-methoxyphenyl)ethyl]pyrimidine-2,4-diamine

Prepared according to general procedure 7 from 2-(2-methoxyphenyl)ethan-1-amine and 4-chloro-6-(2,3-dimethylphenyl)pyrimidin-2-amine. LCMS [M+H]$^+$ 349.

Example 127

6-(2,3-dimethylphenyl)-4-N-[2-(4-methylphenyl)ethyl]pyrimidine-2,4-diamine

Prepared according to general procedure 7 from 2-(4-methylphenyl)ethan-1-amine and 4-chloro-6-(2,3-dimethylphenyl)pyrimidin-2-amine. LCMS [M+H]$^+$ 333.

Example 128

4-N-[2-(4-chlorophenyl)ethyl]-6-(2,3-dimethylphenyl)pyrimidine-2,4-diamine

Prepared according to general procedure 7 from 2-(4-chlorophenyl)ethan-1-amine and 4-chloro-6-(2,3-dimethylphenyl)pyrimidin-2-amine. LCMS [M+H]$^+$ 353.

Example 129

6-(2,3-dimethylphenyl)-4-N-[2-(pyridin-2-yl)ethyl]pyrimidine-2,4-diamine

Prepared according to general procedure 7 from 2-(pyridin-2-yl)ethan-1-amine and 4-chloro-6-(2,3-dimethylphenyl)pyrimidin-2-amine. LCMS [M+H]$^+$ 320.

Example 130

6-(2,3-dimethylphenyl)-4-N-(2-phenylpropyl)pyrimidine-2,4-diamine

Prepared according to general procedure 7 from 2-phenylpropan-1-amine and 4-chloro-6-(2,3-dimethylphenyl)pyrimidin-2-amine. LCMS [M+H]$^+$ 333.

Example 131

6-(2,3-dimethylphenyl)-4-N-(3-phenylpropyl)pyrimidine-2,4-diamine

Prepared according to general procedure 7 from 3-phenylpropan-1-amine and 4-chloro-6-(2,3-dimethylphenyl)pyrimidin-2-amine. LCMS [M+H]$^+$ 333.

Example 132

6-(2,3-dimethylphenyl)-4-N-(2-phenoxyethyl)pyrimidine-2,4-diamine

Prepared according to general procedure 7 from (2-aminoethoxy)benzene and 4-chloro-6-(2,3-dimethylphenyl)pyrimidin-2-amine. LCMS [M+H]$^+$ 335.

Example 133

6-(2,3-dimethylphenyl)-4-N-[2-(phenylamino)ethyl]pyrimidine-2,4-diamine

Prepared according to general procedure 7 from N-(2-aminoethyl)aniline and 4-chloro-6-(2,3-dimethylphenyl)pyrimidin-2-amine. LCMS [M+H]$^+$ 334.

Example 134

6-(2,3-dimethylphenyl)-4-N-[2-(1H-indol-3-yl)ethyl]pyrimidine-2,4-diamine

Prepared according to general procedure 7 from 2-(1H-indol-3-yl)ethan-1-amine and 4-chloro-6-(2,3-dimethylphenyl)pyrimidin-2-amine. LCMS [M+H]$^+$ 358.

Example 135

6-(2,3-dimethylphenyl)-4-N-pentylpyrimidine-2,4-diamine

Prepared according to general procedure 7 from pentan-1-amine and 4-chloro-6-(2,3-dimethylphenyl)pyrimidin-2-amine. LCMS [M+H]$^+$ 285.

Example 136

1-(2-{[2-amino-6-(2,3-dimethylphenyl)pyrimidin-4-yl]amino}ethyl)imidazolidin-2-one Prepared according to general procedure 7 from 1-(2-aminoethyl)imidazolidin-2-one and 4-chloro-6-(2,3-dimethylphenyl)pyrimidin-2-amine. LCMS [M+H]$^+$ 327.

Example 137

1-(3-{[2-amino-6-(2,3-dimethylphenyl)pyrimidin-4-yl]amino}propyl)pyrrolidin-2-one Prepared according to general procedure 7 from 1-(3-aminopropyl)pyrrolidin-2-one and 4-chloro-6-(2,3-dimethylphenyl)pyrimidin-2-amine. LCMS [M+H]$^+$ 340.

Example 138

4-[2-amino-6-(methylamino)pyrimidin-4-yl]-2,6-dimethylphenol

Prepared according to general procedure 6 from (4-hydroxy-3,5-dimethylphenyl)boronic acid. LCMS [M+H]$^+$

Example 139

4-[2-amino-6-(methylamino)pyrimidin-4-yl]-2-methoxyphenol

Prepared according to general procedure 6 from (4-hydroxy-3-methoxyphenyl)boronic acid and 6-iodo-4-N-methylpyrimidine-2,4-diamine. LCMS [M+H]$^+$ 247; $^1$H NMR (400 MHz, CD$_3$OD) δ ppm 7.46 (1H, s), 7.33 (1H, d, J=8.4 Hz), 6.86 (1H, d, J=8.0 Hz), 6.17 (1H, s), 3.34 (3H, s), 2.92 (3H, s).

Example 140

4-[2-amino-6-(methylamino)pyrimidin-4-yl]-2-fluorophenol

Prepared according to general procedure 6 from (3-fluoro-4-hydroxyphenyl)boronic acid and 6-iodo-4-N-methylpyrimidine-2,4-diamine. LCMS [M+H]$^+$ 235.

Example 141

5-[2-amino-6-(methylamino)pyrimidin-4-yl]pyridin-2-ol

Prepared according to general procedure 6 from (6-hydroxypyridin-3-yl)boronic acid and 6-iodo-4-N-methylpyrimidine-2,4-diamine. LCMS [M+H]$^+$ 218; $^1$H NMR (400 MHz, CD$_3$OD) δ ppm 7.99 (1H, s), 7.86 (1H, d, J=9.6 Hz), 6.68 (1H, dd, J=9.6 and 0.4 Hz), 6.21 (1H, s), 3.04 (3H, s).

Example 142

{4-[2-amino-6-(methylamino)pyrimidin-4-yl]phenyl}methanol

Prepared according to general procedure 6 from [4-(hydroxymethyl)phenyl]boronic acid and 6-iodo-4-N-methylpyrimidine-2,4-diamine. LCMS [M+H]$^+$ 231; $^1$H NMR (400 MHz, CD$_3$OD) δ ppm 7.79 (2H, d, J=8.0 Hz), 7.43 (2H, d, J=8.4 Hz), 6.21 (1H, s), 4.65 (2H, s), 2.91 (3H, s).

Example 143

4-N-methyl-6-(2-methylphenyl)pyrimidine-2,4-diamine

Prepared according to general procedure 6 from (2-methylphenyl)boronic acid and 6-iodo-4-N-methylpyrimidine-2,4-diamine. LCMS [M+H]$^+$ 215; $^1$H NMR (400 MHz, CD$_3$OD) δ ppm 7.29-7.23 (4H, m), 5.83 (1H, s), 2.90 (3H, s), 2.33 (3H, s).

Example 144

6-[1-(4-chlorobenzenesulfonyl)-1H-indol-3-yl]-4-N-methylpyrimidine-2,4-diamine

Prepared according to general procedure 8 from [1-(4-chlorobenzenesulfonyl)-1H-indol-3-yl]boronic acid and 6-chloro-4-N-methylpyrimidine-2,4-diamine. LCMS [M+H]$^+$ 414; $^1$H NMR (400 MHz, CD$_3$OD) δ ppm 8.15 (1H, s), 8.08 (1H, d, J=8.0 Hz), 8.04 (1H, d, J=8.0 Hz), 8.00-7.98 (2H, m), 7.57-7.55 (2H, m), 7.41 (1H, td, J=8.4 and 1.2 Hz), 7.35 (1H, td, J=8.0 and 0.8 Hz), 6.28 (1H, s), 2.29 (3H, s).

Example 145

4-N-methyl-6-(4-methyl-1H-indazol-5-yl)pyrimidine-2,4-diamine

Prepared according to general procedure 6 from (4-methyl-1H-indazol-5-yl)boronic acid and 6-iodo-4-N-methylpyrimidine-2,4-diamine. LCMS [M+H]$^+$ 255.

Example 146

4-N-methyl-6-(6-methyl-1H-indazol-5-yl)pyrimidine-2,4-diamine

Prepared according to general procedure 6 from (6-methyl-1H-indazol-5-yl)boronic acid and 6-iodo-4-N-methylpyrimidine-2,4-diamine. LCMS [M+H]$^+$ 255; $^1$H NMR (400 MHz, CD$_3$OD) δ ppm 8.12 (1H, d, J=0.8 Hz), 7.88 (1H, s), 7.56 (1H, d, J=0.8 Hz), 6.09 (1H, s), 3.07 (3H, s), 2.50 (3H, d, J=0.8 Hz).

Example 147

4-N-methyl-6-(3-methylphenyl)pyrimidine-2,4-diamine

Prepared according to general procedure 6 from (3-methylphenyl)boronic acid. LCMS [M+H]$^+$ 215; $^1$H NMR (400 MHz, CD$_3$OD) δ ppm 7.56 (1H, s), 7.51-7.47 (3H, m), 6.32 (1H, s), 3.06 (3H, s), 2.47 (3H, s).

Example 148

6-(1H-indol-5-yl)-4-N-methylpyrimidine-2,4-diamine

Prepared according to general procedure 6 from (1H-indol-5-yl)boronic acid and 6-iodo-4-N-methylpyrimidine-2,4-diamine. LCMS [M+H]$^+$ 240; $^1$H NMR (400 MHz, CD$_3$OD) δ ppm 8.00 (1H, dd, J=1.6 and 0.4 Hz), 7.59 (1H, td, J=8.4 and 0.8 Hz), 7.47 (1H, dd, J=8.4 and 1.6 Hz), 7.42 (1H, d, J=3.2 Hz), 6.63 (1H, dd, J=3.2 and 1.2 Hz), 6.35 (1H, s), 3.06 (3H, s).

Example 149

6-(3-chloropyridin-4-yl)-4-N-methylpyrimidine-2,4-diamine

Prepared according to general procedure 6 from (3-chloropyridin-4-yl)boronic acid and 6-iodo-4-N-methylpyrimidine-2,4-diamine. LCMS [M+H]$^+$ 236; $^1$H NMR (400 MHz, CD$_3$OD) δ ppm 8.83 (1H, s), 8.71 (1H, d, J=5.2 Hz), 7.62 (1H, d, J=4.8 Hz), 6.24 (1H, s), 3.07 (3H, s).

Example 150

{5-[2-amino-6-(methylamino)pyrimidin-4-yl]pyridin-2-yl}methanol

Prepared according to general procedure 6 from [6-(hydroxymethyl)pyridin-3-yl]boronic acid and 6-iodo-4-N-methylpyrimidine-2,4-diamine. LCMS [M+H]$^+$ 232.

Example 151

4-N-cyclobutyl-6-(2,3-dimethylphenyl)pyrimidine-2,4-diamine

Prepared according to general procedure 2 from (2,3-dimethylphenyl)boronic acid and 6-chloro-4-N-cyclobutylpyrimidine-2,4-diamine. LCMS [M+H]$^+$ 269; $^1$H NMR (400 MHz, CD$_3$OD) δ ppm 7.20 (1H, d, J=7.2 Hz), 7.13 (1H, t, J=7.2 Hz), 7.08 (1H, d, J=7.2 Hz), 5.77 (1H, s), 4.44 (1H, br s), 2.44-2.36 (2H, m), 2.34 (3H, s), 2.21 (3H, s), 2.04-1.94 (m, 2H), 1.82-1.73 (m, 2H).

Example 152

4-N-cyclobutyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclobutylpyrimidine-2,4-diamine. LCMS [M+H]$^+$ 434; $^1$H NMR (400 MHz, CD$_3$OD) δ ppm 8.39 (1H, s), 8.09 (1H, d, J =8.4 Hz), 7.96-7.94 (2H, m), 7.84 (1H, d, J=8.0 Hz), 7.50 (1H, td, J=7.2 and 0.8 Hz), 7.35 (1H, td, J=7.2 and 0.8 Hz), 7.41-7.39 (2H, m), 6.44 (1H, s), 4.66 (1H, quintet, J=8.4 Hz), 2.47-2.41 (2H, m), 2.39 (3H, s), 2.14-2.04 (2H, m), 1.89-1.82 (2H, m).

Example 153

4-N-cyclopentyl-6-(2,3-dimethylphenyl)pyrimidine-2,4-diamine

Prepared according to general procedure 2 from (2,3-dimethylphenyl)boronic acid and 6-chloro-4-N-cyclopentylpyrimidine-2,4-diamine. LCMS [M+H]$^+$ 283; $^1$H NMR (400 MHz, CD$_3$OD) δ ppm 7.19 (1H, d, J=7.2 Hz), 7.13 (1H, t, J=7.6 Hz), 7.08 (1H, dd, J=7.6 and 1.6 Hz), 5.81 (1H, s), 4.25 (1H, br s), 2.33 (3H, s), 2.22 (3H, s), 2.06-2.00 (2H, m), 1.81-1.74 (2H, m), 1.71-1.63 (2H, m), 1.58-1.51 (2H, m).

Example 154

4-N-cyclopentyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclopentylpyrimidine-2,4-diamine. LCMS [M+H]$^+$ 448; $^1$H NMR (400 MHz, CD$_3$OD) δ ppm 8.38 (1H, s), 8.10 (1H, d, J =8.4 Hz), 7.96-7.94 (2H, m), 7.84 (1H, d, J=8.0 Hz), 7.50 (1H, td, J=7.2 and 1.2 Hz), 7.42 (1H, td, J=7.2 and 0.8 Hz), 7.41-7.39 (2H, m), 6.48 (1H, s), 4.51 (1H, quintet, J=6.8 Hz), 2.39 (3H, s), 2.14-2.05 (2H, m), 1.84-1.78 (2H, m), 1.75-1.66 (2H, m), 1.63-1.57 (2H, m).

Example 155

4-N-methyl-6-{1-[4-(trifluoromethyl)benzenesulfonyl]-1H-indol-3-yl}pyrimidine-2,4-diamine Prepared according to general procedure 8 from {1-[4-(trifluoromethyl)benzenesulfonyl]-1H-indol-3-yl}boronic acid and 6-chloro-4-N-methylpyrimidine-2,4-diamine. LCMS [M+H]$^+$ 448; $^1$H NMR (400 MHz, CD$_3$OD) δ ppm 8.19 (2H, d, J=8.4 Hz), 8.16 (1H, s), 8.08-8.04 (2H, m), 7.84 (2H, d, J=8.4 Hz), 7.41 (1H, td, J=7.6 and 0.8 Hz), 7.34 (1H, td, J=8.0 and 0.8 Hz), 6.26 (1H, s), 2.92 (s, 3H).

Example 156

4-N-cyclohexyl-6-(2,3-dimethylphenyl)pyrimidine-2,4-diamine

Prepared according to general procedure 2 from (2,3-dimethylphenyl)boronic acid and 6-chloro-4-N-cyclohexylpyrimidine-2,4-diamine. LCMS [M+H]$^+$ 297; $^1$H NMR (400 MHz, CD$_3$OD) δ ppm 7.19 (1H, d, J=7.2 Hz), 7.12 (1H, t, J=7.6 Hz), 7.08 (1H, dd, J=7.6 and 1.6 Hz), 5.78 (1H, s), 3.82 (1H, br s), 2.33 (3H, s), 2.21 (3H, s), 2.03-1.99 (2H, m), 1.83-1.78 (2H, m), 1.71-1.66 (1H, m), 1.48-1.37 (2H, m), 1.31-1.21 (3H, m).

Example 157

4-N-cyclohexyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclohexylpyrimidine-2,4-diamine. LCMS [M+H]$^+$ 462; $^1$H NMR (400 MHz, CD$_3$OD) δ ppm 8.36 (1H, s), 8.08 (1H, d, J=8.0 Hz), 7.95-7.93 (2H, m), 7.83 (1H, d, J=8.0 Hz), 7.48 (1H, td, J=7.2 and 0.8 Hz), 7.41 (1H, td, J=8.0 and 1.2 Hz), 7.40-7.38 (2H, m), 6.46 (1H, s), 4.11-4.05 (1H, m), 2.38 (3H, s), 2.04-2.00 (2H, m), 1.86-1.82 (2H, m), 1.72-1.68 (1H, m), 1.48-1.26 (5H, m).

Example 158

6-(2,3-dimethylphenyl)-4-N-ethylpyrimidine-2,4-diamine

Prepared according to general procedure 2 from (2,3-dimethylphenyl)boronic acid and 6-chloro-4-N-ethylpyrimidine-2,4-diamine. LCMS [M+H]$^+$ 243; $^1$H NMR (400 MHz, CD$_3$OD) δ ppm 7.19 (1H, d, J=7.2 Hz), 7.13 (1H, t, J=7.6 Hz), 7.08 (1H, dd, J=7.6 and 1.2 Hz), 5.80 (1H, s), 3.41-3.36 (2H, m), 2.33 (3H, s), 2.21 (3H, s), 1.23 (3H, t, J=7.2 Hz).

Example 159

4-N-ethyl-6-[1-(4-methylbenzenesulfonyl)-1H-indol-3-yl]pyrimidine-2,4-diamine

Prepared according to general procedure 8 from [1-(4-methylbenzenesulfonyl)-1H-indol-3-yl]boronic acid and 6-chloro-4-N-ethylpyrimidine-2,4-diamine. LCMS [M+H]$^+$ 408; $^1$H NMR (400 MHz, CD$_3$OD) δ ppm 8.12 (1H, s), 8.05-8.01 (2H, m), 7.87-7.85 (2H, m), 7.37 (1H, td, J=7.2 and 1.2 Hz), 7.34-7.32 (2H, m), 7.30 (1H, td, J=8.0 and 1.2 Hz), 6.26 (1H, s), 3.39 (2H, q, J=7.2 Hz), 2.34 (3H, s), 1.24 (3H, t, J=7.2 Hz).

Example 160

4-N-tert-butyl-6-(2,3-dimethylphenyl)pyrimidine-2,4-diamine

Prepared according to general procedure 2 from (2,3-dimethylphenyl)boronic acid and 4-N-tert-butyl-6-chloropyrimidine-2,4-diamine. LCMS [M+H]$^+$ 271; $^1$H NMR (400 MHz, CD$_3$OD) δ ppm 7.18 (1H, d, J=7.2 Hz), 7.12 (1H, t, J=7.6 Hz), 7.07 (1H, dd, J=7.6 and 1.6 Hz), 5.81 (1H, s), 2.33 (3H, s), 2.21 (3H, s), 1.49 (9H, s).

Example 161

4-N-tert-butyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 4-N-tert-butyl-6-chloropyrimidine-2,4-diamine. LCMS [M+H]$^+$ 436; $^1$H NMR (400 MHz, CD$_3$OD) δ ppm 8.36 (1H, s), 8.08 (1H, d, J=8.4 Hz), 7.95-7.93 (2H, m), 7.84 (1H, d, J=7.6 Hz), 7.48 (1H, td, J=7.2 and 1.2 Hz), 7.40 (1H, td, J=8.4 and 1.2 Hz), 7.40-7.38 (2H, m), 6.52 (1H, s), 2.38 (3H, s), 1.54 (9H, s).

Example 162

6-(2,3-dimethylphenyl)-4-N-(propan-2-yl)pyrimidine-2,4-diamine

Prepared according to general procedure 2 (2,3-dimethylphenyl)boronic acid and 6-chloro-4-N-(propan-2-yl)pyrimidine-2,4-diamine. LCMS [M+H]$^+$ 257; $^1$H NMR (400 MHz, CD$_3$OD) δ ppm 7.36 (1H, d, J=7.2 Hz), 7.25 (1H, t, J=7.6 Hz), 7.19 (1H, d, J=7.2 Hz), 5.96 (1H, s), 4.39 (1H, septet, J=6.4 Hz), 2.37 (3H, s), 2.26 (3H, s), 1.29 (3H, s), 1.27 (3H, s).

Example 163

6-[1-(4-methylbenzenesulfonyl)-1H-indol-3-yl]-4-N-(propan-2-yl)pyrimidine-2,4-diamine Prepared according to general procedure 8 from [1-(4-methylbenzenesulfonyl)-1H-indol-3-yl]boronic acid and 6-chloro-4-N-(propan-2-yl)pyrimidine-2,4-diamine. LCMS [M+H]$^+$ 422; $^1$H NMR (400 MHz, CD$_3$OD) δ ppm 8.12 (1H, s), 8.05-8.02 (2H, m), 7.89-7.86 (2H, m), 7.40-7.30 (4H, m), 6.25 (1H, s), 4.19 (1H, br s), 2.36 (3H, s), 1.26 (3H, s), 1.24 (3H, s).

Example 164

4-N-(cyclopropylmethyl)-6-(2,3-dimethylphenyl) pyrimidine-2,4-diamine

Prepared according to general procedure 2 from (2,3-dimethylphenyl)boronic acid and 6-chloro-4-N-(cyclopropylmethyl)pyrimidine-2,4-diamine. LCMS [M+H]$^+$ 269.

Example 165

4-N-(cyclopropylmethyl)-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-(cyclopropylmethyl)pyrimidine-2,4-diamine. LCMS [M+H]$^+$ 434; $^1$H NMR (400 MHz, CD$_3$OD) δ ppm 8.14 (1H, s), 8.06-8.02 (2H, m), 7.88-7.86 (2H, m), 7.40-7.30 (5H, m), 6.31 (1H, s), 3.25 (2H, d, J=6.8 Hz), 1.14-1.11 (1H, m), 0.57-0.55 (2H, m), 0.30-0.28 (2H, m).

Example 166

4-N-[(1R)-1-cyclopropylethyl]-6-(2,3-dimethylphenyl)pyrimidine-2,4-diamine

Prepared according to general procedure 2 from (2,3-dimethylphenyl)boronic acid and 6-chloro-4-N-[(1R)-1-cyclopropylethyl]pyrimidine-2,4-diamine. LCMS [M+H]$^+$ 283; $^1$H NMR (400 MHz, CD$_3$OD) δ ppm 7.19 (1H, d, J=6.8 Hz), 7.13 (1H, t, J=7.6 Hz), 7.09 (1H, dd, J=7.6 and 1.2 Hz), 5.80 (1H, s), 3.58 (1H, br s), 2.34 (3H, s), 2.22 (3H, s), 1.28 (3H, d, J=6.4 Hz), 0.99-0.92 (1H, m), 0.57-0.45 (2H, m), 0.44-0.38 (1H, m), 0.29-0.23 (1H, m).

Example 167

4-N-[(1R)-1-cyclopropylethyl]-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-[(1R)-1-cyclopropylethyl]pyrimidine-2,4-diamine. LCMS [M+H]$^+$ 448; $^1$H NMR (400 MHz, CD$_3$OD) δ ppm 8.37 (1H, s), 8.08 (1H, d, J=8.0 Hz), 7.95-7.93 (2H, m), 7.84 (1H, d, J=7.6 Hz), 7.49 (1H, dt, J=7.6 and 1.2 Hz), 7.42 (1H, dt, J=8.0 and 0.8 Hz), 7.40-7.38 (2H, m), 6.47 (1H, s), 3.78-3.71 (1H, m), 2.38 (3H, s), 1.33 (3H, d, J=6.8 Hz), 1.04-0.99 (1H, m), 0.64-0.57 (1H, m), 0.56-0.49 (1H, m), 0.47-0.41 (1H, m), 0.33-0.27 (1H, m).

Example 168

4-N-[(1S)-1-cyclopropylethyl]-6-(2,3-dimethylphenyl)pyrimidine-2,4-diamine

Prepared according to general procedure 2 from (2,3-dimethylphenyl)boronic acid and 6-chloro-4-N-[(1S)-1-cyclopropylethyl]pyrimidine-2,4-diamine. LCMS [M+H]$^+$ 283; $^1$H NMR (400 MHz, CD$_3$OD) δ ppm 7.18 (1H, d, J=6.8 Hz), 7.11 (1H, t, J=7.6 Hz), 7.07 (1H, dd, J=7.6 and 1.6 Hz), 5.78 (1H, s), 3.56 (1H, br s), 2.32 (3H, s), 2.20 (3H, s), 1.27 (3H, d, J=6.4 Hz), 0.98-0.91 (1H, m), 0.56-0.43 (2H, m), 0.42-0.36 (1H, m), 0.27-0.21 (1H, m).

Example 169

4-N-[(1S)-1-cyclopropylethyl]-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-[(1S)-1-cyclopropylethyl]pyrimidine-2,4-diamine. LCMS [M+H]$^+$ 448; $^1$H NMR (400 MHz, CD$_3$OD) δ ppm 8.37 (1H, s), 8.09 (1H, d, J=8.4 Hz), 7.96-7.94 (2H, m), 7.85 (1H, d, J=8.0 Hz), 7.49 (1H, dt, J=7.6 and 1.2 Hz), 7.42 (1H, dt, J=8.0 and 1.2 Hz), 7.41-7.39 (2H, m), 6.47 (1H, s), 3.78-3.71 (1H, m), 2.39 (3H, s), 1.33 (3H, d, J=6.8 Hz), 1.05-0.98 (1H, m), 0.63-0.58 (1H, m), 0.57-0.50 (1H, m), 0.48-0.42 (1H, m), 0.33-0.27 (1H, m).

Example 170

6-(1-benzofuran-3-yl)-4-N-methylpyrimidine-2,4-diamine

Prepared according to general procedure 6 from (1-benzofuran-3-yl)boronic acid and 6-iodo-4-N-methylpyrimidine-2,4-diamine. LCMS [M+H]+ 241; ¹H NMR (400 MHz, CD₃OD) δ ppm 8.27 (1H, s), 8.07 (1H, dd, J=8.0 and 1.2 Hz), 7.58-7.56 (1H, m), 7.35 (2H, dt, J=7.6 and 1.2 Hz), 6.32 (1H, s), 2.95 (3H, s).

Example 171

6-(2-chloro-5-methylphenyl)-4-N-methylpyrimidine-2,4-diamine

Prepared according to general procedure 2 from (2-chloro-5-methylphenyl)boronic acid and 6-chloro-4-N-methylpyrimidine-2,4-diamine. LCMS [M+H]+ 249; ¹H NMR (400 MHz, CD₃OD) δ ppm 7.35 (1H, d, J=8.0 Hz), 7.28 (1H, d, J=2.0 Hz), 7.23-7.20 (1H, m), 5.97 (1H, s), 2.92 (3H, s), 2.38 (3H, s).

Example 172

6-(1-benzothiophen-3-yl)-4-N-methylpyrimidine-2,4-diamine

Prepared according to general procedure 2 from (1-benzothiophen-3-yl)boronic acid and 6-chloro-4-N-methylpyrimidine-2,4-diamine. LCMS [M+H]+ 257; ¹H NMR (400 MHz, CD₃OD) δ 8.27 (1H, d, J=7.2 Hz), 7.97-7.94 (1H, m), 7.92 (1H, s), 7.45 (1H, dt, J=7.2 and 1.6 Hz), 7.41 (1H, dt, J=7.2 and 1.6 Hz), 6.20 (1H, s), 2.95 (3H, s).

Example 173

2-{4-[2-amino-6-(methylamino)pyrimidin-4-yl]phenyl}propan-2-ol

Prepared according to general procedure 2 from [4-(2-hydroxypropan-2-yl)phenyl]boronic acid and 6-chloro-4-N-methylpyrimidine-2,4-diamine. LCMS [M+H]+ 259; ¹H NMR (400 MHz, CD₃OD) δ ppm 7.82-7.80 (2H, m), 7.60-7.57 (2H, m), 6.23 (1H, s), 2.94 (3H, s), 1.58 (6H, s).

Example 174

6-(1H-indol-4-yl)-4-N-methylpyrimidine-2,4-diamine

Prepared according to general procedure 2 from (1H-indol-4-yl)boronic acid and 6-chloro-4-N-methylpyrimidine-2,4-diamine. LCMS [M+H]+ 240; ¹H NMR (400 MHz, CD₃OD) δ ppm 7.50-7.48 (1H, m), 7.38 (1H, dd, J=7.6 and 0.8 Hz), 7.34 (1H, d, J=3.2 Hz), 7.21 (1H, t, J=7.6 Hz), 6.80 (1H, dd, J=3.2 and 0.8 Hz), 6.31 (1H, s), 2.96 (3H, s).

Example 175

4-N-cyclohexyl-6-(2,3-dichlorophenyl)pyrimidine-2,4-diamine

Prepared according to general procedure 3 from cyclohexanamine and 4-chloro-6-(2,3-dichlorophenyl)pyrimidin-2-amine. LCMS [M+H]+ 337; ¹H NMR (400 MHz, CD₃OD) δ ppm 7.63-7.61 (1H, m), 7.40 (1H, d, J=2.0 Hz), 7.39 (1H, s), 5.93 (1H, s), 3.88 (1H, br s), 2.06-2.02 (2H, m), 1.86-1.81 (2H, m), 1.73-1.69 (1H, m), 1.50-1.40 (2H, m), 1.34-1.25 (3H, m).

Example 176

6-(2,3-dichlorophenyl)-4-N-(propan-2-yl)pyrimidine-2,4-diamine

Prepared according to general procedure 3 from propan-2-amine and 4-chloro-6-(2,3-dichlorophenyl)pyrimidin-2-amine. LCMS [M+H]+ 297; ¹H NMR (400 MHz, CD₃OD) δ ppm 7.61-7.59 (1H, m), 7.38 (1H, d, J=2.0 Hz), 7.37 (1H, s), 5.92 (1H, s), 4.17 (1H, br s), 1.25 (3H, s), 1.24 (3H, s).

Example 177

4-N-(cyclopropylmethyl)-6-(2,3-dichlorophenyl)pyrimidine-2,4-diamine

Prepared according to general procedure 3 from cyclopropylmethanamine and 4-chloro-6-(2,3-dichlorophenyl)pyrimidin-2-amine. LCMS [M+H]+ 309.

Example 178

4-N-[(1S)-1-cyclopropylethyl]-6-(2,3-dichlorophenyl)pyrimidine-2,4-diamine

Prepared according to general procedure 3 from (1S)-1-cyclopropylethan-1-amine and 4-chloro-6-(2,3-dichlorophenyl)pyrimidin-2-amine. LCMS [M+H]+ 323; ¹H NMR (400 MHz, CD₃OD) δ ppm 7.61-7.59 (1H, m), 7.38 (1H, d, J=2.0 Hz), 7.37 (1H, s), 5.92 (1H, s), 3.59 (1H, br s), 1.28 (3H, d, J=6.8 Hz), 0.99-0.92 (2H, m), 0.53-0.48 (2H, m), 0.46-0.38 (1H, m), 0.29-0.23 (1H, m).

Example 179

4-N-[(1R)-1-cyclopropylethyl]-6-(2,3-dichlorophenyl)pyrimidine-2,4-diamine

Prepared according to general procedure 3 from (1R)-1-cyclopropylethan-1-amine and 4-chloro-6-(2,3-dichlorophenyl)pyrimidin-2-amine. LCMS [M+H]+ 323; ¹H NMR (400 MHz, CD₃OD) δ ppm 7.61-7.59 (1H, m), 7.38 (1H, d, J=2.0 Hz), 7.37 (1H, s), 5.92 (1H, s), 3.59 (1H, br s), 1.28 (3H, d, J=6.8 Hz), 0.99-0.92 (2H, m), 0.58-0.47 (2H, m), 0.46-0.38 (1H, m), 0.29-0.23 (1H, m).

Example 180

6-(2,3-dichlorophenyl)-4-N-(2,2-dimethylpropyl)pyrimidine-2,4-diamine

Prepared according to general procedure 3 from 2,2-dimethylpropan-1-amine and 4-chloro-6-(2,3-dichlorophenyl)pyrimidin-2-amine. LCMS [M+H]+ 325; ¹H NMR (400 MHz, CD₃OD) δ ppm 7.61-7.58 (1H, m), 7.38 (1H, d, J=2.0 Hz), 7.36 (1H, s), 6.01 (1H, s), 3.27 (2H, br s), 0.98 (9H, s).

Example 181

6-(2,3-dimethylphenyl)-4-N-(2,2-dimethylpropyl)pyrimidine-2,4-diamine

Prepared according to general procedure 5 from (2,3-dimethylphenyl)boronic acid and 6-chloro-4-N-(2,2-dimethylpropyl)pyrimidine-2,4-diamine. LCMS [M+H]⁺ 285; ¹H NMR (400 MHz, CD₃OD) δ ppm 7.20 (1H, d, J=6.8 Hz), 7.14 (1H, t, J=7.6 Hz), 7.10 (1H, dd, J=7.6 and 1.6 Hz), 5.90 (1H, s), 2.34 (3H, s), 2.22 (3H, s), 1.00 (9H, s).

Example 182

4-N-(2,2-dimethylpropyl)-6-[1-(4-methylbenzene-sulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-(2,2-dimethylpropyl)pyrimidine-2,4-diamine. LCMS [M+H]⁺ 450; ¹H NMR (400 MHz, CD₃OD) δ ppm 8.14 (1H, s), 8.08 (1H, d, J=7.6), 8.04 (1H, dt, J=8.0 and 1.2 Hz), 7.90-7.88 (2H, m), 7.39 (1H, td, J=7.2 and 1.2 Hz), 7.37-7.34 (2H, m), 7.33 (1H, td, J=7.2 and 1.2 Hz), 6.38 (1H, s), 3.27 (2H, s), 2.37 (3H, s), 1.02 (9H, s).

Example 183

6-(5-bromo-2-methoxyphenyl)-4-N-methylpyrimidine-2,4-diamine

Prepared according to general procedure 6 from (5-bromo-2-methoxyphenyl)boronic acid and 6-iodo-4-N-methylpyrimidine-2,4-diamine. LCMS [M+H]⁺ 309; ¹H NMR (400 MHz, CD₃OD) δ ppm 7.72 (1H, d, J=2.4 Hz), 7.52 (1H, dd, J=8.8 and 2.8 Hz), 7.04 (1H, d, J=9.2 Hz), 6.25 (1H, s), 3.87 (3H, s), 2.91 (s, 3H).

Example 184

6-(2,5-dimethylphenyl)-4-N-methylpyrimidine-2,4-diamine

Prepared according to general procedure 6 from (2,5-dimethylphenyl)boronic acid and 6-iodo-4-N-methylpyrimidine-2,4-diamine. LCMS [M+H]⁺ 229; ¹H NMR (400 MHz, CD₃OD) δ ppm 7.16-7.13 (2H, m), 7.11 (1H, s), 5.84 (1H, s), 2.92 (3H, s), 2.35 (3H, s), 2.29 (3H, s).

Example 185

4-N-methyl-6-[2-(trifluoromethyl)pyridin-3-yl]pyrimidine-2,4-diamine

Prepared according to general procedure 6 from [2-(trifluoromethyl)pyridin-3-yl]boronic acid and 6-iodo-4-N-methylpyrimidine-2,4-diamine. LCMS [M+H]⁺ 270.

Example 186

6-(3-chloro-2-methyl-phenyl)-N4-[2-(3-methylsulfonylanilino)ethyl]pyrimidine-2,4-diamine Step 1. N'-(3-methylsulfonylphenyl)ethane-1,2-diamine was prepared according to general procedure 13 from 1-bromo-3-methylsulfonyl-benzene.
Step 2. The title compound was prepared according to general procedure 9 from intermediate 24 and N'-(3-methylsulfonylphenyl)ethane-1,2-diamine. [M+H]⁺ 432.
¹H NMR (400 MHz, CHLOROFORM-d) δ ppm 7.37 (dd, J=7.3, 1.9 Hz, 1 H), 7.28-7.33 (m, 2 H), 7.20-7.24 (m, 1 H), 7.12-7.20 (m, 2 H), 6.82 (ddd, J=8.2, 2.5, 0.9 Hz, 1 H), 5.76 (s, 1 H), 5.18 (br. s., 3 H), 4.66-4.79 (m, 1 H), 3.62 (d, J=6.3 Hz, 2 H), 3.38-3.45 (m, 2 H), 3.05-3.08 (m, 3 H), 2.36 (s, 3 H).

Example 187

6-[4-(benzyloxy)-2-methylphenyl]-4-N-methylpyrimidine-2,4-diamine

Prepared according to general procedure 6 from [4-(benzyloxy)-2-methylphenyl]boronic acid and 6-iodo-4-N-methylpyrimidine-2,4-diamine. LCMS [M+H]⁺ 321; ¹H NMR (400 MHz, CD₃OD) δ ppm 7.47-7.46 (2H, m), 7.41-7.38 (2H, m), 7.35-7.32 (1H, m), 7.24 (1H, d, J=8.4 Hz), 6.92-6.87 (2H, m), 5.84 (1H, s), 5.14 (2H, s), 2.91 (3H, s), 2.34 (3H, s).

Example 188

6-(4-methoxy-2,5-dimethylphenyl)-4-N-methylpyrimidine-2,4-diamine

Prepared according to general procedure 6 from (4-methoxy-2,5-dimethylphenyl)boronic acid and 6-iodo-4-N-methylpyrimidine-2,4-diamine. LCMS [M+H]⁺ 259; ¹H NMR (400 MHz, CD₃OD) δ ppm 7.08 (1H, s), 6.79 (1H, s), 5.83 (1H, s), 3.86 (3H, s), 2.91 (3H, s), 2.34 (3H, s), 2.19 (3H, s).

Example 189

4-N-methyl-6-(2,4,5-trimethylphenyl)pyrimidine-2,4-diamine

Prepared according to general procedure 6 from (2,4,5-trimethylphenyl)boronic acid and 6-iodo-4-N-methylpyrimidine-2,4-diamine. LCMS [M+H]⁺ 243; ¹H NMR (400 MHz, CD₃OD) δ ppm 7.07 (1H, s), 7.03 (1H, s), 5.83 (1H, s), 2.91 (3H, s), 2.28 (9H, s).

Example 190

2-[2-amino-6-(methylamino)pyrimidin-4-yl]-4-chlorobenzonitrile

Prepared according to general procedure 6 from (5-chloro-2-cyanophenyl)boronic acid and 6-iodo-4-N-methylpyrimidine-2,4-diamine. LCMS [M+H]⁺ 260.

Example 191

6-(4,5-dichloro-2-methylphenyl)-4-N-methylpyrimidine-2,4-diamine

Prepared according to general procedure 6 from (4,5-dichloro-2-methylphenyl)boronic acid and 6-iodo-4-N-methylpyrimidine-2,4-diamine. LCMS [M+H]⁺ 283; ¹H NMR (400 MHz, CD₃OD) δ ppm 7.62 (1H, s), 7.61 (1H, s), 6.06 (1H, s), 3.04 (3H, s), 2.36 (3H, s).

Example 192

6-(2,5-dichloro-4-methoxyphenyl)-4-N-methylpyrimidine-2,4-diamine

Prepared according to general procedure 6 from (2,5-dichloro-4-methoxyphenyl)boronic acid and 6-iodo-4-N- methylpyrimidine-2,4-diamine. LCMS [M+H]+ 299; 1H NMR (400 MHz, CD3OD) δ ppm 7.52 (1H, s), 7.22 (1H, s), 6.03 (1H, s), 3.96 (3H, s), 2.92 (3H, s).

Example 193

6-(4-fluoro-2,5-dimethylphenyl)-4-N-methylpyrimidine-2,4-diamine

Prepared according to general procedure 6 from (4-fluoro-2,5-dimethylphenyl)boronic acid and 6-iodo-4-N-methylpyrimidine-2,4-diamine. LCMS [M+H]+ 247; 1H NMR (400 MHz, CD3OD) δ ppm 7.16 (1H, d, J=8.0 Hz), 6.95 (1H, d, J=10.8 Hz), 5.83 (1H, s), 2.91 (3H, s), 2.30 (3H, s), 2.27 (3H, s).

Example 194

4-N-methyl-6-[2-methyl-5-(trifluoromethyl)phenyl]pyrimidine-2,4-diamine

Prepared according to general procedure 6 from [2-methyl-5-(trifluoromethyl)phenyl]boronic acid and 6-iodo-4-N-methylpyrimidine-2,4-diamine. LCMS [M+H]+ 283; 1H NMR (400 MHz, CD3OD) δ ppm 7.78-7.73 (2H, m), 7.61 (1H, d, J=8.0 Hz), 6.08 (1H, s), 3.05 (3H, s), 2.46 (3H, s).

Example 195

6-[5-chloro-2-methyl-4-(trifluoromethyl)phenyl]-4-N-methylpyrimidine-2,4-diamine Prepared according to general procedure 6 from [5-chloro-2-methyl-4-(trifluoromethyl)phenyl]boronic acid and 6-iodo-4-N-methylpyrimidine-2,4-diamine. LCMS [M+H]+ 317; 1H NMR (400 MHz, CD3OD) δ ppm 7.69 (1H, s), 7.53 (1H, s), 5.89 (1H, s), 2.93 (3H, s), 2.40 (3H, s).

Example 196

6-[2,5-bis(trifluoromethyl)phenyl]-4-N-methylpyrimidine-2,4-diamine

Prepared according to general procedure 6 from [2,5-bis(trifluoromethyl)phenyl]boronic acid and 6-iodo-4-N-methylpyrimidine-2,4-diamine. LCMS [M+H]+ 337; 1H NMR (400 MHz, CD3OD) δ ppm 8.20-8.15 (2H, m), 8.10 (1H, s), 6.15 (1H, s), 3.08 (3H, s).

Example 197

6-(5-tert-butyl-2-methoxyphenyl)-4-N-methylpyrimidine-2,4-diamine

Prepared according to general procedure 6 from (5-tert-butyl-2-methoxyphenyl)boronic acid and 6-iodo-4-N-methylpyrimidine-2,4-diamine. LCMS [M+H]+ 287; 1H NMR (400 MHz, CD3OD) δ ppm 7.64 (1H, dd, J=8.8 and 2.4 Hz), 7.51 (1H, s), 7.17 (1H, d, J=8.8 Hz), 6.25 (1H, s), 3.94 (3H, s), 3.05 (3H, s), 1.37 (9H, s).

Example 198

6-[2-methoxy-5-(propan-2-yl)phenyl]-4-N-methylpyrimidine-2,4-diamine

Prepared according to general procedure 6 from [2-methoxy-5-(propan-2-yl)phenyl]boronic acid and 6-iodo-4-N-methylpyrimidine-2,4-diamine. LCMS [M+H]+ 273; 1H NMR (400 MHz, CD3OD) δ ppm 7.49 (1H, dd, J=8.4 and 2.0 Hz), 7.39 (1H, s), 7.17 (1H, d, J=8.8 Hz), 6.28 (1H, s), 3.95 (3H, s), 3.06 (3H, s), 2.98 (1H, sept, J=6.8 Hz), 1.31 (3H, s), 1.30 (3H, s).

Example 199

6-[2-chloro-5-(trifluoromethyl)phenyl]-4-N-methylpyrimidine-2,4-diamine

Prepared according to general procedure 6 from [2-chloro-5-(trifluoromethyl)phenyl]boronic acid and 6-iodo-4-N-methylpyrimidine-2,4-diamine. LCMS [M+H]+ 303; 1H NMR (400 MHz, CD3OD) δ ppm 7.87 (1H, br s), 7.82 (1H, d, J=2.0 Hz), 7.81 (1H, s), 6.14 (1H, s), 3.03 (3H, s).

Example 200

6-(2-fluoro-5-methylphenyl)-4-N-methylpyrimidine-2,4-diamine

Prepared according to general procedure 6 from (2-fluoro-5-methylphenyl)boronic acid and 6-iodo-4-N-methylpyrimidine-2,4-diamine. LCMS [M+H]+ 233; 1H NMR (400 MHz, CD3OD) δ ppm 7.58 (1H, dd, J=7.2 and 2.0 Hz), 7.28-7.25 (1H, m), 7.10-7.06 (1H, m), 6.02 (1H, d, J=1.6 Hz), 2.94 (3H, s), 2.40 (3H, s).

Example 201

6-(5-chloro-2-methoxyphenyl)-4-N-methylpyrimidine-2,4-diamine

Prepared according to general procedure 6 from (5-chloro-2-methoxyphenyl)boronic acid and 6-iodo-4-N-methylpyrimidine-2,4-diamine. LCMS [M+H]+ 265; 1H NMR (400 MHz, CD3OD) δ 7.58-7.57 (1H, m), 7.56 (1H, d, J=2.8 Hz), 7.23 (1H, d, J=9.6 Hz), 6.27 (1H, s), 3.96 (3H, s), 3.05 (3H, s).

Example 202

6-(5-fluoro-2-methylphenyl)-4-N-methylpyrimidine-2,4-diamine

Prepared according to general procedure 6 from (5-fluoro-2-methylphenyl)boronic acid and 6-iodo-4-N-methylpyrimidine-2,4-diamine. LCMS [M+H]+ 233; 1H NMR (400 MHz, CD3OD) δ ppm 7.31-7.27 (1H, m), 7.08-7.04 (2H, m), 5.87 (1H, s), 2.94 (3H, s), 2.33 (3H, s).

Example 203

6-(2,5-dimethoxyphenyl)-4-N-methylpyrimidine-2,4-diamine

Prepared according to general procedure 6 from (2,5-dimethoxyphenyl)boronic acid and 6-iodo-4-N-methylpyrimidine-2,4-diamine. LCMS [M+H]+ 261; 1H NMR (400

MHz, CD₃OD) δ ppm 7.18 (1H, d, J=3.2 Hz), 7.04 (1H, d, J=9.2 Hz), 6.98 (1H, dd, J=8.8 and 3.2 Hz), 6.27 (1H, s), 3.83 (6H, s), 2.93 (3H, s).

Example 204

6-(2-methoxy-5-methylphenyl)-4-N-methylpyrimidine-2,4-diamine

Prepared according to general procedure 6 from (2-methoxy-5-methylphenyl)boronic acid and 6-iodo-4-N-methylpyrimidine-2,4-diamine. LCMS [M+H]⁺ 245; ¹H NMR (400 MHz, CD₃OD) δ 7.36 (1H, s), 7.20 (1H, d, J=8.8 Hz), 6.98 (1H, d, J=8.8 Hz), 6.20 (1H, s), 3.83 (3H, s), 2.91 (3H, s), 2.33 (3H, s).

Example 205

6-(2-chloro-5-fluorophenyl)-4-N-methylpyrimidine-2,4-diamine

Prepared according to general procedure 6 from (2-chloro-5-fluorophenyl)boronic acid and 6-iodo-4-N-methylpyrimidine-2,4-diamine. LCMS [M+H]⁺ 253; ¹H NMR (400 MHz, CD₃OD) δ ppm 7.54-7.50 (1H, m), 7.25 (1H, dd, J=9.2 and 3.2 Hz), 7.19 (1H, td, J=8.8 and 3.2 Hz), 6.01 (1H, s), 2.93 (3H, s).

Example 206

3-[2-amino-6-(methylamino)pyrimidin-4-yl]-4-fluorobenzonitrile

Prepared according to general procedure 6 from (5-cyano-2-fluorophenyl)boronic acid and 6-iodo-4-N-methylpyrimidine-2,4-diamine. LCMS [M+H]⁺ 244; ¹H NMR (400 MHz, CD₃OD) δ ppm 8.26 (1H, dd, J=6.8 and 2.0 Hz), 7.87-7.84 (1H, m), 7.45-7.40 (1H, m), 6.27 (1H, d, J=2.0 Hz), 2.93 (3H, s).

Example 207

6-(2-chloro-5-methoxyphenyl)-4-N-methylpyrimidine-2,4-diamine

Prepared according to general procedure 6 from (2-chloro-5-methoxyphenyl)boronic acid and 6-iodo-4-N-methylpyrimidine-2,4-diamine. LCMS [M+H]⁺ 265; ¹H NMR (400 MHz, CD₃OD) δ ppm 7.39 (1H, d, J=8.8 Hz), 7.02 (1H, d, J=3.2 Hz), 6.98 (1H, dd, J=8.8 and 3.2 Hz), 5.99 (1H, s), 3.84 (3H, s), 2.92 (3H, s).

Example 208

6-[5-fluoro-2-(trifluoromethyl)phenyl]-4-N-methylpyrimidine-2,4-diamine

Prepared according to general procedure 6 from [5-fluoro-2-(trifluoromethyl)phenyl]boronic acid and 6-iodo-4-N-methylpyrimidine-2,4-diamine. LCMS [M+H]⁺ 287; ¹H NMR (400 MHz, CD₃OD) δ ppm 7.87-7.83 (1H, m), 7.39-7.34 (1H, m), 7.25 (1H, dd, J=9.2 and 2.8 Hz), 5.89 (1H, s), 2.92 (3H, s).

Example 209

6-(2,5-dichlorophenyl)-4-N-methylpyrimidine-2,4-diamine

Prepared according to general procedure 6 from (2,5-dichlorophenyl)boronic acid and 6-iodo-4-N-methylpyrimidine-2,4-diamine. LCMS [M+H]⁺ 269; ¹H NMR (400 MHz, CD₃OD) δ ppm 7.51-7.49 (2H, m), 7.42 (1H, dd, J=8.4 and 2.4 Hz), 6.01 (1H, s), 2.92 (3H, s).

Example 210

6-(5-chloro-2-fluorophenyl)-4-N-methylpyrimidine-2,4-diamine

Prepared according to general procedure 6 from (5-chloro-2-fluorophenyl)boronic acid and 6-iodo-4-N-methylpyrimidine-2,4-diamine. LCMS [M+H]⁺ 253; ¹H NMR (400 MHz, CD₃OD) δ ppm 7.75-7.23 (1H, m), 7.69-7.65 (1H, m), 7.40 (1H, m), 6.31 (1H, s), 3.07 (3H, s).

Example 211

3-[2-amino-6-(methylamino)pyrimidin-4-yl]-4-methylbenzonitrile

Prepared according to general procedure 6 from (5-cyano-2-methylphenyl)boronic acid and 6-iodo-4-N-methylpyrimidine-2,4-diamine. LCMS [M+H]⁺ 240; ¹H NMR (400 MHz, CD₃OD) δ 7.68-7.66 (2H, m), 7.48 (1H, d, J=7.6 Hz), 5.88 (1H, s), 2.93 (3H, s), 2.44 (3H, s).

Example 212

3-[2-amino-6-(methylamino)pyrimidin-4-yl]-4-methoxybenzonitrile

Prepared according to general procedure 6 from (5-cyano-2-methoxyphenyl)boronic acid and 6-iodo-4-N-methylpyrimidine-2,4-diamine. LCMS [M+H]⁺ 256; ¹H NMR (400 MHz, CD₃OD) δ ppm 7.95 (1H, d, J=2.4 Hz), 7.98 (1H, dd, J=8.8 and 2.0 Hz), 7.27 (1H, d, J=8.8 Hz), 6.26 (1H, s), 3.97 (3H, s), 2.92 (3H, s).

Example 213

6-(2-chloro-5-fluoro-4-methylphenyl)-4-N-methylpyrimidine-2,4-diamine

Prepared according to general procedure 6 from (2-chloro-5-fluoro-4-methylphenyl)boronic acid and 6-iodo-4-N-methylpyrimidine-2,4-diamine. LCMS [M+H]⁺ 267; ¹H NMR (400 MHz, CD₃OD) δ ppm 7.39 (1H, d, J=6.8 Hz), 7.19 (1H, d, J=9.6 Hz), 6.02 (1H, s), 2.92 (3H, s), 2.32 (3H, d, J=1.6 Hz).

Example 214

6-(5-chloro-2-fluoro-4-methylphenyl)-4-N-methylpyrimidine-2,4-diamine

Prepared according to general procedure 6 from (5-chloro-2-fluoro-4-methylphenyl)boronic acid and 6-iodo- 4-N-methylpyrimidine-2,4-diamine. LCMS [M+H]+ 267; $^1$H NMR (400 MHz, CD$_3$OD) δ 7.72 (1H, d, J=6.8 Hz), 7.19 (1H, d, J=11.2 Hz), 6.31 (1H, s), 3.05 (3H, s), 2.48 (3H, s).

Example 215

6-(2-chloro-4-fluoro-5-methylphenyl)-4-N-methyl-pyrimidine-2,4-diamine

Prepared according to general procedure 6 from (2-chloro-4-fluoro-5-methylphenyl)boronic acid, and 6-iodo-4-N-methylpyrimidine-2,4-diamine LCMS [M+H]+ 267; $^1$H NMR (400 MHz, CD$_3$OD) δ ppm 7.36 (1H, d, J=8.4 Hz), 7.23 (1H, d, J=9.6 Hz), 5.96 (1H, s), 2.91 (3H, s), 2.29 (3H, d, J=1.6 Hz).

Example 216

4-N-cyclopropyl-6-(4-fluoro-2,5-dimethylphenyl)pyrimidine-2,4-diamine

Prepared according to general procedure 2 from (4-fluoro-2,5-dimethylphenyl)boronic acid and 6-chloro-4-N-cyclopropylpyrimidine-2,4-diamine. LCMS [M+H]+ 273; $^1$H NMR (400 MHz, CD$_3$OD) δ ppm 7.19 (1H, d, J=8.0 Hz), 6.97 (1H, d, J=10.4 Hz), 6.03 (1H, s), 2.63 (1H, br s), 2.33 (3H, s), 2.28 (3H, s), 0.84-0.79 (2H, m), 0.60-0.56 (2H, m).

Example 217

4-N-cyclopropyl-6-(4-methoxy-2,5-dimethylphenyl)pyrimidine-2,4-diamine

Prepared according to general procedure 2 from (4-methoxy-2,5-dimethylphenyl)boronic acid and 6-chloro-4-N-cyclopropylpyrimidine-2,4-diamine. LCMS [M+H]+ 285.

Example 218

4-N-cyclopropyl-6-(2,5-dimethylphenyl)pyrimidine-2,4-diamine

Prepared according to general procedure 2 from (2,5-dimethylphenyl)boronic acid and 6-chloro-4-N-cyclopropylpyrimidine-2,4-diamine. LCMS [M+H]+ 255; $^1$H NMR (400 MHz, CD$_3$OD) δ ppm 7.30-7.28 (2H, m), 7.23 (1H, s), 6.00 (1H, s), 3.06 (1H, br s), 2.40 (3H, s), 2.36 (3H, s), 0.93-0.88 (2H, m), 0.69-0.66 (2H, m).

Example 219

6-(5-chloro-2-methylphenyl)-4-N-cyclopropylpyrimidine-2,4-diamine

Prepared according to general procedure 2 from (5-chloro-2-methylphenyl)boronic acid and 6-chloro-4-N-cyclopropylpyrimidine-2,4-diamine. LCMS [M+H]+ 275; $^1$H NMR (400 MHz, CD$_3$OD) δ ppm 7.33-7.27 (3H, m), 6.05 (1H, s), 2.65 (1H, br s), 0.84-0.79 (2H, m), 0.60-0.56 (2H, m).

Example 220

6-(5-chloro-2-methylphenyl)-4-N-cyclobutylpyrimidine-2,4-diamine

Prepared according to general procedure 2 from (5-chloro-2-methylphenyl)boronic acid and 6-chloro-4-N-cyclobutylpyrimidine-2,4-diamine. LCMS [M+H]+ 289; $^1$H NMR (400 MHz, CD$_3$OD) δ ppm 7.33-7.26 (3H, m), 5.81 (1H, s), 4.45 (1H, br s), 2.44-2.37 (2H, m), 2.32 (3H, s), 2.05-1.95 (2H, m), 1.83-1.74 (2H, m).

Example 221

6-(5-chloro-2-methylphenyl)-4-N-ethylpyrimidine-2,4-diamine

Prepared according to general procedure 2 from (5-chloro-2-methylphenyl)boronic acid and 6-chloro-4-N-ethylpyrimidine-2,4-diamine. LCMS [M+H]+ 263; $^1$H NMR (400 MHz, CD$_3$OD) δ ppm 7.51-7.46 (2H, m), 7.41 (1H, d, J=8.4 Hz), 6.05 (1H, s), 3.57 (2H, q, J=6.8 Hz), 2.37 (3H, s), 1.28 (3H, t, J=7.2 Hz).

Example 222

6-(5-chloro-2-methylphenyl)-4-N-[2-(4-chlorophenyl)ethyl]pyrimidine-2,4-diamine

Prepared according to general procedure 2 from (5-chloro-2-methylphenyl)boronic acid and 6-chloro-4-N-[2-(4-chlorophenyl)ethyl]pyrimidine-2,4-diamine. LCMS [M+H]+ 373; $^1$H NMR (400 MHz, CD$_3$OD) δ ppm 7.32-7.26 (7H, m), 5.81 (1H, s), 3.64-3.60 (2H, m), 2.92 (2H, t, J=7.6 Hz), 2.31 (3H, s).

Example 223

4-N-[2-(4-chlorophenyl)ethyl]-6-(4-fluoro-2,5-dimethylphenyl)pyrimidine-2,4-diamine Prepared according to general procedure 2 from (4-fluoro-2,5-dimethylphenyl)boronic acid and 6-chloro-4-N-[2-(4-chlorophenyl)ethyl]pyrimidine-2,4-diamine. LCMS [M+H]+ 371; $^1$H NMR (400 MHz, CD$_3$OD) δ ppm 7.32-7.26 (4H, m), 7.14 (1H, d, J=8.0 Hz), 6.94 (1H, d, J=10.8 Hz), 5.79 (1H, s), 3.63-3.59 (2H, m), 2.92 (2H, t, J=7.2 Hz), 2.30 (3H, s), 2.27 (3H, s).

Example 224

4-N-[2-(4-chlorophenyl)ethyl]-6-(2,5-dimethylphenyl)pyrimidine-2,4-diamine

Prepared according to general procedure 2 from (2,5-dimethylphenyl)boronic acid and 6-chloro-4-N-[2-(4-chlorophenyl)ethyl]pyrimidine-2,4-diamine. LCMS [M+H]+ 353; $^1$H NMR (400 MHz, CD$_3$OD) δ 7.32-7.26 (4H, m), 7.16-7.09 (3H, m), 5.80 (1H, s), 3.61 (2H, t, J=6.4 Hz), 2.92 (2H, t, J=7.2 Hz), 2.35 (3H, s), 2.28 (3H, s).

Example 225

1-(3-{[2-amino-6-(quinolin-5-yl)pyrimidin-4-yl]amino}propyl)pyrrolidin-2-one

Prepared according to general procedure 2 from (quinolin-5-yl)boronic acid and 1-{3-[(2-amino-6-chloropyrimidin-4-yl)amino]propyl}pyrrolidin-2-one. LCMS [M+H]+ 363; $^1$H NMR (400 MHz, CD$_3$OD) δ ppm 8.90 (1H, dd, J=4.0 and 1.6 Hz), 8.64 (1H, d, J=8.8 Hz), 8.12 (1H, d, J=8.4 Hz), 7.88-7.84 (1H, m), 7.71 (1H, d, J=7.2 Hz), 7.59-7.56

(1H, m), 6.07 (1H, s), 3.53 (2H, t, J=6.8 Hz), 3.42 (4H, t, J=6.8 Hz), 2.42 (2H, t, J=8.0 Hz), 2.12-2.05 (2H, m), 1.93-1.86 (2H, m).

Example 226

6-(2-chloro-3-methylphenyl)-4-N-methylpyrimidine-2,4-diamine

Prepared according to general procedure 3 from methanamine and 4-chloro-6-(2-chloro-3-methylphenyl)pyrimidin-2-amine. LCMS [M+H]$^+$ 249; $^1$H NMR (400 MHz, CD$_3$OD) δ ppm 7.56-7.54 (1H, m), 7.42-7.37 (2H, m), 6.11 (1H, s), 3.05 (3H, s), 2.49 (3H, s).

Example 227

6-(2-chloro-3-methylphenyl)-4-N-cyclopropylpyrimidine-2,4-diamine

Prepared according to general procedure 3 from cyclopropanamine and 4-chloro-6-(2-chloro-3-methylphenyl)pyrimidin-2-amine. LCMS [M+H]$^+$ 275; $^1$H NMR (400 MHz, CD$_3$OD) δ ppm 7.56 (1H, d, J=5.6 Hz), 7.42-7.39 (2H, m), 6.07 (1H, s), 3.09 (1H, br s), 2.50 (3H, s), 0.92-0.90 (2H, m), 0.68 (2H, br s).

Example 228

6-(2-chloro-3-methylphenyl)-4-N-[2-(4-chlorophenyl)ethyl]pyrimidine-2,4-diamine

Prepared according to general procedure 3 from 2-(4-chlorophenyl)ethan-1-amine and 4-chloro-6-(2-chloro-3-methylphenyl)pyrimidin-2-amine. LCMS [M+H]$^+$ 373; $^1$H NMR (400 MHz, CD$_3$OD) δ ppm 7.57-7.55 (1H, m), 7.41 (1H, t, J=7.6 Hz), 7.37 (1H, dd, J=8.0 and 2.0 Hz), 7.34-7.28 (4H, m), 6.08 (1H, s), 3.79 (2H, t, J=7.2 Hz), 2.97 (2H, t, J=7.2 Hz), 2.49 (3H, s).

Example 229

1-(3-{[2-amino-6-(2-chloro-3-methylphenyl)pyrimidin-4-yl]amino}propyl)pyrrolidin-2-one Prepared according to general procedure 3 from 1-(3-aminopropyl)pyrrolidin-2-one and 4-chloro-6-(2-chloro-3-methylphenyl)pyrimidin-2-amine. LCMS [M+H]$^+$ 360; $^1$H NMR (400 MHz, CD$_3$OD) δ ppm 7.57-7.55 (1H, m), 7.44-7.38 (2H, m), 6.13 (1H, s), 3.55 (2H, t, J=5.6 Hz), 3.52 (2H, t, J=7.2 Hz), 3.41 (2H, t, J=6.8 Hz), 2.49 (3H, s), 2.42 (2H, t, J=8.0 Hz), 2.09 (2H, quintet, J=7.6 Hz), 1.92 (2H, quintet, J=7.2 Hz).

Example 230

4-N-cyclopropyl-6-(1H-indol-4-yl)pyrimidine-2,4-diamine

Prepared according to general procedure 3 from cyclopropanamine and 4-chloro-6-(1H-indol-4-yl)pyrimidin-2-amine. LCMS [M+H]$^+$ 266; $^1$H NMR (400 MHz, CD$_3$OD) δ ppm 7.67 (1H, d, J=7.6 Hz), 7.50 (1H, s), 7.33 (2H, d, J=7.2 Hz), 6.71 (1H, s), 6.43 (1H, s), 3.10 (1H, br s), 0.92 (2H, br s), 0.69 (2H, br s).

Example 231

4-N-[2-(4-chlorophenyl)ethyl]-6-(1H-indol-4-yl)pyrimidine-2,4-diamine

Prepared according to general procedure 3 from 2-(4-chlorophenyl)ethan-1-amine and 4-chloro-6-(1H-indol-4-yl)pyrimidin-2-amine. LCMS [M+H]$^+$ 364; $^1$H NMR (400 MHz, CD$_3$OD) δ ppm 7.67-7.66 (1H, m), 7.52-7.46 (1H, m), 7.35-7.29 (6H, m), 6.86 (1H, s), 6.44 (1H, s), 3.80 (2H, t, J=7.2 Hz), 2.95 (2H, t, J=6.8 Hz).

Example 232

4-N-cyclopropyl-6-(quinolin-5-yl)pyrimidine-2,4-diamine

Prepared according to general procedure 3 from cyclopropanamine and 4-chloro-6-(quinolin-5-yl)pyrimidin-2-amine. LCMS [M+H]$^+$ 278; $^1$H NMR (400 MHz, CD$_3$OD) δ ppm 8.91 (1H, dd, J=4 and 1.6 Hz), 8.66 (1H, d, J=8.4 Hz), 8.14 (1H, d, J=8.4 Hz), 7.89-7.85 (1H, m), 7.74 (1H, d, J=6.8 Hz), 7.59-7.56 (1H, m), 6.26 (1H, s), 2.69 (1H, br s), 0.85-0.80 (2H, m), 0.62-0.59 (2H, m).

Example 233

(2E)-3-{4-[2-amino-6-(methylamino)pyrimidin-4-yl]phenyl}prop-2-enoic acid

Prepared according to general procedure 6 from (2E)-3-[4-(dihydroxyboranyl)phenyl]prop-2-enoic acid and 6-iodo-4-N-methylpyrimidine-2,4-diamine. LCMS [M+H]$^+$ 271.

Example 234 tert-butyl 3-({[2-amino-6-(2,3-dimethylphenyl)pyrimidin-4-yl]amino}methyl)-azetidine-1-carboxylate Prepared according to general procedure 3 from tert-butyl 3-(aminomethyl)azetidine-1-carboxylate and 4-chloro-6-(2,3-dimethylphenyl)-pyrimidin-2-amine. LCMS [M+H]$^+$ 384; $^1$H NMR (400 MHz, CD$_3$OD) δ ppm 7.19 (1H, d, J=7.6 Hz), 7.12 (1H, t, J=7.6 Hz), 7.07 (1H, d, J=7.6 Hz), 5.82 (s, 1H), 4.05-4.00 (2H, m), 3.73-3.69 (2H, m), 3.60-3.59 (2H, m), 2.92-2.82 (1H, m), 2.33 (3H, s), 2.21 (3H, s), 1.45 (9H, s).

Example 235

4-N-cyclopropyl-6-(1H-indol-5-yl)pyrimidine-2,4-diamine

Prepared according to general procedure 2 from (1H-indol-5-yl)boronic acid and 6-chloro-4-N-cyclopropylpyrimidine-2,4-diamine. LCMS [M+H]$^+$ 266.

Example 236

1-(3-{[2-amino-6-(1H-indol-5-yl)pyrimidin-4-yl]amino}propyl)pyrrolidin-2-one

Prepared according to general procedure 2 from (1H-indol-5-yl)boronic acid and 1-{3-[(2-amino-6-chloropyrimidin-4-yl)amino]propyl}pyrrolidin-2-one. LCMS [M+H]$^+$ 351; $^1$H NMR (400 MHz, CD$_3$OD) δ ppm 8.02 (1H, d, J=1.6 Hz), 7.59 (1H, d, J=8.4 Hz), 7.48 (1H, dd, J=8.4 and 2.0 Hz), 7.42 (1H, d, J=3.2 Hz), 6.64 (1H, d, J=3.2 Hz), 6.37 (1H, s), 3.57-3.51 (4H, m), 3.42 (2H, t, J=7.2 Hz), 2.43 (2H, t, J=8.0 Hz), 2.10 (2H, quintet, J=8.4 Hz), 1.93 (2H, quintet, J=7.2 Hz).

Example 237 tert-Butyl 4-((2-amino-6-(2,3-dimethylphenyl)pyrimidin-4-yl)amino)piperidine-1-carboxylate Prepared according to general procedure 3 from 4-chloro-6-(2,3-dimethylphenyl)pyrimidin-2-amine and tert-butyl 4-aminopiperidine-1-carboxylate. LCMS [M+H]$^+$ 398; $^1$H NMR (400 MHz, CD$_3$OD) δ ppm 7.19 (1H, d, J=6.8 Hz), 7.13 (1H, t, J=7.6 Hz), 7.08 (1H, dd, J=7.2 and 0.8 Hz), 5.82 (1H, s), 4.07-4.05 (2H, m), 2.99 (2H, m), 2.33 (3H, s), 2.22 (3H, s), 2.03-1.99 (2H, s), 1.49 (9H, s), 1.42-1.39 (2H, m).

Example 238

Ethyl 4-((2-amino-6-(2,3-dimethylphenyl)pyrimidin-4-yl)amino)piperidine-1-carboxylate Prepared according to general procedure 3 from 4-chloro-6-(2,3-dimethylphenyl)pyrimidin-2-amine and ethyl 4-aminopiperidine-1-carboxylate. LCMS [M+H]$^+$ 370; $^1$H NMR (400 MHz, CD$_3$OD) δ ppm 7.19 (1H, d, J=7.2 Hz), 7.11 (1H, t, J=7.2 Hz), 7.08 (1H, d, J=7.6 Hz), 5.82 (1H, s), 4.15 (2H, q, J=7.2 Hz), 4.15-4.09 (3H, m), 3.07-2.98 (2H, m), 2.33 (3H, s), 2.21 (3H, s), 2.04-2.01 (2H, m), 1.48-1.39 (2H, m), 1.29 (4H, t, J=7.2 Hz).

Example 239 tert-Butyl (3-((2-amino-6-(2,3-dimethylphenyl)pyrimidin-4-yl)amino)-2,2-dimethyl-propyl)carbamate Prepared according to general procedure 3 from 4-chloro-6-(2,3-dimethylphenyl)pyrimidin-2-amine and tert-butyl N-(3-amino-2,2-dimethylpropyl)carbamate. LCMS [M+H]$^+$ 400.

Example 240

6-(5-chloro-4-methoxy-2-methylphenyl)-4-N-methylpyrimidine-2,4-diamine

Prepared according to general procedure 6 from (5-chloro-4-methoxy-2-methylphenyl)boronic acid and 6-iodo-4-N-methylpyrimidine-2,4-diamine. LCMS [M+H]$^+$ 279.

Example 241

6-(3-chloro-2-methylphenyl)-4-N-[(1R)-1-phenylethyl]pyrimidine-2,4-diamine

4-Chloro-6-(3-chloro-2-methylphenyl)pyrimidin-2-amine (25 mg, 0,098 mmol) and (+)1-phenylethan-1-amine (0,050 mL) were stirred neat at 150° C. for 1 hour. The crude material was dissolved in MeOH (2 mL) and purified by preparative HPLC to give the desired product. LCMS [M+H]$^+$ 339; $^1$H NMR (400 MHz, DMSO-d$_6$) δ ppm 9.25 (1 H, d, J=8.08 Hz) 7.62-7.71 (1 H, m) 7.24-7.47 (7 H, m) 6.23 (0.1H, s) 6.09 (0.9 H, s) 5.35 (1 H, quin, J=7.26 Hz) 2.31 (2.7 H, s) 2.13 (0.3 H, s) 1.46-1.57 (3 H, m).

Example 242

6-(3-chloro-2-methylphenyl)-4-N-(2-phenylpropan-2-yl)pyrimidine-2,4-diamine

4-Chloro-6-(3-chloro-2-methylphenyl)pyrimidin-2-amine (25 mg, 0,098 mmol) and 2-phenylpropan-2-amine (0,050 mL) were stirred neat at 150° C. for 24 hours. The crude material was dissolved in MeOH (2 mL) and purified by preparative HPLC to give the desired product. LCMS [M+H]$^+$ 353; $^1$H NMR (400 MHz, DMSO-d$_6$) δ ppm 12.45 (1 H, br. s.) 8.96 (1 H, br. s.) 7.12-7.79 (8 H, m) 6.22 (1 H, s) 2.31 (3 H, s) 1.79 (6 H, br. s.)

Example 243

6-(3-chloro-2-methylphenyl)-4-N-[1-(1H-indol-3-yl)propan-2-yl]pyrimidine-2,4-diamine 4-Chloro-6-(3-chloro-2-methylphenyl)pyrimidin-2-amine (25 mg, 0,098 mmol) and 1-(1H-indol-3-yl)propan-2-amine (0,050 mL) were stirred neat at 150° C. for 1 hour. The crude material was dissolved in MeOH (2 mL) and purified by preparative HPLC to give the desired product. LCMS [M+H]$^+$ 392; $^1$H NMR (400 MHz, DMSO-d$_6$) δ ppm 12.34 (1 H, br. s.) 10.90 (0.9 H, s) 10.85 (0.1 H, br. s.) 8.79 (0.9 H, d, J=7.83 Hz) 8.63 (0.1 H, d, J=9.09 Hz) 7.66 (0.9 H, dd, J=7.20, 2.15 Hz) 7.62 (0.1 H, d, J=7.58 Hz) 7.54 (1 H, d, J=7.83 Hz) 7.28-7.43 (3 H, m) 7.20 (0.9 H, d, J=2.27 Hz) 6.95-7.13 (2 H, m) 6.89-6.95 (0.1 H, m) 5.99 (0.9 H, s) 5.93 (0.1 H, s) 4.39-4.50 (1 H, m) 2.86-3.03 (2 H, m) 2.30 (2.7 H, s) 2.14 (0.3 H, s) 1.27 (0.3 H, d, J=6.32 Hz) 1.20 (2.7 H, d, J=6.57 Hz).

Example 244

4-N-{bicyclo[2.2.1]heptan-2-yl}-6-(3-chloro-2-methylphenyl)pyrimidine-2,4-diamine 4-Chloro-6-(3-chloro-2-methylphenyl)pyrimidin-2-amine (25 mg, 0,098 mmol) and bicyclo[2.2.1]heptan-2-amine (0,050 mL) were stirred neat at 150° C. for 1 hour. The crude material was dissolved in MeOH (~2 mL) and purified by preparative HPLC to give the desired product. LCMS [M+H]$^+$ 329; $^1$H NMR (400 MHz, DMSO-d$_6$) δ ppm 8.66 (1 H, br. s.) 7.62-7.69 (1 H, m) 7.35-7.44 (2 H, m) 5.99 (1 H, s) 3.87 (1 H, br. s.) 2.30 (3H, s) 2.27-2.35 (1 H, m) 2.24 (1 H, d, J=3.28 Hz) 1.70-1.80 (1 H, m) 1.33-1.60 (4 H, m) 1.09-1.26 (3 H, m)

Example 245

6-(3-chloro-2-methylphenyl)-4-N-ethylpyrimidine-2,4-diamine

4-Chloro-6-(3-chloro-2-methylphenyl)pyrimidin-2-amine (25 mg, 0,098 mmol), 70% ethanamine (0,050 mL) and n-butanol (2 mL) were stirred in a sealed tube at 120° C. for 8 hours. The solvent was removed in vacuo and the crude material was dissolved in MeOH (2 mL) and purified by preparative HPLC to give the desired product. LCMS [M+H]$^+$ 263; $^1$H NMR (400 MHz, DMSO-d$_6$) δ ppm 12.49 (1 H, br. s.) 8.86 (0.9 H, t, J=5.18 Hz) 8.63-8.73 (0.1 H, m) 7.60-7.70 (1 H, m) 7.34-7.45 (2 H, m) 6.34 (0.1 H, br. s.) 6.02 (0.9 H, s) 3.23-3.58 (2 H, m) 2.33 (0.3 H, s) 2.30 (2.7 H, s) 1.18 (2.7 H, t, J=7.20 Hz) 1.08-1.14 (0.3 H, m)

Example 246

6-(3-chloro-2-methylphenyl)-4-N-(propan-2-yl)pyrimidine-2,4-diamine

4-Chloro-6-(3-chloro-2-methylphenyl)pyrimidin-2-amine (25 mg, 0,098 mmol), propan-2-amine (0,050 mL) and n-butanol (2 mL) were stirred in a sealed tube at 120° C. for 8 hours. The solvent was removed in vacuo and the crude material was dissolved in MeOH (2 mL) and purified by preparative HPLC to give the desired product. LCMS [M+H]$^+$ 277.

Example 247

4-N-[2-(2-chlorophenoxy)ethyl]-6-(2,3-dimethylphenyl)pyrimidine-2,4-diamine

4-Chloro-6-(2,3-dimethylphenyl)pyrimidin-2-amine (13 mg, 0,054 mmol) and 1-(2-aminoethoxy)-2-chlorobenzene (18 mg, 0.11 mmol) were stirred neat at 150° C. for 1 h. The crude material was dissolved in MeOH (1 mL) and purified by preparative HPLC to give the desired product. LCMS [M+H]$^+$ 369.

Example 248

4-N-[2-(5-chloro-1H-1,3-benzodiazol-2-yl)ethyl]-6-(2,3-dimethylphenyl)pyrimidine-2,4-diamine 4-Chloro-6-(3-chloro-2-methylphenyl)pyrimidin-2-amine (23 mg, 0.10 mmol), 2-(5-chloro-1H-1,3-benzodiazol-2-yl)ethan-1-amine (20 mg, 0.10 mmol), Et$_3$N (0,040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]$^+$ 393.

Example 249

4-N-[2-(2,5-dimethyl-1H-indol-3-yl)ethyl]-6-(2,3-dimethylphenyl)pyrimidine-2,4-diamine 4-Chloro-6-(2,3-dimethylphenyl)pyrimidin-2-amine (12 mg, 0,050 mmol) and 2-(2,5-dimethyl-1H-indol-3-yl)ethan-1-amine (0,020 mL) were stirred neat at 150° C. for 1 hour. The crude material was dissolved in MeOH (1 mL) and purified by preparative HPLC to give the desired product. LCMS [M+H]$^+$ 386; $^1$H NMR (400 MHz, DMSO-d$_6$) δ ppm 12.30 (1 H, br. s.) 10.65 (0.9 H, s) 10.60 (0.1 H, s) 8.82 (0.9 H, t, J=5.56 Hz) 8.56-8.67 (0.1 H, m) 7.06-7.41 (5 H, m) 6.70-6.85 (1 H, m) 5.97 (0.9 H, s) 5.76 (0.1 H, s) 3.58 (1.8 H, q, J=6.65 Hz) 3.48 (0.2 H, d, J=6.32 Hz) 2.93 (0.8 H, t, J=7.07 Hz) 2.80-2.89 (0.2 H, m) 2.23-2.38 (9 H, m) 2.17 (2.7 H, s) 2.06 (0.3 H, s)

Example 250

6-(2,3-dimethylphenyl)-4-N-[2-(pyridin-3-yloxy)propyl]pyrimidine-2,4-diamine

4-Chloro-6-(2,3-dimethylphenyl)pyrimidin-2-amine (12 mg, 0,050 mmol) and 3-[(1-aminopropan-2-yl)oxy]pyridine (15 mg, 0.10 mmol) were stirred neat at 150° C. for 1 h. The crude material was dissolved in MeOH (1 mL) and purified by preparative HPLC to give the desired product. LCMS [M+H]$^+$ 350.

Example 251

6-(2,3-dimethylphenyl)-4-N-(1H-indazol-5-ylmethyl)pyrimidine-2,4-diamine

4-Chloro-6-(2,3-dimethylphenyl)pyrimidin-2-amine (12 mg, 0,050 mmol), 1H-indazol-5-ylmethanamine (15 mg, 0.10 mmol), Et$_3$N (0.040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]$^+$ 345.

Example 252

6-(2,3-dimethylphenyl)-4-N-(1H-indazol-6-ylmethyl)pyrimidine-2,4-diamine

4-Chloro-6-(2,3-dimethylphenyl)pyrimidin-2-amine (12 mg, 0,050 mmol), 1H-indazol-6-ylmethanamine (15 mg, 0.10 mmol), Et3N (0.040 mL), 0.30 mmol) and 1-butanol (0.20 mL) were stirred at 100° C. for 20 h. MeOH (1 mL) was added and the mixture was purified by preparative HPLC to give the desired product. LCMS [M+H]$^+$ 345

Example 253

6-(2,3-dimethylphenyl)-4-N-[(2-methoxypyridin-4-yl)methyl]pyrimidine-2,4-diamine 4-Chloro-6-(2,3-dimethylphenyl)pyrimidin-2-amine (12 mg, 0,050 mmol), (2-methoxypyridin-4-yl)methanamine (14 mg, 0.10 mmol), Et$_3$N (0,040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]$^+$ 336.

Example 254

4-N-[(5-chloropyrazin-2-yl)methyl]-6-(2,3-dimethylphenyl)pyrimidine-2,4-diamine

4-Chloro-6-(2,3-dimethylphenyl)pyrimidin-2-amine (12 mg, 0,050 mmol), (5-chloropyrazin-2-yl)methanamine (14 mg, 0.10 mmol), Et$_3$N (0,040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]$^+$ 341.

Example 255

6-(2,3-dimethylphenyl)-4-N-{imidazo[1,2-a]pyridin-2-ylmethyl}pyrimidine-2,4-diamine 4-Chloro-6-(2,3-dimethylphenyl)pyrimidin-2-amine (12 mg, 0,050 mmol), imidazo[1,2-a]pyridin-2-ylmethanamine (14 mg, 0.10 mmol), Et$_3$N (0,040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]$^+$ 345.

Example 256 tert-butyl 4-{4-[2-amino-6-(methylamino)pyrimidin-4-yl]-2-(methoxymethyl)phenoxymethyl}piperidine-1-carboxylate A mixture of 6-chloro-4-N-methylpyrimidine-2,4-diamine (24 mg, 0.15 mmol), tert-butyl 4-[4-(dimethoxyboranyl)-2-(methoxymethyl)phenoxymethyl]piperidine-1-carboxylate (67 mg, 0.17 mmol), potassium carbonate (41 mg, 0.30 mmol) and palladium tetrakis(triphenylphosphine)palladium (0) (9 mg, 0.008 mmol) in 1,4-dioxane (5 mL) and water (1.5 mL) was heated in a sealed tube at 90° C. overnight. The reaction mixture was concentrated and purified by preparative HPLC. LCMS [M+H]$^+$ 458.

Example 257

6-[3-(methoxymethyl)-4-(piperidin-4-ylmethoxy) phenyl]-4-N-methylpyrimidine-2,4-diamine Hydrochloride A solution of tert-butyl 4-{4-[2-amino-6-(methylamino) pyrimidin-4-yl]-2-(methoxymethyl)-phenoxymethyl}piperidine-1-carboxylate (45 mg, 0.10 mmol; Example 256) in methanol (3 mL) was treated with 4M HCl in 1,4-dioxane (1 mL). The mixture was stirred at r.t. for 3 h, concentrated and dried in vacuo to give the desired product. LCMS [M+H]$^+$ 358.

Example 258

3-[2-amino-6-(methylamino)pyrimidin-4-yl]-2-methylbenzonitrile

A mixture of 6-chloro-4-N-methylpyrimidine-2,4-diamine (24 mg, 0.15 mmol), (3-cyano-2-methylphenyl)boronic acid (29 mg, 0.18 mmol), potassium carbonate (41 mg, 0.30 mmol) and palladium tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]$^+$ 240.

Example 259

6-(4-methoxy-2,3-dimethylphenyl)-4-N-methylpyrimidine-2,4-diamine

A mixture of 6-chloro-4-N-methylpyrimidine-2,4-diamine (24 mg, 0.15 mmol), (4-methoxy-2,3-dimethylphenyl)boronic acid (32 mg, 0.18 mmol), potassium carbonate (41 mg, 0.30 mmol) and tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]$^+$ 259.

Example 260

6-(4-fluoro-2,3-dimethylphenyl)-4-N-methylpyrimidine-2,4-diamine

A mixture of 6-chloro-4-N-methylpyrimidine-2,4-diamine (24 mg, 0.15 mmol), (4-fluoro-2,3-dimethylphenyl) boronic acid (30 mg, 0.18 mmol), potassium carbonate (41 mg, 0.30 mmol) and tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]$^+$ 247.

Example 261

6-(2,3-dihydro-1-benzofuran-7-yl)-4-N-methylpyrimidine-2,4-diamine

A mixture of 6-chloro-4-N-methylpyrimidine-2,4-diamine (24 mg, 0.15 mmol), (2,3-dihydro-1-benzofuran-7-yl)boronic acid (30 mg, 0.18 mmol), potassium carbonate (41 mg, 0.30 mmol) and tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]$^+$ 243.

Example 262

4-N-methyl-6-[2-methyl-5-(morpholine-4-sulfonyl) phenyl]pyrimidine-2,4-diamine

A mixture of 6-chloro-4-N-methylpyrimidine-2,4-diamine (24 mg, 0.15 mmol), [2-methyl-5-(morpholine-4-sulfonyl)phenyl]boronic acid (51 mg, 0.18 mmol), potassium carbonate (41 mg, 0.30 mmol) and tetrakis(triphenylphosphine)-palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]$^+$ 364.

Example 263

4-N-[2-(4-chlorophenyl)ethyl]-6-(2,3-dichlorophenyl)pyrimidine-2,4-diamine

A mixture of 4-chloro-6-(2,3-dichlorophenyl)pyrimidin-2-amine (28 mg, 0.10 mmol), 2-(4-chlorophenyl)ethan-1-amine (22 mg, 0.14 mmol) and Hünig's base (36 µL, 0.20 mmol) in n-butanol (2 mL) was heated in a sealed tube at 85° C. overnight. The reaction mixture was concentrated and purified by preparative HPLC. LCMS [M+H]$^+$ 393. 1H NMR (400 MHz, DMSO-d6) δ ppm 12.56 (br. s., 1 H), 8.90 (br. s., 1 H), 7.83-7.89 (m, 1 H), 7.51-7.59 (m, 2 H), 7.35-7.41 (m, 2 H), 7.28-7.34 (m, 2 H), 6.11 (s, 1 H), 3.63 (q, J=6.4 Hz, 2 H), 2.89 (t, J=7.1 Hz, 2 H).

Example 264

4-N-[2-(4-chlorophenyl)ethyl]-6-(2-methylphenyl) pyrimidine-2,4-diamine

A mixture of 6-chloro-4-N-[2-(4-chlorophenyl)ethyl]pyrimidine-2,4-diamine (34 mg, 0.12 mmol), (2-methylphenyl)boronic acid (20 mg, 0.14 mmol), potassium carbonate (33 mg, 0.24 mmol) and palladium tetrakis(triphenylphosphine)-palladium (0) (7 mg, 0.006 mmol) in 1,4-dioxane/ water (4 mL; 4:1) was heated in a sealed tube at 90° C. overnight. The reaction mixture was concentrated and purified by preparative HPLC. LCMS [M+H]$^+$ 339.

Example 265

4-N-[2-(4-chlorophenyl)ethyl]-6-[3-(trifluoromethyl) phenyl]pyrimidine-2,4-diamine A mixture of 6-chloro-4-N-[2-(4-chlorophenyl)ethyl]pyrimidine-2,4-diamine (34 mg, 0.12 mmol), [3-(trifluoromethyl)phenyl]boronic acid (27 mg, 0.14 mmol), potassium carbonate (33 mg, 0.24 mmol) and palladium tetrakis(triphenylphosphine)palladium (0) (7 mg, 0.006 mmol) in 1,4-dioxane/water (4 mL; 4:1) was heated in a sealed tube at 90° C. overnight. The reaction mixture was concentrated and purified by preparative HPLC. LCMS [M+H]$^+$ 393.

Example 266

4-N-[2-(4-chlorophenyl)ethyl]-6-(quinolin-5-yl)pyrimidine-2,4-diamine

A mixture of 6-chloro-4-N-[2-(4-chlorophenyl)ethyl]pyrimidine-2,4-diamine (34 mg, 0.12 mmol), (quinolin-5-yl)boronic acid (25 mg, 0.14 mmol), potassium carbonate (33 mg, 0.24 mmol) and palladium tetrakis(triphenylphosphine)palladium (0) (7 mg, 0.006 mmol) in 1,4-dioxane/water (4 mL; 4:1) was heated in a sealed tube at 90° C. overnight. The reaction mixture was concentrated and purified by preparative HPLC. LCMS [M+H]$^+$ 376.

Example 267

4-N-[2-(4-chlorophenyl)cyclopropyl]-6-(2,3-dimethylphenyl)pyrimidine-2,4-diamine A mixture of 4-chloro-6-(2,3-dimethylphenyl)pyrimidin-2-amine (28 mg, 0.12 mmol), 2-(4-chlorophenyl)cyclopropan-1-amine (43 mg, 0.26 mmol) and Hünig's base (90 µL, 0.52 mmol) in n-butanol (2 mL) was heated in a sealed tube at 85° C. overnight. The reaction mixture was concentrated and purified by preparative HPLC. LCMS [M+H]$^+$ 365.

Example 268

6-(2,3-dimethylphenyl)-4-N-[2-(pyridin-3-yl)ethyl]pyrimidine-2,4-diamine

A mixture of 4-chloro-6-(2,3-dimethylphenyl)pyrimidin-2-amine (28 mg, 0.12 mmol), 2-(pyridin-3-yl)ethan-1-amine (21 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 320.

Example 269

3-(2-{[2-amino-6-(2,3-dimethylphenyl)pyrimidin-4-yl]amino}ethyl)phenol

A mixture of 4-chloro-6-(2,3-dimethylphenyl)pyrimidin-2-amine (28 mg, 0.12 mmol), 3-(2-aminoethyl)phenol (23 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 335.

Example 270

6-(2,3-dimethylphenyl)-4-N-[3-(morpholin-4-yl)propyl]pyrimidine-2,4-diamine

A mixture of 4-chloro-6-(2,3-dimethylphenyl)pyrimidin-2-amine (28 mg, 0.12 mmol), 3-(morpholin-4-yl)propan-1-amine (24 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 342.

Example 271 tert-butyl N-(2-{[2-amino-6-(2,3-dimethylphenyl)pyrimidin-4-yl]amino}ethyl)-carbamate A mixture of 4-chloro-6-(2,3-dimethylphenyl)pyrimidin-2-amine (28 mg, 0.12 mmol), tert-butyl N-(2-aminoethyl)carbamate (27 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 358.

Example 272

N-(2-{[2-amino-6-(2,3-dimethylphenyl)pyrimidin-4-yl]amino}ethyl)acetamide

A mixture of 4-chloro-6-(2,3-dimethylphenyl)pyrimidin-2-amine (28 mg, 0.12 mmol), N-(2-aminoethyl)acetamide (17 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 300.

Example 273

Benzyl N-(2-{[2-amino-6-(2,3-dimethylphenyl)pyrimidin-4-yl]amino}ethyl)-carbamate A mixture of 4-chloro-6-(2,3-dimethylphenyl)pyrimidin-2-amine (28 mg, 0.12 mmol), benzyl N-(2-aminoethyl)carbamate hydrochloride (39 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 392.

Example 274 tert-butyl N-(2-{[2-amino-6-(2,3-dimethylphenyl)pyrimidin-4-yl]amino}ethyl)-N-methylcarbamate A mixture of 4-chloro-6-(2,3-dimethylphenyl)pyrimidin-2-amine (28 mg, 0.12 mmol), tert-butyl N-(2-aminoethyl)-N-methylcarbamate (29 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 372.

Example 275 tert-butyl N-(3-{[2-amino-6-(2,3-dimethylphenyl)pyrimidin-4-yl]amino}propyl)-carbamate A mixture of 4-chloro-6-(2,3-dimethylphenyl)pyrimidin-2-amine (28 mg, 0.12 mmol), tert-butyl N-(3-aminopropyl)carbamate (29 mg, 0.17 mmol) and Hünig's base (42 µL, 0.24 mmol) in n-butanol (2 mL) was heated in a sealed tube

Example 276

6-(2,3-dimethylphenyl)-4-N-[3-(5-methyl-1H-pyrazol-3-yl)propyl]pyrimidine-2,4-diamine A mixture of 4-chloro-6-(2,3-dimethylphenyl)pyrimidin-2-amine (28 mg, 0.12 mmol), 3-(5-methyl-1H-pyrazol-4-yl)propan-1-amine (23 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]$^+$ 337.

Example 277

3-{[2-amino-6-(2,3-dimethylphenyl)pyrimidin-4-yl]amino}-1-(morpholin-4-yl)propan-1-one A mixture of 4-chloro-6-(2,3-dimethylphenyl)pyrimidin-2-amine (23 mg, 0.10 mmol), 3-amino-1-(morpholin-4-yl)propan-1-one (22 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC.
LCMS [M+H]$^+$ 356.

Example 278

4-N-[(4-benzylmorpholin-2-yl)methyl]-6-(2,3-dimethylphenyl)pyrimidine-2,4-diamine A mixture of 4-chloro-6-(2,3-dimethylphenyl)pyrimidin-2-amine (23 mg, 0.10 mmol), (4-benzylmorpholin-2-yl)methanamine (29 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC.
LCMS [M+H]$^+$ 404.

Example 279

6-(2,3-dimethylphenyl)-4-N-[(4-methanesulfonylphenyl)methyl]pyrimidine-2,4-diamine A mixture of 4-chloro-6-(2,3-dimethylphenyl)pyrimidin-2-amine (23 mg, 0.10 mmol), (4-methanesulfonylphenyl)methanamine hydrochloride (31 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]$^+$ 383.

Example 280

6-(2,3-dimethylphenyl)-4-N-{[4-(4-methylpiperazin-1-yl)phenyl]methyl}pyrimidine-2,4-diamine A mixture of 4-chloro-6-(2,3-dimethylphenyl)pyrimidin-2-amine (23 mg, 0.10 mmol), [4-(4-methylpiperazin-1-yl)phenyl]methanamine (29 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]$^+$ 403.

Example 281

4-N-[(3S)-1-azabicyclo[2.2.2]octan-3-yl]-6-(2,3-dimethylphenyl)pyrimidine-2,4-diamine A mixture of 4-chloro-6-(2,3-dimethylphenyl)pyrimidin-2-amine (23 mg, 0.10 mmol), (S)-quinuclidin-3-amine hydrochloride (29 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]$^+$ 324.

Example 282 tert-butyl 2-({[2-amino-6-(2,3-dimethylphenyl)pyrimidin-4-yl]amino}methyl)-pyrrolidine-1-carboxylate A mixture of 4-chloro-6-(2,3-dimethylphenyl)pyrimidin-2-amine (23 mg, 0.10 mmol), tert-butyl 2-(aminomethyl)pyrrolidine-1-carboxylate (28 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]$^+$ 398.

Example 283 tert-butyl 4-({[2-amino-6-(2,3-dimethylphenyl)pyrimidin-4-yl]amino}methyl)-piperidine-1-carboxylate A mixture of 4-chloro-6-(2,3-dimethylphenyl)pyrimidin-2-amine (23 mg, 0.10 mmol), tert-butyl 4-(aminomethyl)piperidine-1-carboxylate (30 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]$^+$ 412.

Example 284

1-(3-{[2-amino-6-(2,3-dichlorophenyl)pyrimidin-4-yl]amino}propyl)pyrrolidin-2-one A mixture of 4-chloro-6-(2,3-dichlorophenyl)pyrimidin-2-amine (19 mg, 0.070 mmol) and 1-(3-aminopropyl)pyrrolidin-2-one (49 µL, 0.35 mmol) in n-butanol (1 mL) was heated in a sealed tube at 110° C. overnight. The reaction mixture was concentrated and purified by preparative HPLC. LCMS [M+H]$^+$ 380.

Example 285

1-(3-{[2-amino-6-(3-chloro-2-methylphenyl)pyrimidin-4-yl]amino}propyl)pyrrolidin-2-one A mixture of 4-chloro-6-(3-chloro-2-methylphenyl)pyrimidin-2-amine (19 mg, 0.076 mmol) and 1-(3-aminopropyl)pyrrolidin-2-one (53 µL, 0.38 mmol) in n-butanol (1 mL) was heated in a sealed tube at 110° C. overnight. The (continuation from previous page) at 85° C. overnight. The reaction mixture was concentrated and purified by preparative HPLC. LCMS [M+H]$^+$ 372.

reaction mixture was concentrated and purified by preparative HPLC. LCMS [M+H]+ 360.

Example 286

1-(3-{[2-amino-6-(4-fluoro-2,3-dimethylphenyl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (4-fluoro-2,3-dimethylphenyl)boronic acid (18 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 358.

Example 287

1-(3-{[2-amino-6-(4-methoxy-2,3-dimethylphenyl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (4-methoxy-2,3-dimethylphenyl)boronic acid (20 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 370.

Example 288

1-(3-{[2-amino-6-(4-methyl-1H-indazol-5-yl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (4-methyl-1H-indazol-5-yl)boronic acid (19 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 366.

Example 289

1-[3-({2-amino-6-[2-methyl-5-(morpholine-4-sulfonyl)phenyl]pyrimidin-4-yl}amino)propyl]pyrrolidin-2-one A mixture of 1-{3-[(2-amino-6-chloropyrimidin-4-yl)amino]propyl}pyrrolidin-2-one (27 mg, 0.10 mmol), [2-methyl-5-(morpholine-4-sulfonyl)phenyl]boronic acid (31 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 475.

Example 290

1-(3-{[2-amino-6-(2,3-dihydro-1-benzofuran-7-yl)pyrimidin-4-yl]amino}propyl)pyrrolidin-2-one A mixture of 1-{3-[(2-amino-6-chloropyrimidin-4-yl)amino]propyl}pyrrolidin-2-one. (27 mg, 0.10 mmol), (2,3-dihydro-1-benzofuran-7-yl)boronic acid (18 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 354.

Example 291

1-(3-{[2-amino-6-(2,5-dimethylphenyl)pyrimidin-4-yl]amino}propyl)pyrrolidin-2-one A mixture of 1-{3-[(2-amino-6-chloropyrimidin-4-yl)amino]propyl}pyrrolidin-2-one. (27 mg, 0.10 mmol), (2,5-dimethylphenyl)boronic acid (17 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 340.

Example 292

1-(3-{[2-amino-6-(5-chloro-2-methylphenyl)pyrimidin-4-yl]amino}propyl)pyrrolidin-2-one A mixture of 1-{3-[(2-amino-6-chloropyrimidin-4-yl)amino]propyl}pyrrolidin-2-one. (27 mg, 0.10 mmol), (5-chloro-2-methylphenyl)boronic acid (19 mg, 0.11 mmol), potassium carbonate (28 mg, 0.20 mmol) and palladium tetrakis(triphenyl-phosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 360.

Example 293

1-[3-({2-amino-6-[2-(trifluoromethyl)phenyl]pyrimidin-4-yl}amino)propyl]pyrrolidin-2-one A mixture of 1-{3-[(2-amino-6-chloropyrimidin-4-yl)amino]propyl}pyrrolidin-2-one (27 mg, 0.10 mmol), [2-(trifluoromethyl)phenyl]boronic acid (21 mg, 0.11 mmol), potassium carbonate (28 mg, 0.20 mmol) and palladium tetrakis-(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 380.

Example 294

1-(3-{[2-amino-6-(1H-indol-4-yl)pyrimidin-4-yl]amino}propyl)pyrrolidin-2-one

A mixture of 1-{3-[(2-amino-6-chloropyrimidin-4-yl)amino]propyl}pyrrolidin-2-one (27 mg, 0.10 mmol), (1H-indol-4-yl)boronic acid (18 mg, 0.11 mmol), potassium carbonate (28 mg, 0.20 mmol) and palladium tetrakis(triphenylphosphine)-palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 351.

Example 295

4-N-{[1-(4-chlorophenyl)cyclopropyl]methyl}-6-(2,3-dimethylphenyl)pyrimidine-2,4-diamine A mixture of 4-chloro-6-(2,3-dimethylphenyl)pyrimidin-2-amine (47 mg, 0.20 mmol), [1-(4-chlorophenyl)cyclopropyl]methanamine hydrochloride (65 mg, 0.30 mmol) and Hünig's base (70 µL, 0.40 mmol) in n-butanol (1.5 mL) was heated in a sealed tube at 130° C. overnight. The reaction mixture was concentrated and purified by preparative HPLC. LCMS [M+H]$^+$ 379.

Example 296

4-(2-{[2-amino-6-(2,3-dichlorophenyl)pyrimidin-4-yl]amino}ethyl)benzene-1-sulfonamide A mixture of 4-chloro-6-(2,3-dichlorophenyl)pyrimidin-2-amine (41 mg, 0.15 mmol), 4-(2-aminoethyl)benzene-1-sulfonamide (45 mg, 0.23 mmol) and Hünig's base (39 µL, 0.23 mmol) in n-butanol (2 mL) was heated in a sealed tube at 90° C. for 48 h. The reaction mixture was concentrated and purified by preparative HPLC. LCMS [M+H]$^+$ 438.

Example 297

4-(2-{[2-amino-6-(3-chloro-2-methylphenyl)pyrimidin-4-yl]amino}ethyl)benzene-1-sulfonamide A mixture of 4-chloro-6-(3-chloro-2-methylphenyl)pyrimidin-2-amine (38 mg, 0.15 mmol), 4-(2-aminoethyl)benzene-1-sulfonamide (45 mg, 0.23 mmol) and Hünig's base (39 µL, 0.23 mmol) in n-butanol (2 mL) was heated in a sealed tube at 90° C. for 48 h. The reaction mixture was concentrated and purified by preparative HPLC. LCMS [M+H]$^+$ 418. 1H NMR (400 MHz, DMSO-d6) δ ppm 7.85 (d, J=8.5 Hz, 2 H), 7.46 (d, J=8.5 Hz, 2 H), 7.43 (dd, J=7.58, 1.74 Hz, 1 H), 7.25-7.18 (m, 2H), 5.80 (1H, s), 3.66 (m, 2H), 3.02 (t, J=7.3 Hz, 2H), 2.33 (s, 3H).

Example 298

4-N-(Adamantan-1-yl)-6-(2,3-dichlorophenyl)pyrimidine-2,4-diamine

A mixture of the 4-chloro-6-(2,3-dichlorophenyl)pyrimidin-2-amine (25 mg) and adamantylamine (50 mg) was heated at 150° C. for 1 h. The mixture was cooled, diluted in methanol then purified by preparative HPLC. LCMS [M+H]$^+$ 389.

Example 299

6-(2,3-dichlorophenyl)-4-N-[(1R,2R,3R,5S)-2,6,6-trimethylbicyclo[3.1.1]heptan-3-yl]pyrimidine-2,4-diamine A mixture of 4-chloro-6-(2,3-dichlorophenyl)pyrimidin-2-amine (25 mg) and (1R,2R,3R,5S)-2,6,6-trimethylbicyclo[3.1.1]heptan-3-amine (50 mg) was heated at 150° C. for 1 h. The mixture was cooled, diluted in methanol then purified by preparative HPLC. LCMS [M+H]$^+$ 391.

Example 300

6-(2,3-Dichlorophenyl)-4-N-({3-[(4-methylpiperidin-1-yl)methyl]phenyl}methyl)-pyrimidine-2,4-diamine A mixture of 4-chloro-6-(2,3-dichlorophenyl)pyrimidin-2-amine (25 mg) and {3-[(4-methylpiperidin-1-yl)methyl]phenyl}methanamine (50 mg) was heated at 150° C. for 1 h. The mixture was cooled, diluted in methanol and then purified by preparative HPLC. LCMS [M+H]$^+$ 456.

Example 301

4-(2-{[2-Amino-6-(2,3-dichlorophenyl)pyrimidin-4-yl]amino}ethyl)phenol

A mixture of 4-chloro-6-(2,3-dichlorophenyl)pyrimidin-2-amine (25 mg) and 4-(2-aminoethyl)phenol (50 mg) was heated at 150° C. for 1 h. The mixture was cooled, diluted in methanol then purified by preparative HPLC. LCMS [M+H]$^+$ 375.

Example 302

Ethyl 4-{[2-amino-6-(2,3-dichlorophenyl)pyrimidin-4-yl]amino}piperidine-1-carboxylate A mixture of 4-chloro-6-(2,3-dichlorophenyl)pyrimidin-2-amine (25 mg) and ethyl 4-aminopiperidine-1-carboxylate (50 mg) was heated at 150° C. for 1 h. The mixture was cooled, diluted in methanol then purified by preparative HPLC. LCMS [M+H]$^+$ 410.

Example 303

N-(4-{[2-Amino-6-(2,3-dichlorophenyl)pyrimidin-4-yl]amino}butyl)acetamide

A solution of 4-chloro-6-(2,3-dichlorophenyl)pyrimidin-2-amine (25 mg; 0.1 mmol) in n-BuOH (1.0 ml) was heated at 130° C. with N-(4-aminobutyl)acetamide (1 equiv.) and triethylamine (1 eq). After 18 h the reaction was halted and evaporated. The residue was purified by preparative HPLC. LCMS [M+H]$^+$ 368.

Example 304

6-(2,3-Dichlorophenyl)-4-N-{tricyclo[3.3.1.0$^{3,7}$]nonan-3-yl}pyrimidine-2,4-diamine A solution of 4-chloro-6-(2,3-dichlorophenyl)pyrimidin-2-amine (25 mg; 0.1 mmol) in n-BuOH (1.0 ml) was heated at 130° C. with tricyclo[3.3.1.0$^{3,7}$]nonan-3-amine (1 eq) and triethylamine (1 eq). After 18 h the reaction was halted and evaporated. The residue was purified by preparative HPLC. LCMS [M+H]$^+$ 375.

Example 305

6-(2,3-Dichlorophenyl)-4-N-{[4-(1,2,3-thiadiazol-4-yl)phenyl]methyl}pyrimidine-2,4-diamine A solution of 4-chloro-6-(2,3-dichlorophenyl)pyrimidin-2-amine (25 mg; 0.1 mmol) in n-BuOH (1.0 ml) was heated at 130° C. with [4-(1,2,3-thiadiazol-4-yl)phenyl]methanamine (1 eq) and triethylamine (1 eq). After 18 h the reaction was halted and evaporated. The residue was purified by preparative HPLC. LCMS [M+H]+ 429.

Example 306

4-N-[2-(1-Benzylpiperidin-4-yl)ethyl]-6-(2,3-dichlorophenyl)pyrimidine-2,4-diamine A solution of 4-chloro-6-(2,3-dichlorophenyl)pyrimidin-2-amine (25 mg; 0.1 mmol) in n-BuOH (1.0 ml) was heated at 130° C. with 2-(1-benzylpiperidin-4-yl)ethan-1-amine (1 eq) and triethylamine (1 eq). After 18 h the reaction was halted and evaporated. The residue was purified by preparative HPLC. LCMS [M+H]+ 456.

Example 307

6-[2-[[2-amino-6-(2,3-dichlorophenyl)pyrimidin-4-yl]amino]ethylamino]-3,3-dimethyl-4H-1,4-benzoxazin-2-one Step 1. 6-(2-aminoethylamino)-4H-1,4-benzoxazin-3-one was prepared according to general procedure 13 from 6-bromo-3,3-dimethyl-4H-1,4-benzoxazin-2-one.
Step 2. The title compound was prepared according to general procedure 9 from intermediate 21 and 6-(2-aminoethylamino)-4H-1,4-benzoxazin-3-one [M+H]+ 473. $^1$H NMR (400 MHz, METHANOL-d$_4$) δ ppm 7.76-7.82 (m, 1 H), 7.48-7.51 (m, 2 H), 6.80 (d, J=8.5 Hz, 1 H), 6.48 (dd, J=8.7, 2.7 Hz, 1 H), 6.40 (d, J=2.5 Hz, 1 H), 6.13 (s, 1 H), 3.76 (t, J=6.0 Hz, 3 H), 3.44 (t, J=6.0 Hz, 3 H), 1.42 (s, 6 H).

Example 308

N-{3-[2-amino-6-(methylamino)pyrimidin-4-yl]phenyl}-3-hydroxypyridine-2-carboxamide Equimolar quantities of 3-hydroxypyridine-2-carboxylic acid (0.24 mmol) and 6-(3-aminophenyl)-4-N-methyl-pyrimidine-2,4-diamine were dissolved in 2 ml DMF followed by addition of hydroxybenzotriazole (1.0 eq) and N,N'-dicyclohexylcarbodiimide (1.5 eq). The solution was stirred at rt overnight. The mixture was then filtrated and purified by preparative HPLC.
LCMS [M+H]+ 337; $^1$H NMR (400 MHz, DMSO-d$_6$) δ ppm 12.15 (1H, br. s.), 11.17 (1 H, s), 8.86 (1 H, m, J=5.05 Hz), 8.25-8.35 (2 H, m), 8.03 (1 H, dd, J=8.08, 1.26 Hz), 7.59-7.68 (2 H, m), 7.52 (2 H, dd, J=8.46, 1.39 Hz), 6.36 (1 H, s), 2.95 (3 H, d, J=4.80 Hz).

Example 309

N-{3-[2-Amino-6-(methylamino)pyrimidin-4-yl]phenyl}prop-2-enamide

To a stirred suspension of 6-(3-aminophenyl)-4-N-methyl-pyrimidine-2,4-diamine (0.29 mmol) and triethylamine (1.5 equiv.) in acetonitrile (2 mL) at 0° C. was slowly added prop-2-enoyl chloride (1.0 equiv.). The mixture was allowed to warm to rt and stirred for 3 h. The mixture was concentrated and purified by preparative HPLC. LCMS [M+H]+ 270; $^1$H NMR (400 MHz, DMSO-d$_6$) δ ppm 10.35 (1 H, s), 8.23 (1 H, t, J=1.89 Hz), 7.79 (1 H, d, J=8.08 Hz), 7.56-7.69 (4 H, m), 7.34-7.52 (4 H, m), 6.88 (1 H, s), 6.84 (1 H, s), 6.18 (1 H, s), 5.98 (2 H, s), 2.80 (3 H, d, J=4.80 Hz).

Example 310

(2E)-N-{3-[2-Amino-6-(methylamino)pyrimidin-4-yl]phenyl}-3-phenylprop-2-enamide

To a suspension of the 6-(3-aminophenyl)-4-N-methyl-pyrimidine-2,4-diamine (0.25 mmol) and triethylamine (1.5 equiv.) in acetonitrile (2 mL) at 0° C. was added drop wise, with stirring, the (E)-3-phenylprop-2-enoyl chloride (1.0 equiv.). The mixture was allowed to warm to rt, and stirred for 3 h. The mixture was concentrated and purified by preparative HPLC. LCMS [M+H]+ 346; $^1$H NMR (400 MHz, DMSO-d$_6$) δ ppm 10.35 (s, 1 H), 8.23 (t, J=1.89 Hz, 1 H), 7.79 (d, J=8.08 Hz, 1 H), 7.56-7.69 (m, 4 H), 7.34-7.52 (m, 4 H), 6.88 (s, 1 H), 6.84 (s, 1 H), 6.18 (s, 1 H), 5.98 (s, 2 H), 2.80 (d, J=4.80 Hz, 3 H).

Example 311

N-{3-[2-Amino-6-(methylamino)pyrimidin-4-yl]-2-methylphenyl}prop-2-enamide

To a suspension of 6-(3-amino-2-methyl-phenyl)-4-N-methyl-pyrimidine-2,4-diamine (0.39 mmol) and triethylamine (1.5 equiv.) in acetonitrile (3 ml) at 0° C. was added drop wise, with stirring, prop-2-enoyl chloride (1.0 equiv.). The mixture was allowed to warm to rt, and stirred for 3 h. The mixture was concentrated and purified by preparative HPLC. LCMS [M+H]+ 284; $^1$H NMR (400 MHz, DMSO-d$_6$) δ ppm 9.57 (1 H, s), 7.41 (1 H, d, J=7.58 Hz), 7.20 (1 H, t, J=7.83 Hz), 7.10 (1 H, d, J=6.82 Hz), 6.83 (1 H, br. s.), 6.54 (1 H, dd, J=17.05, 10.23 Hz), 6.25 (1 H, dd, J=17.05, 2.15 Hz), 5.97 (2 H, s), 5.73-5.78 (1 H, m), 5.71 (1 H, s), 2.77 (3H, d, J=4.55 Hz), 2.14 (3 H, s).

Example 312

(2E)-N-{3-[2-Amino-6-(methylamino)pyrimidin-4-yl]phenyl}-4-(dimethylamino)but-2-enamide To a solution of 6-(3-aminophenyl)-4-N-methylpyrimidine-2,4-diamine (0.29 mol) in acetonitrile (4 mL) was added successively (E)-4-(dimethylamino)but-2-enoic acid; hydrochloride (1.0 equiv.), triethylamine (3.0 equiv.) and n-propanephosphonic acid anhydride (T3P, 2.0 equiv.). The resulting mixture was stirred at rt overnight. The solution was then filtrated and purified by preparative HPLC. LCMS [M+H]+ 327; $^1$H NMR (400 MHz, DMSO-d$_6$) δ ppm 10.17 (1 H, s), 8.20 (1 H, t, J=1.77 Hz), 7.71 (1 H, d, J=8.08 Hz), 7.58 (1 H, d, J=7.83 Hz), 7.36 (1 H, t, J=7.83 Hz), 6.81-6.96 (1 H, m), 6.70-6.80 (1 H, m), 6.28 (1 H, dt, J=15.35, 1.55 Hz), 6.16 (1 H, s), 5.97 (2 H, s), 3.06 (2 H, dd, J=6.06, 1.52 Hz), 2.79 (3 H, d, J=4.80 Hz), 2.18 (6 H, s).

Example 313

N-{3-[2-amino-6-(methylamino)pyrimidin-4-yl]phenyl}ethene-1-sulfonamide

To a suspension of 6-(3-aminophenyl)-4-N-methyl-pyrimidine-2,4-diamine (0.20 mmol) and triethylamine (1.1 equiv.) in acetonitrile (1.5 mL) at −60° C. was added drop wise, with stirring, ethenesulfonyl chloride (0.9 equiv.) in 0.5 ml acetonitrile. The mixture was allowed to warm to rt, and stirred for 2 h. The solution was then filtrated and purified by preparative HPLC. LCMS [M+H]+ 306; ¹H NMR (400 MHz, DMSO-d₆) δ ppm 11.98 (1 H, br. s.), 10.38 (1 H, br. s.), 8.79 (1 H, br. s.), 7.31-7.60 (4 H, m), 6.85 (1 H, dd, J=16.42, 9.85 Hz), 6.25 (1 H, s), 6.18 (1 H, d, J=16.42 Hz), 6.08 (1 H, d, J=9.85 Hz), 2.93 (3 H, d, J=4.80 Hz).

Example 314

N-{3-[2-Amino-6-(methylamino)pyrimidin-4-yl] phenyl}prop-2-ynamide

To a solution of 6-(3-aminophenyl)-4-N-methyl-pyrimidine-2,4-diamine (0.30 mol) in acetonitrile (5 mL) at 0° C. was added successively prop-2-ynoic acid (1.0 equiv.), triethylamine (2.0 equiv.) and n-propanephosphonic acid anhydride (T3P, 1.7 equiv.). The resulting mixture was stirred at rt overnight. The solution was then filtrated and purified by preparative HPLC. LCMS [M+H]+ 268; ¹H NMR (400 MHz, DMSO-d₆) δ ppm 8.19 (1 H, br. s.), 7.84 (1 H, d, J=7.83 Hz), 7.65 (1 H, d, J=7.83 Hz), 7.46 (1 H, d, J=13.39 Hz), 7.38 (1 H, t, J=7.83 Hz), 7.00 (1 H, d, J=13.89 Hz), 6.28 (1 H, br. s.), 5.97 (2 H, s), 2.78 (3 H, d, J=4.55 Hz).

Example 315

N-{3-[2-Amino-6-(methylamino)pyrimidin-4-yl] phenyl}-2-oxopropanamide

To a solution of 6-(3-aminophenyl)-4-N-methyl-pyrimidine-2,4-diamine (0.39 mol) in acetonitrile (4 mL) was added successively pyruvic acid (1.0 equiv.), triethylamine (2.5 equiv.) and n-propanephosphonic acid anhydride (T3P, 2.0 equiv.). The resulting mixture was stirred at rt overnight. The solution was then filtrated and purified by preparative HPLC. LCMS [M+H]+ 286.

Example 316

N-{3-[2-Amino-6-(methylamino)pyrimidin-4-yl] phenyl}-2-oxo-2-phenylacetamide

To a solution of 6-(3-aminophenyl)-4-N-methyl-pyrimidine-2,4-diamine (0.42 mol) in acetonitrile (4 mL) was added successively 2-oxo-2-phenyl-acetic acid (0.9 equiv.), triethylamine (2.5 equiv.) and n-propanephosphonic acid anhydride (T3P, 2.0 equiv.). The resulting mixture was stirred at rt overnight. The mixture was concentrated and purified by preparative HPLC. LCMS [M+H]+ 348; ¹H NMR (400 MHz, DMSO-d₆) δ ppm 8.30-8.36 (1 H, m), 8.00-8.11 (2 H, m), 7.66-7.84 (3 H, m), 7.59-7.66 (2 H, m), 7.45 (1 H, t, J=7.96 Hz), 6.90 (1 H, br. s.), 6.19 (1 H, s), 6.01 (2 H, s), 2.80 (3 H, d, J=4.80 Hz).

Example 317

N-{4-[2-Amino-6-(methylamino)pyrimidin-4-yl] phenyl}prop-2-enamide

To a suspension of 6-(4-aminophenyl)-4-N-methyl-pyrimidine-2,4-diamine (0.29 mmol) and triethylamine (1.5 equiv.) in tetrahydrofuran (2 ml) at 0° C. was added drop wise, with stirring, prop-2-enoyl chloride (1.0 equiv.). The mixture was allowed to warm to rt, and stirred for 3 h. The mixture was concentrated and purified by preparative HPLC. LCMS [M+H]+ 270; ¹H NMR (400 MHz, DMSO-d6) δ ppm 10.28 (1 H, s), 7.89 (2 H, d, J=8.8 Hz), 7.58-7.75 (2 H, m), 6.76 (1 H, br. s.), 6.40-6.49 (1 H, m), 6.24-6.30 (1 H, m), 6.17 (1 H, s), 5.94 (2 H, s), 5.58-5.80 (1 H, m), 2.79 (3 H, d, J=4.8 Hz).

Example 318

N-({4-[2-Amino-6-(methylamino)pyrimidin-4-yl] phenyl}methyl)prop-2-enamide

To a suspension of 6-[4-(aminomethyl)phenyl]-4-N-methyl-pyrimidine-2,4-diamine (0.29 mmol) and triethylamine (1.5 equiv.) in tetrahydrofuran (2 ml) at 0° C. was added drop wise, with stirring, prop-2-enoyl chloride (1.0 equiv.). The mixture was allowed to warm to rt and stirred for 3 h. The mixture was concentrated and purified by preparative HPLC. LCMS [M+H]+ 284.

Example 319

N-({3-[2-Amino-6-(methylamino)pyrimidin-4-yl] phenyl}methyl)prop-2-enamide

To a suspension of 6-[3-(aminomethyl)phenyl]-4-N-methyl-pyrimidine-2,4-diamine (0.16 mmol) and triethylamine (1.5 equiv.) acetonitrile (4 mL) at 0° C. was added drop wise, with stirring, prop-2-enoyl chloride (1.0 equiv.). The mixture was allowed to warm to room temperature, and stirred for 3 h. The mixture was concentrated and purified by preparative HPLC. LCMS [M+H]+ 284.

Example 320

N-{3-[2-Amino-6-(ethylamino)pyrimidin-4-yl]-4-methylphenyl}prop-2-enamide

To a suspension of 6-(5-amino-2-methyl-phenyl)-4-N-methyl-pyrimidine-2,4-diamine (0.48 mmol) and triethylamine (1.7 equiv.) in acetonitrile (3 mL) at 0° C. was added drop wise, with stirring, prop-2-enoyl chloride (1.0 equiv.). The mixture was allowed to warm to rt and stirred for 3 h. The mixture was concentrated and purified by preparative HPLC. LCMS [M+H]+ 284; ¹H NMR (400 MHz, DMSO-d₆) δ ppm 10.10 (1 H, s), 7.46-7.75 (2 H, m), 7.16 (1 H, d, J=8.34 Hz), 6.80 (1 H, br. s.), 6.37-6.46 (1 H, m), 6.23 (1 H, dd, J=17.05, 2.15 Hz), 5.95 (2 H, s), 5.62-5.84 (2 H, m), 2.77 (3 H, d, J=4.55 Hz), 2.27 (3 H, s).

Example 321

N-{3-[2-Amino-6-(methylamino)pyrimidin-4-yl] phenyl}-5-chloro-2-hydroxybenzamide Equimolar quantities of 5-chloro-2-hydroxy-benzoic acid and 6-(3-aminophenyl)-4-N-methyl-pyrimidine-2,4-diamine (0.24 mmol) were dissolved in DMF (2 mL) followed by adding hydroxybenzotriazole (1.0 eq) and N,N'-dicyclohexyl-carbodiimide (1.5 eq). The solution was stirred under rt overnight. The mixture was then filtrated and purified by preparative HPLC. LCMS [M+H]+ 370; ¹H NMR (400 MHz, DMSO-d₆) δ ppm 15.10 (1 H, br. s.), 8.08-8.16 (1 H, m), 7.86 (1 H, d, J=7.58 Hz), 7.64 (1 H, d, J=3.03 Hz), 7.49 (1 H, d, J=7.33 Hz), 7.32 (1 H, t, J=7.96 Hz), 6.93 (1 H, dd, J=8.84, 3.03 Hz), 6.78-6.89 (1 H, m), 6.40 (1 H, d, J=8.84 Hz), 6.20 (1 H, s), 6.03 (2 H, s), 2.80 (3 H, d, J=4.55 Hz).

Example 322

N-{3-[2-Amino-6-(methylamino)pyrimidin-4-yl]phenyl}-2-hydroxyacetamide

Equimolar quantities of 2-hydroxyacetic acid and 6-(3-aminophenyl)-4-N-methyl-pyrimidine-2,4-diamine (0.24 mmol) were dissolved in 2 ml DMF followed by adding hydroxybenzotriazole (1.0 eq) in 1 mL DMF and N,N'-dicyclohexylcarbodiimide (1.5 eq, dissolved in xylene). The solution was stirred under room temperature overnight. The mixture was then filtrated and purified by preparative. LCMS [M+H]$^+$ 274; $^1$H NMR (400 MHz, DMSO-d$_6$) δ ppm 12.06 (1 H, br. s.), 9.75-10.10 (1 H, m), 8.83 (1 H, d, J=4.55 Hz), 8.22 (1 H, s), 7.84 (1 H, d, J=9.35 Hz), 7.54 (1 H, t, J=7.96 Hz), 7.40 (1 H, d, J=8.08 Hz), 6.30 (1 H, s), 5.61-5.97 (1 H, m), 4.03 (2 H, s), 2.94 (3 H, d, J=4.80 Hz).

Example 323

N-{3-[2-Amino-6-(methylamino)pyrimidin-4-yl]phenyl}-2-(4-chlorophenyl)-2-hydroxyacetamide Equimolar quantities of 6-(3-aminophenyl)-4-N-methyl-pyrimidine-2,4-diamine (0.24 mmol) and 2-(4-chlorophenyl)-2-hydroxy-acetic acid were dissolved in 2 ml DMF followed by adding hydroxybenzotriazole (1.0 eq) in 1 mL DMF and N,N'-dicyclohexylcarbodiimide (1.5 equiv.; as a solution in xylene). The solution was stirred at rt overnight. The mixture was then filtrated and purified by preparative HPLC. LCMS [M+H]$^+$ 384; $^1$H NMR (400 MHz, DMSO-d$_6$) δ ppm 10.05 (1 H, s), 8.22 (1 H, t, J=1.89 Hz), 7.69 (1 H, d, J=8.59 Hz), 7.59 (1 H, d, J=6.57 Hz), 7.52-7.57 (2 H, m), 7.40-7.45 (2 H, m), 7.34 (1 H, t, J=7.96 Hz), 6.85 (1H, br. s.), 6.14 (1 H, s), 6.04 (2 H, br. s.), 5.97 (1 H, s), 5.14 (1 H, s), 2.78 (3 H, d, J=4.80 Hz).

Example 324

N-{3-[2-Amino-6-(methylamino)pyrimidin-4-yl]phenyl}-2-hydroxy-2-phenylacetamide

Equimolar quantities of 2-hydroxy-2-phenyl-acetic acid and 6-(3-aminophenyl)-4-N-methyl-pyrimidine-2,4-diamine (0.24 mmol) were dissolved in DMF (2 mL) followed by adding hydroxybenzotriazole (1.0 eq) in DMF (1 mL) and N,N'-dicyclohexylcarbodiimide (1.5 eq, dissolved in xylene). The solution was stirred under rt overnight. The mixture was then filtrated and purified by preparative HPLC. LCMS [M+H]$^+$ 350; $^1$H NMR (400 MHz, DMSO-d$_6$) δ ppm 11.86 (1 H, br. s.), 10.25 (2 H, s), 8.25 (1 H, s), 7.85 (1 H, d, J=8.59 Hz), 7.48-7.63 (3 H, m), 7.26-7.46 (4 H, m), 6.56 (1 H, d, J=4.29 Hz), 6.28 (1 H, s), 5.15 (1 H, d, J=3.79 Hz), 2.93 (3 H, d, J=4.80 Hz).

Example 325

N-{3-[2-Amino-6-(methylamino)pyrimidin-4-yl]phenyl}-4-oxo-4-(pyrrolidin-1-yl)butanamide Equimolar quantities of 4-oxo-4-pyrrolidin-1-yl-butanoic acid and 6-(3-amino-phenyl)-4-N-methyl-pyrimidine-2,4-diamine (0.24 mmol) were dissolved in DMF (2 mL) followed by adding hydroxybenzotriazole (1.0 eq) in DMF (1 mL) and N,N'-dicyclohexylcarbodiimide (1.5 eq, dissolved in xylene). The solution was stirred at rt overnight. The mixture was then filtrated and purified by preparative HPLC. LCMS [M+H]$^+$ 369.

Example 326.

N-{3-[2-Amino-6-(methylamino)pyrimidin-4-yl]phenyl}-2-hydroxybenzamide

Equimolar quantities of 2-hydroxybenzoic acid and 6-(3-aminophenyl)-4-N-methyl-pyrimidine-2,4-diamine (0.24 mmol) were dissolved in MeCN (2 mL) followed by adding N,N'-dicyclohexylcarbodiimide (1.25 eq). The solution was stirred at rt overnight. The mixture was then filtrated and purified by preparative HPLC. LCMS [M+H]$^+$ 336.

Example 327

1-{4-[2-Amino-6-(methylamino)pyrimidin-4-yl]phenyl}-2,2,2-trifluoroethan-1-one

Tetrakis(triphenylphosphine)palladium (0) (5 mol %) was added to a stirred mixture of 6-chloro-4-N-methylpyrimidine-2,4-diamine (0.25 mmol), [4-(trifluoroacetyl)phenyl]boronic ester (1.3 equiv.), sodium carbonate (3.2 equiv.), dioxane (2 mL) and water (0.5 mL) in a tube. The tube was sealed and the reaction was heated at 90° C. for 5 hours. The mixture was then filtrated and purified by preparative HPLC. LCMS [M+H]$^+$ 297.

Example 328

6-[3-(Aminomethyl)phenyl]-4-N-methylpyrimidine-2,4-diamine

Tetrakis(triphenylphosphine)palladium (0) (5 mol %) was added to a stirred mixture of 6-chloro-4-N-methylpyrimidine-2,4-diamine (2.00 mmol), [3-(aminomethyl)phenyl]boronic acid (1.3 equiv.), sodium carbonate (3.2 equiv.), dioxane (4 mL) and water (1 mL) in a tube. The tube was sealed and the reaction was heated at 90° C. overnight. The solvent were removed in vacuum and to the remaining solid was added ethyl acetate and washed with water. The organic phase was dried over magnesium sulfate. The crude material was then purified by flash chromatography (0→15% MeOH/DCM) to give the title compound. LCMS [M+H]$^+$ 230; $^1$H NMR (400 MHz, DMSO-d$_6$ δ ppm 7.90 (1 H, s), 7.75 (1 H, d, J=6.32 Hz), 7.35-7.42 (3 H, m), 6.82 (1 H, br. S), 6.21 (1 H, s), 5.98 (2 H, s), 3.79 (2 H, s), 2.79 (3 H, d, J=4.80 Hz).

Example 329

6-[4-(Aminomethyl)phenyl]-4-N-methylpyrimidine-2,4-diamine

Tetrakis(triphenylphosphine)palladium (0) (5 mol %) was added to a stirred mixture of 6-chloro-4-N-methylpyrimidine-2,4-diamine (1.00 mmol), [4-(aminomethyl)phenyl]boronic acid (1.3 equiv.), sodium carbonate (4.2 equiv.), dioxane (4 ml) and water (1 ml) in a tube. The tube was sealed and the reaction was heated at 90° C. overnight. The solvent were removed in vacuum and to the remaining solid was added ethyl acetate and washed with water. The organic phase was dried over magnesium sulfate. The crude material was then purified by flash chromatography (0→15% MeOH/DCM) to give the title compound. LCMS [M+H]$^+$ 230; $^1$H NMR (400 MHz, DMSO-d$_6$) δ ppm 7.86 (2 H, d, J=7.58 Hz), 7.38 (2 H, d, J=8.59 Hz), 6.19 (1 H, s), 5.96 (2 H, s), 3.76 (2 H, s), 2.79 (3 H, d, J=4.80 Hz).

Example 330

4-(2-{[2-Amino-6-(2,3-dimethylphenyl)pyrimidin-4-yl]amino}ethyl)benzene-1-sulfonamide A mixture of 4-chloro-6-(2,3-dimethylphenyl)pyrimidin-2-amine (0.12 mmol), 4-(2-aminoethyl)benzene-1-sulfonamide (0.9 equiv.) and triethylamine (1.5 equiv.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 398; $^1$H NMR (400 MHz, DMSO-d$_6$) δ ppm 12.28 (1 H, br. s.), 8.87 (1 H, br. s.), 7.77 (2 H, d, J=8.34 Hz), 7.48 (2 H, d, J=8.34 Hz), 7.37 (1 H, d, J=7.33 Hz), 7.32 (2 H, s), 7.23-7.28 (1 H, m), 7.18-7.23 (1 H, m), 5.99 (1 H, s), 3.67 (2 H, q, J=6.82 Hz), 2.98 (2 H, t, J=7.20 Hz), 2.31 (3 H, s), 2.17 (3 H, s).

Example 331

6-(2,3-Dimethylphenyl)-4-N-[2-(4-methanesulfonylphenyl)ethyl]pyrimidine-2,4-diamine A mixture of 4-chloro-6-(2,3-dimethylphenyl)pyrimidin-2-amine (0.15 mmol), 2-(4-methanesulfonylphenyl)ethan-1-amine (1.2 equiv.) and N,N-diisopropylethylamine (2.25 equiv.) in n-butanol (0.3 mL) was heated in a sealed tube at 110° C. overnight. Methanol was added and the mixture was filtered and purified by preparative HPLC. LCMS [M+H]$^+$ 397.

Example 332

6-(2,3-Dimethylphenyl)-4-N-[2-(5-methyl-1H-1,2,4-triazol-3-yl)ethyl]pyrimidine-2,4-diamine A mixture of 4-chloro-6-(2,3-dimethylphenyl)pyrimidin-2-amine (0.15 mmol), 2-(5-methyl-1H-1,2,4-triazol-3-yl)ethan-1-amine (0.9 equiv.) and triethylamine (1.5 equiv.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 324.

Example 333

4-(2-{[2-Amino-6-(2,3-dimethylphenyl)pyrimidin-4-yl]amino}ethyl)benzonitrile

A mixture of 4-chloro-6-(2,3-dimethylphenyl)pyrimidin-2-amine (0.15 mmol), 4-(2-aminoethyl)benzonitrile (1.2 equiv.) and N,N-diisopropylethylamine (2.25 equiv.) in n-butanol (0.3 mL) was heated in a sealed tube at 110° C. overnight. Methanol was added, and the mixture was filtered and purified by preparative HPLC. LCMS [M+H]$^+$ 344; $^1$H NMR (400 MHz, DMSO-d$_6$) δ ppm 12.36 (1 H, br. s.), 8.87 (1 H, t, J=5.31 Hz), 7.80 (2 H, d, J=8.08 Hz), 7.51 (2 H, d, J=8.34 Hz), 7.37 (1 H, d, J=7.33 Hz), 7.23-7.28 (1 H, m), 7.16-7.22 (1 H, m), 5.98 (1 H, s), 3.67 (2 H, q, J=6.65 Hz), 2.99 (2 H, t, J=7.20 Hz), 2.31 (3 H, s), 2.17 (3 H, s).

Example 334

6-(2,3-Dimethylphenyl)-4-N-[2-(pyridin-4-yl)ethyl]pyrimidine-2,4-diamine

A mixture of 4-chloro-6-(2,3-dimethylphenyl)pyrimidin-2-amine (0.15 mmol), 2-(pyridin-4-yl)ethan-1-amine (1.2 equiv.) and N,N-diisopropylethylamine (1.25 equiv.) in n-butanol (0.3 ml) was heated in a sealed tube at 110° C. overnight. Methanol was added, and the mixture was filtered and purified by preparative HPLC. LCMS [M+H]$^+$ 320; $^1$H NMR (400 MHz, DMSO-d$_6$) δ ppm 12.45 (1 H, br. s.), 8.93 (1 H, t, J=5.56 Hz), 8.76 (2 H, d, J=6.32 Hz), 7.80 (2 H, d, J=6.32 Hz), 7.37 (1 H, d, J=7.33 Hz), 7.25 (1 H, t, J=7.58 Hz), 7.17-7.21 (1 H, m), 5.99 (1 H, s), 3.68-3.83 (2 H, m), 3.13 (2 H, t, J=7.07 Hz), 2.31 (3 H, s), 2.17 (3 H, s).

Example 335

4-(2-{[2-Amino-6-(2,3-dimethylphenyl)pyrimidin-4-yl]amino}ethoxy)benzonitrile

A mixture of 4-chloro-6-(2,3-dimethylphenyl)pyrimidin-2-amine (0.15 mmol), 4-(2-aminoethoxy)benzonitrile (1.2 equiv.) and N,N-diisopropylethylamine (1.25 equiv.) in n-butanol (0.3 mL) was heated in a sealed tube at 110° C. overnight. Methanol was added, and the mixture was filtered and purified by preparative HPLC. LCMS [M+H]$^+$ 360; $^1$H NMR (400 MHz, DMSO-d$_6$) δ ppm 12.37 (1 H, br. s.), 9.02 (1 H, t, J=5.31 Hz), 7.77-7.83 (2 H, m), 7.37 (1 H, d, J=7.33 Hz), 7.23-7.29 (1 H, m), 7.18-7.22 (1 H, m), 7.12-7.18 (2 H, m), 6.06 (1 H, s), 4.29 (2 H, t, J=5.43 Hz), 3.82 (2 H, q, J=5.22 Hz), 2.31 (3 H, s), 2.17 (3 H, s).

Example 336

4-({[2-Amino-6-(2,3-dimethylphenyl)pyrimidin-4-yl]amino}methyl)benzene-1-sulfonamide A mixture of 4-chloro-6-(2,3-dimethylphenyl)pyrimidin-2-amine (0.08 mmol), 4-(aminomethyl)benzene-1-sulfonamide (0.9 equiv.) and triethylamine (1.5 equiv.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 384; $^1$H NMR (400 MHz, DMSO-d$_6$ δ ppm 7.74-7.81 (2 H, m), 7.49-7.54 (2 H, m), 7.46 (1 H, t, J=5.68 Hz), 7.30 (2 H, s), 7.12-7.21 (1 H, m), 7.01-7.12 (2 H, m), 6.00 (2 H, s), 5.76 (1 H, br. s.), 4.57 (2 H, br. s.), 2.26 (3 H, s), 2.15 (3 H, s).

Example 337

1-(2-{[2-Amino-6-(2,3-dimethylphenyl)pyrimidin-4-yl]amino}ethyl)-1,2-dihydropyridin-2-one A mixture of 4-chloro-6-(2,3-dimethylphenyl)pyrimidin-2-amine (0.11 mmol), 1-(2-aminoethyl)-1,2-dihydropyridin-2-one (0.9 equiv.) and triethylamine (1.5 equiv.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 336.

Example 338

3-({[2-Amino-6-(2,3-dimethylphenyl)pyrimidin-4-yl]amino}methyl)-1,2-dihydropyridin-2-one A mixture of 4-chloro-6-(2,3-dimethylphenyl)pyrimidin-2-amine (0.11 mmol), 3-(aminomethyl)-1,2-dihydropyridin-2-one (0.9 equiv.) and triethylamine (1.5 equiv.) in acetonitrile/ethanol/methanol 5:3:2 (1 ml) was heated in a sealed tube at 95° C. overnight. Methanol was added, and the mixture was filtered and purified by preparative HPLC. LCMS [M+H]$^+$ 322.

Example 339

6-(3-{[2-Amino-6-(2,3-dimethylphenyl)pyrimidin-4-yl]amino}propyl)-5H,6H, 7H-pyrrolo[3,4-b]pyridin-5-one A mixture of 4-chloro-6-(2,3-dimethylphenyl)pyrimidin-2-amine (0.12 mmol), 6-(3-aminopropyl)-5H,6H,7H-pyrrolo[3,4-b]pyridin-5-one (0.9 equiv.) and triethylamine (1.5 equiv.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 389.

Example 340

6-({[2-Amino-6-(2,3-dimethylphenyl)pyrimidin-4-yl]amino}methyl)pyridin-3-ol

A mixture of 4-chloro-6-(2,3-dimethylphenyl)pyrimidin-2-amine (0.08 mmol), 6-(aminomethyl)pyridin-3-ol hydrochloride (0.9 equiv.) and triethylamine (2.5 equiv.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 322.

Example 341

4-N-[2-(3-Chlorophenyl)ethyl]-6-(2,3-dimethylphenyl)pyrimidine-2,4-diamine

Prepared according to general procedure 9 from 2-(3-chlorophenyl)ethan-1-amine and 4-chloro-6-(2,3-dimethylphenyl)pyrimidin-2-amine. LCMS [M+H]$^+$ 353; $^1$H NMR (400 MHz, CDCl$_3$) δ ppm 2.24 (s, 3 H) 2.31 (s, 3 H) 2.88 (t, J=7.07 Hz, 2 H) 3.56 (d, J=5.81 Hz, 2 H) 4.86-5.12 (m, 3 H) 5.79 (s, 1 H) 7.07-7.15 (m, 3 H) 7.17 (q, J=4.04 Hz, 1 H) 7.20-7.26 (m, 3 H).

Example 342

6-(2,3-Dimethylphenyl)-4-N-[3-(1H-imidazol-1-yl)propyl]pyrimidine-2,4-diamine

Prepared according to general procedure 9 from 3-(1H-imidazol-1-yl)propan-1-amine and 4-chloro-6-(2,3-dimethylphenyl)pyrimidin-2-amine. LCMS [M+H]$^+$ 323; $^1$H NMR (400 MHz, CD$_3$OD) δ ppm 2.11 (t, J=6.82 Hz, 2 H) 2.20 (s, 3 H) 2.32 (s, 3 H) 3.38 (br. s., 2 H) 4.13 (t, J=6.95 Hz, 2 H) 5.82 (s, 1 H) 6.98 (br. s., 1 H) 7.05-7.23 (m, 4 H) 7.69 (br. s., 1 H).

Example 343

4-N-[2-(4-Chlorophenyl)propyl]-6-(2,3-dimethylphenyl)pyrimidine-2,4-diamine

Prepared according to general procedure 9 from 2-(4-chlorophenyl)propan-1-amine and 4-chloro-6-(2,3-dimethylphenyl)pyrimidin-2-amine. LCMS [M+H]$^+$ 367; $^1$H NMR (400 MHz, CDCl$_3$) δ ppm 1.31 (d, J=7.07 Hz, 3 H) 2.23 (s, 3 H) 2.31 (s, 3 H) 2.97-3.09 (m, 1 H) 3.28-3.40 (m, 1 H) 3.46-3.66 (m, 1 H) 4.74 (br. s., 1 H) 4.95 (br. s., 2 H) 5.74 (s, 1 H) 7.09-7.14 (m, 2 H) 7.14-7.19 (m, 3 H) 7.28-7.33 (m, 2 H).

Example 344

6-(2,3-Dimethylphenyl)-4-N-[2-(4-fluorophenyl)ethyl]pyrimidine-2,4-diamine

Prepared according to general procedure 9 from 2-(4-fluorophenyl)ethan-1-amine and 4-chloro-6-(2,3-dimethylphenyl)pyrimidin-2-amine. LCMS [M+H]$^+$ 337; $^1$H NMR (400 MHz, CDCl$_3$) δ ppm 2.23 (s, 3 H) 2.29-2.34 (m, 3 H) 2.89-2.96 (m, 3 H) 3.49-3.60 (m, 1 H) 3.76 (d, J=6.06 Hz, 3 H) 5.77 (s, 4 H) 7.00-7.07 (m, 3 H) 7.08-7.12 (m, 2 H) 7.13-7.22 (m, 5 H) 7.28-7.32 (m, 1 H).

Example 345

6-(2,3-Dimethylphenyl)-4-N-[2-(4-methoxyphenyl)-2-(pyrrolidin-1-yl)ethyl]pyrimidine-2,4-diamine Prepared according to general procedure 9 from 2-(4-methoxyphenyl)-2-(pyrrolidin-1-yl)ethan-1-amine and 4-chloro-6-(2,3-dimethylphenyl)pyrimidin-2-amine. LCMS [M+H]$^+$ 418; $^1$H NMR (400 MHz, CDCl$_3$) δ ppm 1.74-1.81 (m, 4 H) 2.22 (s, 3H) 2.30 (s, 3H) 2.46-2.69 (m, 5H) 3.49 (br. s., 2H) 3.81 (s, 3 H) 4.88 (br. s., 2 H) 5.04-5.18 (m, 1 H) 5.74 (s, 1 H) 6.85-6.90 (m, 2 H) 7.09-7.12 (m, 2 H) 7.13-7.17 (m, 1 H) 7.24-7.29 (m, 2 H).

Example 346

4-N-{[4-(Dimethylamino)phenyl]methyl}-6-(2,3-dimethylphenyl)pyrimidine-2,4-diamine Prepared according to general procedure 9 from 4-(aminomethyl)-N,N-dimethylaniline and 4-chloro-6-(2,3-dimethylphenyl)pyrimidin-2-amine. LCMS [M+H]$^+$ 348.

Example 347

4-N-[2-(Benzenesulfonyl)ethyl]-6-(2,3-dimethylphenyl)pyrimidine-2,4-diamine

Prepared according to general procedure 9 from 2-(benzenesulfonyl)ethan-1-amine and 4-chloro-6-(2,3-dimethylphenyl)pyrimidin-2-amine. LCMS [M+H]$^+$ 383; $^1$H NMR (400 MHz, CDCl$_3$) δ ppm 2.22 (s, 3 H) 2.31 (s, 3 H) 3.41-3.46 (m, 2 H) 3.86 (q, J=6.06 Hz, 2 H) 5.10 (br. s., 2 H) 5.41-5.53 (m, 1 H) 5.76 (s, 1 H) 7.07-7.16 (m, 2 H) 7.16-7.20 (m, 1 H) 7.57-7.63 (m, 2 H) 7.66-7.71 (m, 1 H) 7.92-7.97 (m, 2 H),

Example 348

6-(2,3-Dimethylphenyl)-4-N-{[1-(4-fluorophenyl)-1H-pyrazol-4-yl]methyl}pyrimidine-2,4-diamine Prepared according to general procedure 9 from [1-(4-fluorophenyl)-1H-pyrazol-4-yl]methanamine and 4-chloro-6-(2,3-dimethylphenyl)pyrimidin-2-amine. LCMS [M+H]$^+$ 389; $^1$H NMR (400 MHz, CDCl$_3$) δ ppm 2.22 (s, 3 H) 2.29 (s, 3 H) 4.47 (d, J=5.31 Hz, 2 H) 5.11-5.41 (m, 3 H) 5.85 (s, 1 H) 7.10-7.19 (m, 5 H) 7.59-7.65 (m, 2 H) 7.68 (s, 1 H) 7.85 (s, 1 H)

Example 349

6-(2,3-dimethylphenyl)-4-N-{2-[5-(pyridin-4-yl)-1H-1,2,4-triazol-3-yl]ethyl}pyrimidine-2,4-diamine Prepared according to general procedure 9 from 2-[5-(pyridin-4-yl)-1H-1,2,4-triazol-3-yl]ethan-1-amine and 4-chloro-6-(2,3-dimethylphenyl)pyrimidin-2-amine. LCMS [M+H]$^+$ 387.

Example 350

6-(2,3-Dimethylphenyl)-4-N-{[1-(pyrimidin-2-yl)piperidin-3-yl]methyl}pyrimidine-2,4-diamine Prepared according to general procedure 9 from [1-(pyrimidin-2-yl)piperidin-3-yl]methanamine and 4-chloro-6-(2,3-dimethylphenyl)pyrimidin-2-amine. LCMS [M+H]$^+$ 390; $^1$H NMR (400 MHz, CDCl$_3$) δ ppm 1.41 (m, 1 H) 1.48-1.60 (m, 1 H) 1.75 (m, 1 H) 1.85-1.98 (m, 2 H) 2.24 (s, 3 H) 2.31 (s, 3 H) 3.13-3.48 (m, 4 H) 4.15-4.24 (m, 1 H) 4.30 (m, 1 H) 5.11 (br. s., 2 H) 5.39 (br. s., 1 H) 5.82 (s, 1 H) 6.45 (t, J=4.80 Hz, 1 H) 7.10-7.19 (m, 3 H) 8.28-8.31 (d, J=4.80 Hz, 2 H).

Example 351

6-(2,3-Dimethylphenyl)-4-N-[2-(6-methoxy-1H-1,3-benzodiazol-2-yl)ethyl]pyrimidine-2,4-diamine Prepared according to general procedure 9 from 2-(6-methoxy-1H-1,3-benzodiazol-2-yl)ethan-1-amine and 4-chloro-6-(2,3-dimethylphenyl)pyrimidin-2-amine. LCMS [M+H]$^+$ 389; $^1$H NMR (400 MHz, CDCl$_3$) δ ppm 7.40 (d, J=8.59 Hz, 1 H) 7.12 (d, J=6.82 Hz, 1 H) 7.05 (t, J=7.58 Hz, 1 H) 7.01 (d, J=8.08 Hz, 2 H) 6.85 (dd, J=8.72, 2.40 Hz, 1 H) 5.88 (br. s., 1 H) 5.79 (s, 1 H) 5.11-5.43 (m, 2 H) 3.82-3.90 (m, 2 H) 3.81 (s, 3 H) 3.12 (t, J=6.19 Hz, 2 H) 2.24 (s, 3 H) 2.16 (s, 3 H)

Example 352

6-(2,3-Dimethylphenyl)-4-N-[2-(4-methyl-1,3-thiazol-5-yl)ethyl]pyrimidine-2,4-diamine Prepared according to general procedure 9 from 2-(4-methyl-1,3-thiazol-5-yl)ethan-1-amine and 4-chloro-6-(2,3-dimethylphenyl)pyrimidin-2-amine. LCMS [M+H]$^+$ 340; $^1$H NMR (400 MHz, CDCl$_3$) δ ppm 2.23 (s, 3 H) 2.40 (s, 3 H) 3.07 (t, J=6.82 Hz, 2 H) 3.56 (q, J=6.48 Hz, 2 H) 5.01 (br. s., 3 H) 5.79 (s, 1 H) 7.11-7.14 (m, 2 H) 7.17 (q, J=4.55 Hz, 1 H) 8.59 (s, 1 H).

Example 353

4-N-[(3-Cyclopropyl-1H-pyrazol-5-yl)methyl]-6-(2,3-dimethylphenyl)pyrimidine-2,4-diamine Prepared according to general procedure 9 from (3-cyclopropyl-1H-pyrazol-5-yl)methanamine and 4-chloro-6-(2,3-dimethylphenyl)pyrimidin-2-amine. LCMS [M+H]$^+$ 335; $^1$H NMR (400 MHz, CD$_3$OD) δ ppm 0.63-0.71 (m, 2 H) 0.93 (br. d, J=7.33 Hz, 2 H) 1.83-1.93 (m, 1 H) 2.18 (s, 3 H) 2.31 (s, 3 H) 4.50 (br. s., 2 H) 5.86 (s, 1 H) 5.92 (s, 1 H) 7.03-7.22 (m, 3 H).

Example 354

4-N-[3-(3,5-Dimethyl-1H-pyrazol-1-yl)propyl]-6-(2,3-dimethylphenyl)pyrimidine-2,4-diamine Prepared according to general procedure 9 from 3-(3,5-dimethyl-1H-pyrazol-1-yl)propan-1-amine and 4-chloro-6-(2,3-dimethylphenyl)pyrimidin-2-amine. LCMS [M+H]$^+$ 351; $^1$H NMR (400 MHz, CDCl$_3$) δ ppm 2.05 (quin, J=6.44 Hz, 2 H) 2.20 (s, 3 H) 2.21 (d, J=0.51 Hz, 3 H) 2.23 (s, 3 H) 2.31 (s, 3 H) 3.28-3.38 (m, 2 H) 4.07 (t, J=6.57 Hz, 2 H) 5.00 (br. s., 2 H) 5.36 (br. s., 1 H) 5.74 (s, 1 H) 5.78 (s, 1 H) 7.10-7.14 (m, 2 H) 7.16 (q, J=4.29 Hz, 1 H).

Example 355

6-(2,3-Dimethylphenyl)-4-N-{[1-(pyridin-2-yl)piperidin-3-yl]methyl}pyrimidine-2,4-diamine Prepared according to general procedure 9 from [1-(pyridin-2-yl)piperidin-3-yl]methanamine and 4-chloro-6-(2,3-dimethylphenyl)pyrimidin-2-amine. LCMS [M+H]$^+$ 389; $^1$H NMR (400 MHz, CDCl$_3$) δ ppm 1.28-1.40 (m, 1 H) 1.53-1.67 (m, 1 H) 1.73-1.83 (m, 1 H) 1.88-2.00 (m, 2 H) 2.24 (s, 3 H) 2.31 (s, 3 H) 3.00 (br. t, J=11.40 Hz, 1 H) 3.09 (ddd, J=12.95, 10.04, 3.28 Hz, 1 H) 3.17-3.40 (m, 2 H) 3.91 (dt, J=12.88, 4.29 Hz, 1 H) 4.10 (dd, J=12.88, 3.03 Hz, 1 H) 4.99 (br. s., 2 H) 5.31 (d, J=2.02 Hz, 1 H) 5.83 (s, 1 H) 6.57 (ddd, J=7.07, 4.93, 0.88 Hz, 1 H) 6.62-6.67 (m, 1 H) 7.12-7.19 (m, 3 H) 7.45 (ddd, J=8.91, 7.01, 2.02 Hz, 1 H) 8.16 (ddd, J=4.93, 2.02, 0.88 Hz, 1 H).

Example 356

6-(2,3-Dimethylphenyl)-4-N-[(2-phenyl-2H-1,2,3-triazol-4-yl)methyl]pyrimidine-2,4-diamine Prepared according to general procedure 9 from (2-phenyl-2H-1,2,3-triazol-4-yl)methanamine and 4-chloro-6-(2,3-dimethylphenyl)pyrimidin-2-amine. LCMS [M+H]$^+$ 372; $^1$H NMR (400 MHz, CDCl$_3$) δ ppm 2.21 (s, 3 H) 2.28 (s, 3 H) 4.67 (br d, J=5.31 Hz, 2 H) 5.17 (br. s., 2 H) 5.58-5.70 (m, 1 H) 5.87 (s, 1 H) 7.08-7.18 (m, 3 H) 7.32-7.38 (m, 1 H) 7.45-7.51 (m, 2 H) 7.74 (s, 1 H) 8.01-8.06 (m, 2 H).

Example 357

N-(3-{[2-Amino-6-(2,3-dimethylphenyl)pyrimidin-4-yl]amino}propyl)-4-chlorobenzene-1-sulfonamide Prepared according to general procedure 10 from 4-chlorobenzene-1-sulfonyl chloride and 4-N-(3-aminopropyl)-6-(2,3-dimethylphenyl)pyrimidine-2,4-diamine. LCMS [M+H]$^+$ 446; $^1$H NMR (400 MHz, CDCl$_3$) δ ppm 1.72 (quin, J=6.06 Hz, 2 H) 2.21 (s, 3 H) 2.30 (s, 3 H) 2.90 (d, J=5.05 Hz, 2 H) 3.49 (q, J=6.32 Hz, 2 H) 3.44-3.52 (m, 2 H) 5.33-5.43 (m, 1 H) 5.57 (br. s., 2 H) 5.78 (s, 1 H) 7.05-7.09 (m, 1 H) 7.09-7.13 (m, 1 H) 7.16-7.20 (m, 1 H) 7.41-7.46 (m, 2 H) 7.79-7.84 (m, 2 H).

Example 358

3-(3-{[2-Amino-6-(2,3-dimethylphenyl)pyrimidin-4-yl]amino}propyl)-1-(4-chlorophenyl)urea Prepared according to general procedure 11 from 1-chloro-4-isocyanatobenzene and 4-N-(3-aminopropyl)-6-(2,3-dimethylphenyl)pyrimidine-2,4-diamine. LCMS [M+H]$^+$ 425; $^1$H NMR (400 MHz, CD$_3$OD) δ ppm 1.85 (t, J=6.69 Hz, 2 H) 2.23 (s, 3 H) 2.34 (s, 3 H) 3.28 (overlap with methanol) 3.50-3.61 (m, 2 H) 5.97 (s, 1 H) 7.15 (s, 1 H) 7.17-7.25 (m, 3 H) 7.28-7.37 (m, 3 H).

Example 359

N-(3-{[2-Amino-6-(2,3-dimethylphenyl)pyrimidin-4-yl]amino}propyl)-3,5-dimethyl-1,2-oxazole-4-sulfonamide Prepared according to general procedure 10 from dimethyl-1,2-oxazole-4-sulfonyl chloride and 4-N-(3-aminopropyl)-6-(2,3-dimethylphenyl)pyrimidine-2,4-diamine. LCMS [M+H]$^+$ 431; $^1$H NMR (400 MHz, CDCl$_3$) δ ppm 1.79 (br. quin, J=6.0 Hz, 2 H) 2.23 (s, 3 H) 2.30 (s, 3 H) 2.42 (s, 3 H) 2.64 (s, 3 H) 3.01 (br. q, J=5.90 Hz, 2 H) 3.53 (br. q, J=6.00 Hz, 2 H) 5.89 (s, 1 H) 7.05-7.13 (m, 2 H) 7.18-7.21 (m, 1 H).

Example 360

N-(3-{[2-Amino-6-(2,3-dimethylphenyl)pyrimidin-4-yl]amino}propyl)-2-(dimethylamino)acetamide In a vial 4-N-(3-aminopropyl)-6-(2,3-dimethylphenyl)pyrimidine-2,4-diamine (10 mg, 0.037 mmol) and 2-(dimethylamino)acetyl chloride hydrochloride (50 mg, 0.32 mmol) were suspended in DCM (1.0 ml), then Et$_3$N (0.013 ml, 0.092 mmol) was added. The resulting reaction mixture was stirred at r.t. for 1 h. Then MeOH was added and the mixture was stirred 30 min after which the mixture was concentrated and purified by preparative HPLC. LCMS [M+H]$^+$ 357; $^1$H NMR (400 MHz, CDCl$_3$) δ ppm 1.70-1.78 (m, 2 H) 2.28 (s, 3 H) 2.31 (s, 3 H) 2.35 (s, 6 H) 3.06 (s, 2 H) 3.34-3.41 (m, 2 H) 3.48-3.55 (m, 2 H) 5.85 (s, 1 H) 7.12-7.16 (m, 2 H) 7.17-7.22 (m, 1 H).

Example 361

3-(3-{[2-Amino-6-(2,3-dimethylphenyl)pyrimidin-4-yl]amino}propyl)-1-(2,6-dichloropyridin-4-yl)urea Prepared according to general procedure 11 from 2,6-dichloro-4-isocyanatopyridine and 4-N-(3-aminopropyl)-6-(2,3-dimethylphenyl)pyrimidine-2,4-diamine. LCMS [M+H]$^+$ 460; $^1$H NMR (400 MHz, CDCl$_3$) δ ppm 1.86 (br. quint, J=6.7 Hz, 2 H) 2.24 (s, 3 H) 2.34 (s, 3 H) 3.30-3.34 (m [overlap w MeOH], 2H) 3.55 (br. s., 3 H) 5.98 (s, 1 H) 7.11-7.24 (m, 2 H) 7.27-7.33 (m, 1 H) 7.46 (s, 2 H).

Example 362

3-(3-{[2-Amino-6-(2,3-dimethylphenyl)pyrimidin-4-yl]amino}propyl)-1-(3,4-difluorophenyl)urea Prepared according to general procedure 11 from 1,2-difluoro-4-isocyanatobenzene and 4-N-(3-aminopropyl)-6-(2,3-dimethylphenyl)pyrimidine-2,4-diamine. LCMS [M+H]$^+$ 427; $^1$H NMR (400 MHz, CDCl$_3$) δ ppm 1.81-1.89 (m, 2 H) 2.24 (s, 3 H) 2.34 (s, 3 H) 3.25-3.30 (m [overlap w MeOH], 2H) 3.55 (br. s., 2 H) 5.98 (s, 1 H) 6.94-7.01 (m, 1 H) 7.06-7.17 (m, 2 H) 7.17-7.23 (m, 1 H) 7.27-7.33 (m, 1 H) 7.45-7.54 (m, 1 H).

Example 363

N-[3-(3-{[2-Amino-6-(2,3-dimethylphenyl)pyrimidin-4-yl]amino}propoxy)phenyl]acetamide Prepared according to general procedure 9 from N-[3-(3-aminopropoxy)phenyl]acetamide and 4-chloro-6-(2,3-dimethylphenyl)pyrimidin-2-amine. LCMS [M+H]$^+$ 406; $^1$H NMR (400 MHz, DMSO-d$_6$) δ ppm 1.96 (t, J=6.32 Hz, 2 H) 2.02 (s, 3 H) 2.15 (s, 3 H) 2.25 (s, 3 H) 4.00 (t, J=6.32 Hz, 2 H) 5.70 (s, 1 H) 5.92 (br. s., 2 H) 6.61 (dd, J=8.46, 1.64 Hz, 1 H) 6.85-6.99 (m, 1 H) 6.99-7.10 (m, 3 H) 7.11-7.19 (m, 2 H) 7.31 (s, 1 H) 9.88 (s, 1 H). A signal from one of the CH$_2$-groups is overlapping with solvent peaks and is not observed by NMR.

Example 364

6-(2,3-Dimethylphenyl)-4-N-[(2-methyl-1H-indol-5-yl)methyl]pyrimidine-2,4-diamine Prepared according to general procedure 9 from (2-methyl-1H-indol-5-yl)methanamine and 4-chloro-6-(2,3-dimethylphenyl)pyrimidin-2-amine. LCMS [M+H]$^+$ 358; $^1$H NMR (400 MHz, CDCl$_3$) δ ppm 2.22 (s, 3 H) 2.29 (s, 3 H) 2.45 (d, J=0.76 Hz, 3 H) 4.57 (br. s., 2 H) 5.16-5.32 (m, 2 H) 5.85 (s, 1 H) 6.18-6.21 (m, 1 H) 7.05-7.15 (m, 3 H) 7.15-7.19 (m, 1 H) 7.24-7.28 (m, 1 H) 7.47 (s, 1 H) 7.97 (br. s., 1 H).

Example 365

4-N-[2-(3,5-Dimethyl-1H-pyrazol-1-yl)ethyl]-6-(2,3-dimethylphenyl)pyrimidine-2,4-diamine Prepared according to general procedure 9 from 2-(3,5-dimethyl-1H-pyrazol-1-yl)ethan-1-amine and 4-chloro-6-(2,3-dimethylphenyl)pyrimidin-2-amine. LCMS [M+H]$^+$ 337; $^1$H NMR (400 MHz, CDCl$_3$) δ ppm 2.17 (d, J=0.51 Hz, 3 H) 2.18 (s, 3 H) 2.21 (s, 3 H) 2.29 (s, 3 H) 2.51-2.63 (m, 1 H) 3.68-3.76 (m, 2 H) 4.13 (t, J=5.56 Hz, 2 H) 5.03 (s, 2 H) 5.37-5.47 (m, 1 H) 5.71 (s, 1 H) 5.77 (s, 1H) 7.07-7.12 (m, 2 H) 7.12-7.17 (m, 1 H).

Example 366

6-(2,3-Dimethylphenyl)-4-N-[4-(pyrrolidin-1-yl)butyl]pyrimidine-2,4-diamine

Prepared according to general procedure 9 from 4-(pyrrolidin-1-yl)butan-1-amine and 4-chloro-6-(2,3-dimethylphenyl)pyrimidin-2-amine. LCMS [M+H]⁺ 340; ¹H NMR (400 MHz, CDCl₃) δ ppm 1.60-1.73 (m, 4 H) 1.78-1.86 (m, 4 H) 2.24 (s, 3 H) 2.31 (s, 3 H) 2.49-2.60 (m, 6 H) 3.31 (br. s., 2 H) 4.79 (s, 2 H) 5.46-5.58 (m, 1 H) 5.78 (s, 1 H) 7.09-7.18 (m, 3 H).

Example 367

N-(3-{[2-Amino-6-(2,3-dimethylphenyl)pyrimidin-4-yl]amino}propyl)-3-bromobenzamide 4-N-(3-aminopropyl)-6-(2,3-dimethylphenyl)pyrimidine-2,4-diamine (1.0 eq) was dissolved in THF (0.50 mL) and NMP (0.050 mL), then Et₃N (1.5 eq) and 3-bromobenzoyl chloride (1.2 eq) were added. The resulting reaction mixture was stirred at rt overnight. The mixture was then concentrated and purified by column chromatography. LCMS [M+H]⁺ 454; ¹H NMR (400 MHz, CDCl₃) δ ppm 1.80-1.89 (m, 2 H) 2.23 (s, 3 H) 2.30 (s, 3 H) 2.37-2.59 (m, 1 H) 3.47-3.58 (m, 4 H) 5.14 (br. s., 2 H) 5.55-5.69 (m, 1 H) 5.85 (s, 1 H) 7.07-7.13 (m, 2 H) 7.17 (dd, J=6.19, 2.91 Hz, 1 H) 7.31 (t, J=7.83 Hz, 1 H) 7.63 (ddd, J=7.89, 1.96, 1.01 Hz, 1 H) 7.75 (dd, J=7.83, 1.01 Hz, 1 H) 7.98 (t, J=1.77 Hz, 1 H).

Example 368

N-(3-{[2-Amino-6-(2,3-dimethylphenyl)pyrimidin-4-yl]amino}propyl)benzamide

In a vial 4-N-(3-aminopropyl)-6-(2,3-dimethylphenyl)pyrimidine-2,4-diamine (1.0 eq) was dissolved in NMP (0.050 mL) and THF (0.50 mL), then Et₃N (1.5 eq) and benzoyl chloride (1.0 eq) were added. The resulting reaction mixture was stirred at rt for 1 h. The mixture was then concentrated and purified by column chromatography. LCMS [M+H]⁺ 376; ¹H NMR (400 MHz, CDCl₃) δ ppm 1.86 (t, J=6.06 Hz, 2 H) 2.22 (s, 3 H) 2.29 (s, 3 H) 3.54 (dt, J=12.32, 6.09 Hz, 4 H) 5.36-5.54 (m, 1 H) 5.89 (s, 1 H) 6.14-6.31 (m, 1 H) 7.06-7.13 (m, 2 H) 7.16-7.20 (m, 1 H) 7.40-7.46 (m, 2 H) 7.47-7.53 (m, 1 H) 7.80-7.85 (m, 2 H).

Example 369

1-(3-{[2-Amino-6-(2,3-dimethylphenyl)pyrimidin-4-yl]amino}propyl)-3-(propan-2-yl)urea Prepared according to general procedure 11 from 2-isocyanatopropane and 4-N-(3-aminopropyl)-6-(2,3-dimethylphenyl)pyrimidine-2,4-diamine. LCMS [M+H]⁺ 357; ¹H NMR (400 MHz, CDCl₃) δ ppm 1.12 (d, J=6.57 Hz, 6 H) 1.78 (t, J=6.69 Hz, 2 H) 2.24 (s, 3 H) 2.35 (s, 3 H) 3.20 (t, J=6.82 Hz, 2 H) 3.45-3.57 (m, 2 H) 3.74-3.85 (m, 1 H) 5.97 (s, 1 H) 7.19 (d, J=14.65 Hz, 2 H) 7.30 (s, 1 H).

Example 370 tert-Butyl N-(4-{[2-amino-6-(2,3-dimethylphenyl)pyrimidin-4-yl]amino}butyl)-carbamate Prepared according to general procedure 9 from tert-butyl N-(4-aminobutyl)carbamate. LCMS [M+H]⁺ 386; ¹H NMR (400 MHz, CDCl₃) δ ppm 1.45 (s, 9 H) 1.54-1.72 (m, 6 H) 2.24-2.28 (m, 3 H) 2.31 (s, 3 H) 3.20 (d, J=6.32 Hz, 3 H) 3.33-3.43 (m, 2 H) 4.79-4.91 (m, 1 H) 5.79-5.83 (m, 1 H) 7.14 (s, 2 H) 7.16-7.21 (m, 1 H).

Example 371 tert-Butyl N-(5-{[2-amino-6-(2,3-dimethylphenyl)pyrimidin-4-yl]amino}pentyl)-carbamate Step 1: 4-N-(5-Aminopentyl)-6-(2,3-dimethylphenyl)pyrimidine-2,4-diamine was prepared according to general procedure 9 from pentane-1,5-diamine and 4-chloro-6-(2,3-dimethylphenyl)pyrimidin-2-amine.

Step 2: 4-N-(5-Aminopentyl)-6-(2,3-dimethylphenyl)pyrimidine-2,4-diamine (15 mg, 0.028 mmol) and tert-butoxycarbonyl tert-butyl carbonate (7.2 mg, 0.033 mmol) were dissolved in THF (0.50 mL). Then Et₃N (0.011 mL, 0.085 mmol) was added and the resulting mixture was stirred at room temperature for 16 h. The reaction mixture was concentrated and purified by column chromatography (0→5% in DCM) to afford tert-butyl N-[5-[[2-amino-6-(2,3-dimethylphenyl)pyrimidin-4-yl]amino]pentyl]carbamate. LCMS [M+H]⁺ 400; ¹H NMR (400 MHz, CDCl₃) δ ppm 1.35-1.47 (m, 11 H) 1.52 (d, J=7.07 Hz, 2 H) 1.58-1.68 (m, 2 H) 2.24 (s, 3 H) 2.29 (s, 3 H) 3.13 (d, J=6.06 Hz, 2 H) 3.26-3.37 (m, 2 H) 4.58-4.68 (m, 1 H) 5.89 (s, 1 H) 7.11 (d, J=4.80 Hz, 2 H) 7.18 (d, J=4.80 Hz, 1 H).

Example 372 tert-Butyl N-(2-{[2-amino-6-(2,3-dimethylphenyl)pyrimidin-4-yl]amino}cyclohexyl)-carbamate Step 1: 4-N-(2-Aminocyclohexyl)-6-(2,3-dimethylphenyl)pyrimidine-2,4-diamine was prepared according to general procedure 9 from cyclohexane-1,2-diamine and 4-chloro-6-(2,3-dimethylphenyl)pyrimidin-2-amine.

Step 2: 4-N-(2-Aminocyclohexyl)-6-(2,3-dimethylphenyl)pyrimidine-2,4-diamine (15 mg, 0.028 mmol) and tert-butoxycarbonyl tert-butyl carbonate (7.0 mg, 0.032 mmol) were dissolved in THF (0.50 mL). Then Et₃N (0.0050 mL, 0.036 mmol) was added and the resulting mixture was stirred at rt for 16 h. The reaction mixture was concentrated and purified by column chromatography (0→5% in DCM) to afford tert-butyl N-[2-[[2-amino-6-(2,3-dimethylphenyl)pyrimidin-4-yl]amino]cyclohexyl]carbamate. LCMS [M+H]⁺ 412; NMR: mixture of cis- and trans-diastereomers: ¹H NMR (400 MHz, CDCl₃) δ ppm 1.16-1.37 (m, 6 H) 1.38-1.42 (m, 18 H) 1.53 (br. s., 6 H) 1.79 (br. s., 4 H) 2.00-2.08 (m, 1 H) 2.18-2.23 (m, 1 H) 2.25 (d, J=3.79 Hz, 6 H) 2.31 (s, 6 H) 3.40-3.51 (m, 1 H) 3.62-3.75 (m, 1 H) 3.83-3.92 (m, 1 H) 3.97-4.10 (m, 1 H) 4.80-4.93 (m, 1 H) 4.97-5.10 (m, 1 H) 5.15-5.37 (m, 2 H) 5.43-5.67 (m, 2 H) 5.75 (s, 1 H) 5.83 (s, 1 H) 7.09-7.15 (m, 4 H) 7.16-7.21 (m, 2 H).

Example 373 tert-Butyl N-(1-{[2-amino-6-(2,3-dimethylphenyl)pyrimidin-4-yl]amino}-2-methylpropan-2-yl)carbamate Step 1: 4-N-(2-Amino-2-methyl-propyl)-6-(2,3-dimethylphenyl)pyrimidine-2,4-diamine was prepared according to general procedure 9 from 2-methylpropane-1,2-diamine and 4-chloro-6-(2,3-dimethylphenyl)pyrimidin-2-amine.

Step 2: 4-N-(2-Amino-2-methylpropyl)-6-(2,3-dimethylphenyl)pyrimidine-2,4-diamine (15 mg, 0,029 mmol) and tert-butoxycarbonyl tert-butyl carbonate (7.8 mg, 0.036 mmol) were dissolved in THF (0.50 mL). Then Et₃N (0.0061 mL, 0.044 mmol) was added and the resulting mixture was stirred at rt for 16 h. The reaction mixture was concentrated and purified by column chromatography (0→5% in DCM) to afford tert-butyl N-[2-[[2-amino-6-(2,3-dimethylphenyl)pyrimidin-4-yl]amino]-1,1-dimethylethyl]carbamate. LCMS [M+H]$^+$ 386; $^1$H NMR (400 MHz, CDCl$_3$) δ ppm 1.34 (s, 6 H) 1.43 (s, 9 H) 2.26 (s, 3 H) 2.31 (s, 3 H) 3.53 (d, J=5.81 Hz, 2 H) 5.14-5.47 (m, 2 H) 5.87 (s, 1 H) 7.10-7.16 (m, 2 H) 7.18 (d, J=3.28 Hz, 1 H).

Example 374

N-(3-{[2-Amino-6-(2,3-dimethylphenyl)pyrimidin-4-yl]amino}propyl)-3-cyanobenzene-1-sulfonamide Prepared according to general procedure 10 from 3-cyanobenzene-1-sulfonyl chloride and 4-N-(3-aminopropyl)-6-(2,3-dimethylphenyl)pyrimidine-2,4-diamine. LCMS [M+H]$^+$ 437; $^1$H NMR (400 MHz, CDCl$_3$) δ ppm 1.70-1.82 (m, 4 H) 2.23 (s, 3 H) 2.31 (s, 3 H) 2.98 (d, J=5.31 Hz, 2 H) 3.54 (d, J=5.81 Hz, 2 H) 4.71-4.80 (m, 1 H) 5.29 (br. s., 2 H) 5.76 (s, 1 H) 7.07-7.21 (m, 3 H) 7.59-7.65 (m, 1 H) 7.82 (dt, J=7.64, 1.36 Hz, 1 H) 8.14 (dq, J=7.96, 0.97 Hz, 1 H) 8.18-8.21 (m, 1 H).

Example 375

N-(3-{[2-Amino-6-(2,3-dimethylphenyl)pyrimidin-4-yl]amino}propyl)-4-methanesulfonylbenzene-1-sulfonamide Prepared according to general procedure 10 from 4-methanesulfonylbenzene-1-sulfonyl chloride and 4-N-(3-aminopropyl)-6-(2,3-dimethylphenyl)pyrimidine-2,4-diamine. LCMS [M+H]$^+$ 490; $^1$H NMR (400 MHz, CDCl$_3$) δ ppm 1.73-1.80 (m, 2 H) 2.23 (s, 3 H) 2.32 (s, 3 H) 2.95-3.01 (m, 2 H) 3.08 (s, 3 H) 3.51-3.58 (m, 2 H) 4.69-4.77 (m, 1 H) 5.31 (s, 2 H) 5.77 (s, 1 H) 7.08-7.21 (m, 3 H) 8.09 (q, J=8.76 Hz, 4 H).

Example 376

N-(3-{[2-Amino-6-(2,3-dimethylphenyl)pyrimidin-4-yl]amino}propyl)benzene-sulfonamide Prepared according to general procedure 10 from benzenesulfonyl chloride and 4-N-(3-aminopropyl)-6-(2,3-dimethylphenyl)pyrimidine-2,4-diamine. LCMS [M+H]$^+$ 412; $^1$H NMR (400 MHz, CDCl$_3$) δ ppm 1.72 (dt, J=12.06, 5.97 Hz, 2 H) 1.76-1.89 (m, 1 H) 2.22 (s, 3 H) 2.31 (s, 3 H) 2.93 (q, J=6.15 Hz, 2 H) 3.49 (q, J=6.40 Hz, 2 H) 4.70-4.82 (m, 1 H) 5.28 (br. s., 2 H) 5.72-5.74 (m, 1 H) 7.08-7.15 (m, 2 H) 7.16-7.20 (m, 1 H) 7.45-7.51 (m, 1 H) 7.52-7.57 (m, 1 H) 7.87-7.92 (m, 2 H).

Example 377

N-(3-{[2-Amino-6-(2,3-dimethylphenyl)pyrimidin-4-yl]amino}-2,2-dimethylpropyl)-3-fluorobenzene-1-sulfonamide Step 1: tert-butyl N-(3-{[2-amino-6-(2,3-dimethylphenyl)pyrimidin-4-yl]amino}-2,2-dimethylpropyl)carbamate (prepared in example 239) (180 mg, 0.45 mmol) was dissolved in trifluoroacetic acid (2 ml) and stirred at reflux for 1 h. The TFA was evaporated and the crude residue was purified by silica gel chromatography using a gradient of 2-30% MeOH [containing 1 v/v % NH$_4$OH] in DCM which afforded 4-N-(3-amino-2,2-dimethyl-propyl)-6-(2,3-dimethylphenyl)pyrimidine-2,4-diamine (110 mg, 0.37 mmol). LCMS [M+H]$^+$ 300.

Step 2: N-(3-{[2-Amino-6-(2,3-dimethylphenyl)pyrimidin-4-yl]amino}-2,2-dimethylpropyl)-3-fluorobenzene-1-sulfonamide was prepared according to general procedure 10 from 3-fluorobenzene-1-sulfonyl chloride and 4-N-(3-amino-2,2-dimethyl-propyl)-6-(2,3-dimethylphenyl)pyrimidine-2,4-diamine (prepared in step 1). LCMS [M+H]$^+$ 458; $^1$H NMR (400 MHz, CDCl$_3$) δ ppm 0.92 (s, 6 H) 2.16-2.20 (m, 3 H) 2.29 (s, 3 H) 2.69 (d, J=7.07 Hz, 2 H) 3.38 (d, J=6.82 Hz, 2 H) 5.91 (s, 1 H) 6.53 (s, 1 H) 7.04-7.08 (m, 1 H) 7.09-7.15 (m, 1 H) 7.23-7.30 (m, 1 H) 7.38-7.45 (m, 1 H) 7.46-7.56 (m, 2 H) 7.64 (d, J=7.83 Hz, 1 H).

Example 378

N-(3-{[2-Amino-6-(2,3-dimethylphenyl)pyrimidin-4-yl]amino}-2,2-dimethylpropyl)-4-(morpholine-4-sulfonyl)benzene-1-sulfonamide Step 1: tert-butyl N-(3-{[2-amino-6-(2,3-dimethylphenyl)pyrimidin-4-yl]amino}-2,2-dimethylpropyl)carbamate (prepared in example 239) (180 mg, 0.45 mmol) was dissolved in trifluoroacetic acid (2 ml) and stirred at reflux for 1 h. The TFA was evaporated and the crude residue was purified by silica gel chromatography using a gradient of 2-30% MeOH [containing 1 v/v % NH$_4$OH] in DCM which afforded 4-N-(3-amino-2,2-dimethyl-propyl)-6-(2,3-dimethylphenyl)pyrimidine-2,4-diamine (110 mg, 0.37 mmol). LCMS [M+H]$^+$ 300.

Step 2: N-(3-{[2-Amino-6-(2,3-dimethylphenyl)pyrimidin-4-yl]amino}-2,2-dimethylpropyl)-4-(morpholine-4-sulfonyl)benzene-1-sulfonamide was prepared according to general procedure 10 from 4-(morpholine-4-sulfonyl)benzene-1-sulfonyl chloride and 4-N-(3-amino-2,2-dimethyl-propyl)-6-(2,3-dimethyl-phenyl)pyrimidine-2,4-diamine (prepared in step 1 above). LCMS [M+H]$^+$ 589; $^1$H NMR (400 MHz, CDCl$_3$) δ ppm 0.92 (s, 6 H) 2.18 (d, J=0.51 Hz, 3 H) 2.28 (s, 3 H) 2.71 (d, J=6.82 Hz, 2 H) 2.99-3.06 (m, 4 H) 3.38 (d, J=6.82 Hz, 2 H) 3.70-3.78 (m, 4 H) 5.93 (s, 1 H) 6.94 (s, 1 H) 7.03-7.08 (m, 1 H) 7.09-7.15 (m, 1 H) 7.25 (d, J=7.58 Hz, 1 H) 7.42 (s, 1 H) 7.87 (d, J=8.59 Hz, 2 H) 8.02 (d, J=8.59 Hz, 2 H).

Example 379

6-(2,3-Dimethylphenyl)-4-N-(prop-2-en-1-yl)pyrimidine-2,4-diamin.

Prepared according to general procedure 9 from prop-2-en-1-amine and 4-chloro-6-(2,3-dimethylphenyl)pyrimidin-2-amine. LCMS [M+H]$^+$ 255; $^1$H NMR (400 MHz, CDCl$_3$) δ ppm 2.23 (s, 3 H) 2.31 (s, 3 H) 3.92 (br. s., 2 H) 4.95 (br. s., 3 H) 5.18 (dq, J=10.23, 1.47 Hz, 1 H) 5.26 (dq, J=17.18, 1.60 Hz, 1 H) 5.81 (s, 1 H) 5.85-5.96 (m, 1 H) 7.10-7.15 (m, 2 H) 7.15-7.19 (m, 1 H).

Example 380

1-(3-{[2-Amino-6-(2,3-dimethylphenyl)pyrimidin-4-yl]amino}propyl)imidazolidin-2-one Prepared according to general procedure 9 from 1-(3-aminopropyl)imidazolidin-2-one and 4-chloro-6-(2,3-dimethylphenyl)pyrimidin-2-amine. LCMS [M+H]$^+$ 341.

Example 381

N-(3-{[2-Amino-6-(2,3-dimethylphenyl)pyrimidin-4-yl]amino}propyl)-3-fluorobenzene-1-sulfonamide Prepared according to general procedure 10 from 3-fluorobenzene-1-sulfonyl chloride and 4-N-(3-aminopropyl)-6-(2,3-dimethylphenyl)pyrimidine-2,4-diamine. LCMS [M+H]$^+$ 430.

Example 382

N-{4-[(3-{[2-Amino-6-(2,3-dimethylphenyl)pyrimidin-4-yl]amino}propyl)sulfamoyl]-phenyl}acetamide Prepared according to general procedure 10 from 4-acetamidobenzene-1-sulfonyl chloride and 4-N-(3-aminopropyl)-6-(2,3-dimethylphenyl)pyrimidine-2,4-diamine. LCMS [M+H]$^+$ 469.

Example 383

N-(3-{[2-Amino-6-(2,3-dimethylphenyl)pyrimidin-4-yl]amino}propyl)methanesulfonamide Prepared according to general procedure 10 from methanesulfonyl chloride and 4-N-(3-aminopropyl)-6-(2,3-dimethylphenyl)pyrimidine-2,4-diamine. LCMS [M+H]$^+$ 350.

Example 384

N-(2-{[2-Amino-6-(2,3-dimethylphenyl)pyrimidin-4-yl]amino}ethyl)-3-fluorobenzene-1-sulfonamide Prepared according to general procedure 10 from 3-fluorobenzene-1-sulfonyl chloride and 4-N-(2-aminoethyl)-6-(2,3-dimethylphenyl)pyrimidine-2,4-diamine. LCMS [M+H]$^+$ 416.

Example 385

N-(2-{[2-Amino-6-(2,3-dimethylphenyl)pyrimidin-4-yl]amino}ethyl)-4-methoxybenzene-1-sulfonamide Prepared according to general procedure 10 from 4-methoxybenzene-1-sulfonyl chloride and 4-N-(2-aminoethyl)-6-(2,3-dimethylphenyl)pyrimidine-2,4-diamine. LCMS [M+H]$^+$ 428.

Example 386

6-(2,3-Dimethylphenyl)-4-N-(prop-2-yn-1-yl)pyrimidine-2,4-diamine

Prepared according to general procedure 9 from prop-2-yn-1-amine and 4-chloro-6-(2,3-dimethylphenyl)pyrimidin-2-amine. LCMS [M+H]$^+$ 253.

Example 387

2-{[2-Amino-6-(2,3-dimethylphenyl)pyrimidin-4-yl]amino}acetamide

Prepared according to general procedure 9 from 2-aminoacetamide and 4-chloro-6-(2,3-dimethylphenyl)pyrimidin-2-amine. LCMS [M+H]$^+$ 272.

Example 388

N-(3-{[2-Amino-6-(2,3-dimethylphenyl)pyrimidin-4-yl]amino}propyl)-4,5-dichlorothiophene-2-sulfonamide Prepared according to general procedure 10 from 4,5-dichlorothiophene-2-sulfonyl chloride and 4-N-(3-aminopropyl)-6-(2,3-dimethylphenyl)pyrimidine-2,4-diamine. LCMS [M+H]$^+$ 486.

Example 389

N-(3-{[2-Amino-6-(2,3-dimethylphenyl)pyrimidin-4-yl]amino}propyl)-5-chloro-1,3-dimethyl-1H-pyrazole-4-sulfonamide Prepared according to general procedure 10 from 5-chloro-1,3-dimethyl-1H-pyrazole-4-sulfonyl chloride and 4-N-(3-aminopropyl)-6-(2,3-dimethylphenyl)-pyrimidine-2,4-diamine. LCMS [M+H]$^+$ 464.

Example 390

2-{[2-Amino-6-(2,3-dimethylphenyl)pyrimidin-4-yl]amino}acetonitrile

Prepared according to general procedure 9 from 2-aminoacetonitrile and 4-chloro-6-(2,3-dimethylphenyl)pyrimidin-2-amine. LCMS [M+H]$^+$ 254.

Example 391

N-(3-{[2-Amino-6-(2,3-dimethylphenyl)pyrimidin-4-yl]amino}propyl)-1,2-dimethyl-1H-imidazole-4-sulfonamide Prepared according to general procedure 10 from 1,2-dimethyl-1H-imidazole-4-sulfonyl chloride and 4-N-(3-aminopropyl)-6-(2,3-dimethylphenyl)pyrimidine-2,4-diamine. LCMS [M+H]$^+$ 430; $^1$H NMR (400 MHz, CD$_3$OD) δ ppm 7.69 (s, 2 H), 7.33-7.38 (m, 1 H), 7.21-7.27 (m, 1 H), 7.16-7.20 (m, 1 H), 6.00 (s, 1 H), 3.71 (s, 3 H), 3.58 (s, 2 H), 3.06 (s, 2 H), 2.45 (s, 3 H), 2.36 (s, 3 H), 2.25 (s, 3 H), 1.80-1.90 (m, 2 H).

Example 392

N-(2-{[2-Amino-6-(2,3-dimethylphenyl)pyrimidin-4-yl]amino}ethyl)-5-chloro-1,3-dimethyl-1H-pyrazole-4-sulfonamide Prepared according to general procedure 10 from 5-chloro-1,3-dimethyl-1H-pyrazole-4-sulfonyl chloride and 4-N-(2-aminoethyl)-6-(2,3-dimethylphenyl)-pyrimidine-2,4-diamine. LCMS [M+H]$^+$ 450.

Example 393

4-N-{2-[(1,3-Benzoxazol-2-yl)amino]ethyl}-6-(2,3-dimethylphenyl)pyrimidine-2,4-diamine Prepared according to general procedure 12 from 2-chloro-1,3-benzoxazole and 4-N-(2-aminoethyl)-6-(2,3-dimethylphenyl)pyrimidine-2,4-diamine. LCMS [M+H]$^+$ 375.

Example 394

6-(2,3-Dimethylphenyl)-4-N-(4-phenylbutan-2-yl)pyrimidine-2,4-diamine

Prepared according to general procedure 9 from 4-phenylbutan-2-amine and 4-chloro-6-(2,3-dimethylphenyl)pyrimidin-2-amine. LCMS [M+H]$^+$ 347.

Example 395

4-N-(2,2-Dimethyloxan-4-yl)-6-(2,3-dimethylphenyl)pyrimidine-2,4-diamine

Prepared according to general procedure 9 from 2,2-dimethyloxan-4-amine and 4-chloro-6-(2,3-dimethylphenyl)pyrimidin-2-amine. LCMS [M+H]$^+$ 327.

Example 396

Ethyl 2-{[2-amino-6-(2,3-dimethylphenyl)pyrimidin-4-yl]amino}acetate

Prepared according to general procedure 9 from ethyl 2-aminoacetate and 4-chloro-6-(2,3-dimethylphenyl)pyrimidin-2-amine. LCMS [M+H]$^+$ 301.

Example 397

6-[(2-{[2-Amino-6-(2,3-dimethylphenyl)pyrimidin-4-yl]amino}ethyl)amino]pyridine-3-carbonitrile Prepared according to general procedure 12 from 6-chloropyridine-3-carbonitrile and 4-N-(2-aminoethyl)-6-(2,3-dimethylphenyl)pyrimidine-2,4-diamine. LCMS [M+H]$^+$ 360; $^1$H NMR (400 MHz, CD$_3$OD) δ ppm 8.32-8.34 (m, 1 H), 7.59-7.64 (m, 1 H), 7.34-7.38 (m, 1 H), 7.22-7.27 (m, 2 H), 7.15-7.18 (m, 1 H), 6.55-6.59 (m, 1 H), 5.97 (s, 1 H), 3.72-3.77 (m, 3 H), 3.66-3.71 (m, 3 H), 2.36 (s, 4 H), 2.24 (s, 3 H).

Example 398

4-N-{2-[(3-Bromo-1,2,4-thiadiazol-5-yl)amino]ethyl}-6-(2,3-dimethylphenyl)pyrimidine-2,4-diamine Prepared according to general procedure 12 from 3-bromo-5-chloro-1,2,4-thiadiazole and 4-N-(2-aminoethyl)-6-(2,3-dimethylphenyl)pyrimidine-2,4-diamine. LCMS [M+H]$^+$ 420.

Example 399

6-(2,3-Dimethylphenyl)-4-N-[(5-methyl-4H-1,2,4-triazol-3-yl)methyl]pyrimidine-2,4-diamine Prepared according to general procedure 9 from (5-methyl-4H-1,2,4-triazol-3-yl)methanamine and 4-chloro-6-(2,3-dimethylphenyl)pyrimidin-2-amine. LCMS [M+H]$^+$ 310; $^1$H NMR (400 MHz, CD$_3$OD) δ ppm 7.37-7.41 (m, 1 H), 7.25-7.30 (m, 1 H), 7.20-7.24 (m, 1 H), 6.12 (s, 1 H), 4.79 (s, 2 H), 2.47 (s, 3 H), 2.38 (s, 3 H), 2.29 (s, 3 H).

Example 400

6-(2,3-Dimethylphenyl)-4-N-{2-[5-(4-fluorophenyl)-1,3,4-oxadiazol-2-yl]ethyl}pyrimidine-2,4-diamine Prepared according to general procedure 9 from 2-[5-(4-fluorophenyl)-1,3,4-oxadiazol-2-yl]ethan-1-amine and 4-chloro-6-(2,3-dimethylphenyl)pyrimidin-2-amine. LCMS [M+H]$^+$ 405.

Example 401

N-(2-{[2-Amino-6-(2,3-dimethylphenyl)pyrimidin-4-yl]amino}ethyl)-4-methanesulfonylbenzene-1-sulfonamide Prepared according to general procedure 10 from 4-methanesulfonylbenzene-1-sulfonyl chloride and 4-N-(2-aminoethyl)-6-(2,3-dimethylphenyl)pyrimidine-2,4-diamine. LCMS [M+H]$^+$ 476; $^1$H NMR (400 MHz, CD$_3$OD) δ ppm 8.10-8.14 (m, 3H), 8.05-8.09 (m, 3 H), 7.16-7.20 (m, 1 H), 7.09-7.14 (m, 1 H), 7.05-7.08 (m, 1H), 5.73-5.76 (m, 1 H), 3.42-3.49 (m, 2 H), 3.14 (s, 6 H), 2.31 (s, 4 H), 2.18 (s, 3 H).

Example 402

N-(3-{[2-Amino-6-(2,3-dimethylphenyl)pyrimidin-4-yl]amino}propyl)-3-methanesulfonylbenzene-1-sulfonamide Prepared according to general procedure 10 from 3-methanesulfonylbenzene-1-sulfonyl chloride and 4-N-(3-aminopropyl)-6-(2,3-dimethylphenyl)pyrimidine-2,4-diamine. LCMS [M+H]$^+$ 490; $^1$H NMR (400 MHz, CDCl$_3$) δ ppm 8.43-8.45 (m, 1 H), 8.18 (ddd, J=7.8, 1.8, 1.0 Hz, 3 H), 8.11 (ddd, J=7.8, 1.8, 1.0 Hz, 3 H), 7.67-7.73 (m, 1 H), 7.15-7.19 (m, 1 H), 7.09-7.13 (m, 1 H), 7.08 (d, J=2.0 Hz, 1 H), 5.74 (s, 1 H), 5.31 (br. s., 2 H), 4.82-5.00 (m, 1 H), 3.50 (d, J=5.8 Hz, 2 H), 3.09 (s, 3 H), 2.94 (d, J=4.0 Hz, 2 H), 2.29 (s, 3 H), 2.20 (s, 3 H), 1.71 (t, J=5.8 Hz, 2 H).

Example 403

N-(3-{[2-Amino-6-(2,3-dimethylphenyl)pyrimidin-4-yl]amino}propyl)-2-methanesulfonylbenzene-1-sulfonamide Prepared according to general procedure 10 from 2-methanesulfonylbenzene-1-sulfonyl chloride and 4-N-(3-aminopropyl)-6-(2,3-dimethylphenyl)pyrimidine-2,4-diamine. LCMS [M+H]$^+$ 490; $^1$H NMR (400 MHz, CD$_3$OD) δ ppm 8.20-8.33 (m, 3 H), 8.10-8.17 (m, 1 H), 7.84-7.90 (m, 5 H), 7.68-7.80 (m, 3 H), 7.16-7.21 (m, 3H), 7.12 (s, 3 H), 7.08 (d, J=1.5 Hz, 3 H), 5.74 (s, 3 H), 3.46 (s, 3 H), 3.43 (s, 8 H), 3.32-3.36 (m, 3 H), 3.07 (t, J=6.7 Hz, 5 H), 2.31 (s, 8 H), 2.19 (s, 3 H), 1.66 (t, J=6.7 Hz, 5 H).

Example 404

6-(2,3-Dimethylphenyl)-4-N-[2-(4-methanesulfonylphenyl)ethyl]pyrimidine-2,4-diamine A mixture of 4-chloro-6-(2,3-dimethylphenyl)pyrimidin-2-amine (0.15 mmol), 2-(4-methylsulfonylphenyl)ethanamine (1.2 equiv.) and N,N-diisopropylethylamine (2.25 equiv.) in n-butanol (0.3 mL) was heated in a sealed tube at 110° C. overnight. Methanol was added and the mixture was filtered and purified by preparative HPLC. LCMS [M+H]+ 397.

Example 405

6-(2,3-Dimethylphenyl)-4-N-[2-(4-methanesulfonyl-phenyl)ethyl]pyrimidine-2,4-diamine A mixture of 4-chloro-6-(2,3-dichlorophenyl)pyrimidin-2-amine (0.08 mmol), 2-(4-methylthiazol-5-yl)ethanamine; dihydrobromide (1.2 equiv.) and N,N-diisopropylethylamine (4.25 equiv.) in n-butanol (0.3 ml) was heated in a sealed tube at 110° C. overnight. Methanol was added and the mixture was filtered and purified by preparative HPLC. LCMS [M+H]+ 380.

Example 406

6-(2,3-Dimethylphenyl)-4-N-[2-(4-methanesulfonyl-phenyl)ethyl]pyrimidine-2,4-diamine A mixture of 4-chloro-6-(3-chloro-2-methyl-phenyl)pyrimidin-2-amine (0.14 mmol), 2-(4-methylthiazol-5-yl)ethanamine; dihydrobromide (1.2 equiv.) and N,N-diisopropylethylamine (4.25 equiv.) in n-butanol (0.3 mL) was heated in a sealed tube at 110° C. overnight. Methanol was added and the mixture was filtered and purified by preparative HPLC. LCMS [M+H]+ 360.

Example 407

6-(2,3-Dimethylphenyl)-4-N-[2-(4-methanesulfonyl-phenyl)ethyl]pyrimidine-2,4-diamine A mixture of 4-chloro-6-(2,3-dimethylphenyl)pyrimidin-2-amine (0.13 mmol), [2-(difluoromethyl)-4-pyridyl]methanamine; hydrochloride (1.2 equiv.) and N,N-diisopropylethylamine (3.25 equiv.) in n-butanol (0.3 ml) was heated in a sealed tube at 110° C. overnight. Methanol was added and the mixture was filtered and purified by preparative HPLC. LCMS [M+H]+ 356.

Example 408

6-(2,3-Dimethylphenyl)-4-N-[2-(4-methanesulfonyl-phenyl)ethyl]pyrimidine-2,4-diamine A mixture of 4-chloro-6-(2,3-dimethylphenyl)pyrimidin-2-amine (0.13 mmol), 2-(1H-imidazol-4-yl)ethanamine; dihydrochloride (1.2 equiv.) and N,N-diisopropylethylamine (3.25 equiv.) in n-butanol (0.3 mL) was heated in a sealed tube at 110° C. overnight. Methanol was added and the mixture was filtered and purified by preparative HPLC. LCMS [M+H]+ 309.

Example 409

6-(2,3-Dimethylphenyl)-4-N-[2-(4-methanesulfonyl-phenyl)ethyl]pyrimidine-2,4-diamine A mixture of 4-chloro-6-(2,3-dimethylphenyl)pyrimidin-2-amine (0.13 mmol), 3-(1H-benzimidazol-2-yl)propan-1-amine (1.2 equiv.) and N,N-diisopropylethylamine (3.25 equiv.) in n-butanol (0.3 mL) was heated in a sealed tube at 110° C. overnight. Methanol was added and the mixture was filtered and purified by preparative HPLC. LCMS [M+H]+ 373.

Example 410

6-(2,3-Dimethylphenyl)-4-N-[2-(4-methanesulfonyl-phenyl)ethyl]pyrimidine-2,4-diamine A mixture of 4-chloro-6-(2,3-dimethylphenyl)pyrimidin-2-amine (0.14 mmol), (1-methylbenzimidazol-2-yl)methanamine (1.2 equiv.) and N,N-diisopropylethylamine (1.25 equiv.) in n-butanol (0.3 mL) was heated in a sealed tube at 110° C. overnight. Methanol was added and the mixture was filtered and purified by preparative HPLC. LCMS [M+H]+ 359.

Example 411

6-(2,3-Dimethylphenyl)-4-N-[2-(4-methanesulfonyl-phenyl)ethyl]pyrimidine-2,4-diamine A mixture of 4-chloro-6-(2,3-dimethylphenyl)pyrimidin-2-amine (0.13 mmol), (2-phenylthiazol-5-yl)methanamine hydrochloride (1.2 equiv.) and N,N-diisopropylethylamine (2.25 equiv.) in n-butanol (0.3 mL) was heated in a sealed tube at 110° C. overnight. Methanol was added and the mixture was filtered and purified by preparative HPLC. LCMS [M+H]+ 388.

Example 412

6-(3-chloro-2-methylphenyl)-4-N-[2-(5-methyl-1H-1,2,4-triazol-3-yl)ethyl]pyrimidine-2,4-diamine A mixture 4-chloro-6-(3-chloro-2-methyl-phenyl)pyrimidin-2-amine (0.14 mmol), 2-(5-methyl-1H-1,2,4-triazol-3-yl)ethanamine hydrochloride (1.2 equiv.) and N,N-diisopropylethylamine (3.25 equiv.) in n-butanol (0.3 mL) was heated in a sealed tube at 110° C. overnight. Methanol was added and the mixture was filtered and purified by preparative HPLC. LCMS [M+H]+ 344.

Example 413

6-(2,3-dichlorophenyl)-4-N-[2-(5-methyl-1H-1,2,4-triazol-3-yl)ethyl]pyrimidine-2,4-diamine A mixture of 4-chloro-6-(2,3-dichlorophenyl)pyrimidin-2-amine (0.13 mmol), 2-(5-methyl-1H-1,2,4-triazol-3-yl)ethanamine hydrochloride (1.0 equiv.) and N,N-diisopropylethylamine (3.25 equiv.) in n-butanol (0.3 mL) was heated in a sealed tube at 110° C. overnight. Methanol was added and the mixture was filtered and purified by preparative HPLC. LCMS [M+H]+ 364.

Example 414

4-(2-{[2-amino-6-(3-chloro-2-methylphenyl)pyrimidin-4-yl]amino}ethyl)-N,N-dimethylbenzene-1-sulfonamide A mixture of 4-chloro-6-(3-chloro-2-methyl-phenyl)pyrimidin-2-amine (0.14 mmol), 4-(2-aminoethyl)-N,N-dimethyl-benzenesulfonamide (1.0 equiv.) and N,N-diisopropylethylamine (2.25 equiv.) in n-butanol (0.3 mL) was heated in a sealed tube at 110° C. overnight. Methanol was added and the mixture was filtered and purified by preparative HPLC. LCMS [M+H]+ 446.

Example 415

4-(2-{[2-amino-6-(2,3-dichlorophenyl)pyrimidin-4-yl]amino}ethyl)-N,N-dimethylbenzene-1-sulfonamide A mixture of 4-chloro-6-(2,3-dichlorophenyl)pyrimidin-2-amine (0.13 mmol), 4-(2-aminoethyl)-N, N-dimethyl-benzenesulfonamide (1.0 equiv.) and N,N-diisopropyl-ethylamine (2.25 equiv.) in n-butanol (0.3 mL) was heated in a sealed tube at 110° C. overnight. Methanol was added and the mixture was filtered and purified by preparative HPLC. LCMS [M+H]+ 466.

Example 416

4-(2-{[2-amino-6-(2,3-dimethylphenyl)pyrimidin-4-yl]amino}ethyl)-N,N-dimethylbenzene-1-sulfonamide A mixture of 4-chloro-6-(2,3-dimethylphenyl)pyrimidin-2-amine (0.15 mmol), 4-(2-aminoethyl)-N, N-dimethyl-benzenesulfonamide (1.0 equiv.) and N,N-diisopropylethylamine (2.25 equiv.) in n-butanol (0.3 mL) was heated in a sealed tube at 110° C. overnight. Methanol was added and the mixture was filtered and purified by preparative HPLC. LCMS [M+H]+ 426.

Example 417

4-N-{1-[(4-Chlorophenyl)methyl]cyclopropyl}-6-(2,3-dimethylphenyl)pyrimidine-2,4-diamine A mixture of 4-chloro-6-(2,3-dimethylphenyl)pyrimidin-2-amine (47 mg, 0.20 mmol), 1-[(4-chlorophenyl)methyl]cyclopropan-1-amine hydrochloride (52 mg, 0.24 mmol) and triethylamine (50 μL, 0.36 mmol) in n-butanol (3 mL) was heated in a sealed tube at 130° C. overnight. The reaction mixture was concentrated and purified by preparative HPLC. LCMS [M+H]+ 379.

Example 418

4-N-Cyclopropyl-6-(2,3,4-trichlorophenyl)pyrimidine-2,4-diamine

A mixture of 4-chloro-6-(2,3,4-trichlorophenyl)pyrimidin-2-amine (21 mg, 0.050 mmol), cyclopropanamine (25 μL, 0.36 mmol) and triethylamine (25 μL, 0.18 mmol) in n-butanol (1.5 mL) was heated in a sealed tube at 90° C. overnight. The reaction mixture was concentrated and purified by preparative HPLC. LCMS [M+H]+ 329.

Example 419

4-N-[2-(4-Chlorophenyl)ethyl]-6-(2,3,4-trichlorophenyl)pyrimidine-2,4-diamine

A mixture of 4-chloro-6-(2,3,4-trichlorophenyl)pyrimidin-2-amine (21 mg, 0.050 mmol), 2-(4-chlorophenyl)ethan-1-amine (30 μL, 0.24 mmol) and triethylamine (25 μL, 0.18 mmol) in n-butanol (1.5 mL) was heated in a sealed tube at 90° C. overnight. The reaction mixture was concentrated and purified by preparative HPLC. LCMS [M+H]+ 427.

Example 420

6-(2,3-dimethylphenyl)-4-N-($^2$H$_3$)methylpyrimidine-2,4-diamine

A solution of 4-chloro-6-(2,3-dimethylphenyl)pyrimidin-2-amine (0.15 mmol) and d$_3$-methanamine hydrochloride (70 mg; 1 mmol) and triethylamine (101 mg; 1 mmol) in n-BuOH (2.0 mL) was heated at 95° C. overnight. The reaction mixture was concentrated and purified by preparative HPLC. LCMS [M+H]+ 232.

Example 421

6-(2,3-dichlorophenyl)-4-N-($^2$H$_3$)methylpyrimidine-2,4-diamine

A solution of 4-chloro-6-(2,3-dichlorophenyl)pyrimidin-2-amine (0.15 mmol) and d$_3$-methanamine hydrochloride (70 mg; 1 mmol) and triethylamine (101 mg; 1 mmol) in n-BuOH (2.0 mL) was heated at 95° C. overnight. The reaction mixture was concentrated and purified by preparative HPLC to afford the product. LCMS [M+H]+ 272.

Example 422

6-(2-chloro-3-methylphenyl)-4-N-($^2$H$_3$)methylpyrimidine-2,4-diamine

A solution of 4-chloro-6-(2-chloro-3-methylphenyl)pyrimidin-2-amine (0.15 mmol) and d$_3$-methanamine hydrochloride (70 mg; 1 mmol) and triethylamine (101 mg; 1 mmol) in n-BuOH (2.0 mL) was heated at 95° C. overnight. The reaction mixture was concentrated and purified by preparative HPLC to afford the product. LCMS [M+H]+ 252.

Example 423

4-N-[2-(4-Chlorophenyl)ethyl]-6-(1H-pyrrol-2-yl)pyrimidine-2,4-diamine

Prepared according to general procedure 2 from 6-chloro-4-N-[2-(4-chlorophenyl)ethyl]pyrimidine-2,4-diamine and (1-tert-butoxycarbonylpyrrol-2-yl)boronic acid. The t-butoxycarbonyl group was removed during work-up. LCMS [M+H]+ 314; $^1$H NMR (400 MHz, CD$_3$OD) δ ppm 7.29-7.33 (m, 5 H), 7.27 (s, 2 H), 7.10-7.13 (m, 1 H), 6.88-6.92 (m, 1 H), 6.33-6.37 (m, 1 H), 6.12 (s, 1 H), 3.70-3.76 (m, 2 H), 2.91-2.96 (m, 2 H).

Example 424

N-(4-{[2-amino-6-(2,3-dimethylphenyl)pyrimidin-4-yl]amino}butyl)-4-methanesulfonylbenzene-1-sulfonamide Prepared according to general procedure 10 from 4-(methylsulfonyl)-benzenesulfonyl chloride and 4-N-(4-aminobutyl)-6-(2,3-dimethylphenyl)-pyrimidine-2,4-diamine. LCMS [M+H]+ 504; $^1$H NMR (400 MHz, CD$_3$OD) δ ppm 8.12-8.17 (m, 2 H), 8.06-8.10 (m, 2 H), 7.16-7.20 (m, 1 H), 7.09-7.14 (m, 1 H), 7.05-7.09 (m, 1 H), 5.76-5.79 (m, 1 H), 3.18 (s, 3 H), 2.94-2.99 (m, 2 H), 2.31 (s, 3 H), 2.19 (s, 3 H), 1.50-1.66 (m, 4 H).

Example 425

4-(2-{[2-amino-6-(4-fluoro-2,3-dimethylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 4-fluoro-2,3-dimethyl-benzeneboronic acid. LCMS [M+H]$^+$ 416; $^1$H NMR (400 MHz, CD$_3$OD) δ ppm 7.81-7.85 (m, 2 H), 7.44 (d, J=8.6 Hz, 2 H), 7.07 (dd, J=8.5, 5.9 Hz, 1 H), 6.92 (t, J=8.8 Hz, 1 H), 5.75 (s, 1 H), 3.63 (br. s., 2 H), 2.99 (t, J=7.2 Hz, 2 H), 2.20-2.23 (m, 6 H).

Example 426

4-(2-{[2-amino-6-(3-cyano-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 3-cyano-2-methyl-benzene-boronic acid. LCMS [M+H]$^+$ 409; $^1$H NMR (400 MHz, CD$_3$OD) δ ppm 7.80-7.86 (m, 2 H), 7.70 (dd, J=7.8, 1.3 Hz, 1 H), 7.53 (d, J=6.8 Hz, 1 H), 7.37-7.47 (m, 3 H), 5.80 (s, 1 H), 3.65 (br. s., 2 H), 3.00 (t, J=7.2 Hz, 2 H), 2.49 (s, 3 H).

Example 427

4-(2-{[2-amino-6-(5-chloro-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 5-chloro-2-methyl-benzeneboronic acid. LCMS [M+H]$^+$ 418; $^1$H NMR (400 MHz, CD$_3$OD) δ ppm 7.81-7.85 (m, 2 H), 7.44 (d, J=8.3 Hz, 2 H), 7.21-7.29 (m, 3 H), 5.80 (s, 1 H), 3.64 (br. s., 2 H), 2.99 (t, J=7.2 Hz, 2 H), 2.28 (s, 3 H).

Example 428

4-(2-{[2-amino-6-(3,4-dichloro-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 3,4-dichloro-2-methyl-benzeneboronic acid. LCMS [M+H]$^+$ 452; $^1$H NMR (400 MHz, CDCl$_3$) δ ppm 7.88 (d, J=8.3 Hz, 2 H), 7.38 (d, J=8.3 Hz, 2 H), 7.33-7.36 (m, 1 H), 7.15 (s, 1 H), 5.73 (s, 1 H), 4.87 (s, 2 H), 4.81-4.84 (m, 2 H), 4.70-4.77 (m, 1 H), 3.61-3.69 (m, 2 H), 3.01 (s, 2 H), 2.41 (s, 3 H).

Example 429

6-(3-chloro-2-methylphenyl)-4-N-(prop-2-yn-1-yl)pyrimidine-2,4-diamine

Prepared according to general procedure 7 from propargylamine and 4-chloro-6-(3-chloro-2-methyl-phenyl)pyrimidin-2-amine. LCMS [M+H]$^+$ 273; $^1$H NMR (400 MHz, CD$_3$OD) δ ppm 7.40-7.43 (m, 1 H), 7.21 (s, 2 H), 5.85-5.88 (m, 1 H), 4.13-4.18 (m, 2 H), 2.59 (s, 1 H), 2.33 (s, 3 H).

Example 430

6-(4-fluoro-2,3-dimethylphenyl)-4-N-[2-(4-methanesulfonylphenyl)ethyl]pyrimidine-2,4-diamine Prepared according to general procedure 2 from 6-chloro-4-N-[2-(4-methylsulfonylphenyl)ethyl]pyrimidine-2,4-diamine and 4-fluoro-2,3-dimethyl-benzeneboronic acid. LCMS [M+H]$^+$ 415; $^1$H NMR (400 MHz, CD$_3$OD) δ ppm 7.88 (s, 2 H), 7.53-7.58 (m, 2 H), 7.06-7.11 (m, 1 H), 6.91-6.97 (m, 1 H), 5.76 (s, 1 H), 3.64-3.72 (m, 2 H), 3.11 (s, 3 H), 3.02-3.08 (m, 2 H), 2.22-2.25 (m, 6 H).

Example 431

6-(3,4-dichloro-2-methylphenyl)-4-N-[2-(4-methanesulfonylphenyl)ethyl]pyrimidine-2,4-diamine Prepared according to general procedure 2 from 6-chloro-4-N-[2-(4-methylsulfonylphenyl)ethyl]pyrimidine-2,4-diamine and 3,4-dichloro-2-methyl-benzeneboronic acid. LCMS [M+H]$^+$ 451; $^1$H NMR (400 MHz, CD$_3$OD) δ ppm 7.89 (d, J=8.6 Hz, 2 H), 7.57 (s, 2 H), 7.43-7.46 (m, 1 H), 7.17-7.21 (m, 1 H), 5.78 (s, 1 H), 3.63-3.75 (m, 2 H), 3.11 (s, 3 H), 3.03-3.08 (m, 2 H), 2.39 (s, 3 H).

Example 432

4-(2-{[2-amino-6-(4-chloro-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 4-chloro-2-methyl-benzene-boronic acid. LCMS [M+H]$^+$ 418; $^1$H NMR (400 MHz, CD$_3$OD) δ ppm 7.81-7.85 (m, 2 H), 7.42-7.46 (m, 2 H), 7.27-7.28 (m, 1 H), 7.23 (d, J=1.3 Hz, 2 H), 5.78 (s, 1 H), 3.63 (br. s., 2 H), 2.99 (t, J=7.1 Hz, 2 H), 2.30 (d, J=0.8 Hz, 3 H).

Example 433

4-(2-{[2-amino-6-(2-chloro-4-fluorophenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 2-chloro-4-fluoro-benzene-boronic acid. LCMS [M+H]$^+$ 422.

Example 434

4-(2-{[2-amino-6-(2,3,4-trifluorophenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 2,3,4-trifluorobenzeneboronic acid. LCMS [M+H]$^+$ 424.

Example 435

4-(2-{[2-amino-6-(4-fluoro-3-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 4-fluoro-3-methyl-benzene-boronic acid. LCMS [M+H]⁺ 402; ¹H NMR (400 MHz, CD₃OD) δ ppm 7.80-7.85 (m, 2 H), 7.67-7.72 (m, 1 H), 7.59-7.65 (m, 1 H), 7.41-7.46 (m, 2 H), 7.07 (dd, J=9.6, 8.6 Hz, 1 H), 6.12 (s, 1 H), 3.64 (t, J=7.2 Hz, 2 H), 2.99 (t, J=7.1 Hz, 2 H), 2.31 (d, J=2.0 Hz, 3 H).

Example 436

4-N-cyclopropyl-6-(4-fluoro-2,3-dimethylphenyl)pyrimidine-2,4-diamine

Prepared according to general procedure 2 from 6-chloro-4-N-cyclopropyl-pyrimidine-2,4-diamine and 4-fluoro-2,3-dimethyl-benzeneboronic acid. LCMS [M+H]⁺ 273; ¹H NMR (400 MHz, CD₃OD) δ ppm 7.08-7.15 (m, 1 H), 6.90-6.98 (m, 1 H), 5.90-6.07 (m, 1 H), 2.53-2.66 (m, 1 H), 2.21-2.26 (m, 6 H), 0.78 (dd, J=7.1, 2.0 Hz, 2 H), 0.54 (dd, J=3.7, 1.9 Hz, 2 H).

Example 437

3-[2-amino-6-(cyclopropylamino)pyrimidin-4-yl]-2-methylbenzonitrile

Prepared according to general procedure 2 from 6-chloro-4-N-cyclopropyl-pyrimidine-2,4-diamine and 3-cyano-2-methyl-benzeneboronic acid. LCMS [M+H]⁺ 266; ¹H NMR (400 MHz, CD₃OD) δ ppm 7.73-7.77 (m, 1 H), 7.58-7.63 (m, 1 H), 7.42-7.48 (m, 1 H), 5.91-6.17 (m, 1 H), 2.59-2.70 (m, 1 H), 2.54 (s, 3H), 0.81 (d, J=4.8 Hz, 2 H), 0.54-0.59 (m, 2 H).

Example 438

6-(2,3-dichlorophenyl)-4-N-(prop-2-yn-1-yl)pyrimidine-2,4-diamine

Prepared according to general procedure 9 from 4-chloro-6-(2,3-dichlorophenyl)pyrimidin-2-amine and propargyl amine. LCMS [M+H]⁺ 293.

Example 439

4-(2-{[2-amino-6-(4-fluoro-2,5-dimethylphenyl)pyrimidin-4-yl]amino}ethyl)benzene-1-sulfonamide Prepared according to general procedure 9 from 4-chloro-6-(4-fluoro-2,5-dimethyl-phenyl)pyrimidin-2-amine and 2-(4-sulfamoylphenyl)ethylammonium chloride. LCMS [M+H]⁺ 416.

Example 440

4-N-[2-(3,5-dimethyl-1H-pyrazol-4-yl)ethyl]-6-(2,3-dimethylphenyl)pyrimidine-2,4-diamine Prepared according to general procedure 9 from 4-chloro-6-(2,3-dimethylphenyl)pyrimidin-2-amine and 2-(3,5-dimethyl-1H-pyrazol-1-ium-4-yl)ethylammonium dichloride. [M+H]+ 337; ¹H NMR (400 MHz, CD₃OD) δ ppm 7.34 (s, 1 H), 7.21-7.26 (m, 1 H), 7.18 (dd, J=1.0, 0.5 Hz, 1 H), 6.00 (s, 1 H), 3.70 (t, J=6.8 Hz, 2 H), 2.83 (t, J=6.9 Hz, 2 H), 2.39 (s, 6 H), 2.35 (s, 3 H), 2.24 (s, 3 H).

Example 441

4-N-{2-[(6-chloropyridazin-3-yl)amino]ethyl}-6-(2,3-dimethylphenyl)pyrimidine-2,4-diamine Prepared according to general procedure 12 from 4-N-(2-aminoethyl)-6-(2,3-dimethylphenyl)pyrimidine-2,4-diamine and 3,6-dichloropyridazine. [M+H]+ 370.

Example 442

2-[(2-{[2-amino-6-(2,3-dimethylphenyl)pyrimidin-4-yl]amino}ethyl)amino]pyridine-4-carbonitrile Prepared according to general procedure 12 from 4-N-(2-aminoethyl)-6-(2,3-dimethylphenyl)pyrimidine-2,4-diamine and 2-chloropyridine-4-carbonitrile. LCMS [M+H]⁺ 360.

Example 443

6-[(2-{[2-amino-6-(2,3-dimethylphenyl)pyrimidin-4-yl]amino}ethyl)amino]pyridine-3-sulfonamide Prepared according to general procedure 12 from 4-N-(2-aminoethyl)-6-(2,3-dimethylphenyl)pyrimidine-2,4-diamine and 6-chloropyridine-3-sulfonamide. LCMS [M+H]⁺ 414.

Example 444

1-N-(3-{[2-amino-6-(2,3-dimethylphenyl)pyrimidin-4-yl]amino}propyl)benzene-1,4-disulfonamide Prepared according to general procedure 10 from 4-N-(4-aminopropyl)-6-(2,3-dimethylphenyl)pyrimidine-2,4-diamine and 4-(aminosulfonyl)benzenesulfonyl chloride. LCMS [M+H]⁺ 491; ¹H NMR (400 MHz, CD₃OD) δ ppm 8.04-8.08 (m, 2 H), 7.98-8.02 (m, 2 H), 7.28 (d, J=7.1 Hz, 1 H), 7.16-7.22 (m, 1 H), 7.15 (d, J=1.5 Hz, 1 H), 5.91 (s, 1 H), 3.48 (d, J=1.5 Hz, 2 H), 2.98 (t, J=6.8 Hz, 2 H), 2.34 (s, 3 H), 2.22 (s, 3 H), 1.78 (t, J=6.8 Hz, 2 H).

Example 445

6-(2,3-dichlorophenyl)-4-N-[2-(4-methanesulfonylphenyl)ethyl]pyrimidine-2,4-diamine Prepared according to general procedure 2 from 6-chloro-4-N-[2-(4-methylsulfonylphenyl)ethyl]pyrimidine-2,4-diamine and 2,3-dichlorobenzene-boronic acid. LCMS [M+H]⁺ 437; ¹H NMR (400 MHz, CD₃OD) δ ppm 7.90 (d, J=8.6 Hz, 2 H), 7.78 (t, J=4.9 Hz, 1 H), 7.56 (d, J=8.6 Hz, 2 H), 7.49 (dd, J=4.9, 0.6 Hz, 2 H), 6.08 (s, 1 H), 3.84 (s, 2 H), 3.06-3.11 (m, 5 H).

Example 446

6-(2,3-dimethylphenyl)-4-N-[1-(1H-pyrazol-1-yl)propan-2-yl]pyrimidine-2,4-diamine Prepared according to general procedure 9 from 4-chloro-6-(2,3-dimethylphenyl)-pyrimidin-2-amine and 1-pyrazol-1-ylpropan-2-amine. LCMS [M+H]⁺ 323; ¹H NMR (400

MHz, CDCl₃) δ ppm 7.71 (d, J=7.8 Hz, 1 H), 7.57 (d, J=1.8 Hz, 1 H), 7.51 (d, J=2.3 Hz, 1 H), 7.24 (d, J=7.3 Hz, 1 H), 7.12 (t, J=7.6 Hz, 1 H), 7.04-7.08 (m, 1H), 6.30 (t, J=2.3 Hz, 1 H), 5.85 (s, 1 H), 4.65-4.75 (m, 1 H), 4.34-4.41 (m, 1H), 4.23 (dd, J=14.1, 6.3 Hz, 1 H), 2.29 (s, 3 H), 2.18 (s, 3 H), 1.16 (d, J=6.8 Hz, 3 H).

Example 447

6-(2,3-dimethylphenyl)-4-N-{2-[(3-methoxyphenyl)amino]ethyl}pyrimidine-2,4-diamine Prepared according to general procedure 9 from 4-chloro-6-(2,3-dimethylphenyl)pyrimidin-2-amine and N'-(3-methoxyphenyl)ethane-1,2-diamine. LCMS [M+H]⁺ 364; ¹H NMR (400 MHz, CDCl₃) δ ppm 7.18-7.26 (m, 1 H), 7.01-7.07 (m, 1 H), 6.96-7.00 (m, 1 H), 6.95 (t, J=2.0 Hz, 1 H), 6.84 (d, J=7.8 Hz, 1H), 6.76 (dd, J=8.3, 2.0 Hz, 1 H), 5.91 (s, 1 H), 3.82 (d, J=4.8 Hz, 2 H), 3.75 (s, 3H), 3.48 (br. s., 2 H), 2.24 (s, 3 H), 2.10 (s, 3 H).

Example 448

6-(2,3-dimethylphenyl)-4-N-{2-[(3-fluoro-4-methylphenyl)amino]ethyl}pyrimidine-2,4-diamine Step 1: A vial was charged with 2-fluoro-4-iodo-1-methyl-benzene (240 mg, 1.0 mmol), ethane-1,2-diamine (0.20 mL, 3.0 mmol), CuCl (9.9 mg, 0.10 mmol), and KOH (110 mg, 2.0 mmol). The vial was then flushed with nitrogen and sealed. The mixture was stirred at r.t. for 16 h, thereafter the mixture was extracted with EtOAc. The combined organic phases were dried, concentrated and purified by column chromatography to afford N'-(3-fluoro-4-methylphenyl)ethane-1,2-diamine.
Step 2: A mixture of 6-(2,3-dimethylphenyl)-4-chloropyrimidin-2-amine (30 mg, 0.13 mmol), N'-(3-fluoro-4-methyl-phenyl)ethane-1,2-diamine (20 mg, 0.12 mmol), and diisopropylethylamine (0.040 mL, 0.23 mmol) in 2-propanol (0.50 mL) was heated in a sealed tube at 150° C. for 30 min in a microwave reactor. The reaction mixture was then concentrated and purified by preparative HPLC. LCMS [M+H]⁺ 366; ¹H NMR (400 MHz, CD₃OD) δ ppm 7.33-7.37 (m, 1 H), 7.21-7.27 (m, 1 H), 7.15-7.18 (m, 1 H), 6.93-6.99 (m, 1 H), 6.38-6.45 (m, 2 H), 5.99 (s, 1 H), 3.72 (s, 2 H), 3.39 (s, 2 H), 2.36 (s, 3 H), 2.24 (s, 3 H), 2.11 (d, J=1.5 Hz, 3 H).

Example 449

4-N-{2-[(3,4-dichlorophenyl)amino]ethyl}-6-(2,3-dimethylphenyl)pyrimidine-2,4-diamine Prepared according to general procedure 9 from 4-chloro-6-(2,3-dimethylphenyl)pyrimidin-2-amine and N'-(3,4-dichlorophenyl)ethane-1,2-diamine. LCMS [M+H]⁺ 402; ¹H NMR (400 MHz, CD₃OD) δ ppm 7.33-7.37 (m, 1 H), 7.24 (s, 1 H), 7.18 (m, 2 H), 6.76 (d, J=2.8 Hz, 1 H), 6.57 (dd, J=8.8, 2.8 Hz, 1 H), 5.97 (s, 3 H), 3.69-3.73 (m, 2 H), 3.37-3.42 (m, 2 H), 2.35 (s, 3 H), 2.23 (s, 3 H).

Example 450

4-N-{2-[(5-chloropyridin-2-yl)amino]ethyl}-6-(2,3-dimethylphenyl)pyrimidine-2,4-diamine Prepared according to general procedure 9 from 4-chloro-6-(2,3-dimethylphenyl)pyrimidin-2-amine and N'-(5-chloro-2-pyridyl)ethane-1,2-diamine. LCMS [M+H]⁺ 369; ¹H NMR (400 MHz, CDCl₃) δ ppm 7.61-7.69 (m, 2 H), 7.30 (d, J=7.6 Hz, 1 H), 7.10-7.22 (m, 3 H), 6.17 (br. s., 1 H), 3.71 (br. s., 4 H), 2.33 (s, 3 H), 2.24 (s, 3 H).

Example 451

4-N-{2-[(5-bromopyridin-2-yl)amino]ethyl}-6-(2,3-dimethylphenyl)pyrimidine-2,4-diamine Prepared according to general procedure 9 from 4-chloro-6-(2,3-dimethylphenyl)pyrimidin-2-amine and N'-(5-bromo-2-pyridyl)ethane-1,2-diamine. LCMS [M+H]⁺ 413; ¹H NMR (400 MHz, CD₃OD) δ ppm 8.07 (dd, J=2.3, 0.8 Hz, 1H), 7.86 (dd, J=9.3, 2.3 Hz, 2 H), 7.33-7.37 (m, 2 H), 7.24 (t, J=7.6 Hz, 1 H), 7.15-7.19 (m, 1 H), 6.90 (dd, J=9.5, 0.6 Hz, 1 H), 6.03 (s, 1 H), 3.77-3.82 (m, 2H), 3.64-3.69 (m, 2 H), 2.35 (s, 3 H), 2.24 (s, 3 H).

Example 452

4-[(2-{[2-amino-6-(2,3-dimethylphenyl)pyrimidin-4-yl]amino}ethyl)amino]benzene-1-sulfonamide Prepared according to general procedure 9 from 4-chloro-6-(2,3-dimethylphenyl)pyrimidin-2-amine and 4-(2-aminoethylamino)benzene-sulfonamide. LCMS [M+H]⁺ 413; ¹H NMR (400 MHz, CD₃OD) δ ppm 7.64 (d, J=9.1 Hz, 2 H), 7.33-7.37 (m, 1 H), 7.24 (s, 1 H), 7.15-7.19 (m, 1 H), 6.70 (d, J=9.1 Hz, 2 H), 6.00 (s, 1 H), 3.72-3.77 (m, 2 H), 3.45-3.50 (m, 2 H), 2.35 (s, 3H), 2.24 (s, 3 H).

Example 453

4-N-[2-(4-chlorophenyl)ethyl]-6-(dimethyl-1,2-oxazol-4-yl)pyrimidine-2,4-diamine Prepared according to general procedure 2 from 6-chloro-4-N-[2-(4-chlorophenyl)ethyl]pyrimidine-2,4-diamine and (3,5-dimethylisoxazol-4-yl)boronic acid. LCMS [M+H]⁺ 344.

Example 454

6-(2,3-dimethylphenyl)-4-N-{2-[(pyridin-3-yl)amino]ethyl}pyrimidine-2,4-diamine

Prepared according to general procedure 9 from 4-chloro-6-(2,3-dimethylphenyl)pyrimidin-2-amine and N'-(3-pyridyl)ethane-1,2-diamine. LCMS [M+H]⁺ 335; ¹H NMR (400 MHz, CD₃OD) δ ppm 8.10-8.12 (m, 1 H), 7.97-8.00 (m, 1 H), 7.72-7.80 (m, 2 H), 7.34-7.38 (m, 1 H), 7.22-7.27 (m, 1 H), 7.19 (dd, J=1.0, 0.5 Hz, 1 H), 6.04 (s, 1 H), 3.75-3.80 (m, 2 H), 3.54 (t, J=6.2 Hz, 2 H), 2.36 (s, 3 H), 2.25 (s, 3 H).

Example 455

6-(3-chloro-2-methylphenyl)-4-N-[2-(4-methanesulfonylphenyl)ethyl]pyrimidine-2,4-diamine A solution of 4-chloro-6-(3-chloro-2-methylphenyl)pyrimidin-2-amine (300 mg; 1.2 mmol) and the 2-(4-methylsulfonylphenyl)ethanamine (HCl salt) (300 mg; 1.27 mmol) in n-Butanol (2.0 ml) was treated with Hunigs base (400 mg; 3 mmol) and heated at 140° overnight. The mixture was purified by preparative HPLC (basic column to afford the product 390 mg. LCMS [M+H]⁺ 417; ¹H NMR (400 MHz, CD₃OD) δ ppm 7.89 (d, J=Hz, 2H), 7.56 (d, J=Hz, 2H), 7.44-7.41 (m, 1H), 7.25-7.18 (m, 2H), 5.79 (s, 1H), 3.68 (m, 2H), 3.11 (s, 3H), 3.07-3.03 (m, 2H) and 2.33 (s, 3H).

Example 456

[4-[2-[[2-amino-6-(3-chloro-2-methyl-phenyl)pyrimidin-4-yl]amino]ethyl]phenyl]-morpholinomethanone The title compound was prepared according to general procedure 2 from intermediate 52 and (3-chloro-2-methylphenyl)boronic acid. [M+H]⁺ 452.

Example 457

6-[(3-{[2-amino-6-(2,3-dimethylphenyl)pyrimidin-4-yl]amino}propyl)amino]pyridine-3-sulfonamide In a closed vial a mixture of intermediate 36 and 6-chloropyridine-3-sulfonamide (1.2 equiv.) were stirred neat at 150° C. for 16 h. The reaction mixture was purified by preparative LC. LCMS [M+H]⁺ 428. 1H NMR (400 MHz, METHANOL-d4) δ ppm 8.34-8.37 (m, 2 H), 8.01-8.08 (m, 2 H), 7.35-7.41 (m, 2 H), 7.24-7.29 (m, 2 H), 7.19-7.24 (m, 3 H), 6.96-7.02 (m, 2 H), 6.04 (s, 1 H), 3.68 (s, 2 H), 3.55 (s, 2 H), 2.38 (s, 3 H), 2.27 (s, 3 H), 2.05 (s, 2 H).

Example 458

6-[(2-{[2-amino-6-(2,3-dimethylphenyl)pyrimidin-4-yl]amino}ethyl)amino]-N-methylpyridine-3-sulfonamide The title compound was prepared according to general procedure 12 from 6-chloro-N-methyl-pyridine-3-sulfonamide and intermediate 35. LCMS [M+H]⁺ 428 1H NMR (400 MHz, METHANOL-d4) δ ppm 8.36-8.39 (m, 1 H), 7.74-7.79 (m, 1 H), 7.33-7.38 (m, 1 H), 7.22-7.27 (m, 1 H), 7.15-7.19 (m, 1 H), 6.65-6.71 (m, 1 H), 5.96-5.99 (m, 1 H), 3.75-3.79 (m, 2 H), 3.68-3.73 (m, 2 H), 2.51 (s, 3H), 2.35-2.37 (m, 2 H), 2.23-2.25 (m, 3 H).

Example 459

6-(2,3-dichlorophenyl)-4-N-{2-[(pyridin-4-yl)amino]ethyl}pyrimidine-2,4-diamine

Step 1: N'-(4-pyridyl)ethane-1,2-diamine was prepared according to general procedure 13 from 4-iodopyridine.
Step 2: The title compound was prepared according to general procedure 9 from the crude material in step 1 and intermediate 21. LCMS [M+H]⁺ 375. 1H NMR (400 MHz, METHANOL-d4) δ ppm 8.19 (dd, J=7.2, 1.1 Hz, 1 H), 8.04 (dd, J=7.1, 1.0 Hz, 1 H), 7.80 (dd, J=6.2, 3.4 Hz, 1 H), 7.48-7.51 (m, 2H), 7.03 (dd, J=7.2, 2.7 Hz, 1 H), 6.91 (dd, J=7.1, 2.8 Hz, 1 H), 6.18 (s, 1 H), 3.82 (dd, J=6.6, 6.0 Hz, 2 H), 3.69 (dd, J=6.6, 6.0 Hz, 2 H).

Example 460

4-(2-{[2-amino-6-(5-methylfuran-2-yl)pyrimidin-4-yl]amino}ethyl)benzene-1-sulfonamide The title compound was prepared according to general procedure 14 from intermediate 25 and potassium trifluoro (5-methylfuran-2-yl)boranuide. LCMS [M+H]⁺ 374. 1H NMR (400 MHz, METHANOL-d4) δ ppm 7.86 (d, J=8.3 Hz, 2 H), 7.46 (d, J=8.3 Hz, 2 H), 7.15 (d, J=3.5 Hz, 1 H), 6.37 (dd, J=3.5, 1.0 Hz, 1 H), 6.25 (s, 1 H), 3.77-3.83 (m, 2 H), 3.02-3.07 (m, 2 H), 2.44 (s, 3 H).

Example 461

6-(3-chloro-2-methylphenyl)-4-N-[2-(4-chlorophenyl)ethyl]pyrimidine-2,4-diamine

Prepared according to general procedure 3 from Intermediate 24 and 2-(4-chlorophenyl) ethanamine. LCMS [M+H]⁺ 373; ¹H NMR (400 MHz, DMSO-d₆) δ ppm 7.43 (dd, J=7.7, 1.4 Hz, 1 H), 7.27-7.38 (m, 4 H), 7.21-7.26 (m, 1 H), 7.17-7.21 (m, 1 H), 7.03 (br. s., 1 H), 6.05 (br. s., 2 H), 5.72 (s, 1 H), 3.41-3.55 (m, 2H), 2.82 (t, J=7.2 Hz, 2 H), 2.29 (s, 3 H).

Example 462

6-[(2-{[2-amino-6-(2,3-dimethylphenyl)pyrimidin-4-yl]amino}ethyl)amino]pyridine-3-carboxamide The title compound was prepared according to general procedure 12 from intermediate 35 and 6-chloropyridine-3-carboxamide. LCMS [M+H]⁺ 378. 1H NMR (400 MHz, METHANOL-d4) δ ppm 8.49 (dd, J=2.3, 0.8 Hz, 1 H), 8.15 (dd, J=9.5, 1.9 Hz, 1 H), 7.36 (d, J=7.6 Hz, 1 H), 7.25 (t, J=7.5 Hz, 1 H), 7.14-7.19 (m, 1 H), 6.92 (d, J=8.8 Hz, 1 H), 6.02 (s, 1 H), 3.79-3.85 (m, 2 H), 3.70-3.75 (m, 2 H), 2.36 (s, 3 H), 2.24 (s, 3 H).

Example 463

4-N-methyl-6-(thiophen-3-yl)pyrimidine-2,4-diamine

The title compound was prepared according to general procedure 14 from intermediate 20 and potassium trifluoro (3-thienyl)boranuide.
LCMS [M+H]⁺ 207. 1H NMR (400 MHz, METHANOL-d4) δ ppm 8.10 (dd, J=2.9, 1.1 Hz, 1 H), 7.68 (dd, J=5.1, 2.9 Hz, 1 H), 7.51 (dd, J=5.1, 1.1 Hz, 1 H), 6.33 (s, 1 H), 3.02 (s, 3 H).

Example 464

4-N-methyl-6-(4-methylthiophen-2-yl)pyrimidine-2,4-diamine

The title compound was prepared according to general procedure 14 from intermediate 20 and potassium trifluoro-(4-methyl-2-thienyl)boranuide. LCMS [M+H]⁺ 221. 1H NMR (400 MHz, METHANOL-d4) δ ppm 6.00 (s, 1 H), 5.84 (s, 1 H), 4.70-4.72 (m, 1 H), 1.48 (s, 3 H), 0.79 (d, J=1.0 Hz, 3 H).

Example 465

4-N-methyl-6-(1-methyl-1H-pyrazol-5-yl)pyrimidine-2,4-diamine

The title compound was prepared according to general procedure 14 from intermediate 20 and potassium trifluoro (1-methyl-1H-pyrazol-5-yl)boranuide. LCMS [M+H]⁺ 205. 1H NMR (400 MHz, DMSO-d6) δ ppm 7.41 (d, J=2.0 Hz, 1 H), 6.90 (br. s., 1 H), 6.56 (br. s., 1 H), 6.11 (br. s., 2 H), 6.01 (s, 1 H), 4.11 (s, 3 H), 2.77 (d, J=4.8 Hz, 3 H).

Example 466

4-N-{2-[(5-bromopyridin-2-yl)amino]ethyl}-6-(2,3-dichlorophenyl)pyrimidine-2,4-diamine Step 1: A mixture of 5-bromo-2-chloro-pyridine and ethane-1,2-diamine was stirred at 90° C. for 16 h. The mixture was concentrated, diluted with KOH (2 M), and extracted with EtOAc ×10. The combined organic extracts were concentrated and used in step 2 without further purification.
Step 2: The title compound was prepared according to general procedure 9 from the crude material in step 1 and intermediate 21.
LCMS [M+H]$^+$ 453 1H NMR (400 MHz, METHANOL-d4) δ ppm 8.06 (dd, J=2.3, 0.8 Hz, 1 H), 7.83 (dd, J=9.3, 2.3 Hz, 1 H), 7.77-7.80 (m, 1 H), 7.49 (d, J=6.8 Hz, 1 H), 7.49 (d, J=3.0 Hz, 1 H), 6.85 (d, J=9.3 Hz, 1 H), 6.15 (s, 1 H), 3.77-3.82 (m, 2 H), 3.63-3.68 (m, 2 H).

Example 467

4-N-methyl-6-(3-methyl-1H-pyrazol-4-yl)pyrimidine-2,4-diamine

The title compound was prepared according to general procedure 14 from intermediate 20 and potassium trifluoro-(3-methyl-1H-pyrazol-4-yl)boranuide. LCMS [M+H]$^+$ 205.

Example 468

4-N-methyl-6-(1H-pyrrol-3-yl)pyrimidine-2,4-diamine

The title compound was prepared according to general procedure 17 from intermediate 20 and triisopropoxy-[3-(4,4,5,5-tetramethyl-1,3,2-dioxaborolan-2-yl)-pyrrol-1-yl]silane. LCMS [M+H]$^+$ 190. 1H NMR (400 MHz, METHANOL-d4) δ ppm 7.46 (s, 1 H), 6.89-6.92 (m, 1 H), 6.54-6.57 (m, 1 H), 6.15 (s, 1 H), 2.99 (s, 3 H).

Example 469

N-(4-{[2-amino-6-(2,3-dichlorophenyl)pyrimidin-4-yl]amino}butyl)-2-methoxyacetamide The title compound was prepared according to general procedure 15 from Intermediate 46 and 2-methoxyacetic. LCMS [M+H]$^+$ 398. 1H NMR (400 MHz, METHANOL-d4) δ ppm 7.80 (dd, J=5.8, 3.8 Hz, 1H), 7.50-7.53 (m, 2H), 6.13 (s, 1 H), 3.90 (s, 2 H), 3.57 (t, J=6.7 Hz, 2 H), 3.43 (s, 3 H), 3.30-3.35 (m, 2H, signal obscured by solvent), 1.66 (d, J=11.9 Hz, 4 H).

Example 470

N-(4-{[2-amino-6-(2,3-dichlorophenyl)pyrimidin-4-yl]amino}butyl)-2,2,2-trifluoroacetamide The title compound was prepared according to general procedure 15 from Intermediate 46 and trifluoroacetic acid. LCMS [M+H]$^+$ 422. 1H NMR (400 MHz, METHANOL-d4) δ ppm 7.77 (dd, J=6.3, 3.5 Hz, 2 H), 7.48-7.51 (m, 2 H), 6.12 (s, 1 H), 3.56 (s, 2 H), 3.33-3.38 (m, 2 H), 1.67 (d, J=6.6 Hz, 5 H).

Example 471

N-(4-{[2-amino-6-(2,3-dichlorophenyl)pyrimidin-4-yl]amino}butyl)-4-methanesulfonylbenzamide The title compound was prepared according to general procedure 15 from Intermediate 46 and 4-methylsulfonylbenzoic acid. LCMS [M+H]$^+$ 508. 1H NMR (400 MHz, METHANOL-d4) δ ppm 8.03-8.10 (m, 4 H), 7.80 (dd, J=5.3, 4.5 Hz, 1 H), 7.50-7.53 (m, 2 H), 6.13 (s, 1 H), 3.61 (s, 2 H), 3.47-3.53 (m, 2 H), 3.17-3.19 (m, 3 H), 1.71-1.81 (m, 4 H).

Example 472

N-(4-{[2-amino-6-(2,3-dichlorophenyl)pyrimidin-4-yl]amino}butyl)-1,2-oxazole-5-carboxamide The title compound was prepared according to general procedure 15 from Intermediate 46 and isoxazole-5-carboxylic acid. LCMS [M+H]$^+$ 421. 1H NMR (400 MHz, METHANOL-d4) δ ppm 8.52 (d, J=1.8 Hz, 1 H), 7.77-7.80 (m, 1 H), 7.49-7.51 (m, 2 H), 6.94-6.95 (m, 1 H), 6.11 (s, 1 H), 3.55-3.60 (m, 2 H), 3.42-3.47 (m, 2 H), 1.69-1.75 (m, 5 H).

Example 473

N-(4-{[2-amino-6-(2,3-dichlorophenyl)pyrimidin-4-yl]amino}butyl)-3,4-dichlorobenzamide A mixture of Intermediate 46 (1.0 equiv.), 3,4-dichlorobenzoyl chloride (1.3 equiv.), and diisopropylethylamine (5 equiv.) in DCM was stirred at 20° C. for 16 h. After completion the mixture was concentrated and purified by preparative LC. LCMS [M+H]$^+$ 498.

Example 474

N-(4-{[2-amino-6-(2,3-dichlorophenyl)pyrimidin-4-yl]amino}butyl)-2,2-dimethylpropanamide A mixture of Intermediate 46 (1.0 equiv.), trimethylacetyl chloride (1.3 equiv.), and diisopropylethylamine (5 equiv.) in DCM was stirred at 20° C. for 16 h. After completion the mixture was concentrated and purified by preparative LC. LCMS [M+H]$^+$ 410. 1H NMR (400 MHz, METHANOL-d4) δ ppm 7.75-7.81 (m, 1 H), 7.50 (d, J=4.3 Hz, 2 H), 6.12 (s, 1 H), 3.54 (t, J=6.6 Hz, 2 H), 3.24 (t, J=6.6 Hz, 2H), 1.54-1.70 (m, 4 H), 1.17 (s, 9 H).

Example 475

N-(4-{[2-amino-6-(2,3-dichlorophenyl)pyrimidin-4-yl]amino}butyl)-4-methanesulfonylbenzene-1-sulfonamide The title compound was prepared according to general procedure 10 from Intermediate 46 and 4-methylsulfonylbenzenesulfonyl chloride. LCMS [M+H]$^+$ 544. 1H NMR (400 MHz, METHANOL-d4) δ ppm 8.14-8.17 (m, 2 H), 8.07-8.10 (m, 2 H), 7.78 (dd, J=6.9, 2.7 Hz, 1 H), 7.49-7.52

(m, 2 H), 6.10 (s, 1 H), 3.49 (t, J=6.9 Hz, 2 H), 3.19 (s, 3 H), 2.97 (t, J=6.8 Hz, 2 H), 1.62-1.71 (m, 2 H), 1.52-1.61 (m, 2 H).

Example 476

3-(4-{[2-amino-6-(2,3-dichlorophenyl)pyrimidin-4-yl]amino}butyl)-1-[4-(methylsulfanyl)phenyl]urea A mixture of intermediate 46 (1.0 equiv), 1-isocyanato-4-methylsulfanyl-benzene (1.1 equiv), and diisopropylethylamine (2.1 equiv) in acetonitrile was stirred at room temperature for 15 h. The mixture was concentrated and purified by preparative HPLC to afford the title compound. LCMS [M+H]$^+$ 491. 1H NMR (400 MHz, METHANOL-d4) δ ppm 7.74-7.79 (m, 1 H), 7.47-7.49 (m, 2 H), 7.28-7.32 (m, 2 H), 7.17-7.21 (m, 2 H), 6.11 (s, 1 H), 3.56 (t, J=6.8 Hz, 2 H), 3.26 (t, J=6.8 Hz, 2 H), 2.42 (s, 3 H), 1.66-1.75 (m, 2 H), 1.57-1.66 (m, 2 H).

Example 477

3-(4-{[2-amino-6-(2,3-dichlorophenyl)pyrimidin-4-yl]amino}butyl)-1-(4-methanesulfinylphenyl)urea In a vial [4-(2,3-dichlorophenyl)-6-[4-[(4-methylsulfanylphenyl)carbamoylamino]butylamino]pyrimidin-2-yl] ammonium trifluoroacetate (from example 476) was dissolved in 2-propanol, then 0.2 ml H$_2$O$_2$ (30 wt %) was added and the resulting mixture was stirred 2 h at 20° C. The crude mixture was then purified by preparative LC. LCMS [M+H]$^+$ 507.

Example 478

4-N-methyl-6-(2-methylfuran-3-yl)pyrimidine-2,4-diamine

The title compound was prepared according to general procedure 17 from intermediate 20 and 4,4,5,5-tetramethyl-2-(2-methyl-3-furyl)-1,3,2-dioxaborolane. LCMS [M+H]$^+$ 205. 1H NMR (400 MHz, METHANOL-d4) δ ppm 7.56 (d, J=2.0 Hz, 1 H), 6.69-6.71 (m, 1 H), 6.09 (s, 1 H), 3.01 (s, 3 H), 2.50 (s, 3 H).

Example 479

4-N-methyl-6-[5-(pyrrolidin-1-ylmethyl)thiophen-2-yl]pyrimidine-2,4-diamine

The title compound was prepared according to general procedure 17 from intermediate 20 and 1-[[5-(4,4,5,5-tetramethyl-1,3,2-dioxaborolan-2-yl)-2-thienyl]methyl]pyrrolidine. LCMS [M+H]$^+$ 290. 1H NMR (400 MHz, METHANOL-d4) δ ppm 7.49 (d, J=3.5 Hz, 1 H), 6.98 (d, J=3.8 Hz, 1 H), 6.16 (s, 1 H), 3.84 (s, 2 H), 2.88 (s, 3 H), 2.57-2.65 (m, 4 H), 1.82 (dt, J=6.2, 3.0 Hz, 4 H).

Example 480

6-(4-fluoro-2,5-dimethylphenyl)-4-N-{2-[(5-nitropyridin-2-yl)amino]ethyl}pyrimidine-2,4-diamine The title compound was prepared according to general procedure 9 from Intermediate 49 and N'-(5-nitro-2-pyridyl)ethane-1,2-diamine. LCMS [M+H]$^+$ 398. 1H NMR (400 MHz, CHLOROFORM-d) δ ppm 9.01 (d, J=2.8 Hz, 1 H), 8.15 (dd, J=9.0, 2.7 Hz, 1 H), 7.15 (d, J=8.1 Hz, 1 H), 6.87 (d, J=10.6 Hz, 1 H), 6.37 (dd, J=9.3, 0.5 Hz, 1 H), 5.82 (s, 1 H), 5.12-5.24 (m, 1 H), 4.85-4.98 (m, 2 H), 2.31 (s, 3 H), 2.22-2.25 (m, 3 H), 1.73-1.84 (m, 1 H).

Example 481

[2-(2-amino-6-{[2-(4-chlorophenyl)ethyl]amino}pyrimidin-4-yl)phenyl]methanol 6-chloro-4-N-[2-(4-chlorophenyl)ethyl]pyrimidine-2,4-diamine (intermediate 22) (30 mg, 0.11 mmol), 1,3-dihydro-2,1-benzoxaborol-1-ol (17 mg, 0.13 mmol), K$_2$CO$_3$ (53 mg, 0.38 mmol), Tetrakis(triphenylphosphine)palladium(O) (3.1 mg, 0,0030 mmol), MeCN (2 mL) and water (0.5 mL) were heated in the micro for 15 min at 120° C. The organic phase was filtered and purified by basic prep-HPLC to afford [2-(2-amino-6-{[2-(4-chlorophenyl)ethyl]amino}pyrimidin-4-yl)phenyl]methanol LCMS [M+H]$^+$ 355

Example 482

6-(3-chloro-2-methylphenyl)-4-N-cyclopropylpyrimidine-2,4-diamine

A mixture of 6-chloro-4-N-cyclopropylpyrimidine-2,4-diamine (37 mg, 0.20 mmol; Intermediate 10), (3-chloro-2-methylphenyl)boronic acid (41 mg, 0.24 mmol), tetrakis (triphenylphosphine)palladium (0) (12 mg, 0.010 mmol) and potassium carbonate (55 mg, 0.40 mmol) in 1,4-dioxane (4 mL) and water (1 mL) was heated in a sealed tube at 95° C. for 1.5 h. Concentrated and purified by preparative HPLC. LCMS [M+H]$^+$ 275.

Example 483

6-(3-chloro-2-methylphenyl)-4-N-(2-fluoroethyl)pyrimidine-2,4-diamine

Step 1: A mixture of 4,6-dichloropyrimidin-2-amine (164 mg, 1.00 mmol), 2-fluoroethan-1-amine hydrochloride (149 mg, 1.50 mmol) and triethylamine (300 µL, 2.15 mmol) in DMSO (4 mL) was heated at 160° C. for 10 min using microwave irradiation. The reaction mixture was purified by preparative HPLC to afford 6-chloro-4-N-(2-fluoroethyl)pyrimidine-2,4-diamine; trifluoroacetic acid.

Step 2: A mixture of 6-chloro-4-N-(2-fluoroethyl)pyrimidine-2,4-diamine; trifluoroacetic acid (40 mg, 0.13 mmol), (3-chloro-2-methylphenyl)boronic acid (29 mg, 0.17 mmol), tetrakis(triphenylphosphine)palladium (0) (8 mg, 0.0070 mmol) and potassium carbonate (36 mg, 0.26 mmol) in 1,4-dioxane (4 mL) and water (1 mL) was heated in a sealed tube at 95° C. for 1 h. Concentrated and purified by preparative HPLC. LCMS [M+H]$^+$ 281; $^1$H NMR (400 MHz, DMSO-d$_6$) δ ppm 9.03 (br. s., 1 H) 7.63-7.69 (m, 1 H) 7.37-7.43 (m, 2 H) 6.09 (s, 1 H) 4.51-4.71 (m, 2 H) 3.65-3.82 (m, 2 H) 2.30 (s, 3 H).

Example 484

6-(2,3-dimethylphenyl)-4-N-(2-fluoroethyl)pyrimidine-2,4-diamine

A mixture of 6-chloro-4-N-(2-fluoroethyl)pyrimidine-2,4-diamine; trifluoroacetic acid (40 mg, 0.13 mmol; Example 483, Step 1), (2,3-dimethylphenyl)boronic acid (26 mg, 0.17 mmol), tetrakis(triphenylphosphine)palladium (0) (8 mg, 0.0070 mmol) and potassium carbonate (36 mg, 0.26 mmol) in 1,4-dioxane (4 mL) and water (1 mL) was heated in a sealed tube at 95° C. for 1 h. Concentrated and purified by preparative HPLC. LCMS [M+H]$^+$ 261.

Example 485

4-(2-{[2-amino-6-(3-chloro-2-methylphenyl)pyrimidin-4-yl]amino}ethyl)benzoic acid A mixture of 4-chloro-6-(3-chloro-2-methylphenyl)pyrimidin-2-amine (25 mg, 0.10 mmol; Intermediate 24), 4-(2-aminoethyl)benzoic acid hydrochloride (30 mg, 0.15 mmol) and triethylamine (40 µL, 0.30 mmol) in n-butanol (1.5 mL) was heated in a sealed tube at 130° C. overnight. Concentrated and purified by preparative HPLC. LCMS [M+H]$^+$ 383.

Example 486

4-(2-{[6-(2-acetylthiophen-3-yl)-2-aminopyrimidin-4-yl]amino}ethyl)benzene-1-sulfonamide The title compound was prepared according to general procedure 14 from intermediate 25 and potassium (2-acetylthiophen-3-yl)trifluoroboranuide. LCMS [M+H]$^+$ 418. 1H NMR (400 MHz, METHANOL-d4) δ ppm 7.96 (d, J=5.1 Hz, 1 H), 7.84-7.88 (m, 2 H), 7.46-7.50 (m, 2 H), 7.39 (d, J=5.1 Hz, 1 H), 6.12 (s, 1 H), 3.82 (t, J=7.1 Hz, 2 H), 3.06 (t, J=7.1 Hz, 2 H), 2.62 (s, 3 H).

Example 487

3-{4-[2-amino-6-(methylamino)pyrimidin-4-yl]-1H-pyrazol-1-yl}propanamide

The title compound was prepared according to general procedure 17 from intermediate 20 and 3-[4-(4,4,5,5-tetramethyl-1,3,2-dioxaborolan-2-yl)pyrazol-1-yl]-propanamide. LCMS [M+H]$^+$ 262. 1H NMR (400 MHz, METHANOL-d4) δ ppm 8.11 (s, 1 H), 7.95 (s, 1 H), 6.09 (s, 1 H), 4.47 (t, J=6.7 Hz, 2 H), 2.90-2.92 (m, 3H), 2.82 (t, J=6.7 Hz, 2 H).

Example 488

N-{6-[(2-{[2-amino-6-(4-fluoro-2,5-dimethylphenyl)pyrimidin-4-yl]amino}ethyl)amino]pyridin-3-yl}acetamide Step 1: In a flask 6-(4-fluoro-2,5-dimethyl-phenyl)-N4-[2-[(5-nitro-2-pyridyl)amino]ethyl]pyrimidine-2,4-diamine (from example 480) was dissolved in MeOH, then the flask was evacuated and the atmosphere was changed to H$_2$. The mixture was stirred at 20° C. for 16 h and then passed through a syringe filter and concentrated.
Step 2. The crude mixture from step 1 was dissolved in DCM, then Hünig's base (2.0 equiv) and acetyl chloride (1.1 equiv) were added and the mixture was stirred 3 h at 20° C. Then the mixture was concentrated and purified by preparative LC. LCMS [M+H]$^+$ 410. 1H NMR (400 MHz, METHANOL-d4) δ ppm 8.50 (dd, J=2.5, 0.8 Hz, 1 H), 7.90 (dd, J=9.7, 2.4 Hz, 1 H), 7.28 (d, J=7.6 Hz, 1 H), 7.08-7.15 (m, 2 H), 6.07 (s, 1 H), 3.81-3.87 (m, 2 H), 3.67-3.73 (m, 2 H), 2.34 (s, 3 H), 2.28-2.31 (m, 3 H), 2.16 (s, 3 H).

Example 489

N-{6-[(2-{[2-amino-6-(4-fluoro-2,5-dimethylphenyl)pyrimidin-4-yl]amino}ethyl)amino]pyridin-3-yl}methanesulfonamide Step 1: In a flask 6-(4-fluoro-2,5-dimethyl-phenyl)-N4-[2-[(5-nitro-2-pyridyl)amino]ethyl]pyrimidine-2,4-diamine (from example 480) was dissolved in MeOH, then the flask was evacuated and the atmosphere was changed to H$_2$. The mixture was stirred at 20° C. for 16 h and then passed through a syringe filter and concentrated.
Step 2: The crude mixture from step 1 was dissolved in DCM, then Hünig's base (2.0 equiv) and methanesulfonyl chloride (1.1 equiv) were added and the mixture was stirred 3 h at 20° C. Then the mixture was concentrated and purified by preparative LC. LCMS [M+H]$^+$ 446. 1H NMR (400 MHz, METHANOL-d4) δ ppm 7.84-7.88 (m, 2 H), 7.29 (d, J=7.3 Hz, 2 H), 7.08-7.13 (m, 5 H), 6.07 (s, 2 H), 3.81-3.86 (m, 2 H), 3.68-3.73 (m, 2 H), 3.04 (s, 3 H), 2.35 (s, 3 H), 2.29-2.32 (m, 3 H).

Example 490

6-(2,3-dimethylphenyl)-4-N-{2-[(6-methoxy-4-methylpyridin-3-yl)amino]ethyl}pyrimidine-2,4-diamine Step 1: N'-(6-methoxy-4-methyl-3-pyridyl)ethane-1,2-diamine was prepared according to general procedure 13 from 5-bromo-2-methoxy-4-methyl-pyridine.
Step 2: The title compound was prepared according to general procedure 9 from the crude material in step 1 and intermediate 19. LCMS [M+H]$^+$ 379. 1H NMR (400 MHz, METHANOL-d4) δ ppm 7.55 (br. s., 1 H), 7.39 (d, J=7.6 Hz, 1 H), 7.24-7.30 (m, 1 H), 7.19-7.23 (m, 1 H), 7.14 (br. s., 1 H), 6.05 (s, 1 H), 4.03 (s, 3 H), 3.81 (t, J=6.3 Hz, 2 H), 3.47 (t, J=6.3 Hz, 2 H), 2.38 (s, 3 H), 2.36 (s, 3 H), 2.27 (s, 3 H).

Example 491

6-(2,3-dimethylphenyl)-4-N-{2-[(6-methanesulfonylpyridin-3-yl)amino]ethyl}pyrimidine-2,4-diamine Step 1: N'-(6-methylsulfonyl-3-pyridyl)ethane-1,2-diamine was prepared according to general procedure 13 from 5-bromo-2-methylsulfonyl-pyridine.
Step 2: The title compound was prepared according to general procedure 9 from the crude material in step 1 and intermediate 19. LCMS [M+H]$^+$ 413. 1H NMR (400 MHz, METHANOL-d4) δ ppm 8.13 (d, J=2.8 Hz, 1 H), 7.85 (dd, J=8.6, 0.5 Hz, 1 H), 7.38 (d, J=7.3 Hz, 1 H), 7.23-7.29 (m, 1 H), 7.15-7.21 (m, 2 H), 6.01 (s, 1 H), 3.75-3.80 (m, 2 H), 3.55 (t, J=6.2 Hz, 2 H), 3.12 (s, 3 H), 2.38 (s, 3 H), 2.26 (s, 3 H).

Example 492

5-[(2-{[2-amino-6-(2,3-dimethylphenyl)pyrimidin-4-yl]amino}ethyl)amino]pyridine-3-sulfonamide Step 1: 5-(2-aminoethylamino)pyridine-3-sulfonamide was prepared according to general procedure 13 from 5-bromopyridine-3-sulfonamide.
Step 2: The title compound was prepared according to general procedure 9 from the crude material in step 1 and intermediate 19. LCMS [M+H]$^+$ 414. 1H NMR (400 MHz, METHANOL-d4) δ ppm 8.14-8.39 (m, 2 H), 7.78 (s, 1 H), 7.36-7.41 (m, 1 H), 7.24-7.29 (m, 1 H), 7.20-7.24 (m, 1 H), 6.01 (s, 1 H), 3.70-3.75 (m, 2H), 3.52-3.57 (m, 2 H), 2.38 (s, 3 H), 2.27 (s, 3 H).

Example 493

[4-[2-[[2-amino-6-(3,5-dichloro-2-methyl-phenyl)pyrimidin-4-yl]amino]ethyl]phenyl]-morpholino-methanone The title compound was prepared according to general procedure 2 from intermediate 52 and (3,5-dichloro-2-methyl-phenyl)boronic acid. [M+H]$^+$ 486.

Example 494 tert-butyl 4-(2-amino-6-{[2-(4-methanesulfonylphenyl)ethyl]amino}pyrimidin-4-yl)-1,2,3,6-tetrahydro-pyridine-1-carboxylate Tetrakis(triphenylphosphine) palladium (0) (0.05 equiv.) was added after degassing with nitrogen to a stirred mixture of intermediate 33, tert-butyl 4-(4,4,5,5-tetramethyl-1,3,2-dioxaborolan-2-yl)-3,6-dihydro-2H-pyridine-1-carboxylate (1.1 equiv.), potassium carbonate 1 M (2.5 equiv.) and dioxane in a tube. The tube was sealed and the reaction was heated at 80° C. for 5 hours. The mixture was purified by preparative HPLC (acetonitrile/ammonium bicarbonate buffer) to give the title compound. LCMS [M+H]+ 474; 1H NMR (400 MHz, DMSO-d6) δ ppm 7.81-7.87 (m, 2 H), 7.49-7.55 (m, 2 H), 6.94 (br. s., 1 H), 6.62 (br. s., 1 H), 5.85 (s, 2 H), 5.77 (s, 1 H), 3.93-4.03 (m, 2 H), 3.42-3.54 (m, 4 H), 3.18 (s, 3 H), 2.92 (t, J=7.1 Hz, 2 H), 2.28-2.37 (m, 2 H), 1.41 (s, 9 H).

Example 495

4-[(1R,2S)-2-{[2-amino-6-(3-chloro-2-methylphenyl)pyrimidin-4-yl]amino}cyclopropyl]benzene-1-sulfonamide Step 1: 6-chloro-N4-[(1S,2R)-2-phenylcyclopropyl]pyrimidine-2,4-diamine: A mixture of 4,6-dichloropyrimidin-2-amine, (1S,2R)-2-phenylcyclopropanamine hydrochloride and N,N-Diisopropylethylamine in n-butanol was heated in a sealed tube at 80° C. for 16 h. After cooling was the solid washed with ethanol to obtain the title product. LCMS [M+H]$^+$ 261.
Step 2: 4-[(1R,2S)-2-[(2-amino-6-chloro-pyrimidin-4-yl)amino]cyclopropyl]benzenesulfonyl chloride:
To 6-chloro-N4-[(1S,2R)-2-phenylcyclopropyl]pyrimidine-2,4-diamine at 0° C. in DCM was chlorosulfonic acid added dropwise. The mixture was then stirred at rt for 2 h. The solution was poured into crushed ice, extracted with DCM. The combined organic phases were washed with water, dried, filtered, and concentrated to obtain the title compound. LCMS [M+H]$^+$ 359.
Step 3: 4-[(1R,2S)-2-[(2-amino-6-chloro-pyrimidin-4-yl)amino]cyclopropyl]benzenesulfonamide:
Aqueous ammonia was added drop wise to a stirred, ice-chilled solution of 4-[(1R,2S)-2-[(2-amino-6-chloro-pyrimidin-4-yl)amino]cyclopropyl]benzenesulfonyl chloride in acetonitrile. The resulting mixture was stirred for 20 min at RT and diluted with water, extracted with EtOAc. The organic layers were dried over Na$_2$SO$_4$ and concentrated in vacuo to give the title compound. LCMS [M+H]$^+$ 340.

Step 4: 4-[(1R,2S)-2-{[2-amino-6-(3-chloro-2-methylphenyl)pyrimidin-4-yl]amino}cyclopropyl]benzene-1-sulfonamide was prepared according to general procedure 2 from 4-[(1R,2S)-2-[(2-amino-6-chloro-pyrimidin-4-yl)amino]cyclopropyl]benzenesulfonamide and (3-chloro-2-methyl-phenyl)boronic acid. LCMS [M+H]$^+$ 430; $^1$H NMR (400 MHz, DMSO-d$_6$) δ ppm 7.69 (d, J=8.1 Hz, 2 H), 7.42-7.45 (m, 1 H), 7.40 (d, J=3.3 Hz, 1 H), 7.32 (d, J=8.3 Hz, 2 H), 7.15-7.28 (m, 4 H), 6.07 (s, 2 H), 5.71 (s, 1 H), 2.52-2.52 (m, 1 H), 2.28 (s, 3 H), 2.10 (ddd, J=8.8, 6.2, 3.2 Hz, 1 H), 1.28-1.42 (m, 2 H).

Example 496

4-N-[2-(4-methanesulfonylphenyl)ethyl]-6-(1,2,3,6-tetrahydropyridin-4-yl)pyrimidine-2,4-diamine To tert-butyl 4-(2-amino-6-{[2-(4-methanesulfonylphenyl)ethyl]amino}pyrimidin-4-yl)-1,2,3,6-tetrahydropyridine-1-carboxylate was added 5 M HCl in dioxan and the mixture was stirred at rt for 20 min. The solvent was removed to obtain the title compound. LCMS [M+H]$^+$ 374.

Example 497

4-N-[2-(4-methanesulfonylphenyl)ethyl]-6-[1-(4-methylbenzenesulfonyl)-1,2,3,6-tetrahydropyridin-4-yl]pyrimidine-2,4-diamine Prepared according to general procedure 16 from N4-[2-(4-methylsulfonylphenyl)ethyl]-6-(1,2,3,6-tetrahydropyridin-4-yl)pyrimidine-2,4-diamine hydrochloride and 4-methylbenzenesulfonyl chloride. LCMS [M+H]$^+$ 528. $^1$H NMR (400 MHz, DMSO-d$_6$) δ ppm 11.58 (br. s., 1 H), 8.85 (t, J=5.7 Hz, 1 H), 7.83-7.88 (m, 2 H), 7.67-7.72 (m, 2 H), 7.53 (d, J=8.3 Hz, 2 H), 7.46 (dd, J=8.5, 0.6 Hz, 2 H), 6.49 (br. s., 2 H), 5.97 (s, 1 H), 3.72-3.78 (m, 2 H), 3.57-3.69 (m, 2 H), 3.12-3.21 (m, 5 H), 2.97 (t, J=7.1 Hz, 2 H), 2.35-2.42 (m, 5 H).

Example 498

2-[3-(2-amino-6-{[2-(4-chlorophenyl)ethyl]amino}pyrimidin-4-yl)phenoxy]acetamide 4-N-[2-(4-chlorophenyl)ethyl]-6-iodopyrimidine-2,4-diamine (25 mg, 0,070 mmol), [3-(carbamoylmethoxy)phenyl]boronic acid (26 mg, 0.13 mmol), K$_2$CO$_3$ (55 mg, 0.40 mmol), Tetrakis(triphenylphosphine)palladium(O) (3.8 mg, 0,0030 mmol), MeCN (1.5 mL) and water (0.5 mL) were heated in the micro for 10 min at 120° C. The organic phase was filtered and purified by basic prep-HPLC to afford 2-[3-(2-amino-6-{[2-(4-chlorophenyl)ethyl]amino}pyrimidin-4-yl)phenoxy]acetamide. LCMS [M+H]$^+$ 398

Example 499

2-[(2-{[2-amino-6-(2,3-dimethylphenyl)pyrimidin-4-yl]amino}ethyl)amino]pyrimidine-4-carboxamide The title compound was prepared according to general procedure 12 from intermediate 35 and 2-chloropyrimidine-4-carboxamide. LCMS [M+H]$^+$ 379. 1H NMR (400 MHz, METHANOL-d4) δ ppm 8.49 (d, J=4.8 Hz, 1 H), 7.35 (d, J=7.3 Hz, 1 H), 7.19-7.26 (m, 2 H), 7.13-7.17 (m, 1 H), 5.94 (s, 1 H), 3.77 (s, 4 H), 2.35 (s, 3 H), 2.22 (s, 3 H).

Example 500

6-(2,3-dimethylphenyl)-4-N-{2-[(pyrazin-2-yl)amino]ethyl}pyrimidine-2,4-diamine

The title compound was prepared according to general procedure 12 from intermediate 35 and 2-chloropyrazine. LCMS [M+H]$^+$ 336.

Example 501

4-N-{2-[(6-chloropyrimidin-4-yl)amino]ethyl}-6-(2,3-dimethylphenyl)pyrimidine-2,4-diamine The title compound was prepared according to general procedure 12 from intermediate 35 and 4,6-dichloropyrimidine. LCMS [M+H]$^+$ 370. 1H NMR (400 MHz, METHANOL-d4) δ ppm 8.26 (s, 1 H), 7.36 (d, J=7.3 Hz, 1 H), 7.24 (t, J=7.6 Hz, 1 H), 7.17 (d, J=7.6 Hz, 1 H), 6.54 (br. s., 1 H), 5.97 (s, 1 H), 3.67-3.78 (m, 4H), 2.36 (s, 3 H), 2.23 (s, 3 H).

Example 502

6-(3-chloro-2-methyl-phenyl)-N4-[3-(3-methylsulfonylanilino)propyl]pyrimidine-2,4-diamine Step 1. A mixture of 1-bromo-3-methylsulfonyl-benzene (1.0 equiv.), CuCl (0.10 equiv.), KOH (2.0 equiv.), and 1,3-propanediamine (4.50 equiv.) were stirred at 90° C. for 16 h in a sealed vial. The mixture was allowed to cool and was then extracted with hot EtOAc ×5. The combined organics were concentrated and the excess of 1,3-propanediamine was removed by co-evaporation with toluene. The crude material was used without further purification.

Step 2. The title compound was prepared according to general procedure 9 from material from step 1 and intermediate 24. [M+H]+ 446. $^1$H NMR (400 MHz, METHANOL-d$_4$) δ ppm 7.38-7.42 (m, 1 H), 7.28-7.34 (m, 1 H), 7.20 (d, J=7.6 Hz, 2 H), 7.11 (d, J=1.3 Hz, 2 H), 6.87-6.94 (m, 1 H), 5.82 (s, 1 H), 3.44-3.55 (m, 2 H), 3.21-3.27 (m, 3 H), 3.05 (s, 3 H), 2.31 (s, 3 H), 1.93 (t, J=6.8 Hz, 2 H).

Example 503

4-[2-[[2-amino-6-(3-chloro-2-methyl-phenyl)pyrimidin-4-yl]amino]ethyl]benzenecarbothioamide A mixture of 4-[2-[[2-amino-6-(3-chloro-2-methyl-phenyl)pyrimidin-4-yl]amino]ethyl]benzonitrile (intermediate 53), O,O'-Diethyl dithiophosphate, and water was stirred at 20° C. for 2 days. The mixture was then diluted with water and extracted with DCM. The combined organics were purified by silica gel chromatography. LCMS [M+H]$^+$ 398.

Example 504

3-(2-amino-6-{[2-(4-methanesulfonylphenyl)ethyl]amino}pyrimidin-4-yl)-N-tert-butylthiophene-2-sulfonamide The title compound was prepared according to general procedure 14 from intermediate 33 and potassium [2-(tert-butylsulfamoyl)-3-thienyl]-trifluoro-boranuide. LCMS [M+H]$^+$ 510, 1H NMR (400 MHz, METHANOL-d4) δ ppm 7.87-7.92 (m, 2 H), 7.64-7.67 (m, 2 H), 7.55 (d, J=8.3 Hz, 2 H), 6.31 (s, 1 H), 3.82 (t, J=7.1 Hz, 2 H), 3.10 (s, 3 H), 3.05-3.09 (m, 2 H), 1.28 (s, 9 H).

Example 505 tert-butyl N-{[5-(2-amino-6-{[2-(4-methanesulfonylphenyl)ethyl]amino}pyrimidin-4-yl)thiophen-2-yl]methyl}carbamate The title compound was prepared according to general procedure 14 from intermediate 33 and potassium [2-(tert-butylsulfamoyl)-3-thienyl]-trifluoro-boranuide. LCMS [M+H]$^+$ 504. 1H NMR (400 MHz, METHANOL-d4) δ ppm 7.89 (d, J=8.6 Hz, 2 H), 7.56-7.60 (m, 1 H), 7.54 (d, J=8.3 Hz, 2 H), 7.07 (d, J=3.8 Hz, 1 H), 6.19 (s, 1 H), 4.42 (s, 2 H), 3.79 (t, J=7.1 Hz, 2 H), 3.10 (s, 3 H), 3.06 (t, J=7.1 Hz, 2 H), 1.46 (s, 9 H).

Example 506

N-[4-(2-{[2-amino-6-(2,3-dimethylphenyl)pyrimidin-4-yl]amino}ethyl)phenyl]acetamide The title compound was prepared according to general procedure 18 from Intermediate 50 and acetyl chloride. LCMS [M+H]$^+$ 376. 1H NMR (400 MHz, METHANOL-d4) δ ppm 7.46-7.51 (m, 2 H), 7.33-7.37 (m, 1 H), 7.20-7.26 (m, 3 H), 7.15-7.19 (m, 1 H), 5.96 (s, 1 H), 3.75 (t, J=7.2 Hz, 2 H), 2.91 (t, J=7.2 Hz, 2 H), 2.35 (s, 3 H), 2.24 (s, 3 H), 2.11 (s, 3 H).

Example 507

N-[4-(2-{[2-amino-6-(2,3-dimethylphenyl)pyrimidin-4-yl]amino}ethyl)phenyl]methanesulfonamide The title compound was prepared according to general procedure 18 from Intermediate 50 and methanesulfonyl chloride. LCMS [M+H]$^+$ 412. 1H NMR (400 MHz, METHANOL-d4) δ ppm 7.35 (d, J=7.1 Hz, 1 H), 7.14-7.28 (m, 6 H), 5.97 (s, 1 H), 3.76 (t, J=7.2 Hz, 2 H), 2.91-2.95 (m, 5 H), 2.36 (s, 3 H), 2.24 (s, 3 H).

Example 508

{2-[2-amino-6-(methylamino)pyrimidin-4-yl]phenyl}methanol 6-chloro-4-N-methylpyrimidine-2,4-diamine (20 mg, 0.13 mmol), 1,3-dihydro-2,1-benzoxaborol-1-ol (25 mg, 0.19 mmol), K$_2$CO$_3$ (78 mg, 0.57 mmol), Tetrakis(triphenylphosphine)palladium(O) (7.3 mg, 0,0060 mmol), MeCN (1.5 mL) and water (0.5 mL) were heated in the micro for 10 min at 120° C. The organic phase was filtered and purified by basic prep-HPLC to afford {2-[2-amino-6-(methylamino)pyrimidin-4-yl]phenyl}methanol. LCMS [M+H]$^+$ 231

Example 509

4-[2-({2-amino-6-[2-(hydroxymethyl)phenyl]pyrimidin-4-yl}amino)ethyl]benzene-1-sulfonamide 4-{2-[(2-amino-6-chloropyrimidin-4-yl)amino]ethyl}benzene-1-sulfonamide (20 mg, 0,060 mmol), 1,3-dihydro-2,1-benzoxaborol-1-ol (12 mg, 0,090 mmol), K$_2$CO$_3$ (38 mg, 0.27 mmol), Tetrakis(triphenylphosphine)

palladium(0) (3.5 mg, 0,0030 mmol), MeCN (1.5 mL) and water (0.5 mL) were heated in the micro for 10 min at 120° C. The organic phase was filtered and purified by basic prep-HPLC to afford 4-[2-({2-amino-6-[2-(hydroxymethyl) phenyl]pyrimidin-4-yl}amino)ethyl]benzene-1-sulfonamide. LCMS [M+H]$^+$ 400

Example 510

4-[(2-{[2-amino-6-(2,3-dimethylphenyl)pyrimidin-4-yl]amino}ethyl)amino]-N-methylbenzene-1-sulfonamide Step 1: 4-(2-aminoethylamino)-N-methyl-benzenesulfonamide was prepared according to general procedure 13 from 4-iodo-N-methyl-benzenesulfonamide.
Step 2: The title compound was prepared according to general procedure 9 from the crude material in step 1 and intermediate 19. LCMS [M+H]$^+$ 427. 1H NMR (400 MHz, METHANOL-d4) δ ppm 7.54-7.59 (m, 2 H), 7.33-7.37 (m, 1 H), 7.21-7.27 (m, 1 H), 7.15-7.20 (m, 1 H), 6.71-6.75 (m, 2 H), 5.98 (s, 1 H), 3.75 (t, J=6.2 Hz, 2 H), 3.49 (t, J=6.1 Hz, 2 H), 2.45-2.47 (m, 3 H), 2.36 (s, 3 H), 2.24 (s, 3 H).

Example 511

N-{4-[(2-{[2-amino-6-(2,3-dimethylphenyl)pyrimidin-4-yl]amino}ethyl)amino]-2-methylphenyl}acetamide Step 1: N-[4-(2-aminoethylamino)-2-methyl-phenyl]acetamide was prepared according to general procedure 13 from N-(4-iodo-2-methyl-phenyl)acetamide.
Step 2: The title compound was prepared according to general procedure 9 from the crude material in step 1 and intermediate 19. LCMS [M+H]$^+$ 405. 1H NMR (400 MHz, METHANOL-d4) δ ppm 7.36 (d, J=7.6 Hz, 2 H), 7.22-7.28 (m, 3 H), 7.16-7.20 (m, 1 H), 6.92 (d, J=2.5 Hz, 1 H), 6.87 (dd, J=8.3, 2.5 Hz, 1 H), 6.03 (s, 1 H), 3.75-3.81 (m, 2 H), 3.55 (t, J=5.9 Hz, 2 H), 2.36 (s, 3 H), 2.25 (s, 3 H), 2.22 (s, 3 H), 2.14 (s, 3 H).

Example 512

6-[(2-{[2-amino-6-(2,3-dimethylphenyl)pyrimidin-4-yl]amino}ethyl)amino]-3,4-dihydro-2H-1,4-benzoxazin-3-one Step 1: 6-(2-aminoethylamino)-4H-1,4-benzoxazin-3-one was prepared according to general procedure 13 from (6-bromo-4H-1,4-benzoxazin-3-one.
Step 2: The title compound was prepared according to general procedure 9 from the crude material in step 1 and intermediate 19. LCMS [M+H]$^+$ 405. 1H NMR (400 MHz, METHANOL-d4) δ ppm 7.35-7.38 (m, 1 H), 7.25 (t, J=7.6 Hz, 1 H), 7.16-7.20 (m, 1 H), 6.93 (d, J=8.6 Hz, 1 H), 6.70 (dd, J=8.7, 2.7 Hz, 1 H), 6.65 (d, J=2.5 Hz, 1 H), 6.03 (s, 1 H), 4.53 (s, 2 H), 3.79 (t, J=6.1 Hz, 2 H), 3.53 (t, J=5.9 Hz, 2 H), 2.36 (s, 3 H), 2.25 (s, 3 H).

Example 513

2-[(2-{[2-amino-6-(2,3-dimethylphenyl)pyrimidin-4-yl]amino}ethyl)amino]benzamide Step 1: 2-(2-aminoethylamino)benzamide was prepared according to general procedure 13 from 2-bromobenzamide.
Step 2: The title compound was prepared according to general procedure 9 from the crude material in step 1 and intermediate 19. LCMS [M+H]$^+$ 377. 1H NMR (400 MHz, METHANOL-d4) δ ppm 7.57 (dd, J=7.8, 1.3 Hz, 1 H), 7.31-7.37 (m, 2H), 7.22-7.27 (m, 1 H), 7.17-7.21 (m, 1 H), 6.83 (dd, J=8.3, 0.8 Hz, 1 H), 6.64 (ddd, J=8.0, 7.1, 1.0 Hz, 1 H), 6.01 (s, 1 H), 3.79 (t, J=5.9 Hz, 2 H), 3.49 (t, J=5.9 Hz, 2 H), 2.36 (s, 3 H), 2.25 (s, 3 H).

Example 514

2-[(2-{[2-amino-6-(2,3-dimethylphenyl)pyrimidin-4-yl]amino}ethyl)amino]pyridine-4-carboxamide The title compound was prepared according to general procedure 12 from intermediate 35 and 6-chloropyridine-3-carboxamide. LCMS [M+H]$^+$ 378.

Example 515

6-(2-{[2-amino-6-(2,3-dimethylphenyl)pyrimidin-4-yl]amino}ethoxy)pyridine-3-carboxamide A mixture of 2-[[2-amino-6-(2,3-dimethylphenyl)pyrimidin-4-yl]amino]ethanol, 6-chloropyridine-3-carboxamide (1.5 equiv.) and potassium carbonate (3.5 equiv.) in DMSO was heated in a sealed tube at 90° C. for 16 h. After cooling was methanol added to the solution, followed by filtration and purification by preparative HPLC acetonitrile/trifluoroacetic acid buffer to furnish the title compound. LCMS [M+H]$^+$ 379.

Example 516

N-[3-(2-amino-6-{[2-(4-methanesulfonylphenyl) ethyl]amino}pyrimidin-4-yl)-2-methylphenyl]-4-chloro-2-hydroxybenzamide Prepared according to general procedure 2 from intermediate 33 and (4-chloro-2-hydroxy-N-[2-methyl-3-(4,4,5,5-tetramethyl-1,3,2-dioxaborolan-2-yl)phenyl]benzamide. LCMS [M+H]$^+$ 552.

Example 517

3-(2-{[2-amino-6-(2,3-dimethylphenyl)pyrimidin-4-yl]amino}ethyl)-1H-indol-5-ol

The title compound was prepared according to general procedure 9 from 3-(2-aminoethyl)-1H-indol-5-ol hydrogen chloride and intermediate 19. LCMS [M+H]$^+$ 374. 1H NMR (400 MHz, METHANOL-d4) δ ppm 7.16 (d, J=8.8 Hz, 1 H), 7.09 (t, J=7.4 Hz, 1 H), 6.95-7.06 (m, 3 H), 6.67 (dd, J=8.7, 2.4 Hz, 1 H), 5.75 (s, 1 H), 3.61 (br. s., 2 H), 2.96 (t, J=7.3 Hz, 2 H), 2.30 (s, 3 H), 2.17 (s, 3 H).

Example 518

4-N-{2-[5-(benzyloxy)-1H-indol-3-yl]ethyl}-6-(2,3-dimethylphenyl)pyrimidine-2,4-diamine The title compound was prepared according to general procedure 9 from 5-benzyloxy tryptamine-HCl and intermediate 19. LCMS [M+H]$^+$ 464. 1H NMR (400 MHz, METHANOL-d4) δ ppm 7.37-7.43 (m, 2 H), 7.29-7.35 (m, 2 H), 7.24-7.28 (m, 1 H), 7.22 (d, J=8.8 Hz, 1 H), 7.09-7.16 (m, 2 H), 7.03-7.08 (m, 2 H), 7.00 (br. s., 1 H), 6.82 (dd, J=8.7, 2.4 Hz, 1 H), 5.74 (s, 1 H), 5.02 (s, 2 H), 3.60 (br. s., 2 H), 2.98 (t, J=7.0 Hz, 2 H), 2.27 (s, 3 H), 2.15 (s, 3 H).

Example 519

4-N-[2-(5-bromo-1H-indol-3-yl)ethyl]-6-(2,3-dimethylphenyl)pyrimidine-2,4-diamine The title compound was prepared according to general procedure 9 from 5-bromotryptamine-HCl and intermediate 19. LCMS [M+H]+ 436. 1H NMR (400 MHz, METHANOL-d4) δ ppm 7.73 (s, 1 H), 7.22-7.26 (m, 1 H), 7.16 (dd, J=8.8, 1.9 Hz, 2 H), 7.06-7.13 (m, 2 H), 7.04 (br. s., 1 H), 5.74 (s, 1 H), 3.61 (br. s., 2 H), 2.99 (t, J=7.1 Hz, 2 H), 2.29 (s, 3 H), 2.17 (s, 3 H).

Example 520

6-(2,3-dimethylphenyl)-4-N-[2-(5-methoxy-1H-indol-3-yl)ethyl]pyrimidine-2,4-diamine The title compound was prepared according to general procedure 9 from 5-methoxytryptamine and intermediate 19. LCMS [M+H]+ 388. 1H NMR (400 MHz, METHANOL-d4) δ ppm 7.21 (dd, J=8.8, 0.6 Hz, 1 H), 7.15-7.18 (m, 1 H), 7.10 (t, J=7.6 Hz, 1 H), 6.99-7.07 (m, 3 H), 6.74 (dd, J=8.8, 2.2 Hz, 1 H), 5.76 (s, 1 H), 3.77 (br. s, 3 H), 3.63 (br. s., 2 H), 3.01 (t, J=7.1 Hz, 2 H), 2.31 (s, 3 H), 2.17 (s, 3 H).

Example 521

6-(2,3-dimethylphenyl)-4-N-[2-(7-methyl-1H-indol-3-yl)ethyl]pyrimidine-2,4-diamine The title compound was prepared according to general procedure 9 from 7-methyltryptamine and intermediate 19. LCMS [M+H]+ 372.

Example 522

4-N-{2-[7-(benzyloxy)-1H-indol-3-yl]ethyl}-6-(2,3-dimethylphenyl)pyrimidine-2,4-diamine The title compound was prepared according to general procedure 9 from 7-benzyloxytryptamine and intermediate 19. LCMS [M+H]+ 464.

Example 523

6-(2,3-dimethylphenyl)-4-N-[2-(6-methoxy-1H-indol-3-yl)ethyl]pyrimidine-2,4-diamine The title compound was prepared according to general procedure 9 from 6-methoxytryptamine and intermediate 19. LCMS [M+H]+ 388. 1H NMR (400 MHz, METHANOL-d4) δ ppm 7.43 (d, J=8.8 Hz, 1 H), 7.15-7.19 (m, 1 H), 7.10 (t, J=7.6 Hz, 1 H), 7.02 (br. s., 1 H), 6.96 (s, 1 H), 6.87 (d, J=2.5 Hz, 1 H), 6.67 (dd, J=8.5, 2.2 Hz, 1 H), 5.74 (s, 1 H), 3.80 (s, 3 H), 3.62 (br. s., 2 H), 3.00 (t, J=7.1 Hz, 2 H), 2.31 (s, 3 H), 2.18 (s, 3 H).

Example 524

6-(2,3-dichlorophenyl)-4-N-(2-methylcyclopropyl) pyrimidine-2,4-diamine

A mixture of 4-chloro-6-(2,3-dichlorophenyl)pyrimidin-2-amine (41 mg, 0.15 mmol; Intermediate 21), 2-methylcyclopropan-1-amine (21 mg, 0.30 mmol) and triethylamine (50 μL, 0.36 mmol) in n-butanol (1 mL) was heated in a sealed tube at 95° C. overnight. Concentrated and purified by preparative HPLC. LCMS [M+H]+ 309.

Example 525 tert-butyl 4-(2-amino-6-{[2-(4-sulfamoylphenyl) ethyl]amino}pyrimidin-4-yl)-1,2,3,6-tetrahydropyridine-1-carboxylate Tetrakis(triphenylphosphine) palladium (0) (0.05 equiv.) was added after degassing with nitrogen to a stirred mixture of intermediate 25, tert-butyl 4-(4,4,5,5-tetramethyl-1,3,2-dioxaborolan-2-yl)-3,6-dihydro-2H-pyridine-1-carboxylate (1.1 equiv.), potassium carbonate 1 M (2.5 equiv.) and dioxane in a tube. The tube was sealed and the reaction was heated at 90° C. for 3 hours. The mixture was purified by preparative HPLC (acetonitrile/ammonium bicarbonate buffer) to give the title compound. LCMS [M+H]+ 475.

Example 526

4-(2-{[2-amino-6-(3-hydroxyphenyl)pyrimidin-4-yl] amino}ethyl)benzene-1-sulfonamide Prepared according to general procedure 2 from intermediate 25 and (3-hydroxyphenyl)boronic acid. LCMS [M+H]+ 386.

Example 527

4-(2-{[2-amino-6-(cyclohept-1-en-1-yl)pyrimidin-4-yl]amino}ethyl)benzene-1-sulfonamide Tetrakis(triphenylphosphine) palladium (0) (0.05 equiv.) was added after degassing with nitrogen to a stirred mixture of intermediate 25, 2-(cyclohepten-1-yl)-4,4,5,5-tetramethyl-1,3,2-dioxaborolane (1.2 equiv.), potassium carbonate 1 M (2.5 equiv.) and dioxane in a tube. The tube was sealed and the reaction was heated at 90° C. for 16 hours. The mixture was purified by preparative HPLC (acetonitrile/ ammonium bicarbonate buffer) to give the title compound. LCMS [M+H]+ 388.

Example 528

Ethyl 6-[(2-{[2-amino-6-(2,3-dimethylphenyl)pyrimidin-4-yl]amino}ethyl)amino]pyridine-3-carboxylate Step 1. A mixture of ethyl 6-chloropyridine-3-carboxylate (1.0 equiv.) and ethane-1,2-diamine (1.1 equiv.) were stirred at 90° C. for 16 h. The mixture was purified by preparative LC which afforded ethyl 6-(2-aminoethylamino)pyridine-3-carboxylate.

Step 2: The title compound was prepared according to general procedure 9 from ethyl 6-(2-aminoethylamino)pyridine-3-carboxylate and intermediate 19. LCMS [M+H]+ 407. 1H NMR (400 MHz, METHANOL-d4) δ ppm 8.53 (dd, J=2.2, 0.6 Hz, 1 H), 8.23 (d, J=9.2 Hz, 1 H), 7.36 (d, J=7.6 Hz, 1 H), 7.24 (t, J=7.6 Hz, 1 H), 7.14-7.18 (m, 1 H), 7.01 (d, J=8.2 Hz, 1 H), 6.03 (s, 1 H), 4.37 (q, J=7.3 Hz, 2 H), 3.80-3.87 (m, 2 H), 3.73-3.79 (m, 2 H), 2.35 (s, 3 H), 2.23 (s, 3 H), 1.38 (t, J=7.1 Hz, 3 H).

Example 529

4-[(2-{[2-amino-6-(2,3-dimethylphenyl)pyrimidin-4-yl]amino}ethyl)amino]-2-(trifluoromethyl)benzene-1-sulfonamide Step 1: 4-(2-aminoethylamino)-2-(trifluoromethyl)benzenesulfonamide was prepared according to general procedure 13 from 4-bromo-2-(trifluoromethyl)benzenesulfonamide.

Step 2: The title compound was prepared according to general procedure 9 from the compound from step 1 and intermediate 19. LCMS [M+H]$^+$ 481. 1H NMR (400 MHz, METHANOL-d4) δ ppm 7.96 (d, J=8.8 Hz, 1 H), 7.35 (d, J=7.6 Hz, 1 H), 7.24 (t, J=7.7 Hz, 1 H), 7.14-7.19 (m, 1 H), 7.03 (d, J=2.5 Hz, 1 H), 6.85 (dd, J=9.2, 2.5 Hz, 1 H), 5.97 (s, 1 H), 3.71-3.79 (m, 2 H), 3.51-3.56 (m, 2 H), 2.35 (s, 3 H), 2.23 (s, 3 H).

Example 530

4-[(2-{[2-amino-6-(2,3-dimethylphenyl)pyrimidin-4-yl]amino}ethyl)amino]benzamide Step 1: 4-(2-aminoethylamino)benzamide was prepared according to general procedure 13 from 4-iodobenzamide.

Step 2: The title compound was prepared according to general procedure 9 from the compound from step 1 and intermediate 19. LCMS [M+H]$^+$ 377. 1H NMR (400 MHz, METHANOL-d4) δ ppm 7.66-7.72 (m, 2 H), 7.35 (d, J=7.6 Hz, 1 H), 7.23 (t, J=7.6 Hz, 1 H), 7.13-7.17 (m, 1 H), 6.64-6.69 (m, 2 H), 5.97 (s, 1 H), 3.75 (s, 2 H), 3.48 (s, 2 H), 2.35 (s, 3 H), 2.22 (s, 3 H).

Example 531

Ethyl N-[4-(2-{[2-amino-6-(2,3-dimethylphenyl)pyrimidin-4-yl]amino}ethyl)phenyl]carbamate The title compound was prepared according to general procedure 18 Intermediate 50 and ethyl chloroformate. LCMS [M+H]$^+$ 406. 1H NMR (400 MHz, METHANOL-d4) δ ppm 7.34 (d, J=8.5 Hz, 1 H), 7.16 (d, J=8.2 Hz, 2 H), 7.10 (t, J=7.6 Hz, 1 H), 7.02-7.06 (m, 1 H), 5.75 (s, 1 H), 4.17 (q, J=7.3 Hz, 2 H), 3.55 (br. s., 2 H), 2.84 (t, J=7.3 Hz, 2 H), 2.30 (s, 3 H), 2.18 (s, 3 H), 1.29 (t, J=7.1 Hz, 3 H).

Example 532

5-[(2-{[2-amino-6-(2,3-dimethylphenyl)pyrimidin-4-yl]amino}ethyl)amino]-2-methoxybenzene-1-sulfonamide Step 1: 5-(2-aminoethylamino)-2-methoxy-benzenesulfonamide was prepared according to general procedure 13 from 5-bromo-2-methoxy-benzenesulfonamide.

Step 2: The title compound was prepared according to general procedure 9 from the compound from step 1 and intermediate 19. LCMS [M+H]$^+$ 443. 1H NMR (400 MHz, METHANOL-d4) δ ppm 7.44 (d, J=2.8 Hz, 1 H), 7.34-7.38 (m, 1 H), 7.22-7.27 (m, 1 H), 7.18-7.22 (m, 1 H), 7.07-7.11 (m, 1 H), 7.01-7.05 (m, 1 H), 6.00 (s, 1 H), 3.92 (s, 3 H), 3.70 (t, J=6.8 Hz, 2 H), 3.43-3.48 (m, 2 H), 2.36 (s, 3 H), 2.25 (s, 3 H).

Example 533 tert-butyl 4-(2-amino-6-{[2-(4-sulfamoylphenyl)ethyl]amino}pyrimidin-4-yl)piperidine-1-carboxylate Palladium 10% on carbon was added to tert-butyl 4-[2-amino-6-[2-(4-sulfamoylphenyl)ethylamino]pyrimidin-4-yl]-3,6-dihydro-2H-pyridine-1-carboxylate in methanol. The solution was purged with N$_2$ for 5 minutes followed by dropwise addition of formic acid (3 equiv.) and the resulting mixture was stirred at 50° C. for 5 h. The mixture was then filtered and purified by preparative HPLC to give the title compound. LCMS [M+H]$^+$ 477.

Example 534

4-{2-[(2-amino-6-cycloheptylpyrimidin-4-yl)amino]ethyl}benzene-1-sulfonamide

Palladium 10% on carbon was added to 4-[2-[[2-amino-6-(cyclohepten-1-yl)pyrimidin-4-yl]amino]ethyl]benzenesulfonamide in methanol. The solution was purged with N$_2$ for 5 minutes followed by dropwise addition of formic acid (3 equiv.) and the resulting mixture was stirred at 90° C. for 4 h. The mixture was then filtered and purified by preparative HPLC to give the title compound. LCMS [M+H]$^+$ 390.

Example 535

3-(2-amino-6-{[2-(4-sulfamoylphenyl)ethyl]amino}pyrimidin-4-yl)phenyl methanesulfonate To a dried tube was added 4-[2-[[2-amino-6-(3-hydroxyphenyl)pyrimidin-4-yl]amino]ethyl]benzenesulfonamide, dry THF and pyridine. The reaction mixture was then cooled to 0° C. and methane sulfonyl chloride (1.1 equiv) was added dropwise. The reaction was stirred at RT for 16 h followed by quenching with water, filtration and purification by preparative HPLC. LCMS [M+H]$^+$ 464.

Example 536

3-(2-amino-6-{[2-(4-sulfamoylphenyl)ethyl]amino}pyrimidin-4-yl)phenyl trifluoromethanesulfonate 4-[2-[[2-amino-6-(3-hydroxyphenyl)pyrimidin-4-yl]amino]ethyl]benzenesulfonamide, N-phenylbis(trifluoromethane-sulfonimide), K$_2$CO$_3$, and THF were added to a tube and heated to 90° C. for 2 h. After cooling was methanol added to the solution followed by filtration and purification by preparative HPLC to give the title compound. LCMS [M+H]$^+$ 518.

Example 537

4-(2-{[2-amino-6-(2,3-dimethylphenyl)pyrimidin-4-yl]amino}ethyl)benzoic Acid

The title compound was prepared according to general procedure 9 from intermediate 19 and 2-(4-carboxyphenyl)ethylammonium chloride. LCMS [M+H]$^+$ 363.

Example 538

6-[(2-{[2-amino-6-(3-chloro-2-methylphenyl)pyrimidin-4-yl]amino}ethyl)amino]-3,4-dihydro-2H-1,4-benzoxazin-3-one Step 1: 6-(2-aminoethylamino)-4H-1,4-benzoxazin-3-one was prepared according to general procedure 13 from 6-bromo-4H-1,4-benzoxazin-3-one.

Step 2: The title compound was prepared according to general procedure 9 from the compound from step 1 and intermediate 24. LCMS [M+H]$^+$ 425. 1H NMR (400 MHz, METHANOL-d4) δ ppm 7.61 (dd, J=7.7, 1.7 Hz, 1 H), 7.30-7.39 (m, 2 H), 6.90 (d, J=8.5 Hz, 1 H), 6.58-6.67 (m, 2 H), 6.06 (s, 1 H), 4.52 (s, 2 H), 3.79 (t, J=6.0 Hz, 2 H), 3.51 (t, J=6.0 Hz, 2 H), 2.38 (s, 3 H).

Example 539

6-(2,3-dimethylphenyl)-4-N-{2-[(2-methyl-1,3-benzothiazol-6-yl)amino]ethyl}pyrimidine-2,4-diamine Step 1: N'-(2-methyl-1,3-benzothiazol-6-yl)ethane-1,2-diamine was prepared according to general procedure 13 from 6-iodo-2-methyl-1,3-benzothiazole.

Step 2: The title compound was prepared according to general procedure 9 from the compound from step 1 and intermediate 19. LCMS [M+H]$^+$ 405. 1H NMR (400 MHz, METHANOL-d4) δ ppm 7.68 (d, J=8.8 Hz, 1 H), 7.34 (d, J=7.6 Hz, 1 H), 7.26 (d, J=2.5 Hz, 1 H), 7.22 (t, J=7.6 Hz, 1 H), 7.11 (d, J=7.3 Hz, 1 H), 7.01 (dd, J=8.8, 2.2 Hz, 1 H), 5.97 (s, 1 H), 3.79 (t, J=6.0 Hz, 2 H), 3.53 (t, J=6.0 Hz, 2 H), 2.79 (s, 3 H), 2.34 (s, 3 H), 2.21 (s, 3 H).

Example 540

6-[(2-{[2-amino-6-(3-chlorophenyl)pyrimidin-4-yl]amino}ethyl)amino]-3,4-dihydro-2H-1,4-benzoxazin-3-one The title compound was isolated as a by-product from the reaction mixture in example 541 (step 2). LCMS [M+H]$^+$ 411. 1H NMR (400 MHz, METHANOL-d4) δ ppm 7.77 (t, J=1.9 Hz, 1 H), 7.62-7.67 (m, 2 H), 7.55-7.61 (m, 1 H), 6.87-6.97 (m, 2 H), 6.66 (dd, J=8.5, 2.5 Hz, 1 H), 6.61 (d, J=2.5 Hz, 1 H), 6.35 (s, 1 H), 4.50 (s, 2 H), 3.79 (t, J=6.0 Hz, 2 H), 3.51 (t, J=6.0 Hz, 2 H).

Example 541

6-[(2-{[2-amino-6-(2,3-dichlorophenyl)pyrimidin-4-yl]amino}ethyl)amino]-3,4-dihydro-2H-1,4-benzoxazin-3-one Step 1: 6-(2-aminoethylamino)-4H-1,4-benzoxazin-3-one was prepared according to general procedure 13 from 6-bromo-4H-1,4-benzoxazin-3-one.

Step 2: The title compound was prepared according to general procedure 9 from the crude compound from step 1 and intermediate 21. LCMS [M+H]$^+$ 445. 1H NMR (400 MHz, METHANOL-d4) δ ppm 7.76-7.80 (m, 1 H), 7.48-7.51 (m, 2H), 6.85 (d, J=8.5 Hz, 1 H), 6.52 (dd, J=8.7, 2.7 Hz, 1 H), 6.47 (d, J=2.5 Hz, 1 H), 6.15 (s, 1 H), 4.49 (s, 2 H), 3.77 (t, J=6.0 Hz, 2 H), 3.45 (t, J=6.0 Hz, 2 H).

Example 542

6-(2,3-dichlorophenyl)-4-N-{2-[(2-methyl-1,3-benzothiazol-6-yl)amino]ethyl}pyrimidine-2,4-diamine Step 1: N'-(2-methyl-1,3-benzothiazol-6-yl)ethane-1,2-diamine was prepared according to general procedure 13 from 6-iodo-2-methyl-1,3-benzothiazole.

Step 2: The title compound was prepared according to general procedure 9 from the crude compound from step 1 and intermediate 21. LCMS [M+H]$^+$ 445. $^1$H NMR (400 MHz, METHANOL-d4) δ ppm 7.77 (dd, J=7.9, 1.6 Hz, 1 H), 7.63 (d, J=8.8 Hz, 1 H), 7.45-7.50 (m, 1 H), 7.42 (d, J=1.6 Hz, 1 H), 7.16 (d, J=2.2 Hz, 1H), 6.93 (d, J=2.5 Hz, 1 H), 6.09 (s, 1 H), 3.77-3.81 (m, 2 H), 3.48-3.53 (m, 2H), 2.76 (s, 3 H).

Example 543

6-(2,3-dimethylphenyl)-4-N-(2-{[4-(1H-1,2,3,4-tetrazol-5-yl)phenyl]amino}ethyl)pyrimidine-2,4-diamine Step 1: N'-[4-(1H-tetrazol-5-yl)phenyl]ethane-1,2-diamine was prepared according to general procedure 13 from 5-(4-bromophenyl)-1H-tetrazole.

Step 2: The title compound was prepared according to general procedure 9 from the compound from step 1 and intermediate 19. LCMS [M+H]$^+$ 402. 1H NMR (400 MHz, METHANOL-d4) δ ppm 7.73-7.78 (m, 2 H), 7.33 (s, 1 H), 7.17-7.23 (m, 1H), 7.14 (d, J=0.9 Hz, 1 H), 6.77-6.82 (m, 2 H), 5.97 (s, 1 H), 3.77 (t, J=6.0 Hz, 2H), 3.51 (t, J=6.0 Hz, 2 H), 2.33 (s, 3 H), 2.20 (s, 3 H).

Example 544

6-(2,3-dimethylphenyl)-4-N-{2-[(3-methanesulfonylphenyl)amino]ethyl}pyrimidine-2,4-diamine Step 1: N'-(3-methylsulfonylphenyl)ethane-1,2-diamine was prepared according to general procedure 13 from 1-bromo-3-methylsulfonyl-benzene.

Step 2: The title compound was prepared according to general procedure 9 from the compound from step 1 and intermediate 19. LCMS [M+H]$^+$ 412. 1H NMR (400 MHz, METHANOL-d4) δ ppm 7.34 (s, 3 H), 7.23 (d, J=7.6 Hz, 1 H), 7.20 (d, J=1.3 Hz, 1 H), 7.14 (ddd, J=7.6, 1.9, 0.9 Hz, 1 H), 6.94 (ddd, J=8.2, 2.5, 0.9 Hz, 1 H), 5.99 (s, 1 H), 3.70 (s, 2 H), 3.48 (s, 2 H), 3.09 (s, 3 H), 2.36 (s, 3 H), 2.25 (s, 3 H).

Example 545

5-[(2-{[2-amino-6-(2,3-dimethylphenyl)pyrimidin-4-yl]amino}ethyl)amino]-2-methoxybenzene-1-sulfonic Acid Step 1: 5-(2-aminoethylamino)-2-methoxy-benzenesulfonic acid was prepared according to general procedure 13 from 4-bromo-2-methoxy-benzenesulfonic acid.

Step 2: The title compound was prepared according to general procedure 9 from the compound from step 1 and intermediate 19. LCMS [M+H]$^+$ 444.

Example 546

4-[(2-{[2-amino-6-(2,3-dimethylphenyl)pyrimidin-4-yl]amino}ethyl)amino]-3-fluorobenzene-1-sulfonamide Step 1: 4-(2-aminoethylamino)-3-fluoro-benzenesulfonamide was prepared according to general procedure 13 from 4-bromo-3-fluoro-benzenesulfonamide.

Step 2: The title compound was prepared according to general procedure 9 from the compound from step 1 and intermediate 19. LCMS [M+H]$^+$ 431.

Example 547

4-(2-{[2-amino-6-(3-chloro-2-methylphenyl)pyrimidin-4-yl]amino}ethyl)benzamide

Step 1: A mixture of 4,6-dichloropyrimidin-2-amine (600 mg, 3.66 mmol), 4-(2-aminoethyl)benzoic acid hydrochloride (812 mg, 4.02 mmol) and triethylamine (1.5 mL, 4.02 mmol) in n-butanol (20 mL) was heated in a sealed tube at 110° C. overnight. The reaction mixture was concentrated and the crude material was recrystallized from a mixture of 2-propanol, methanol and water. The solid material was collected by filtration, washed with 2-propanol and dried under vacuum to afford 4-{2-[(2-amino-6-chloropyrimidin-4-yl)amino]ethyl}benzoic acid.

Step 2: A mixture of 4-{2-[(2-amino-6-chloropyrimidin-4-yl)amino]ethyl}benzoic acid (59 mg, 0.20 mmol), ammonia (1.0 mL, 0.50 mmol; as a 0.50 M solution in 1,4-dioxane), HATU coupling reagent (91 mg, 0.24 mmol) and triethylamine (in DMF (3 mL) was stirred at rt for 1.5 h. Purified by preparative HPLC to afford 4-{2-[(2-amino-6-chloropyrimidin-4-yl)amino]ethyl}benzamide.

Step 3: A mixture of 4-{2-[(2-amino-6-chloropyrimidin-4-yl)amino]ethyl}benzamide (27 mg, 0.093 mmol), (3-chloro-2-methylphenyl)boronic acid (21 mg, 0.12 mmol), palladium tetrakis(triphenylphosphine)palladium (0) (12 mg, 0.010 mmol) and potassium carbonate (26 mg, 0.19 mmol) in 1,4-dioxane (4 mL) and water (1 mL) was heated in a sealed tube at 95° C. for 1 h. Concentrated and purified by preparative HPLC. LCMS [M+H]$^+$ 382; 1H NMR (400 MHz, CD$_3$OD) δ ppm 7.79-7.84 (2H, m) 7.34-7.43 (3 H, m) 7.15-7.24 (2 H, m) 5.76 (1 H, s) 3.61 (2 H, s) 2.98 (2 H, t, J=7.11 Hz) 2.31 (3 H, s).

Example 548

4-(2-{[2-amino-6-(2,3-dimethylphenyl)pyrimidin-4-yl]amino}ethyl)benzamide

A mixture of 4-[2-[[2-amino-6-(2,3-dimethylphenyl)pyrimidin-4-yl]amino]ethyl]benzoic acid (from example 537) and O-(Benzotriazol-1-yl)-N,N,N',N'-tetramethyluronium tetrafluoroborate was dissolved in DMF. Then NH3 in dioxane was added. The mixture was stirred at 20° C. for 4 h and then purified by preparative LC. LCMS [M+H]$^+$ 362. 1H NMR (400 MHz, METHANOL-d4) δ ppm 7.81-7.86 (m, 2 H), 7.34-7.41 (m, 4 H), 7.22-7.27 (m, 1 H), 7.15-7.20 (m, 1 H), 5.96 (s, 1 H), 3.81 (t, J=7.3 Hz, 2 H), 3.03 (t, J=7.1 Hz, 2 H), 2.36 (s, 3H), 2.24 (s, 3 H).

Example 549

4-N-{2-[(2-amino-9H-purin-6-yl)amino]ethyl}-6-(2,3-dimethylphenyl)pyrimidine-2,4-diamine Step 1: N6-(2-aminoethyl)-9H-purine-2,6-diamine was prepared according to general procedure 13 from 6-bromo-9H-purin-2-amine.

Step 2: The title compound was prepared according to general procedure 9 from the compound from step 1 and intermediate 19. LCMS [M+H]$^+$ 391. 1H NMR (400 MHz, METHANOL-d4) δ ppm 8.04 (s, 1 H), 7.35 (d, J=7.3 Hz, 1 H), 7.23 (t, J=7.7 Hz, 1 H), 7.13-7.18 (m, 1 H), 5.99 (s, 1 H), 3.92 (d, J=6.0 Hz, 2 H), 3.82-3.89 (m, 2 H), 2.35 (s, 3 H), 2.22 (s, 3 H).

Example 550

4-(2-{[6-(1-acetyl-1,2,3,6-tetrahydropyridin-4-yl)-2-aminopyrimidin-4-yl]amino}ethyl)benzene-1-sulfonamide Prepared according to general procedure 16 4-[2-[[2-amino-6-(1,2,3,6-tetrahydropyridin-4-yl)pyrimidin-4-yl]amino]ethyl]benzenesulfonamide hydrochloride and acetyl chloride. LCMS [M+H]$^+$ 417.

Example 551

4-[2-({2-amino-6-[1-(2-methylpropanoyl)-1,2,3,6-tetrahydropyridin-4-yl]pyrimidin-4-yl}amino)ethyl]benzene-1-sulfonamide Prepared according to general procedure 16 from 4-[2-[[2-amino-6-(1,2,3,6-tetrahydropyridin-4-yl)pyrimidin-4-yl]amino]ethyl]benzenesulfonamide hydrochloride and 2-methylpropanoyl chloride. LCMS [M+H]$^+$ 445.

Example 552

4-(2-{[2-amino-6-(1-methanesulfonyl-1,2,3,6-tetrahydropyridin-4-yl)pyrimidin-4-yl]amino}ethyl)benzene-1-sulfonamide Prepared according to general procedure 16 from 4-[2-[[2-amino-6-(1,2,3,6-tetrahydropyridin-4-yl)pyrimidin-4-yl]amino]ethyl]benzenesulfonamide hydrochloride and methanesulfonyl chloride. LCMS [M+H]$^+$ 453.

Example 553

4-[2-({2-amino-6-[1-(1,2-oxazole-5-carbonyl)-1,2,3,6-tetrahydropyridin-4-yl]pyrimidin-4-yl}amino)ethyl]benzene-1-sulfonamide Prepared according to general procedure 16 from 4-[2-[[2-amino-6-(1,2,3,6-tetrahydropyridin-4-yl)pyrimidin-4- yl]amino]ethyl]benzenesulfonamide hydrochloride and isoxazole-5-carbonyl chloride. LCMS [M+H]⁺ 470.

Example 554

4-(2-{[2-amino-6-(1-cyclopentanecarbonyl-1,2,3,6-tetrahydropyridin-4-yl)pyrimidin-4-yl]amino}ethyl)benzene-1-sulfonamide Prepared according to general procedure 16 from 4-[2-[[2-amino-6-(1,2,3,6-tetrahydropyridin-4-yl)pyrimidin-4-yl]amino]ethyl]benzenesulfonamide hydrochloride and cyclopentanecarbonyl chloride. LCMS [M+H]⁺ 471.

Example 555

4-[2-({2-amino-6-[1-(cyclopropanesulfonyl)-1,2,3,6-tetrahydropyridin-4-yl]pyrimidin-4-yl}amino)ethyl]benzene-1-sulfonamide Prepared according to general procedure 16 from 4-[2-[[2-amino-6-(1,2,3,6-tetrahydropyridin-4-yl)pyrimidin-4-yl]amino]ethyl]benzenesulfonamide hydrochloride and cyclopropanesulfonyl chloride. LCMS [M+H]⁺ 479.

Example 556

4-[2-({2-amino-6-[1-(2-cyclopentylacetyl)-1,2,3,6-tetrahydropyridin-4-yl]pyrimidin-4-yl}amino)ethyl]benzene-1-sulfonamide Prepared according to general procedure 16 from 4-[2-[[2-amino-6-(1,2,3,6-tetrahydropyridin-4-yl)pyrimidin-4-yl]amino]ethyl]benzenesulfonamide hydrochloride and 2-cyclopentylacetyl chloride. LCMS [M+H]⁺ 485.

Example 557

4-[2-({2-amino-6-[1-(4-methylbenzoyl)-1,2,3,6-tetrahydropyridin-4-yl]pyrimidin-4-yl}amino)ethyl]benzene-1-sulfonamide Prepared according to general procedure 16 from 4-[2-[[2-amino-6-(1,2,3,6-tetrahydropyridin-4-yl)pyrimidin-4-yl]amino]ethyl]benzenesulfonamide hydrochloride and 4-methylbenzoyl chloride. LCMS [M+H]⁺ 493. ¹H NMR (400 MHz, DMSO-d₆) δ ppm 11.59 (br. s., 1 H), 8.70-8.94 (m, 1 H), 7.70-7.79 (m, 2 H), 7.45 (d, J=8.2 Hz, 2 H), 7.23-7.38 (m, 6 H), 6.60 (br. s., 2 H), 6.03 (s, 1 H), 4.14-4.41 (m, 2 H), 3.57-3.71 (m, 4 H), 2.94 (t, J=7.1 Hz, 2 H), 2.38-2.43 (m, 2H), 2.35 (s, 3 H).

Example 558

N-[3-(2-{[2-amino-6-(3-chloro-2-methylphenyl)pyrimidin-4-yl]amino}ethyl)phenyl]acetamide The title compound was prepared according to General procedure 18 from Intermediate 47 and acetyl chloride. LCMS [M+H]⁺ 396. 1H NMR (400 MHz, METHANOL-d4) δ ppm 7.63 (d, J=0.9 Hz, 1 H), 7.58-7.61 (m, 1 H), 7.32-7.38 (m, 2 H), 7.24-7.26 (m, 2 H), 7.02 (qd, J=2.8, 1.9 Hz, 1 H), 6.00 (s, 1 H), 3.78 (t, J=7.3 Hz, 2 H), 2.94 (t, J=7.3 Hz, 2 H), 2.37 (s, 3 H), 2.12 (s, 3 H).

Example 559

Ethyl N-[3-(2-{[2-amino-6-(3-chloro-2-methylphenyl)pyrimidin-4-yl]amino}ethyl)phenyl]carbamate The title compound was prepared according to general procedure 18 from Intermediate 47 and ethyl chloroformate. LCMS [M+H]⁺ 426. 1H NMR (400 MHz, METHANOL-d4) δ ppm 7.58-7.61 (m, 1 H), 7.45-7.48 (m, 1 H), 7.33-7.35 (m, 2 H), 7.16-7.24 (m, 3 H), 6.93-6.96 (m, 1 H), 6.00 (s, 1 H), 4.13-4.20 (m, 2 H), 3.77 (s, 2 H), 2.93 (s, 2 H), 2.37 (s, 3 H), 1.30 (t, J=7.1 Hz, 3 H).

Example 560

6-(2-{[2-amino-6-(3-chloro-2-methylphenyl)pyrimidin-4-yl]amino}ethyl)-3,4-dihydro-2H-1,4-benzoxazin-3-one Step 1: 6-(2-aminoethyl)-4H-1,4-benzoxazin-3-one was prepared according to general procedure 19 from 6-bromo-4H-1,4-benzoxazin-3-one.
Step 2: The title compound was prepared according to general procedure 9 from 6-(2-aminoethyl)-4H-1,4-benzoxazin-3-one and intermediate 24. LCMS [M+H]⁺ 410. 1H NMR (400 MHz, METHANOL-d4) δ ppm 7.38-7.42 (m, 1 H), 7.19-7.23 (m, 1 H), 7.15-7.19 (m, 1 H), 6.86 (d, J=0.9 Hz, 2 H), 6.78-6.81 (m, 1 H), 5.73-5.77 (m, 1 H), 4.52 (s, 2 H), 3.52-3.61 (m, 2 H), 2.79-2.85 (m, 2 H), 2.31 (s, 3 H).

Example 561

4-N-(2-{[2-amino-6-(2,3-dimethylphenyl)pyrimidin-4-yl]amino}ethyl)-6-(2,3-dimethylphenyl)pyrimidine-2,4-diamine The title compound was prepared according to general procedure 12 from intermediate 35 and intermediate 19. LCMS [M+H]⁺ 455. 1H NMR (400 MHz, METHANOL-d4) δ ppm 7.34-7.39 (m, 2 H), 7.22-7.27 (m, 2 H), 7.15-7.20 (m, 2 H), 6.03 (s, 2 H), 3.81-3.84 (m, 4 H), 2.36 (s, 6 H), 2.25 (s, 6 H).

Example 562 methyl 5-[(2-{[2-amino-6-(2,3-dimethylphenyl)pyrimidin-4-yl]amino}ethyl)amino]pyrazine-2-carboxylate The title compound was prepared according to general procedure 12 from intermediate 35 and methyl 5-chloropyrazine-2-carboxylate. LCMS [M+H]⁺ 394. 1H NMR (400 MHz, METHANOL-d4) δ ppm 8.63-8.72 (m, 1 H), 7.86-7.97 (m, 1 H), 7.33-7.39 (m, 1 H), 7.20-7.27 (m, 1 H), 7.13-7.17 (m, 1 H), 5.93-5.96 (m, 1 H), 3.90 (s, 3 H), 3.73-3.81 (m, 4 H), 2.36 (s, 3 H), 2.23 (s, 3 H).

Example 563 methyl 2-[(2-{[2-amino-6-(2,3-dimethylphenyl)pyrimidin-4-yl]amino}ethyl)amino]-6-methylpyrimidine-4-carboxylate The title compound was prepared according to general procedure 12 from intermediate 35 and methyl 2-chloro-6- methyl-pyrimidine-4-carboxylate. LCMS [M+H]⁺ 408. 1H NMR (400 MHz, METHANOL-d4) δ ppm 7.36 (d, J=7.3 Hz, 1 H), 7.24 (t, J=7.6 Hz, 1 H), 7.16 (d, J=6.6 Hz, 1 H), 7.12 (s, 1 H), 6.02 (s, 1 H), 3.91 (s, 3 H), 3.70-3.78 (m, 4 H), 2.40 (s, 3 H), 2.36 (s, 3 H), 2.24 (s, 3 H).

Example 564

4-N-(2-{[2-amino-6-(2,3-dimethylphenyl)pyrimidin-4-yl]amino}ethyl)pyrimidine-2,4-diamine The title compound was prepared according to general procedure 12 from intermediate 35 and 4-chloropyrimidin-2-amine. LCMS [M+H]⁺ 351. 1H NMR (400 MHz, METHANOL-d4) δ ppm 7.57 (d, J=7.3 Hz, 1 H), 7.36 (d, J=7.6 Hz, 1 H), 7.25 (t, J=7.6 Hz, 1 H), 7.15-7.19 (m, 1 H), 6.09 (d, J=7.3 Hz, 1 H), 6.01 (s, 1 H), 3.77 (m, 4 H), 2.36 (s, 3 H), 2.25 (s, 3 H).

Example 565

6-(2,3-dimethylphenyl)-4-N-{2-[(9H-purin-6-yl)amino]ethyl}pyrimidine-2,4-diamine The title compound was prepared according to general procedure 12 from intermediate 35 and 6-chloro-9H-purine. LCMS [M+H]⁺ 376. 1H NMR (400 MHz, METHANOL-d4) δ ppm 8.46 (br. s., 1 H), 8.30 (s, 1 H), 7.35 (d, J=7.3 Hz, 1 H), 7.24 (t, J=7.6 Hz, 1 H), 7.13-7.18 (m, 1 H), 5.98 (s, 1 H), 4.01 (br. s., 2 H), 3.85-3.92 (m, 2 H), 2.35 (s, 3 H), 2.22 (s, 3 H).

Example 566

1-[4-[2-[[2-amino-6-(3-chloro-2-methyl-phenyl)pyrimidin-4-yl]amino]ethyl]phenyl]-3-ethyl-urea The title compound was prepared according to general procedure 21 from ethyl isocyanate and intermediate 48. LCMS [M+H]⁺ 425.

Example 567

6-(3-chloro-2-methylphenyl)-4-N-[2-(3-methanesulfonylphenyl)ethyl]pyrimidine-2,4-diamine Step 1: 2-(3-methylsulfonylphenyl)ethanamine was prepared according to general procedure 19 from 1-bromo-3-methylsulfonyl-benzene.
Step 2: The title compound was prepared according to general procedure 9 from 2-(3-methylsulfonylphenyl)ethanamine and intermediate 24. LCMS [M+H]⁺ 417. 1H NMR (400 MHz, METHANOL-d4) δ ppm 7.82-7.90 (m, 2 H), 7.65-7.70 (m, 1 H), 7.58-7.64 (m, 2 H), 7.35-7.38 (m, 2 H), 6.01 (s, 1 H), 3.86 (s, 2 H), 3.14 (s, 5 H), 2.38 (s, 3 H).

Example 568

5-N-(2-{[2-amino-6-(2,3-dimethylphenyl)pyrimidin-4-yl]amino}ethyl)pyridine-2,5-diamine Step 1: N-[5-(2-aminoethylamino)-2-pyridyl]acetamide was prepared according to general procedure 13 from N-(5-bromo-2-pyridinyl)acetamide.
Step 2: A mixture of the crude material from step 1 (2 equiv.), intermediate 19 (1 equiv.), and diisopropylethylamine (9 equiv.) in methanol was stirred at 150° C. for 1 h. The N-acetyl group was hydrolyzed under these reaction conditions and the title compound was isolated after preparative LC. LCMS [M+H]⁺ 350. 1H NMR (400 MHz, METHANOL-d4) δ ppm 7.52-7.57 (m, 1 H), 7.34-7.38 (m, 1 H), 7.22-7.27 (m, 1 H), 7.16-7.20 (m, 1 H), 7.13 (dd, J=2.8, 0.6 Hz, 1 H), 6.91 (dd, J=9.5, 0.6 Hz, 1 H), 6.04 (s, 1 H), 3.73 (t, J=6.5 Hz, 2 H), 3.30-3.35 (m, 2H, signal obscured by solvent), 2.36 (s, 3 H), 2.25 (s, 3 H).

Example 569

1-N-(2-{[2-amino-6-(2,3-dimethylphenyl)pyrimidin-4-yl]amino}ethyl)-2-fluorobenzene-1,4-diamine Step 1: N-[4-(2-aminoethylamino)-3-fluoro-phenyl]acetamide was prepared according to general procedure 13 from N-(4-bromo-3-fluorophenyl)acetamide.
Step 2: A mixture of the crude material from step 1 (2 equiv.), intermediate 19 (1 equiv.), and diisopropylethylamine (9 equiv.) in methanol was stirred at 150° C. for 1 h. The N-acetyl group was hydrolyzed under these reaction conditions and the title compound was isolated after preparative LC. LCMS [M+H]⁺ 367.

Example 570

1-[4-[2-[[2-amino-6-(3-chloro-2-methyl-phenyl)pyrimidin-4-yl]amino]ethyl]phenyl]-3-tert-butyl-urea The title compound was prepared according to general procedure 21 from t-butyl isocyanate and intermediate 48. LCMS [M+H]⁺ 453. ¹H NMR (400 MHz, METHANOL-d₄) δ ppm 7.57-7.62 (m, 1 H), 7.33 (d, J=1.9 Hz, 2 H), 7.23-7.27 (m, 2 H), 7.16 (s, 2 H), 5.99 (s, 1 H), 3.70-3.77 (m, 2 H), 2.85-2.91 (m, 2 H), 2.37 (s, 3 H), 1.34-1.38 (m, 9 H).

Example 571

1-allyl-3-[4-[2-[[2-amino-6-(3-chloro-2-methyl-phenyl)pyrimidin-4-yl]amino]ethyl]phenyl]urea The title compound was prepared according to general procedure 21 from allyl isocyanate and intermediate 48. LCMS [M+H]⁺ 437. ¹H NMR (400 MHz, METHANOL-d₄) δ ppm 7.59 (d, J=7.3 Hz, 1 H), 7.29-7.38 (m, 4 H), 7.17 (d, J=8.5 Hz, 2 H), 5.99 (s, 1 H), 5.83-5.95 (m, 1 H), 5.18-5.25 (m, 1 H), 5.11 (dd, J=10.4, 1.6 Hz, 1 H), 3.81 (dt, J=5.3, 1.6 Hz, 2 H), 3.74 (t, J=7.3 Hz, 2 H), 2.89 (t, J=7.1 Hz, 2 H), 2.37 (s, 3 H).

Example 572

Ethyl N-[[4-[2-[[2-amino-6-(3-chloro-2-methyl-phenyl)pyrimidin-4-yl]amino]ethyl]phenyl]carbamoyl]carbamate The title compound was prepared according to general procedure 21 from ethyl N-(oxomethylene)carbamate and intermediate 48. LCMS [M+H]⁺ 469.

Example 573

1-[4-[2-[[2-amino-6-(3-chloro-2-methyl-phenyl)pyrimidin-4-yl]amino]ethyl]phenyl]-3-sec-butyl-urea The title compound was prepared according to general procedure 21 from sec-butyl isocyanate and intermediate 48.

LCMS [M+H]⁺ 453. ¹H NMR (400 MHz, METHANOL-d₄) δ ppm 7.59 (d, J=7.3 Hz, 1 H), 7.31-7.38 (m, 2 H), 7.26-7.31 (m, 2 H), 7.13-7.18 (m, 2 H), 5.99 (s, 1 H), 3.74 (t, J=7.3 Hz, 2 H), 3.65-3.72 (m, 1 H), 2.89 (t, J=7.3 Hz, 2 H), 2.37 (s, 3 H), 1.44-1.55 (m, 2 H), 1.15 (d, J=6.3 Hz, 3 H), 0.92-0.98 (m, 3 H).

Example 574

1-[4-[2-[[2-amino-6-(3-chloro-2-methyl-phenyl)pyrimidin-4-yl]amino]ethyl]phenyl]-3-ethyl-thiourea A mixture of intermediate 48 (1.0 equiv.) and ethyl isothiocyanate (2.4 equiv.) in DCM was stirred at 20° C. for 48 h. The reaction mixture was then concentrated and purified by preparative LC. LCMS [M+H]⁺ 441.

Example 575

N-[4-[2-[[2-amino-6-(3-chloro-2-methyl-phenyl)pyrimidin-4-yl]amino]ethyl]phenyl]morpholine-4-carboxamide A mixture of intermediate 48 (1.0 equiv.), morpholine-4-carbonyl chloride, and diisopropylethylamine in DCM was stirred at reflux for 2 h. The mixture was then concentrated and purified by preparative LC. LCMS [M+H]⁺ 467. ¹H NMR (400 MHz, METHANOL-d₄) δ ppm 7.60 (dd, J=7.4, 2.4 Hz, 1 H), 7.33-7.38 (m, 2 H), 7.29-7.32 (m, 2 H), 7.16-7.21 (m, 2 H), 5.99 (s, 1 H), 3.75 (t, J=7.3 Hz, 2 H), 3.68-3.72 (m, 4 H), 3.48-3.52 (m, 4 H), 2.91 (t, J=7.3 Hz, 2 H), 2.37 (s, 3 H).

Example 576 isopropyl N-[4-[2-[[2-amino-6-(3-chloro-2-methyl-phenyl)pyrimidin-4-yl]amino]ethyl]phenyl]carbamate The title compound was prepared according to general procedure 18 from intermediate 48 and isopropyl carbonochloridate. LCMS [M+H]⁺ 440. ¹H NMR (400 MHz, CHLOROFORM-d) δ ppm 7.44-7.49 (m, 1 H), 7.32 (d, J=7.9 Hz, 2H), 7.07-7.25 (m, 4 H), 6.62-6.78 (m, 1 H), 6.37 (br. s., 1 H), 5.79 (s, 1 H), 5.00 (d, J=6.3 Hz, 1 H), 3.72 (d, J=6.0 Hz, 2 H), 2.87 (t, J=7.0 Hz, 3 H), 2.31 (s, 3 H), 1.27-1.34 (m, 6 H).

Example 577

Isobutyl N-[4-[2-[[2-amino-6-(3-chloro-2-methyl-phenyl)pyrimidin-4-yl]amino]ethyl]phenyl]carbamate The title compound was prepared according to general procedure 18 from intermediate 48 and isobutyl carbonochloridate. LCMS [M+H]⁺ 454. ¹H NMR (400 MHz, CHLOROFORM-d) δ ppm 7.45-7.49 (m, 1 H), 7.31 (d, J=7.6 Hz, 2 H), 7.11-7.22 (m, 5 H), 6.71-6.88 (m, 1 H), 6.44 (br. s., 1 H), 5.81 (s, 1 H), 3.94 (d, J=6.3 Hz, 2 H), 3.73 (d, J=6.0 Hz, 2 H), 2.87 (t, J=7.0 Hz, 2 H), 2.29-2.33 (m, 3H), 1.97 (s, 1 H), 0.93-0.99 (m, 6 H).

Example 578

2,2-dimethylpropyl N-[4-[2-[[2-amino-6-(3-chloro-2-methyl-phenyl)pyrimidin-4-yl]amino]ethyl]phenyl]carbamate The title compound was prepared according to general procedure 18 from intermediate 48 and 2,2-dimethylpropyl carbonochloridate. LCMS [M+H]⁺ 468. ¹H NMR (400 MHz, CHLOROFORM-d) δ ppm 7.45 (d, J=7.6 Hz, 1 H), 7.32 (d, J=7.6 Hz, 2 H), 7.09-7.20 (m, 4 H), 6.78-6.90 (m, 1 H), 6.61-6.69 (m, 1 H), 5.82 (s, 1H), 3.85 (s, 2 H), 3.65-3.74 (m, 2 H), 2.86 (br. s., 2 H), 2.30 (s, 3 H), 0.93-0.99 (m, 9 H).

Example 579

2-methoxyethyl N-[4-[2-[[2-amino-6-(3-chloro-2-methyl-phenyl)pyrimidin-4-yl]amino]ethyl]phenyl]carbamate The title compound was prepared according to general procedure 18 from intermediate 48 and 2-methoxyethyl carbonochloridate. LCMS [M+H]⁺ 456. ¹H NMR (400 MHz, CHLOROFORM-d) δ ppm 7.45 (dd, J=7.6, 1.3 Hz, 1 H), 7.32 (d, J=8.2 Hz, 2 H), 7.10-7.21 (m, 4 H), 6.89 (s, 1 H), 6.36 (br. s., 1 H), 5.75 (s, 1 H), 4.29-4.35 (m, 2 H), 3.67-3.74 (m, 2 H), 3.63-3.67 (m, 2 H), 3.41-3.44 (m, 3 H), 2.87 (s, 2 H), 2.31 (s, 3 H).

Example 580

6-[2-[[2-amino-6-(3-chlorophenyl)pyrimidin-4-yl]amino]ethylamino]-3,3-dimethyl-4H-1,4-benzoxazin-2-one The title compound was isolated as a side product from the experiment described in example 307. [M+H]⁺ 439. ¹H NMR (400 MHz, METHANOL-d₄) δ ppm 7.75-7.77 (m, 1 H), 7.64 (dd, J=3.8, 1.9 Hz, 2 H), 7.56-7.61 (m, 1 H), 6.75 (d, J=8.8 Hz, 1 H), 6.36-6.41 (m, 1 H), 6.28-6.32 (m, 2 H), 3.74 (t, J=6.2 Hz, 2 H), 3.38 (t, J=6.0 Hz, 2 H), 1.40 (s, 6 H).

Example 581

6-(3-chloro-2-methylphenyl)-4-N-(2-methylcyclopropyl)pyrimidine-2,4-diamine

A mixture of 4-chloro-6-(3-chloro-2-methylphenyl)pyrimidin-2-amine (38 mg, 0.15 mmol; Intermediate 24), 2-methylcyclopropan-1-amine (21 mg, 0.30 mmol) and triethylamine (50 µL, 0.36 mmol) in n-butanol (2 mL) was heated in a sealed tube at 95° C. for 48 h. Concentrated and purified by preparative HPLC. LCMS [M+H]⁺ 289.

Example 582

3-(2-{[2-amino-6-(3-chloro-2-methylphenyl)pyrimidin-4-yl]amino}ethyl)benzene-1-sulfonamide Step 1: 3-(2-aminoethyl)benzenesulfonamide was prepared according to general procedure 19 from 3-bromobenzenesulfonamide.
Step 2: The title compound was prepared according to general procedure 9 from 3-(2-aminoethyl)benzenesulfonamide and intermediate 24. LCMS [M+H]⁺ 418.

Example 583

3-(2-{[2-amino-6-(2,3-dichlorophenyl)pyrimidin-4-yl]amino}ethyl)benzene-1-sulfonamide Step 1: 3-(2-aminoethyl)benzenesulfonamide was prepared according to general procedure 19 from 3-bromobenzenesulfonamide.
Step 2: The title compound was prepared according to general procedure 9 from 3-(2-aminoethyl)benzenesulfonamide and intermediate 21. LCMS [M+H]$^+$ 438.

Example 584

But-2-ynyl N-[4-[2-[[2-amino-6-(3-chloro-2-methyl-phenyl)pyrimidin-4-yl]amino]ethyl]phenyl]carbamate The title compound was prepared according to general procedure 18 from intermediate 48 and but-2-ynyl carbonochloridate. LCMS [M+H]$^+$ 450. $^1$H NMR (400 MHz, CHLOROFORM-d) δ ppm 7.45-7.49 (m, 1 H), 7.32 (d, J=7.9 Hz, 2 H), 7.11-7.23 (m, 4 H), 6.83 (br. s., 1 H), 6.33-6.40 (m, 1 H), 5.80 (s, 1 H), 4.74 (dt, J=4.4, 2.2 Hz, 2 H), 3.73 (d, J=6.0 Hz, 2 H), 2.88 (t, J=7.0 Hz, 2 H), 2.29-2.34 (m, 3 H), 1.84-1.89 (m, 3 H).

Example 585

[4-[2-[[2-amino-6-(3-chloro-2-methyl-phenyl)pyrimidin-4-yl]amino]ethyl]phenyl]cyanamide A mixture of 4-[2-[[2-amino-6-(3-chloro-2-methyl-phenyl)pyrimidin-4-yl]amino]ethyl]-N'-hydroxy-benzamidine (1.0 equiv.), 4-toluenesulfonyl chloride (1.1 equiv.), and diisopropylethylamine (1.1 equiv.) in DCM was stirred at 20° C. for 2 h. The mixture was then diluted with NaHCO$_3$ and extracted with DCM ×3. The combined organics were concentrated and purified by silica gel chromatography. LCMS [M+H]$^+$ 379. $^1$H NMR (400 MHz, METHANOL-d$_4$) δ ppm 7.39-7.44 (m, 1 H), 7.15-7.26 (m, 4 H), 6.91 (d, J=8.5 Hz, 2 H), 5.76 (br. s., 1 H), 3.50-3.65 (m, 2 H), 2.85 (s, 2 H), 2.31 (s, 3 H).

Example 586

6-(2-{[2-amino-6-(3-chloro-2-methylphenyl)pyrimidin-4-yl]amino}ethoxy)pyridine-3-carboxamide A mixture of 2-[[2-amino-6-(3-chloro-2-methyl-phenyl)pyrimidin-4-yl]amino]ethanol, 6-chloropyridine-3-carboxamide (1.5 equiv.) and Cs$_2$CO$_3$ (2.0 equiv.) in DMSO was heated in a sealed tube at 90° C. for 16 h. After cooling was methanol added to the solution followed by filtration and purification by preparative HPLC to give the title compound. LCMS [M+H]$^+$ 399.

Example 587

6-[(2-{[2-amino-6-(3-chloro-2-methylphenyl)pyrimidin-4-yl]amino}ethyl)amino]-2,2-dimethyl-3,4-dihydro-2H-1,4-benzoxazin-3-one Step 1: 6-(2-aminoethylamino)-2,2-dimethyl-4H-1,4-benzoxazin-3-one was prepared according to general procedure 13 from 6-bromo-2,2-dimethyl-4H-1,4-benzoxazin-3-one Step 2: The title compound was prepared according to general procedure 9 from 6-(2-aminoethylamino)-2,2-dimethyl-4H-1,4-benzoxazin-3-one and intermediate 24. LCMS [M+H]$^+$ 453. 1H NMR (400 MHz, METHANOL-d4) δ ppm 7.40 (dd, J=7.7, 1.7 Hz, 1 H), 7.14-7.23 (m, 2 H), 6.70 (d, J=8.5 Hz, 1 H), 6.28-6.34 (m, 1 H), 6.23 (d, J=2.5 Hz, 1 H), 5.80 (s, 1 H), 3.52-3.63 (m, 2 H), 3.27 (t, J=6.2 Hz, 2 H), 2.31 (s, 3 H), 1.40 (s, 6 H).

Example 588

4-[2-[[2-amino-6-(3-chloro-2-methyl-phenyl)pyrimidin-4-yl]amino]ethyl]benzamidine A mixture of 4-[2-[[2-amino-6-(3-chloro-2-methyl-phenyl)pyrimidin-4-yl]amino]ethyl]benzenecarbothioamide and iodomethane (2.0 equiv.) in acetone was stirred at reflux for 2 h. Thereafter the mixture was concentrated and suspended in acetonitrile. Then ammonium acetate was added and the mixture was stirred at 20° C. for 16 h. The reaction mixture was diluted with MeOH and purified by preparative LC. LCMS [M+H]$^+$ 381. $^1$H NMR (400 MHz, METHANOL-d$_4$) δ ppm 7.77-7.81 (m, 2 H), 7.59-7.64 (m, 1 H), 7.57 (d, J=8.5 Hz, 2 H), 7.31-7.39 (m, 2 H), 6.01 (s, 1 H), 3.79-3.86 (m, 2 H), 3.08-3.13 (m, 2 H), 2.38 (s, 3 H).

Example 589

4-N-(azetidin-3-yl)-6-(2,3-dimethylphenyl)pyrimidine-2,4-diamine

The title compound was isolated as a side product from the reaction mixture described in example 590. LCMS [M+H]$^+$ 270. 1H NMR (400 MHz, METHANOL-d4) δ ppm 7.16-7.20 (m, 1 H), 7.11 (t, J=7.4 Hz, 1 H), 7.04-7.08 (m, 1 H), 5.67 (s, 1 H), 4.28 (app. t, J=8.2 Hz, 2 H), 3.87-3.95 (m, 1 H), 3.75 (app. dd, J=9.2, 5.4 Hz, 2 H), 2.31 (s, 3 H), 2.18 (s, 3 H).

Example 590 tert-butyl 3-{[2-amino-6-(2,3-dimethylphenyl)pyrimidin-4-yl]amino}azetidine-1-carboxylate The title compound was prepared according to general procedure 9 from tert-butyl 3-aminoazetidine-1-carboxylate and intermediate 19. LCMS [M+H]$^+$ 370. 1H NMR (400 MHz, METHANOL-d4) δ ppm 7.16-7.20 (m, 1 H), 7.11 (t, J=7.6 Hz, 1 H), 7.04-7.08 (m, 1 H), 5.82 (s, 1 H), 4.65-4.74 (m, 1 H), 4.22-4.30 (m, 2 H), 3.77-3.84 (m, 2 H), 2.31 (s, 3 H), 2.19 (s, 3 H), 1.45 (s, 9 H).

Example 591

2-(2-{[2-amino-6-(3-chloro-2-methylphenyl)pyrimidin-4-yl]amino}ethoxy)pyrimidine-4-carboxamide A mixture of 2-[[2-amino-6-(3-chloro-2-methyl-phenyl)pyrimidin-4-yl]amino]ethanol, 2-chloropyrimidine-4-carboxamide (1.5 equiv.) and Cs$_2$CO$_3$ (2.0 equiv.) in DMSO was heated in a sealed tube at 90° C. for 16 h. After cooling was methanol added to the solution followed by filtration and purification by preparative HPLC to give the title compound. LCMS [M+H]$^+$ 400. $^1$H NMR (400 MHz, METHANOL-d$_4$) δ ppm 8.78 (d, J=5.1 Hz, 1 H), 7.68 (d, J=5.1 Hz, 1 H), 7.40 (dd, J=7.4, 1.7 Hz, 1 H), 7.16-7.24 (m, 2 H), 5.82 (br. s., 1 H), 4.67 (t, J=5.5 Hz, 2 H), 3.73-3.92 (m, 2 H), 2.31 (s, 3 H).

Example 592

2-(2-{[2-amino-6-(3-chloro-2-methylphenyl)pyrimidin-4-yl]amino}ethoxy)pyrimidine-4-carboxylic Acid A mixture of 2-[[2-amino-6-(3-chloro-2-methyl-phenyl)pyrimidin-4-yl]amino]ethanol, 2-chloropyrimidine-4-carboxamide (1.5 equiv.) and $Cs_2CO_3$ (2.0 equiv.) in DMSO was heated in a sealed tube at 90° C. for 16 h. After cooling was methanol added to the solution followed by filtration and purification by preparative HPLC to give the title compound. LCMS [M+H]$^+$ 401. $^1$H NMR (400 MHz, METHANOL-d$_4$) δ ppm 8.63 (br. s., 1 H), 7.50 (dd, J=6.6, 2.5 Hz, 2 H), 7.16-7.37 (m, 2 H), 6.00 (s, 1 H), 4.61-4.71 (m, 2 H), 3.89 (br. s., 2 H), 2.34 (s, 3 H).

Example 593

N-[4-(2-{[2-amino-6-(3-chloro-2-methylphenyl)pyrimidin-4-yl]amino}ethyl)phenyl]-2,2-dimethylpropanamide The title compound was prepared according to general procedure 18 from Intermediate 48 and 2,2-dimethylpropanoyl chloride. LCMS [M+H]$^+$ 438. 1H NMR (400 MHz, METHANOL-d4) δ ppm 7.42-7.47 (m, 2 H), 7.41 (dd, J=7.4, 1.4 Hz, 1H), 7.14-7.24 (m, 4 H), 5.76 (s, 1 H), 3.50-3.66 (m, 2 H), 2.83-2.91 (m, 2 H), 2.31 (s, 3 H), 1.29 (s, 9 H).

Example 594

N-[4-(2-{[2-amino-6-(3-chloro-2-methylphenyl)pyrimidin-4-yl]amino}ethyl)phenyl]-2,2,2-trifluoroethane-1-sulfonamide The title compound was prepared according to general procedure 18 from Intermediate 48 and 2,2,2-trifluoroethanesulfonyl chloride. LCMS [M+H]$^+$ 500. 1H NMR (400 MHz, METHANOL-d4) δ ppm 7.58-7.62 (m, 1 H), 7.31-7.38 (m, 2H), 7.26-7.31 (m, 2 H), 7.20-7.25 (m, 2 H), 6.00 (s, 1 H), 4.07 (q, J=9.5 Hz, 2H), 3.77 (t, J=7.1 Hz, 2 H), 2.94 (t, J=7.1 Hz, 2 H), 2.37 (s, 3 H).

Example 595

1-[4-(2-{[2-amino-6-(3-chloro-2-methylphenyl)pyrimidin-4-yl]amino}ethyl)phenyl]-3-(propan-2-yl)urea A mixture of Intermediate 48 and isopropyl isocyanate were stirred in DCM at 20° C. for 24 h. The desired compound precipitated and the solid was filtered off and washed with DCM. LCMS [M+H]$^+$ 439. 1H NMR (400 MHz, METHANOL-d4) δ ppm 7.38-7.43 (m, 1 H), 7.24-7.29 (m, 2 H), 7.11-7.24 (m, 4 H), 5.75 (s, 1 H), 3.87 (dt, J=13.0, 6.6 Hz, 1 H), 3.52-3.62 (m, 2 H), 2.83 (t, J=7.3 Hz, 2 H), 2.31 (s, 3 H), 1.17 (d, J=6.6 Hz, 6 H).

Example 596 tert-butyl N-[4-(2-{[2-amino-6-(3-chloro-2-methylphenyl)pyrimidin-4-yl]amino}ethyl)phenyl]carbamate The title compound was prepared according to general procedure 18 from Intermediate 48 and di-tert-butyl dicarbonate. LCMS [M+H]$^+$ 454. 1H NMR (400 MHz, METHANOL-d4) δ ppm 7.38-7.43 (m, 1 H), 7.31 (d, J=8.5 Hz, 2 H), 7.12-7.24 (m, 4 H), 5.75 (s, 1 H), 3.49-3.63 (m, 2 H), 2.83 (s, 2 H), 2.31 (s, 3 H), 1.49-1.53 (m, 9 H).

Example 597

N-[4-(2-{[2-amino-6-(3-chloro-2-methylphenyl)pyrimidin-4-yl]amino}ethyl)phenyl]cyclopropanecarboxamide The title compound was prepared according to general procedure 18 from Intermediate 48 and cyclopropanecarbonyl chloride. LCMS [M+H]$^+$ 422. 1H NMR (400 MHz, METHANOL-d4) δ ppm 7.44-7.49 (m, 2 H), 7.41 (dd, J=7.6, 1.3 Hz, 1H), 7.14-7.24 (m, 4 H), 5.75 (s, 1 H), 3.58 (br. s., 2 H), 2.86 (t, J=7.3 Hz, 2 H), 2.31 (s, 3 H), 1.75 (tt, J=7.9, 4.7 Hz, 1 H), 0.91-0.96 (m, 2 H), 0.81-0.87 (m, 2H).

Example 598

6-(2,3-dimethylphenyl)-4-N-[2-(thiophen-2-yl)ethyl]pyrimidine-2,4-diamine

The title compound was prepared according to general procedure 9 from intermediate 19 and 2-(2-thienyl)ethanamine. LCMS [M+H]$^+$ 325. 1H NMR (400 MHz, METHANOL-d4) δ ppm 7.36 (d, J=7.6 Hz, 1 H), 7.22-7.27 (m, 2 H), 7.16-7.21 (m, 1 H), 6.93-6.97 (m, 1 H), 6.90-6.93 (m, 1 H), 5.99 (s, 1 H), 3.79 (t, J=7.1 Hz, 2 H), 3.16-3.21 (m, 2 H), 2.36 (s, 3 H), 2.25 (s, 3 H).

Example 599

6-(3-chloro-2-methylphenyl)-4-N-[2-(3,4-dichlorophenyl)ethyl]pyrimidine-2,4-diamine The title compound was prepared according to general procedure 9 from intermediate 24 and 2-(3,4-dichlorophenyl)ethanamine. LCMS [M+H]$^+$ 407. 1H NMR (400 MHz, METHANOL-d4) δ ppm 7.58-7.62 (m, 1 H), 7.44-7.47 (m, 2 H), 7.31-7.38 (m, 2 H), 7.21-7.24 (m, 1 H), 5.99 (s, 1 H), 3.75-3.81 (m, 2 H), 2.92-2.98 (m, 2 H), 2.37 (s, 3 H).

Example 600

6-(3-chloro-2-methylphenyl)-4-N-[2-(2,4-dichlorophenyl)ethyl]pyrimidine-2,4-diamine The title compound was prepared according to general procedure 9 from intermediate 24 and 2-(2,4-dichlorophenyl)ethanamine. LCMS [M+H]$^+$ 407. 1H NMR (400 MHz, METHANOL-d4) δ ppm 7.58-7.63 (m, 1 H), 7.47 (d, J=1.9

Hz, 1 H), 7.27-7.38 (m, 4 H), 5.98 (s, 1 H), 3.80 (t, J=7.0 Hz, 2 H), 3.10 (t, J=7.1 Hz, 2 H), 2.37 (s, 3 H).

Example 601

N-[4-(2-{[2-amino-6-(3-chloro-2-methylphenyl)pyrimidin-4-yl]amino}ethyl)phenyl]ethane-1-sulfonamide The title compound was prepared according to general procedure 18 from Intermediate 48 and ethanesulfonyl chloride. 1H NMR (400 MHz, METHANOL-d4) δ ppm 7.57-7.61 (m, 1 H), 7.31-7.37 (m, 2 H), 7.22-7.26 (m, 2 H), 7.18-7.22 (m, 2 H), 6.00 (s, 1 H), 3.76 (t, J=7.1 Hz, 2 H), 3.05 (q, J=7.4 Hz, 2 H), 2.92 (t, J=7.1 Hz, 2 H), 2.37 (s, 3 H), 1.26-1.32 (m, 3 H).
LCMS [M+H]$^+$ 446.

Example 602

4-(2-{[2-amino-6-(2,4,5-trimethylphenyl)pyrimidin-4-yl]amino}ethyl)benzene-1-sulfonamide The title compound was prepared according to general procedure 2 from (2,4,5-trimethylphenyl)boronic acid and intermediate 25. LCMS [M+H]$^+$ 412.

Example 603

4-(2-{[2-amino-6-(4-methoxy-2,5-dimethylphenyl)pyrimidin-4-yl]amino}ethyl)benzene-1-sulfonamide The title compound was prepared according to general procedure 2 from (4-methoxy-2,5-dimethyl-phenyl)boronic acid and intermediate 25. LCMS [M+H]$^+$ 428.

Example 604

4-(2-{[2-amino-6-(4,5-dichloro-2-methylphenyl)pyrimidin-4-yl]amino}ethyl)benzene-1-sulfonamide The title compound was prepared according to general procedure 2 from (4,5-dichloro-2-methyl-phenyl)boronic acid and intermediate 25. LCMS [M+H]$^+$ 452.

Example 605

4-(2-{[2-amino-6-(5-chloro-4-methoxy-2-methylphenyl)pyrimidin-4-yl]amino}ethyl)benzene-1-sulfonamide The title compound was prepared according to general procedure 2 from (5-chloro-4-methoxy-2-methyl-phenyl)boronic acid and intermediate 25. LCMS [M+H]$^+$ 448.

Example 606

4-(2-{[2-amino-6-(1H-indol-4-yl)pyrimidin-4-yl]amino}ethyl)benzene-1-sulfonamide The title compound was prepared according to general procedure 2 from 1H-indol-4-ylboronic acid and intermediate 25. LCMS [M+H]$^+$ 409.

Example 607

4-(2-{[2-amino-6-(2,5-dimethylphenyl)pyrimidin-4-yl]amino}ethyl)benzene-1-sulfonamide The title compound was prepared according to general procedure 2 from (2,5-dimethylphenyl)boronic acid and intermediate 25. LCMS [M+H]$^+$ 398.

Example 608

4-(2-{[2-amino-6-(5-fluoro-2-methylphenyl)pyrimidin-4-yl]amino}ethyl)benzene-1-sulfonamide The title compound was prepared according to general procedure 2 from (5-fluoro-2-methyl-phenyl)boronic acid and intermediate 25. LCMS [M+H]$^+$ 402.

Example 609

4-(2-{[2-amino-6-(3,4,5-trichloro-2-methylphenyl)pyrimidin-4-yl]amino}ethyl)benzene-1-sulfonamide The title compound was prepared according to general procedure 2 from (3,4,5-trichloro-2-methyl-phenyl)boronic acid and intermediate 25. LCMS [M+H]$^+$ 486.

Example 610

4-(2-{[2-amino-6-(5-chloro-2-fluoro-3-methylphenyl)pyrimidin-4-yl]amino}ethyl)benzene-1-sulfonamide The title compound was prepared according to general procedure 2 from (5-chloro-2-fluoro-3-methyl-phenyl)boronic acid and intermediate 25. LCMS [M+H]$^+$ 436.

Example 611

4-(2-{[2-amino-6-(3,5-dichloro-2-methylphenyl)pyrimidin-4-yl]amino}ethyl)benzene-1-sulfonamide The title compound was prepared according to general procedure 2 from (3,5-dichloro-2-methyl-phenyl)boronic acid and intermediate 25. LCMS [M+H]$^+$ 452.

Example 612

4-(2-{[2-amino-6-(3,4,5-trichloro-2-methylphenyl)pyrimidin-4-yl]amino}ethyl)benzamide The title compound was prepared according to general procedure 2 from (3,4,5-trichloro-2-methyl-phenyl)boronic acid and Intermediate 45. LCMS [M+H]$^+$ 450.

Example 613

4-(2-{[2-amino-6-(3,5-dichloro-2-methylphenyl)pyrimidin-4-yl]amino}ethyl)benzamide The title compound was prepared according to general procedure 2 from (3,5-dichloro-2-methyl-phenyl)boronic acid and Intermediate 45. LCMS [M+H]$^+$ 416.

Example 614

4-(2-{[2-amino-6-(4-fluoro-2,3-dimethylphenyl)pyrimidin-4-yl]amino}ethyl)benzamide The title compound was prepared according to general procedure 2 from (4-fluoro-2,3-dimethyl-phenyl)boronic acid and Intermediate 45. LCMS [M+H]$^+$ 380.

Example 615

4-(2-{[2-amino-6-(3,4-dichloro-2-methylphenyl)pyrimidin-4-yl]amino}ethyl)benzamide The title compound was prepared according to general procedure 2 from (3,4-dichloro-2-methyl-phenyl)boronic acid and Intermediate 45. LCMS [M+H]$^+$ 416.

Example 616

4-(2-{[2-amino-6-(5-chloro-2-fluoro-3-methylphenyl)pyrimidin-4-yl]amino}ethyl)benzamide The title compound was prepared according to general procedure 2 from (5-chloro-2-fluoro-3-methyl-phenyl)boronic acid and Intermediate 45. LCMS [M+H]$^+$ 400.

Example 617

4-(2-{[2-amino-6-(3-chloro-2-fluorophenyl)pyrimidin-4-yl]amino}ethyl)benzamide

The title compound was prepared according to general procedure 2 from (3-chloro-2-fluoro-phenyl)boronic acid and Intermediate 45. LCMS [M+H]$^+$ 386.

Example 618

N-[3-(2-{[2-amino-6-(3-chloro-2-methylphenyl)pyrimidin-4-yl]amino}ethyl)phenyl]-2,2-dimethylpropanamide The title compound was prepared according to general procedure 18 from Intermediate 47 and 2,2-dimethylpropanoyl chloride. LCMS [M+H]$^+$ 438.

Example 619

1-[3-(2-{[2-amino-6-(3-chloro-2-methylphenyl)pyrimidin-4-yl]amino}ethyl)phenyl]-3-(propan-2-yl)urea A mixture of Intermediate 47 and isopropyl isocyanate were stirred in DCM at 20° C. for 24 h. The desired compound precipitated and the solid was filtered off and washed with DCM. LCMS [M+H]$^+$ 439.

Example 620 tert-butyl N-[3-(2-{[2-amino-6-(3-chloro-2-methylphenyl)pyrimidin-4-yl]amino}ethyl)phenyl]carbamate The title compound was prepared according to general procedure 18 from Intermediate 47 and di-tert-butyl dicarbonate. LCMS [M+H]$^+$ 454.

Example 621

N-[3-(2-{[2-amino-6-(3-chloro-2-methylphenyl)pyrimidin-4-yl]amino}ethyl)phenyl]cyclopropanecarboxamide The title compound was prepared according to general procedure 18 from Intermediate 47 and cyclopropanecarbonyl chloride. LCMS [M+H]$^+$ 422.

Example 622

N-[3-(2-{[2-amino-6-(3-chloro-2-methylphenyl)pyrimidin-4-yl]amino}ethyl)phenyl]-2-methylpropane-1-sulfonamide The title compound was prepared according to general procedure 18 from Intermediate 47 and isobutylsulfonyl chloride. LCMS [M+H]$^+$ 474.

Example 623

N-[4-(2-{[2-amino-6-(3-chloro-2-methylphenyl)pyrimidin-4-yl]amino}ethyl)phenyl]propane-2-sulfonamide The title compound was prepared according to general procedure 18 from Intermediate 48 and isopropylsulfonyl chloride. LCMS [M+H]$^+$ 460.

Example 624

N-[4-(2-{[2-amino-6-(3-chloro-2-methylphenyl)pyrimidin-4-yl]amino}ethyl)phenyl]-2-methylpropane-1-sulfonamide The title compound was prepared according to general procedure 18 from Intermediate 48 and isobutylsulfonyl chloride. LCMS [M+H]$^+$ 474.

Example 625

4-(2-{[2-amino-6-(3-chloro-2-methylphenyl)pyrimidin-4-yl]amino}ethyl)benzonitrile 4-chloro-6-(3-chloro-2-methylphenyl)pyrimidin-2-amine (150 mg, 0.59 mmol), 4-(2-aminoethyl)benzonitrile hydrochloride (110 mg, 0.59 mmol), K$_2$CO$_3$ (240 mg, 1.8 mmol) and MeCN (5 mL) were heated (microwave reactor) for 1 hour at 170° C. ~400 mL was taken out, added some MeOH and purified by basic prep-HPLC to afford 4-(2-{[2-amino-6-(3-chloro-2-methylphenyl)pyrimidin-4-yl]amino}ethyl)benzonitrile. LCMS [M+H]$^+$ 364

Example 626

4-N-methyl-6-(2-phenylethynyl)pyrimidine-2,4-diamine

N$_2$ was flushed trough a mixture of 6-iodo-4-N-methylpyrimidine-2,4-diamine (intermediate 17) (50 mg, 0.20 mmol), ethynylbenzene (100 mg, 1.0 mmol), K$_2$CO$_3$ (110 mg, 0.80 mmol), DME (0.75 mL) and water (0.75 mL). Pd(dppf)Cl$_2$.CH$_2$Cl$_2$ (33 mg, 0,040 mmol) and CuI (7.6 mg, 0.040 mmol) were added and the mixture was heated in a sealed tube at 90° C. for 90 min. The organic phase was removed in vacuo. The crude material was dissolved in MeOH and purified by prep-HPLC, to afford 4-N-methyl-6-(2-phenylethynyl)pyrimidine-2,4-diamine. LCMS [M+H]+ 225.

Example 627

3-[2-[[2-amino-6-(3-chloro-2-methyl-phenyl)pyrimidin-4-yl]amino]ethyl]benzamide

Step 1. 3-(2-aminoethyl)benzamide was prepared according to general procedure 19 from 3-bromobenzamide.
Step 2. The title compound was prepared according to general procedure 9 from 3-(2-aminoethyl)benzamide and intermediate 24. LCMS [M+H]+ 382.

Example 628

4-[2-[[2-amino-6-(3-chloro-2-methyl-phenyl)pyrimidin-4-yl]amino]ethyl]-N-methyl-benzamide Step 1. A mixture of 4-[2-[(2-amino-6-chloro-pyrimidin-4-yl)amino]ethyl]benzoic acid (from step 1 of the synthesis of intermediate 45, 1.0 equiv.), TBTU (1.2 equiv.), and DMF was stirred at 20° C. for 5 min. Then methyl amine (3.0 equiv.) was added and the resulting mixture was stirred at 20° C. for 16 h. The mixture was then diluted with NaHCO$_3$ and extracted with DCM ×3. The combined organics were dried and purified by silica gel chromatography.
Step 2. The title compound was prepared according to general procedure 2 from the material from step 1 and (3-chloro-2-methyl-phenyl)boronic acid. LCMS [M+H]+ 396.

Example 629

[4-[2-[[2-amino-6-(3-chloro-2-methyl-phenyl)pyrimidin-4-yl]amino]ethyl]phenyl]-pyrrolidin-1-yl-methanone Step 1. A mixture of 4-[2-[(2-amino-6-chloro-pyrimidin-4-yl)amino]ethyl]benzoic acid (from step 1 of the synthesis of intermediate 45, 1.0 equiv.), TBTU (1.2 equiv.), and DMF was stirred at 20° C. for 5 min. Then pyrrolidine (3.0 equiv.) was added and the resulting mixture was stirred at 20° C. for 16 h. The mixture was then diluted with NaHCO$_3$ and extracted with DCM ×3. The combined organics were dried and purified by silica gel chromatography.
Step 2. The title compound was prepared according to general procedure 2 from the material from step 1 and (3-chloro-2-methyl-phenyl)boronic acid. LCMS [M+H]+ 436.

Example 630

7-[2-[[2-amino-6-(3-chloro-2-methyl-phenyl)pyrimidin-4-yl]amino]ethylamino]-4H-1,4-benzoxazin-3-one Step 1. 7-(2-aminoethylamino)-4H-1,4-benzoxazin-3-one was prepared according to general procedure 13 from 7-bromo-4H-1,4-benzoxazin-3-one.
Step 2. The title compound was prepared according to general procedure 9 from the material from step 1 and intermediate 24. LCMS [M+H]+ 425. $^1$H NMR (400 MHz, METHANOL-d$_4$) δ ppm 7.59-7.62 (m, 1 H), 7.30-7.39 (m, 2 H), 6.77 (d, J=8.5 Hz, 1 H), 6.56 (d, J=2.5 Hz, 1 H), 6.49 (dd, J=8.5, 2.5 Hz, 1 H), 6.04 (s, 1 H), 4.52 (s, 2 H), 3.74 (t, J=6.2 Hz, 2 H), 3.45 (t, J=6.0 Hz, 2 H), 2.38 (s, 3 H).

Example 631

6-[2-[[2-amino-6-(3-chloro-2-methyl-phenyl)pyrimidin-4-yl]amino]ethylamino]-4-methyl-1,4-benzoxazin-3-one Step 1. 6-(2-aminoethylamino)-4-methyl-1,4-benzoxazin-3-one was prepared according to general procedure 13 from 6-bromo-4-methyl-1,4-benzoxazin-3-one.
Step 2. The title compound was prepared according to general procedure 9 from 6-(2-aminoethylamino)-4-methyl-1,4-benzoxazin-3-one and intermediate 24. [M+H]+ 439. $^1$H NMR (400 MHz, METHANOL-d$_4$) δ ppm 7.61 (dd, J=7.6, 1.3 Hz, 1 H), 7.30-7.39 (m, 2 H), 6.88 (d, J=8.5 Hz, 1 H), 6.63 (d, J=2.8 Hz, 1 H), 6.54 (dd, J=8.5, 2.5 Hz, 1 H), 6.04 (s, 1 H), 4.52 (d, J=0.6 Hz, 2 H), 3.75-3.80 (m, 2 H), 3.49 (t, J=6.0 Hz, 2 H), 3.33 (s, 3 H), 2.37 (s, 3 H).

Example 632

7-[2-[[2-amino-6-(3-chloro-2-methyl-phenyl)pyrimidin-4-yl]amino]ethylamino]-3H-quinazolin-4-one Step 1. 6-(2-aminoethylamino)-3H-quinazolin-4-one was prepared according to general procedure 13 from 7-bromo-3H-quinazolin-4-one.
Step 2. The title compound was prepared according to general procedure 9 from 6-(2-aminoethylamino)-3H-quinazolin-4-one and intermediate 24. [M+H]+ 422. $^1$H NMR (400 MHz, METHANOL-d$_4$) δ ppm 8.08-8.10 (m, 1 H), 7.69-7.72 (m, 1 H), 7.59-7.63 (m, 1 H), 7.48-7.52 (m, 1 H), 7.32-7.40 (m, 1H), 7.20-7.25 (m, 1 H), 6.04 (s, 1 H), 3.68 (dd, J=8.8, 5.7 Hz, 2 H), 3.49-3.54 (m, 2 H), 2.39 (s, 3 H).

Example 633

6-[2-[[2-amino-6-(2,3-dichlorophenyl)pyrimidin-4-yl]amino]ethylamino]-4-methyl-1,4-benzoxazin-3-one Step 1. 6-(2-aminoethylamino)-4-methyl-1,4-benzoxazin-3-one was prepared according to general procedure 13 from 6-bromo-4-methyl-1,4-benzoxazin-3-one.
Step 2. The title compound was prepared according to general procedure 9 from 6-(2-aminoethylamino)-4-methyl-1,4-benzoxazin-3-one and intermediate 21. [M+H]+ 459. $^1$H NMR (400 MHz, METHANOL-d$_4$) δ ppm 7.79 (dd, J=7.0, 2.8 Hz, 1 H), 7.47-7.53 (m, 2 H), 6.93 (d, J=8.8 Hz, 1 H), 6.77 (d, J=2.5 Hz, 1 H), 6.67 (dd, J=8.5, 2.5 Hz, 1 H), 6.15 (s, 1 H), 4.55 (s, 2 H), 3.77-3.83 (m, 2 H), 3.53-3.58 (m, 2 H), 3.34 (s, 3 H).

Example 634

6-(3-chloro-2-methylphenyl)-4-N-[2-(3-nitrophenyl)ethyl]pyrimidine-2,4-diamine

Step 1: A mixture of 2-amino-4,6-dichloropyrimidine (1.0 equiv.), 2-(3-nitrophenyl)ethylammonium chloride (1.3 equiv.), and diisopropylethylamine (2.5 equiv.) in 2-propanol was stirred at 100° C. in a sealed vial for 16 h. The reaction mixture was then diluted with NaHCO$_3$ (aq) and extracted with DCM. The crude material was then purified by silica gel chromatography.

Step 2: A mixture of the product from step 1 (1.0 equiv.), (3-chloro-2-methyl-phenyl)boronic acid (1.2 equiv.), $K_2CO_3$ (3.0 equiv.) and $Pd(PPh_3)_4$ (0.05 equiv.) in 1,4-dioxane and water was stirred at 90° C. for 16 h. Thereafter water was added and the mixture was extracted with DCM ×3. The combined organic phases were concentrated and purified by silica gel chromatography. LCMS [M+H]+ 384.

Example 635

4-[2-[[2-amino-6-(2-chloro-3-methyl-phenyl)pyrimidin-4-yl]amino]ethyl]benzenesulfonamide The title compound was prepared according to general procedure 9 from 4-(2-aminoethyl)benzenesulfonamide and intermediate 37. LCMS [M+H]$^+$ 418. $^1$H NMR (400 MHz, METHANOL-$d_4$) δ ppm 7.83-7.87 (m, 2 H), 7.51-7.55 (m, 1 H), 7.44-7.49 (m, 2 H), 7.36-7.41 (m, 1 H), 7.33-7.36 (m, 1 H), 6.06 (s, 1 H), 3.81 (t, J=7.3 Hz, 2 H), 3.05 (t, J=7.1 Hz, 2 H), 2.47 (s, 3 H).

Example 636

4-[2-[[2-amino-6-(2,3,5-trichlorophenyl)pyrimidin-4-yl]amino]ethyl]benzenesulfonamide Step 1. A mixture of 4,6-dichloropyrimidin-2-amine (0.10 g, 0.64 mmol), (2,3,5-trichlorophenyl)boronic acid (0.12 g, 0.53 mmol), potassium carbonate (0.22 g, 1.60 mmol) and palladium tetrakis(triphenylphosphine)palladium (0) (0.031 g, 0.027 mmol) in 1,4-dioxane/water (5 mL; 4:1) was heated in a sealed tube at 60° C. for 4 h. The mixture was then diluted with $NaHCO_3$ and extracted with DCM ×3. The combined organics were concentrated and purified by silica gel chromatography. LCMS [M+H]$^+$ 308.

Step 2. The title compound was prepared according to general procedure 9 from 4-(2-aminoethyl)benzenesulfonamide and the material from step 1. LCMS [M+H]$^+$ 472. $^1$H NMR (400 MHz, METHANOL-$d_4$) δ ppm 7.89-7.90 (m, 1 H), 7.85 (d, J=8.5 Hz, 2 H), 7.61-7.62 (m, 1 H), 7.46 (d, J=8.5 Hz, 2 H), 6.11 (s, 1 H), 3.82 (s, 2 H), 3.05 (s, 2 H).

Example 637

4-[2-[[2-amino-6-(2,3,4-trichlorophenyl)pyrimidin-4-yl]amino]ethyl]benzenesulfonamide The title compound was prepared according to general procedure 9 from 4-(2-aminoethyl)benzenesulfonamide and intermediate 26. LCMS [M+H]$^+$ 472. $^1$H NMR (400 MHz, METHANOL-$d_4$) δ ppm 7.82-7.87 (m, 2 H), 7.71 (d, J=8.5 Hz, 1 H), 7.44-7.50 (m, 3 H), 6.10 (s, 1 H), 3.81 (t, J=7.1 Hz, 2 H), 3.05 (t, J=7.1 Hz, 2 H).

Example 638

4-[2-[[2-amino-6-(2,4-dichloro-3-methoxy-phenyl)pyrimidin-4-yl]amino]ethyl]benzenesulfonamide Step 1. A mixture of 4,6-dichloropyrimidin-2-amine (0.10 g, 0.64 mmol), (2,4-dichloro-3-methoxy-phenyl)boronic acid (0.12 g, 0.53 mmol), potassium carbonate (0.22 g, 1.60 mmol) and palladium tetrakis(triphenylphosphine)palladium (0) (0.031 g, 0.027 mmol) in 1,4-dioxane/water (5 mL; 4:1) was heated in a sealed tube at 60° C. for 4 h. The mixture was then diluted with $NaHCO_3$ and extracted with DCM ×3. The combined organics were concentrated and purified by silica gel chromatography. LCMS [M+H]$^+$ 304.

Step 2. The title compound was prepared according to general procedure 9 from 4-(2-aminoethyl)benzenesulfonamide and the material from step 1.

LCMS [M+H]$^+$ 468. $^1$H NMR (400 MHz, METHANOL-$d_4$) δ ppm 7.83-7.87 (m, 2 H), 7.57 (d, J=8.5 Hz, 1 H), 7.46 (d, J=8.5 Hz, 2 H), 7.29 (d, J=8.5 Hz, 1 H), 6.09 (s, 1 H), 3.92-3.94 (m, 3 H), 3.81 (t, J=7.3 Hz, 2 H), 3.05 (t, J=7.1 Hz, 2 H).

Example 639

6-(3-chloro-2-methyl-phenyl)-N4-[2-(2-methyl-5-nitro-imidazol-1-yl)ethyl]pyrimidine-2,4-diamine The title compound was prepared according to general procedure 9 from 2-(2-methyl-5-nitro-imidazol-3-ium-1-yl)ethylammonium dichloride and intermediate 24. [M+H]$^+$ 388. $^1$H NMR (400 MHz, METHANOL-$d_4$) δ ppm 7.98 (br. s., 1 H), 7.61 (dd, J=7.9, 1.6 Hz, 1 H), 7.33-7.39 (m, 1 H), 7.29-7.33 (m, 1 H), 5.98 (s, 1H), 4.65-4.70 (m, 2 H), 3.97 (t, J=5.8 Hz, 2 H), 2.53 (s, 3 H), 2.36 (s, 3 H).

Example 640

6-(3-chloro-2-methyl-phenyl)-N4-[2-[(2-methyl-1,3-benzothiazol-6-yl)amino]ethyl]pyrimidine-2,4-diamine Step 1. N'-(2-methyl-1,3-benzothiazol-6-yl)ethane-1,2-diamine was prepared according to general procedure 13 from 6-iodo-2-methyl-1,3-benzothiazole.

Step 2. The title compound was prepared according to general procedure 9 from intermediate 24 and N'-(2-methyl-1,3-benzothiazol-6-yl)ethane-1,2-diamine. [M+H]$^+$ 425. $^1$H NMR (400 MHz, CHLOROFORM-d) δ ppm 7.86 (d, J=8.8 Hz, 1 H), 7.74 (br. s., 1 H), 7.41-7.49 (m, 2 H), 7.18 (dd, J=8.8, 2.2 Hz, 1 H), 7.04-7.13 (m, 2 H), 5.91 (s, 1 H), 3.86-3.93 (m, 2 H), 3.52-3.58 (m, 2 H), 2.89 (s, 3 H), 2.25 (s, 3 H).

Example 641

4-[2-[[2-amino-6-(benzothiophen-3-yl)pyrimidin-4-yl]amino]ethyl]benzenesulfonamide The title compound was prepared according to general procedure 2 from intermediate 25 and benzothiophen-3-ylboronic acid. [M+H]$^+$ 426. $^1$H NMR (400 MHz, METHANOL-$d_4$) δ ppm 8.16 (s, 1 H), 8.02-8.06 (m, 1 H), 7.96-8.00 (m, 1 H), 7.83-7.88 (m, 2 H), 7.45-7.57 (m, 4 H), 6.34 (s, 1 H), 3.84 (t, J=7.1 Hz, 2 H), 3.07 (t, J=7.1 Hz, 2 H).

Example 642

N4-[2-(4-aminophenyl)ethyl]-6-(3-chloro-2-methyl-phenyl)pyrimidine-2,4-diamine

Step 1. A mixture of 4-(2-aminoethyl)aniline (1 equiv.), 4-chloro-6-(2,3-dimethylphenyl)pyrimidin-2-amine (1 equiv.), and Hünigs base (1.1 equiv.) in 2-propanol was stirred at 110° C. for 4 h. The mixture was then cooled, poured into saturated $NaHCO_3$ and extracted with DCM ×3. The combined organics were dried with $MgSO_4$ and concentrated. The crude material was suspended in hot MeOH and filtered. Evaporation of the solvent afforded N4-[2-(4-aminophenyl)ethyl]-6-chloro-pyrimidine-2,4-diamine. [M+H]⁺ 264.

Step 2. The title compound was produced according to general procedure 9 from the material in step 1 and (3-chloro-2-methyl-phenyl)boronic acid. [M+H]⁺ 354.

Example 643

4-[3-[[2-amino-6-(3-chloro-2-methyl-phenyl)pyrimidin-4-yl]amino]propylamino]benzamide Step 1. 4-(3-aminopropylamino)benzamide was prepared according to general procedure 13 from 4-iodobenzamide and propane-1,3-diamine.

Step 2. The title compound was produced according to general procedure 9 from 4-(3-aminopropylamino)benzamide and intermediate 24. [M+H]⁺ 411. ¹H NMR (400 MHz, METHANOL-d₄) δ ppm 7.63-7.69 (m, 2 H), 7.40 (dd, J=7.7, 1.4 Hz, 1 H), 7.13-7.24 (m, 2 H), 6.62 (d, J=8.8 Hz, 2 H), 5.82 (s, 1 H), 3.48 (br. s., 2 H), 3.24 (t, J=6.6 Hz, 2 H), 2.31 (s, 3 H), 1.92 (t, J=6.8 Hz, 2 H).

Example 644

4-[3-[[2-amino-6-(3-chloro-2-methyl-phenyl)pyrimidin-4-yl]amino]propylamino]-N-methyl-benzenesulfonamide Step 1. 4-(3-aminopropylamino)-N-methyl-benzenesulfonamide was prepared according to general procedure 13 from 4-iodo-N-methyl-benzenesulfonamide and propane-1,3-diamine.

Step 2. The title compound was produced according to general procedure 9 from 4-(3-aminopropylamino)-N-methyl-benzenesulfonamide and intermediate 24. [M+H]⁺ 461. ¹H NMR (400 MHz, METHANOL-d₄) δ ppm 7.51-7.56 (m, 2 H), 7.38-7.43 (m, 1 H), 7.15-7.24 (m, 2 H), 6.68 (d, J=8.8 Hz, 2 H), 5.82 (s, 1 H), 3.48 (br. s., 2 H), 3.25 (t, J=6.8 Hz, 2 H), 2.46 (s, 3 H), 2.32 (s, 3 H), 1.92 (quin, J=6.9 Hz, 2 H).

Example 645

6-(3-chloro-2-methyl-phenyl)-N4-[3-[(2-methyl-1,3-benzothiazol-6-yl)amino]propyl]pyrimidine-2,4-diamine Step 1. N'-(2-methyl-1,3-benzothiazol-6-yl)propane-1,3-diamine was prepared according to general procedure 13 from 6-iodo-2-methyl-1,3-benzothiazole and propane-1,3-diamine.

Step 2. The title compound was produced according to general procedure 9 from N'-(2-methyl-1,3-benzothiazol-6-yl)propane-1,3-diamine and intermediate 24. [M+H]⁺ 439. ¹H NMR (400 MHz, METHANOL-d₄) δ ppm 7.83 (d, J=8.8 Hz, 1 H), 7.58-7.63 (m, 2 H), 7.30-7.39 (m, 2 H), 7.26 (dd, J=8.8, 2.5 Hz, 1 H), 6.04 (s, 1 H), 3.67 (t, J=6.8 Hz, 2 H), 3.40-3.46 (m, 2 H), 2.84 (s, 3 H), 2.37 (s, 3 H), 2.07 (quin, J=7.1 Hz, 2 H).

Example 646

2-[2-[[2-amino-6-(3-chloro-2-methyl-phenyl)pyrimidin-4-yl]amino]ethylamino]pyrimidine-4-carboxamide The title compound was produced according to general procedure 12 from intermediate 58 and 2-chloropyrimidine-4-carboxamide. LCMS [M+H]⁺ 399. ¹H NMR (400 MHz, METHANOL-d₄) δ ppm 8.49 (d, J=5.4 Hz, 1 H), 7.60 (dd, J=8.1, 1.4 Hz, 1 H), 7.28-7.39 (m, 2 H), 7.18-7.22 (m, 1 H), 5.97 (s, 1 H), 3.77 (s, 4 H), 2.35 (s, 3 H).

Example 647

The title compound was produced according to general procedure 12 from intermediate 58 and 6-chloropyridine-3-carboxamide. LCMS [M+H]⁺ 398. ¹H NMR (400 MHz, METHANOL-d₄) δ ppm 8.48 (d, J=1.9 Hz, 1 H), 8.23 (d, J=9.2 Hz, 1 H), 7.61 (dd, J=7.6, 1.6 Hz, 1 H), 7.30-7.40 (m, 2 H), 7.01 (d, J=9.5 Hz, 1 H), 6.06 (s, 1 H), 3.80-3.87 (m, 2 H), 3.70-3.78 (m, 2 H), 2.37 (s, 3 H).

Example 648

1-[3-[2-[[2-amino-6-(3-chloro-2-methyl-phenyl)pyrimidin-4-yl]amino]ethyl]phenyl]-3-ethyl-urea The title compound was produced according to general procedure 21 from intermediate 47 and ethyl isocyanate. LCMS [M+H]⁺ 425. ¹H NMR (400 MHz, METHANOL-d₄) δ ppm 7.40 (dd, J=7.4, 1.7 Hz, 1 H), 7.32 (s, 1 H), 7.14-7.24 (m, 4 H), 6.88 (d, J=6.6 Hz, 1 H), 5.78 (s, 1 H), 3.59 (br. s., 2 H), 3.22 (q, J=7.3 Hz, 2 H), 2.85 (t, J=7.3 Hz, 2 H), 2.32 (s, 3 H), 1.12-1.17 (m, 3 H).

Example 649

1-[3-[2-[[2-amino-6-(3-chloro-2-methyl-phenyl)pyrimidin-4-yl]amino]ethyl]phenyl]-3-tert-butyl-urea The title compound was produced according to general procedure 21 from intermediate 47 and tert-butyl isocyanate. LCMS [M+H]⁺ 453. ¹H NMR (400 MHz, METHANOL-d₄) δ ppm 7.56-7.62 (m, 1 H), 7.45 (t, J=1.7 Hz, 1 H), 7.32-7.36 (m, 2 H), 7.14-7.19 (m, 1 H), 6.99 (ddd, J=8.1, 2.2, 1.1 Hz, 1 H), 6.87 (dq, J=7.6, 0.8 Hz, 1 H), 6.01 (s, 1 H), 3.77 (s, 2 H), 2.90 (s, 2 H), 2.37 (s, 3 H), 1.34-1.37 (m, 9 H).

Example 650

N-[3-[2-[[2-amino-6-(3-chloro-2-methyl-phenyl)pyrimidin-4-yl]amino]ethyl]phenyl]morpholine-4-carboxamide A mixture of N4-[2-(3-aminophenyl)ethyl]-6-(3-chloro-2-methyl-phenyl)pyrimidine-2,4-diamine (intermediate 47) (1 equiv.), morpholine-4-carbonyl chloride (1.4 equiv.), and diisopropylethylamine (1.6 equiv.) in DCM was stirred at reflux for 16 h. The reaction mixture was concentrated and purified by preparative LC. LCMS [M+H]⁺ 467. ¹H NMR (400 MHz, METHANOL-d₄) δ ppm 7.58-7.62 (m, 1 H), 7.41 (t, J=1.7 Hz, 1 H), 7.33-7.36 (m, 2 H), 7.19-7.24 (m, 1 H), 7.11-7.14 (m, 1 H), 6.94-6.98 (m, 1 H), 6.00 (s, 1 H), 3.78 (t, J=7.1 Hz, 2 H), 3.68-3.73 (m, 4 H), 3.48-3.53 (m, 4 H), 2.92 (t, J=7.1 Hz, 2 H), 2.37 (s, 3 H).

Example 651

3-[3-[2-[[2-amino-6-(3-chloro-2-methyl-phenyl)pyrimidin-4-yl]amino]ethyl]phenyl]-1,1-dimethyl-urea A mixture of N4-[2-(3-aminophenyl)ethyl]-6-(3-chloro-2-methyl-phenyl)pyrimidine-2,4-diamine (intermediate 47)

(1 equiv.), N,N-dimethylcarbamoyl chloride (1.3 equiv.), and diisopropylethylamine (1.6 equiv.) was stirred at 150° C. for 10 min. The reaction mixture was concentrated and purified by preparative LC. LCMS [M+H]$^+$ 425. $^1$H NMR (400 MHz, METHANOL-d$_4$) δ ppm 7.58-7.62 (m, 1 H), 7.41 (t, J=1.7 Hz, 1 H), 7.33-7.36 (m, 2 H), 7.18-7.24 (m, 1 H), 7.11-7.15 (m, 1 H), 6.92-6.96 (m, 1 H), 6.01 (s, 1 H), 3.78 (t, J=7.1 Hz, 2 H), 3.01-3.03 (m, 6 H), 2.89-2.94 (m, 2 H), 2.37 (s, 3 H).

Example 652

N-[3-[2-[[2-amino-6-(3-chloro-2-methyl-phenyl)pyrimidin-4-yl]amino]ethyl]phenyl]pyrrolidine-1-carboxamide A mixture of N4-[2-(3-aminophenyl)ethyl]-6-(3-chloro-2-methyl-phenyl)pyrimidine-2,4-diamine (intermediate 47) (1 equiv.), pyrrolidine-1-carbonyl chloride (1.3 equiv.), and diisopropylethylamine (1.6 equiv.) was stirred at 150° C. for 10 min. The reaction mixture was concentrated and purified by preparative LC. LCMS [M+H]$^+$ 451. $^1$H NMR (400 MHz, METHANOL-d$_4$) δ ppm 7.58-7.61 (m, 1 H), 7.46 (t, J=1.6 Hz, 1 H), 7.33-7.36 (m, 2 H), 7.17-7.23 (m, 2 H), 6.94 (dt, J=7.1, 1.7 Hz, 2 H), 6.01 (s, 1 H), 3.78 (t, J=7.1 Hz, 2 H), 3.43-3.48 (m, 4 H), 2.92 (t, J=7.1 Hz, 2 H), 2.37 (s, 3 H), 1.95-2.00 (m, 4 H).

Example 653 isopropyl N-[3-[2-[[2-amino-6-(3-chloro-2-methyl-phenyl)pyrimidin-4-yl]amino]ethyl]phenyl]carbamate The title compound was produced according to general procedure 18 from intermediate 47 and isopropyl carbonochloridate. LCMS [M+H]$^+$ 440. $^1$H NMR (400 MHz, METHANOL-d$_4$) δ ppm 7.60 (dd, J=6.3, 2.8 Hz, 1 H), 7.47 (s, 1 H), 7.33-7.36 (m, 2 H), 7.17-7.23 (m, 2 H), 6.92-6.96 (m, 1 H), 6.00 (s, 1 H), 4.91-4.98 (m, 1 H), 3.77 (t, J=7.1 Hz, 2 H), 2.92 (t, J=7.1 Hz, 2 H), 2.37 (s, 3 H), 1.27-1.31 (m, 6 H).

Example 654 isobutyl N-[3-[2-[[2-amino-6-(3-chloro-2-methyl-phenyl)pyrimidin-4-yl]amino]ethyl]phenyl]carbamate The title compound was produced according to general procedure 18 from intermediate 47 and isobutyl carbonochloridate. LCMS [M+H]$^+$ 454. $^1$H NMR (400 MHz, METHANOL-d$_4$) δ ppm 7.58-7.61 (m, 1 H), 7.48 (s, 1 H), 7.33-7.35 (m, 2 H), 7.18-7.24 (m, 2 H), 6.92-6.97 (m, 1 H), 6.00 (s, 1 H), 3.90 (d, J=6.6 Hz, 2 H), 3.77 (t, J=7.1 Hz, 2 H), 2.93 (t, J=7.1 Hz, 2 H), 2.37 (s, 3 H), 1.91-2.03 (m, 1 H), 0.96-1.01 (m, 6 H).

Example 655

2,2-dimethylpropyl N-[3-[2-[[2-amino-6-(3-chloro-2-methyl-phenyl)pyrimidin-4-yl]amino]ethyl]phenyl]carbamate The title compound was produced according to general procedure 18 from intermediate 47 and 2,2-dimethylpropyl carbonochloridate. LCMS [M+H]$^+$ 468. $^1$H NMR (400 MHz, METHANOL-d$_4$) δ ppm 7.57-7.61 (m, 1 H), 7.49 (br. s., 1 H), 7.33-7.35 (m, 2 H), 7.19-7.24 (m, 2 H), 6.95 (dt, J=6.2, 1.9 Hz, 1 H), 6.00 (s, 1 H), 3.83 (s, 2 H), 3.77 (s, 2 H), 2.93 (s, 2 H), 2.37 (s, 3 H), 0.97-1.01 (m, 9 H).

Example 656

1-[6-[2-[[2-amino-6-(3-chloro-2-methyl-phenyl)pyrimidin-4-yl]amino]ethylamino]-3-pyridyl]-3-tert-butyl-urea Step 1. A mixture of intermediate 24 (1 equiv.), N-(2-aminoethyl)-5-nitropyridin-2-amine, (1.3 equiv.), and Hünig's base (1.5 equiv.) was stirred in 2-propanol at 120° C. for 16 h. The mixture was then poured into water and extracted with DCM ×3. The combined organics were dried (MgSO$_4$) and concentrated. The crude material was used in step 2 without further purification.

Step 2. The crude material from step 1 (1 equiv.) was dissolved in EtOH, then SnCl$_2$ (5 equiv.) was added and the resulting mixture was stirred at reflux for 5 h. The mixture was then cooled and basified by addition of NaOH (5 M). The mixture was then extracted with DCM ×3. The combined organics were dried (MgSO$_4$) and concentrated. The crude material was used in step 3 without further purification.

Step 3. A mixture of the crude material from step 2 (1 equiv.) and tert-butyl isocyanate (3 equiv.) in DCM was stirred at reflux for 16 h. The mixture was then concentrated and purified by preparative HPLC. LCMS [M+H]$^+$ 469. $^1$H NMR (400 MHz, METHANOL-d$_4$) δ ppm 8.18 (dd, J=2.5, 0.6 Hz, 1 H), 7.77 (dd, J=9.5, 2.5 Hz, 1 H), 7.60 (dd, J=7.7, 2.1 Hz, 1 H), 7.30-7.38 (m, 2 H), 7.07 (dd, J=9.6, 0.8 Hz, 1 H), 6.07 (s, 1 H), 3.82 (s, 2 H), 3.66 (s, 2 H), 2.36 (s, 3 H), 1.36 (s, 9 H).

Example 657 tert-butyl N-[6-[2-[[2-amino-6-(3-chloro-2-methyl-phenyl)pyrimidin-4-yl]amino]ethylamino]-3-pyridyl]carbamate Step 1. A mixture of intermediate 24 (1 equiv.), N-(2-aminoethyl)-5-nitropyridin-2-amine, (1.3 equiv.), and Hünig's base (1.5 equiv.) was stirred in 2-propanol at 120° C. for 16 h. The mixture was then poured into water and extracted with DCM ×3. The combined organics were dried (MgSO4) and concentrated. The crude material was used in step 2 without further purification.

Step 2. The crude material from step 1 (1 equiv.) was dissolved in EtOH, then SnCl$_2$ (5 equiv.) was added and the resulting mixture was stirred at reflux for 5 h. The mixture was then cooled and basified by addition of NaOH (5 M). The mixture was then extracted with DCM ×3. The combined organics were dried (MgSO$_4$) and concentrated. The crude material was used in step 3 without further purification.

Step 3. A mixture of the crude material from step 2 and di-tert-butyl dicarbonate in DCM was stirred at reflux for 16 h. The mixture was then concentrated and purified by prep-LC. LCMS [M+H]$^+$ 470. $^1$H NMR (400 MHz, METHANOL-d$_4$) δ ppm 8.23 (br. s., 1 H), 7.84 (dd, J=9.5, 2.5 Hz, 1 H), 7.58-7.62 (m, 1 H), 7.28-7.38 (m, 2 H), 7.09 (dd, J=9.8, 0.6 Hz, 1 H), 6.07 (s, 1 H), 3.80-3.86 (m, 2 H), 3.64-3.70 (m, 2 H), 2.36 (s, 3 H), 1.51 (s, 9 H).

Example 658

N2-[2-[[2-amino-6-(3-chloro-2-methyl-phenyl)pyrimidin-4-yl]amino]ethyl]-1,3,5-triazine-2,4,6-triamine The title compound was produced according to general procedure 12 from intermediate 58 and 6-chloro-1,3,5-triazine-2,4-diamine. LCMS [M+H]$^+$ 387.

Example 659

2-[2-[[2-amino-6-(3-chloro-2-methyl-phenyl)pyrimidin-4-yl]amino]ethylamino]-4-(trifluoromethyl)pyrimidine-5-carboxamide The title compound was produced according to general procedure 12 from intermediate 58 and 2-chloro-4-(trifluoromethyl)pyrimidine-5-carboxamide. LCMS [M+H]$^+$ 467. $^1$H NMR (400 MHz, METHANOL-d$_4$) δ ppm 8.50-8.62 (m, 1 H), 7.57-7.61 (m, 1 H), 7.29-7.38 (m, 2 H), 5.99 (d, J=7.3 Hz, 1 H), 3.76 (br. s., 4 H), 2.37 (s, 3 H).

Example 660

N-[2-[[2-amino-6-(3-chloro-2-methyl-phenyl)pyrimidin-4-yl]amino]ethyl]-3-fluoro-benzenesulfonamide A mixture of N4-(2-aminoethyl)-6-(3-chloro-2-methylphenyl)pyrimidine-2,4-diamine (intermediate 58) (1 equiv.), 3-fluorobenzenesulfonyl chloride (1.3 equiv.), and Hünig's base (2.1 equiv.) in DCM was stirred 18 h at 20° C. The reaction mixture was concentrated and purified by prep-LC. LCMS [M+H]$^+$ 436. $^1$H NMR (400 MHz, METHANOL-d$_4$) δ ppm 7.67-7.71 (m, 1 H), 7.56-7.63 (m, 3 H), 7.32-7.42 (m, 3 H), 6.04 (s, 1 H), 3.61 (t, J=6.0 Hz, 2 H), 3.16 (t, J=6.0 Hz, 2H), 2.38 (s, 3 H).

Example 661

2-(2-amino-6-(3-chloro-2-methylphenyl)pyrimidin-4-ylamino)-1-(4-(methylsulfonyl)phenyl)ethanol Step 1:
2-Bromo-1-(4-(methylsulfonyl)phenyl)ethanone To the solution of 1-(4-(methylsulfonyl)phenyl)ethan-1-one (5.00 g, 25.2 mmol) in CHCl$_3$ (100 mL) was added Br$_2$ (4.0 0 g, 25.2 mmol) in CHCl$_3$ (15 mL) dropwise over period of 1 h, the mixture was stirred for 1 h at RT (15° C.). The solution was washed with saturated NaHCO$_3$ (30 mL) and brine (30 mL), dried over Na$_2$SO$_4$. After removal of solvent under reduced pressure, the crude product was recrystallized from EtOH (50 mL) at RT to afford a white solid as product 20 (4.60 g, 16.6 mmol, 66%). $^1$H NMR (300 MHz, CDCl$_3$): δ=3.12 (s, 3 H), 4.48 (s, 2 H), 8.10 (m, 2 H), 8.18 (m, 2 H) ppm.

Step 2: To the solution of 2-Bromo-1-(4-(methylsulfonyl)phenyl)ethanone (5.30 g, 19.1 mmol) in MeCN (53 mL) was added hexamethylenetetramine (2.70 g, 19.3 mmol), the mixture was stirred for 2 h. at R.T. The product was isolated by filtration and dried under high vacuum (7.20 g), and used for next step without further purification.

Step 3:
2-Amino-1-(4-(methylsulfonyl)phenyl)ethanone hydrochloride

To the solution of concentrated HCl (10 mL) in EtOH (40 mL) was added 2-amino-1-(4-(methylsulfonyl)phenyl)ethanone (7.2 g, 17.3 mmol) at RT. The mixture was stirred for 2 h at 50° C. After cooling to 5° C., the resulting white solid was collected by filtration, washed with EtOH (10 mL). The solid was dissolved in the mixture of H$_2$O (12 mL) and concentrated HCl (0.5 mL) at 70° C., the hot solution was filtered and the filtrate was cooled to 5° C., the crystalline white solid was isolated by filtration, washed with ice-cold H$_2$O (5 mL) and EtOH (5 mL), dried under high vacuum to afford the product (2.30 g, 9.2 mmol, 53%). $^1$H NMR (400 MHz, D$_2$O): δ=3.17 (d, J=2.8 Hz, 2 H), 4.64 (s, 3 H), 7.99 (m, 2 H), 8.09 (m, 2 H) ppm.

Step 4:
2-amino-1-(4-(methylsulfonyl)phenyl)ethan-1-ol

At 0° C., NaBH$_4$ (0.30 g, 8.0 mmol) was dissolved in MeOH (30 mL), KOH (0.22 g, 3.9 mmol) in MeOH (4 mL) was added carefully, then 2-Amino-1-(4-(methylsulfonyl)phenyl)ethanone hydrochloride (1.00 g, 4.0 mmol) was added in small portions. The mixture was stirred for 30 min at 0° C. and 30 min at RT. After removal of solvent under reduced pressure, the residue was treated with saturated NaHCO$_3$ (10 mL). After extraction with DCM (20 mL×4), the combined organic layers was washed with brine (5 mL), dried over Na$_2$SO$_4$. Removal of solvent under reduced pressure, gave the product (0.25 g). $^1$H NMR (300 MHz, CDCl$_3$): δ=2.76 (m, 1 H), 3.07 (s, 3 H), 3.12 (m, 1 H), 4.73 (m, 1 H), 7.59 (d, J=8.4 Hz, 2 H), 7.93 (d, J=8.4 Hz, 2 H) ppm.

Step 5: 2-(2-amino-6-(3-chloro-2-methylphenyl)pyrimidin-4-ylamino)-1-(4-(methylsulfonyl)phenyl)ethanol A mixture of 2-amino-1-(4-(methylsulfonyl)phenyl)ethan-1-ol (190 mg, 0.88 mmol), intermediate 24 (266 mg, 1.05 mmol) and triethylamine (0.19 mL, 1.32 mmol) in isopropanol (5 mL) was stirred overnight at 95° C. After cooling to RT and removal of solvent under reduced pressure, the residue was purified by preparative HPLC to yield the product (65 mg). $^1$H NMR (300 MHz, DMSO-d$_6$): δ=2.08 (s, 3 H), 3.20 (s, 3 H), 3.61 (br, 1 H), 4.90 (s, 1 H), 5.81 (s, 1 H), 5.84 (m, 1H), 6.11 (s, 2 H), 7.20 (m, 3 H), 7.26 (m, 1 H), 7.70 (m, 2 H), 7.90 (m, 2 H) ppm.

Example 662

N-[2-[[2-amino-6-(3-chloro-2-methyl-phenyl)pyrimidin-4-yl]amino]ethyl]morpholine-4-carboxamide A mixture of N4-(2-aminoethyl)-6-(3-chloro-2-methylphenyl)pyrimidine-2,4-diamine (intermediate 58) (1 equiv.), morpholine-4-carbonyl chloride (1.4 equiv.), and Hünig's base (2.1 equiv.) in DCM was stirred 18 h at 20° C. The reaction mixture was concentrated and purified by preparative LC. LCMS [M+H]⁺ 391. ¹H NMR (400 MHz, METHANOL-d₄) δ ppm 7.61 (dd, J=7.1, 2.1 Hz, 1 H), 7.31-7.40 (m, 2 H), 6.04 (d, J=0.9 Hz, 1 H), 3.62-3.66 (m, 6 H), 3.40-3.44 (m, 2 H), 3.33-3.37 (m, 4 H), 2.38 (s, 3 H).

Example 663

1-[2-[[2-amino-6-(3-chloro-2-methyl-phenyl)pyrimidin-4-yl]amino]ethyl]-3-(3-fluorophenyl)urea A mixture of N4-(2-aminoethyl)-6-(3-chloro-2-methyl-phenyl)pyrimidine-2,4-diamine (intermediate 58) (1 equiv.) and 3-fluorophenyl isocyanate (1.4 equiv.) in DCM was stirred 18 h at 20° C. The reaction mixture was concentrated and purified by preparative LC. LCMS [M+H]⁺ 415. ¹H NMR (400 MHz, METHANOL-d₄) δ ppm 7.60 (dd, J=7.9, 1.3 Hz, 1 H), 7.29-7.38 (m, 3 H), 7.20-7.26 (m, 1 H), 7.00 (ddd, J=8.2, 2.1, 0.8 Hz, 1 H), 6.66-6.72 (m, 1 H), 6.04 (s, 1 H), 3.63-3.68 (m, 2 H), 3.45-3.49 (m, 2 H), 2.37 (s, 3 H).

Example 664

6-(3-chloro-2-methyl-phenyl)-N4-[2-(4-isopropylsulfonylanilino)ethyl]pyrimidine-2,4-diamine Step 1. N'-(4-isopropylsulfonylphenyl)ethane-1,2-diamine was prepared according to general procedure 13 from 1-bromo-4-isopropylsulfonyl-benzene and ethylenediamine.

Step 2. The title compound was prepared according to general procedure 9 from the crude material of step 1 and intermediate 24. [M+H]⁺ 460. ¹H NMR (400 MHz, METHANOL-d₄) δ ppm 7.51-7.62 (m, 3 H), 7.29-7.39 (m, 2 H), 6.74-6.79 (m, 2 H), 6.01 (s, 1 H), 3.76 (t, J=6.2 Hz, 2 H), 3.51 (t, J=6.2 Hz, 2 H), 3.13-3.22 (m, 1 H), 2.37 (s, 3 H), 1.22 (d, J=7.0 Hz, 6 H).

Example 665

6-(3-chloro-2-methyl-phenyl)-N4-[2-(4-methylsulfinylanilino)ethyl]pyrimidine-2,4-diamine Step 1. N'-(4-methylsulfinylphenyl)ethane-1,2-diamine was prepared according to general procedure 13 from 1-bromo-4-methylsulfinyl-benzene and ethylenediamine.

Step 2. The title compound was prepared according to general procedure 9 from the crude material of step 1 and intermediate 24. LCMS [M+H]⁺ 416.

Example 666

4-[2-[[2-amino-6-(3-chloro-2-methyl-phenyl)pyrimidin-4-yl]amino]ethyl]-3-fluoro-benzamide Step 1. 4-(2-aminoethyl)-3-fluoro-benzamide was prepared according to general procedure 22 from 4-bromo-3-fluoro-benzamide.

Step 2. The title compound was prepared according to general procedure 9 from the material from step 1 and intermediate 24. [M+H]+ 400.

Example 667

6-[3-[[2-amino-6-(3-chloro-2-methyl-phenyl)pyrimidin-4-yl]amino]azetidin-1-yl]pyridine-3-sulfonamide Step 1. A mixture of 4-fluorobenzenesulfonamide (1 equiv.), tert-butyl N-(azetidin-3-yl)carbamate (1.3 equiv.), and diisopropylethylamine (1.3 equiv.) was stirred in acetonitrile at 150° C. for 1 h in a sealed vial. The reaction mixture was then concentrated and purified by silica gel chromatography using MeOH (0-9%) in DCM.

Step 2. Tert-butyl N-[1-(4-sulfamoylphenyl)azetidin-3-yl]carbamate from step 1 was stirred in TFA at 20° C. for 2 h. The reaction mixture was then concentrated and used without further purification in step 3.

Step 3. The title compound was prepared according to general procedure 9 from the material from step 2 and intermediate 24. LCMS [M+H]⁺ 445.

Example 668 tert-butyl N-[3-[[2-amino-6-(3-chloro-2-methyl-phenyl)pyrimidin-4-yl]amino]propyl]carbamate Step 1. A mixture of tert-butyl N-(3-aminopropyl)carbamate (1.25 equiv.), 4,6-dichloropyrimidin-2-amine (1 equiv.), and Hünig's base (1.5 equiv.) in 2-propanol was stirred at 100° C. for 16 h. The reaction mixture was then poured into water and extracted with DCM ×3. The combined organics were dried (MgSO₄) and concentrated. The crude material was purified by silica gel chromatography which afforded tert-butyl N-[3-[(2-amino-6-chloro-pyrimidin-4-yl)amino]propyl]carbamate Step 2. The title compound was prepared according to general procedure 2 from tert-butyl N-[3-[(2-amino-6-chloro-pyrimidin-4-yl)amino]propyl]carbamate (prepared in step 1) and (3-chloro-2-methyl-phenyl)boronic acid. LCMS [M+H]⁺ 392. ¹H NMR (400 MHz, METHANOL-d4) δ ppm 7.57-7.63 (m, 1 H), 7.31-7.40 (m, 2 H), 6.04 (s, 1 H), 3.55 (t, J=6.8 Hz, 2 H), 3.14 (t, J=7.0 Hz, 2 H), 2.39 (s, 3H), 1.81 (t, J=7.0 Hz, 2 H), 1.44 (s, 9 H).

Example 669

4-[3-[[2-amino-6-(3-chloro-2-methyl-phenyl)pyrimidin-4-yl]amino]propylamino]benzenesulfonamide Step 1. 4-(3-aminopropylamino)benzenesulfonamide was prepared according to general procedure 13 from 4-iodo-benzenesulfonamide and propane-1,3-diamine.

Step 2. The title compound was prepared according to general procedure 9 from 4-(3-aminopropylamino)benzenesulfonamide and intermediate 24. LCMS [M+H]⁺ 447.

Example 670

4-[[3-[[2-amino-6-(3-chloro-2-methyl-phenyl)pyrimidin-4-yl]amino]-2,2-dimethyl-propyl]amino]benzenesulfonamide Step 1. A mixture of 4-bromobenzenesulfonamide (1 equiv.), CuCl (0.1 equiv.), and KOH (2 equiv.) were stirred in 2,2-dimethylpropane-1,3-diamine (5 equiv.) at 40° C. for 72 h. the reaction mixture was extracted with hot EtOAc and concentrated. The crude 4-[(3-amino-2,2-dimethyl-propyl)amino]benzenesulfonamide was then washed with diethyl ether and used in step 2.

Step 2. The title compound was prepared according to general procedure 9 from 4-[(3-amino-2,2-dimethyl-propyl)amino]benzenesulfonamide and intermediate 24. LCMS [M+H]⁺ 475.

Example 671

6-(3-chloro-2-methyl-phenyl)-N4-[2,2-dimethyl-3-[(2-methyl-1,3-benzothiazol-6-yl)amino]propyl]pyrimidine-2,4-diamine Step 1. A mixture of 6-iodo-2-methyl-1,3-benzothiazole (1 equiv.), CuCl (0.1 equiv.), and KOH (2 equiv.) were stirred in 2,2-dimethylpropane-1,3-diamine (5 equiv.) at 40° C. for 72 h. the reaction mixture was extracted with hot EtOAc and concentrated. The crude residue was then purified by preparative LC to afford 2,2-dimethyl-N'-(2-methyl-1,3-benzothiazol-6-yl)propane-1,3-diamine. [M+H]$^+$ 250.

Step 2. The title compound was prepared according to general procedure 9 from 2,2-dimethyl-N'-(2-methyl-1,3-benzothiazol-6-yl)propane-1,3-diamine and intermediate 24. LCMS [M+H]$^+$ 467. $^1$H NMR (400 MHz, METHANOL-d4) δ ppm 7.56-7.61 (m, 2 H), 7.31-7.37 (m, 1 H), 7.25-7.30 (m, 1 H), 7.12 (d, J=2.2 Hz, 1 H), 6.92-6.97 (m, 1 H), 6.09 (s, 1 H), 3.59 (s, 2 H), 3.08 (s, 2 H), 2.75 (s, 3 H), 2.32 (s, 3 H), 1.11 (s, 6 H).

Example 672

6-(3-Chloro-2-methyl-phenyl)-N4-[2-(3-isopropylsulfonylanilino)ethyl]pyrimidine-2,4-diamine Step 1. N'-(3-isopropylsulfonylphenyl)ethane-1,2-diamine was prepared according to general procedure 13 from 1-bromo-3-isopropylsulfonyl-benzene and ethylenediamine.

Step 2. The title compound was prepared according to general procedure 9 from N'-(3-isopropylsulfonylphenyl)ethane-1,2-diamine and 4-chloro-6-(3-chloro-2-methyl-phenyl)pyrimidin-2-amine (intermediate 24). LCMS [M+H]$^+$ 460. $^1$H NMR (400 MHz, METHANOL-d$_4$) δ ppm 7.59-7.62 (m, 1 H), 7.35 (s, 3 H), 7.22-7.25 (m, 1 H), 7.05-7.09 (m, 1 H), 6.94-6.98 (m, 1 H), 6.01 (s, 1 H), 3.65-3.70 (m, 2 H), 3.45-3.50 (m, 2 H), 2.38 (s, 3 H), 1.26 (d, J=7.0 Hz, 6 H).

Example 673

6-[3-[[2-amino-6-(3-chloro-2-methyl-phenyl)pyrimidin-4-yl]amino]propylamino]pyridine-3-carboxamide The title compound was prepared according to general procedure 12 from 6-chloropyridine-3-carboxamide and intermediate 59. LCMS [M+H]$^+$ 412.

Example 674

2-[3-[[2-amino-6-(3-chloro-2-methyl-phenyl)pyrimidin-4-yl]amino]propylamino]pyrimidine-4-carboxamide The title compound was prepared according to general procedure 12 from 2-chloropyrimidine-4-carboxamide and intermediate 59. LCMS [M+H]+ 413.

Example 675

6-(3-chloro-2-methyl-phenyl)-N4-[2-(4-isopropylsulfonylphenyl)ethyl]pyrimidine-2,4-diamine Step 1. 2-(4-isopropylsulfonylphenyl)ethanamine was prepared according to general procedure 22 from 1-bromo-4-isopropylsulfonyl-benzene.

Step 2. The title compound was prepared according to general procedure 9 from 2-(4-isopropylsulfonylphenyl)ethanamine and intermediate 24. LCMS [M+H]$^+$ 445.

Example 676

Step 1. 2-(3-isopropylsulfonylphenyl)ethanamine was prepared according to general procedure 22 from 1-bromo-3-isopropylsulfonyl-benzene.

Step 2. The title compound was prepared according to general procedure 9 from 2-(3-isopropylsulfonylphenyl)ethanamine and intermediate 24. LCMS [M+H]$^+$ 445. $^1$H NMR (400 MHz, METHANOL-d4) δ ppm 7.73-7.80 (m, 2 H), 7.67 (s, 1 H), 7.60 (t, J=7.4 Hz, 2 H), 7.31-7.38 (m, 2 H), 5.98 (d, J=1.6 Hz, 1 H), 3.85 (t, J=7.0 Hz, 2 H), 3.34 (obstructed by solvent signal, m, 1 H), 3.10 (t, J=7.0 Hz, 2 H), 2.36 (s, 3 H), 1.24 (d, J=7.0 Hz, 6 H).

Example 677

4-[2-[[2-amino-6-(3-chloro-2-methyl-phenyl)pyrimidin-4-yl]amino]ethyl]-2-fluoro-benzamide Step 1. 4-(2-aminoethyl)-2-fluoro-benzamide was prepared according to general procedure 22 from 4-bromo-2-fluoro-benzamide.

Step 2. The title compound was prepared according to general procedure 9 from 4-(2-aminoethyl)-2-fluoro-benzamide and intermediate 24. LCMS [M+H]$^+$ 400. $^1$H NMR (400 MHz, METHANOL-d4) δ ppm 7.79 (t, J=7.9 Hz, 1 H), 7.58-7.62 (m, 1 H), 7.30-7.38 (m, 2 H), 7.22 (dd, J=7.9, 1.6 Hz, 1 H), 7.18 (dd, J=12.2, 1.4 Hz, 1 H), 6.00 (s, 1 H), 3.82 (t, J=7.1 Hz, 2 H), 3.03 (t, J=7.1 Hz, 2 H), 2.37 (s, 3 H).

Example 678

6-(3-chloro-2-methyl-phenyl)-N4-[2-(3-fluoro-4-methylsulfonyl-phenyl)ethyl]pyrimidine-2,4-diamine Step 1. 2-(3-fluoro-4-methylsulfonyl-phenyl)ethylamine was prepared according to general procedure 22 from 4-bromo-2-fluoro-1-methylsulfonyl-benzene.

Step 2. The title compound was prepared according to general procedure 9 from 2-(3-fluoro-4-methylsulfonyl-phenyl)ethylamine and intermediate 24. LCMS [M+H]$^+$ 435. $^1$H NMR (400 MHz, METHANOL-d4) δ ppm 7.86 (t, J=7.7 Hz, 1 H), 7.58-7.62 (m, 1 H), 7.31-7.38 (m, 4 H), 6.00 (s, 1 H), 3.84 (t, J=7.0 Hz, 2 H), 3.22-3.24 (m, 3 H), 3.08 (t, J=7.0 Hz, 2 H), 2.37 (s, 3 H).

Example 679

5-[2-[[2-amino-6-(3-chloro-2-methyl-phenyl)pyrimidin-4-yl]amino]ethyl]-2-hydroxy-benzamide Step 1. 2-(3-carbamoyl-4-hydroxy-phenyl)ethylamine was prepared according to general procedure 22 from 6-bromo-2,2-dimethyl-3H-1,3-benzoxazin-4-one.

Step 2. The title compound was prepared according to general procedure 9 from 2-(3-carbamoyl-4-hydroxy-phenyl)ethylamine and intermediate 24. LCMS [M+H]$^+$ 398.

Example 680

6-(3-chloro-2-methyl-phenyl)-N4-(4-phenylbutyl)pyrimidine-2,4-diamine

The title compound was prepared according to general procedure 9 from 4-phenylbutan-1-amine and intermediate 24. LCMS [M+H]⁺ 367. ¹H NMR (400 MHz, METHANOL-d4) δ ppm 7.57-7.61 (m, 1 H), 7.33-7.36 (m, 2 H), 7.23-7.28 (m, 2 H), 7.12-7.21 (m, 3 H), 6.01 (s, 1 H), 3.54 (t, J=6.8 Hz, 2 H), 2.65-2.70 (m, 2 H), 2.38 (s, 3 H), 1.62-1.77 (m, 4 H).

Example 681

6-(3-chloro-2-methyl-phenyl)-N4-[2-(cyclohexen-1-yl)ethyl]pyrimidine-2,4-diamine The title compound was prepared according to general procedure 9 from 2-(cyclohexen-1-yl)ethanamine and intermediate 24. LCMS [M+H]⁺ 343. ¹H NMR (400 MHz, METHANOL-d4) δ ppm 7.58-7.62 (m, 1 H), 7.31-7.39 (m, 2 H), 6.03 (s, 1 H), 5.46-5.52 (m, 1 H), 3.62 (t, J=7.1 Hz, 2 H), 2.38 (s, 3 H), 2.26 (t, J=6.6 Hz, 2 H), 1.95-2.07 (m, 4 H), 1.62-1.70 (m, 2 H), 1.53-1.61 (m, 2 H).

Example 682

N4-but-3-enyl-6-(3-chloro-2-methyl-phenyl)pyrimidine-2,4-diamine

The title compound was prepared according to general procedure 9 from but-3-en-1-amine and intermediate 24. LCMS [M+H]⁺ 289. ¹H NMR (400 MHz, METHANOL-d4) δ ppm 7.58-7.62 (m, 1 H), 7.32-7.38 (m, 2 H), 6.03 (s, 1 H), 5.87 (ddt, J=17.1, 10.3, 6.7, 6.7 Hz, 1 H), 5.14 (dq, J=17.1, 1.7 Hz, 1 H), 5.09 (ddt, J=10.2, 2.0, 1.1, 1.1 Hz, 1 H), 3.60 (t, J=7.0 Hz, 2 H), 2.39-2.44 (m, 2 H), 2.38 (s, 3 H).

Example 683

5-[2-[[2-amino-6-(3-chloro-2-methyl-phenyl)pyrimidin-4-yl]amino]ethylamino]naphthalene-1-sulfonic acid The title compound was prepared according to general procedure 9 from 5-(2-aminoethylamino)naphthalene-1-sulfonic acid and intermediate 24. LCMS [M+H]⁺ 484.

Example 684

6-(3-chloro-2-methyl-phenyl)-N4-[2-(cyclopropylmethoxy)ethyl]pyrimidine-2,4-diamine The title compound was prepared according to general procedure 9 from 2-(cyclopropylmethoxy)ethanamine and intermediate 24. LCMS [M+H]⁺ 333. ¹H NMR (400 MHz, METHANOL-d4) δ ppm 7.57-7.63 (m, 1 H), 7.32-7.39 (m, 2 H), 6.09 (s, 1 H), 3.70-3.74 (m, 2 H), 3.65-3.69 (m, 2 H), 3.34-3.37 (m, 2 H), 2.39 (s, 3 H), 1.05 (d, J=8.2 Hz, 1 H), 0.50-0.55 (m, 2 H), 0.19-0.24 (m, 2 H).

Example 685

2-[2-[[2-amino-6-(3-chloro-2-methyl-phenyl)pyrimidin-4-yl]amino]ethylsulfanyl]pyrimidine-4-carboxamide Step 1. A mixture of 2-(2-aminoethylsulfanyl)pyrimidine-4-carboxamide (1 equiv.), 2-(2-aminoethylsulfanyl)pyrimidine-4-carboxamide (1.2 equiv.), and Hünig's base (2 equiv.) in 2-propanol was stirred at 150° C. for 30 min. Thereafter the mixture was concentrated and purified by silica gel chromatography which afforded 2-(2-aminoethylsulfanyl)pyrimidine-4-carboxamide. LCMS [M+H]⁺ 299. ¹H NMR (400 MHz, CHLOROFORM-d) δ ppm 8.80 (br. s., 1 H), 8.74 (d, J=5.1 Hz, 1 H), 7.80 (d, J=4.7 Hz, 1 H), 5.67 (br. s., 1 H), 5.01 (br. s., 1 H), 3.44-3.52 (m, 2 H), 3.23-3.30 (m, 2 H), 1.45 (s, 9 H).

Step 2. A mixture of 2-(2-aminoethylsulfanyl)pyrimidine-4-carboxamide and TFA was stirred at 20° C. for 1 h. Thereafter the mixture was concentrated to afford 2-(2-aminoethylsulfanyl)pyrimidine-4-carboxamide which was used without purification in step 3.

Step 3. The title compound was prepared according to general procedure 9 from 2-(2-aminoethylsulfanyl)pyrimidine-4-carboxamide and intermediate 24. LCMS [M+H]⁺ 416.

Example 686

6-(3-chloro-2-methyl-phenyl)-N4-(3,3-difluoroallyl)pyrimidine-2,4-diamine

The title compound was isolated as a side product in the synthesis of N4-(3-bromo-3,3-difluoro-propyl)-6-(3-chloro-2-methyl-phenyl)pyrimidine-2,4-diamine (prepared in example 687). LCMS [M+H]⁺ 311. ¹H NMR (400 MHz, METHANOL-d4) δ ppm 7.61 (dd, J=7.1, 2.4 Hz, 1 H), 7.34-7.39 (m, 2 H), 6.03 (s, 1 H), 4.62-4.74 (m, 1 H), 4.13 (dt, J=7.7, 1.8 Hz, 2 H), 2.38 (s, 3 H).

Example 687

N4-(3-bromo-3,3-difluoro-propyl)-6-(3-chloro-2-methyl-phenyl)pyrimidine-2,4-diamine The title compound was prepared according to general procedure 9 from 3-bromo-3,3-difluoro-propan-1-amine and intermediate 24. LCMS [M+H]⁺ 391. ¹H NMR (400 MHz, METHANOL-d4) δ ppm 7.59-7.63 (m, 1 H), 7.32-7.40 (m, 2 H), 6.06 (s, 1 H), 3.81 (t, J=7.0 Hz, 2 H), 2.79-2.92 (m, 2 H), 2.38 (s, 3 H).

Example 688

6-(3-chloro-2-methyl-phenyl)-N4-[2-[[5-[(dimethylamino)methyl]-2-furyl]methylsulfanyl]ethyl]pyrimidine-2,4-diamine The title compound was prepared according to general procedure 9 from 2-[[5-[(dimethylamino)methyl]-2-furyl]methylsulfanyl]ethanamine and intermediate 24. LCMS [M+H]⁺ 432.

Example 689

6-(3-chloro-2-methyl-phenyl)-N4-[2-[(4-methylsulfonylphenyl)methylsulfanyl]ethyl]pyrimidine-2,4-diamine Step 1. A mixture of 1-(chloromethyl)-4-methylsulfonylbenzene (1 equiv.), tert-butyl N-(2-sulfanylethyl)carbamate (1 equiv.), and Cs₂CO₃ (1 equiv.) was stirred in DMF at 60° C. for 16 h. Then the mixture was poured into sat. NaHCO₃ and extracted with DCM ×3. The combined organics were dried (MgSO₄), concentrated, and purified by silica gel chromatography to afford tert-butyl N-[2-[(4-methylsulfonylphenyl)methylsulfanyl]ethyl]carbamate. ¹H NMR (400 MHz, CHLOROFORM-d) δ ppm 7.90 (d, J=8.5 Hz, 2 H), 7.55 (d, J=8.5 Hz, 2 H), 3.80 (s, 2 H), 3.27-3.35 (m, 2 H), 3.07 (s, 3 H), 2.55 (t, J=6.8 Hz, 2 H), 1.46 (s, 9 H).

Step 2. A mixture of tert-butyl N-[2-[(4-methylsulfonyl-phenyl)methylsulfanyl]ethyl]carbamate and TFA was stirred at 20° C. for 1 h. Thereafter the mixture was concentrated to afford 2-[(4-methylsulfonylphenyl)methylsulfanyl]ethan-amine which was used without purification in step 3.

Step 3. A mixture of 2-[(4-methylsulfonylphenyl)methyl-sulfanyl]ethanamine (1 equiv.), 4,6-dichloropyrimidin-2-amine (1 equiv.), and Hünig's base (3 equiv.) was stirred in 2-propanol at 120° C. for 16 h. Then the mixture was poured into sat. $NaHCO_3$ and extracted with DCM ×3. The combined organics were dried ($MgSO_4$), concentrated, and purified by silica gel chromatography to afford 6-chloro-N4-[2-[(4-methylsulfonylphenyl)methylsulfanyl]ethyl]pyrimidine-2,4-diamine.

Step 4. The title compound was prepared according to general procedure 2 from 6-chloro-N4-[2-[(4-methylsulfonylphenyl)methylsulfanyl]ethyl]pyrimidine-2,4-diamine and (3-chloro-2-methyl)phenylboronic acid. LCMS [M+H]$^+$ 463. $^1$H NMR (400 MHz, CHLOROFORM-d) δ ppm 7.88-7.93 (m, 2 H), 7.52-7.56 (m, 2 H), 7.39 (dd, J=7.1, 2.4 Hz, 1 H), 7.14-7.21 (m, 2 H), 5.78 (s, 1 H), 4.98-5.06 (m, 1 H), 4.84 (s, 2 H), 3.82 (s, 2 H), 3.49-3.58 (m, 2 H), 3.06 (s, 3 H), 2.68 (t, J=6.5 Hz, 2 H), 2.37 (s, 3 H).

Example 690

6-(3-chloro-2-methylphenyl)-N4-{2-[(2-phenylethyl)sulfanyl]ethyl}pyrimidine-2,4-diamine Step 1. A mixture of 2-bromoethylbenzene (1 equiv.), tert-butyl N-(2-sulfanylethyl)carbamate (1 equiv.), and $Cs_2CO_3$ (1 equiv.) was stirred in DMF at 60° C. for 16 h. Then the mixture was poured into sat. $NaHCO_3$ and extracted with DCM ×3. The combined organics were dried ($MgSO_4$), concentrated, and purified by silica gel chromatography to afford tert-butyl N-[2-(2-phenylethylsulfanyl)ethyl]carbamate. LCMS [M+H]$^+$ 282. $^1$H NMR (400 MHz, CHLOROFORM-d) δ ppm 7.28-7.34 (m, 2 H), 7.19-7.26 (m, 3 H), 3.32 (d, J=6.3 Hz, 2 H), 2.86-2.92 (m, 2 H), 2.77-2.84 (m, 2 H), 2.66 (t, J=6.5 Hz, 2 H), 1.43-1.47 (m, 9 H).

Step 2. A mixture of tert-butyl N-[2-(2-phenylethylsulfa-nyl)ethyl]carbamate and TFA was stirred at 20° C. for 1 h. Thereafter the mixture was concentrated to afford 2-(2-phenylethylsulfanyl)ethanamine which was used without purification in step 3.

Step 3. A mixture of 2-(2-phenylethylsulfanyl)ethanamine (1 equiv.), 4,6-dichloropyrimidin-2-amine (1 equiv.), and Hünig's base (3 equiv.) was stirred in 2-propanol at 120° C. for 16 h. Then the mixture was poured into sat. $NaHCO_3$ and extracted with DCM ×3. The combined organics were dried (MgSO4), concentrated, and purified by silica gel chromatography to afford 6-chloro-N4-[2-(2-phenylethylsulfanyl)ethyl]pyrimidine-2,4-diamine. LCMS [M+H]$^+$ 309.

Step 4. The title compound was prepared according to general procedure 2 from 6-chloro-N4-[2-(2-phenylethyl-sulfanyl)ethyl]pyrimidine-2,4-diamine and (3-chloro-2-methyl)phenylboronic acid. LCMS [M+H]$^+$ 399. $^1$H NMR (400 MHz, CHLOROFORM-d) δ ppm 7.38 (dd, J=7.6, 1.9 Hz, 1 H), 7.28-7.33 (m, 2 H), 7.13-7.25 (m, 4 H), 5.78 (s, 1 H), 5.03-5.16 (m, 1 H), 4.83 (br. s., 2 H), 3.54 (d, J=5.1 Hz, 2 H), 2.88-2.95 (m, 2 H), 2.80-2.86 (m, 2 H), 2.77 (t, J=6.6 Hz, 2 H), 2.36 (s, 3 H).

Example 691

6-(3-chloro-2-methyl-phenyl)-N4-[2-[(4-methylsul-fonylphenyl)methylsulfinyl]ethyl]pyrimidine-2,4-diamine A mixture of 6-(3-chloro-2-methyl-phenyl)-N4-[2-[(4-methylsulfonylphenyl)methylsulfanyl]ethyl]pyrimidine-2,4-diamine (example 689) (1 equiv.) and $H_2O_2$ (3 equiv.) in MeOH was stirred at 20° C. for 2 h. Thereafter the mixture was concentrated and purified by silica gel chromatography to afford the title compound. LCMS [M+H]$^+$ 479. $^1$H NMR (400 MHz, CHLOROFORM-d) δ ppm 7.95-8.00 (m, 2 H), 7.51-7.55 (m, 2 H), 7.36-7.40 (m, 1 H), 7.13-7.19 (m, 2 H), 5.81 (s, 1 H), 5.37 (t, J=5.7 Hz, 1 H), 4.92 (s, 2 H), 4.16 (d, J=13.0 Hz, 1 H), 4.04 (d, J=13.3 Hz, 1 H), 3.83-4.01 (m, 2 H), 3.09-3.17 (m, 1 H), 3.08 (s, 3 H), 2.84 (dt, J=13.1, 5.1 Hz, 1 H), 2.36 (s, 3 H).

Example 692

6-(3-chloro-2-methyl-phenyl)-N4-[2-(2-phenylethyl-sulfinyl)ethyl]pyrimidine-2,4-diamine A mixture of 6-(3-chloro-2-methyl-phenyl)-N4-[2-(2-phenylethylsulfanyl)ethyl]pyrimidine-2,4-diamine (example 690) (1 equiv.) and $H_2O_2$ (4 equiv.) in MeOH was stirred at 20° C. for 2 h. Thereafter the mixture was concentrated and purified by silica gel chromatography to afford the title compound. LCMS [M+H]$^+$ 415. $^1$H NMR (400 MHz, CHLOROFORM-d) δ ppm 7.34-7.38 (m, 1 H), 7.30-7.34 (m, 2 H), 7.21-7.28 (m, 4 H), 7.11-7.19 (m, 2 H), 5.80 (s, 1 H), 5.61 (br. s., 1 H), 4.97 (s, 2 H), 3.93 (d, J=5.4 Hz, 2 H), 3.03-3.19 (m, 4 H), 2.87-3.02 (m, 2 H), 2.35 (s, 3 H).

Example 693

6-(3-chloro-2-methyl-phenyl)-N4-[2-[(4-methylsul-fonylphenyl)methylsulfonyl]ethyl]pyrimidine-2,4-diamine A mixture of 6-(3-chloro-2-methyl-phenyl)-N4-[2-[(4-methylsulfonylphenyl)methylsulfanyl]ethyl]pyrimidine-2,4-diamine (example 691) (1 equiv.) and 3-chloroperbenzoic acid (1.5 equiv.) in DCM was stirred at 20° C. for 1 h. The mixture was concentrated and purified by silica gel chromatography to afford the title compound. LCMS [M+H]$^+$ 495. $^1$H NMR (400 MHz, CHLOROFORM-d) δ ppm 7.97-8.02 (m, 2 H), 7.58-7.63 (m, 2 H), 7.37-7.40 (m, 1 H), 7.13-7.21 (m, 2 H), 5.84 (s, 1 H), 5.24 (t, J=6.2 Hz, 1 H), 4.90 (s, 2 H), 4.36 (s, 2 H), 3.96 (q, J=6.2 Hz, 2 H), 3.30 (t, J=6.0 Hz, 2 H), 3.08 (s, 3 H), 2.36 (s, 3 H).

Example 694

6-(3-chloro-2-methyl-phenyl)-N4-[2-(2-phenylethyl-sulfonyl)ethyl]pyrimidine-2,4-diamine A mixture of 6-(3-chloro-2-methyl-phenyl)-N4-[2-(2-phenylethylsulfanyl)ethyl]pyrimidine-2,4-diamine (example 692) (1 equiv.) and 3-chloroperbenzoic acid (1.5 equiv.) in DCM was stirred at 20° C. for 1 h. The mixture was concentrated and purified by silica gel chromatography to afford the title compound. LCMS [M+H]$^+$ 431. $^1$H NMR (400 MHz, CHLOROFORM-d) δ ppm 7.36-7.40 (m, 1 H), 7.24-7.35 (m, 3 H), 7.18-7.22 (m, 2 H), 7.13-7.18 (m, 2 H), 5.81 (s, 1 H), 5.26 (t, J=6.0 Hz, 1 H), 4.87 (s, 2 H), 3.94 (q, J=6.2 Hz, 2 H), 3.28-3.34 (m, 2 H), 3.24 (t, J=6.0 Hz, 2 H), 3.14-3.19 (m, 2 H), 2.35 (s, 3 H).

Example 695

Isopropyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and $H_2SO_4$ (1 equiv.) was stirred in 2-propanol at reflux for 16 h. The mixture was poured into sat. $NaHCO_3$ and extracted with DCM ×3. The combined organics were dried ($MgSO_4$) and concentrated. The crude isopropyl 4-(2-aminoethyl)benzoate was used in step 2 without further purification. LCMS $[M+H]^+$ 208.

Step 2. The title compound was prepared according to general procedure 9 from isopropyl 4-(2-aminoethyl)benzoate and intermediate 24. LCMS $[M+H]^+$ 425. $^1H$ NMR (400 MHz, DMSO-d6) δ ppm 7.88 (d, J=8.2 Hz, 2 H), 7.42 (d, J=8.2 Hz, 2 H), 7.34-7.38 (m, 1 H), 7.20-7.27 (m, 2 H), 7.06 (br. s., 1 H), 6.06 (br. s., 2 H), 5.84 (s, 1 H), 5.13 (spt, J=6.3 Hz, 1 H), 3.52 (br. s., 2 H), 2.92 (t, J=7.4 Hz, 2 H), 2.38 (s, 3 H), 1.32 (d, J=6.3 Hz, 6 H).

Example 696

1-[3-[2-[[2-amino-6-(3-chloro-2-methyl-phenyl)pyrimidin-4-yl]amino]ethyl]phenyl]guanidine A mixture of Intermediate 47 (1 equiv.) and tert-butyl (N2)-N-[(tert-butoxycarbonylamino)-pyrazol-1-yl-methylene]carbamate (1.4 equiv.) in 2-propanol was stirred at 150° C. for 1 h. The mixture was then concentrated and thereafter dissolved in TFA. The resulting mixture was stirred at 150° C. for 30 min. after which it was concentrated and purified by preparative LC. $[M+H]^+$ 396. $^1H$ NMR (400 MHz, METHANOL-d4) δ ppm 7.58-7.63 (m, 1 H), 7.41-7.47 (m, 1 H), 7.29-7.38 (m, 3 H), 7.22 (t, J=1.7 Hz, 1 H), 7.17 (ddd, J=7.9, 2.2, 1.3 Hz, 1 H), 6.02 (s, 1 H), 3.80 (t, J=7.3 Hz, 2 H), 3.01 (t, J=7.3 Hz, 2 H), 2.38 (s, 3 H).

Example 697

4-(2-(2-Amino-6-(3-chloro-2-methylphenyl)pyrimidin-4-ylamino)-1-hydroxyethyl)benzenesulfonamide Step 1: 4-(2-Bromoacetyl)benzenesulfonamide $Br_2$ (7.2 g, 45.0 mmol, in 10 mL HOAc) was added dropwise to the solution of 4-acetylbenzenesulfonamide (9.0 g, 45.0 mmol) in HOAc (250 mL) at 40° C. The reaction mixture was stirred for 1 h at 40° C. After removal of solvent under reduced pressure, the residue was purified by recrystallization from EtOH (20 mL) to yield the product (6.60 g). $^1H$ NMR (300 MHz, CDCl_3): δ 4.99 (s, 2 H), 7.59 (s, 2 H), 7.98 (m, 2 H), 8.16 (m, 2 H) ppm. LC-MS (ESI): m/z 277.93 $[M+H]^+$.

Step 2: 4-(2-Bromo-1-hydroxyethyl)benzenesulfonamide

To the mixture of 4-(2-Bromoacetyl)benzenesulfonamide (1.00 g, 3.6 mmol) in THF (20 mL) was added borane-dimethylsulphide complex (0.33 g, 4.3 mmol) at 0° C. The mixture was stirred for 24 h at R.T. After removal of solvent under reduced pressure, the residue was purified by column chromatography to afford the product (0.30 g). $^1H$ NMR (300 MHz, CDCl_3): δ 3.63 (m, 1 H), 3.72 (m, 1 H), 4.91 (m, 1 H), 6.00 (d, J=4.8 Hz, 1 H), 7.34 (s, 2 H), 7.57 (d, J=8.4 Hz, 1 H), 7.78 (d, J=8.4 Hz, 2 H) ppm.

Step 3: 4-(2-Amino-1-hydroxyethyl)benzenesulfonamide

The mixture of 4-(2-Bromo-1-hydroxyethyl)benzenesulfonamide (0.30 g, 1.1 mmol) and $NH_4OH$ (15 mL) was stirred for 60 h. at R.T. Removal of solvent under reduced pressure afforded the crude product as a yellow solid (100%), which was used for next step without further purification. $^1H$ NMR (400 MHz, $D_2O$): δ 3.08 (m, 1 H), 3.24 (m, 1 H), 4.99 (m, 1 H), 7.54 (m, 2 H), 7.82 (m, 2 H) ppm.

Step 4: 4-(2-(2-Amino-6-(3-chloro-2-methylphenyl)pyrimidin-4-ylamino)-1-hydroxyethyl)benzenesulfonamide The amine prepared in step 3 above (0.23 g, 1.0 mmol), and intermediate 24 (0.27 g, 1.0 mmol) and $NEt_3$ (0.20 g, 2.0 mmol) in i-PrOH (12 mL) was stirred at 95° C. overnight. After removal of solvent, the residue was purified by preparative HPLC to afford the target compound as a white solid (44 mg, 0.10 mmol, 10%, purity 99.8%). $^1H$ NMR (400 MHz, $D_2O$): δ=2.29 (s, 3 H), 3.22 (m, 1 H), 3.31 (s, 1 H), 3.61 (br, 1 H), 4.86 (s, 1 H), 5.77 (m, 1 H), 5.83 (s, 1 H), 6.12 (s, 2 H), 7.21 (m, 2 H), 7.27 (s, 1 H), 7.43 (m, 1 H), 7.59 (m, 2 H), 7.81 (m, 2 H) ppm.

Example 698

6-[2-[[2-amino-6-(3-chloro-2-methyl-phenyl)pyrimidin-4-yl]amino]ethylsulfanyl]pyridine-3-sulfonamide Step 1. A mixture of 6-chloropyridine-3-sulfonamide (1 equiv.), tert-butyl N-(2-sulfanylethyl)carbamate (1.2 equiv.), and Hünig's base (2 equiv.) in 2-propanol was stirred at 120° C. for 16 h. The mixture was then concentrated, dissolved in DCM and passed through a short plug of silica. After concentration the crude residue was used without further purification in step 2.

Step 2. The crude residue from step 1 was stirred in TFA at 20° C. for 2 h. The TFA was then removed by co-evaporation with 2-propanol. Used without further purification in step 3. LCMS $[M+H]^+$ 234.

Step 3. The title compound was prepared according to general procedure 9 from the material from step 2 and intermediate 24. LCMS [M+H]+ 451.

Example 699 methyl 4-[2-[[2-amino-6-(3-chloro-2-methyl-phenyl)pyrimidin-4-yl]amino]ethylsulfanylmethyl]benzoate Step 1. A mixture of methyl 4-(bromomethyl)benzoate (1 equiv.), tert-butyl N-(2-sulfanylethyl)carbamate (1.3 equiv.), and $K_2CO_3$ (1.1 equiv.) were stirred in DMF at 60° C. for 16 h. The mixture was poured into water and extracted with DCM ×3. The combined organics were dried ($MgSO_4$), concentrated, and purified by silica gel chromatography to afford methyl 4-[2-(tert-butoxycarbonylamino)ethylsulfanylmethyl]benzoate.

Step 2. Methyl 4-[2-(tert-butoxycarbonylamino)ethylsulfanylmethyl]benzoate was stirred in TFA at 20° C. for 2 h. The TFA was then removed by co-evaporation with 2-propanol. Used without further purification in step 3.

Step 3. The title compound was prepared according to general procedure 9 from the material from step 2 and intermediate 24. LCMS [M+H]$^+$ 443. $^1$H NMR (400 MHz, METHANOL-d4) δ ppm 7.94-7.98 (m, 2 H), 7.60 (dd, J=7.0, 2.5 Hz, 1 H), 7.47-7.51 (m, 2 H), 7.33-7.37 (m, 2 H), 6.02 (s, 1 H), 3.89 (s, 3 H), 3.87 (s, 2 H), 3.66 (t, J=6.8 Hz, 2 H), 2.71 (t, J=6.8 Hz, 2 H), 2.38 (s, 3 H).

Example 700

6-(3-chloro-2-methyl-phenyl)-N4-[2-[(5-methylisoxazol-3-yl)methylsulfanyl]ethyl]pyrimidine-2,4-diamine Step 1. A mixture of 3-(chloromethyl)-5-methyl-isoxazole (1 equiv.), tert-butyl N-(2-sulfanylethyl)carbamate (1.3 equiv.), and K$_2$CO$_3$ (1.1 equiv.) were stirred in DMF at 60° C. for 16 h. The mixture was poured into water and extracted with DCM ×3. The combined organics were dried (MgSO$_4$), concentrated, and purified by silica gel chromatography to afford tert-butyl N-[2-[(5-methylisoxazol-3-yl)methylsulfanyl]ethyl]carbamate.

Step 2. Tert-butyl N-[2-[(5-methylisoxazol-3-yl)methylsulfanyl]ethyl]carbamate was stirred in TFA at 20° C. for 2 h. The TFA was then removed by co-evaporation with 2-propanol. Used without further purification in step 3.

Step 3. The title compound was prepared according to general procedure 9 from the material from step 2 and intermediate 24. LCMS [M+H]$^+$ 390. $^1$H NMR (400 MHz, METHANOL-d4) δ ppm 7.58-7.62 (m, 1 H), 7.34-7.37 (m, 2 H), 6.18 (d, J=0.9 Hz, 1 H), 6.05 (s, 1 H), 3.77 (s, 2 H), 3.70 (t, J=6.8 Hz, 2 H), 2.73 (t, J=6.8 Hz, 2 H), 2.40 (d, J=0.9 Hz, 3 H), 2.39 (s, 3 H).

Example 701

6-(3-chloro-2-methyl-phenyl)-N4-[2-(3,5-dimethylisoxazol-4-yl)ethyl]pyrimidine-2,4-diamine The title compound was prepared according to general procedure 9 from 2-(3,5-dimethylisoxazol-4-yl)ethanamine and intermediate 24. LCMS [M+H]$^+$ 358. $^1$H NMR (400 MHz, METHANOL-d4) δ ppm 7.60 (dd, J=7.4, 1.4 Hz, 1 H), 7.34-7.38 (m, 1 H), 7.31-7.34 (m, 1 H), 5.99 (s, 1 H), 3.68 (t, J=7.0 Hz, 2 H), 2.71 (t, J=6.8 Hz, 2 H), 2.37 (s, 3 H), 2.33 (s, 3 H), 2.26 (s, 3 H).

Example 702

6-(3-chloro-2-methyl-phenyl)-N4-propyl-pyrimidine-2,4-diamine

The title compound was prepared according to general procedure 9 from propan-1-amine and intermediate 24. LCMS [M+H]$^+$ 277. $^1$H NMR (400 MHz, METHANOL-d4) δ ppm 7.56-7.62 (m, 1 H), 7.32-7.38 (m, 2 H), 6.03 (s, 1 H), 3.45-3.51 (m, 2 H), 2.38 (s, 3 H), 1.62-1.73 (m, 2 H), 0.97-1.03 (m, 3 H).

Example 703

N4-butyl-6-(3-chloro-2-methyl-phenyl)pyrimidine-2,4-diamine

The title compound was prepared according to general procedure 9 from butan-1-amine and intermediate 24. LCMS [M+H]$^+$ 291. $^1$H NMR (400 MHz, METHANOL-d4) δ ppm 7.58-7.63 (m, 1 H), 7.32-7.38 (m, 2 H), 6.02 (s, 1 H), 3.52 (t, J=7.1 Hz, 2 H), 2.38 (s, 3 H), 1.59-1.68 (m, 2 H), 1.38-1.49 (m, 2 H), 0.96-1.02 (m, 3 H).

Example 704

6-(3-chloro-2-methyl-phenyl)-N4-(2-methoxyethyl)pyrimidine-2,4-diamine

The title compound was prepared according to general procedure 9 from 2-methoxyethanamine and intermediate 24. LCMS [M+H]$^+$ 293. $^1$H NMR (400 MHz, METHANOL-d4) δ ppm 7.58-7.62 (m, 1 H), 7.32-7.39 (m, 2 H), 6.08 (s, 1 H), 3.69-3.73 (m, 2 H), 3.57-3.62 (m, 2 H), 3.39 (s, 3 H), 2.38 (s, 3 H).

Example 705

6-(3-chloro-2-methyl-phenyl)-N4-(3-ethoxypropyl)pyrimidine-2,4-diamine

The title compound was prepared according to general procedure 9 from 3-ethoxypropan-1-amine and intermediate 24. LCMS [M+H]$^+$ 321. $^1$H NMR (400 MHz, METHANOL-d4) δ ppm 7.58-7.63 (m, 1 H), 7.32-7.39 (m, 2 H), 6.03 (s, 1H), 3.60 (t, J=7.0 Hz, 2 H), 3.47-3.56 (m, 4 H), 2.38 (s, 3 H), 1.87-1.94 (m, 2H), 1.17-1.22 (m, 3 H).

Example 706

6-(3-chloro-2-methyl-phenyl)-N4-(tetrahydropyran-4-ylmethyl)pyrimidine-2,4-diamine The title compound was prepared according to general procedure 9 from tetrahydropyran-4-ylmethanamine and intermediate 24. LCMS [M+H]$^+$ 333.

Example 707

6-(3-chloro-2-methyl-phenyl)-N4-(tetrahydrofuran-2-ylmethyl)pyrimidine-2,4-diamine The title compound was prepared according to general procedure 9 from tetrahydrofuran-2-ylmethanamine and intermediate 24. LCMS [M+H]$^+$ 319. $^1$H NMR (400 MHz, METHANOL-d4) δ ppm 7.58-7.62 (m, 1 H), 7.32-7.39 (m, 2 H), 6.09 (s, 1 H), 4.12 (dd, J=7.0, 4.4 Hz, 1 H), 3.87-3.95 (m, 1 H), 3.74-3.81 (m, 1 H), 3.63-3.70 (m, 1 H), 3.54-3.61 (m, 1 H), 2.39 (s, 3 H), 2.00-2.11 (m, 1 H), 1.96 (dtd, J=7.7, 6.5, 6.5, 1.4 Hz, 2 H), 1.65 (dd, J=12.0, 8.5 Hz, 1 H).

Example 708

6-(3-chloro-2-methyl-phenyl)-N4-[(2E)-3,7-dimethylocta-2,6-dienyl]pyrimidine-2,4-diamine The title compound was prepared according to general procedure 9 from geranylamine and intermediate 24. LCMS [M+H]$^+$ 371. $^1$H NMR (400 MHz, METHANOL-d4) δ ppm 7.58-7.61 (m, 1 H), 7.31-7.38 (m, 2 H), 6.02 (s, 1 H), 5.30-5.36 (m, 1 H), 5.11 (ddt, J=8.2, 5.5, 1.5, 1.5 Hz, 1 H), 4.12 (dd, J=7.0, 0.6 Hz, 2 H), 2.38 (s, 3 H), 2.09 (s, 4 H), 1.76 (d, J=1.3 Hz, 3 H), 1.67 (d, J=1.3 Hz, 3 H), 1.61 (d, J=0.6 Hz, 3 H).

Example 709

6-(3-chloro-2-methyl-phenyl)-N4-isobutyl-pyrimidine-2,4-diamine

The title compound was prepared according to general procedure 9 from isobutylamine and intermediate 24. LCMS [M+H]$^+$ 291. $^1$H NMR (400 MHz, METHANOL-d4) δ ppm 7.57-7.62 (m, 1 H), 7.33-7.39 (m, 2 H), 6.05 (s, 1 H), 3.36 (d, J=7.0 Hz, 2 H), 2.39 (s, 3 H), 1.96 (dquin, J=13.6, 6.8, 6.8, 6.8, 6.8 Hz, 1 H), 1.00 (s, 3 H), 0.98 (s, 3 H).

Example 710 methyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and H$_2$SO$_4$ (1 equiv.) was stirred in methanol at reflux for 16 h. The mixture was poured into sat. NaHCO$_3$ and extracted with DCM ×3. The combined organics were dried (MgSO4) and concentrated. The crude methyl 4-(2-aminoethyl)benzoate was used in step 2 without further purification. LCMS [M+H]+ 180.

Step 2. The title compound was prepared according to general procedure 9 from methyl 4-(2-aminoethyl)benzoate and intermediate 24. LCMS [M+H]$^+$ 397. $^1$H NMR (400 MHz, METHANOL-d4) δ ppm 7.94 (d, J=8.2 Hz, 2 H), 7.35-7.43 (m, 3 H), 7.13-7.25 (m, 2 H), 5.76 (s, 1 H), 3.89 (s, 3 H), 3.60-3.71 (m, 2 H), 2.98 (t, J=7.1 Hz, 2 H), 2.30 (s, 3 H).

Example 711

Ethyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and H$_2$SO$_4$ (1 equiv.) was stirred in ethanol at reflux for 16 h. The mixture was poured into sat. NaHCO$_3$ and extracted with DCM ×3. The combined organics were dried (MgSO$_4$) and concentrated. The crude ethyl 4-(2-aminoethyl)benzoate was used in step 2 without further purification. LCMS [M+H]+ 194.

Step 2. The title compound was prepared according to general procedure 9 from ethyl 4-(2-aminoethyl)benzoate and intermediate 24. LCMS [M+H]$^+$ 411. $^1$H NMR (400 MHz, METHANOL-d4) δ ppm 7.94 (d, J=8.2 Hz, 2 H), 7.35-7.43 (m, 3 H), 7.13-7.24 (m, 2 H), 5.75 (s, 1 H), 4.35 (q, J=7.3 Hz, 2 H), 3.64 (br. s., 2 H), 2.98 (t, J=7.1 Hz, 2 H), 2.30 (s, 3 H), 1.38 (t, J=7.1 Hz, 3 H).

Example 712 propyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and H$_2$SO$_4$ (1 equiv.) was stirred in 1-propanol at 90° C. for 16 h. The mixture was poured into sat. NaHCO$_3$ and extracted with DCM ×3. The combined organics were dried (MgSO4) and concentrated. The crude propyl 4-(2-aminoethyl)benzoate was used in step 2 without further purification. LCMS [M+H]+ 208.

Step 2. The title compound was prepared according to general procedure 9 from propyl 4-(2-aminoethyl)benzoate and intermediate 24. LCMS [M+H]$^+$ 425. $^1$H NMR (400 MHz, METHANOL-d4) δ ppm 7.95 (d, J=8.2 Hz, 2 H), 7.36-7.43 (m, 3 H), 7.14-7.24 (m, 2 H), 5.76 (s, 1 H), 4.23-4.29 (m, 2 H), 3.60-3.70 (m, 2 H), 2.99 (t, J=7.1 Hz, 2 H), 2.30 (s, 3 H), 1.73-1.85 (m, 2 H), 1.04 (t, J=7.4 Hz, 3 H).

Example 713

6-(3-chloro-2-methyl-phenyl)-N4-(2-phenylethyl)pyrimidine-2,4-diamine

The title compound was prepared according to general procedure 9 from 2-phenylethanamine and intermediate 24. LCMS [M+H]$^+$ 339.

Example 714

6-(3-chloro-2-methyl-phenyl)-N4-[2-(4-pyridyl)ethyl]pyrimidine-2,4-diamine

The title compound was prepared according to general procedure 9 from 2-(4-pyridyl)ethanamine and intermediate 24. LCMS [M+H]$^+$ 340. $^1$H NMR (400 MHz, CHLOROFORM-d) δ ppm 8.53-8.58 (m, 2 H), 7.39 (dd, J=7.6, 1.9 Hz, 1 H), 7.13-7.22 (m, 2 H), 5.77 (s, 1 H), 4.83 (br. s., 2 H), 4.69-4.77 (m, 1 H), 3.65 (br. s., 2 H), 2.94 (t, J=7.0 Hz, 2 H), 2.37 (s, 3 H).

Example 715

6-(3-chloro-2-methyl-phenyl)-N4-[2-(2-pyridyl)ethyl]pyrimidine-2,4-diamine

The title compound was prepared according to general procedure 9 from 2-(2-pyridyl)ethanamine and intermediate 24. LCMS [M+H]$^+$ 340. $^1$H NMR (400 MHz, CHLOROFORM-d) δ ppm 8.51-8.57 (m, 1 H), 7.63 (td, J=7.7, 1.9 Hz, 1 H), 7.37 (dd, J=7.6, 1.6 Hz, 1 H), 7.12-7.22 (m, 4 H), 5.79 (s, 1 H), 5.56 (t, J=5.2 Hz, 1 H), 4.87 (br. s., 2 H), 3.70-3.81 (m, 2 H), 3.09 (t, J=6.6 Hz, 2 H), 2.36 (s, 3 H).

Example 716

2-hydroxyethyl 4-[2-[[2-amino-6-(3-chloro-2-methyl-phenyl) pyrimidin-4-yl]amino]ethyl]benzoate A mixture of 4-[2-[[2-amino-6-(3-chloro-2-methyl-phenyl)pyrimidin-4-yl]amino]ethyl]benzoic acid (prepared in example 485) (1 equiv.) and H$_2$SO$_4$ (1 equiv.) was stirred in ethylene glycol at 120° C. for 2 h. The mixture was then purified by preparative LC. LCMS [M+H]$^+$ 427.

Example 717

2-methylsulfonylethyl 4-[2-[[2-amino-6-(3-chloro-2-methyl-phenyl)pyrimidin-4-yl]amino]ethyl]benzoate A mixture of 4-[2-[[2-amino-6-(3-chloro-2-methyl-phenyl)pyrimidin-4-yl]amino]ethyl]benzoic acid (prepared in example 485) (1 equiv.) and H$_2$SO$_4$ (1 equiv.) was stirred in 2-methylsulfonylethanol at 120° C. for 2 h. The mixture was then purified by preparative LC. LCMS [M+H]$^+$ 489.

Example 718

2,3-dihydroxypropyl 4-[2-[[2-amino-6-(3-chloro-2-methyl-phenyl)pyrimidin-4-yl]amino]ethyl]benzoate A mixture of 4-[2-[[2-amino-6-(3-chloro-2-methyl-phenyl)pyrimidin-4-yl]amino]ethyl]benzoic acid (prepared in example 485) (1 equiv.) and H₂SO₄ (1 equiv.) was stirred in glycerol at 120° C. for 2 h. The mixture was then purified by preparative LC. LCMS [M+H]⁺ 457.

Example 719

6-(3-chloro-2-methyl-phenyl)-N4-[2-[(6-methylsulfonyl-3-pyridyl)amino]ethyl]pyrimidine-2,4-diamine Step 1. N'-(6-methylsulfonyl-3-pyridyl)ethane-1,2-diamine was prepared according to general procedure 13 from 5-bromo-2-methylsulfonyl-pyridine and ethylenediamine.

Step 2. The title compound was prepared according to general procedure 9 from N'-(6-methylsulfonyl-3-pyridyl)ethane-1,2-diamine and intermediate 24. LCMS [M+H]⁺ 433. ¹H NMR (400 MHz, METHANOL-d4) δ ppm 8.11 (d, J=2.8 Hz, 1 H), 7.83 (d, J=8.8 Hz, 1 H), 7.60 (dd, J=7.6, 1.6 Hz, 1 H), 7.30-7.39 (m, 2 H), 7.15 (dd, J=8.8, 2.8 Hz, 1 H), 6.03 (s, 1 H), 3.73-3.79 (m, 2 H), 3.53 (t, J=6.3 Hz, 2 H), 3.10 (s, 3 H), 2.37 (s, 3 H).

Example 720

N-[4-[2-[[2-amino-6-(3-chloro-2-methyl-phenyl)pyrimidin-4-yl]amino]ethylamino]-2-methyl-phenyl]acetamide Step 1. N-[4-(2-aminoethylamino)-2-methyl-phenyl]acetamide was prepared according to general procedure 13 from N-(4-iodo-2-methyl-phenyl)acetamide and ethylenediamine.

Step 2. The title compound was prepared according to general procedure 9 from N-[4-(2-aminoethylamino)-2-methyl-phenyl]acetamide and intermediate 24. LCMS [M+H]⁺ 425. ¹H NMR (400 MHz, METHANOL-d4) δ ppm 7.61 (dd, J=7.6, 1.6 Hz, 1 H), 7.30-7.40 (m, 2 H), 7.15 (d, J=8.2 Hz, 1 H), 6.75 (d, J=12.6 Hz, 2 H), 6.05 (s, 1 H), 3.77 (t, J=6.0 Hz, 2 H), 3.50 (d, J=5.1 Hz, 2 H), 2.38 (s, 3 H), 2.19 (s, 3 H), 2.13 (s, 3 H).

Example 721

6-(3-chloro-2-methyl-phenyl)-N4-[(2Z)-2-(fluoromethylene)-4-(4-fluorophenyl)butyl]pyrimidine-2,4-diamine The title compound was prepared according to general procedure 9 from (2Z)-2-(fluoromethylene)-4-(4-fluorophenyl)butan-1-ammonium chloride and intermediate 24. LCMS [M+H]⁺ 415. ¹H NMR (400 MHz, METHANOL-d4) δ ppm 7.41 (dd, J=7.4, 2.1 Hz, 1 H), 7.14-7.25 (m, 5 H), 6.94 (t, J=8.7 Hz, 2 H), 6.69 (d, J=85.0 Hz, 1 H), 5.80 (s, 1 H), 3.95 (br. s., 2 H), 2.74-2.81 (m, 2 H), 2.39-2.46 (m, 2 H), 2.31 (s, 3 H).

Example 722

Step 1 2-Bromo-5-(methylsulfonyl)pyridine

Isopropylmagnesium chloride (2.0 M, 13.7 mL, 27.4 mmol) was added to a solution of 3,6-dibromopyridine (5.00 g, 21.1 mmol) in THF (18 mL) at 0° C. at a rate which maintained the temperature below 8° C. The reaction mixture was stirred at 0° C. for 45 min. At −15° C. the solution of methanesulfonyl chloride (3.22 g, 28.1 mmol) in THF (4 mL) was added at a rate which maintained the temperature below 5° C. The reaction mixture was allowed to warm up to room temperature and then quenched by adding water (50 mL) and ethyl acetate (30 mL) to it. After separation, the organic layer was dried over Na₂SO₄. After removal of solvent, the residue was purified by column chromatography to afford the expected product (2.4 g). 1H NMR (400 MHz, DMSO-d6): δ=3.37 (s, 3 H), 7.98 (m, 1 H), 8.26 (m, 1 H), 8.89 (d, J=0.4 Hz, 1 H) ppm.

Step 2 6-(3-Chloro-2-methylphenyl)-N4-(2-(5-(methylsulfonyl)pyridin-2-yloxy)ethyl)pyrimidine-2,4-diamine NaH (60%, 86 mg, 2.154 mmol) was added to the solution of 2-[[2-amino-6-(3-chloro-2-methyl-phenyl)pyrimidin-4-yl]amino]ethanol (intermediate 55) (337 mg, 1.44 mmol) in THF (15 mL). The reaction mixture was stirred for 10 min at RT. After addition of Bromo-5-(methylsulfonyl)pyridine (200 mg, 0.72 mmol), the reaction mixture was stirred for 30 min at RT. The reaction was quenched by adding 6 drops of water. After removal of solvent under reduced pressure, the residue was purified by prep HPLC (eluent: mixture of MeCN and 0.1% aqueous NH₄HCO₃ solution) to afford the product. 1H NMR (400 MHz, DMSO-d6): δ=2.29 (s, 3 H), 3.26 (s, 3 H), 3.69 (s, 2 H), 4.50 (t, J=6.4 Hz, 2 H), 5.78 (s, 1 H), 6.11 (s, 2 H), 7.19 (m, 1 H), 7.22 (m, 3 H), 7.44 (m, 1 H), 8.19 (m, 1 H), 8.67 (s, 1 H) ppm.

Example 723

(2-(2-Amino-6-(4-(methylsulfonyl)phenethylamino)pyrimidin-4-yl)-6-chlorophenyl)methanol The solution of (2-(2-Amino-6-chloropyrimidin-4-yl)-6-chlorophenyl)methanol (prepared in example 750; step 2) (55.3 mg, 0.21 mmol), 2-(4-methanesulfonylphenyl)ethan-1-amine (104 mg, 0.45 mmol) and DIPEA (86.3 mg, 0.67 mmol) in n-BuOH (3 mL) was stirred overnight under reflux. After removal the solvent under the reduced pressure, the residue was purified by preparative HPLC to give the product (14.2 mg). ¹H NMR (300 MHz, DMSO-d₆) δ=2.97 (t, J=7.5 Hz, 2 H), 3.19 (s, 3 H), 3.31 (s, 1 H), 3.54 (m, 2 H), 4.45 (s, 2 H), 5.95 (br, 1 H), 6.34 (s, 1 H), 7.38 (m, 2 H), 7.55 (m, 3 H), 7.86 (m, 2 H) ppm.

Example 724 methyl 4-[2-[[2-amino-6-(3-chloro-2-methyl-phenyl)pyrimidin-4-yl]amino]ethylsulfinylmethyl]benzoate A mixture of methyl 4-[2-[[2-amino-6-(3-chloro-2-methyl-phenyl)pyrimidin-4-yl]amino]ethylsulfanylmethyl]benzoate (example 699) (1 equiv.) and H₂O₂ (5 equiv.) in MeOH was stirred at 20° C. for 16 h. Thereafter the mixture was concentrated and purified by preparative LC to afford the title compound. LCMS [M+H]⁺ 459. ¹H NMR (400 MHz, METHANOL-d4) δ ppm 8.03-8.06 (m, 2 H), 7.61 (dd, J=7.6, 1.9 Hz, 1 H), 7.49-7.53 (m, 2 H), 7.31-7.39 (m, 2 H), 6.06 (s, 1 H), 4.33 (d, J=13.0 Hz, 1 H), 4.19 (d, J=13.0 Hz, 1 H), 3.94-4.00 (m, 2 H), 3.23 (ddd, J=13.7, 7.7, 6.3 Hz, 1 H), 3.00 (dt, J=13.4, 5.4 Hz, 1 H), 2.37 (s, 3 H).

Example 725

6-(3-chloro-2-methyl-phenyl)-N4-[2-[(5-methylisoxazol-3-yl)methylsulfinyl]ethyl]pyrimidine-2,4-diamine A mixture of 6-(3-chloro-2-methyl-phenyl)-N4-[2-[(5-methylisoxazol-3-yl)methylsulfanyl]ethyl]pyrimidine-2,4- diamine (example 700) (1 equiv.) and H₂O₂ (5 equiv.) in MeOH was stirred at 20° C. for 16 h. Thereafter the mixture was concentrated and purified by preparative LC to afford the title compound. LCMS [M+H]⁺ 406. ¹H NMR (400 MHz, METHANOL-d4) δ ppm 7.61 (dd, J=7.0, 2.2 Hz, 1 H), 7.31-7.40 (m, 2 H), 6.25 (s, 1 H), 6.08 (s, 1 H), 4.34 (d, J=13.6 Hz, 1 H), 4.14 (d, J=13.9 Hz, 1 H), 3.94-4.00 (m, 2 H), 3.23-3.29 (m, 1 H), 3.09 (dt, J=13.5, 5.6 Hz, 1 H), 2.45 (s, 3 H), 2.38 (s, 3 H).

Example 726

6-(3-chloro-2-methyl-phenyl)-N4-[2-(4-ethylphenyl)ethyl]pyrimidine-2,4-diamine

The title compound was prepared according to general procedure 9 from 2-(4-ethylphenyl)ethanamine and intermediate 24. LCMS [M+H]⁺ 367. ¹H NMR (400 MHz, METHANOL-d4) δ ppm 7.59 (dd, J=7.6, 1.9 Hz, 1 H), 7.30-7.38 (m, 2 H), 7.12-7.20 (m, 4 H), 6.00 (s, 1 H), 3.75 (t, J=7.3 Hz, 2 H), 2.91 (t, J=7.3 Hz, 2 H), 2.61 (q, J=7.6 Hz, 2 H), 2.37 (s, 3 H), 1.20 (t, J=7.6 Hz, 3 H).

Example 727

4-[2-[[2-amino-6-(3-chloro-2-methyl-phenyl)pyrimidin-4-yl]amino]ethyl]benzene-1,2-diol The title compound was prepared according to general procedure 9 from 2-(3,4-dihydroxyphenyl)ethylamine hydrochloride and intermediate 24. LCMS [M+H]⁺ 371.

Example 728

5-[2-[[2-amino-6-(3-chloro-2-methyl-phenyl)pyrimidin-4-yl]amino]ethyl]benzene-1,2,3-triol The title compound was prepared according to general procedure 9 from 2-(3,4,5-trihydroxyphenyl)ethylamine hydrochloride and intermediate 24. LCMS [M+H]⁺ 387. ¹H NMR (400 MHz, METHANOL-d4) δ ppm 7.56-7.62 (m, 1 H), 7.30-7.38 (m, 2 H), 6.24 (s, 2 H), 6.00 (s, 1 H), 3.65-3.72 (m, 2 H), 2.73 (t, J=7.1 Hz, 2 H), 2.38 (s, 3 H).

Example 729

6-(3-chloro-2-methyl-phenyl)-N4-(2-methylallyl)pyrimidine-2,4-diamine

The title compound was prepared according to general procedure 9 from 2-methylprop-2-en-1-amine and intermediate 24. LCMS [M+H]⁺ 289.

Example 730 methyl 4-[2-[[2-amino-6-(3-chloro-2-methyl-phenyl)pyrimidin-4-yl]amino]ethylsulfonylmethyl]benzoate A mixture of methyl 4-[2-[[2-amino-6-(3-chloro-2-methyl-phenyl)pyrimidin-4-yl]amino]ethylsulfinylmethyl]benzoate (example 724) (1 equiv.) and 3-chloroperbenzoic acid (1.5 equiv.) in DCM was stirred at 20° C. for 2 h. The mixture was concentrated and purified by silica gel chromatography to afford the title compound. LCMS [M+H]⁺ 475. ¹H NMR (400 MHz, METHANOL-d4) δ ppm 8.00-8.04 (m, 2 H), 7.53-7.57 (m, 2 H), 7.42 (dd, J=7.1, 2.1 Hz, 1 H), 7.17-7.25 (m, 2 H), 5.85 (s, 1 H), 4.55 (s, 2 H), 3.91 (s, 3 H), 3.85 (t, J=6.5 Hz, 2 H), 3.37 (t, J=6.3 Hz, 2 H), 2.32 (s, 3 H).

Example 731 methyl 4-[[[2-amino-6-(3-chloro-2-methyl-phenyl)pyrimidin-4-yl]amino]methyl]cyclohexanecarboxylate The title compound was prepared according to general procedure 9 from methyl 4-(aminomethyl)cyclohexanecarboxylate and intermediate 24. LCMS [M+H]⁺ 389.
¹H NMR (400 MHz, METHANOL-d4) δ ppm 7.37-7.44 (m, 1 H), 7.16-7.24 (m, 2 H), 5.81 (s, 1 H), 3.65 (s, 3 H), 3.14-3.28 (m, 2 H), 2.25-2.34 (m, 4 H), 1.99 (br. s., 2 H), 1.86-1.94 (m, 2 H), 1.52-1.66 (m, 1 H), 1.41 (dd, J=12.6, 3.5 Hz, 2 H), 1.06 (d, J=3.5 Hz, 2 H).

Example 732

4-[4-[[2-amino-6-(3-chloro-2-methyl-phenyl)pyrimidin-4-yl]amino]but-2-ynylsulfanyl]benzoic acid Step 1. A mixture of 3-sulfanylbenzoic acid (3 equiv.), 4-chlorobut-2-yn-1-amine hydrochloride (1 equiv.), and Hünig's base (6 equiv.) in 2-propanol was stirred at 120° C. for 16 h. A precipitate formed which was collected by filtration and washed with MeOH and DCM to afford 3-(4-aminobut-2-ynylsulfanyl)benzoic acid. LCMS [M+H]⁺ 222.
Step 2. The title compound was prepared according to general procedure 9 from 3-(4-aminobut-2-ynylsulfanyl)benzoic acid and intermediate 24. LCMS [M+H]⁺ 439. ¹H NMR (400 MHz, METHANOL-d4) δ ppm 8.07-8.10 (m, 1 H), 7.85-7.88 (m, 1 H), 7.59-7.66 (m, 2 H), 7.39-7.45 (m, 1 H), 7.35-7.38 (m, 2 H), 6.03 (s, 1 H), 4.29 (t, J=2.1 Hz, 2 H), 3.78 (t, J=2.2 Hz, 2 H), 2.37 (s, 3 H).

Example 733

6-(3-chloro-2-methyl-phenyl)-N4-[2-(3-pyridyl)ethyl]pyrimidine-2,4-diamine

The title compound was prepared according to general procedure 9 from 2-(3-pyridyl)ethanamine and intermediate 24. LCMS [M+H]⁺ 340. ¹H NMR (400 MHz, METHANOL-d4) δ ppm 8.85 (s, 1 H), 8.76 (d, J=5.7 Hz, 1 H), 8.59 (dt, J=7.8, 1.8 Hz, 1 H), 8.03 (dd, J=7.9, 5.7 Hz, 1 H), 7.58-7.62 (m, 1 H), 7.29-7.39 (m, 2 H), 6.03 (s, 1 H), 3.90 (t, J=6.8 Hz, 2 H), 3.24 (t, J=7.0 Hz, 2 H), 2.37 (s, 3 H).

Example 734

6-(3-chloro-2-methyl-phenyl)-N4-(2-pyrimidin-2-ylethyl)pyrimidine-2,4-diamine

The title compound was prepared according to general procedure 9 from 2-pyrimidin-2-ylethanammonium chloride and intermediate 24. LCMS [M+H]⁺ 341. ¹H NMR (400 MHz, CHLOROFORM-d) δ ppm 9.65-10.54 (m, 2 H), 8.75-8.95 (m, 2 H), 7.48 (dd, J=7.7, 1.4 Hz, 1 H), 7.44 (br. s., 1 H), 7.37 (d, J=4.4 Hz, 1 H), 7.18-7.22 (m, 1 H), 7.14-7.17 (m, 1 H), 5.84 (s, 1 H), 4.04 (br. s., 2 H), 3.39 (br. s., 2 H), 2.32 (s, 3 H).

Example 735

6-(3-chloro-2-methyl-phenyl)-N4-(2-pyrazin-2-yl-ethyl)pyrimidine-2,4-diamine

The title compound was prepared according to general procedure 9 from 2-pyrazin-2-ylethanammonium chloride and intermediate 24. LCMS [M+H]+ 341. ¹H NMR (400 MHz, CHLOROFORM-d) δ ppm 8.47-8.62 (m, 3 H), 7.47 (dd, J=7.6, 1.6 Hz, 1 H), 7.34 (t, J=5.7 Hz, 1 H), 7.14-7.22 (m, 2 H), 5.84 (s, 1 H), 3.95 (q, J=6.0 Hz, 2 H), 3.18 (t, J=6.3 Hz, 2 H), 2.33 (s, 3 H).

Example 736

N4-[2-(4-bromophenyl)ethyl]-6-(3-chloro-2-methyl-phenyl)pyrimidine-2,4-diamine

A mixture of 4-chloro-6-(3-chloro-2-methylphenyl)pyrimidin-2-amine (200 mg, 0.79 mmol; Intermediate 24), 2-(4-bromophenyl)ethan-1-amine (183 µL, 1.18 mmol) and triethylamine (200 µl, 1.43 mmol) in n-butanol (3 mL) was heated in a sealed tube at 120° C. for 72 h. The mixture was left at r.t. for 4 h and the solid material was removed by filtration. The filtrate was concentrated and purified by preparative HPLC. LCMS [M+H]+ 417.

Example 737

4-(2-{[2-amino-6-(3-chloro-2-methylphenyl)pyrimidin-4-yl]amino}ethyl)-N-(1-hydroxypropan-2-yl)benzamide Step 1: A mixture of 4,6-dichloropyrimidin-2-amine (600 mg, 3.66 mmol), 4-(2-aminoethyl)benzoic acid hydrochloride (812 mg, 4.02 mmol) and triethylamine (1.53 mL, 10.98 mmol) in n-butanol (20 mL) was heated in a sealed tube at 110° C. overnight and then concentrated. The residue was recrystallized from a mixture of 2-propanol, methanol and water. The solid material was collected by filtration and dried to give 4-{2-[(2-amino-6-chloropyrimidin-4-yl)amino]ethyl}benzoic acid. LCMS [M+H]+ 293.

Step 2: A mixture of 4-{2-[(2-amino-6-chloropyrimidin-4-yl)amino]ethyl}benzoic acid (58 mg, 0.20 mmol), 2-aminopropan-1-ol (30 µL, 0.39 mmol), HATU coupling reagent (91 mg, 0.24 mmol) and triethylamine (80 µL, 0.59 mmol) in DMF (3 mL) was stirred at r.t. for 2 h. Purified by preparative HPLC to give 4-{2-[(2-amino-6-chloropyrimidin-4-yl)amino]ethyl}-N-(1-hydroxypropan-2-yl)benzamide.

Step 3: A mixture of 4-{2-[(2-amino-6-chloropyrimidin-4-yl)amino]ethyl}-N-(1-hydroxypropan-2-yl)benzamide (40 mg, 0.11 mmol), (3-chloro-2-methylphenyl)boronic acid (25 mg, 0.15 mmol), Pd(PPh₃)₄ (7 mg, 0.010 mmol) and potassium carbonate (32 mg, 0.23 mmol) in 1,4-dioxane/water (5 mL; 4:1) was heated in a sealed tube at 90° C. overnight. The mixture was concentrated and purified by preparative HPLC to give 4-(2-{[2-amino-6-(3-chloro-2-methylphenyl)pyrimidin-4-yl]amino}ethyl)-N-(1-hydroxypropan-2-yl)benzamide. LCMS [M+H]+ 440.

Example 738

Give 6-(3-chloro-2-methylphenyl)-4-N-{2-[4-(4-methylpiperazine-1-carbonyl)phenyl]ethyl}pyrimidine-2,4-diamine Step 1: A mixture of 4-{2-[(2-amino-6-chloropyrimidin-4-yl)amino]ethyl}benzoic acid (59 mg, 0.20 mmol) prepared in example 737 step 1, 1-methylpiperazine (40 µL, 0.36 mmol), HATU coupling reagent (91 mg, 0.24 mmol) and triethylamine (80 µL, 0.59 mmol) in DMF (3 mL) was stirred at r.t. for 2 h. Purified by preparative HPLC to give 6-chloro-4-N-{2-[4-(4-methylpiperazine-1-carbonyl)phenyl]ethyl}pyrimidine-2,4-diamine. LCMS [M+H]+ 375.

Step 2: A mixture of 6-chloro-4-N-{2-[4-(4-methylpiperazine-1-carbonyl)phenyl]ethyl}pyrimidine-2,4-diamine (30 mg, 0.080 mmol), (3-chloro-2-methylphenyl)boronic acid (18 mg, 0.10 mmol), Pd(PPh₃)₄ (5 mg, 0.0043 mmol) and potassium carbonate (22 mg, 0.16 mmol) in 1,4-dioxane/water (5 mL; 4:1) was heated in a sealed tube at 90° C. overnight. The mixture was concentrated and purified by preparative HPLC to give 6-(3-chloro-2-methylphenyl)-4-N-{2-[4-(4-methylpiperazine-1-carbonyl)phenyl]ethyl}pyrimidine-2,4-diamine. LCMS [M+H]+ 465.

Example 739

6-(3-chloro-2-methylphenyl)-N4-[2-(4-methanesulfinylphenyl)ethyl]pyrimidine-2,4-diamine Step 1: A mixture of 1-bromo-4-methanesulfinylbenzene (88 mg, 0.40 mmol), potassium benzyl N-[2-(trifluoroboranuidyl)ethyl]carbamate (160 mg, 0.56 mmol), caesium carbonate (261 mg, 0.80 mmol), Pd(OAc)₂ (9 mg, 0.040 mmol) and 2-dicyclohexylphosphino-2',6'-diisopropoxybiphenyl (37 mg, 0.080 mmol) in 1,4-dioxane/water (5 mL; 4:1) was heated in a sealed tube at 100° C. overnight. The mixture was concentrated and purified by preparative HPLC to give benzyl N-[2-(4-methanesulfinylphenyl)ethyl]carbamate. LCMS [M+H]+ 318.

Step 2: Benzyl N-[2-(4-methanesulfinylphenyl)ethyl]carbamate (39 mg, 0.12 mmol) was heated in TFA (1 mL) at 70° C. overnight. The mixture was concentrated and dried under vacuum to give 2-(4-methanesulfinylphenyl)ethan-1-amine; trifluoroacetic acid. LCMS [M+H]+ 184.

Step 3: A mixture of 4-chloro-6-(3-chloro-2-methylphenyl)pyrimidin-2-amine (25 mg, 0.10 mmol; Intermediate 24), 2-(4-methanesulfinylphenyl)ethan-1-amine; trifluoroacetic acid (33 mg, 0.11 mmol) and potassium carbonate (34 mg, 0.25 mmol) in acetonitrile (2 mL) was heated at 150° C. for 1 h using microwave irradiation. The mixture was concentrated and purified by preparative HPLC to give 6-(3-chloro-2-methylphenyl)-N4-[2-(4-methanesulfinylphenyl)ethyl]pyrimidine-2,4-diamine. LCMS [M+H]+ 401.

Example 740

4-[2-({2-amino-6-[2-methyl-3-(trifluoromethyl)phenyl]pyrimidin-4-yl}amino)ethyl]benzene-1-sulfonamide Step 1: A mixture of 1-bromo-2-methyl-3-(trifluoromethyl)benzene (100 µL, 0.64 mmol), 4,4,5,5-tetramethyl-2-(tetramethyl-1,3,2-dioxaborolan-2-yl)-1,3,2-dioxaborolane (327 mg, 1.29 mmol), PdCl₂dppf.DCM (26 mg, 0.030 mmol) and potassium acetate (158 mg, 1.61 mmol) in 1,4-dioxane (5 mL) was heated in a sealed tube at 80° C. overnight. The mixture was run through a plug of silica (EtOAc), concentrated and purified by preparative HPLC to give 4,4,5,5-tetramethyl-2-[2-methyl-3-(trifluoromethyl)phenyl]-1,3,2-dioxaborolane.

Step 2: A mixture of 4-{2-[(2-amino-6-chloropyrimidin-4-yl)amino]ethyl}benzene-1-sulfonamide (25 mg, 0.080 mmol; Intermediate 25), 4,4,5,5-tetramethyl-2-[2-methyl-3-(trifluoromethyl)phenyl]-1,3,2-dioxaborolane (26 mg, 0.090

237 mmol), Pd(PPh₃)₄ (9 mg, 0.010 mmol) and potassium carbonate (21 mg, 0.15 mmol) in 1,4-dioxane/water (5 mL; 4:1) was heated in a sealed tube at 90° C. overnight. The mixture was concentrated and purified by preparative HPLC to give 4-[2-({2-amino-6-[2-methyl-3-(trifluoromethyl)phenyl]pyrimidin-4-yl}amino)ethyl]benzene-1-sulfonamide. LCMS [M+H]⁺ 452.

Example 741

N4-[2-(4-methanesulfonylphenyl)ethyl]-6-[2-methyl-3-(trifluoromethyl)phenyl]pyrimidine-2,4-diamine A mixture of 6-chloro-4-N-[2-(4-methanesulfonylphenyl)ethyl]pyrimidine-2,4-diamine (25 mg, 0.080 mmol; Intermediate 33), 4,4,5,5-tetramethyl-2-[2-methyl-3-(trifluoromethyl)phenyl]-1,3,2-dioxaborolane (26 mg, 0.090 mmol) prepared in example 740, Step 1), Pd(PPh₃)₄ (9 mg, 0.010 mmol) and potassium carbonate (21 mg, 0.15 mmol) in 1,4-dioxane/water (5 mL; 4:1) was heated in a sealed tube at 90° C. overnight. The mixture was concentrated and purified by preparative HPLC to give N4-[2-(4-methanesulfonylphenyl)ethyl]-6-[2-methyl-3-(trifluoromethyl)phenyl]pyrimidine-2,4-diamine. LCMS [M+H]⁺ 451.

Example 742

4-(3-chloro-2-methylphenyl)-5H,6H,7H-pyrrolo[2,3-d]pyrimidin-2-amine

Step 1: To an oven-dried flask containing 4,6-dichloro-2-(methylsulfanyl)pyrimidine (390 mg, 2.0 mmol) in anhydrous THF (7.5 mL) was added TMPMgCl.LiCl (2.4 mL, 2.4 mmol; as a 1M solution in THF) at r.t. After stirring for 30 min, tert-butyl 1,2,3-oxathiazolidine-3-carboxylate 2,2-dioxide (469 mg, 2.1 mmol) was added and the reaction was stirred for a further 1 h at r.t. To the mixture was added 1M citric acid (7.5 mL) and EtOAc (7.5 mL) followed by vigorous stirring for 5 min. The organic layer concentrated to give tert-butyl N-{2-[4,6-dichloro-2-(methylsulfanyl)pyrimidin-5-yl]ethyl}.

Step 2: The material from Step 1 was stirred in TFA (7.5 mL) for 15 min and then concentrated. The residue was dissolved in acetonitrile (20 mL) and triethylamine (1.1 mL, 8.0 mmol) was added and the resulting mixture was heated at 80° C. for 30 min. The mixture was concentrated and run through a plug of silica (EtOAc) to give 4-chloro-2-(methylsulfanyl)-5H,6H,7H-pyrrolo[2,3-d]pyrimidine.

Step 3: A mixture of 4-chloro-2-(methylsulfanyl)-5H,6H,7H-pyrrolo[2,3-d]pyrimidine (151 mg, 0.75 mmol), (3-chloro-2-methylphenyl)boronic acid (153 mg, 0.90 mmol), Pd(PPh₃)₄ (43 mg, 0.040 mmol) and potassium carbonate (207 mg, 1.5 mmol) in 1,4-dioxane/water (5 mL; 4:1) was heated in a sealed tube at 90° C. for 1.5 h. The mixture was concentrated and purified by preparative HPLC to give 4-(3-chloro-2-methylphenyl)-2-(methylsulfanyl)-5H,6H,7H-pyrrolo[2,3-d]pyrimidine. LCMS [M+H]⁺ 292.

Step 4: A mixture of 4-(3-chloro-2-methylphenyl)-2-(methylsulfanyl)-5H,6H,7H-pyrrolo[2,3-d]pyrimidine; trifluoroacetic acid (70 mg, 0.17 mmol) and Oxone (318 mg, 0.52 mmol) in methanol (4 mL) and water (1.5 mL) was stirred at r.t. overnight. The mixture was concentrated and partitioned between water (15 mL) and EtOAc (30 mL). The organic layer was washed with water (15 mL) and concentrated to give 4-(3-chloro-2-methylphenyl)-2-methanesulfonyl-5H,6H,7H-pyrrolo[2,3-d]pyrimidine.

238

Step 5: A mixture of 4-(3-chloro-2-methylphenyl)-2-methanesulfonyl-5H,6H,7H-pyrrolo[2,3-d]pyrimidine (285 mg, 0.88 mmol), 25% aq NH₄OH (2 mL) and n-propanol (2 mL) was heated at 150° C. for 1 h using microwave irradiation. The mixture was concentrated and purified by preparative HPLC to give 4-(3-chloro-2-methylphenyl)-5H,6H,7H-pyrrolo[2,3-d]pyrimidin-2-amine. LCMS [M+H]⁺ 261; ¹H NMR (400 MHz, CD₃OD) δ ppm 7.55-7.65 (m, 1 H), 7.34-7.41 (m, 2 H), 3.73-3.84 (m, 2 H), 2.78-2.95 (m, 2 H), 2.37 (s, 3 H).

Example 743

(6R)-4-(3-Chloro-2-methylphenyl)-6-methyl-5H,6H,7H-pyrrolo[2,3-d]pyrimidin-2-amine Prepared according to the same procedure as describe for example 742 above starting from 4,6-dichloro-2-(methylsulfanyl)pyrimidine and tert-butyl (R)-4-methyl-1,2,3-oxathiazolidine-3-carboxylate 2,2-dioxide. LCMS [M+H]⁺ 275.

Example 744

6-(3-chloro-2-methylphenyl)-N4-(2-{[5-(trifluoromethyl)pyridin-2-yl]oxy}ethyl)pyrimidine-2,4-diamine A mixture of 2-[[2-amino-6-(3-chloro-2-methyl-phenyl)pyrimidin-4-yl]amino]ethanol (intermediate 55), 2-chloro-5-(trifluoromethyl)pyridine (1.5 equiv.) and Cs₂CO₃ (2.0 equiv.) in DMSO was heated in a sealed tube at 90° C. for 16 h. After cooling was methanol added, followed by filtration and purification by preparative LC to give the title compound. LCMS [M+H]⁺ 424. ¹H NMR (400 MHz, METHANOL-d₄) δ ppm 8.43-8.53 (m, 1 H), 7.88-8.03 (m, 1 H), 7.52-7.67 (m, 1 H), 7.29-7.39 (m, 2 H), 6.95-7.00 (m, 1 H), 6.07 (s, 1 H), 4.50-4.69 (m, 1 H), 3.96 (t, J=5.4 Hz, 2 H), 2.38 (s, 3 H).

Example 745

6-(3-chloro-2-methylphenyl)-N4-(2-{furo[3,2-c]pyridin-4-yloxy}ethyl)pyrimidine-2,4-diamine A mixture of 2-[[2-amino-6-(3-chloro-2-methyl-phenyl)pyrimidin-4-yl]amino]ethanol (intermediate 55), 4-chloro-furo[3,2-c]pyridine (1.5 equiv.) and Cs₂CO₃ (2.0 equiv.) in DMSO was heated in a sealed tube at 110° C. for 16 h. After cooling was methanol added, followed by filtration and purification by preparative LC to give the title compound. LCMS [M+H]⁺ 396. ¹H NMR (400 MHz, METHANOL-d₄) δ ppm 7.97 (d, J=6.0 Hz, 1 H), 7.79 (d, J=2.2 Hz, 1 H), 7.60 (dd, J=7.3, 2.2 Hz, 1 H), 7.29-7.38 (m, 2 H), 7.22 (dd, J=6.0, 0.9 Hz, 1 H), 6.92 (dd, J=2.2, 0.9 Hz, 1 H), 6.07 (s, 1 H), 4.69 (t, J=5.2 Hz, 2 H), 4.01 (t, J=5.4 Hz, 2 H), 2.36 (s, 3 H).

Example 746

6-(3-chloro-2-methylphenyl)-N4-{2-[(5-chloropyridin-2-yl)oxy]ethyl}pyrimidine-2,4-diamine A mixture of 2-[[2-amino-6-(3-chloro-2-methyl-phenyl)pyrimidin-4-yl]amino]ethanol (intermediate 55), 2,5-dichloropyridine (1.5 equiv.) and Cs₂CO₃ (2.0 equiv.) in DMSO was heated in a sealed tube at 110° C. for 16 h. After cooling methanol was added followed, by filtration and purification by preparative LC to give the title compound. LCMS

[M+H]+ 390. ¹H NMR (400 MHz, METHANOL-d₄) δ ppm 8.09-8.13 (m, 1 H), 7.69 (dd, J=8.8, 2.8 Hz, 1 H), 7.58-7.63 (m, 1 H), 7.31-7.39 (m, 2 H), 6.83 (dd, J=8.8, 0.6 Hz, 1 H), 6.07 (s, 1 H), 4.51 (t, J=5.2 Hz, 2 H), 3.92 (t, J=5.4 Hz, 2 H), 2.38 (s, 3 H).

Example 747

4-(2-{[2-amino-6-(3-chloro-2-methylphenyl)pyrimidin-4-yl]amino}ethoxy)benzonitrile A mixture of 4-chloro-6-(3-chloro-2-methylphenyl)pyrimidin-2-amine (intermediate 24), 4-(2-aminoethoxy)benzonitrile (1.5 equiv.) and N,N-Diisopropylethylamine (2 equiv.) in 2-propanol (0.3 mL) was heated in a sealed tube at 100° C. for 30 h. Purification by column chromatography afforded the title compound (70% EtOAc in iso-Hexane). LCMS [M+H]+ 380. ¹H NMR (400 MHz, DMSO-d₆) δ ppm 7.75-7.82 (m, 2 H), 7.44 (dd, J=7.7, 1.4 Hz, 1 H), 7.17-7.28 (m, 3 H), 7.15 (d, J=8.8 Hz, 2 H), 6.10 (br. s., 2 H), 5.79 (s, 1 H), 4.20 (t, J=5.7 Hz, 2 H), 3.60-3.76 (m, 2 H), 2.29 (s, 3 H),

Example 748

(Z)-4-(2-{[2-amino-6-(3-chloro-2-methylphenyl)pyrimidin-4-yl]amino}ethoxy)-N'-hydroxybenzene-1-carboximidamide 4-(2-{[2-amino-6-(3-chloro-2-methylphenyl)pyrimidin-4-yl]amino}ethoxy)benzonitrile (prepared in example 747) was dissolved in DMSO (1 mL). H₂O₂ (4.0 equiv.) and 5M NaOH was added and the reaction was stirred at room temperature for 30 min. Methanol was added followed, by filtration and purification by preparative LC to give the title compound. LCMS [M+H]+ 398. ¹H NMR (400 MHz, DMSO-d₆) δ ppm 7.80-7.89 (m, 4 H), 7.44 (dd, J=7.7, 1.7 Hz, 1H), 7.22-7.27 (m, 1 H), 7.20 (dd, J=7.7, 1.7 Hz, 2 H), 7.01 (d, J=8.8 Hz, 2 H), 6.10 (s, 2 H), 5.80 (s, 1 H), 4.16 (t, J=5.7 Hz, 2 H), 3.59-3.76 (m, 2 H), 2.29 (s, 3 H).

Example 749

6-(3-chloro-2-methylphenyl)-N4-{2-[4-(2H-1,2,3,4-tetrazol-5-yl)phenoxy]ethyl}pyrimidine-2,4-diamine A mixture of 4-[2-[[2-amino-6-(3-chloro-2-methyl-phenyl)pyrimidin-4-yl]amino]ethoxy]benzonitrile, (prepared in example 747) sodium azide (1.2 equiv.), ammonium chloride (1.2 equiv.) in DMF was heated in a sealed dry tube at 130° C. for 24 hours. After cooling methanol was added followed by filtration and purification by preparative LC to give the title compound. LCMS [M+H]+ 423. ¹H NMR (400 MHz, METHANOL-d₄) δ ppm 7.91-7.99 (m, 2 H), 7.35-7.45 (m, 1 H), 7.17-7.24 (m, 2 H), 6.99-7.08 (m, 2 H), 5.90 (s, 1 H), 4.21 (t, J=5.5 Hz, 2 H), 3.73-3.86 (m, 2 H), 2.32 (s, 3 H)

Example 750

4-(2-(2-Amino-6-(3-chloro-2-(hydroxymethyl)phenyl)pyrimidin-4-ylamino)ethyl) Benzenesulfonamide

Step 1: (3-Chloro-2-(hydroxymethyl)phenylboronic Acid

The solution of 2-borono-6-chlorobenzoic acid (1.40 g, 7.0 mmol) in THF (5 mL) was added dropwise to a stirred suspension of LiAlH₄ (1.60 g, 42.0 mmol) in THF (20 mL) at 0° C. The mixture was stirred under reflux for 3 h. The solvent was removed under reduced pressure to give white solid. 1M HCl was added dropwise at 0° C. The mixture was filtered to give the product (0.80 g). ¹H NMR (400 MHz, DMSO-d₆): δ=4.99 (s, 2 H), 7.41 (m, 1 H), 7.53 (m, 1 H), 7.70 (m, 1 H), 9.45 (s, 1 H) ppm.

Step 2: (2-(2-Amino-6-chloropyrimidin-4-yl)-6-chlorophenyl)methanol

To the solution of (3-Chloro-2-(hydroxymethyl)phenylboronic acid (0.80 g, 4.3 mmol), 4,6-dichloropyrimidin-2-amine (1.40 g, 8.6 mmol), and Na₂CO₃ (1.00 g, 9.5 mmol) in dioxane/H₂O (32 mL/8 mL), Pd(PPh₃)₄ (150 mg, 0.13 mmol, 3 mol %) was then added. The mixture was stirred for h at 90° C. The solvent was removed under the reduced pressure. The residue was treated with DCM (10 mL×3). The organic layer was washed with brine (10 mL). After removal of solvent under the reduced pressure, the residue was purified by column chromatography (silica gel, petroleum ether/ethyl acetate=5/1) to give the product (0.10 g). ¹H NMR (400 MHz, CDCl₃): δ=4.69 (s, 2 H), 5.52 (m, 1 H), 6.93 (s, 1 H), 7.36 (m, 3H), 7.55 (m, 1 H) ppm.

Step 3: 4-(2-(2-Amino-6-(3-chloro-2-(hydroxymethyl)phenyl)pyrimidin-4-ylamino)ethyl)benzenesulfonamide To the solution of (2-(2-Amino-6-chloropyrimidin-4-yl)-6-chlorophenyl)methanol (42.7 mg, 0.16 mmol), 4-(2-aminoethyl)benzenesulfonamide (47.6 mg, 0.24 mmol) and DIPEA (41.3 mg, 0.32 mmol), the mixture was refluxed overnight. After removal the solvent under reduced pressure, the residue was purified by preparative TLC to afford the product as white solid (20.3 mg). ¹H NMR (400 MHz, CDCl₃): δ=3.06 (t, J=6.3 Hz, 2 H), 3.82 (t, J=6.6 Hz, 2 H), 4.75 (s, 2 H), 6.20 (s, 1 H), 7.48 (m, 4 H), 7.67 (m, 1 H), 7.86 (m, 2 H) ppm.

Example 751

(Z)-4-(2-{[2-amino-6-(3-chloro-2-methylphenyl)pyrimidin-4-yl]amino}ethoxy)-N'-hydroxybenzene-1-carboximidamide To a solution of 4-[2-[[2-amino-6-(3-chloro-2-methylphenyl)pyrimidin-4-yl]amino]ethoxy]benzonitrile (intermediate 61) methanol was added the hydroxylamine HCL salt (3.0 equiv.) and N,N-Diisopropylethylamine (3.2 equiv.) and stirred at 80° C. for 90 min. The reaction mixture was cooled to 23° C. and concentrated in vacuo. Dichloromethane and water were added, the phases were separated, and the organic layer was washed with brine, dried (Na₂SO₄), filtered, and concentrated in vacuo. The crude was dissolved in methanol, followed by filtration and purification by preparative LC to give the title compound. LCMS [M+H]+ 413.

Example 752

6-(3-chloro-2-methylphenyl)-N4-[3-(4-methanesulfonylphenoxy)propyl]pyrimidine-2,4-diamine A mixture of 3-{[2-amino-6-(3-chloro-2-methylphenyl)pyrimidin-4-yl]amino}propan-1-ol (intermediate 60), 1-fluoro-4-methylsulfonyl-benzene (1.1 equiv.) and Cs₂CO₃ (2.0 equiv.) in DMSO was heated in a sealed tube at 90° C.

for 1 h. After cooling was methanol added to the solution, followed by filtration and purification by preparative LC to furnish the title compound. LCMS [M+H]$^+$ 447. $^1$H NMR (400 MHz, METHANOL-d$_4$) δ ppm 7.85-7.91 (m, 2 H), 7.60 (dd, J=7.4, 2.1 Hz, 1 H), 7.34 (d, J=5.7 Hz, 2 H), 7.10-7.18 (m, 2 H), 6.04 (s, 1 H), 4.22 (t, J=6.0 Hz, 2 H), 3.75 (t, J=6.6 Hz, 2 H), 3.08 (s, 3 H), 2.37 (s, 3 H), 2.18 (quin, J=6.3 Hz, 2 H)

Example 753

2-(3-{[2-amino-6-(3-chloro-2-methylphenyl)pyrimidin-4-yl]amino}propoxy)pyrimidine-4-carboxamide A mixture of 3-{[2-amino-6-(3-chloro-2-methylphenyl)pyrimidin-4-yl]amino}propan-1-ol (intermediate 60), 2-chloropyrimidine-4-carboxamide (1.1 equiv.) and Cs$_2$CO$_3$ (2.0 equiv.) in DMSO was heated in a sealed tube at 90° C. for 2 h. After cooling was methanol added to the solution, followed by filtration and purification by preparative LC to furnish the title compound. LCMS [M+H]$^+$414. $^1$H NMR (400 MHz, METHANOL-d$_4$) δ ppm 8.79 (d, J=5.1 Hz, 1 H), 7.69 (s, 1 H), 7.55-7.63 (m, 1 H), 7.30-7.41 (m, 3 H), 6.04 (s, 1 H), 4.59 (t, J=6.0 Hz, 2 H), 3.76 (t, J=6.8 Hz, 2 H), 2.18 (quin, J=6.3 Hz, 3 H).

Example 754

6-(3-{[2-amino-6-(3-chloro-2-methylphenyl)pyrimidin-4-yl]amino}propoxy)pyridine-3-carboxamide A mixture of 3-{[2-amino-6-(3-chloro-2-methylphenyl)pyrimidin-4-yl]amino}propan-1-ol (intermediate 60), 6-chloropyridine-3-carboxamide (1.1 equiv.) and Cs$_2$CO$_3$ (2.0 equiv.) in DMSO was heated in a sealed tube at 90° C. for 2 h. After cooling was methanol added to the solution, followed by filtration and purification by preparative LC to furnish the title compound. LCMS [M+H]$^+$413. $^1$H NMR (400 MHz, METHANOL-d$_4$) δ ppm 8.67 (dd, J=2.5, 0.6 Hz, 1 H), 8.13 (dd, J=8.8, 2.5 Hz, 1 H), 7.58-7.63 (m, 1 H), 7.29-7.40 (m, 2 H), 6.86 (dd, J=8.8, 0.6 Hz, 1 H), 6.03 (s, 1 H), 4.48 (t, J=6.2 Hz, 2 H), 3.72 (t, J=6.6 Hz, 2 H), 2.37 (s, 3 H), 2.15 (quin, J=6.4 Hz, 2 H).

Example 755

6-(3-chloro-2-methylphenyl)-N4-{2-[4-(morpholine-4-sulfonyl)phenyl]ethyl}pyrimidine-2,4-diamine Morpholine (6 equiv.) and 4-(2-acetamidoethyl)benzene-1-sulfonyl chloride (intermediate 62) (1 equiv.) were heated neat at 70° C. for 30 min. 2.5 M NaOH (26 equiv.) was added and the reaction was heated in the micro wave oven for 15 min at 150° C. The mixture was extracted with DCM and the organic phase was dried over MgSO$_4$ and removed in vacuo. The crude product was dissolved in MeOH and 4-chloro-6-(3-chloro-2-methylphenyl)pyrimidin-2-amine (intermediate 24) (1 equiv.) was added. The solvent was removed and the mixture was melted for 15 min at 160° C. The crude material was dissolved in MeOH and purified by preparative LC to afford the title compound. LCMS [M+H]$^+$ 488. $^1$H NMR (400 MHz, DMSO-d6) δ ppm 2.29 (3 H, s) 2.78-2.88 (4 H, m) 2.96 (2 H, t, J=7.19 Hz) 3.45-3.59 (2 H, m) 3.59-3.67 (4 H, m) 5.74 (1 H, s) 6.06 (2 H, br. s.) 7.07 (1 H, br. s.) 7.17-7.27 (2 H, m) 7.40-7.47 (1 H, m) 7.53-7.59 (2 H, m) 7.63-7.70 (2 H, m)

Example 756

4-(2-{[2-amino-6-(3-chloro-2-methylphenyl)pyrimidin-4-yl]amino}ethyl)-N-(2-methoxyethyl)benzene-1-sulfonamide 2-Methoxyethan-1-amine (6 equiv.) and 4-(2-acetamidoethyl)benzene-1-sulfonyl chloride (intermediate 62) (1 equiv.) were heated neat at 70° C. for 30 min. 2.5M NaOH (26 equiv.) was added and the reaction was heated in the micro for 15 min at 150° C. 12M HCl (26 equiv.) was added and the solvent was removed in vacuo. MeOH was added and NaCl was removed by filtration. 4-chloro-6-(3-chloro-2-methylphenyl)pyrimidin-2-amine (intermediate 24) (1 equiv.) was added and the solvent was evaporated at 80° C. The crude material was melted at 160° C. for 30 min. The crude material was dissolved in MeOH and purified by preparative LC to afford the title compound. LCMS [M+H]$^+$ 476.

Example 757

4-(2-{[2-amino-6-(3-chloro-2-methylphenyl)pyrimidin-4-yl]amino}ethyl)-N-(oxetan-3-yl)benzene-1-sulfonamide Oxetan-3-amine (6 equiv.) and 4-(2-acetamidoethyl)benzene-1-sulfonyl chloride intermediate 62 (1 equiv.) were heated neat at 70° C. for 30 min. 2,5M NaOH (26 equiv.) was added and the reaction was heated in the micro for 15 min at 150° C. 12M HCl (26 equiv.) was added and the solvent was removed in vacuo. MeOH was added and NaCl was removed by filtration. 4-chloro-6-(3-chloro-2-methylphenyl)pyrimidin-2-amine (intermediate 24) (1 equiv.) was added and the solvent was evaporated at 80° C. The crude material was melted at 160° C. for 30 min. The crude material was dissolved in MeOH and purified by preparative LC to afford the title compound. LCMS [M+H]$^+$ 474.

Example 758

4-(2-{[2-amino-6-(3-chloro-2-methylphenyl)pyrimidin-4-yl]amino}ethyl)-N-(oxan-4-yl)benzene-1-sulfonamide oxan-4-amine (6 equiv.) and 4-(2-acetamidoethyl)benzene-1-sulfonyl chloride intermediate 62 (1 equiv.) were heated neat at 70° C. for 30 min. 2,5M NaOH (26 equiv.) was added and the reaction was heated in the micro for 15 min at 150° C. 12M HCl (26 equiv.) was added and the solvent was removed in vacuo. MeOH was added and NaCl was removed by filtration. 4-chloro-6-(3-chloro-2-methylphenyl)pyrimidin-2-amine (intermediate 24) (1 equiv.) was added and the solvent was evaporated at 80° C. The crude material was melted at 160° C. for 30 min. The crude material was dissolved in MeOH and purified by preparative LC to afford the title compound. LCMS [M+H]$^+$ 502.

Example 759

4-(2-{[2-amino-6-(3-chloro-2-methylphenyl)pyrimidin-4-yl]amino}ethyl)-N-methyl-N-(prop-2-yn-1-yl)benzamide Step 1 sodium 4-(2-{[2-amino-6-(3-chloro-2-methylphenyl)pyrimidin-4-yl]amino}ethyl)benzoate Methyl 4-(2-{[2-amino-6-(3-chloro-2-methylphenyl)pyrimidin-4-yl]amino}ethyl)benzoate (prepared in example 710) (1 eq), MeOH and 5M NaOH (1.1 eq) were heated in a sealed tube for 8 hours at 115° C. The title compound was isolated by removing the solvent in vacuo. LCMS [M+H]+ 383.

Step 2 TBTU (1.5 eq) was added to a stirred mixture of sodium 4-(2-{[2-amino-6-(3-chloro-2-methylphenyl)pyrimidin-4-yl]amino}ethyl)benzoate (1 eq), methyl(prop-2-yn-1-yl)amine (3 eq), Hunigs (5 eq) and dry DMF. The mixture was stirred at r.t. in a sealed tube for 4 hours. The mixture was purified by preparative LC to give the title compound. LCMS [M+H]+ 434 1H NMR (400 MHz, DMSO-d6) d ppm 2.26-2.31 (3 H, m) 2.88 (1 H, t, J=7.35 Hz) 2.97 (3 H, br. s.) 3.23-3.40 (1 H, m) 3.51 (2 H, br. s.) 3.95-4.41 (2 H, m) 5.74 (1H, s) 6.06 (2 H, br. s.) 7.08 (1 H, br. s.) 7.18-7.28 (2 H, m) 7.32-7.40 (4 H, m) 7.44 (1 H, dd, J=7.58, 1.74 Hz)

Example 760

6-(3-chloro-2-methylphenyl)-N4-[2-(4-ethynylphenyl)ethyl]pyrimidine-2,4-diamine

Step 1: N4-[2-(4-bromophenyl)ethyl]-6-(3-chloro-2-methylphenyl)pyrimidine-2,4-diamine $N_2$ was bubbled through a mixture of N4-[2-(4-bromophenyl)ethyl]-6-(3-chloro-2-methylphenyl)pyrimidine-2,4-diamine, prepared in example 736, (1 eq), $Et_3N$ (1 eq), PPh3 (0.2 eq), CuI (0.05 eq) and DMF for 3 min. $PdCl_2(PPh_3)_2$ (0.05 eq) and ethynyltrimethylsilane (2 eq) was added and the reaction was heated in a sealed tube for 1 hour at 120° C. The mixture was cold to r.t. and 1M tetrabutyl ammonium fluoride in THF (5 eq) was added. The reaction was stirred for 1 hour at r.t. MeOH was added followed by filtration and purified by preparative LC to give the title compound. LCMS [M+H]+ 363. 1H NMR (400 MHz, DMSO-d6) d ppm 2.29 (3 H, s) 2.84 (2 H, t, J=7.27 Hz) 3.48 (2 H, br. s.) 4.13 (1 H, s) 5.72 (1 H, s) 6.05 (2 H, br. s.) 7.03 (1 H, br. s.) 7.17-7.31 (4 H, m) 7.38-7.46 (3 H, m)

Example 761

6-(2-(2-amino-6-(3-chloro-2-methylphenyl)pyrimidin-4-ylamino)ethoxy)pyridine-3-sulfonamide Step 1: 6-Chloropyridine-3-sulfonamide $SOCl_2$ (24 mL) was added to water (145 mL) containing CuCl (87 mg) at 0° C. over a period of 30 min. The solution was then stirred at RT overnight. 3-amino-6-chloropyridine (10.0 g, 77.8 mmol) was added with stirring to conc. HCl (80 mL) portionwise. The mixture was stirred until all solid was dissolved. At −5° C. a solution of $NaNO_2$ (5.9 g, 85.5 mmol, in 24 mL $H_2O$) was added dropwise while the temperature was kept between −5° C. and 0° C. The resulting mixture was stirred for 30 min after completion of the addition and then added dropwise into the aqueous solution of $SOCl_2$. The temperature was kept below 0° C. during the addition. After the addition the mixture was stirred for 1 h below 0° C. and then filtered. The cake was washed with ice-cold water (5 mL). A yellow solid was obtained as crude product (16 g), which was added with stirring into 50% aqueous ammonia (80 mL) portionwise at 10° C. The mixture was then stirred at RT for 30 min, then was extracted with EA (150 mL×1.50 mL×2), the combined organic layers were washed with brine (50 mL) and dried over $Na_2SO_4$. Removal of solvent under reduced pressure afforded the product $^1$H NMR (400 MHz, DMSO-$d_6$): δ=7.73 (s, 2 H), 7.78 (d, J=8.4 Hz, 1 H), 8.22 (m, 1 H), 8.80 (d, J=2.0 Hz, 1 H) ppm.

Step 2: 6-(2-Aminoethoxy)pyridine-3-sulfonamide

To the solution of 2-aminoethanol (2.4 g, 38.9 mmol) in dioxane (60 mL) was added NaH (60%, 1.40 g, 35.1 mmol) in portions at 10° C. After 30 min stirring at RT, 6-Chloropyridine-3-sulfonamide (1.50 g, 7.8 mmol) was added. The mixture was stirred for 30 min under reflux. After cooling to RT, the reaction was quenched by adding $H_2O$ (0.5 mL). The organic layer was separated and dried over $Na_2SO_4$. After removal of solvent under reduced pressure, the residue was purified by column chromatography. Recrystallization from MeCN afforded a yellow the product (0.42 g). $^1$H NMR (400 MHz, DMSO-$d_6$): δ=2.89 (t, J=6.0 Hz, 2 H), 4.27 (t, J=6.0 Hz, 2 H), 4.62 (br, 2 H), 6.99 (m, 1 H), 8.05 (m, 1 H), 8.55 (m, 1 H) ppm.

Step 3: 6-(2-(2-amino-6-(3-chloro-2-methylphenyl)pyrimidin-4-ylamino)ethoxy)pyridine-3-sulfonamide The mixture of 6-(2-Aminoethoxy)pyridine-3-sulfonamide prepared in step 2 (0.42 g, 1.9 mmol), and intermediate 24 (0.98 g, 3.8 mmol) and TEA (0.59 g, 5.8 mmol) in i-PrOH (15 mL) was stirred at 95° C. overnight. After cooling to RT and removal of solvent under reduced pressure, the residue was purified by column chromatography (to afford a white solid which was purified by prep HPLC to provide the title compound. $^1$H NMR (400 MHz, DMSO-$d_6$): δ=2.29 (s, 2 H), 3.67 (s, 2 H), 4.46 (t, J=5.6 Hz, 2 H), 5.79 (s, 1 H), 6.09 (s, 2 H), 7.01 (d, J=8.8 Hz, 1 H), 7.24 (m, 3 H), 7.44 (m, 1 H), 8.07 (m, 1 H), 8.56 (d, J=2.4 Hz, 1 H) ppm.

Example 1

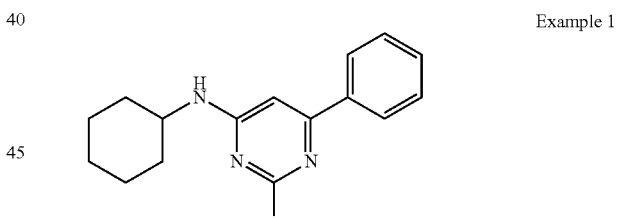

Example 2

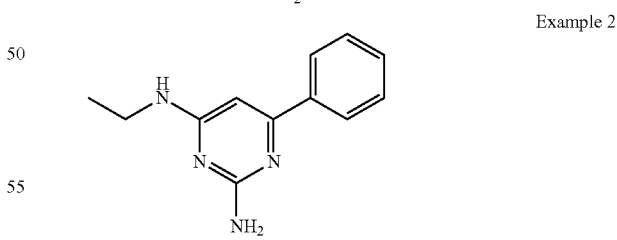

Example 3

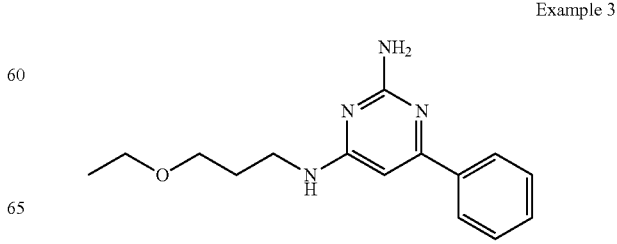

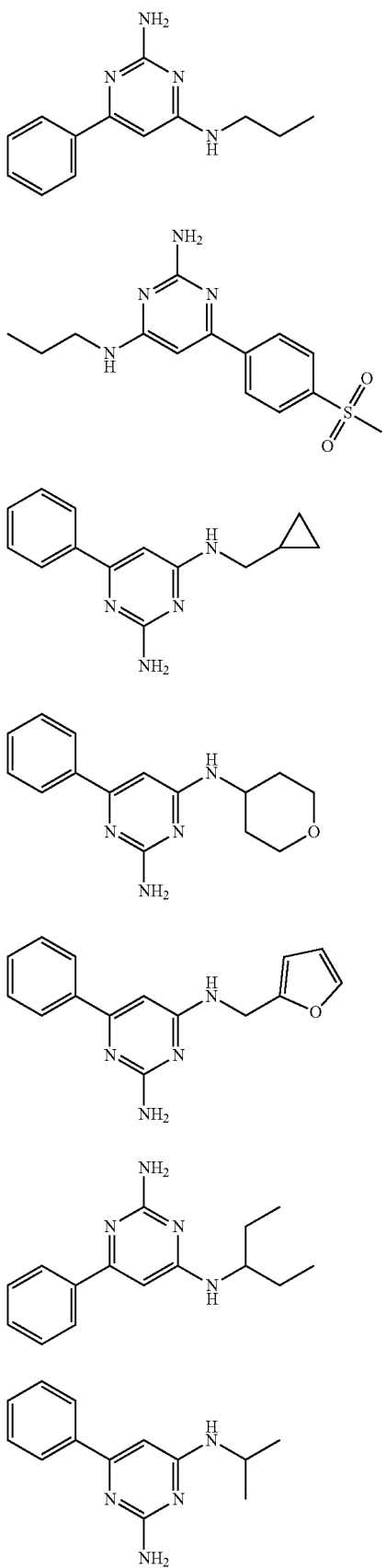
Example 4
Example 5
Example 6
Example 7
Example 8
Example 9
Example 10
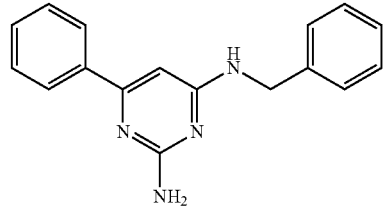
Example 11
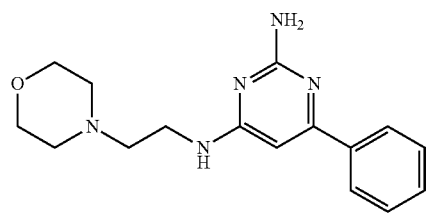
Example 12
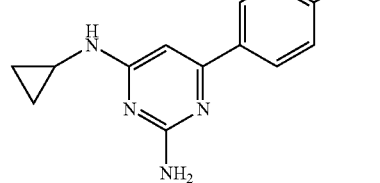
Example 13
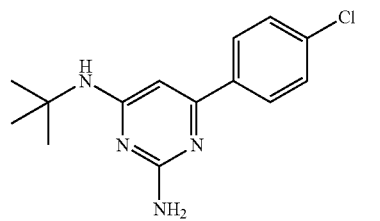
Example 14
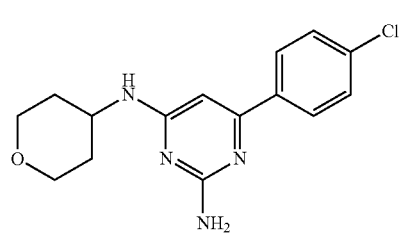
Example 15
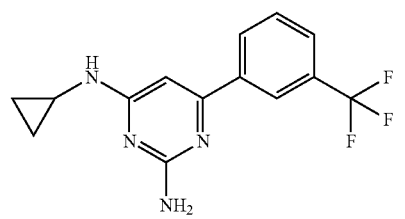
Example 16
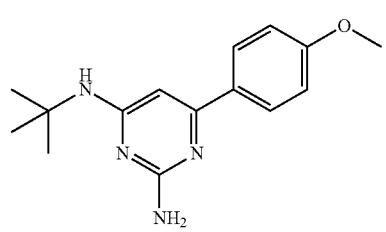
Example 17

Example 18
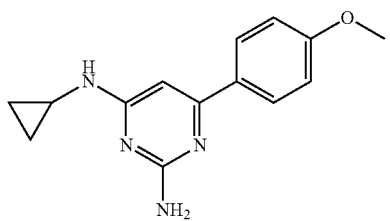
Example 19
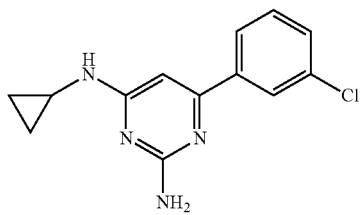
Example 20
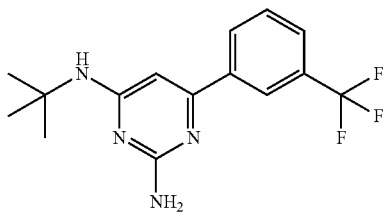
Example 21
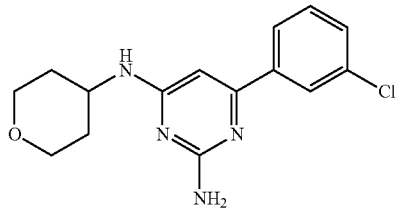
Example 22
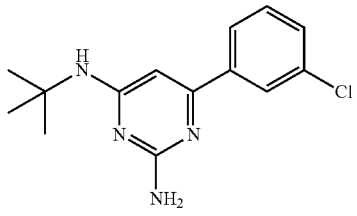
Example 23
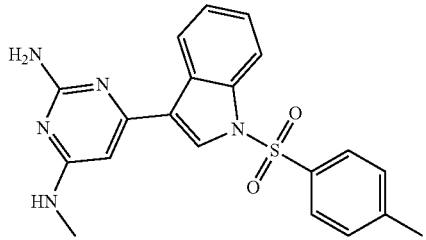
Example 24
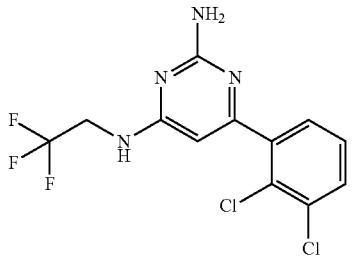
Example 25
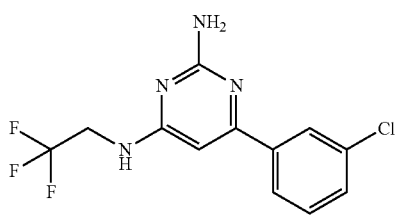
Example 26
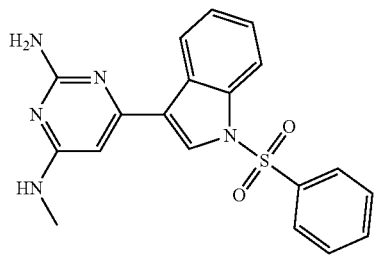
Example 27
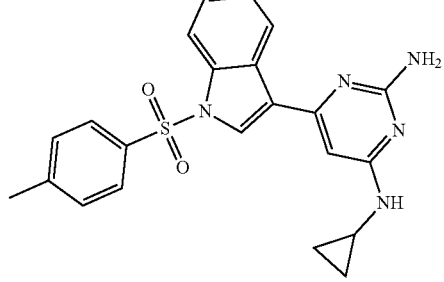
Example 28
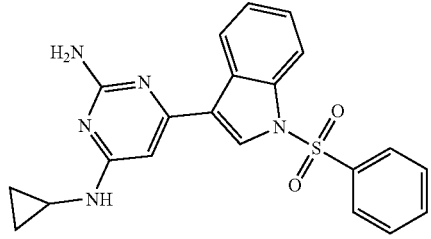
Example 29
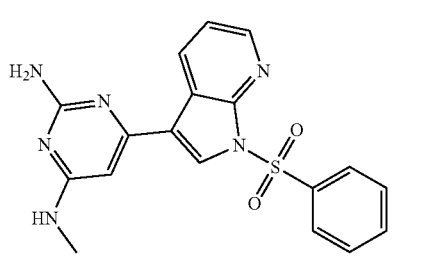
Example 30
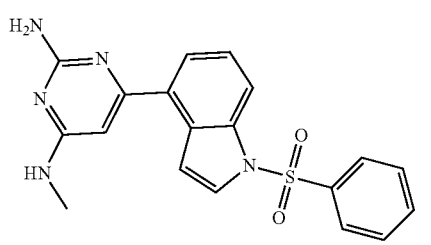

Example 31
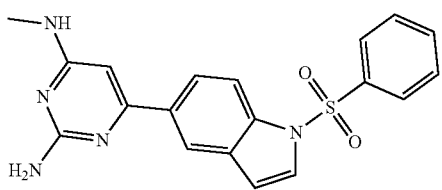
Example 32
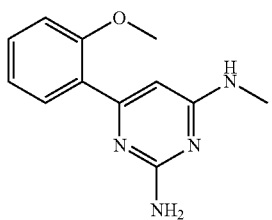
Example 33
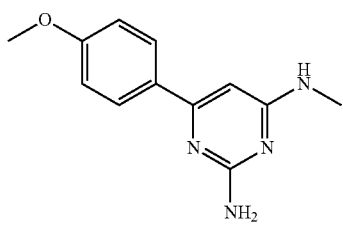
Example 34
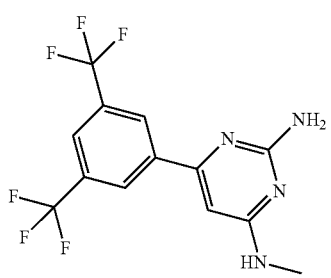
Example 35
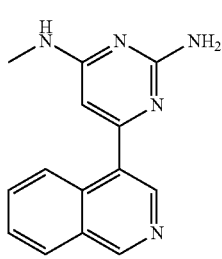
Example 36
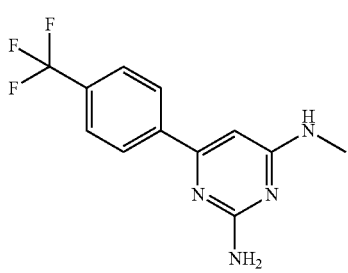
Example 37
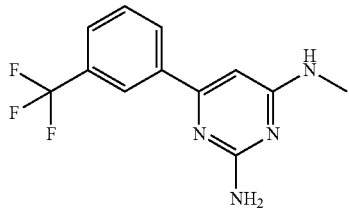
Example 38
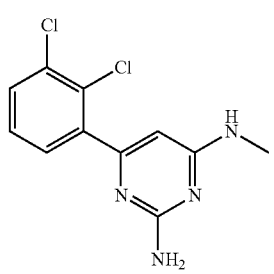
Example 39
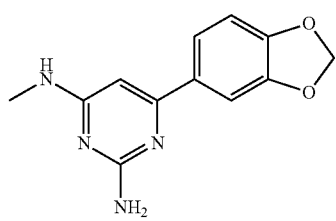
Example 40
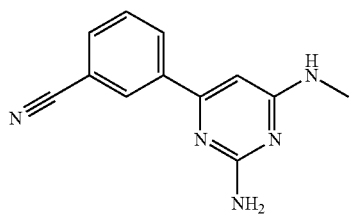
Example 41
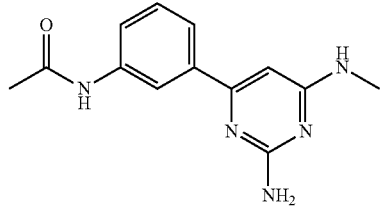
Example 42
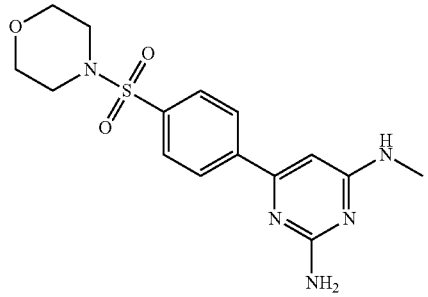

Example 43
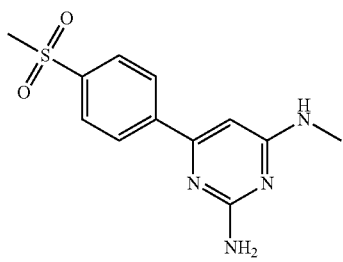
Example 44
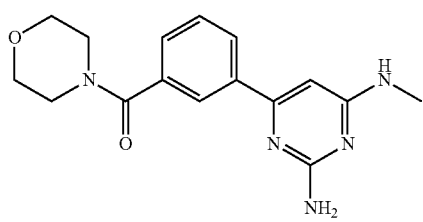
Example 45
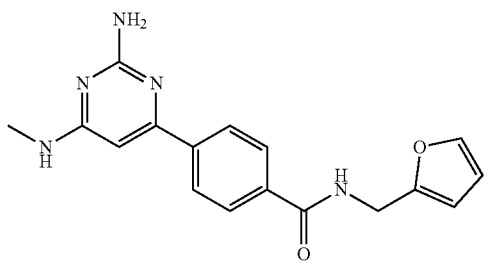
Example 46
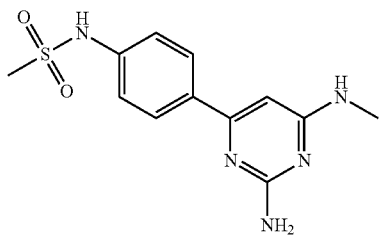
Example 47
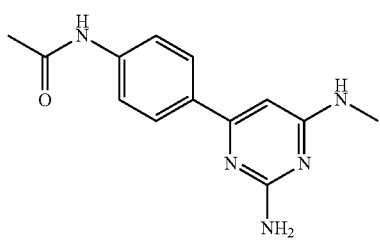
Example 48
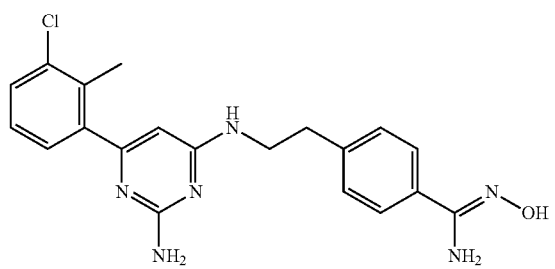
Example 49
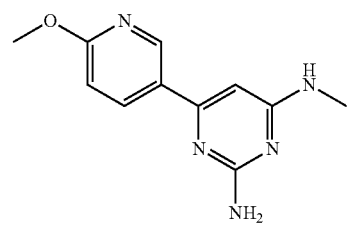
Example 50
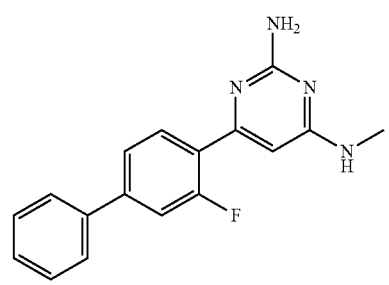
Example 51
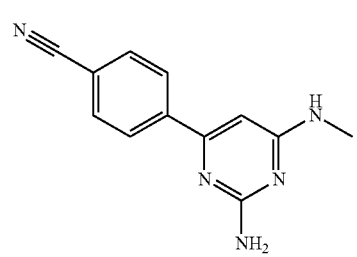
Example 52
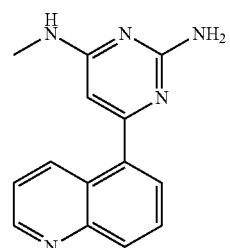
Example 53
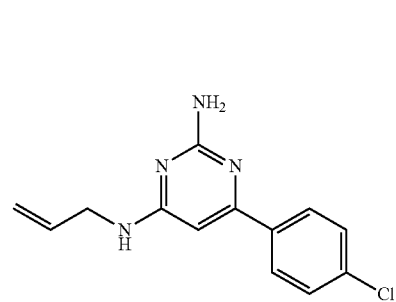
Example 54
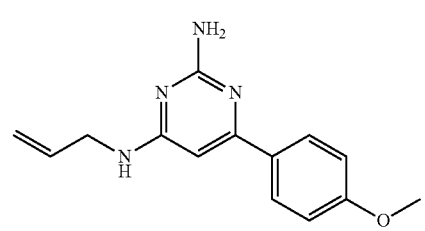

Example 55
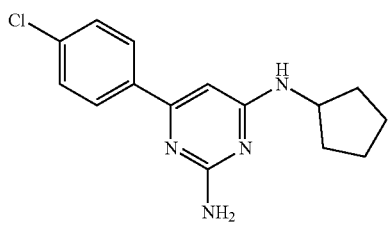
Example 56
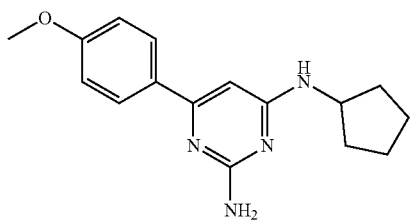
Example 57
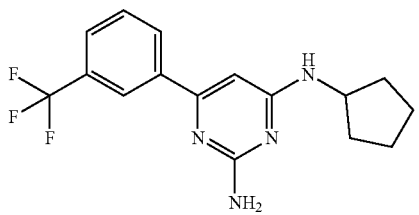
Example 58
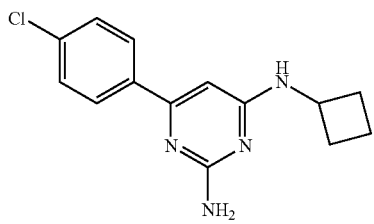
Example 59
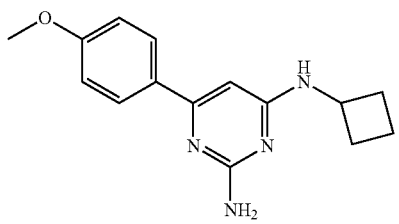
Example 60
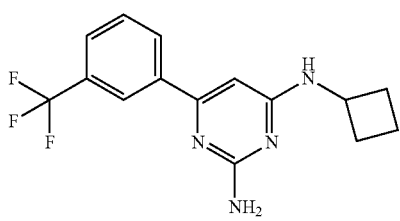
Example 61
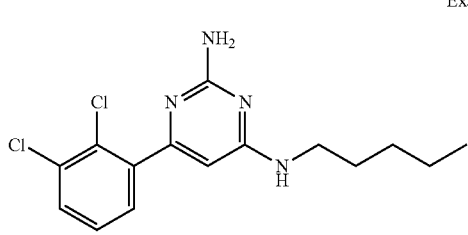
Example 62
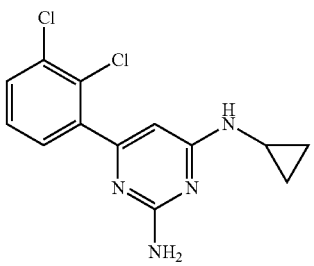
Example 63
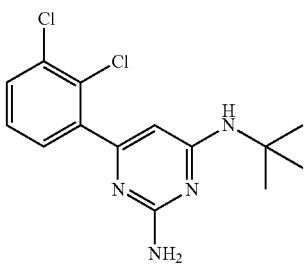
Example 64
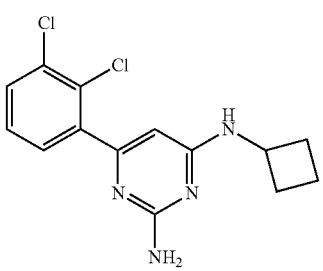
Example 65
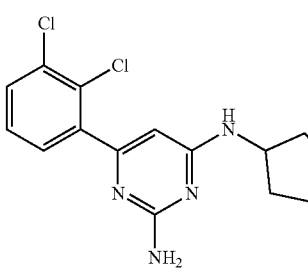
Example 66
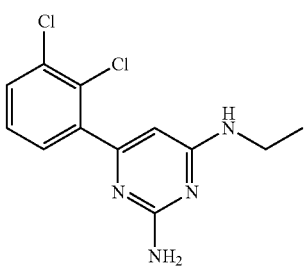
Example 67
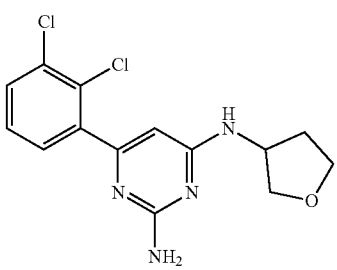

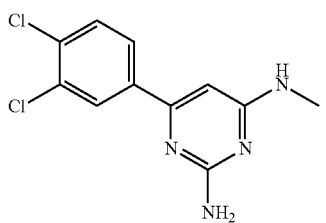
Example 68
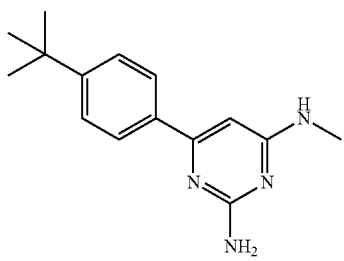
Example 69
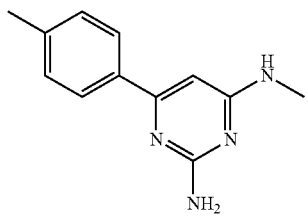
Example 70
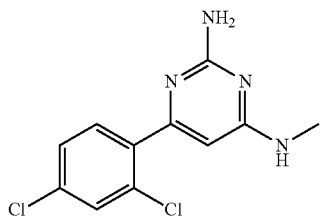
Example 71
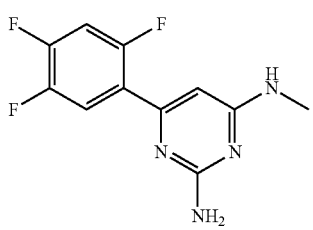
Example 72
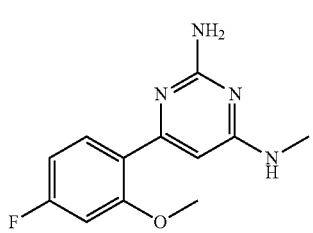
Example 73
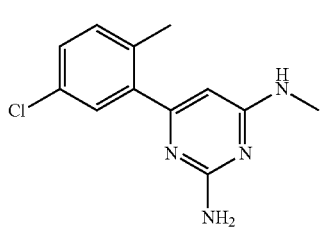
Example 74
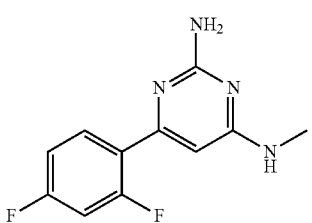
Example 75
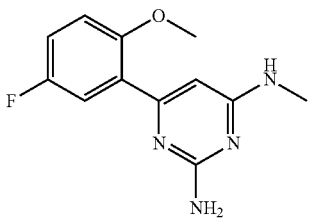
Example 76
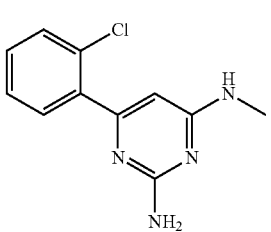
Example 77
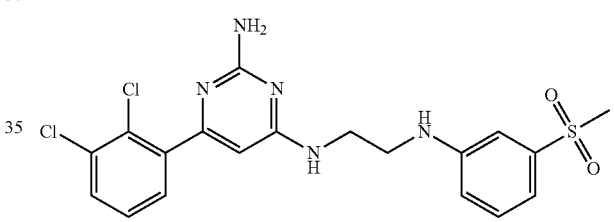
Example 78
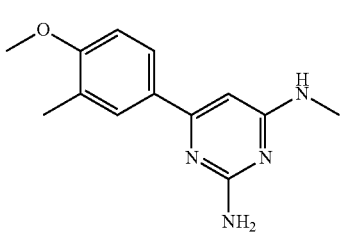
Example 79
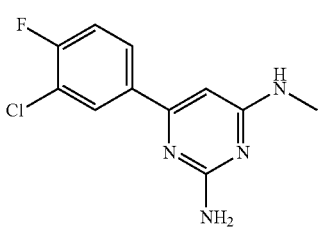
Example 80
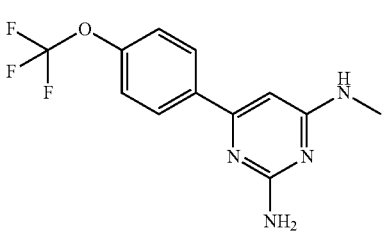
Example 81

Example 82
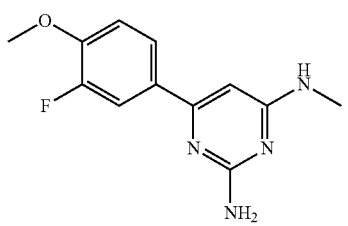
Example 83
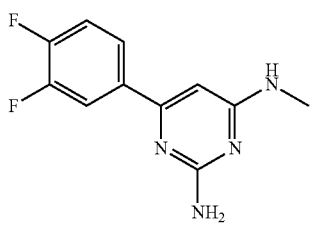
Example 84
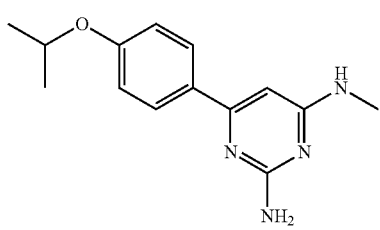
Example 85
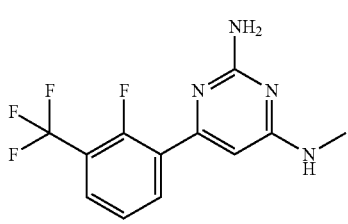
Example 86
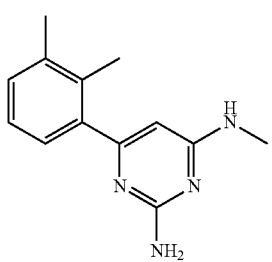
Example 87
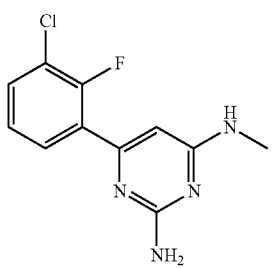
Example 88
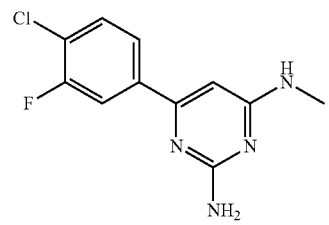
Example 89
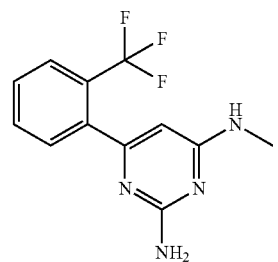
Example 90
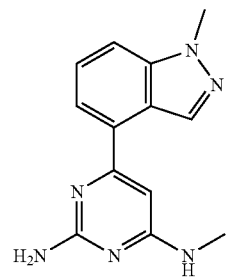
Example 91
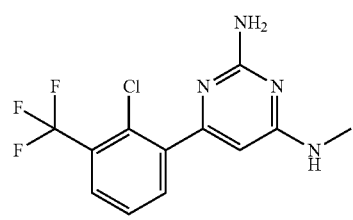
Example 92
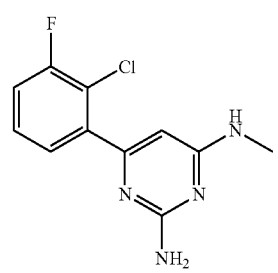
Example 93
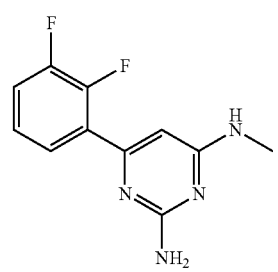

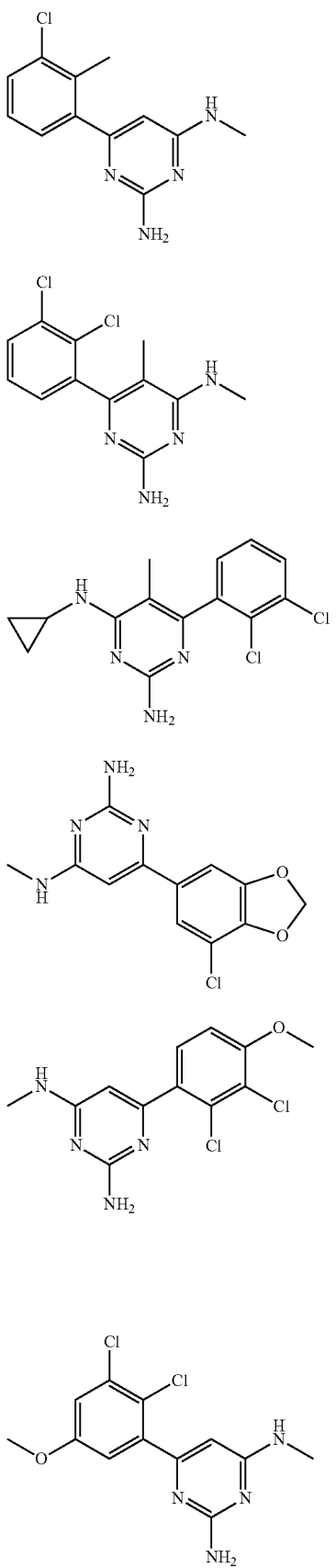
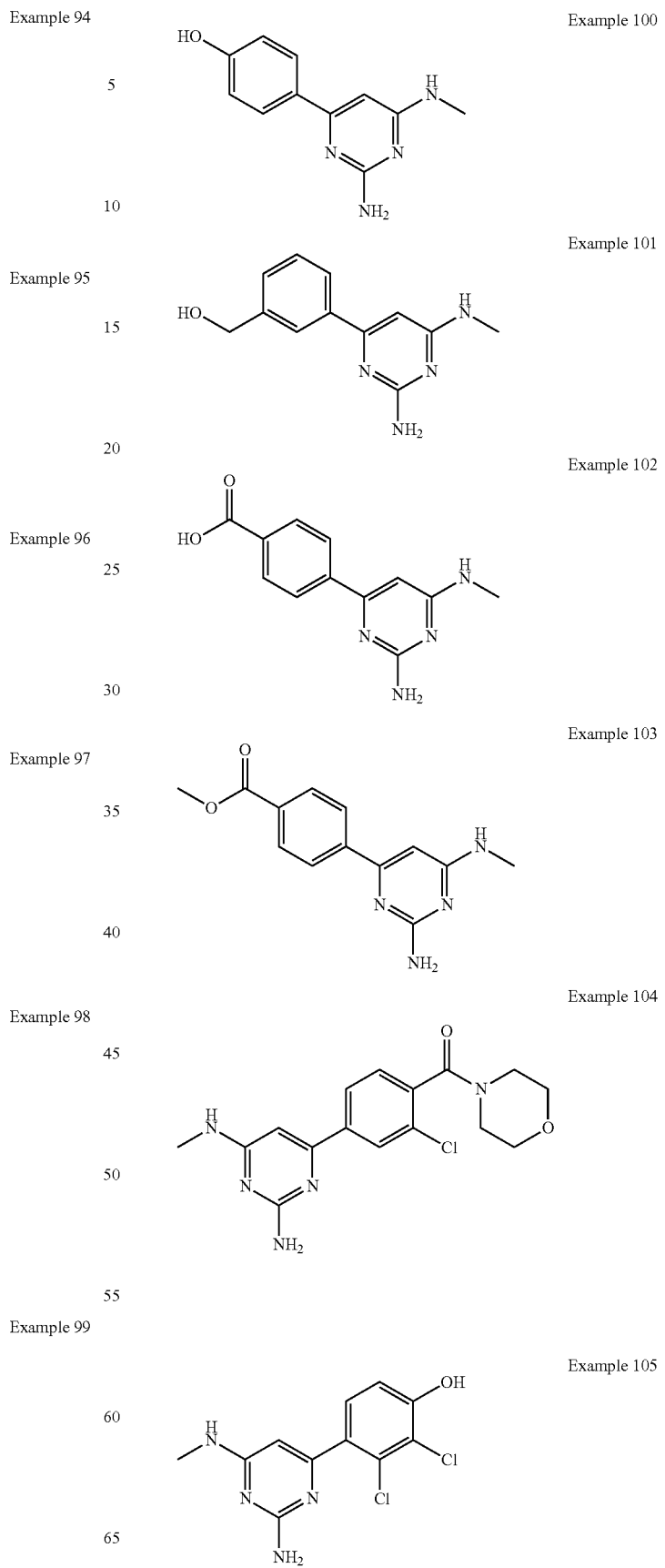
Example 94
Example 95
Example 96
Example 97
Example 98
Example 99
Example 100
Example 101
Example 102
Example 103
Example 104
Example 105

Example 106
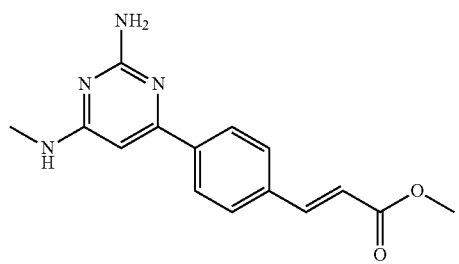
Example 107
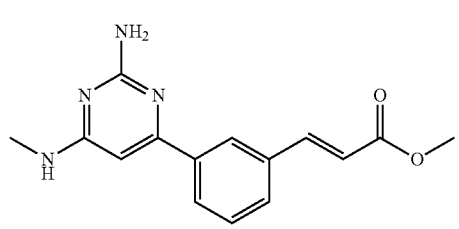
Example 108
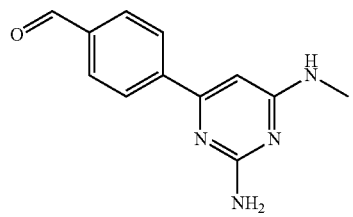
Example 109
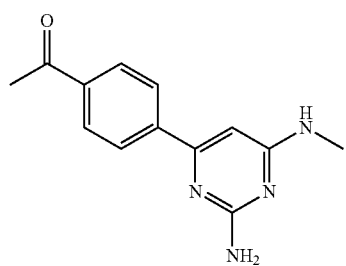
Example 110
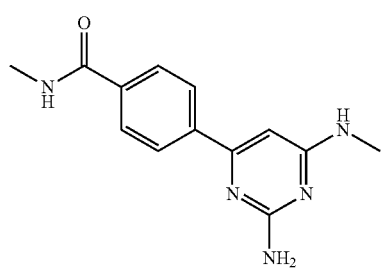
Example 111
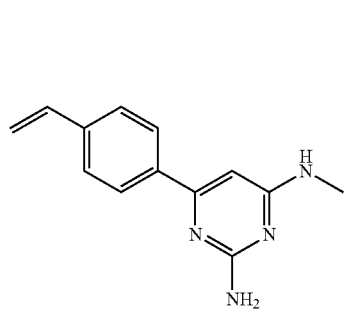
Example 112
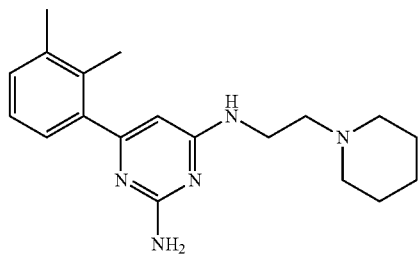
Example 113
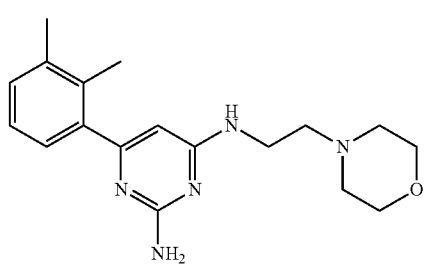
Example 114
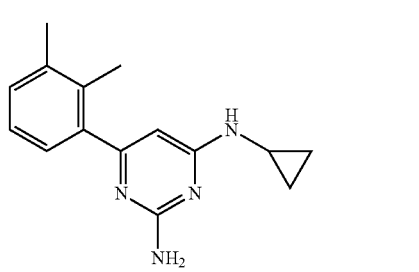
Example 115
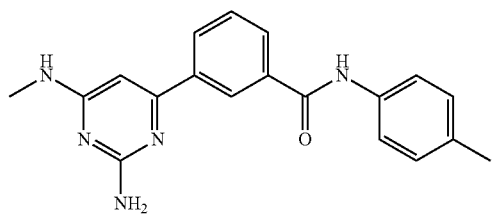
Example 116
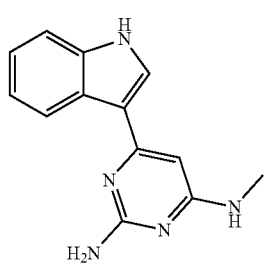
Example 117
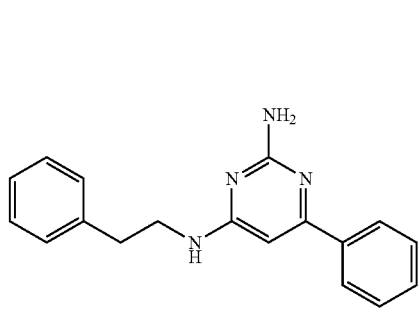

Example 118
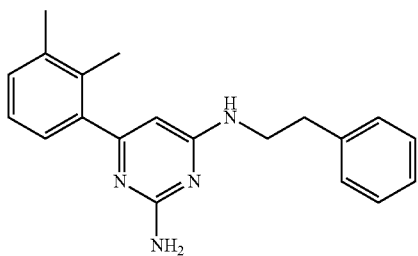
Example 119
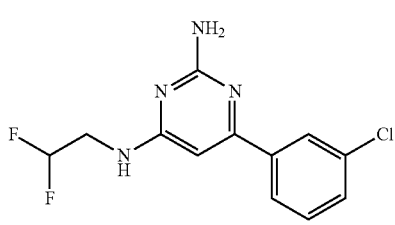
Example 120
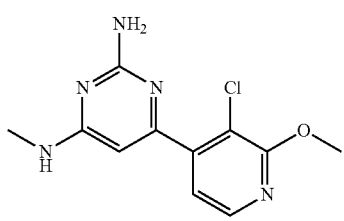
Example 121
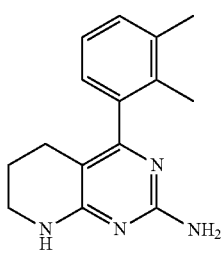
Example 122
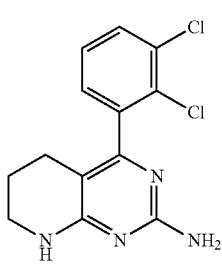
Example 123
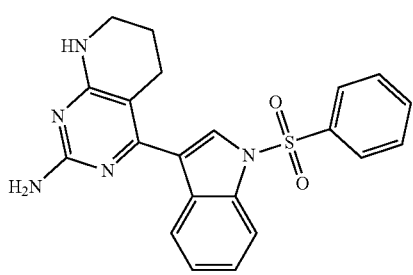
Example 124
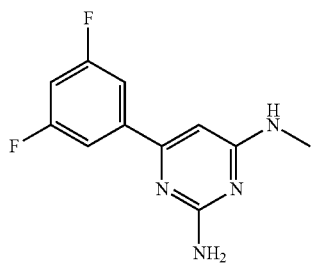
Example 125
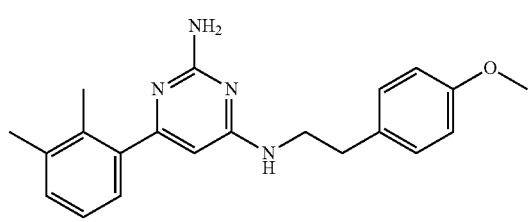
Example 126
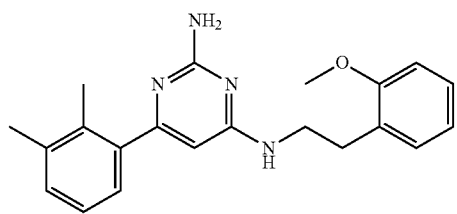
Example 127
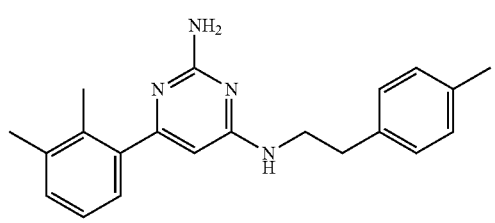
Example 128
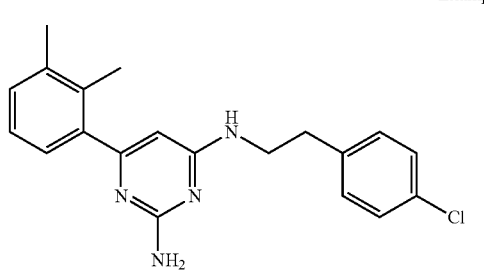
Example 129
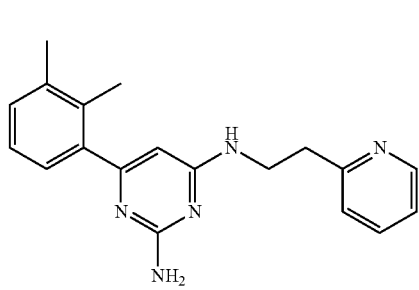

Example 130
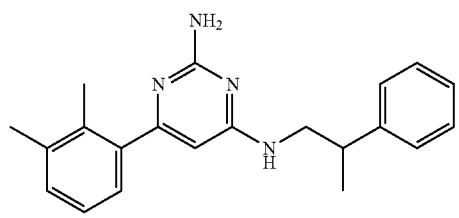
Example 131
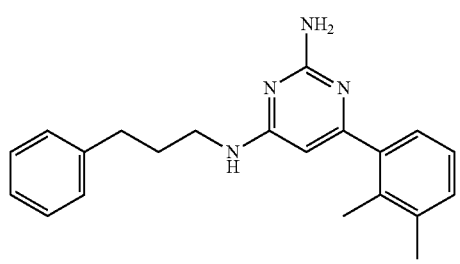
Example 132
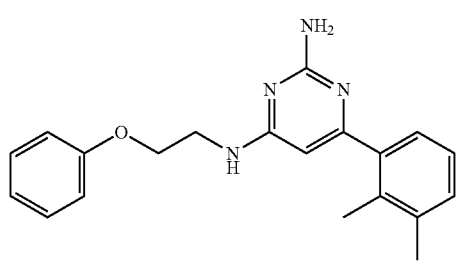
Example 133
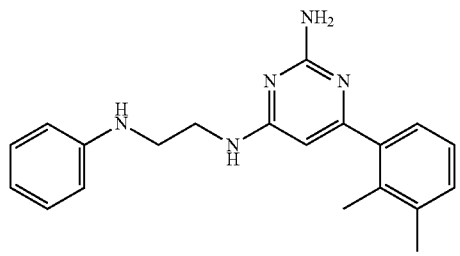
Example 134
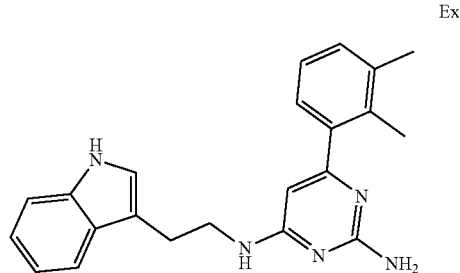
Example 135
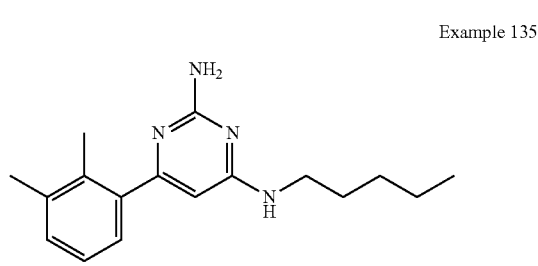
Example 136
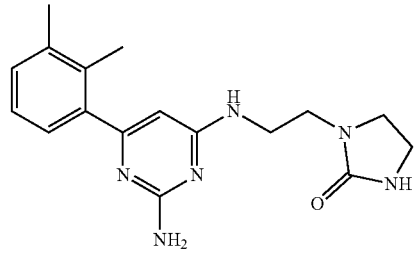
Example 137
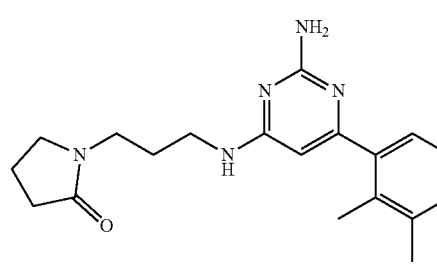
Example 138
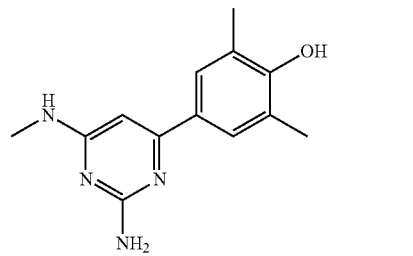
Example 139
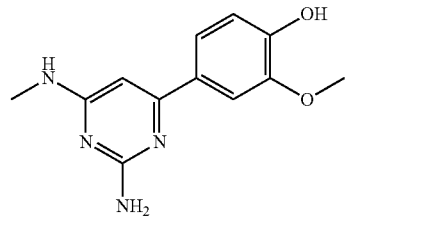
Example 140
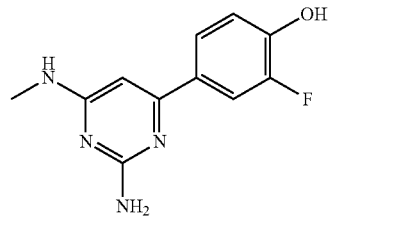
Example 141
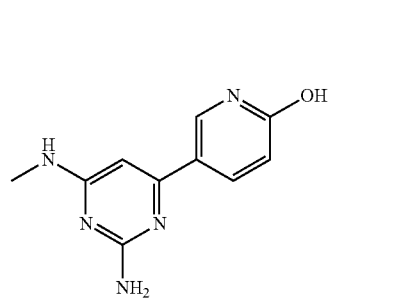

Example 142
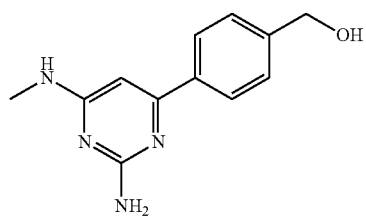
Example 143
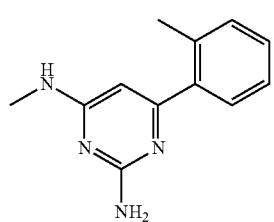
Example 144
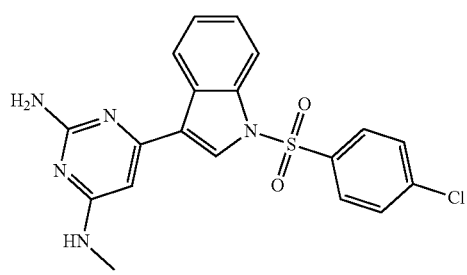
Example 145
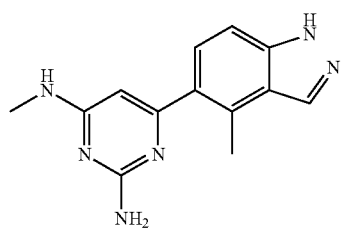
Example 146
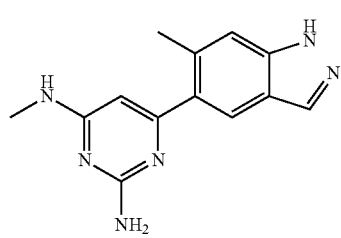
Example 147
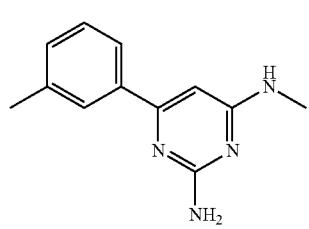
Example 148
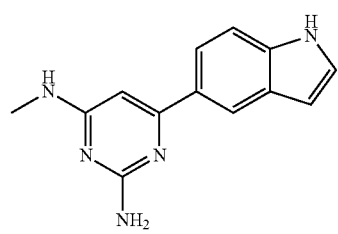
Example 149
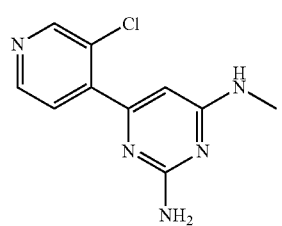
Example 150
Example 151
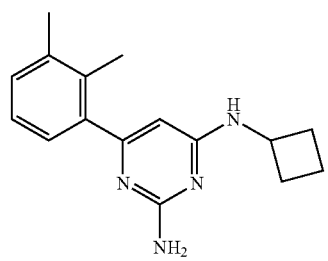
Example 152
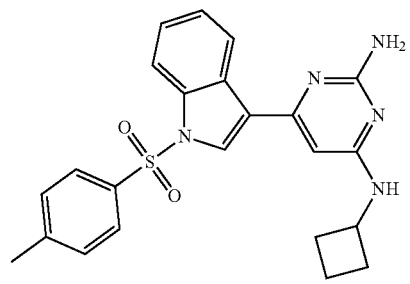
Example 153
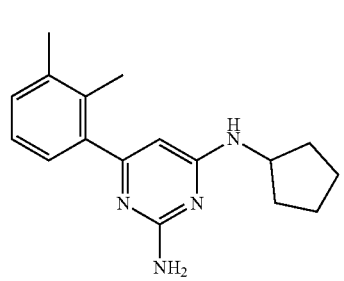

Example 154
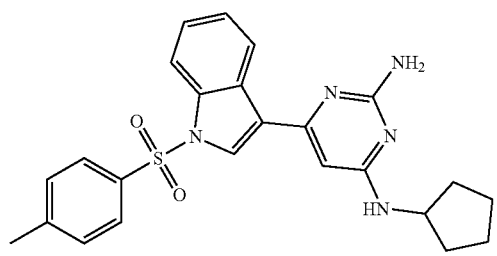
Example 159
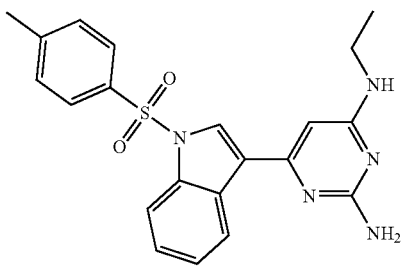
Example 155
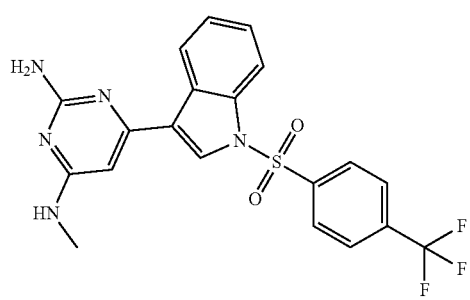
Example 160
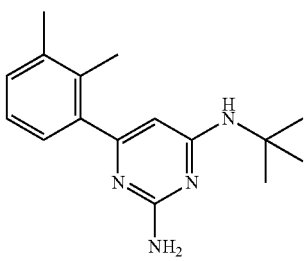
Example 156
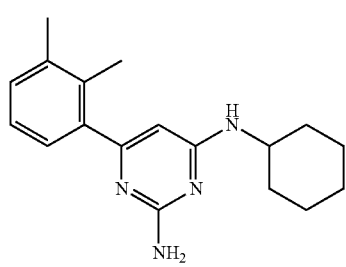
Example 161
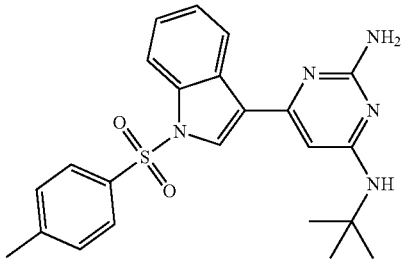
Example 157
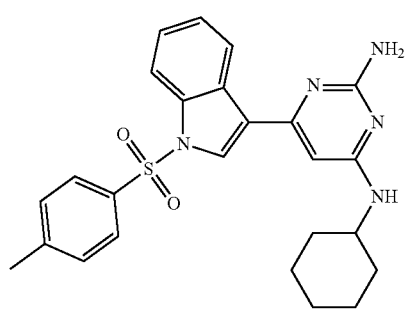
Example 162
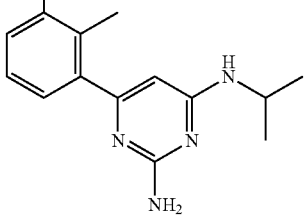
Example 163
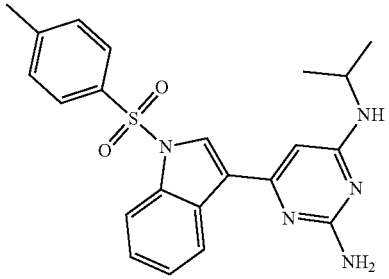
Example 158
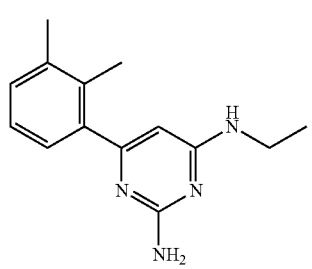
Example 164
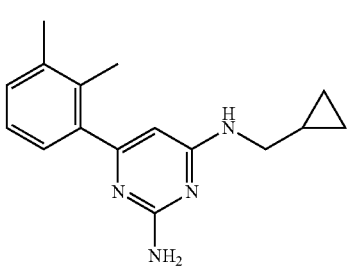

Example 165
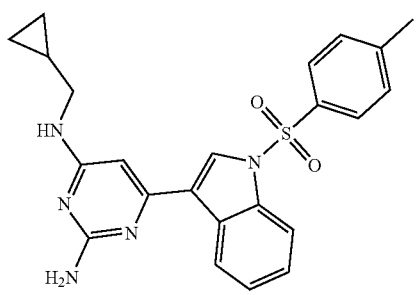
Example 166
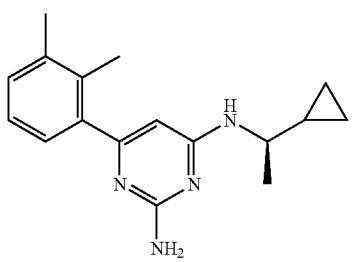
Example 167
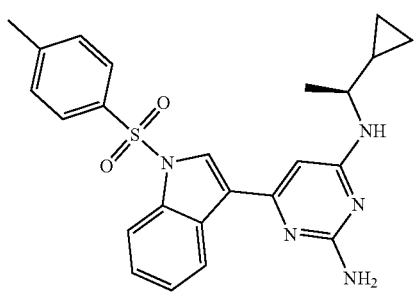
Example 168
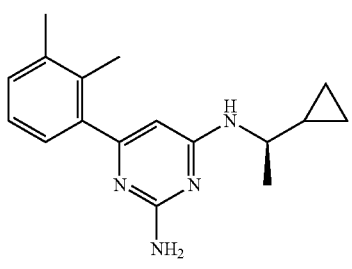
Example 169
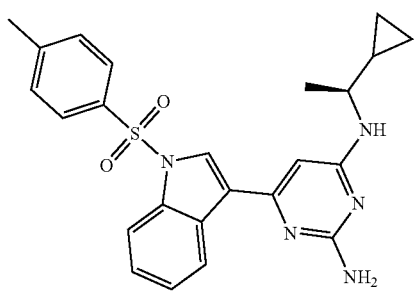
Example 170
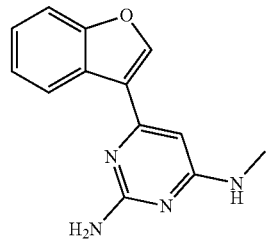
Example 171
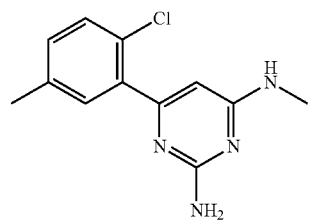
Example 172
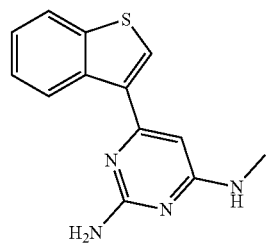
Example 173
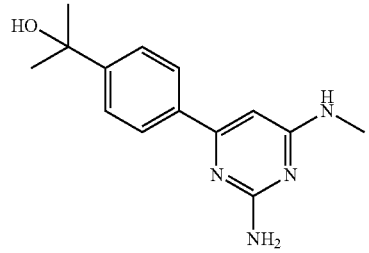
Example 174
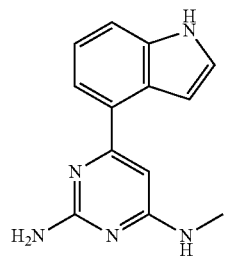
Example 175
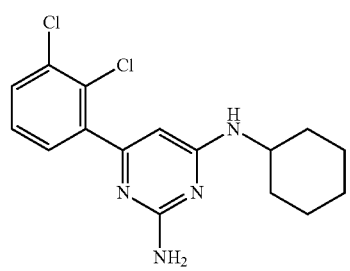

Example 176
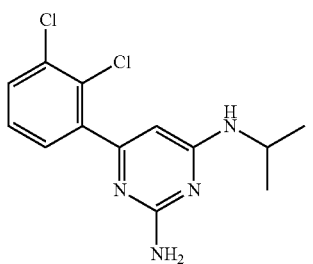
Example 177
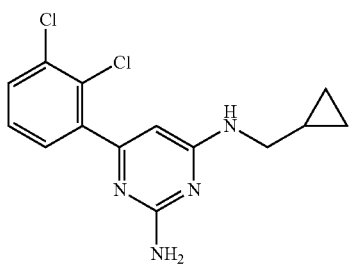
Example 178
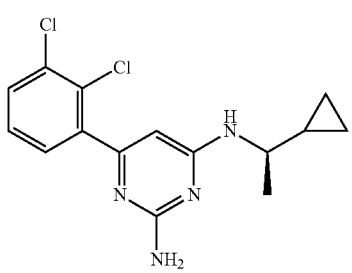
Example 179
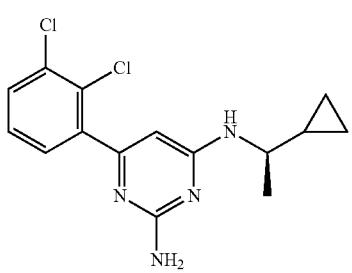
Example 180
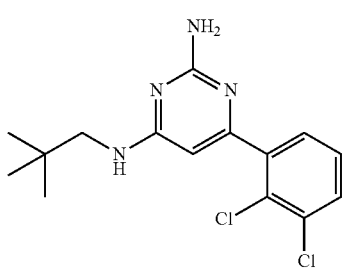
Example 181
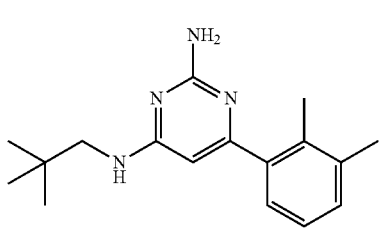
Example 182
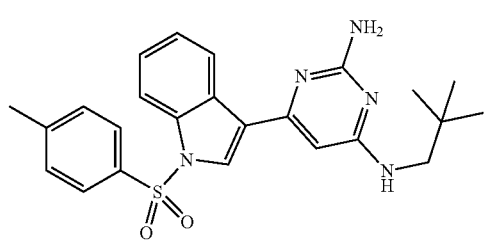
Example 183
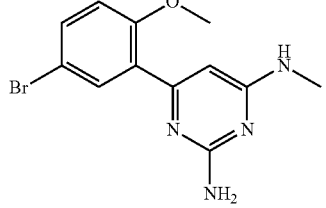
Example 184
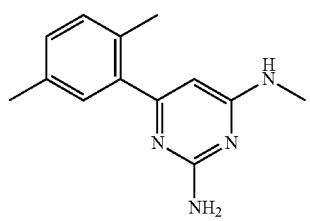
Example 185
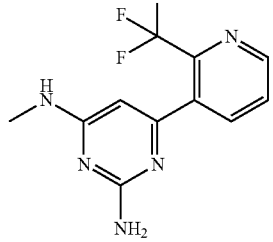
Example 186
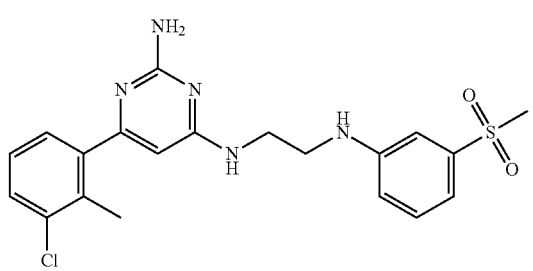
Example 187
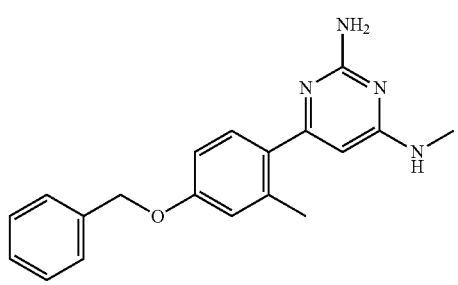

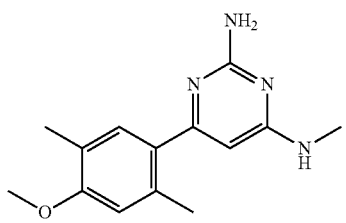 Example 188
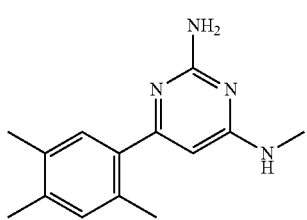 Example 189
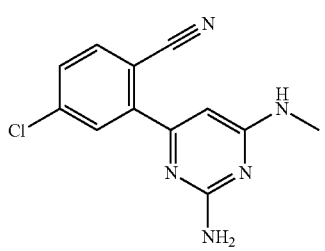 Example 190
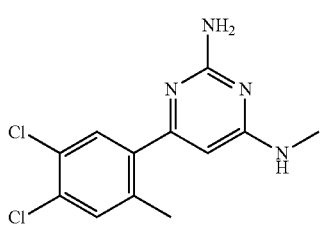 Example 191
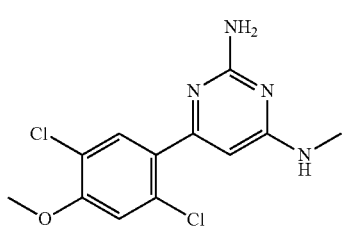 Example 192
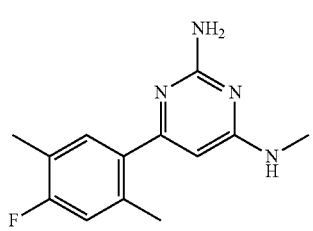 Example 193
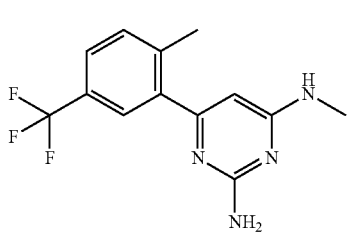 Example 194
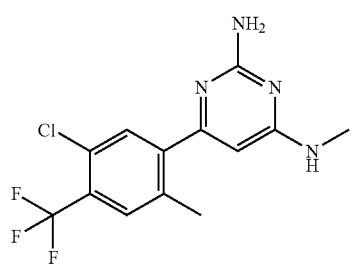 Example 195
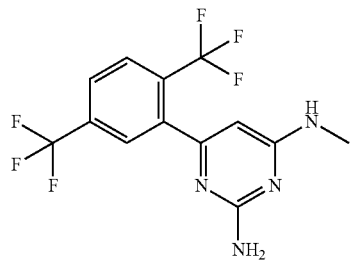 Example 196
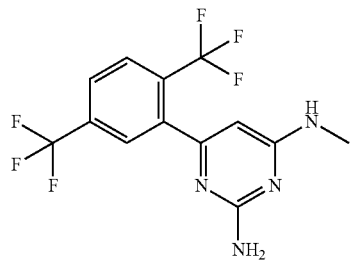 Example 197
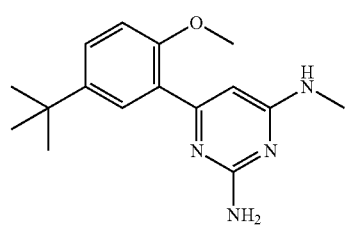 Example 198
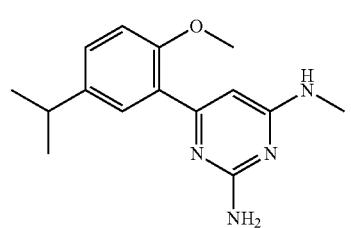 Example 199
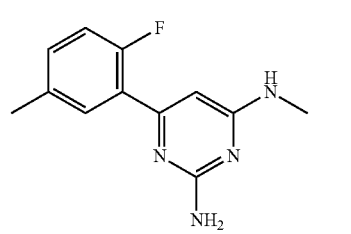 Example 200

-continued
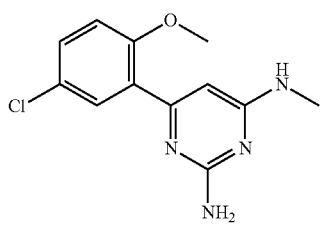
Example 201
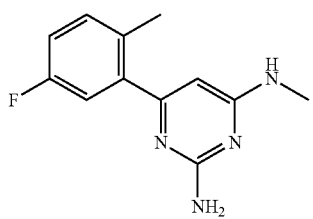
Example 202
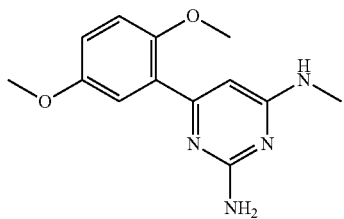
Example 203
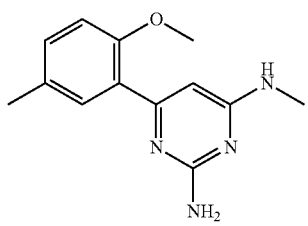
Example 204
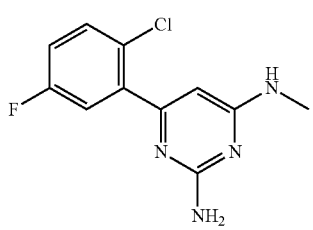
Example 205
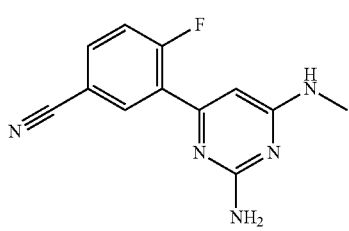
Example 206
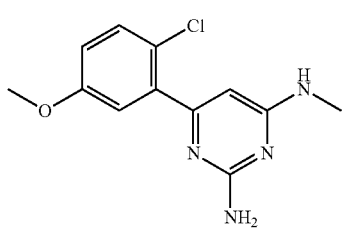
Example 207
-continued
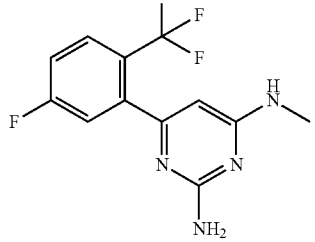
Example 208
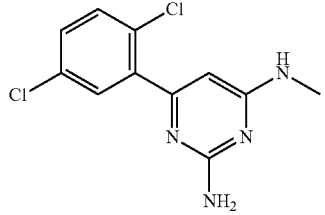
Example 209
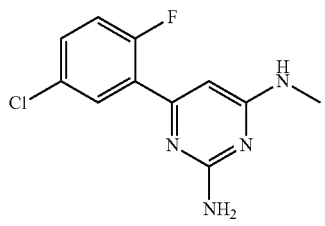
Example 210
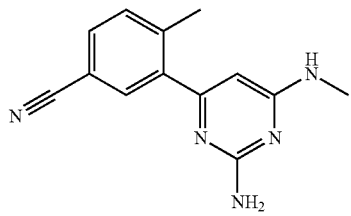
Example 211
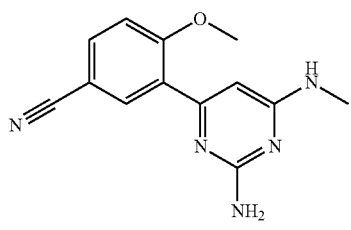
Example 212
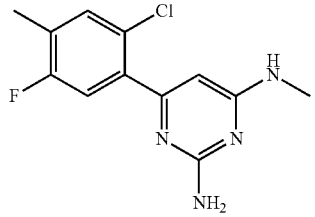
Example 213
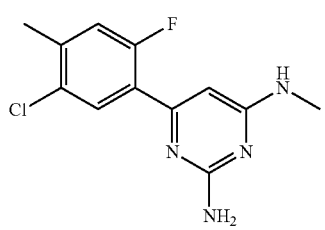
Example 214

-continued
Example 215
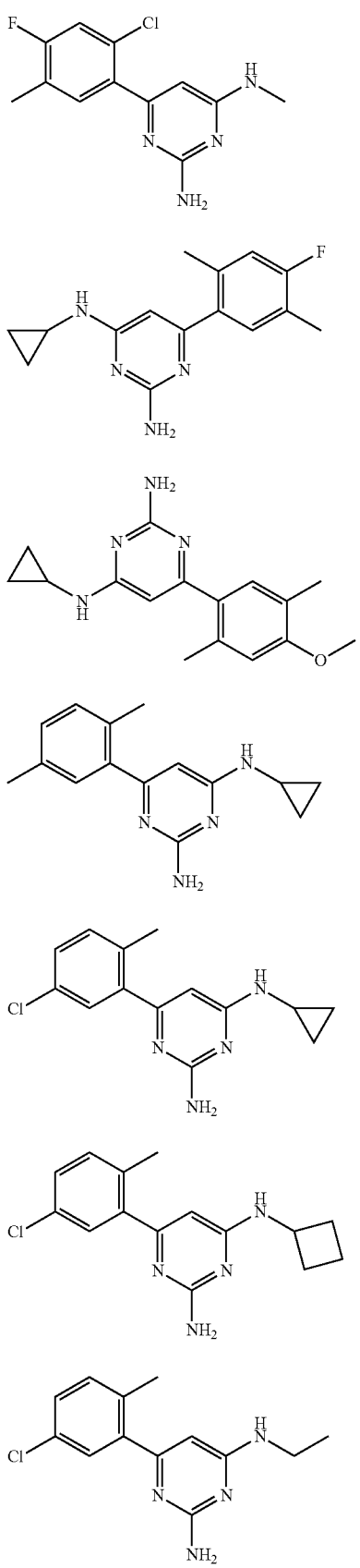
Example 216
Example 217
Example 218
Example 219
Example 220
Example 221
-continued
Example 222
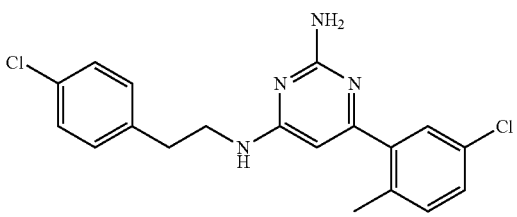
Example 223
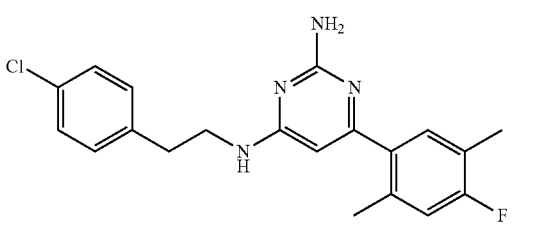
Example 224
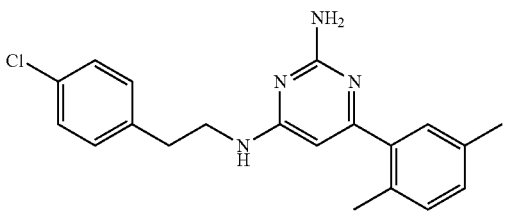
Example 225
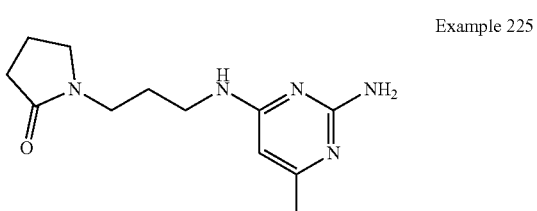
Example 226
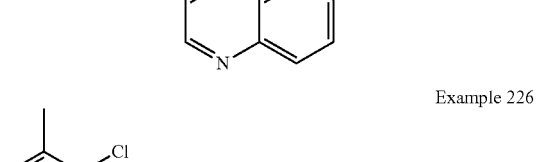
Example 227
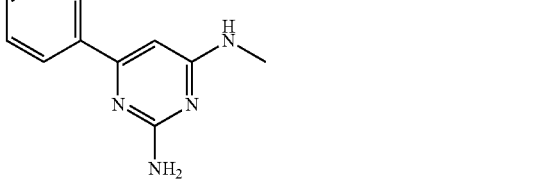

Example 228
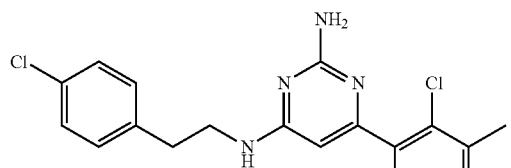
Example 229
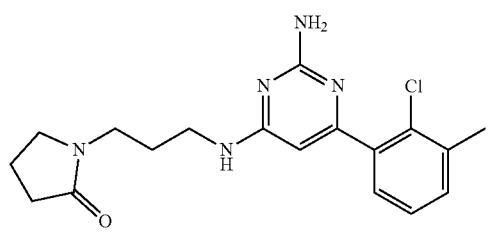
Example 230
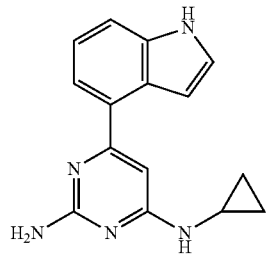
Example 231
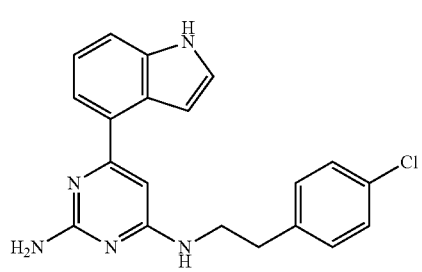
Example 232
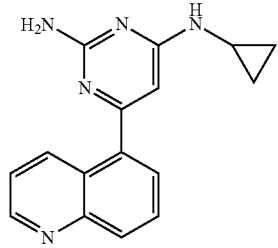
Example 233
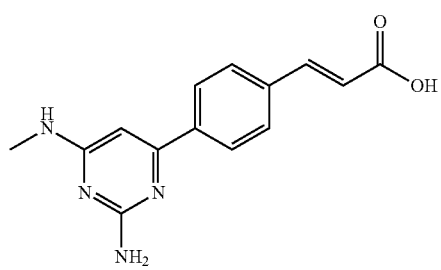
Example 234
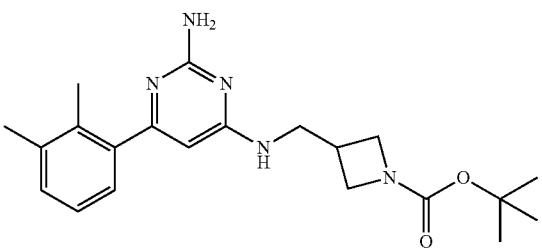
Example 235
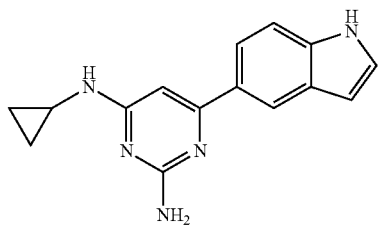
Example 236
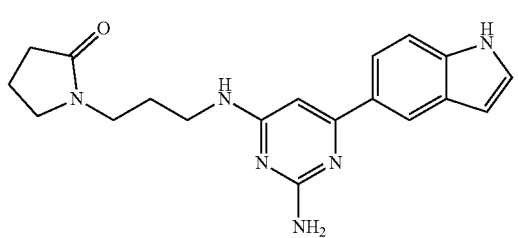
Example 237
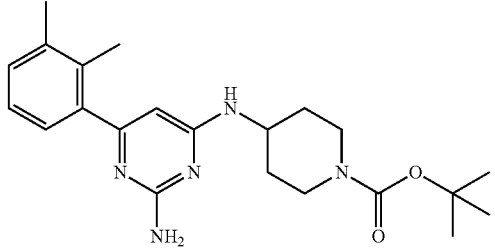
Example 238
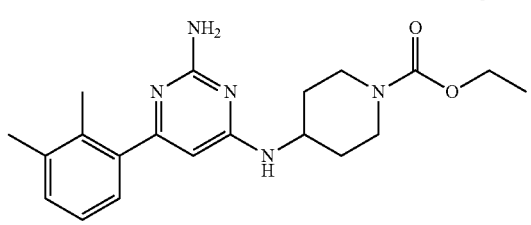
Example 239
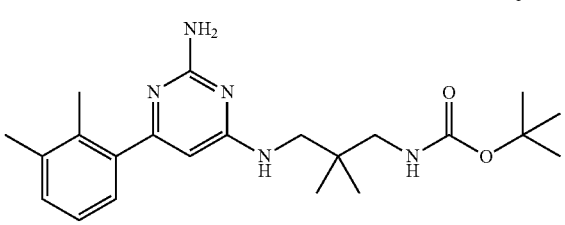

Example 240
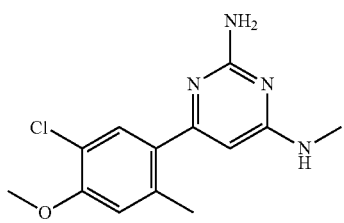
Example 241
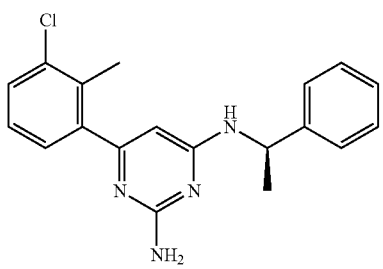
Example 242
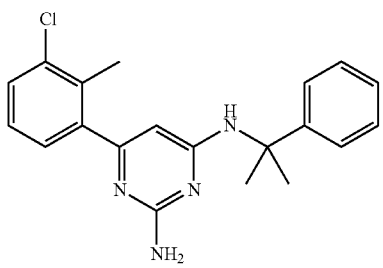
Example 243
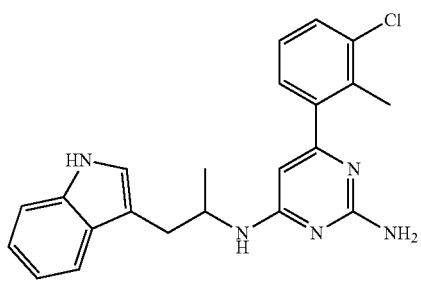
Example 244
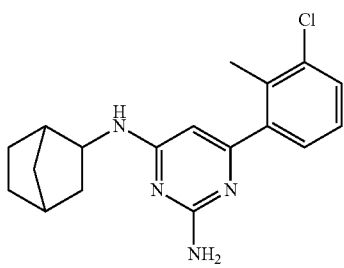
Example 245
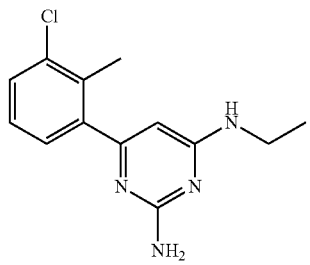
Example 246
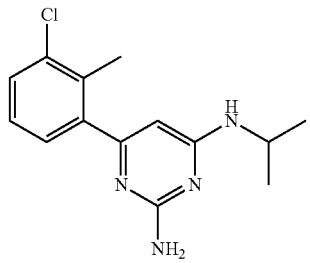
Example 247
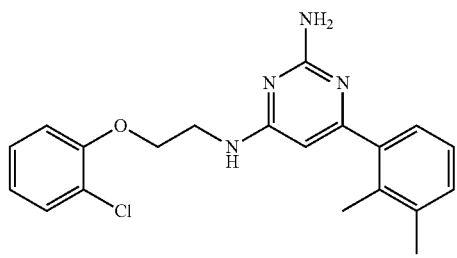
Example 248
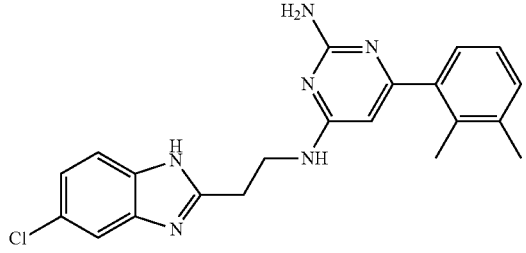
Example 249
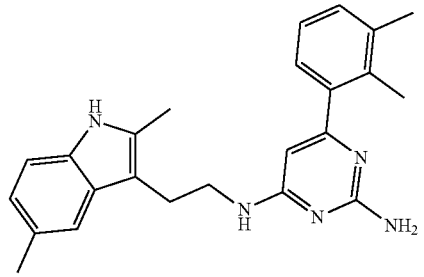

Example 250
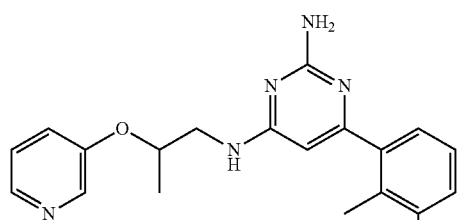
Example 251
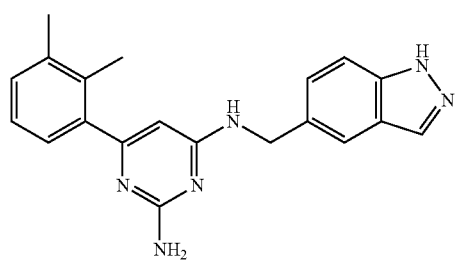
Example 252
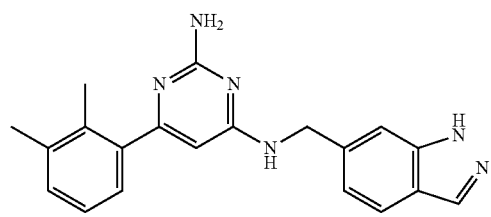
Example 253
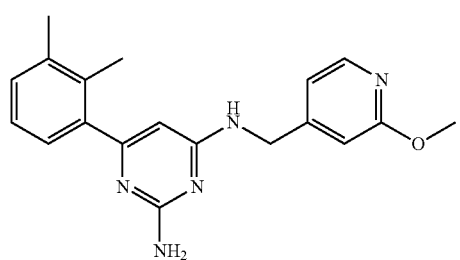
Example 254
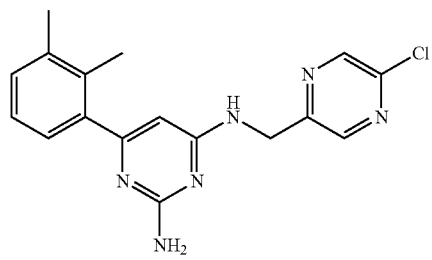
Example 255
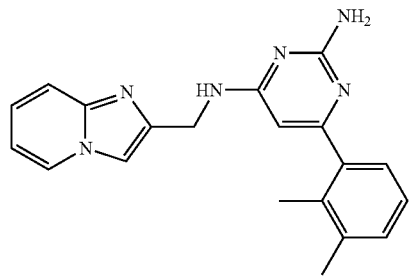
Example 256
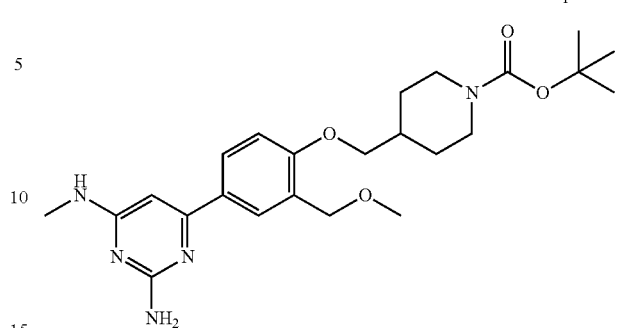
Example 257
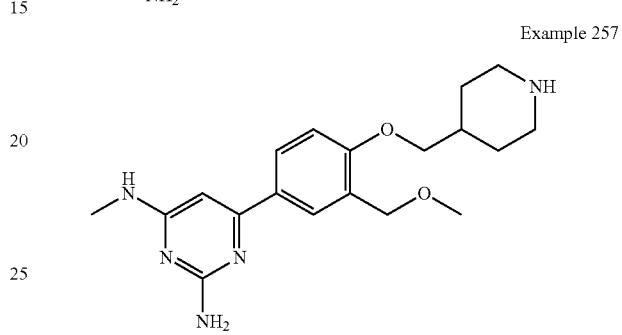
Example 258
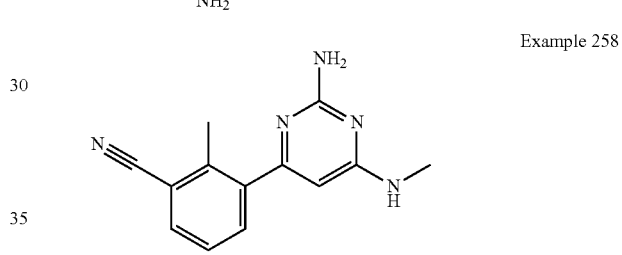
Example 259
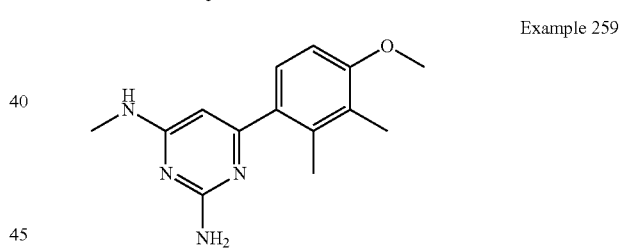
Example 260
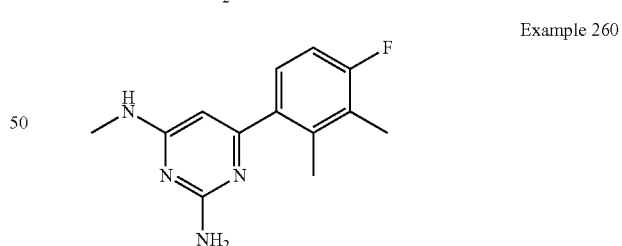
Example 261
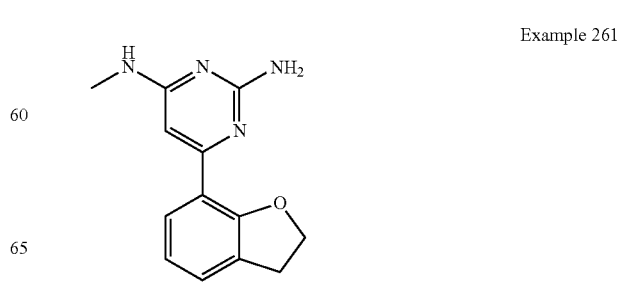

Example 262
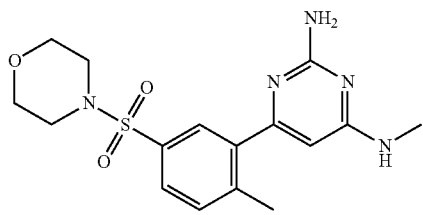
Example 263
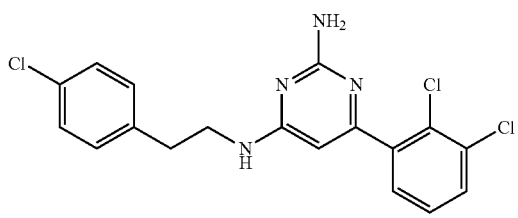
Example 264
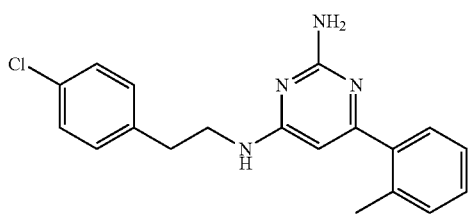
Example 265
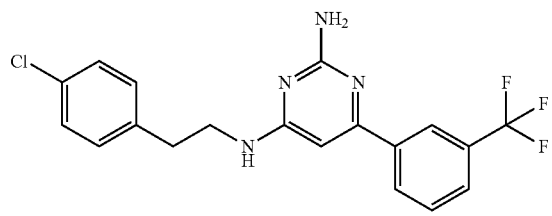
Example 266
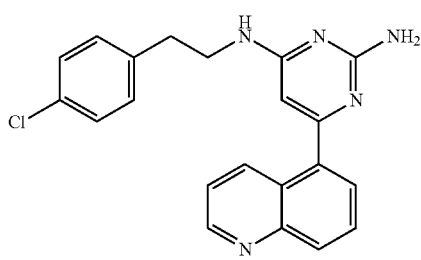
Example 267
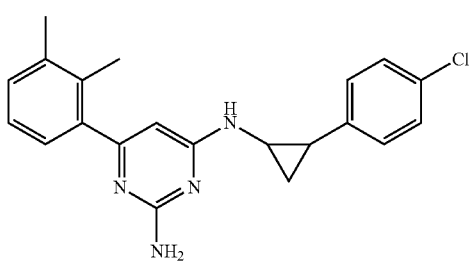
Example 268
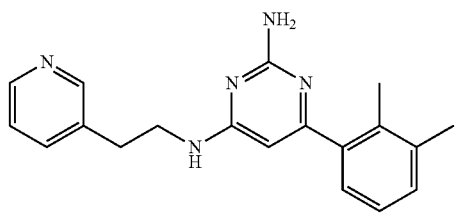
Example 269
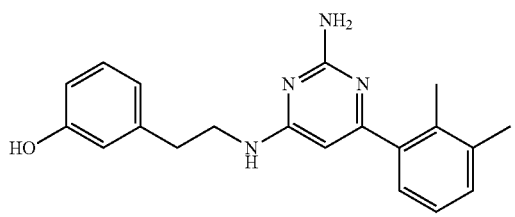
Example 270
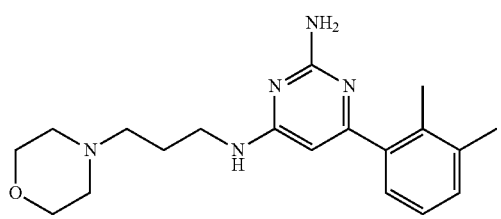
Example 271
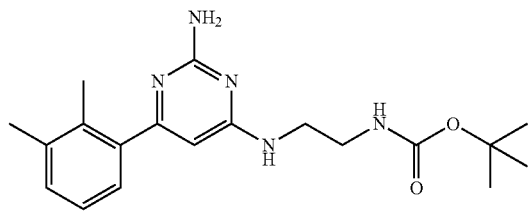
Example 272
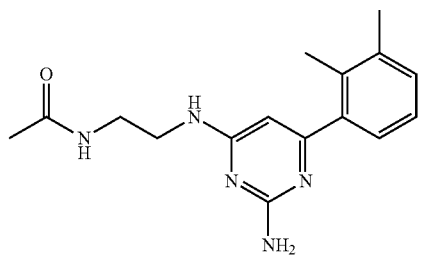
Example 273
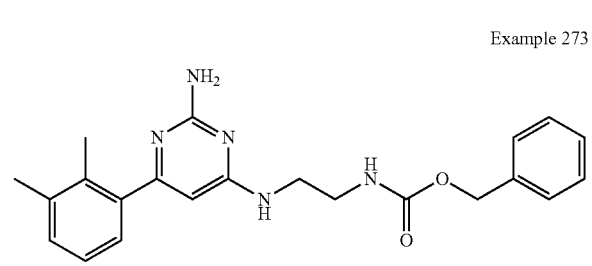

-continued
Example 274
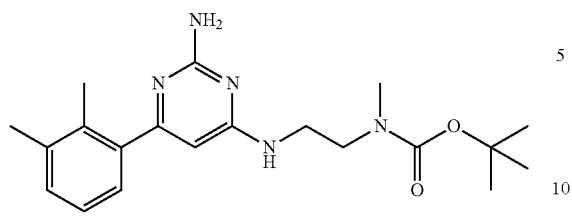
Example 275
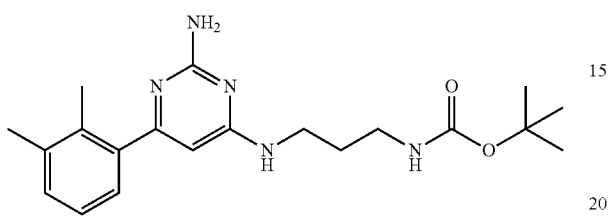
Example 276
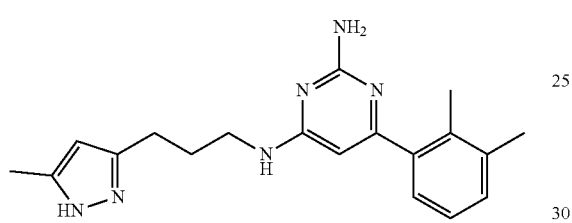
Example 277
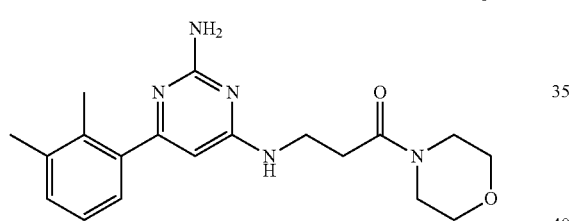
Example 278
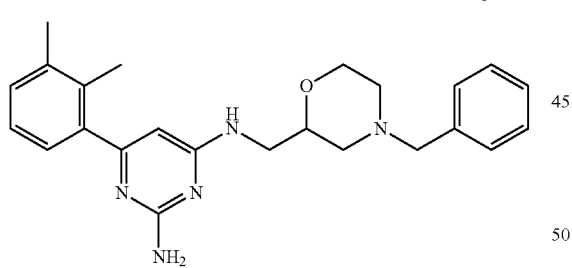
Example 279
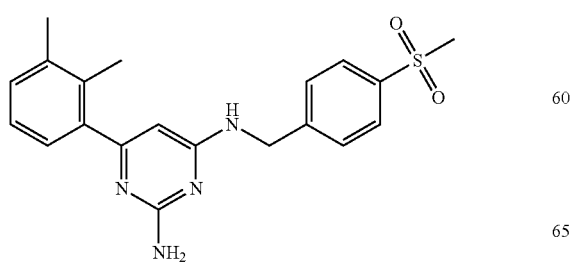
-continued
Example 280
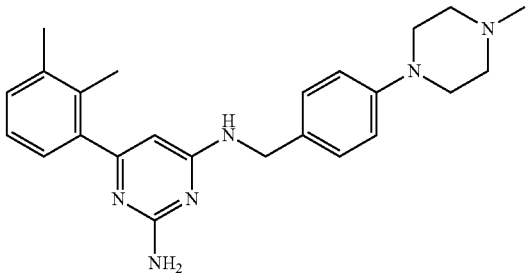
Example 281
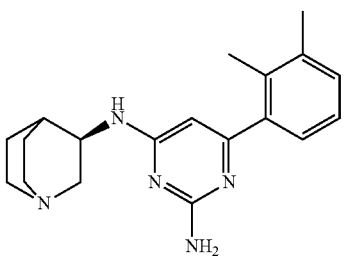
Example 282
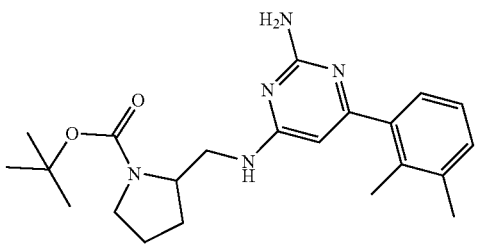
Example 283
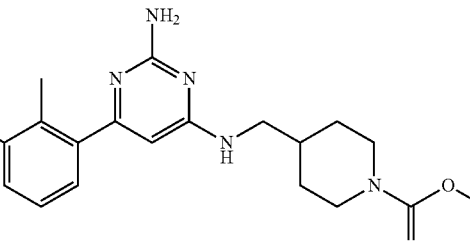
Example 284
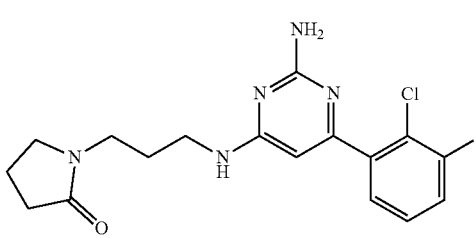
Example 285
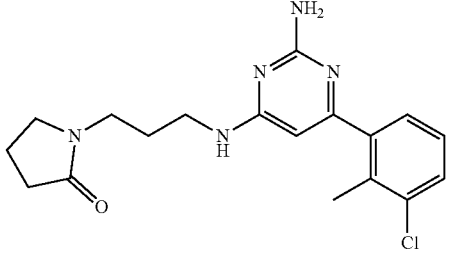

Example 286
Example 287
Example 288
Example 289
Example 290
Example 291
Example 292
Example 293
Example 294
Example 295
Example 296

Example 297
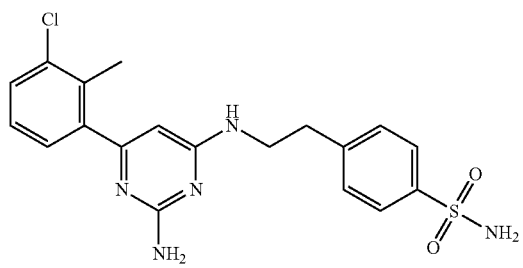
Example 298
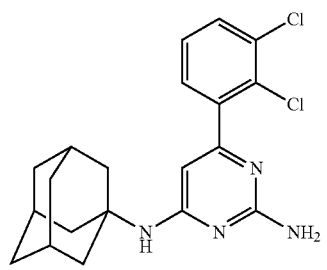
Example 299
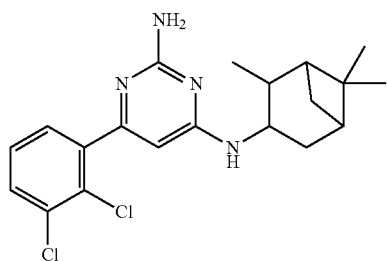
Example 300
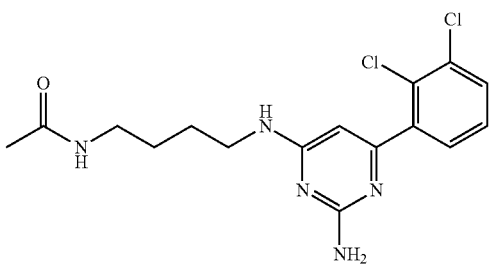
Example 301
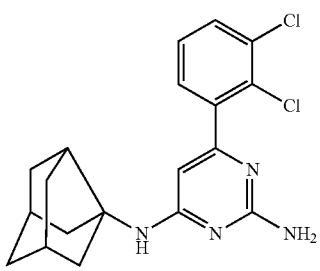
Example 302
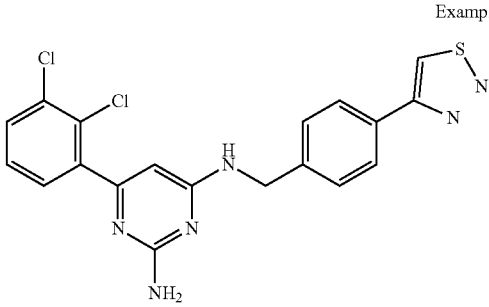
Example 303
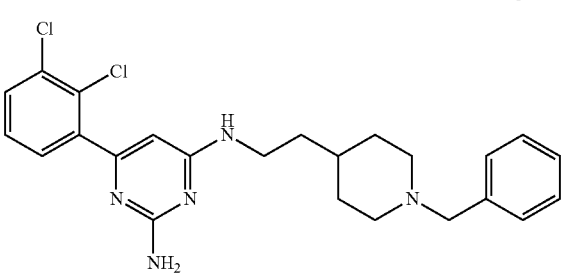
Example 304
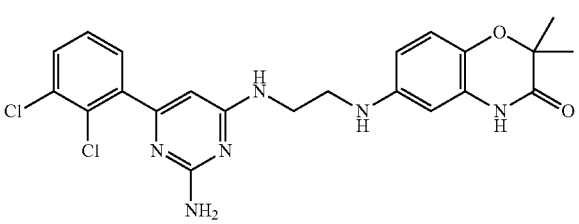
Example 305
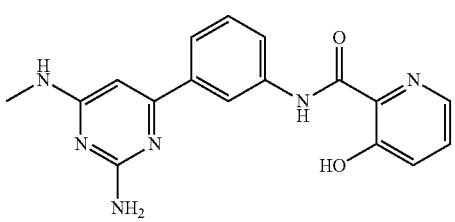
Example 306
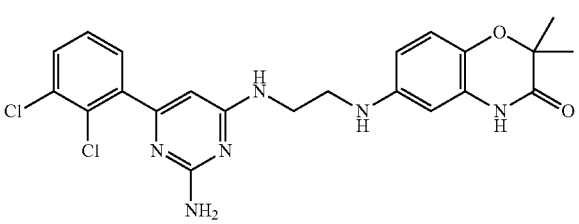
Example 307
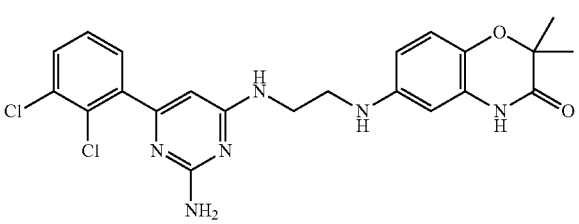
Example 308
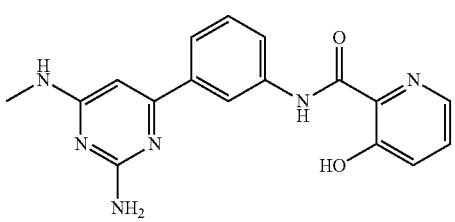

-continued
Example 309
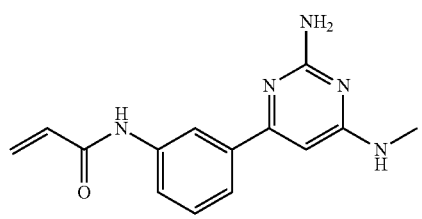
Example 310
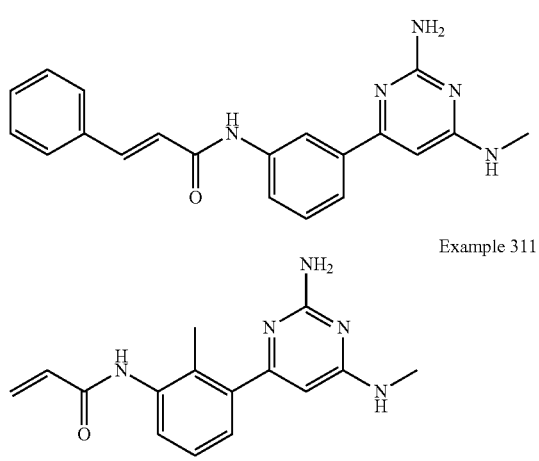
Example 311
Example 312
Example 313
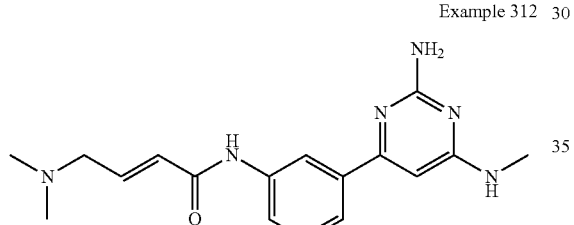
Example 314
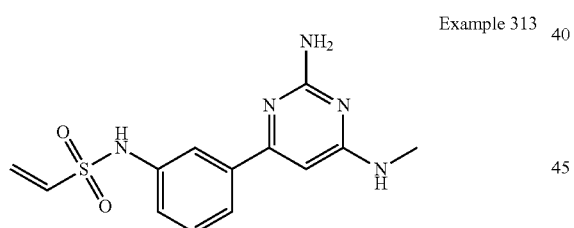
Example 315
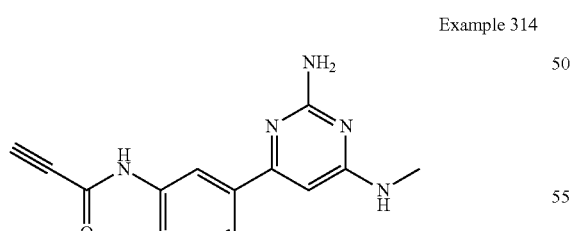
-continued
Example 316
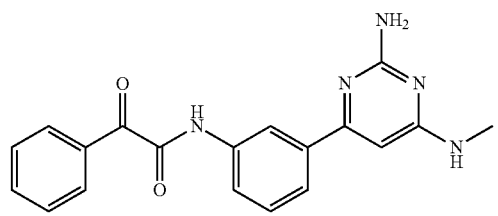
Example 317
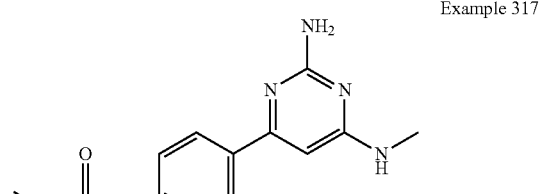
Example 318
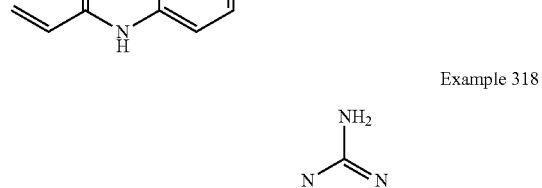
Example 319
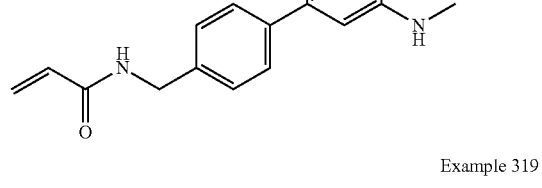
Example 320
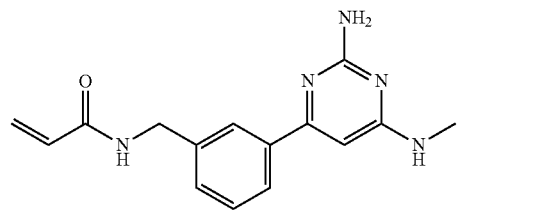
Example 321
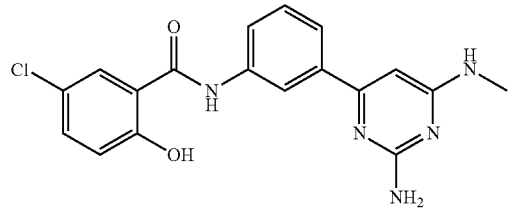

Example 322, 323, 324, 325, 326, 327, 328, 329, 330, 331, 332, 333

Example 334
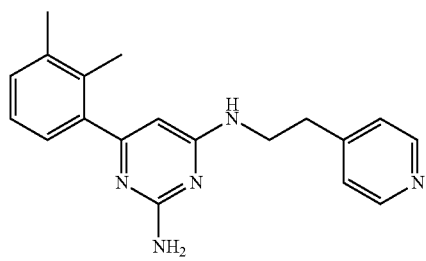
Example 340
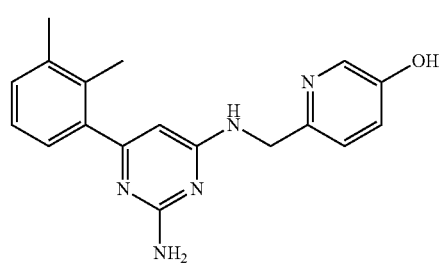
Example 335
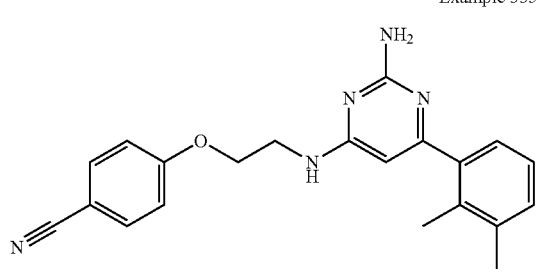
Example 341
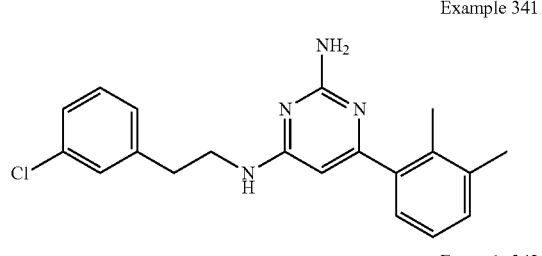
Example 336
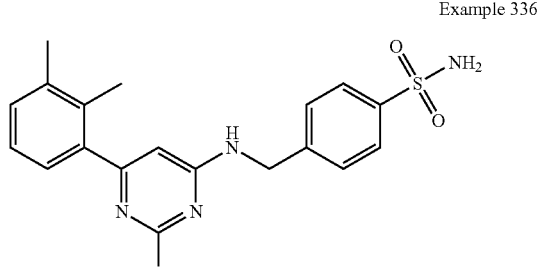
Example 342
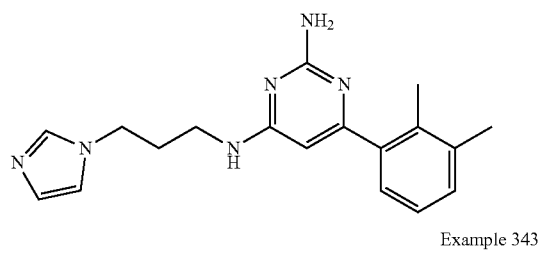
Example 337
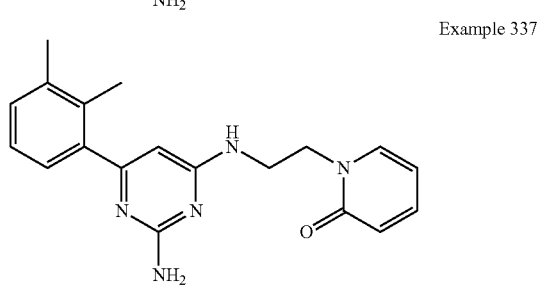
Example 343
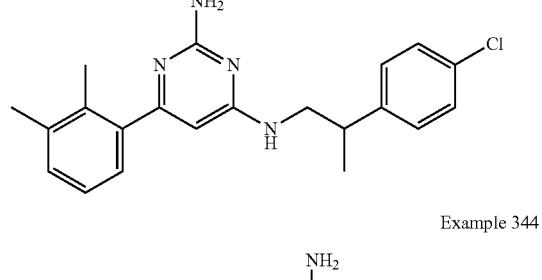
Example 338
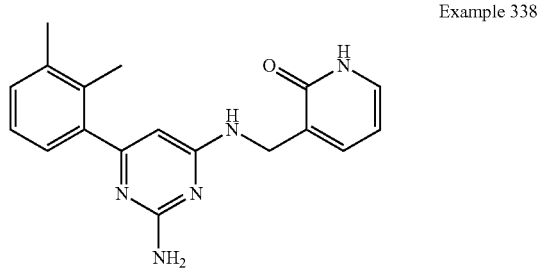
Example 344
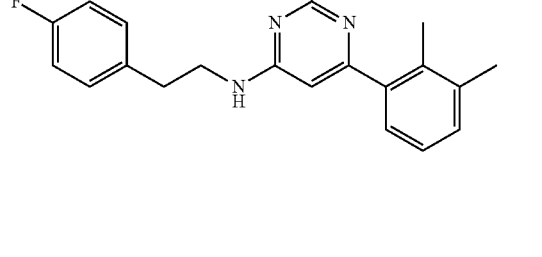
Example 339
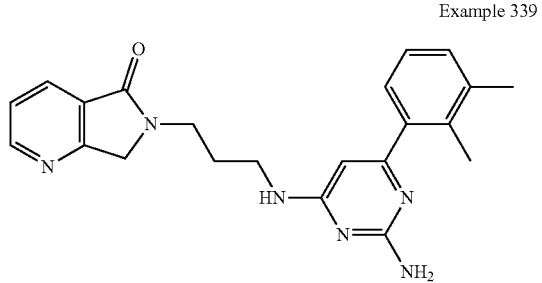
Example 345
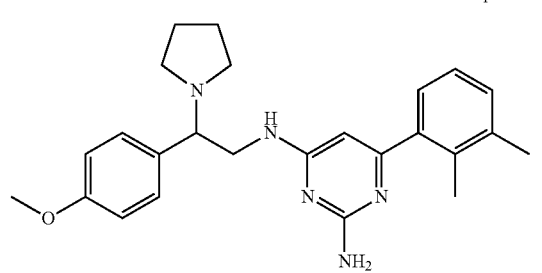

Example 346
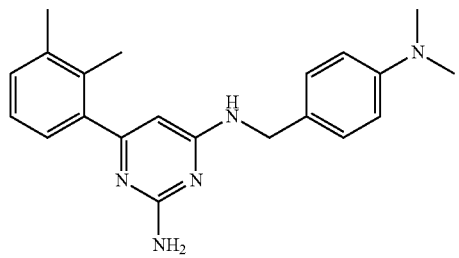
Example 347
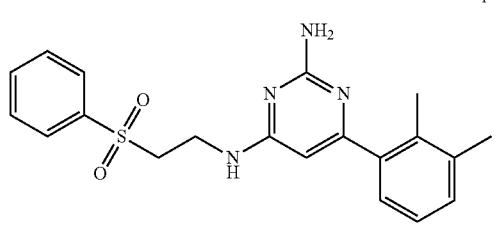
Example 348
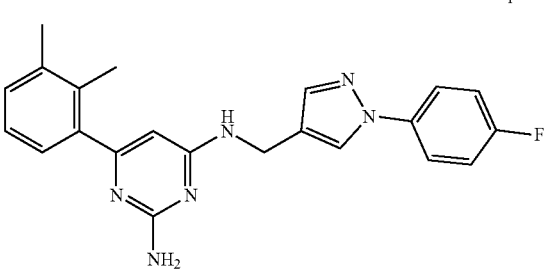
Example 349
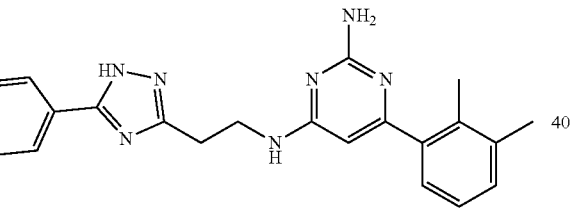
Example 350
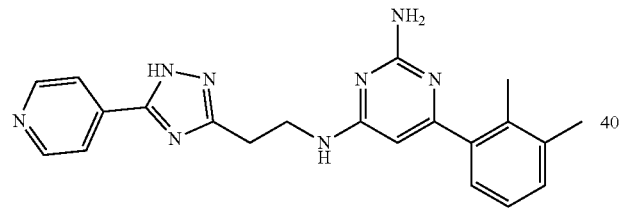
Example 351
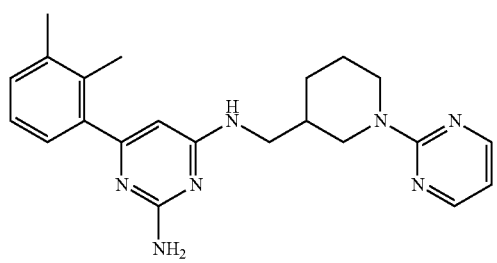
Example 352
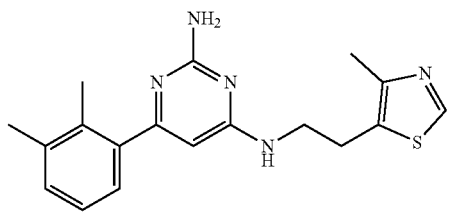
Example 353
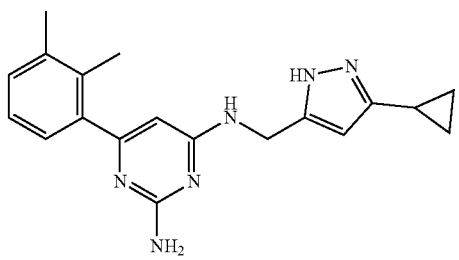
Example 354
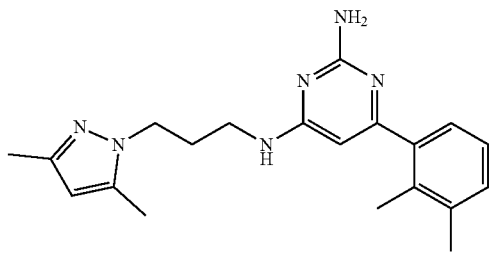
Example 355
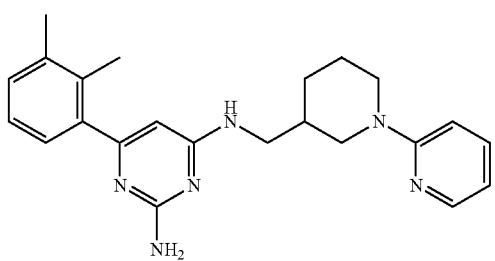
Example 356
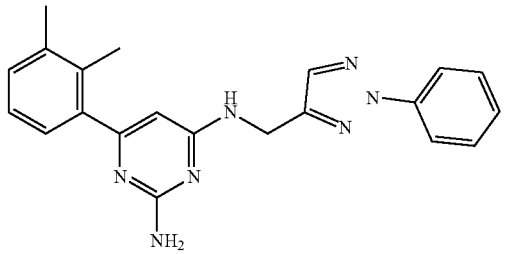
Example 357
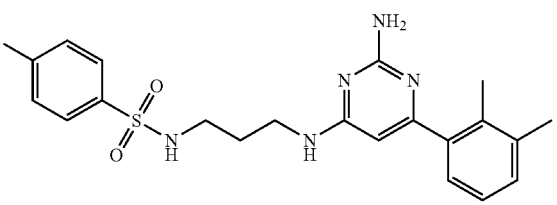

Example 358
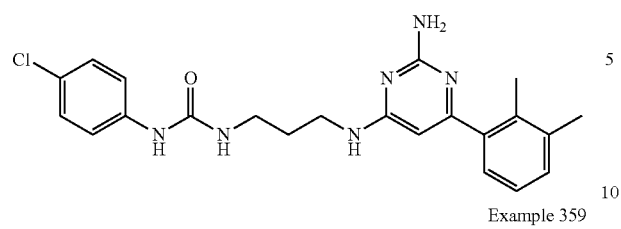
Example 359
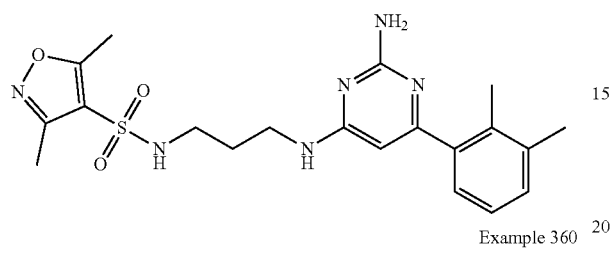
Example 360
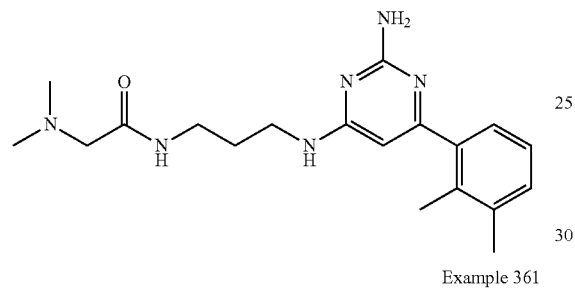
Example 361
Example 362
Example 363
Example 364
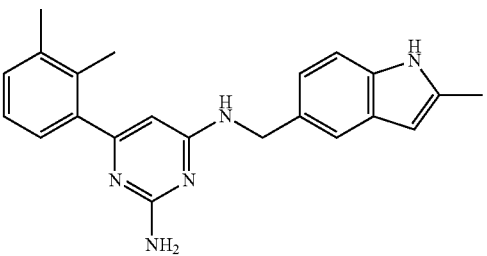
Example 365
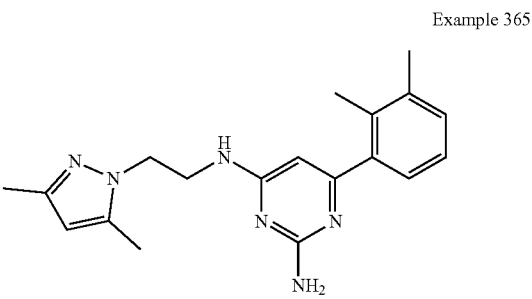
Example 366
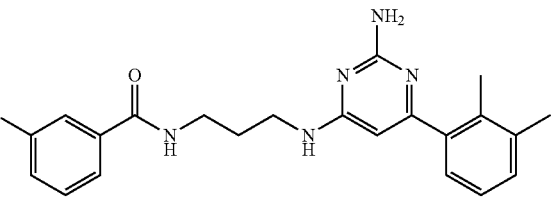
Example 367
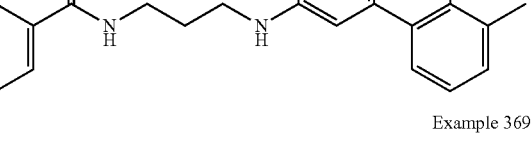
Example 368
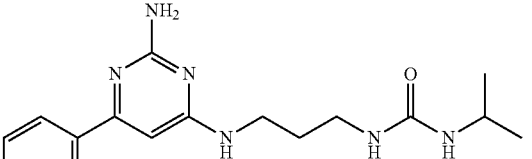
Example 369
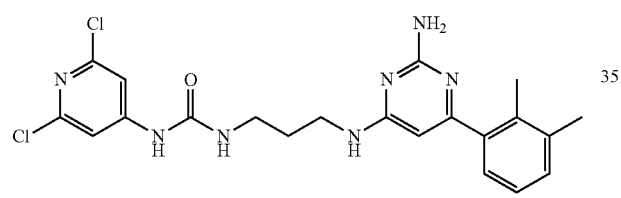
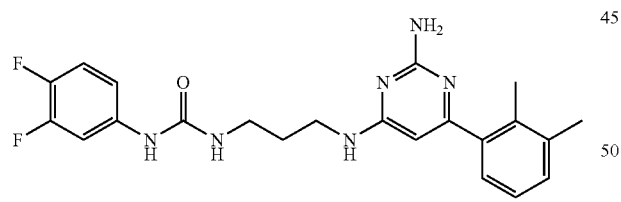
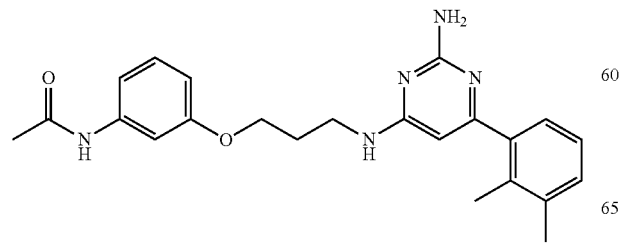

Example 370
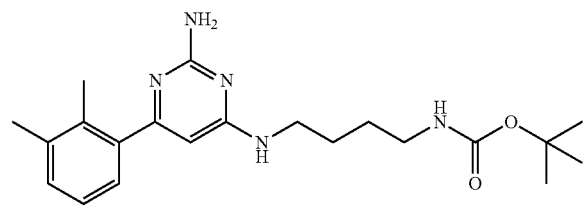
Example 371
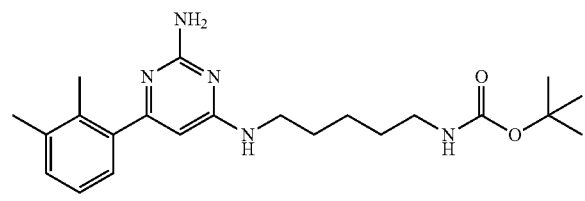
Example 372
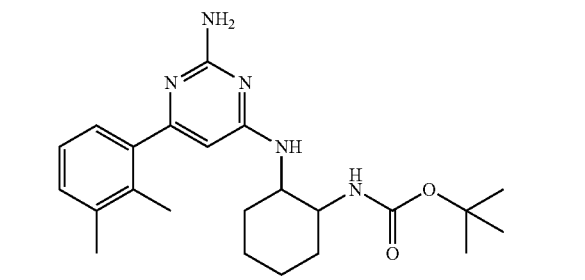
Example 373
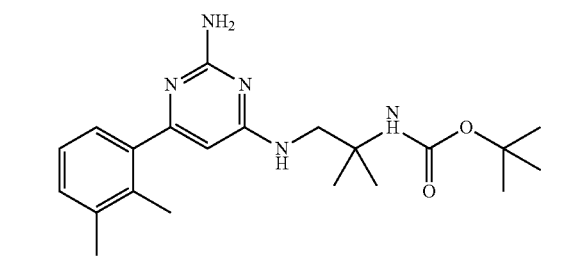
Example 374
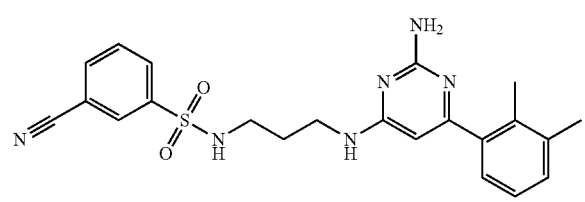
Example 375
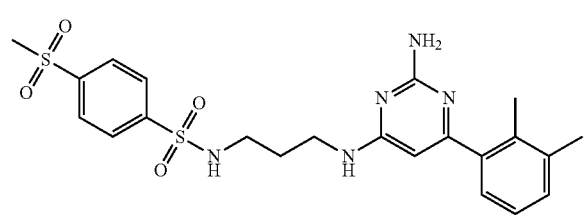
Example 376
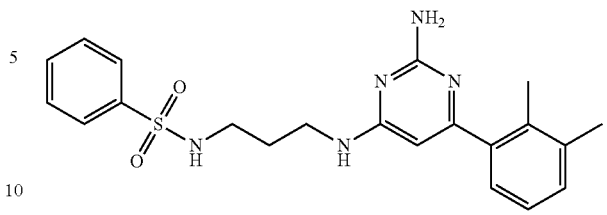
Example 377
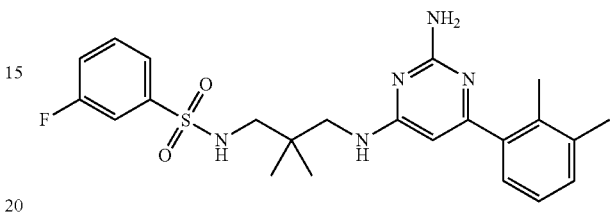
Example 378
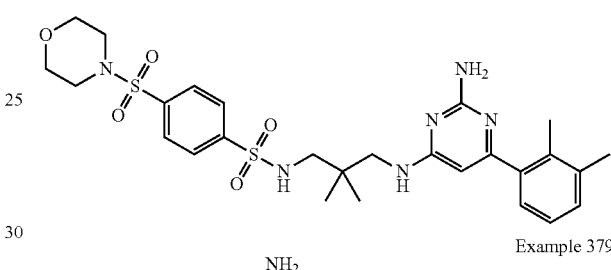
Example 379
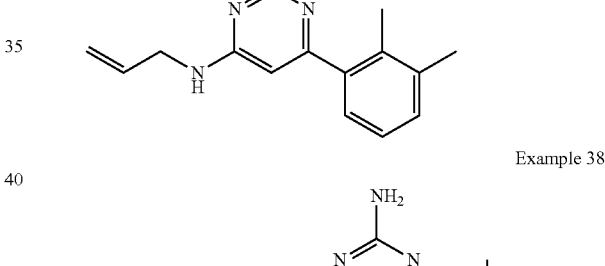
Example 380
Example 381
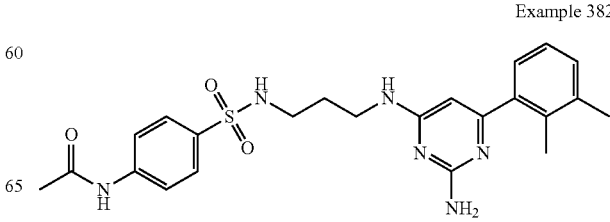
Example 382
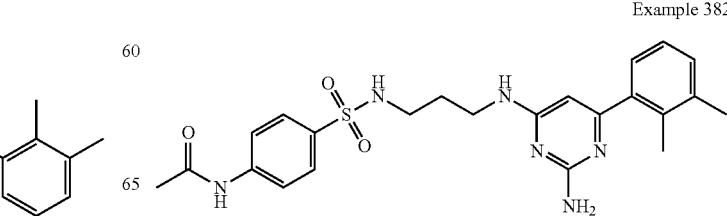

Example 383
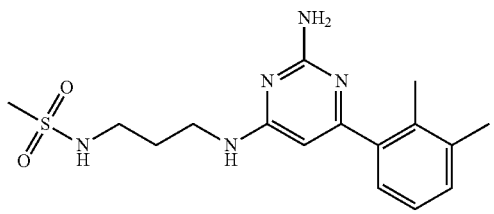
Example 384
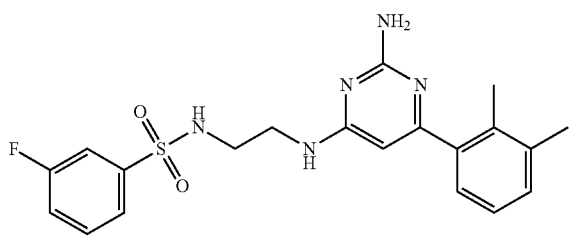
Example 385
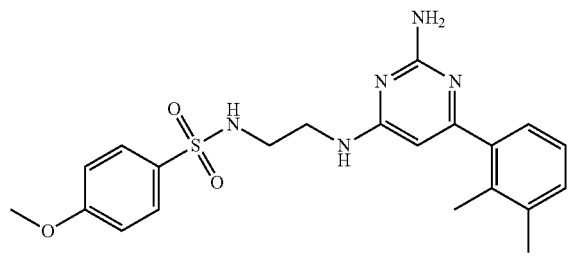
Example 386
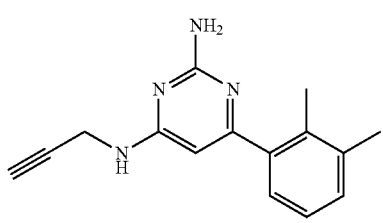
Example 387
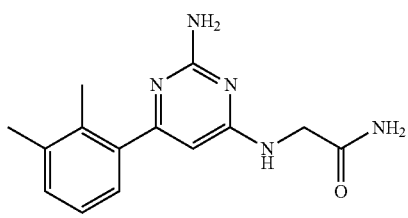
Example 388
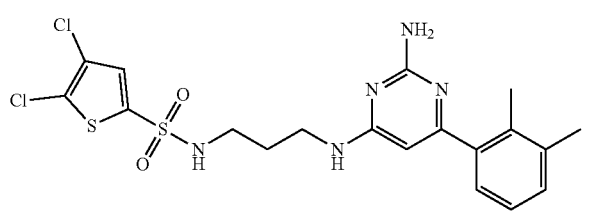
Example 389
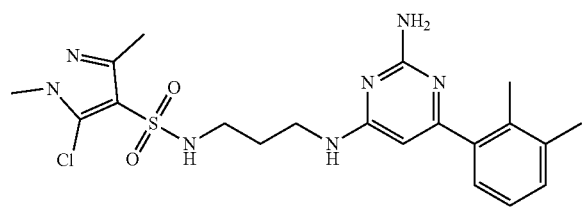
Example 390
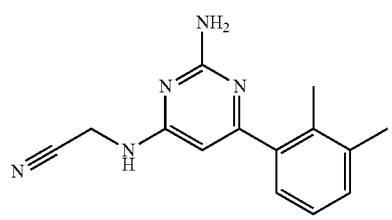
Example 391
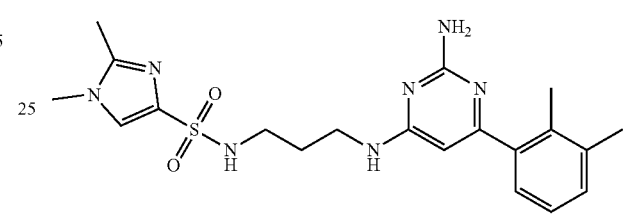
Example 392
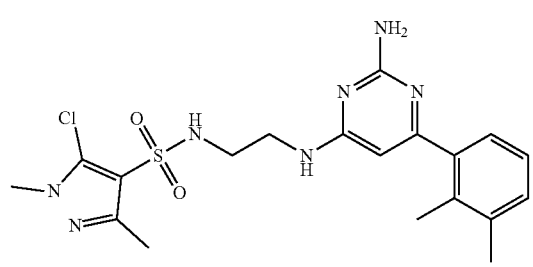
Example 393
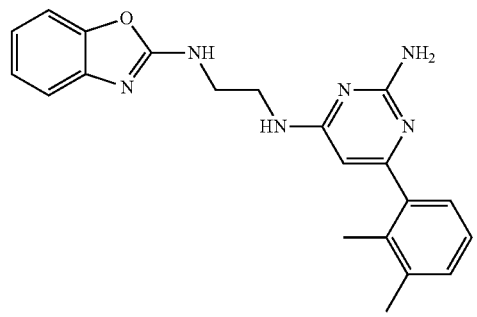
Example 394
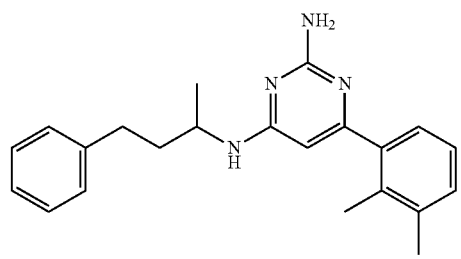

Example 395
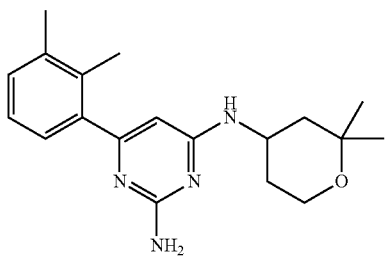
Example 396
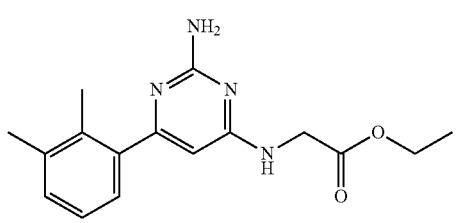
Example 397
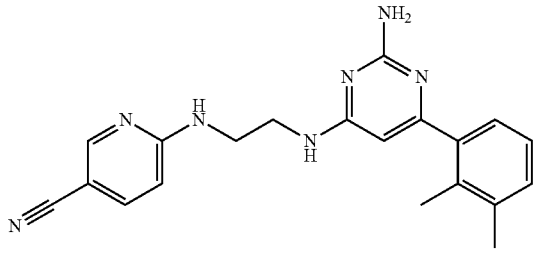
Example 398
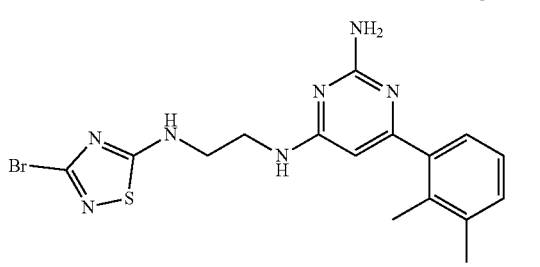
Example 399
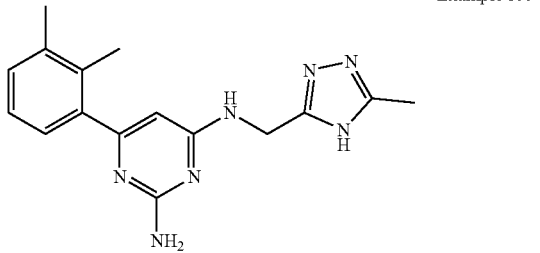
Example 400
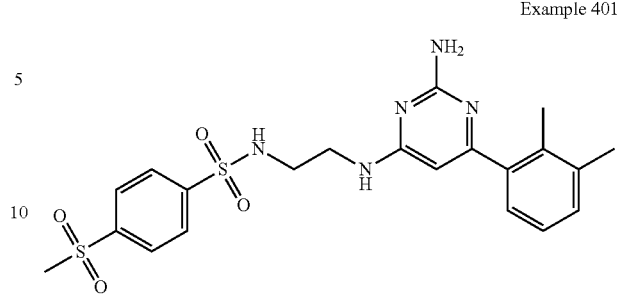
Example 401
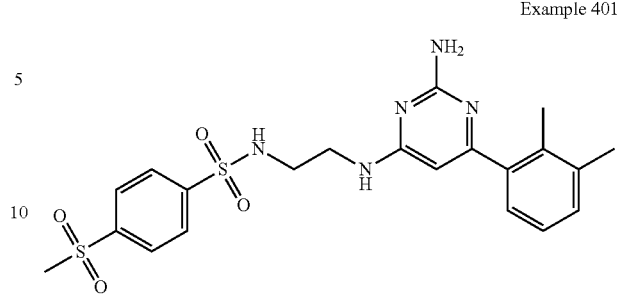
Example 402
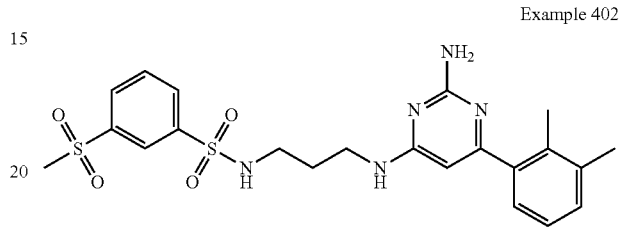
Example 403
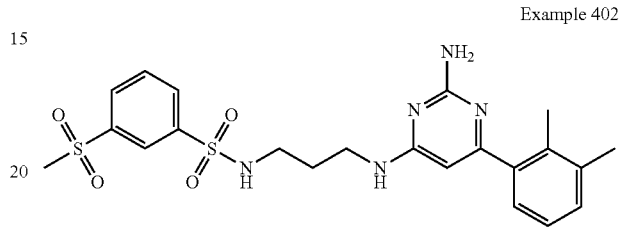
Example 404
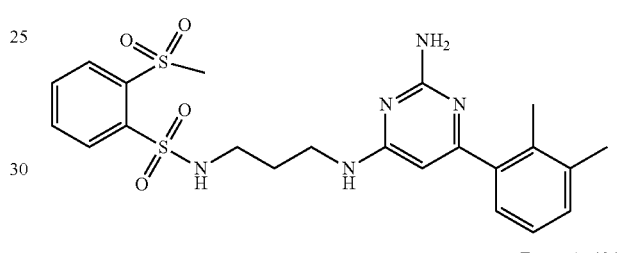
Example 405
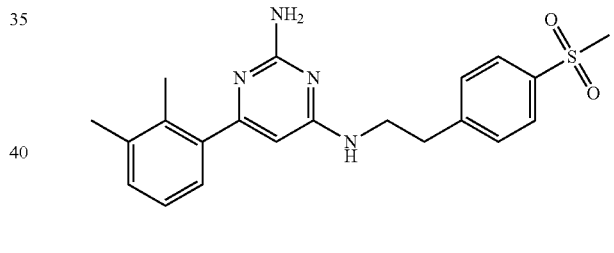
Example 406
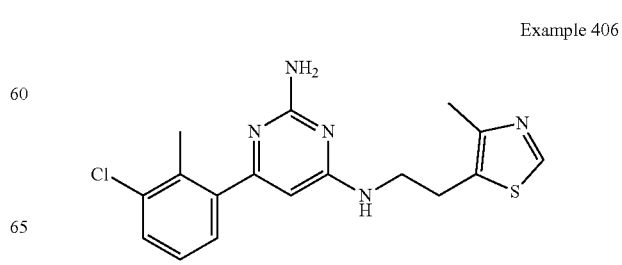

Example 407
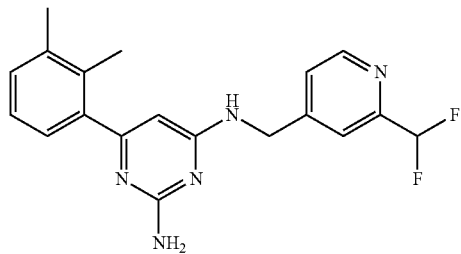
Example 408
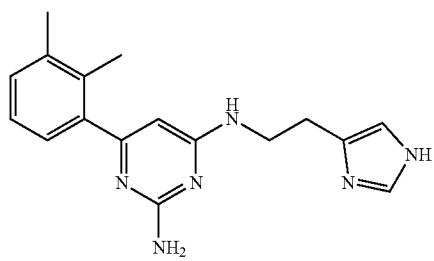
Example 409
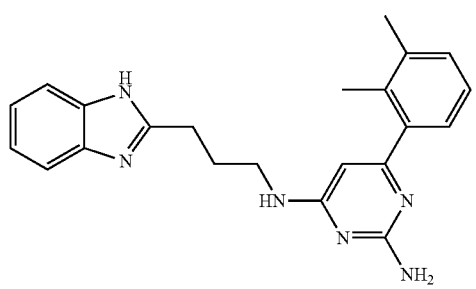
Example 410
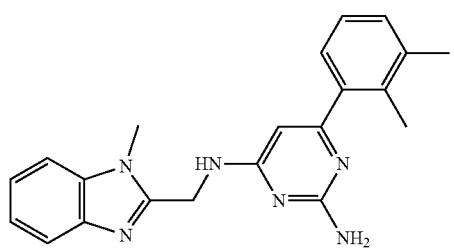
Example 411
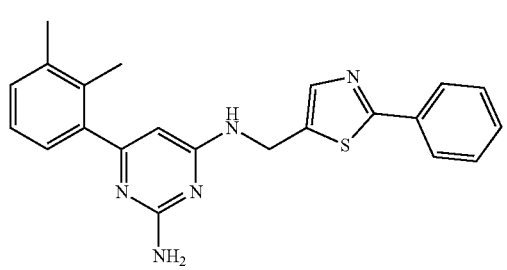
Example 412
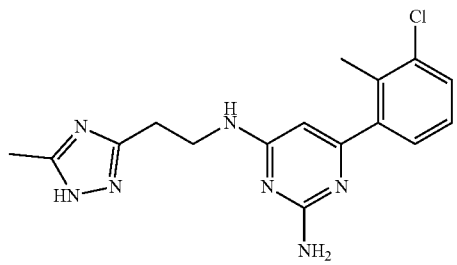
Example 413
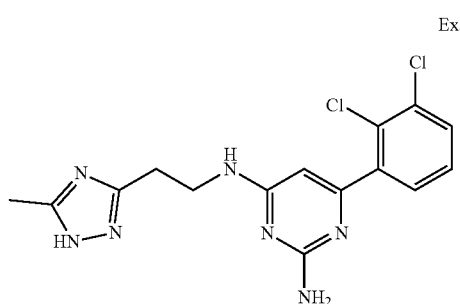
Example 414
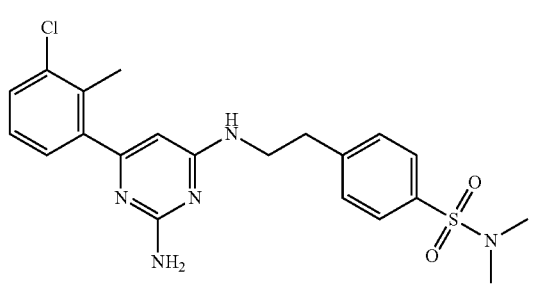
Example 415
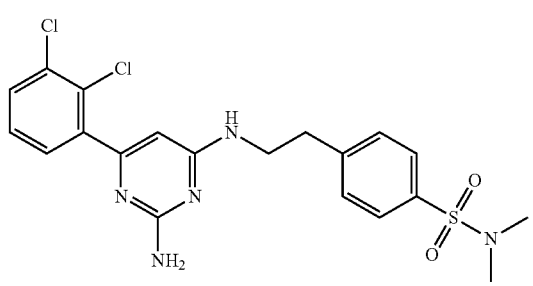
Example 416
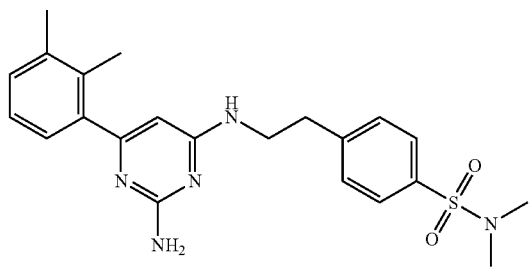

Example 417
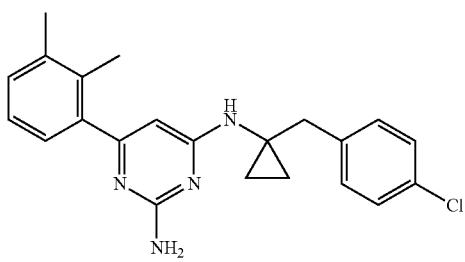
Example 418
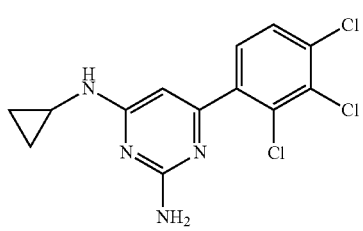
Example 419
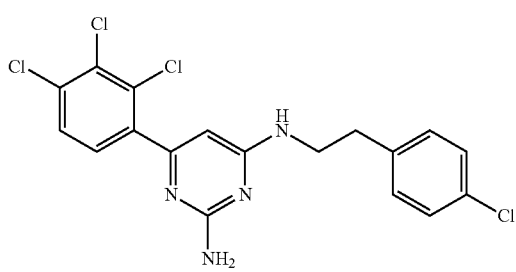
Example 420
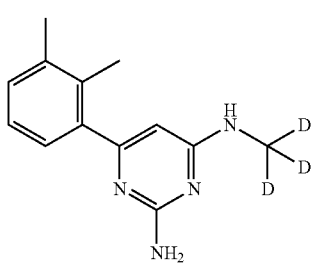
Example 421
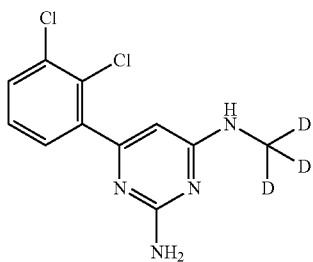
Example 422
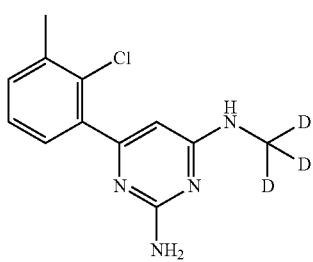
Example 423
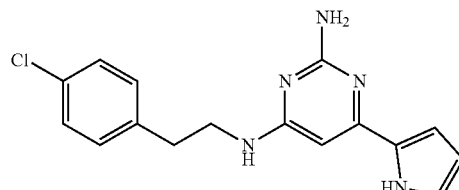
Example 424
Example 425
Example 426
Example 427
Example 428
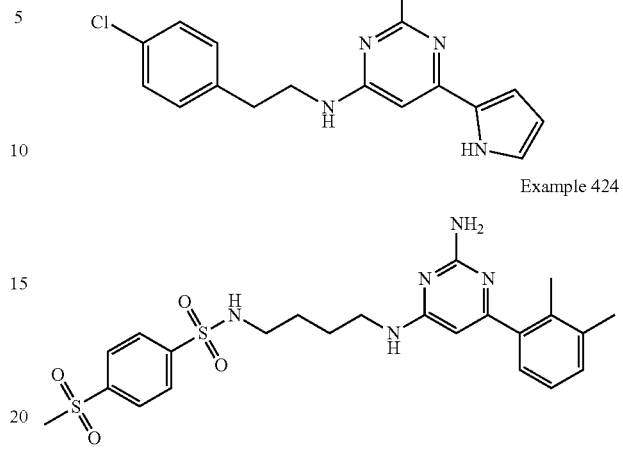

Example 429
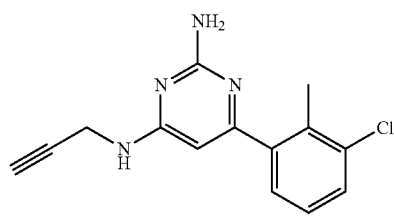
Example 430
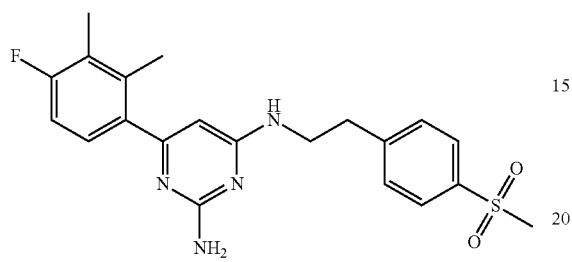
Example 431
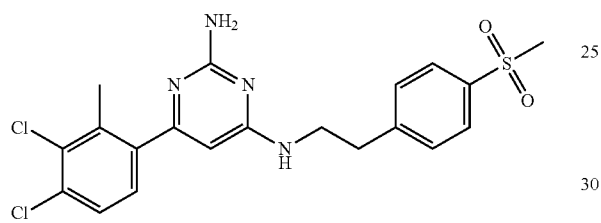
Example 432
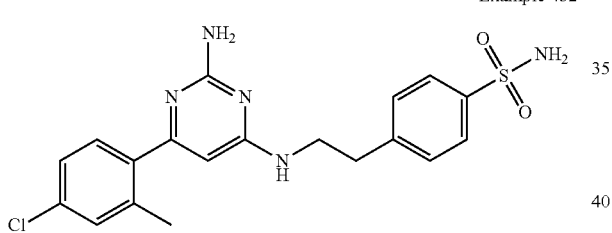
Example 433
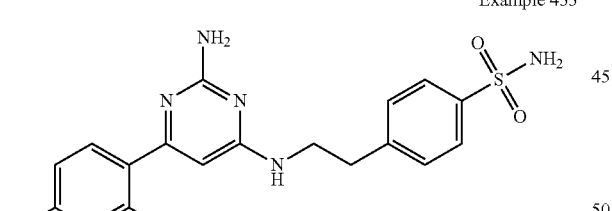
Example 434
Example 435
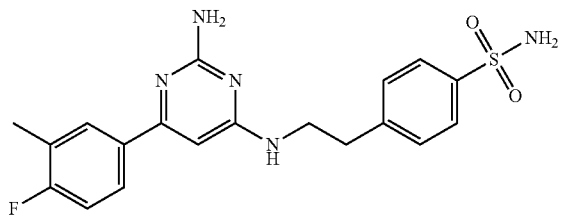
Example 436
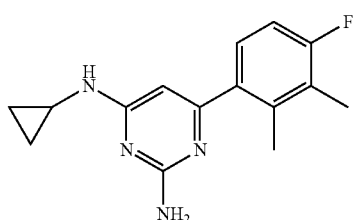
Example 437
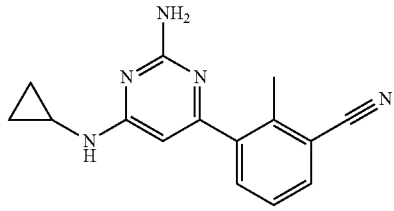
Example 438
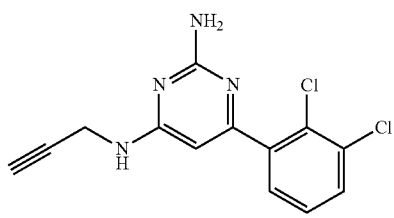
Example 439
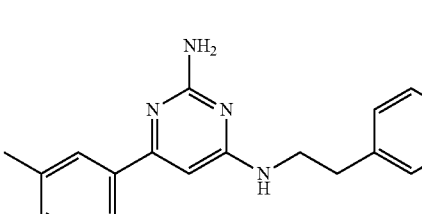
Example 440
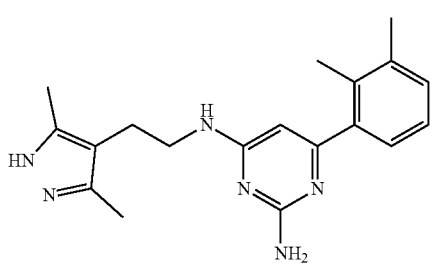

Example 441
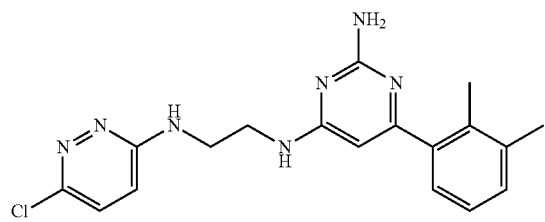
Example 442
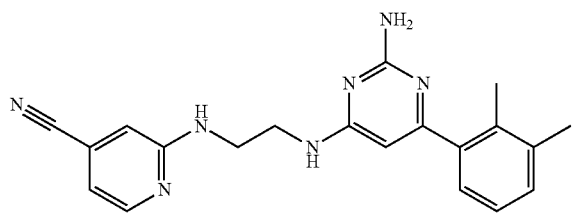
Example 443
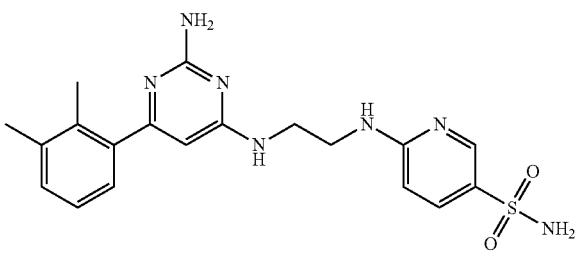
Example 444
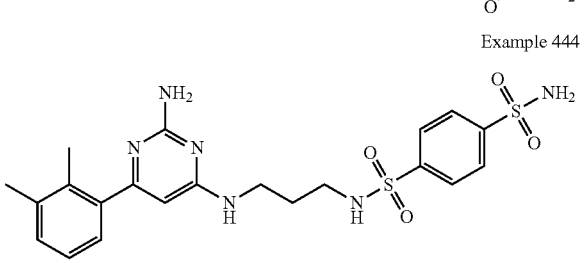
Example 445
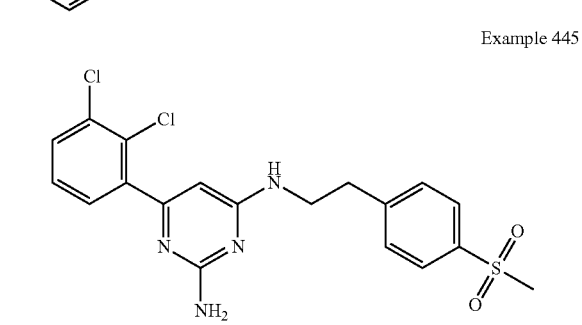
Example 446
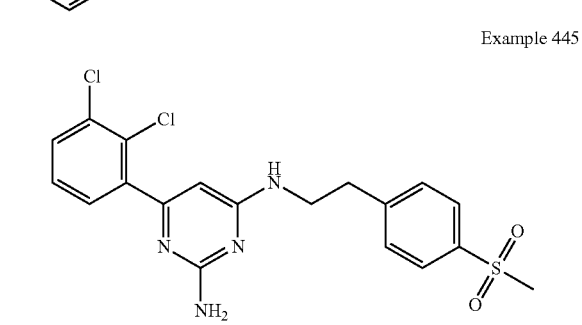
Example 447
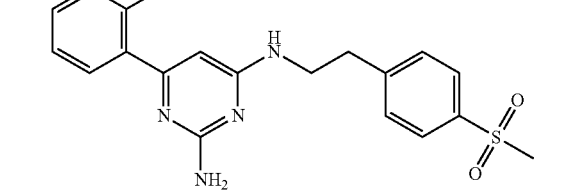
Example 448
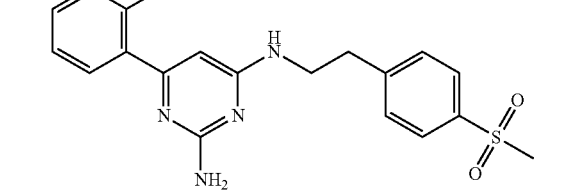
Example 449
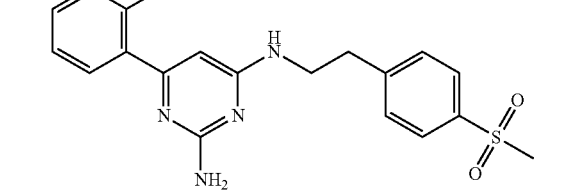
Example 450
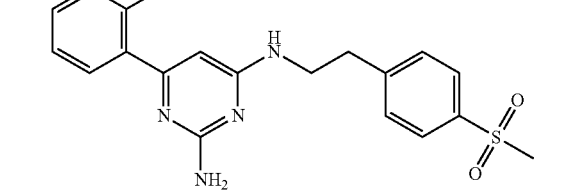
Example 451
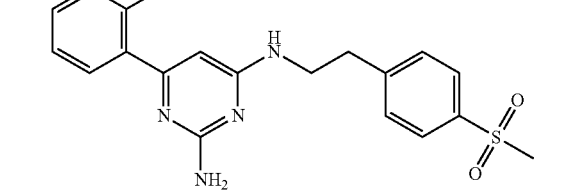
Example 452
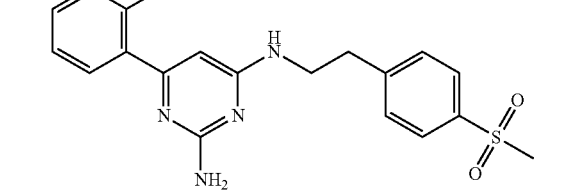

Example 453
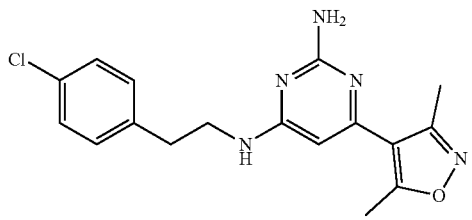
Example 454
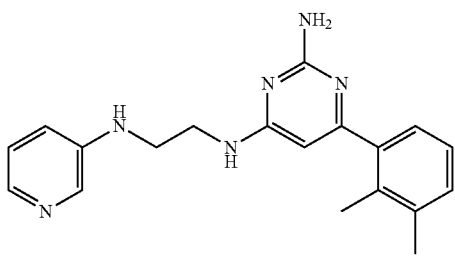
Example 455
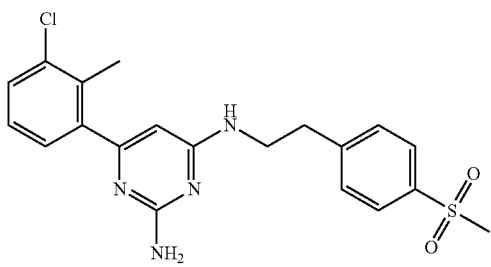
Example 456
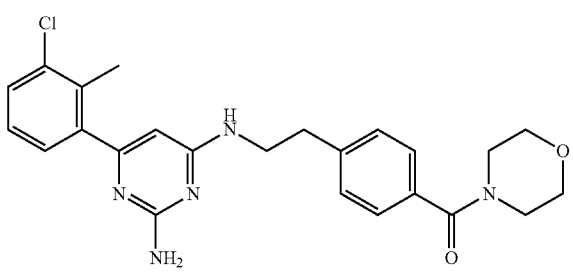
Example 457
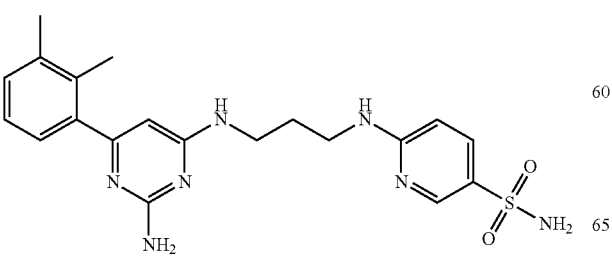
Example 458
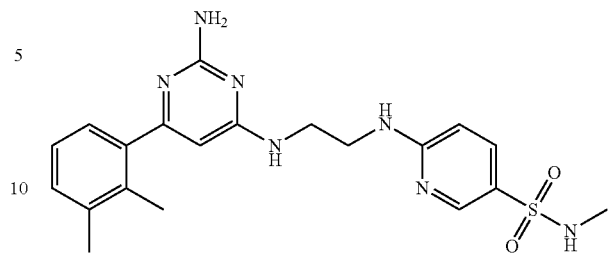
Example 459
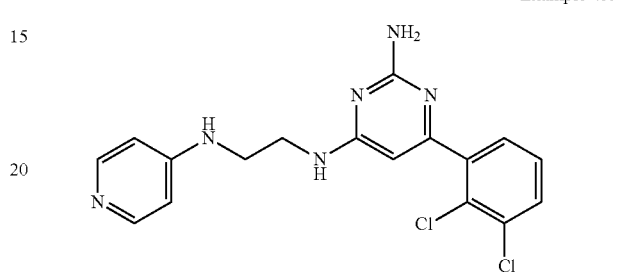
Example 460
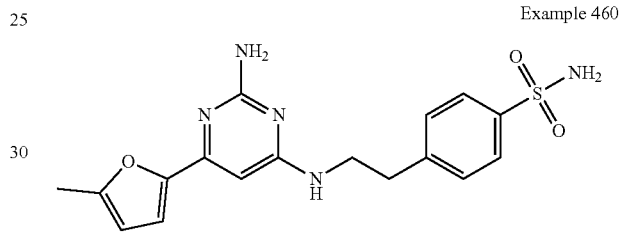
Example 461
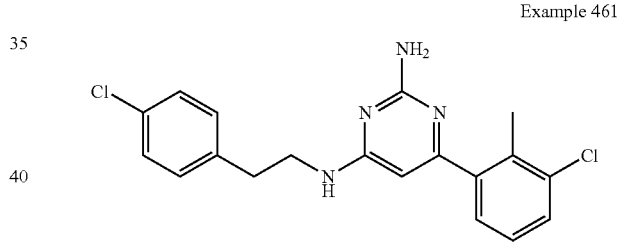
Example 462
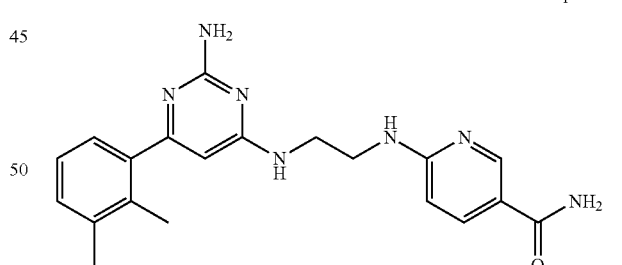
Example 463

-continued
Example 464
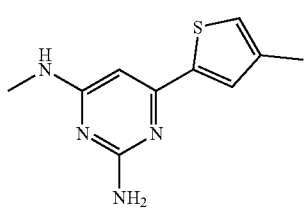
Example 465
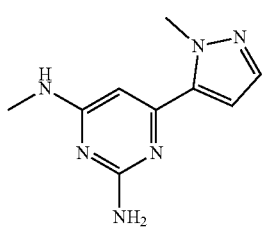
Example 466
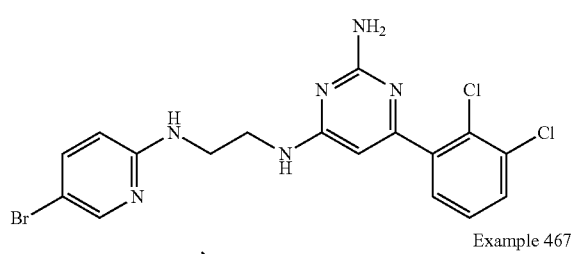
Example 467
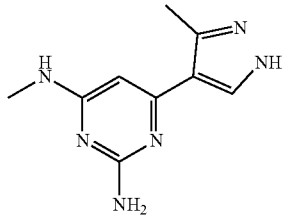
Example 468
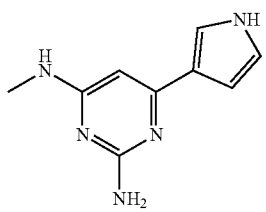
Example 469
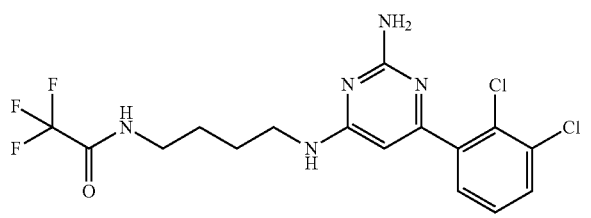
Example 470
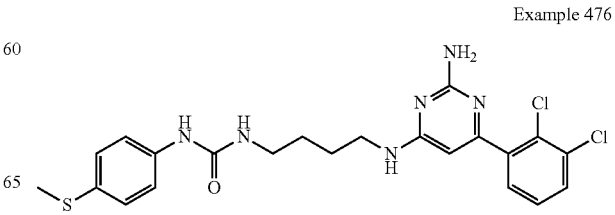
-continued
Example 471
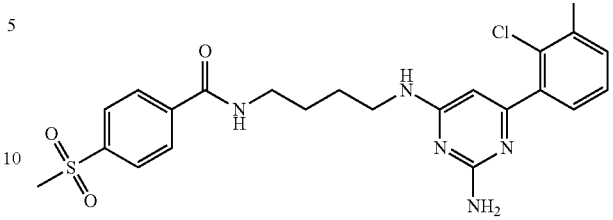
Example 472
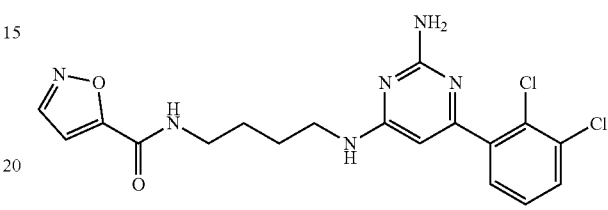
Example 473
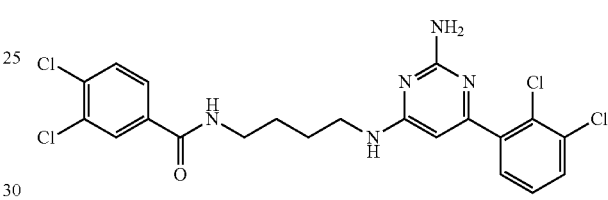
Example 474
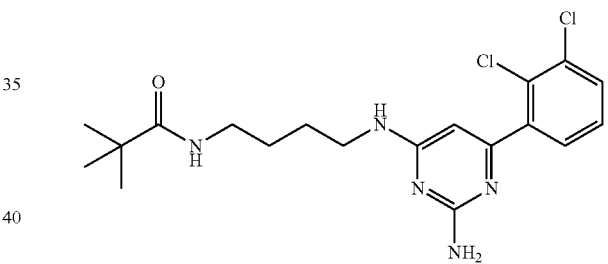
Example 475
Example 476
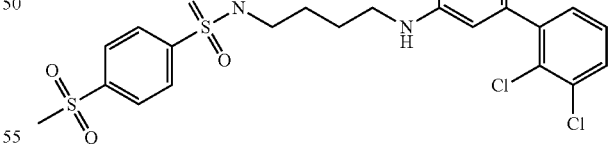

Example 477
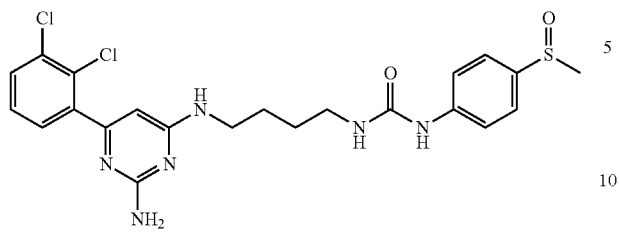
Example 483
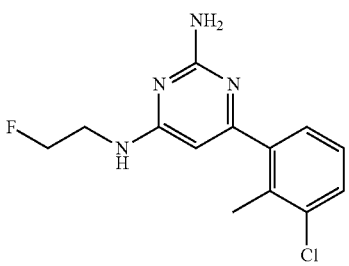
Example 478
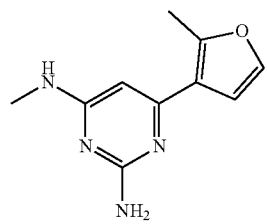
Example 484
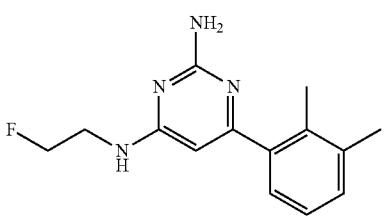
Example 479
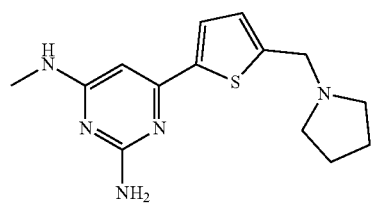
Example 485
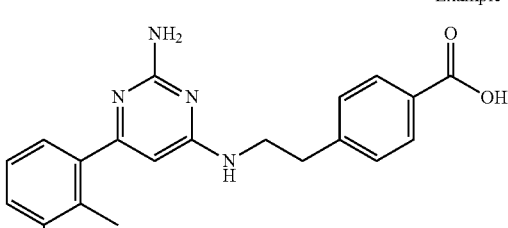
Example 480
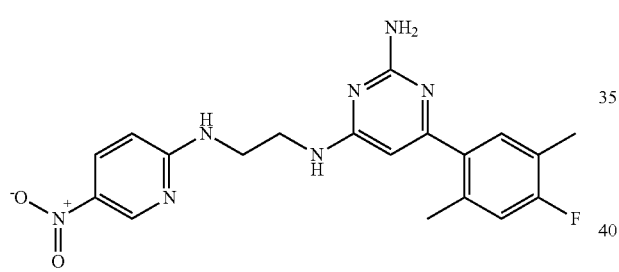
Example 486
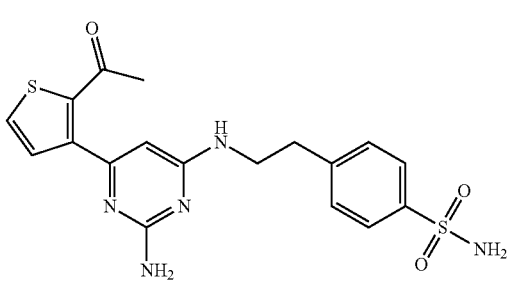
Example 481
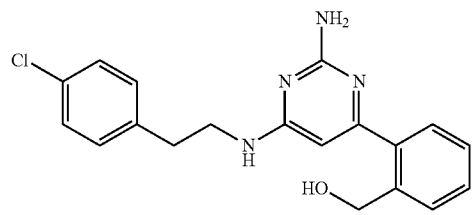
Example 487
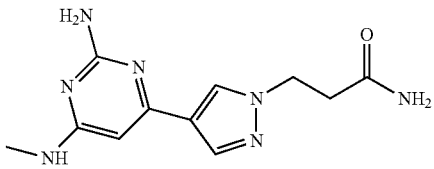
Example 482
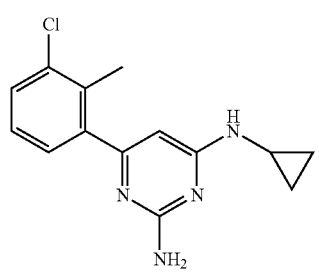
Example 488
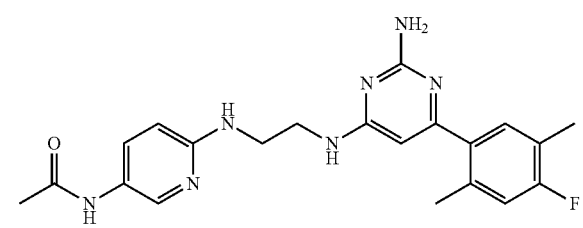

Example 489
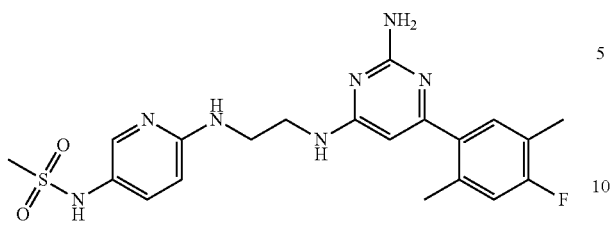
Example 491
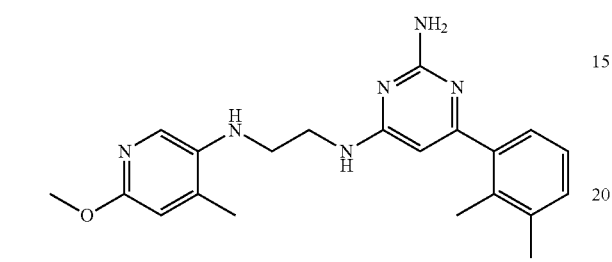
Example 491
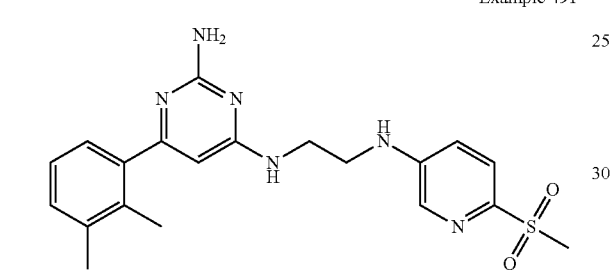
Example 492
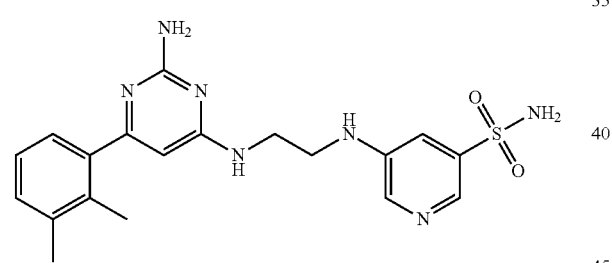
Example 493
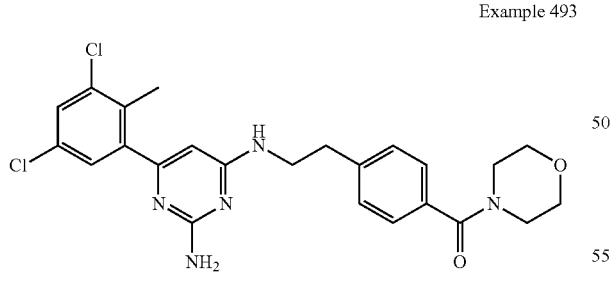
Example 494
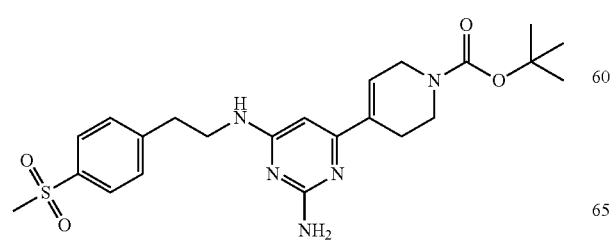
Example 495
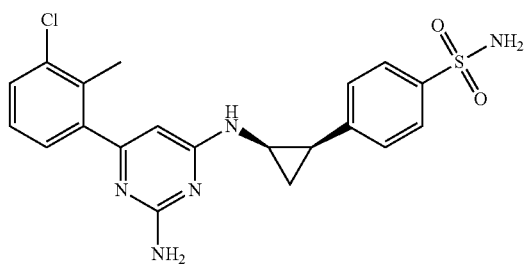
Example 496
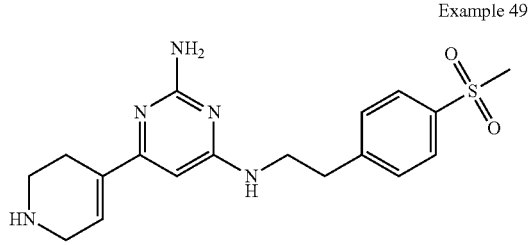
Example 497
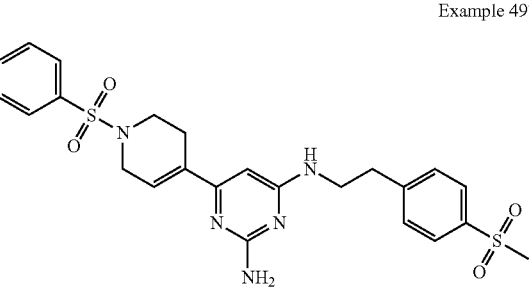
Example 498
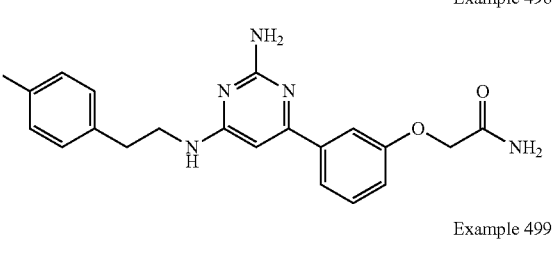
Example 499
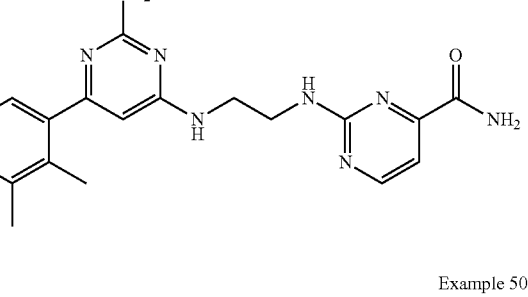
Example 500
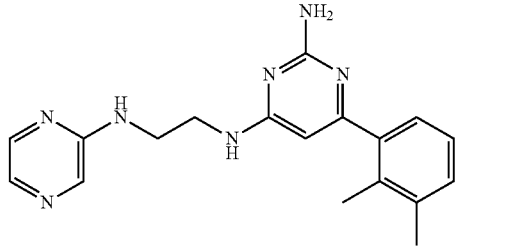

Example 501
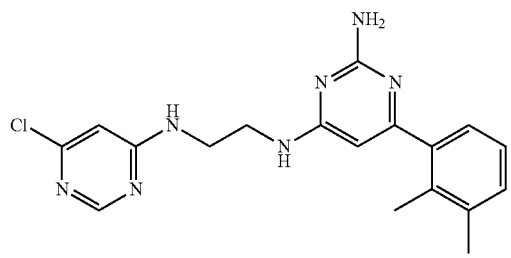
Example 502
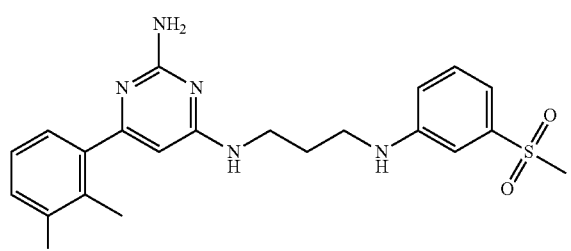
Example 503
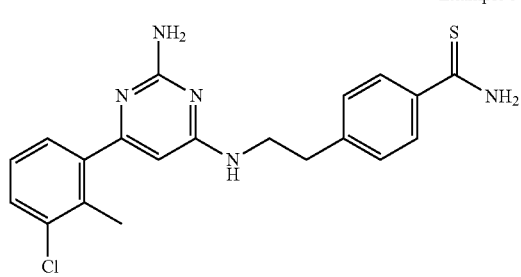
Example 504
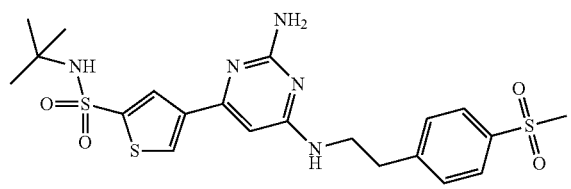
Example 505
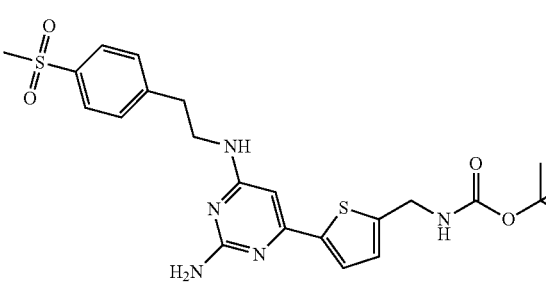
Example 506
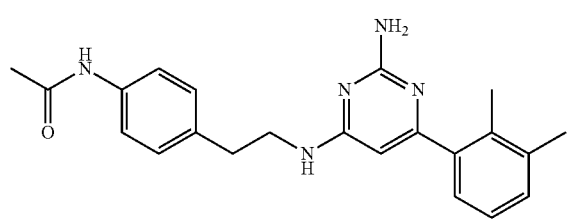
Example 507
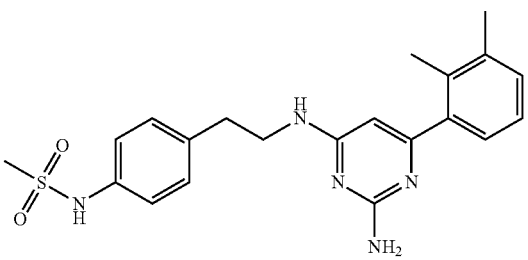
Example 508
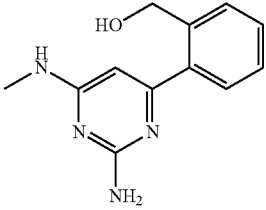
Example 509
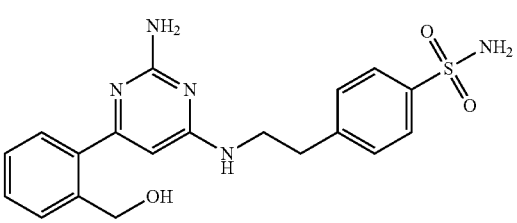
Example 510
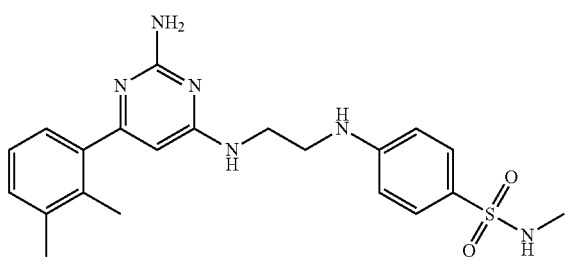
Example 511
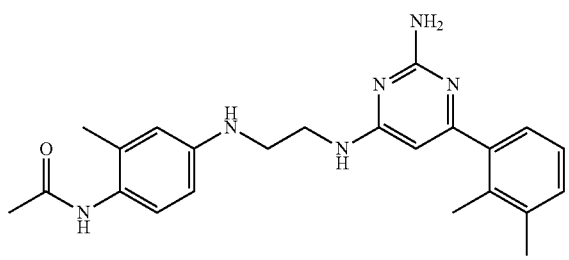
Example 512
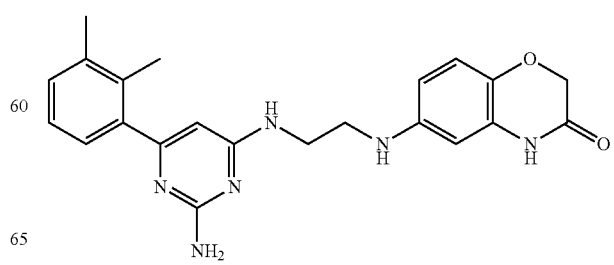

Example 513
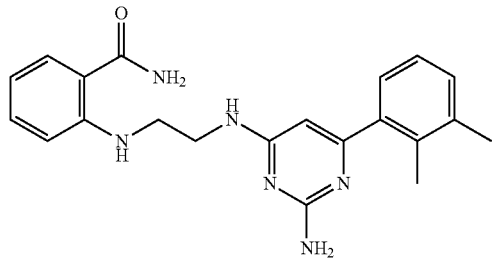
Example 514
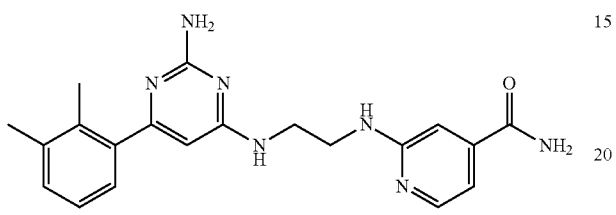
Example 515
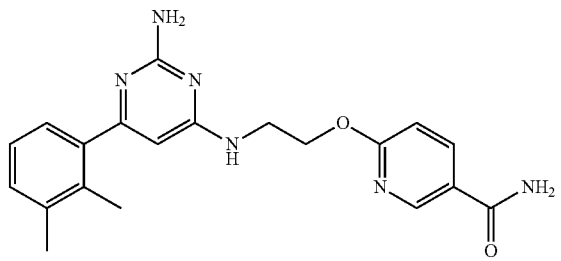
Example 516
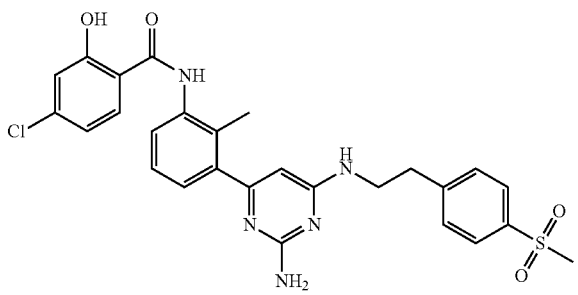
Example 517
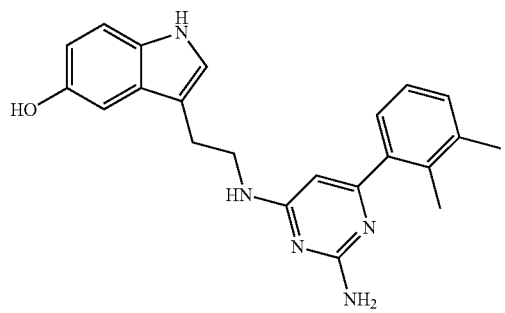
Example 518
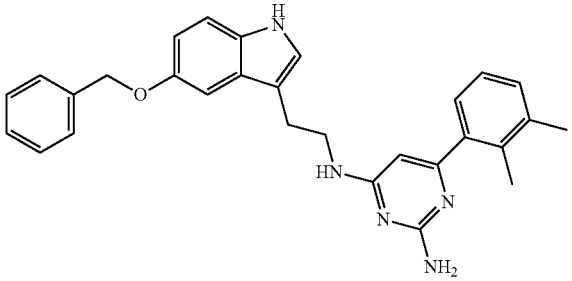
Example 519
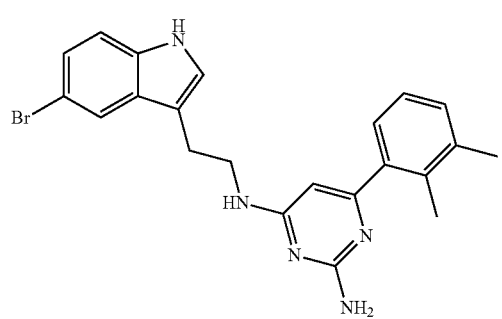
Example 520
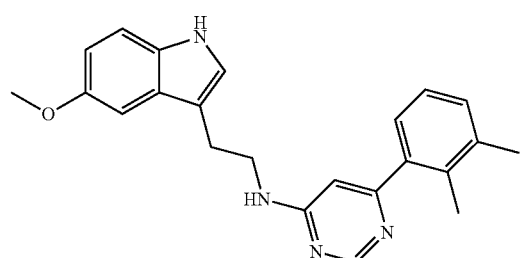
Example 521
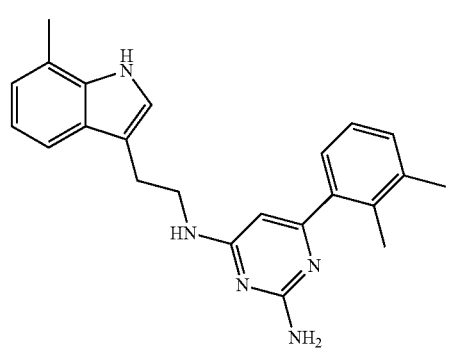
Example 522
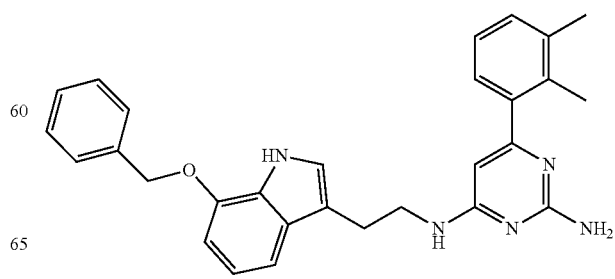

-continued
Example 523
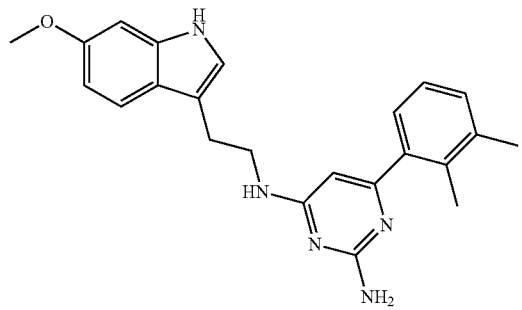
Example 524
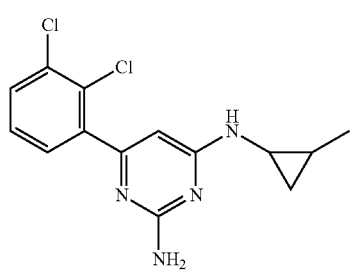
Example 525
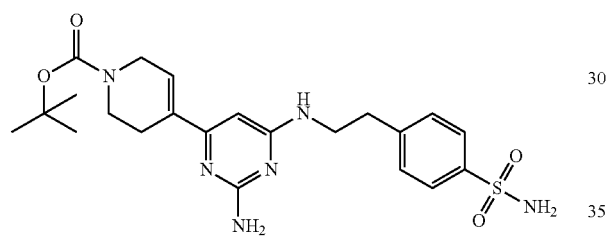
Example 526
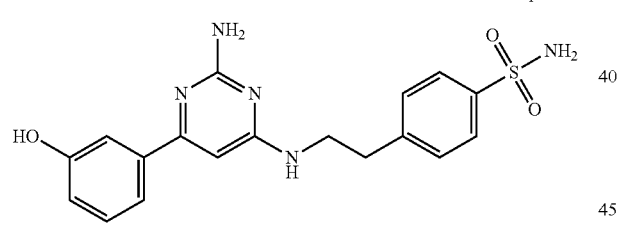
Example 527
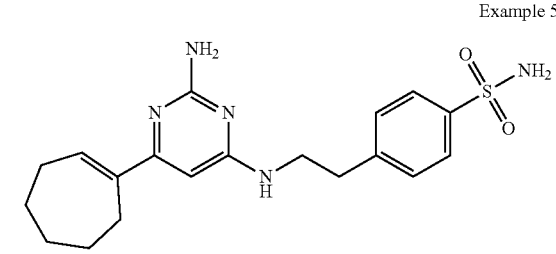
Example 528
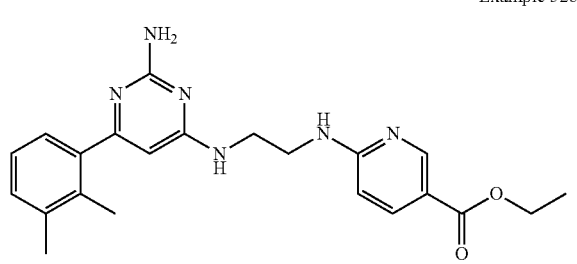
-continued
Example 529
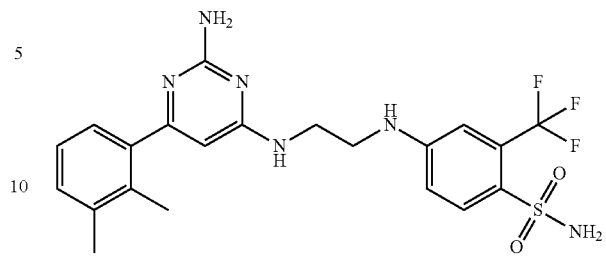
Example 530
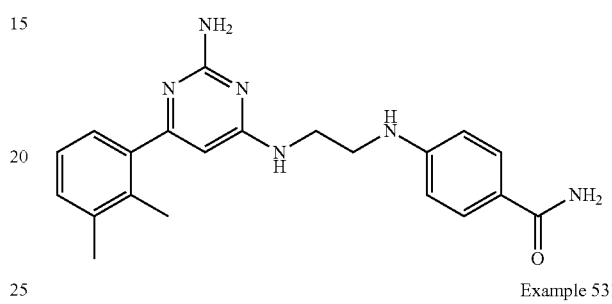
Example 531
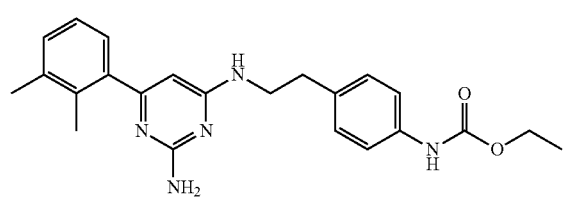
Example 532
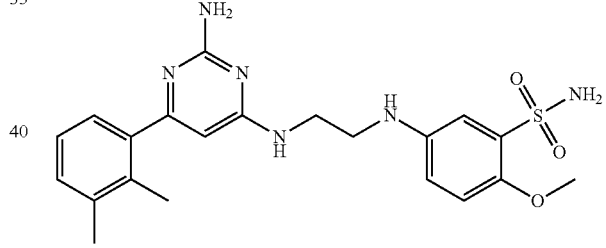
Example 533
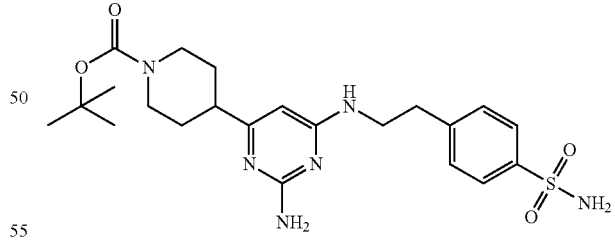
Example 534
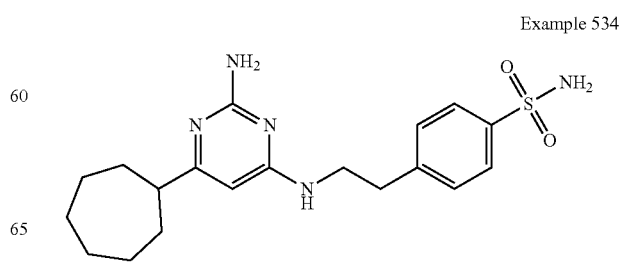

Example 535
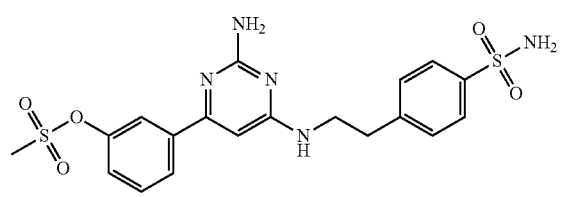
Example 536
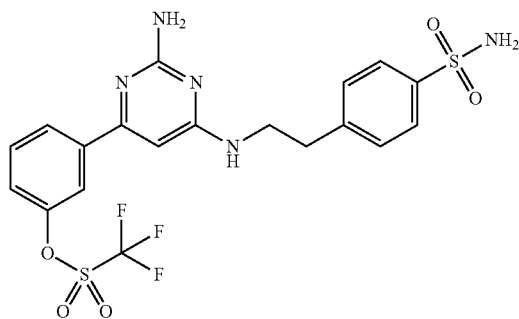
Example 537
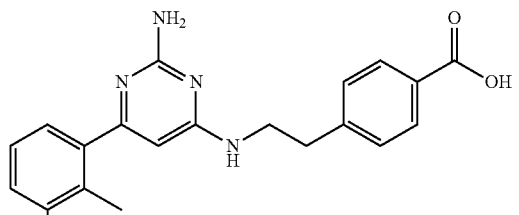
Example 538
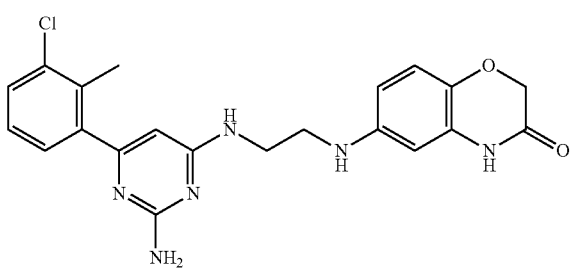
Example 539
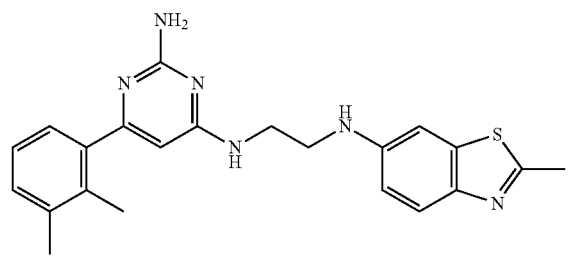
Example 540
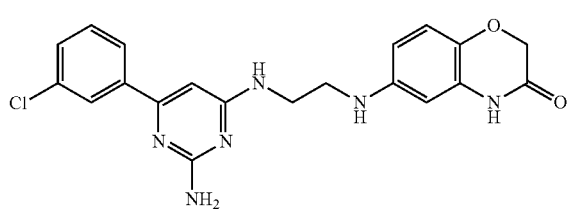
Example 541
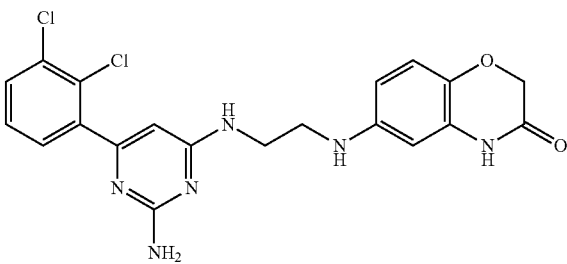
Example 542
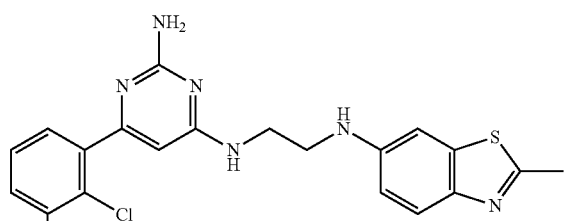
Example 543
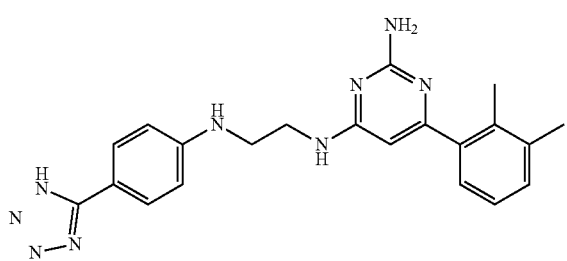
Example 544
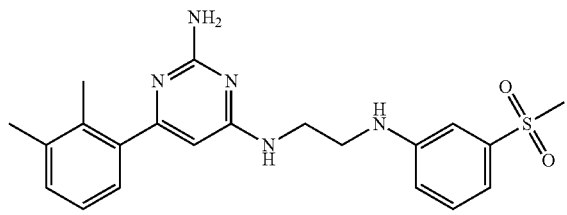
Example 545
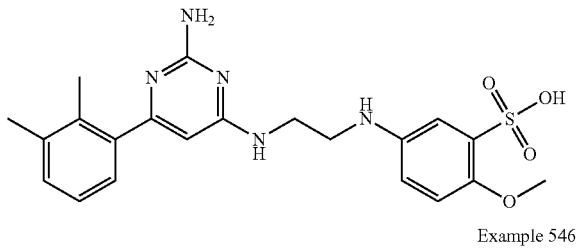
Example 546
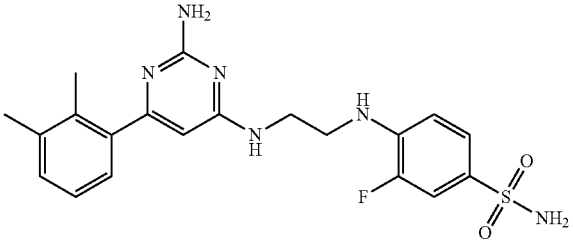

Example 547
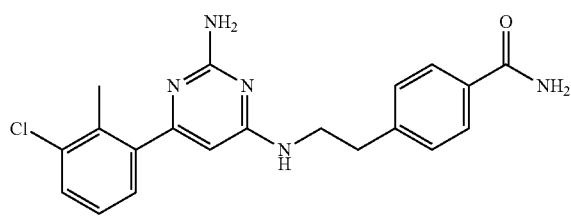
Example 548
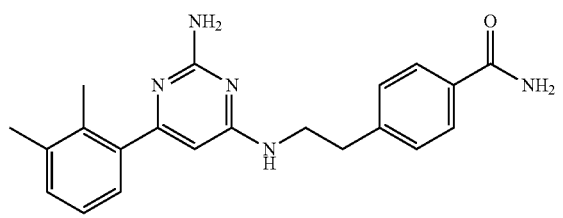
Example 549
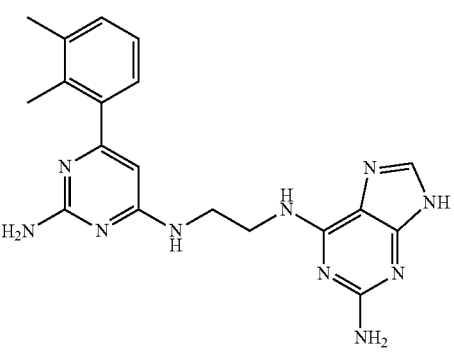
Example 550
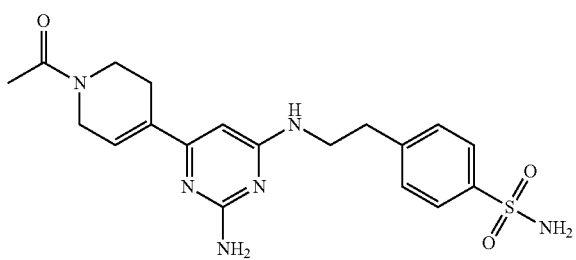
Example 551
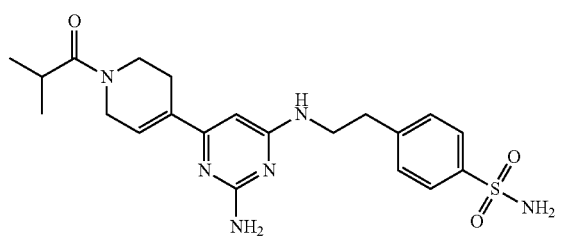
Example 552
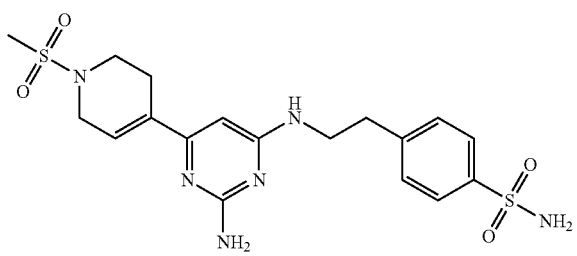
Example 553
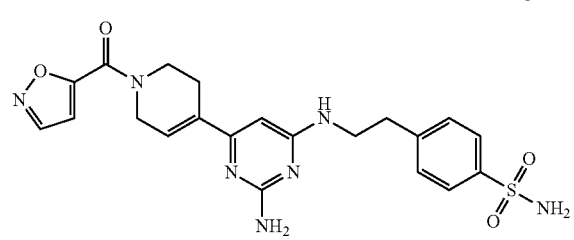
Example 554
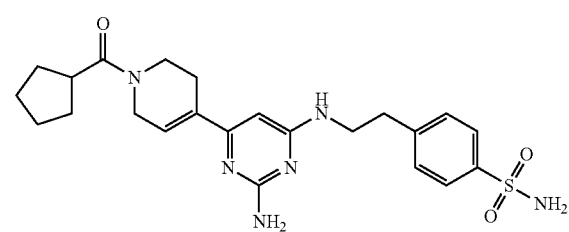
Example 555
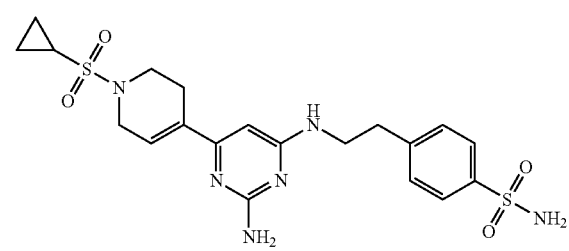
Example 556
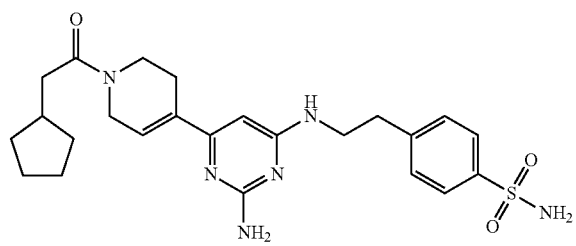
Example 557
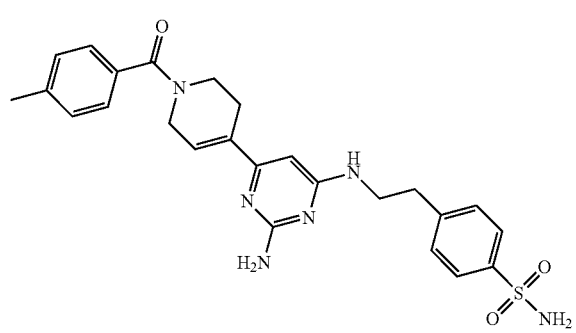

Example 558
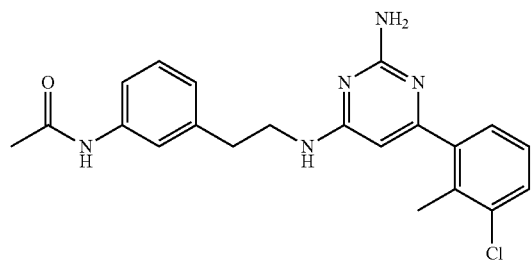
Example 559
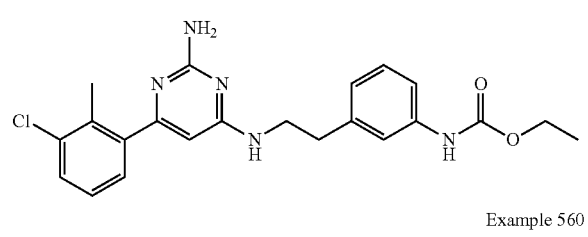
Example 560
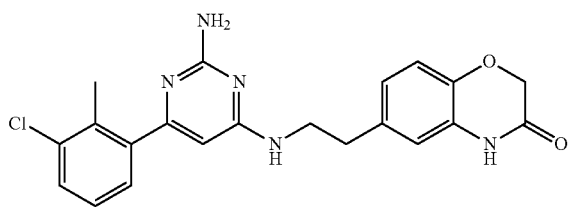
Example 561
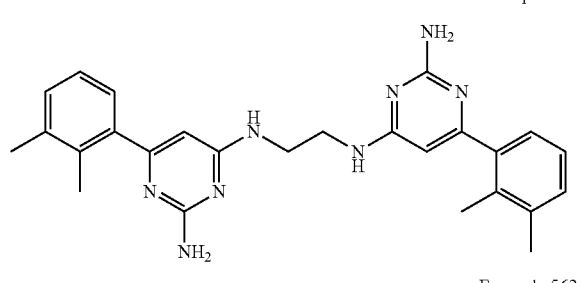
Example 562
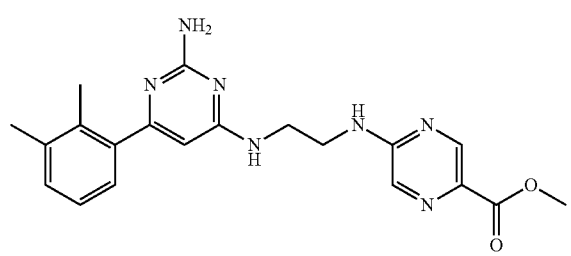
Example 563
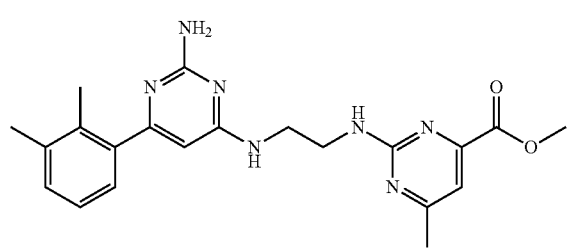
Example 564
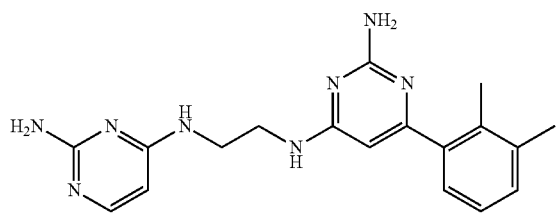
Example 565
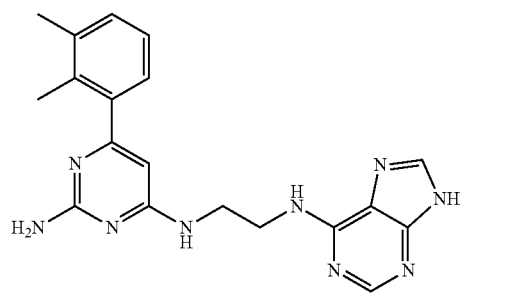
Example 566
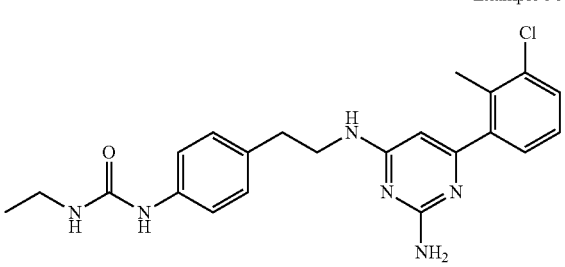
Example 567
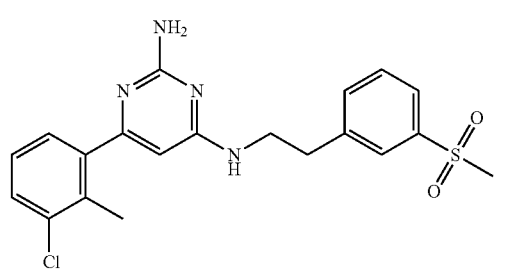
Example 568
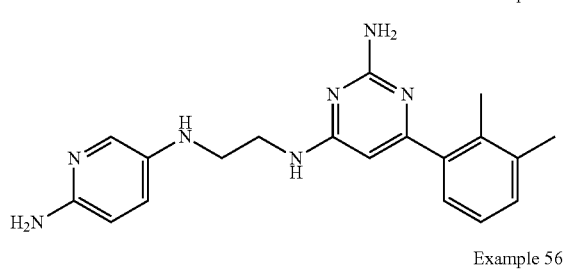
Example 569
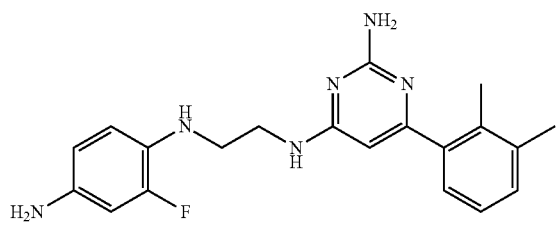

Example 570
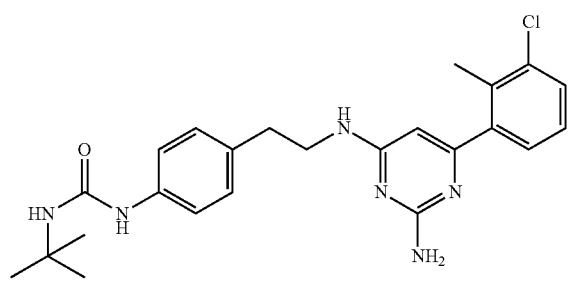
Example 575
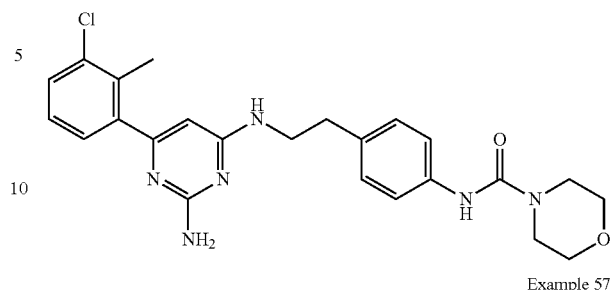
Example 571
Example 576
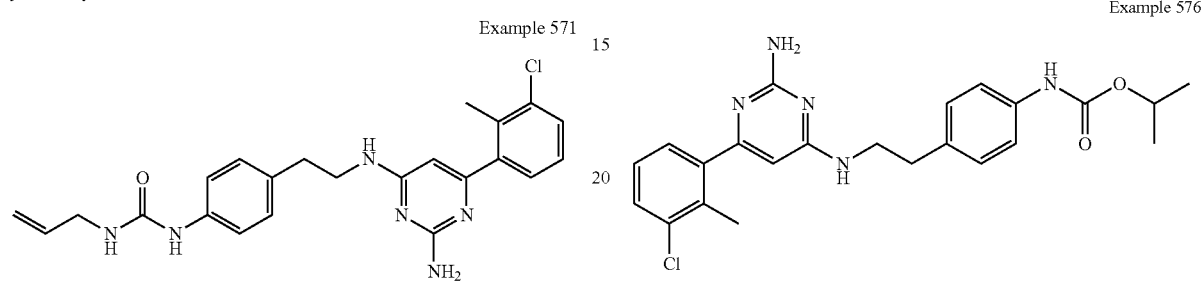
Example 572
Example 577
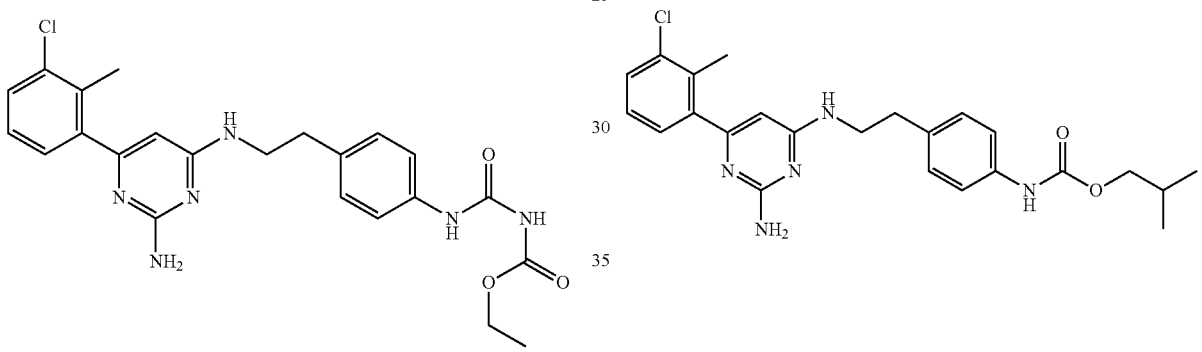
Example 573
Example 578
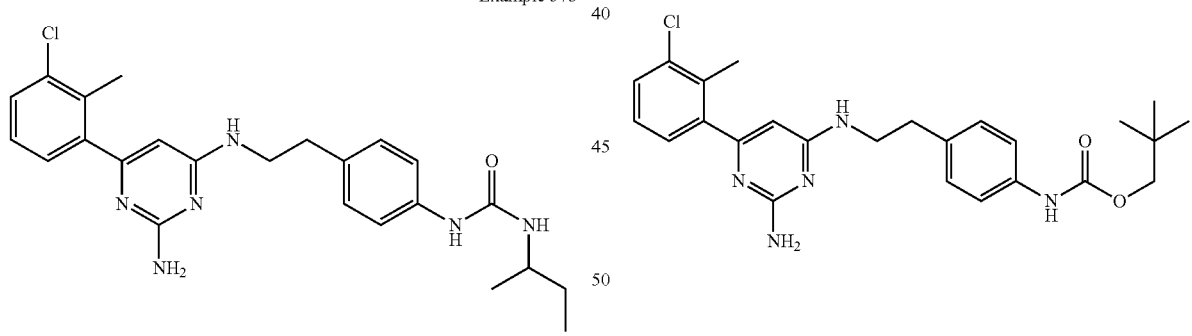
Example 574
Example 579
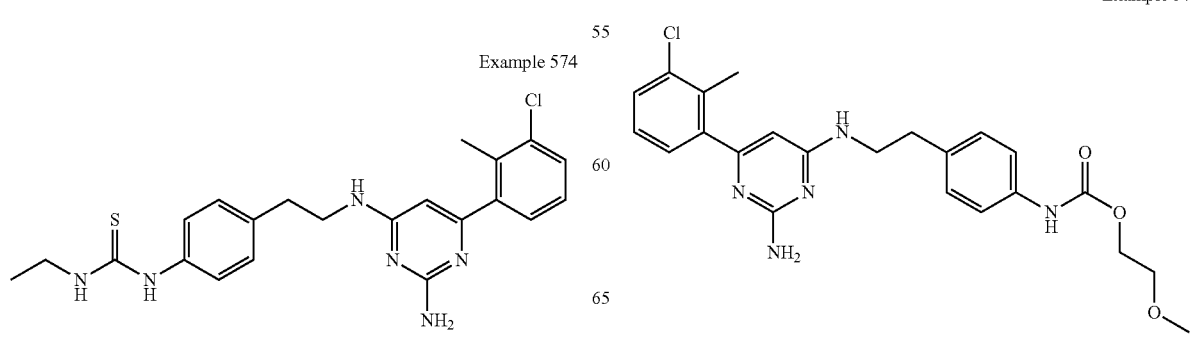

Example 580
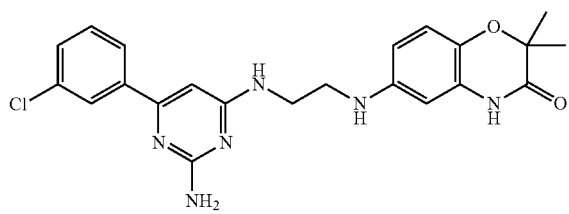
Example 581
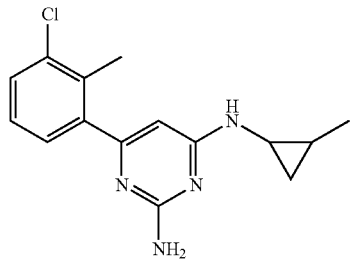
Example 582
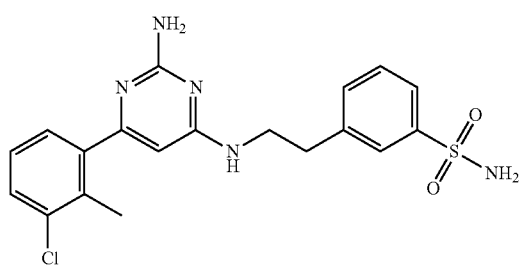
Example 583
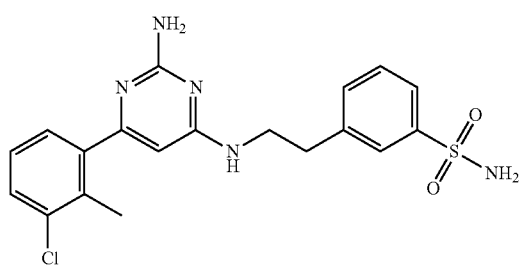
Example 584
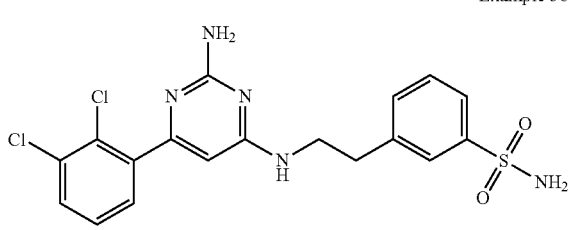
Example 585
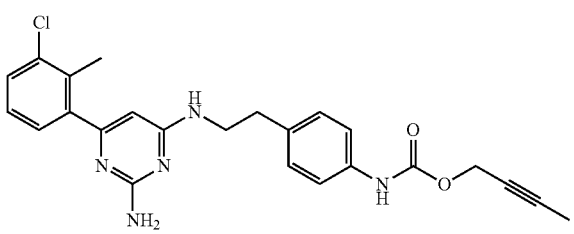
Example 586
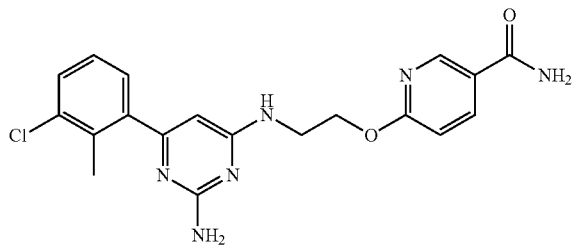
Example 587
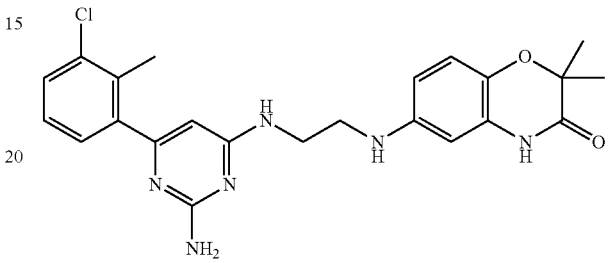
Example 588
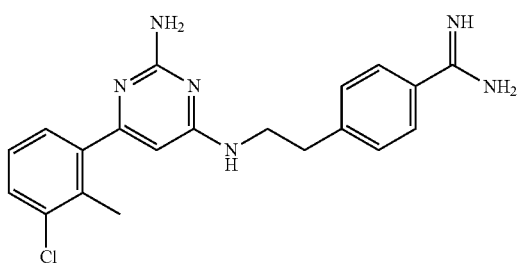
Example 589
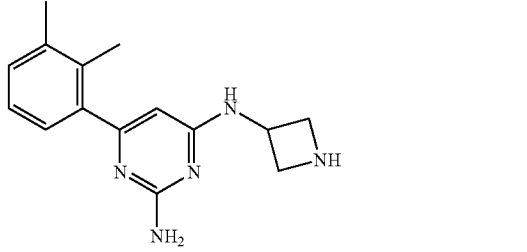
Example 590
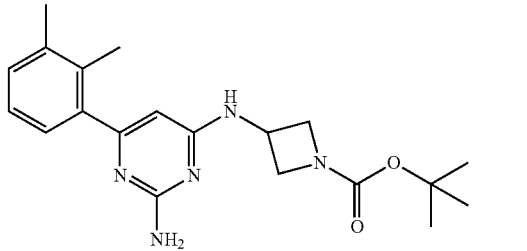
Example 591
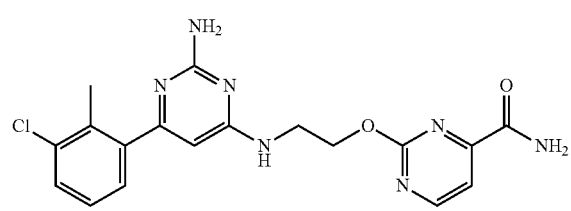

Example 592
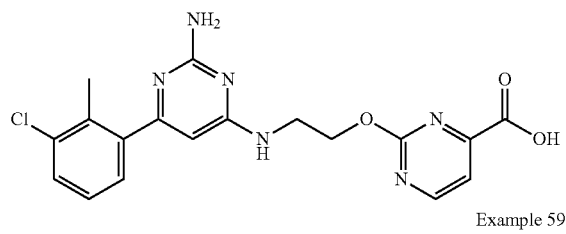
Example 593
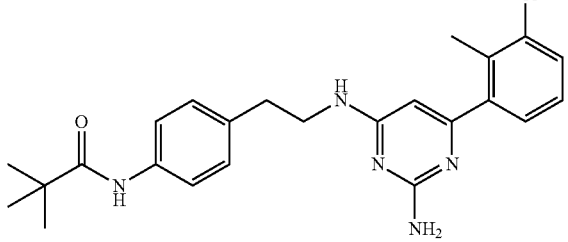
Example 594
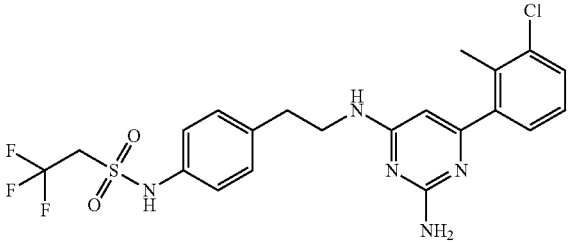
Example 595
Example 596
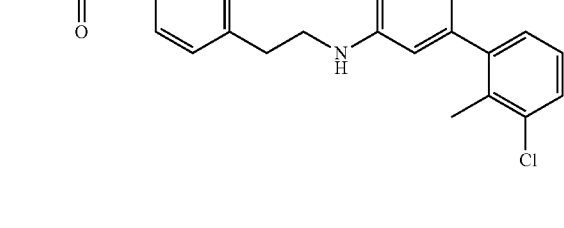
Example 597
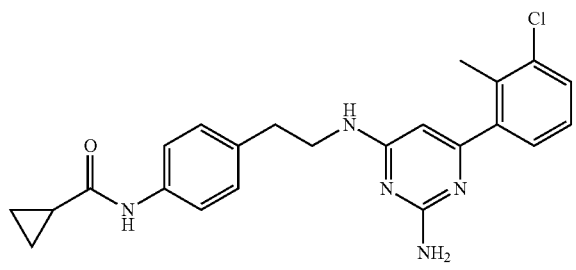
Example 598
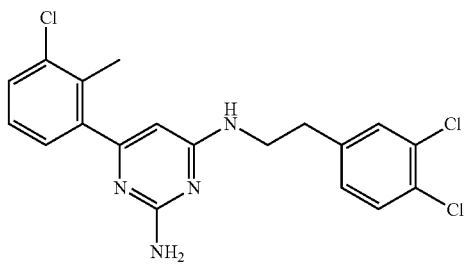
Example 599
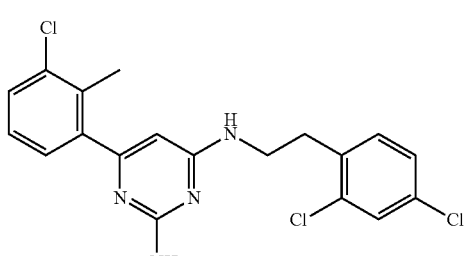
Example 600
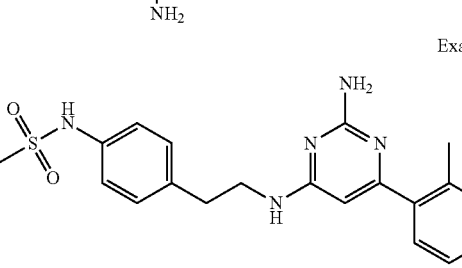
Example 601
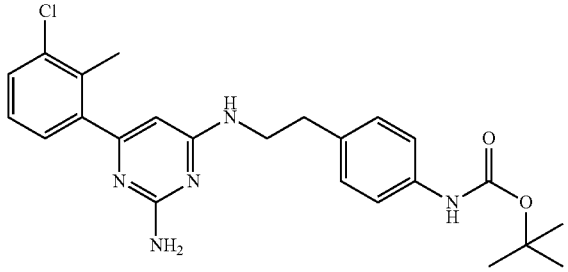
Example 602
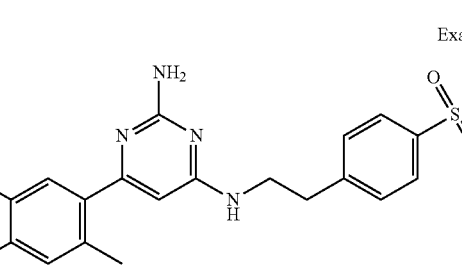

Example 603
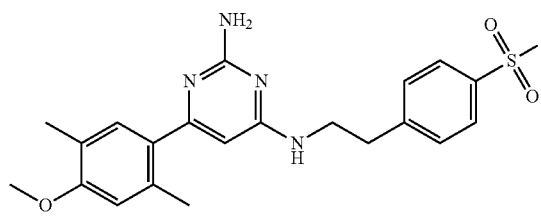
Example 604
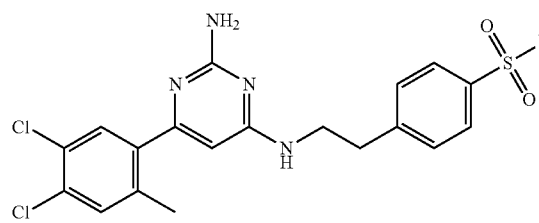
Example 605
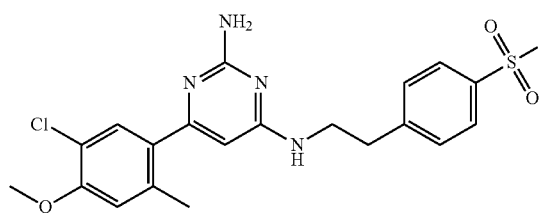
Example 606
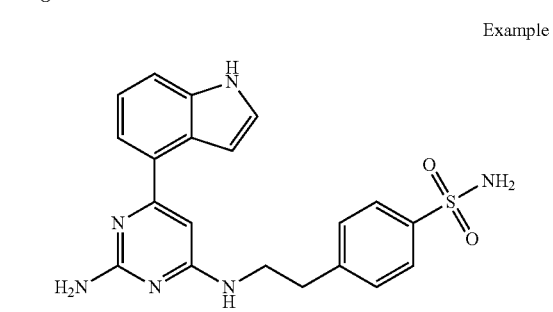
Example 607
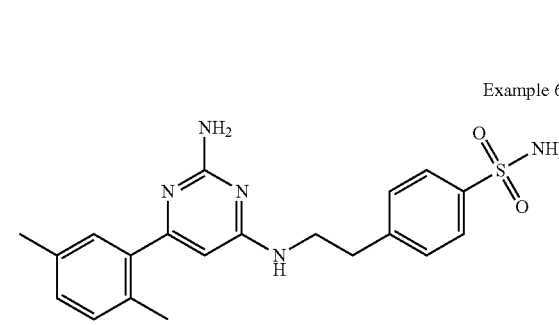
Example 608
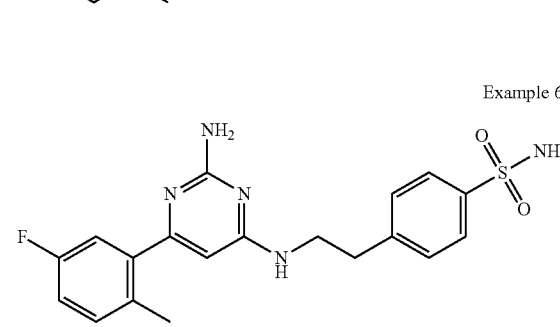
Example 609
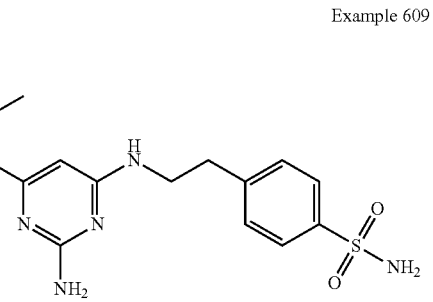
Example 610
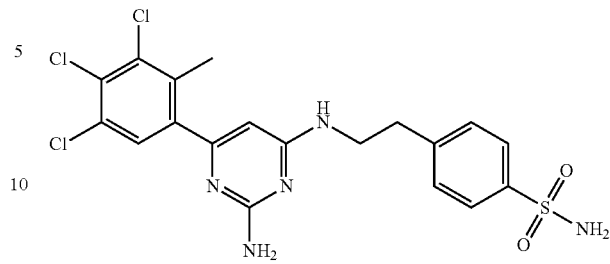
Example 611
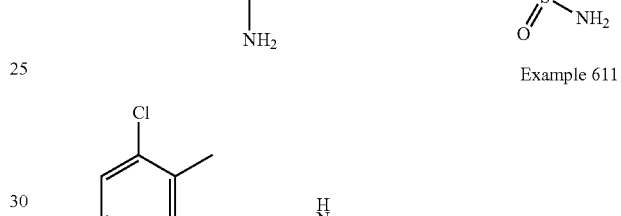
Example 612
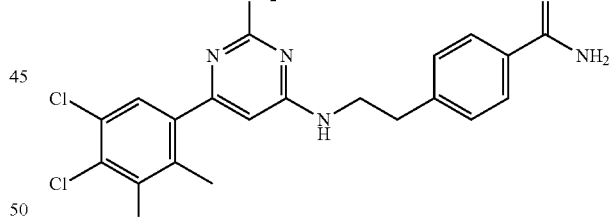
Example 613
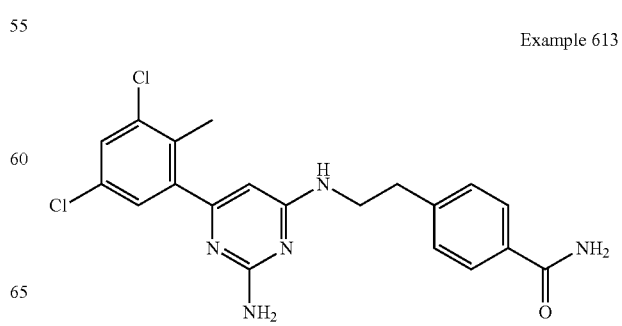

Example 614
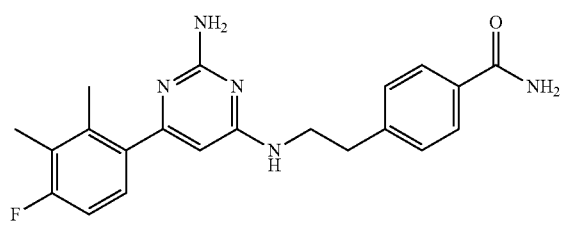
Example 615
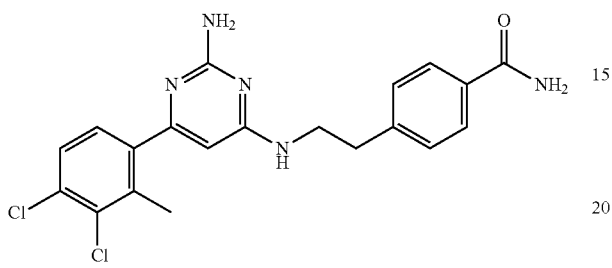
Example 616
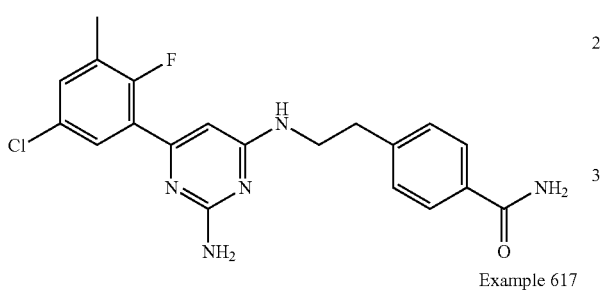
Example 617
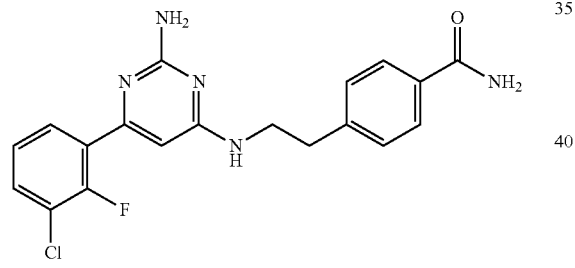
Example 618
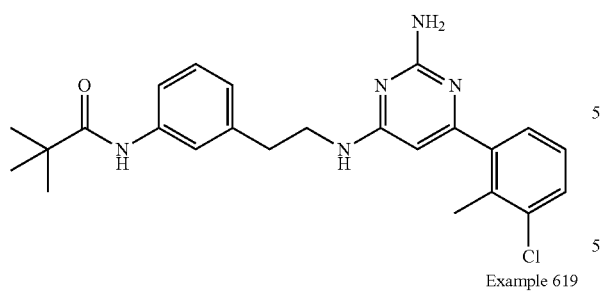
Example 619
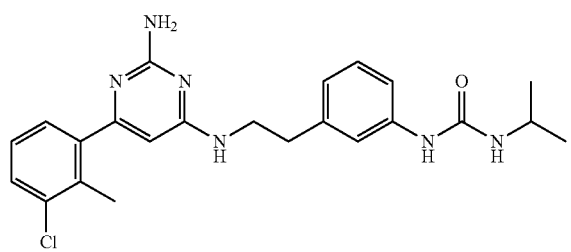
Example 620
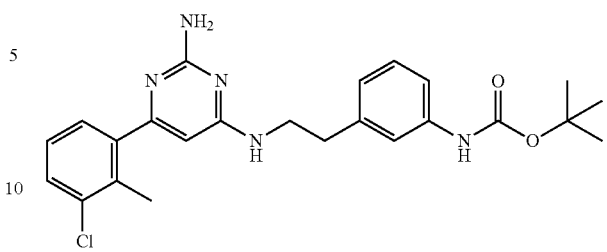
Example 621
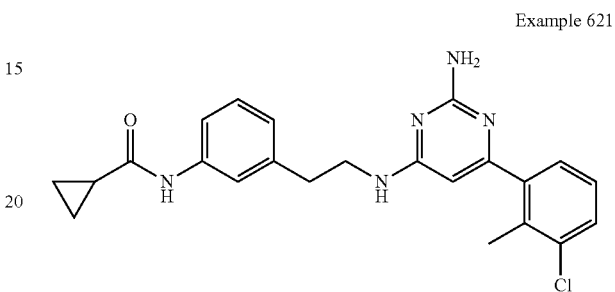
Example 622
Example 623
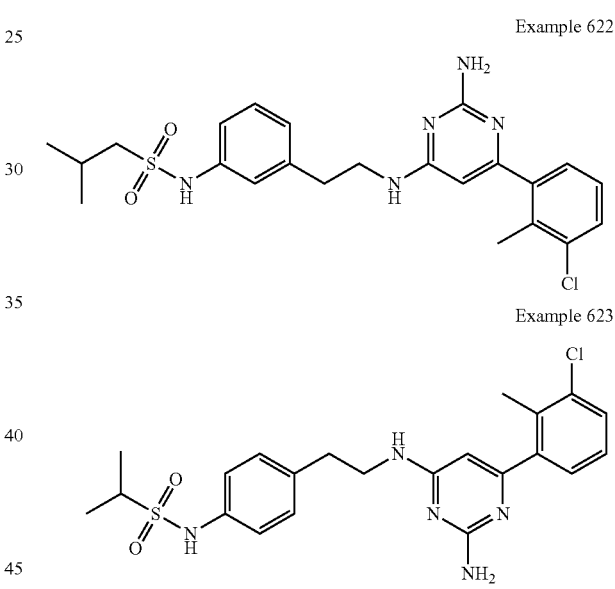
Example 624
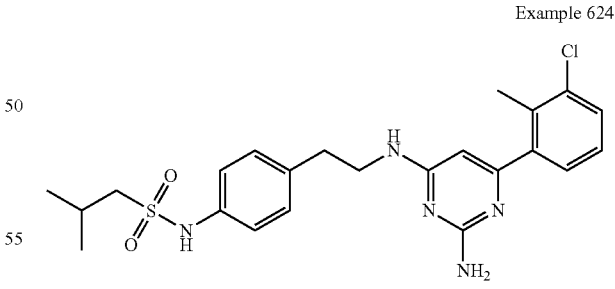
Example 625
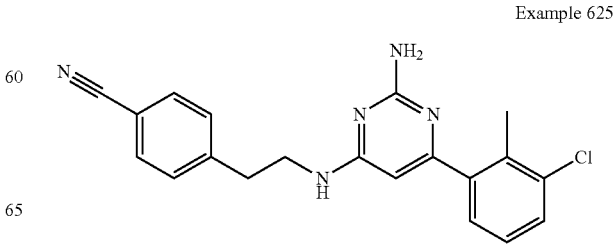

Example 626

Example 627

Example 628

Example 629

Example 630

Example 631

Example 632

Example 633

Example 634

Example 635

Example 636
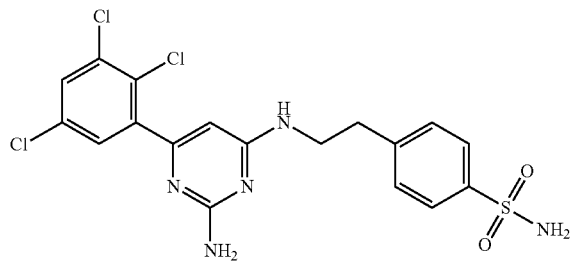
Example 637
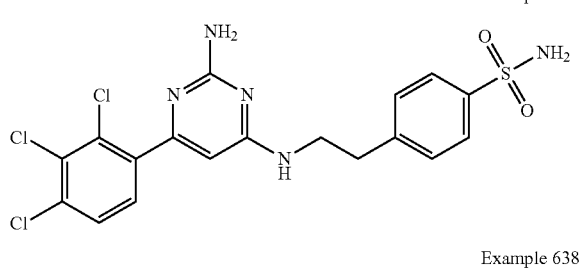
Example 638
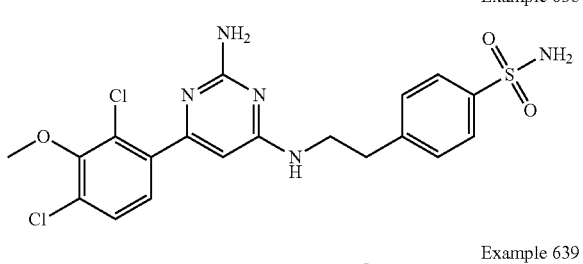
Example 639
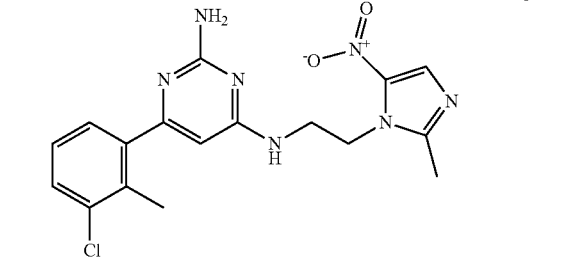
Example 640
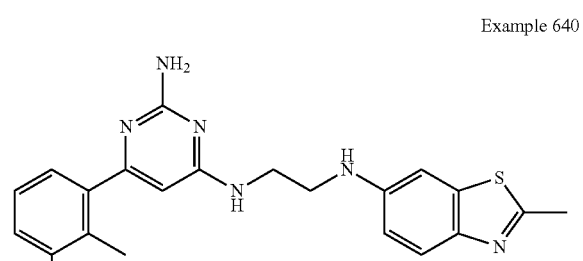
Example 641
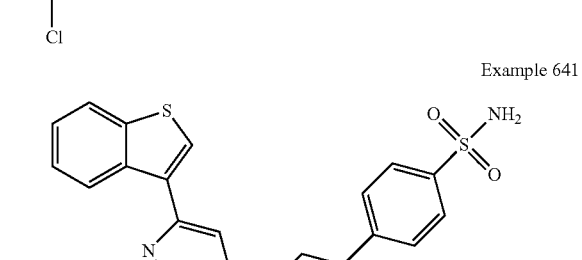
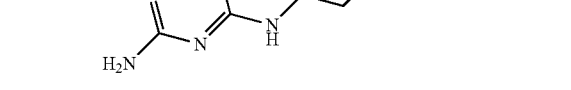
Example 642
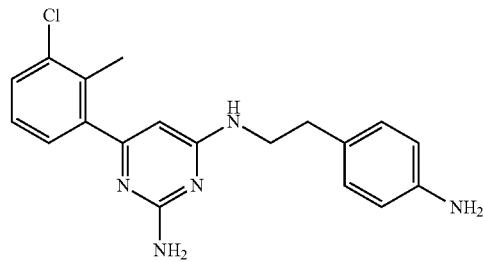
Example 643
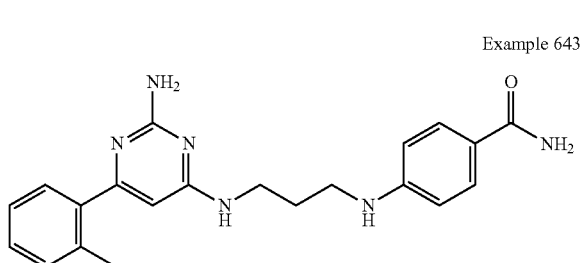
Example 644
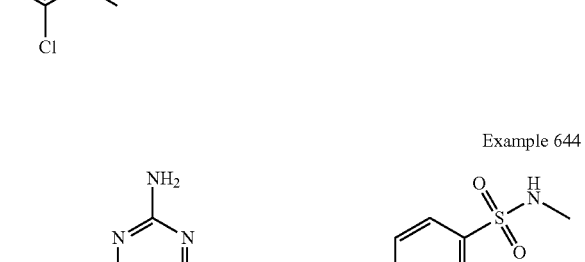
Example 645
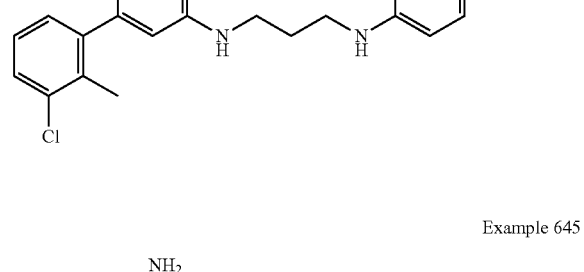
Example 646
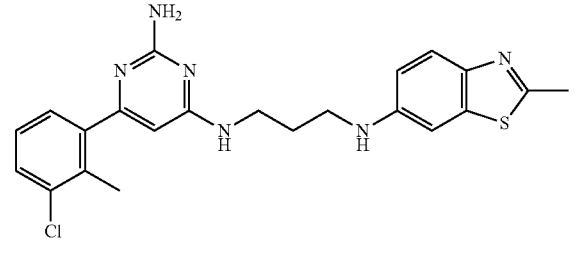

Example 647
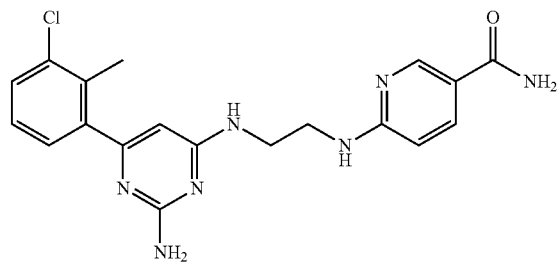
Example 648
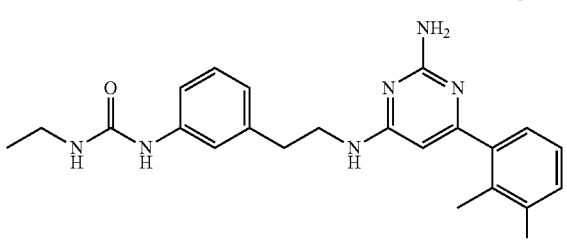
Example 649
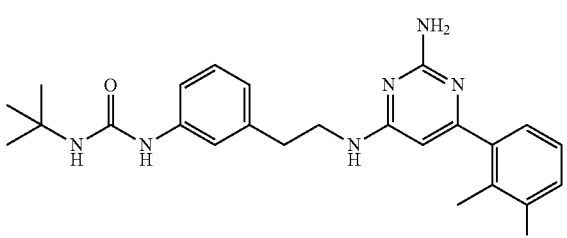
Example 650
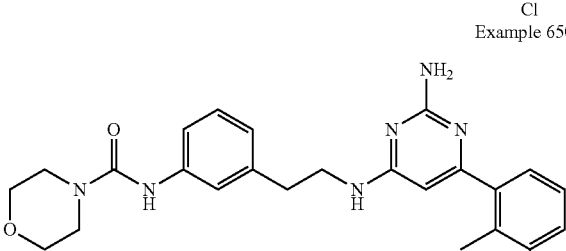
Example 651
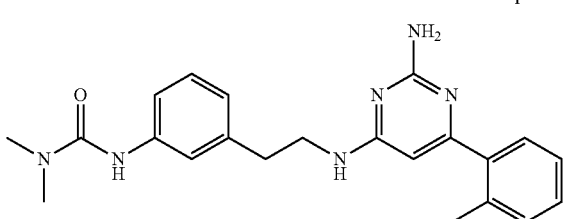
Example 652
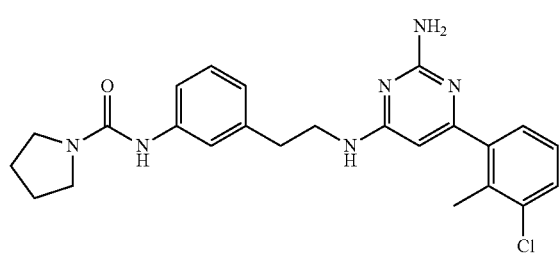
Example 653
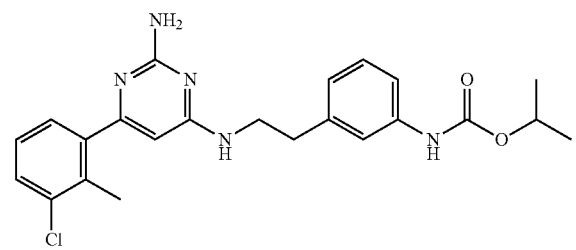
Example 654
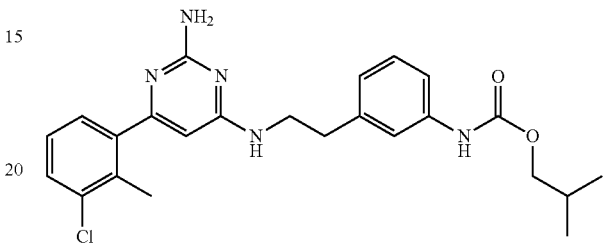
Example 655
Example 656
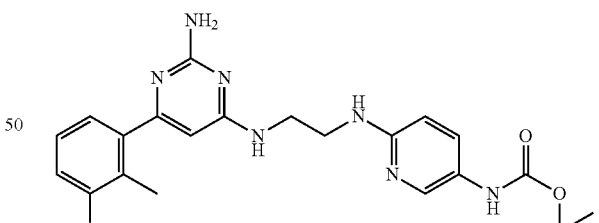
Example 657
Example 658
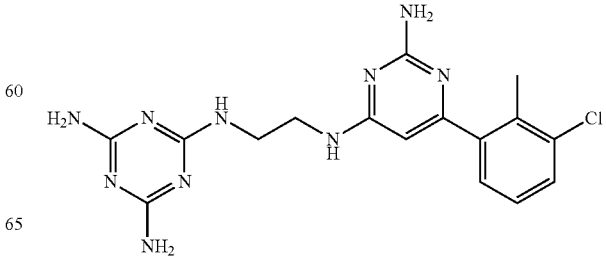

Example 659
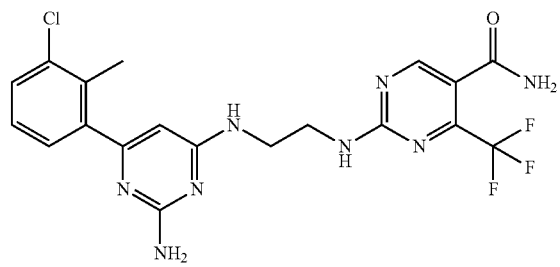
Example 660
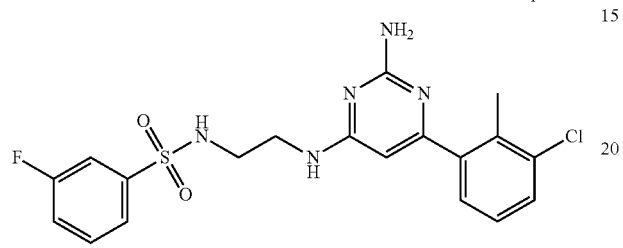
Example 661
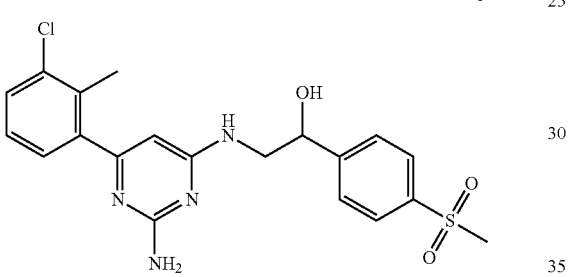
Example 662
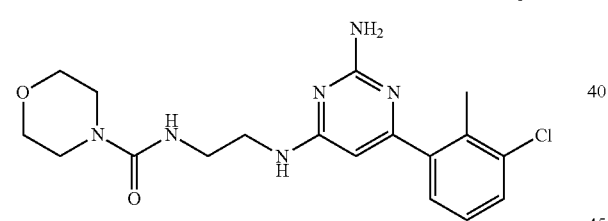
Example 663
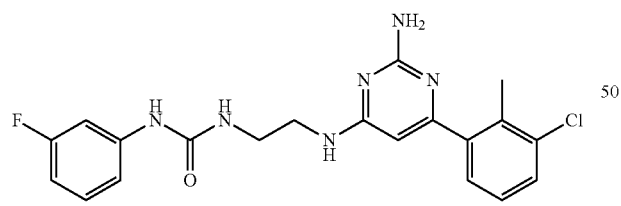
Example 664
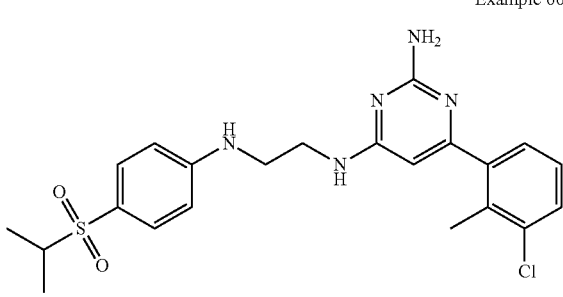
Example 665
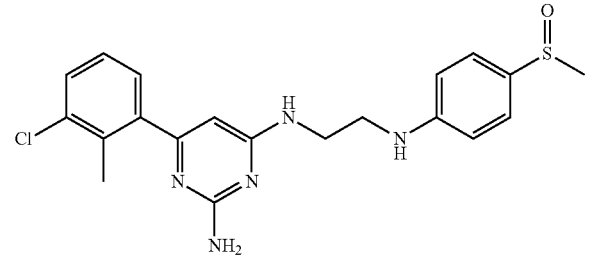
Example 666
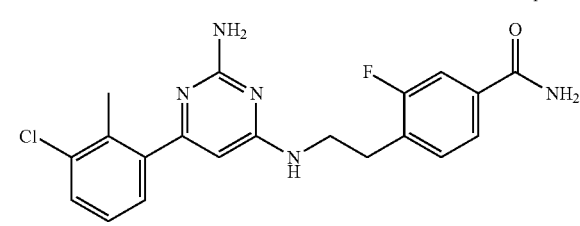
Example 667
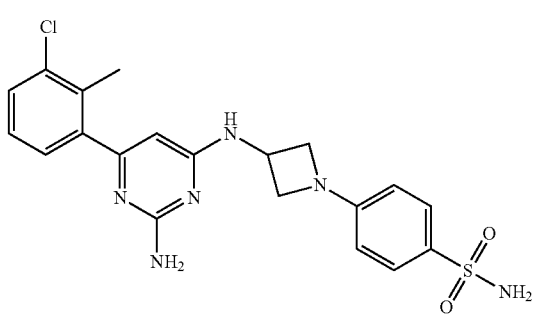
Example 668
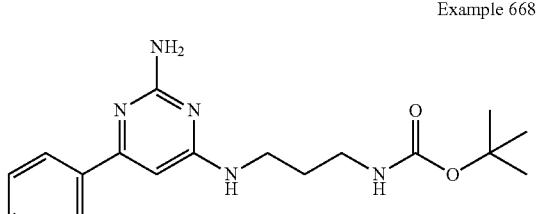
Example 669
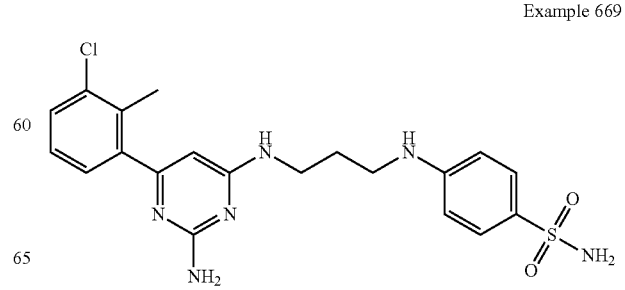

Example 670
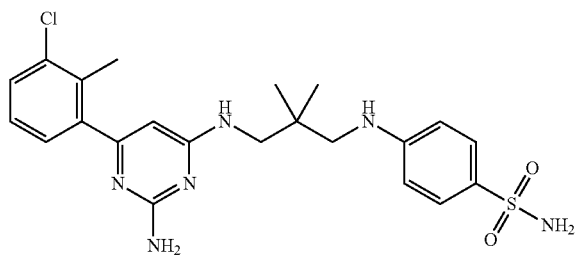
Example 675
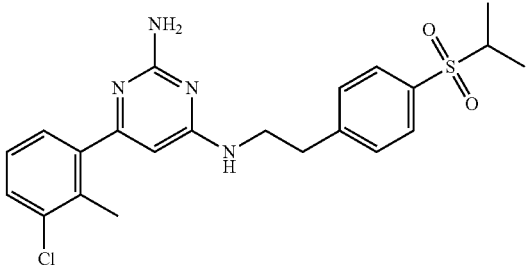
Example 671
Example 676
Example 672
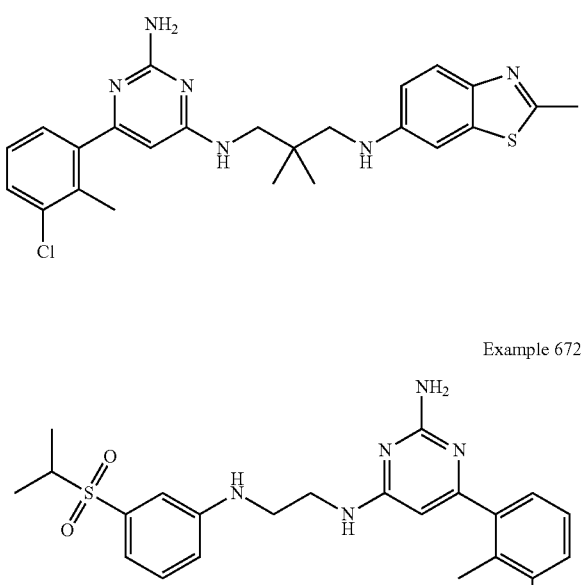
Example 677
Example 678
Example 673
Example 679
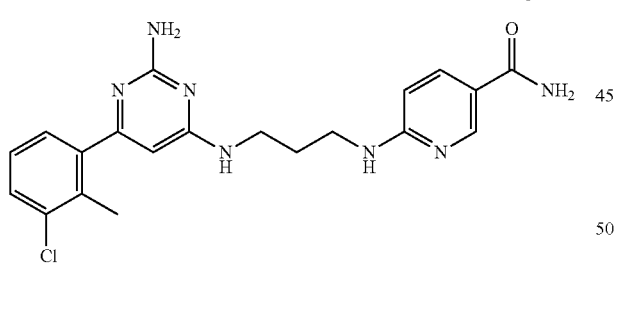
Example 674
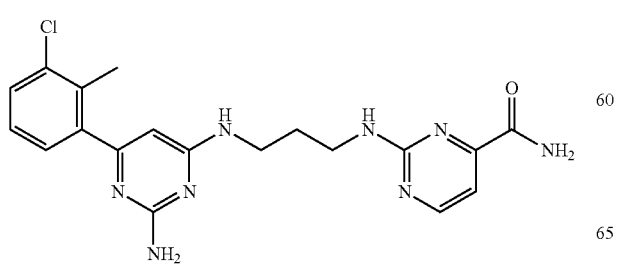
Example 680
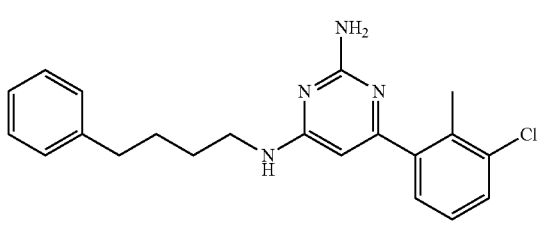

359
-continued

Example 681

Example 682

Example 683

Example 684

Example 685

Example 686

360
-continued

Example 687

Example 688

Example 689

Example 690

Example 691

Example 692

Example 693
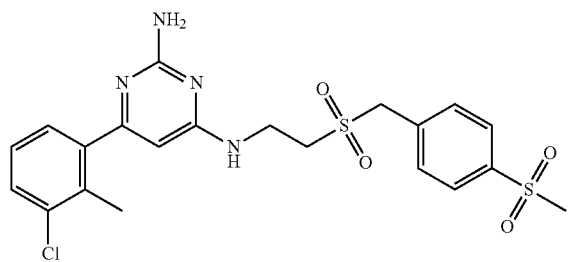
Example 694
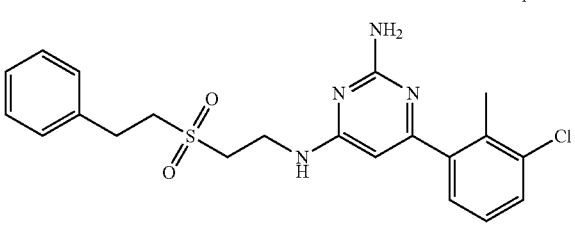
Example 695
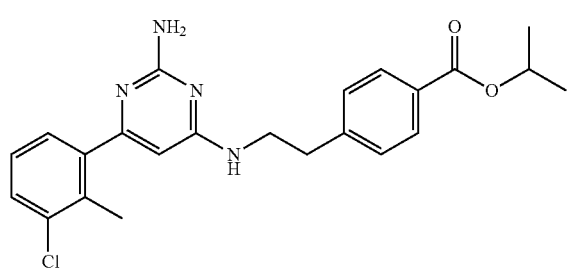
Example 696
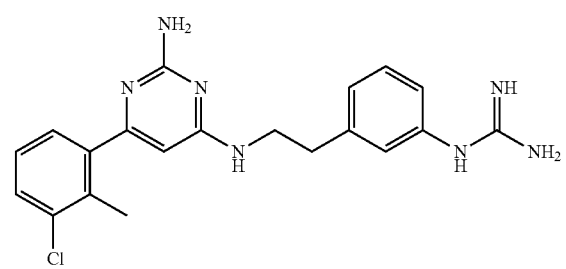
Example 697
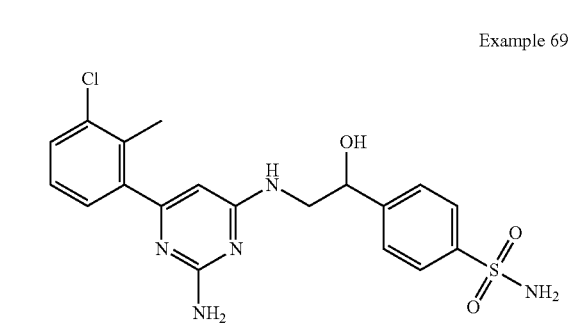
Example 698
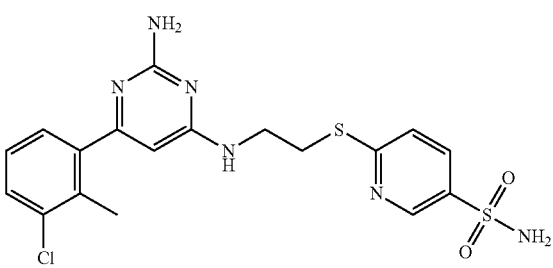
Example 699
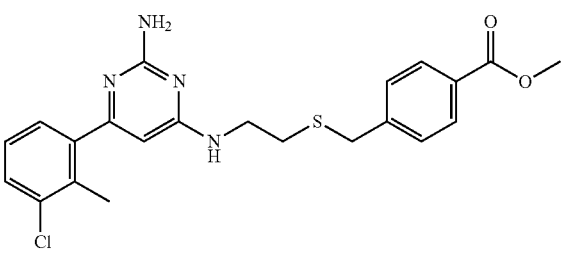
Example 700
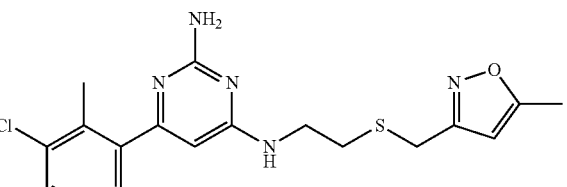
Example 701
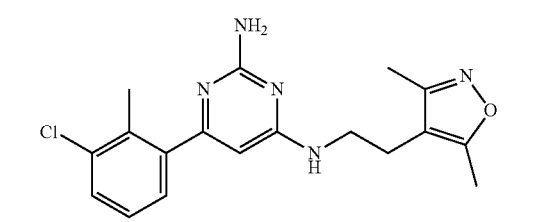
Example 702
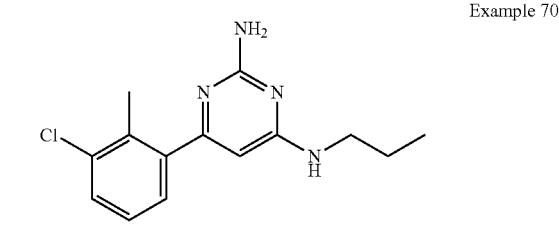
Example 703
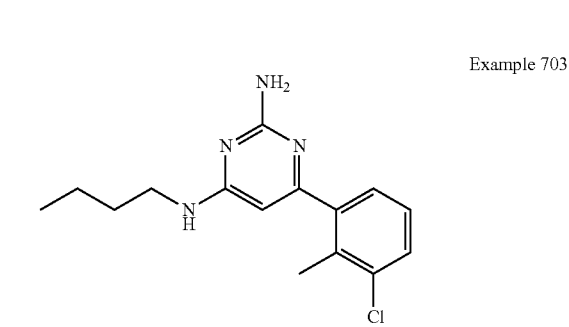

Example 704
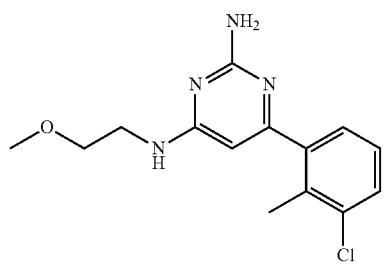
Example 705
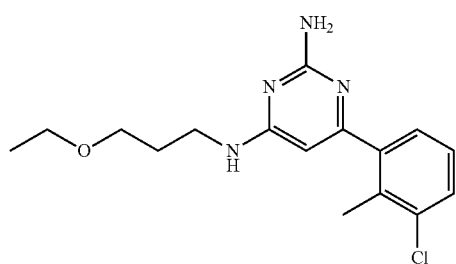
Example 706
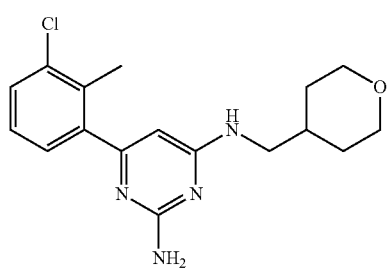
Example 707
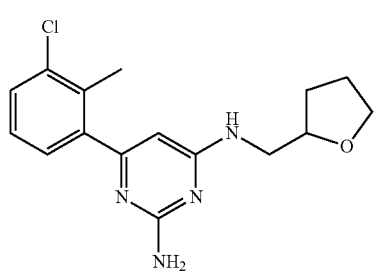
Example 708
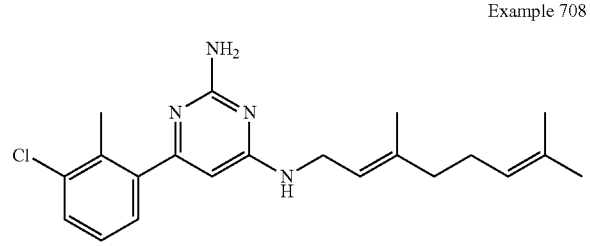
Example 709
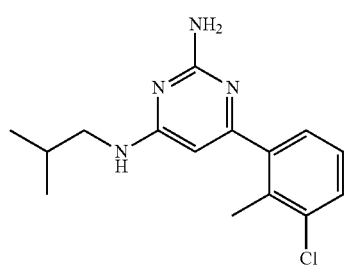
Example 710
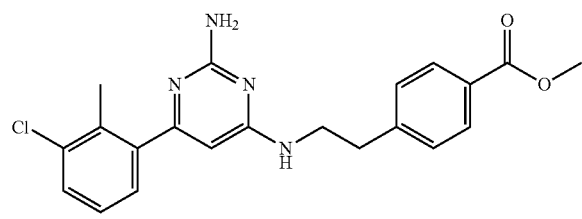
Example 711
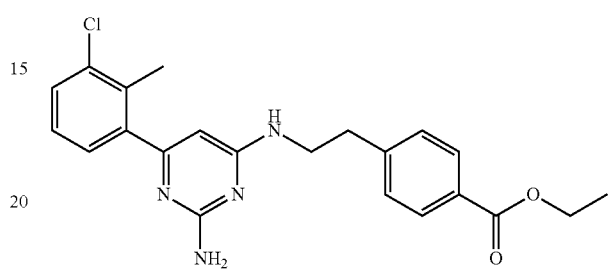
Example 712
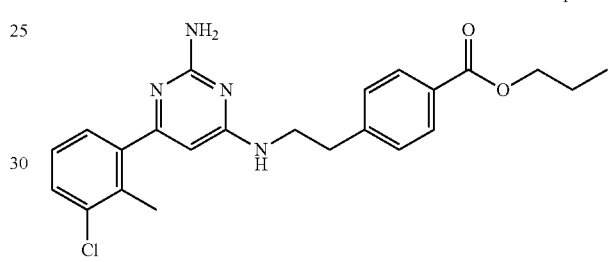
Example 713
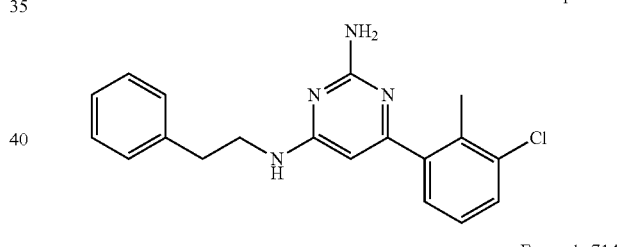
Example 714
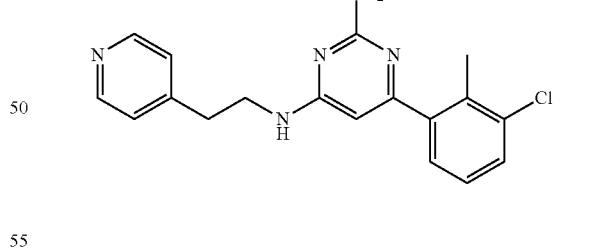
Example 715
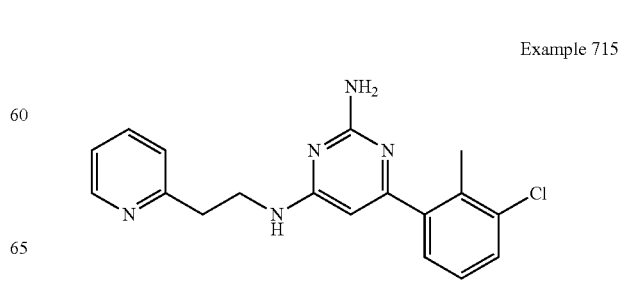

Example 716
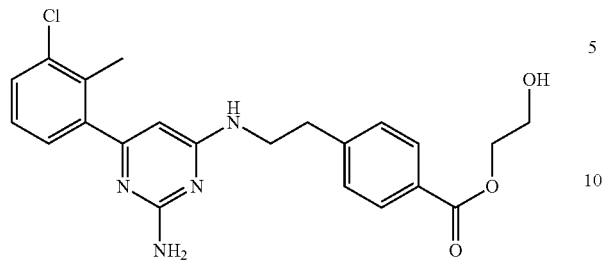
Example 717
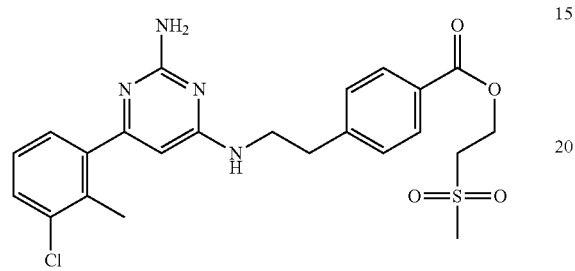
Example 718
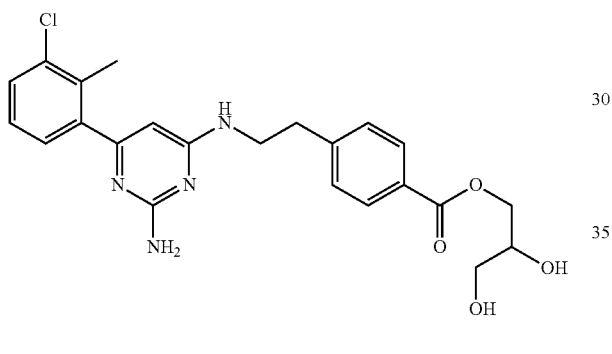
Example 719
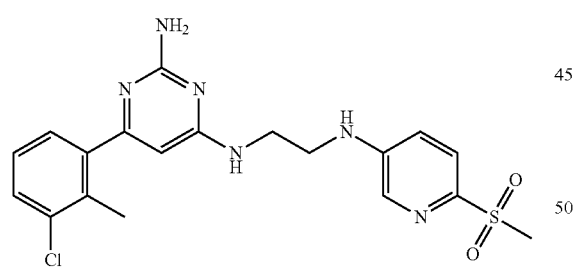
Example 720
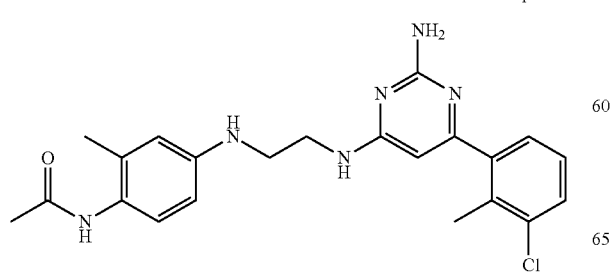
Example 721
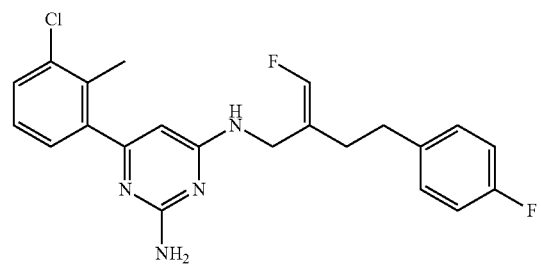
Example 722
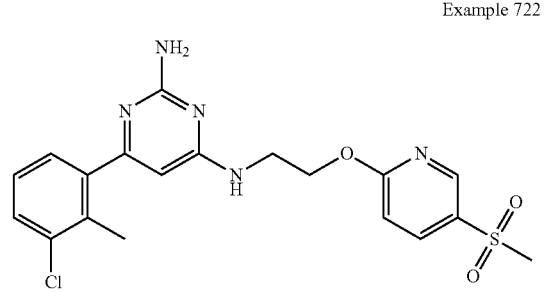
Example 723
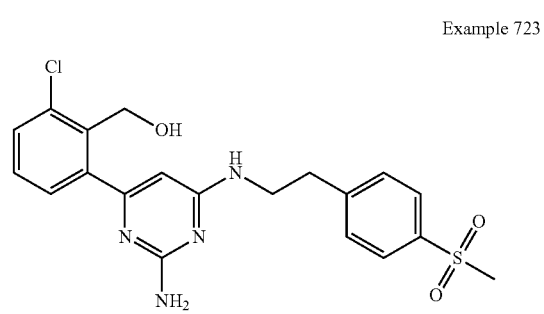
Example 724
Example 725

Example 726
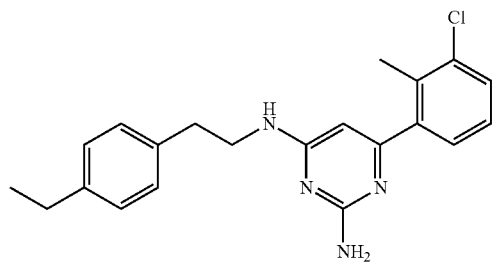
Example 727
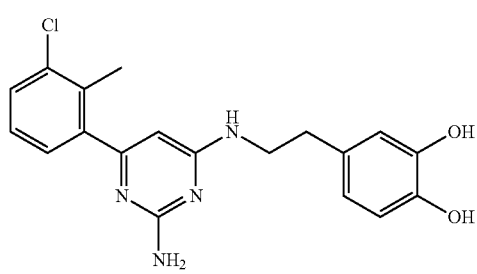
Example 728
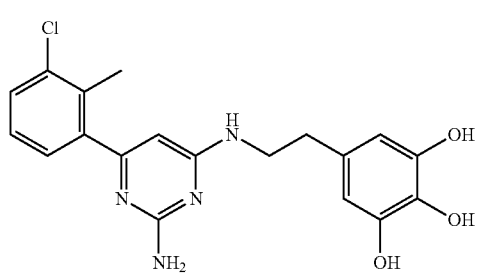
Example 729
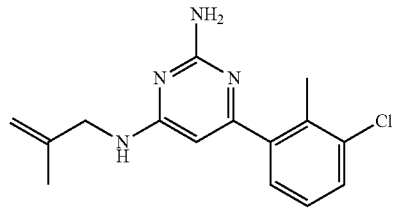
Example 730
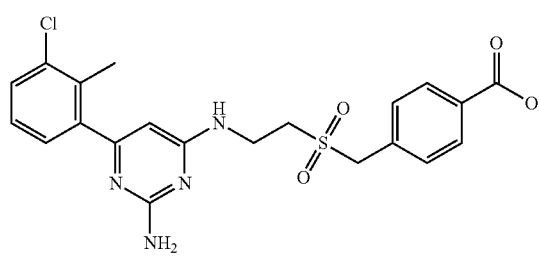
Example 731
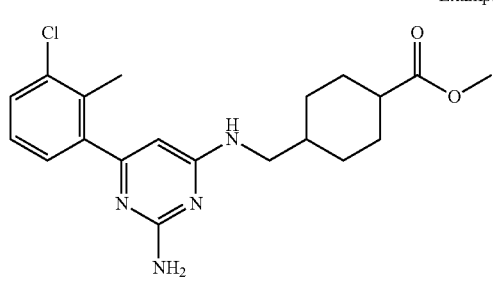
Example 732
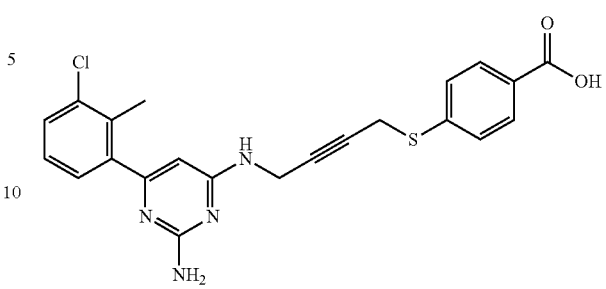
Example 733
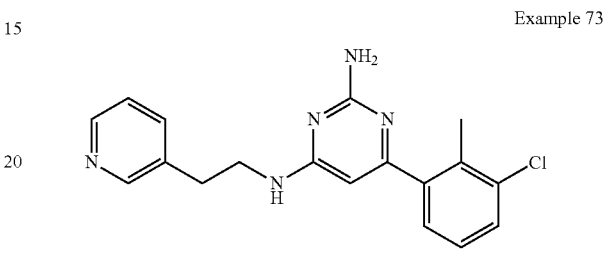
Example 734
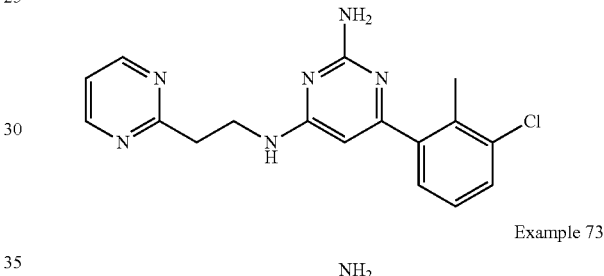
Example 735
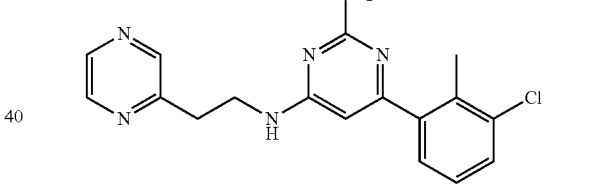
Example 736
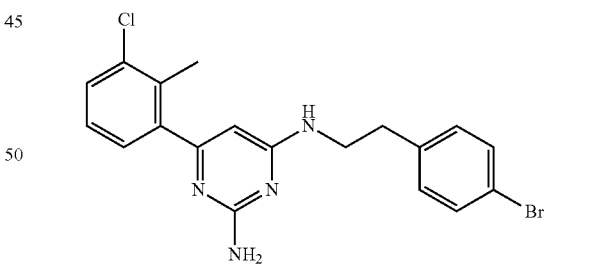
Example 737
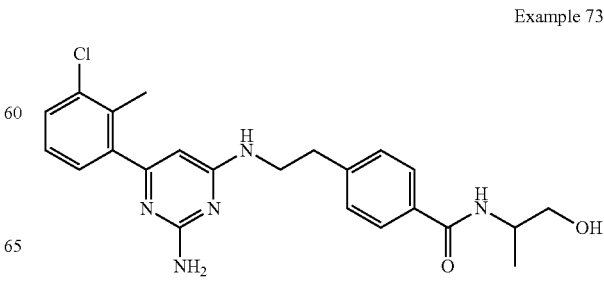

Example 738
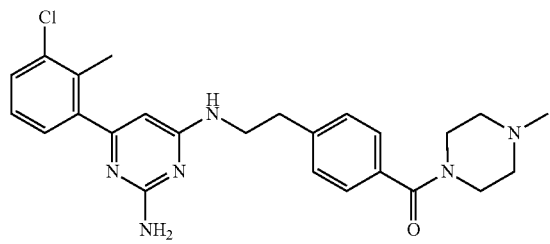
Example 739
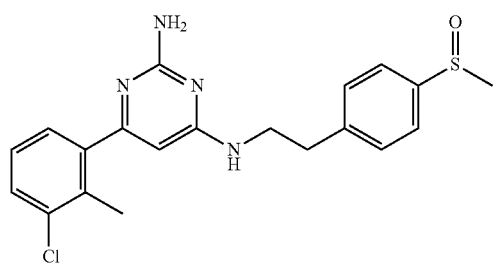
Example 740
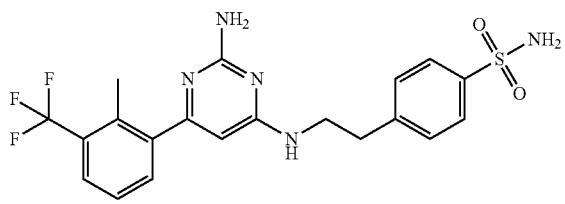
Example 741
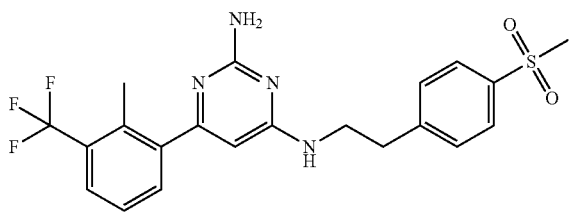
Example 742
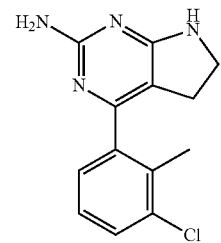
Example 743
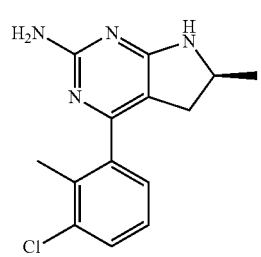
Example 744
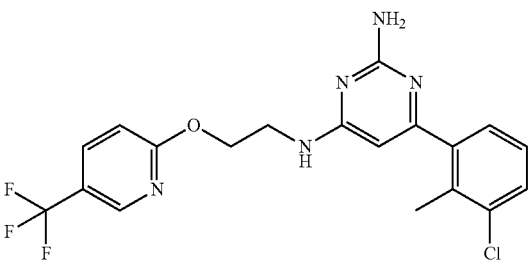
Example 745
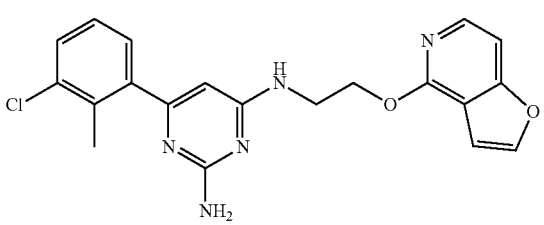
Example 746
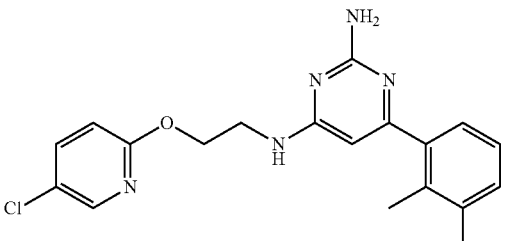
Example 747
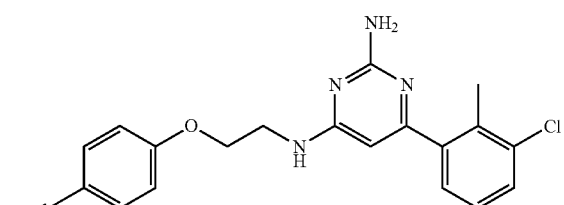
Example 748
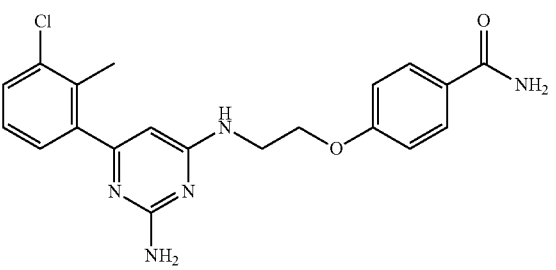
Example 749
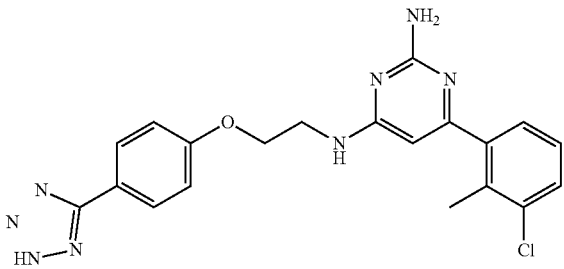

Example 750
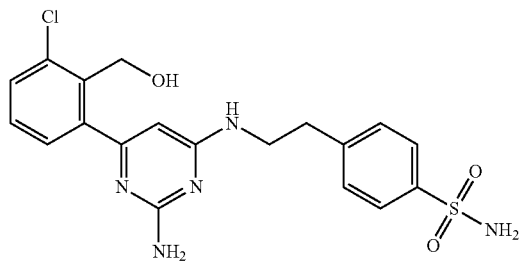
Example 751
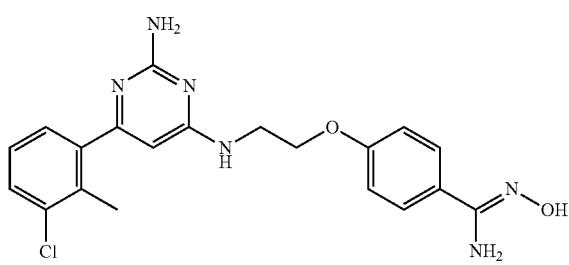
Example 752
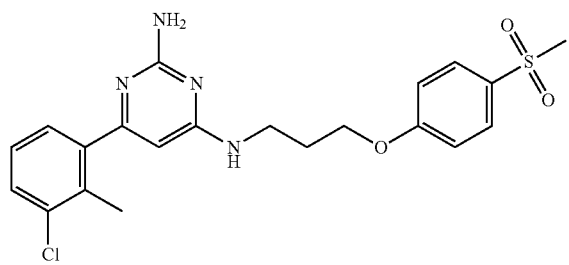
Example 753
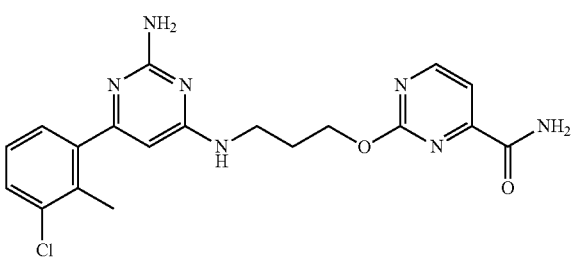
Example 754
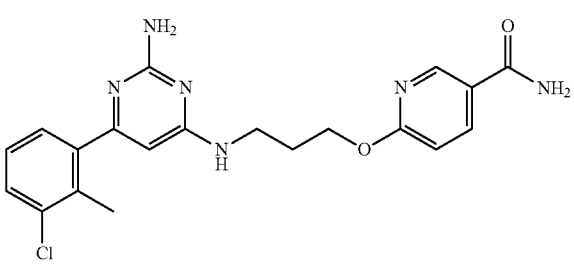
Example 755
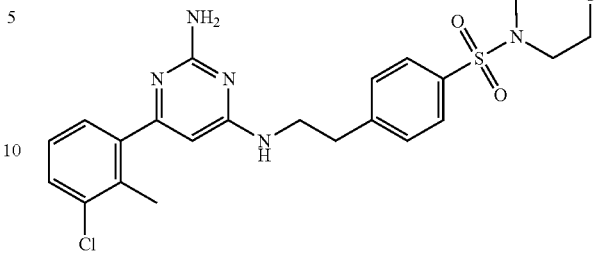
Example 756
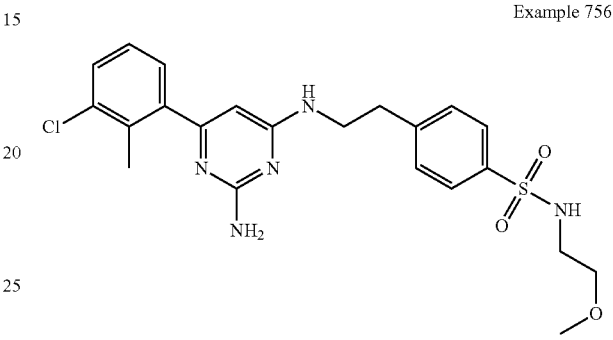
Example 757
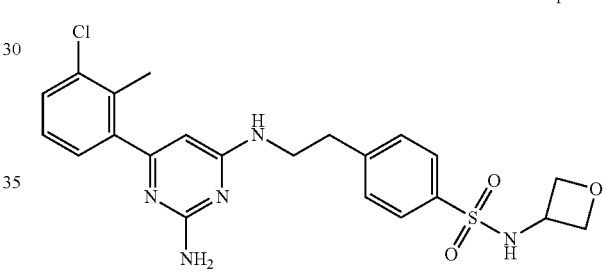
Example 758
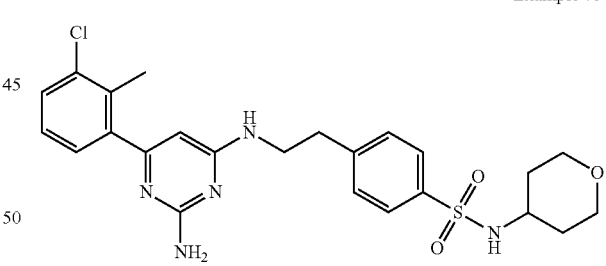
Example 759
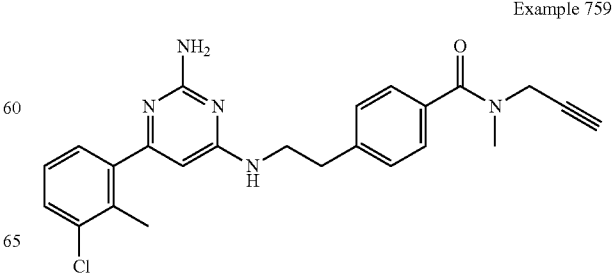

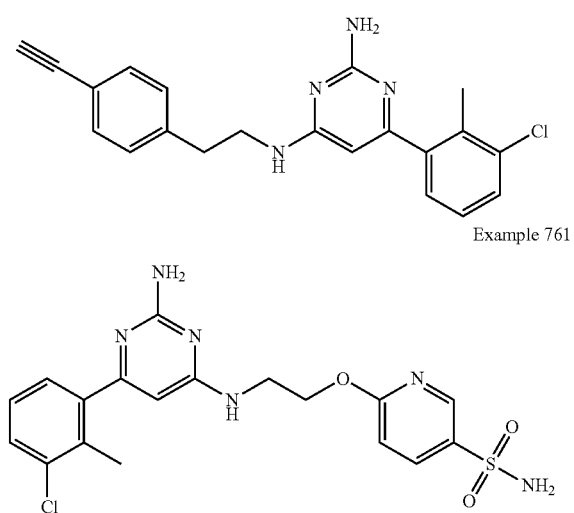

Example 760

Example 761

BIOLOGICAL EXAMPLES

Biological Example 1

MTH1 Enzymatic Assay and IC50 Value Determination

MTH1 catalyzes the hydrolysis of dGTP to dGMP and PPi. By coupling the reaction to pyrophosphatase added in excess PPi is converted to Pi that can be detected by using the malachite green assay reagent. Two different formats were used for IC50 determinations in the enzymatic assay, 96- and 384-well format. 96-well method: Briefly, the compound to be analyzed is diluted in DMSO in a 1:3 dilution series generating 12 different compound concentrations giving a final DMSO concentration of 1% in the assay well. MTH1 diluted in assay buffer (100 mM Tris-acetate, 40 mM NaCl, 10 mM magnesium acetate, 1 mM DTT and 0.005% Tween 20) fortified with E. coli pyrophosphatase (0.2 U/ml) is added to a final concentration of 6 nM. dGTP diluted in assay buffer is added to a final concentration of 100 µM. The reaction mixture is incubated for 15 minutes at 22° C. To 100 µl reaction mixture, 25 µl Malachite green assay regent (0.095% Malachite green in 17% H2SO4, 1.5% Ammonium molybdate, 0.17% Tween 20) is added, followed by incubation with shaking for 15 minutes at 22° C. The absorbance of the assay plate is read at 630 nm using a Hidex Sense Multilabel plate reader. The IC50 value is determined by fitting a dose response curve to the data points using nonlinear regression analysis and the equation Y=Bottom+(Top-Bottom)/(1+10^((Log IC50-X)*HillSlope)), where Y is the read absorbance at 630 nm and X is log [compound].

384-Well Method: The compounds to be tested are nano-dispensed, in 11 concentrations, directly in assay plates, with a final DMSO concentration <1%. The protocol and the reaction mixture are the same as for the 96-well assay, with a total reaction volume of 50 µl/well to which 10 µl of Malachite green reagent is added. All additions to the assay plates are made with multidrop.

Using these approaches the following representative IC50 values were derived. 1, 2, 4, 6, 7, 11, 13, 16, 18, 19, 23, 26, 27, 28, 29, 30, 31, 32, 33, 34, 35, 36, 37, 38, 39, 40, 41, 43, 44, 46, 47, 48, 49, 50, 51, 52, 53, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 97, 98, 99, 100, 101, 103, 104, 105, 106, 107, 108, 109, 110, 111, 114, 115, 116, 118, 120, 121, 122, 123, 124, 125, 126, 127, 128, 129, 130, 131, 132, 133, 134, 135, 136, 137, 138, 139, 140, 142, 143, 144, 145, 146, 147, 148, 149, 151, 152, 153, 155, 156, 158, 159, 163, 164, 165, 168, 170, 171, 172, 173, 174, 175, 176, 177, 183, 184, 185, 186, 187, 188, 189, 190, 191, 192, 193, 194, 195, 196, 197, 198, 200, 201, 202, 203, 204, 205, 206, 207, 208, 209, 210, 211, 213, 214, 215, 216, 217, 218, 219, 220, 221, 222, 223, 224, 226, 227, 228, 230, 231, 232, 233, 234, 235, 239, 240, 243, 244, 245, 246, 247, 248, 249, 250, 251, 252, 253, 254, 256, 257, 258, 259, 260, 261, 262, 263, 264, 266, 267, 268, 269, 271, 273, 274, 275, 276, 279, 280, 282, 283, 295, 296, 297, 300, 301, 303, 304, 305, 307, 308, 309, 310, 311, 312, 313, 314, 315, 316, 317, 321, 322, 323, 324, 325, 326, 327, 328, 329, 330, 331, 332, 333, 334, 335, 336, 337, 338, 341, 342, 343, 344, 346, 348, 349, 350, 351, 352, 355, 356, 357, 359, 361, 362, 363, 364, 367, 370, 371, 374, 375, 376, 379, 381, 382, 385, 386, 388, 389, 391, 393, 394, 397, 398, 400, 401, 402, 403, 404, 405, 406, 407, 408, 409, 411, 412, 414, 415, 416, 417, 418, 419, 420, 421, 422, 424, 425, 426, 427, 428, 429, 430, 431, 432, 433, 434, 435, 436, 437, 438, 439, 440, 441, 442, 443, 444, 445, 447, 448, 449, 450, 451, 452, 453, 454, 455, 456, 457, 458, 460, 461, 462, 463, 464, 465, 466, 468, 469, 470, 471, 472, 473, 474, 475, 476, 477, 478, 479, 480, 481, 482, 483, 484, 485, 486, 487, 488, 489, 490, 491, 492, 493, 494, 495, 497, 498, 499, 500, 501, 502, 503, 505, 506, 507, 508, 509, 510, 511, 512, 513, 514, 515, 516, 517, 518, 519, 520, 521, 522, 523, 524, 525, 526, 527, 528, 529, 530, 531, 532, 534, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 591, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 663, 664, 665, 666, 668, 669, 670, 671, 672, 673, 674, 675, 676, 677, 678, 679, 680, 681, 682, 683, 684, 685, 686, 687, 688, 689, 690, 695, 696, 697, 698, 699, 700, 701, 702, 703, 704, 705, 706, 707, 708, 709, 710, 711, 712, 713, 714, 715, 716, 717, 718, 719, 720, 721, 722, 723, 726, 727, 728, 729, 731, 732, 733, 735, 736, 737, 738, 739, 740, 741, 742, 743, 744, 745, 746, 747, 748, 749, 750, 751, 752, 753, 754, 755, 756, 757, 758, 759, 760 and 761 had IC$_{50}$'s of less than 200 nM Examples 3, 8, 9, 10, 17, 22, 24, 25, 42, 45, 54, 60, 95, 96, 102, 113, 117, 119, 150, 154, 157, 160, 162, 169, 178, 199, 212, 225, 229, 236, 238, 241, 242, 255, 265, 270, 272, 278, 284, 285, 286, 287, 288, 290, 291, 292, 293, 294, 298, 302, 306, 318, 319, 320, 339, 340, 347, 353, 354, 358, 360, 365, 366, 368, 369, 373, 377, 378, 380, 383, 384, 387, 390, 392, 395, 410, 413, 423, 446, 459, 467, 496, 504, 533, 535, 590, 592, 662, 691, 693, 694, 724, 730 and 734 had IC$_{50}$'s of between 200 nM and 2 µM.

Examples 5, 12, 14, 15, 20, 21, 112, 161, 166, 167, 179, 180, 181, 182, 237, 277, 281, 289, 299, 345, 372, 396, 399, 589, 667, 692 and 725 had IC$_{50}$'s of between 2 µM and 10 µM.

Biological Example 2

Cellular Assay and IC50 Value Determination

Primary T-lymphocytes are isolated from donated human blood and thereafter activated with CD3/CD28 Dynabeads.

The T-lymphocytes are treated with an MTH1 inhibitor, positive control or vehicle for 24-96 hrs. Cell viability can be measured by using standard assays, such as for instance a resazurin assay. In some experiments, the cells are stained with Cell Trace Violet at the start of the culture. The dye is diluted as the cells divide and gives a measurement of cell proliferation (see FIG. 1 for an example).

The invention claimed is:
1. A method of treatment of autoimmune diseases and inflammatory conditions, wherein the method comprises administering a therapeutically effective amount of a compound of formula I,

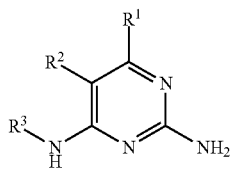

(I)

or a pharmaceutically acceptable salt thereof, to a patient in need of such treatment, wherein:
$R^1$ represents
(i)

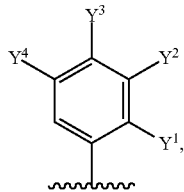

or
(ii) a 6-membered heteroaryl substituted by one or more groups selected from $Y^5$, or
(iii) a 5- to 10-membered monocyclic or bicyclic heteroaryl connected to the pyrimidine ring of the compound of formula I via a carbon atom of the heteroaryl, which heteroaryl is optionally substituted by one or more groups selected from $Y^5$;
$R^2$ represents hydrogen; and
$R^3$ represents —X-L-J, —$C^{1-12}$alkyl optionally substituted by one or more $Z^1$ or heterocycloalkyl optionally substituted by one or more groups selected from $Z^2$;
X represents —$C_{1-6}$alkylene-, optionally substituted by one or more $T^1$, or —$(C(R^A)2)p-C_{2-5}$heterocycloalkylene-$(C(R^A)2)_q$-, where the heterocycloalkylene is optionally substituted by one or more $T^2$;
L represents a single bond or -$L^1$-$L^2$-;
$L^1$ represents —N($R^B$)—, —O—, —S(O)$_m$—, —C(O)N($R^C$)—, —N($R^D$)C(O)—, —S(O)$_n$N($R^E$)—, —N($R^F$)S(O)$_n$— or —N($R^G$)C(O)N($R^H$)—;
$L^2$ represents a single bond or —$C_{1-6}$alkylene-;
J represents
(i) a 6- to 10-membered aryl optionally substituted by $D^1$ and optionally substituted by one or more groups selected from $R^X$, or
(ii) a 5- to 11-membered monocyclic or bicyclic heteroaryl ring, which heteroaryl contains 1 to 3 nitrogen atoms, and/or one oxygen atom and/or one or two sulfur atoms and which heteroaryl is optionally substituted by $D^2$ and optionally substituted by one or more groups selected from $R^Y$;
$Y^1$ represents hydrogen, halogen, —CN, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —$N_3$, —$NO_2$, —O$R^m$ or —S$R^n$;
$Y^2$, $Y^3$ and $Y^4$ each independently represents hydrogen, halogen, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —$N_3$, —$NO_2$, —OH, —O$R^m$ or —S$R^n$;
$Y^5$ represents halogen, $R^a$, -A-C(Q)$R^b$, -A-C(Q)N($R^c$)$R^d$, -A-C(Q)O$R^e$, -A-S(O)$_n$$R^f$, -A-S(N$R^g$)(O)$R^h$, -A-S(O)$_n$N($R^i$)$R^j$, -A-S(O)$_n$O$R^k$, —B(O$R^l$)$_2$, —$N_3$, —$NO_2$, —OH, —O$R^m$ or —S$R^n$;
Q represents =O, =S, =N$R^o$, =NN($R^p$)$R^q$, =N(O$R^r$), =NS(O)$_2$N($R^s$)$R^t$ or =C(H)NO$_2$;
A represents a single bond, —N($R^I$)—, —C(Q)N($R^J$)— or —O—;
each $R^a$, $R^f$, $R^h$ and $R^m$ independently represents $C_{1-6}$ alkyl optionally substituted by one or more groups selected from $W^1$, heterocycloalkyl optionally substituted by one or more groups selected from $W^2$ or aryl or heteroaryl both optionally substituted by one or more groups selected from $W^3$,
each $R^b$, $R^c$, $R^d$, $R^e$, $R^g$, $R^i$, $R^j$, $R^k$, $R^l$, $R^o$, $R^p$, $R^q$, $R^r$, $R^s$ and $R^t$ independently represents hydrogen, $C_{1-6}$ alkyl optionally substituted by one or more groups selected from $W^1$, heterocycloalkyl optionally substituted by one or more groups selected from $W^2$ or aryl or heteroaryl both optionally substituted by one or more groups selected from $W^3$; or
any two $R^c$ and $R^d$, $R^i$ and $R^j$, $R^p$ and $R^q$ and/or $R^s$ and $R^t$ are linked together to form, along with the nitrogen atom to which they are attached, a 3- to 8-membered monocyclic or bicyclic ring, which ring optionally contains one or two further heteroatoms and which ring optionally is substituted by one or more groups selected from $W^2$, $C_{1-3}$alkyl optionally substituted by one or more groups selected from $W^1$, and =O; or
two $R^l$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, $C_{1-3}$alkyl optionally substituted by one or more halogens, and =O;
$W^1$ represents halogen, —CN, -$A^1$-C(O)$R^{b1}$, -$A^1$-C(O)N($R^{c1}$)$R^{d1}$, -$A^1$-C(O)O$R^{e1}$, -$A^1$-S(O)$_n$$R^{f1}$, -$A^1$-S(O)$_n$O$R^{g1}$, —N($R^{h1}$)$R^{i1}$, —O$R^{j1}$ or =O;
$W^2$ represents halogen, —CN, $R^{a1}$, -$A^1$-C(O)$R^{b1}$, -$A^1$-C(O)N($R^{c1}$)$R^{d1}$, -$A^1$-C(O)O$R^{e1}$, -$A^1$-S(O)$_n$$R^{f1}$, -$A^1$-S(O)$_n$O$R^{g1}$, —N($R^{h1}$)$R^{i1}$, —O$R^{j1}$ or =O;
$W^3$ represents halogen, —CN, $R^{a1}$, -$A^1$-C(O)$R^{b1}$, -$A^1$-C(O)N($R^{c1}$)$R^{d1}$, -$A^1$-C(O)O$R^{e1}$, -$A^1$-S(O)$_n$$R^{f1}$, -$A^1$-S(O)$_n$O$R^{g1}$, —O$R^{j1}$, -$A^1$-S(N$R^{k1}$)(O)$R^{l1}$, -$A^1$-S(O)$_n$N($R^{m1}$)$R^{n1}$, —$N_3$, —$NO_2$, —S$R^{o1}$ or =O;
$A^1$ represents a single bond, —N($R^K$)— or —O—;
each $R^{a1}$, $R^{f1}$ and $R^{l1}$ independently represents $C_{1-6}$ alkyl optionally substituted by one or more fluoro;
each $R^{b1}$, $R^{c1}$, $R^{d1}$, $R^{e1}$, $R^{g1}$, $R^{h1}$, $R^{i1}$, $R^{j1}$, $R^{k1}$, $R^{m1}$, $R^{n1}$, and $R^{o1}$ independently represents hydrogen or $C_{1-6}$ alkyl optionally substituted by one or more fluoro; or any two $R^{c1}$ and $R^{d1}$, $R^{h1}$ and $R^{i1}$ and/or $R^{m1}$ and $R^{n1}$ are linked together to form, along with the nitrogen atom to which they are attached, a 3- to 6-membered ring, which ring optionally contains one further heteroatom and which ring optionally is substituted by one or more groups selected from fluoro, $C_{1-3}$alkyl optionally substituted by one or more fluoro, and =O;

$Z^1$ represents halogen, —CN, -$A^2$-C($Q^1$)$R^{b2}$, -$A^2$-C($Q^1$)N($R^{c2}$)$R^{d2}$, -$A^2$-C($Q^1$)O$R^{e2}$, -$A^2$-S(O)$_n$$R^{f2}$, -$A^2$-S(O)$_n$O$R^{g2}$, -$A^2$-S(N$R^{h2}$)(O)$R^{i2}$, -$A^2$-S(O)$_n$N($R^{j2}$)$R^{k2}$, —N($R^{l2}$)$R^{m2}$, —O$R^{n2}$, —S$R^{o2}$ or heterocycloalkyl optionally substituted by one or more groups selected from $W^5$;

$Z^2$ represents halogen, —CN, $R^{a2}$, -$A^2$-C($Q^1$)$R^{b2}$, -$A^2$-C($Q^1$)N($R^{c2}$)$R^{d2}$, -$A^2$-C($Q^1$)O$R^{e2}$, -$A^2$-S(O)$_n$$R^{f2}$, -$A^2$-S(O)$_n$O$R^{g2}$, -$A^2$-S(N$R^{h2}$)(O)$R^{i2}$, -$A^2$-S(O)$_n$N($R^{j2}$)$R^{k2}$, —N($R^{l2}$)$R^{m2}$, —O$R^{n2}$ or =Q1;

$Q^1$ represents =O, =S, =N$R^{p2}$, =NN($R^{q2}$)$R^{r2}$, =N(O$R^{s2}$), =NS(O)$_2$N($R^{t2}$)$R^{u2}$ or =C(H)NO$_2$;

$A^2$ represents a single bond, —N($R^L$)—, —C($Q^1$)N($R^M$)— or —O—;

each $R^{a2}$, $R^{f2}$, $R^{i2}$, $R^{n2}$ and $R^{o2}$ independently represents $C_{1-6}$alkyl optionally substituted by one or more groups selected from $W^4$ or heterocycloalkyl optionally substituted by one or more groups selected from $W^5$;

$R^{m2}$ represents $C_{2-6}$alkyl optionally substituted by one or more groups selected from $W^4$;

each $R^{b2}$, $R^{c2}$, $R^{d2}$, $R^{e2}$, $R^{g2}$, $R^{h2}$, $R^{j2}$, $R^{k2}$, $R^{l2}$, $R^{p2}$, $R^{q2}$, $R^{r2}$, $R^{s2}$, $R^{t2}$ and $R^{u2}$ independently represents hydrogen, $C_{1-6}$alkyl optionally substituted by one or more groups selected from $W^4$, heterocycloalkyl optionally substituted by one or more groups selected from $W^5$; or any two $R^{c2}$ and $R^{d2}$, $R^{j2}$ and $R^{k2}$, $R^{l2}$ and $R^{m2}$, $R^{q2}$ and $R^{r2}$ and/or $R^{t2}$ and $R^{u2}$ are linked together to form, along with the nitrogen atom to which they are attached, a 3- to 8-membered monocyclic or bicyclic ring, which ring optionally contains one or two further heteroatoms and which ring optionally is substituted by one or more groups selected from $W^5$, $C_{1-3}$alkyl optionally substituted by one or more groups selected from $W^4$, and =O;

$W^4$ represents halogen, —CN, -$A^3$-C(O)$R^{b3}$, -$A^3$-C(O)N($R^{c3}$)$R^{d3}$, -$A^3$-C(O)O$R^{e3}$, -$A^3$-S(O)$_n$$R^{f3}$, -$A^3$-S(O)$_n$ O$R^{g3}$, —O$R^{h3}$, =O or $W^6$;

$W^5$ represents halogen, —CN, $R^{a3}$, -$A^3$-C(O)$R^{b3}$, -$A^3$-C(O)N($R^{c3}$)$R^{d3}$, -$A^3$-C(O)O$R^{e3}$, -$A^3$-S(O)$_n$$R^{f3}$, -$A^3$-S(O)$_n$O$R^{g3}$, —O$R^{h3}$, =O or $W^6$;

$W^6$ represents phenyl or heteroaryl, both optionally substituted by one or more groups selected from halogen and $R^{a3}$;

$A^3$ represents a single bond, —N($R^L$)— or —O—;

each $R^{a3}$ and $R^{f3}$ independently represents $C_{1-6}$ alkyl optionally substituted by one or more fluoro;

each $R^{b3}$, $R^{c3}$, $R^{d3}$, $R^{e3}$, $R^{g3}$ and $R^{h3}$ independently represents hydrogen or $C_{1-6}$alkyl optionally substituted by one or more fluoro; or $R^{c3}$ and $R^{d3}$ are linked together to form, along with the nitrogen atom to which they are attached, a 3- to 6-membered ring, which ring optionally contains one further heteroatom and which ring optionally is substituted by one or more groups selected from fluoro, $C_{1-3}$alkyl optionally substituted by one or more fluoro, and =O;

$D^1$ and $D^2$ represent $R^{a4}$, -$A^4$-C($Q^2$)$R^{b4}$, -$A^4$-C($Q^2$)N($R^{c4}$)$R^{d4}$, -$A^4$-C($Q^2$)O$R^{e4}$, -$A^4$-S(O)$_n$$R^{f4}$, -$A^4$-S(O)$_n$C(O)$R^{g4}$, -$A^4$-S(N$R^{h4}$)(O)$R^{i4}$, -$A^4$-S(O)$_n$N($R^{j4}$)$R^{k4}$, -$A^4$-S(O)$_n$O$R^{l4}$, —B(O$R^{m4}$)$_2$, —N$_3$, —N($R^{n4}$)$R^{o4}$, —N(H)CN, —NO$_2$, —ONO$_2$, —O$R^{p4}$, —S$R^{q4}$ or, when J is partly aromatic, =$Q^2$;

$Q^2$ represents =O, =S, =N$R^{r4}$, =NN($R^{s4}$)$R^{t4}$, =N(O$R^{u4}$), =NS(O)$_2$N($R^{v4}$)$R^{w4}$ or =C(H)NO$_2$;

$A^4$ represents a single bond, —N($R^M$)—, —C(Q)N($R^N$)— or —O—;

each $R^X$ and $R^Y$ independently represent halogen, —CN, $R^{a4}$, —N($R^{n4}$)$R^{o4}$, —NO$_2$, —O$R^{p4}$ or =O;

$R^{c4}$ represents hydrogen, $R^{a4}$, —C(O)O$R^{e4}$, —S(O)$_n$$R^{f4}$, —S(O)$_n$N($R^{j4}$)$R^{k4}$, —N($R^{n4}$)$R^{o4}$ or —O$R^{p4}$;

each $R^{a4}$, $R^{f4}$ and $R^{i4}$ independently represent $C_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$;

each $R^{b4}$, $R^{d4}$, $R^{e4}$, $R^{g4}$, $R^{h4}$, $R^{j4}$, $R^{k4}$, $R^{l4}$, $R^{m4}$, $R^{n4}$, $R^{o4}$, $R^{p4}$, $R^{q4}$, $R^{r4}$, $R^{s4}$, $R^{t4}$, $R^{u4}$, $R^{v4}$ and $R^{w4}$ independently represent hydrogen, $C_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$; or any two $R^{c4}$ and $R^{d4}$, $R^{j4}$ and $R^{k4}$, $R^{n4}$ and $R^{o4}$, $R^{s4}$ and $R^{t4}$ and/or $R^{v4}$ and $R^{w4}$ are linked together to form, along with the nitrogen atom to which they are attached, a 3- to 6-membered ring, which ring optionally contains one heteroatom and which ring optionally is substituted by one or more groups selected from fluoro, $C_{1-3}$alkyl optionally substituted by one or more fluoro, and =O; or two $R^{m4}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, $C_{1-3}$alkyl optionally substituted by one or more halogens, and =O;

each $G^1$ is independently selected from halogen, —CN, —N($R^{b5}$)$R^{c5}$, —N(H)C(O)$R^{d5}$, —N(H)S(O)$_n$$R^{h5}$, —O$R^{k5}$, —S(O)$_m$$R^{i2}$ or =O;

each $G^2$ is independently selected from halogen, $R^{a5}$, —CN, —N($R^{b5}$)$R^{c5}$, —N(H)C(O)$R^{d5}$, —N(H)S(O)$_n$$R^{h5}$, —O$R^{k5}$, —S(O)$_m$$R^{i2}$ or =O;

each $G^3$ and $G^4$ are independently selected from halogen, —CN, $R^{a5}$, —N($R^{b5}$)$R^{c5}$, -$A^5$-C(O)$R^{d5}$, -$A^5$-C(O)N($R^{e5}$)$R^{f5}$, -$A^5$-C(O)O$R^{g5}$, -$A^5$-S(O)$_n$$R^{h5}$, -$A^5$-S(O)$_n$N($R^{i5}$)$R^{j5}$, —O$R^{k5}$ or =O;

$A^5$ represents a single bond or —N(H)—;

$R^{a5}$ represents $C_{1-6}$ alkyl optionally substituted by one or more halogens;

each $R^{b5}$, $R^{c5}$, $R^{d5}$, $R^{e5}$, $R^{f5}$, $R^{g5}$, $R^{h5}$, $R^{i5}$, $R^{j5}$, $R^{k5}$ and $R^{l5}$ independently represents hydrogen or $C_{1-6}$ alkyl optionally substituted by one or more halogens; or any two $R^{b5}$ and $R^{c5}$, $R^{e5}$ and $R^{f5}$ and/or $R^{i5}$ and $R^{j5}$ are linked together to form, along with the nitrogen atom to which they are attached, a 3- to 6-membered ring, which ring optionally contains one further heteroatom and which ring optionally is substituted by one or more groups selected from halogen, $C_{1-3}$alkyl optionally substituted by one or more halogens, and =O;

each $R^A$, $R^B$, $R^C$, $R^D$, $R^E$, $R^F$, $R^G$, $R^H$, $R^I$, $R^J$, $R^K$, $R^L$, $R^M$ and $R^N$ independently represents hydrogen or $C_{1-3}$ alkyl optionally substituted by one or more fluoro;

$T^1$ represents halogen, —CN, —N($R^{b6}$)$R^{c6}$ or —OR$^{d6}$;

$T^2$ represents halogen, —CN, $R^{a6}$, —OR$^{d6}$ or =O;

each $R^{a6}$ independently represents $C_{1-6}$alkyl optionally substituted by one or more halogens;

each $R^{b6}$, $R^{c6}$ and $R^{d6}$ independently represents hydrogen or $C_{1-6}$alkyl optionally substituted by one or more halogens; or $R^{b6}$ and $R^{c6}$ are linked together to form, along with the nitrogen atom to which they are attached, a 3- to 6-membered ring;

each p and q independently represents 0, 1 or 2, provided that the sum of p and q is 0, 1 or 2;

each m independently represents 0, 1 or 2; and each n independently represents 1 or 2;

provided that when X represents —CH$_2$CH$_2$—, L represents -L$^1$-L$^2$-, L$^1$ represents —N(H)— or —N(Me)-, L$^2$ represents a single bond and J represents 4-pyrimidinyl, and said 4-pyrimidinyl is unsubstituted or substituted with —CH$_3$, —NH$_2$ or —N(H)CH$_2$CH(CH$_3$)$_2$, then R$^1$ does not represent phenyl, 3-chlorophenyl, 3,5-dichlorophenyl or 5-chloro-2-methoxyphenyl, and provided that formula I does not represent (S)—N$^4$-(1-(2,4-difluorophenyl)ethyl)-6-(pyrazolo[1,5-a]pyrimidin-3-yl)pyrimidine-2,4-diamine.

2. The method as claimed in claim 1 wherein R$^1$ represents (i)

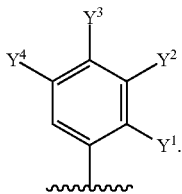

3. The method as claimed in claim 2, wherein
Y$^1$ represents halogen, —CN, R$^a$ or —OR$^m$; and
Y$^2$, Y$^3$ and Y$^4$ each independently represent hydrogen, halogen, R$^a$, -A-C(Q)R$^b$, —C(Q)N(R$^c$)R$^d$, —C(Q)OR$^e$, -A-S(O)$_n$R$^f$, —S(O)$_n$N(R$^i$)R$^j$, —OH or —OR$^m$.

4. The method as claimed in claim 3, wherein at least two of Y$^1$, Y$^2$, Y$^3$ and Y$^4$ are other than hydrogen.

5. The method as claimed in claim 4, wherein Y$^3$ and Y$^4$ are hydrogen; and Y$^1$ and Y$^2$ are independently selected from fluoro, chloro, -Me and —CF$_3$.

6. The method as claimed in claim 1, wherein R$^3$ represents —X-L-J.

7. The method as claimed in claim 6, wherein X represents —CH$_2$—, —CH$_2$CH$_2$—, —CH(Me)-, —C(Me)$_2$-, —CH$_2$CH(Me)-, —CH(Me)CH$_2$—, —CH$_2$CH$_2$CH$_2$—, —CH(Me)CH$_2$CH$_2$—, —CH$_2$CH$_2$CH$_2$—, —CH$_2$C(CH$_3$)$_2$CH$_2$—, -cyclopropylene- or —CH$_2$—=CH$_2$—.

8. The method as claimed in claim 7, wherein X represents —CH$_2$CH$_2$—, —CH$_2$CH$_2$CH$_2$— or -cyclopropylene-.

9. The method as claimed in claim 1, wherein L represents -L$^1$-L$^2$-.

10. The method as claimed in claim 9, wherein L$^1$ represents —N(H)—, —O—, —SO$_2$—, —C(O)N(H)—, —SO$_2$N(H)— or —N(H)C(O)N(H)—.

11. The method as claimed in claim 9, wherein L$^1$ represents —N(H)—, —O— or —N(H)C(O)N(H)—.

12. The method as claimed in claim 9, wherein L$^2$ represents a single bond.

13. The method as claimed in claim 9, wherein L$^2$ represents —CH$_2$— or —CH$_2$CH$_2$—.

14. The method as claimed in claim 1, wherein L represents a single bond.

15. The method as claimed in claim 1, wherein J represents phenyl optionally substituted by D$^1$ and optionally substituted by one or more groups selected from R$^X$.

16. The method as claimed in claim 1, wherein J represents a 5- to 11-membered monocyclic or bicyclic heteroaryl ring, which ring contains 1 to 3 nitrogen atoms, and/or one oxygen atom and/or one or two sulfur atoms and which ring is optionally substituted by D$^2$ and optionally substituted by one or more groups selected from R$^Y$.

17. The method as claimed in claim 1, wherein R$^3$ represents —C$_{1-6}$alkyl optionally substituted by one or more groups selected from Z$^1$.

18. The method as claimed in claim 1, wherein the compound is selected from

4-N-cyclohexyl-6-phenylpyrimidine-2,4-diamine;
4-N-ethyl-6-phenylpyrimidine-2,4-diamine;
4-N-(3-ethoxypropyl)-6-phenylpyrimidine-2,4-diamine;
6-phenyl-4-N-propylpyrimidine-2,4-diamine;
6-(4-methanesulfonylphenyl)-4-N-propylpyrimidine-2,4-diamine;
4-N-(cyclopropylmethyl)-6-phenylpyrimidine-2,4-diamine;
4-N-(oxan-4-yl)-6-phenylpyrimidine-2,4-diamine;
4-N-(furan-2-ylmethyl)-6-phenylpyrimidine-2,4-diamine;
4-N-(pentan-3-yl)-6-phenylpyrimidine-2,4-diamine;
6-phenyl-4-N-(propan-2-yl)pyrimidine-2,4-diamine;
4-N-benzyl-6-phenylpyrimidine-2,4-diamine;
4-N-[2-(morpholin-4-yl)ethyl]-6-phenylpyrimidine-2,4-diamine;
6-(4-chlorophenyl)-4-N-cyclopropylpyrimidine-2,4-diamine;
4-(N-tert-butyl)-6-(4-chlorophenyl)pyrimidine-2,4-diamine;
6-(4-chlorophenyl)-4-N-(oxan-4-yl)pyrimidine-2,4-diamine;
4-N-cyclopropyl-6-[3-(trifluoromethyl)phenyl]pyrimidine-2,4-diamine;
4-N-tert-butyl-6-(4-methoxyphenyl)pyrimidine-2,4-diamine;
4-N-cyclopropyl-6-(4-methoxyphenyl)pyrimidine-2,4-diamine;
6-(3-chlorophenyl)-4-N-cyclopropylpyrimidine-2,4-diamine;
4-N-tert-butyl-6-[3-(trifluoromethyl)phenyl]pyrimidine-2,4-diamine;
6-(3-chlorophenyl)-4-N-(oxan-4-yl)pyrimidine-2,4-diamine;
4-N-tert-butyl-6-(3-chlorophenyl)pyrimidine-2,4-diamine;
4-N-methyl-6-[1-(4-methylbenzenesulfonyl)-1H-indol-3-yl]pyrimidine-2,4-diamine;
6-(2,3-dichlorophenyl)-4-N-(2,2,2-trifluoroethyl)pyrimidine-2,4-diamine;

6-(3-chlorophenyl)-4-N-(2,2,2-trifluoroethyl)pyrimidine-2,4-diamine;
6-[1-(benzenesulfonyl)-1H-indol-3-yl]-4-N-methylpyrimidine-2,4-diamine;
4-N-cyclopropyl-6-[1-(4-methylbenzenesulfonyl)-1H-indol-3-yl]pyrimidine-2,4-diamine;
6-[1-(benzenesulfonyl)-1H-indol-3-yl]-4-N-cyclopropylpyrimidine-2,4-diamine;
6-[1-(benzenesulfonyl)-1H-pyrrolo[2,3-b]pyridin-3-yl]-4-N-methylpyrimidine-2,4-diamine;
6-[1-(benzenesulfonyl)-1H-indol-4-yl]-4-N-methylpyrimidine-2,4-diamine;
6-[1-(benzenesulfonyl)-1H-indol-5-yl]-4-N-methylpyrimidine-2,4-diamine;
6-(2-methoxyphenyl)-4-N-methylpyrimidine-2,4-diamine;
6-(4-methoxyphenyl)-4-N-methylpyrimidine-2,4-diamine;
6-[3,5-bis(trifluoromethyl)phenyl]-4-N-methylpyrimidine-2,4-diamine;
6-(isoquinolin-4-yl)-4-N-methylpyrimidine-2,4-diamine;
4-N-methyl-6-[4-(trifluoromethyl)phenyl]pyrimidine-2,4-diamine;
4-N-methyl-6-[3-(trifluoromethyl)phenyl]pyrimidine-2,4-diamine;
6-(2,3-dichlorophenyl)-4-N-methylpyrimidine-2,4-diamine;
6-(2H-1,3-benzodioxol-5-yl)-4-N-methylpyrimidine-2,4-diamine;
3-[2-amino-6-(methylamino)pyrimidin-4-yl]benzonitrile;
N-{3-[2-amino-6-(methylamino)pyrimidin-4-yl]phenyl}acetamide;
4-N-methyl-6-[4-(morpholine-4-sulfonyl)phenyl]pyrimidine-2,4-diamine;
6-(4-methanesulfonylphenyl)-4-N-methylpyrimidine-2,4-diamine;
4-N-methyl-6-[3-(morpholine-4-carbonyl)phenyl]pyrimidine-2,4-diamine;
4-[2-amino-6-(methylamino)pyrimidin-4-yl]-N-(furan-2-ylmethyl)benzamide;
N-{4-[2-amino-6-(methylamino)pyrimidin-4-yl]phenyl}methanesulfonamide;
N-{4-[2-amino-6-(methylamino)pyrimidin-4-yl]phenyl}acetamide;
4-[2-[[2-amino-6-(3-chloro-2-methyl-phenyl)pyrimidin-4-yl]amino]ethyl]-N'-hydroxy-benzamidine;
6-(6-methoxypyridin-3-yl)-4-N-methylpyrimidine-2,4-diamine;
6-(2-fluoro-4-phenylphenyl)-4-N-methylpyrimidine-2,4-diamine;
4-[2-amino-6-(methylamino)pyrimidin-4-yl]benzonitrile;
6-(4-chlorophenyl)-4-N-(prop-2-en-1-yl)pyrimidine-2,4-diamine;
6-(4-methoxyphenyl)-4-N-(prop-2-en-1-yl)pyrimidine-2,4-diamine;
6-(4-chlorophenyl)-4-N-cyclopentylpyrimidine-2,4-diamine;
4-N-cyclopentyl-6-(4-methoxyphenyl)pyrimidine-2,4-diamine;
4-N-cyclopentyl-6-[3-(trifluoromethyl)phenyl]pyrimidine-2,4-diamine;
6-(4-chlorophenyl)-4-N-cyclobutylpyrimidine-2,4-diamine;
4-N-cyclobutyl-6-(4-methoxyphenyl)pyrimidine-2,4-diamine;
4-N-cyclobutyl-6-[3-(trifluoromethyl)phenyl]pyrimidine-2,4-diamine;
6-(2,3-dichlorophenyl)-4-N-pentylpyrimidine-2,4-diamine;
4-N-cyclopropyl-6-(2,3-dichlorophenyl)pyrimidine-2,4-diamine;
4-N-tert-butyl-6-(2,3-dichlorophenyl)pyrimidine-2,4-diamine;
4-N-cyclobutyl-6-(2,3-dichlorophenyl)pyrimidine-2,4-diamine;
4-N-cyclopentyl-6-(2,3-dichlorophenyl)pyrimidine-2,4-diamine;
6-(2,3-dichlorophenyl)-4-N-ethylpyrimidine-2,4-diamine;
6-(2,3-dichlorophenyl)-4-N-(oxolan-3-yl)pyrimidine-2,4-diamine;
6-(3,4-dichlorophenyl)-4-N-methylpyrimidine-2,4-diamine;
6-(4-tert-butylphenyl)-4-N-methylpyrimidine-2,4-diamine;
4-N-methyl-6-(4-methylphenyl)pyrimidine-2,4-diamine;
6-(2,4-dichlorophenyl)-4-N-methylpyrimidine-2,4-diamine;
4-N-methyl-6-(2,4,5-trifluorophenyl)pyrimidine-2,4-diamine;
6-(4-fluoro-2-methoxyphenyl)-4-N-methylpyrimidine-2,4-diamine;
6-(5-chloro-2-methylphenyl)-4-N-methylpyrimidine-2,4-diamine;
6-(2,4-difluorophenyl)-4-N-methylpyrimidine-2,4-diamine;
6-(5-fluoro-2-methoxyphenyl)-4-N-methylpyrimidine-2,4-diamine;
6-(2-chlorophenyl)-4-N-methylpyrimidine-2,4-diamine;
6-(2,3-dichlorophenyl)-N4-[2-(3-methylsulfonylanilino)ethyl]pyrimidine-2,4-diamine;
6-(4-methoxy-3-methylphenyl)-4-N-methylpyrimidine-2,4-diamine;
6-(3-chloro-4-fluorophenyl)-4-N-methylpyrimidine-2,4-diamine;
4-N-methyl-6-[4-(trifluoromethoxy)phenyl]pyrimidine-2,4-diamine;
6-(3-fluoro-4-methoxyphenyl)-4-N-methylpyrimidine-2,4-diamine;
6-(3,4-difluorophenyl)-4-N-methylpyrimidine-2,4-diamine;
4-N-methyl-6-[4-(propan-2-yloxy)phenyl]pyrimidine-2,4-diamine;
6-[2-fluoro-3-(trifluoromethyl)phenyl]-4-N-methylpyrimidine-2,4-diamine;
6-(2,3-dimethylphenyl)-4-N-methylpyrimidine-2,4-diamine;
6-(3-chloro-2-fluorophenyl)-4-N-methylpyrimidine-2,4-diamine;
6-(4-chloro-3-fluorophenyl)-4-N-methylpyrimidine-2,4-diamine;
4-N-methyl-6-[2-(trifluoromethyl)phenyl]pyrimidine-2,4-diamine;
4-N-methyl-6-(1-methyl-1H-indazol-4-yl)pyrimidine-2,4-diamine;
6-[2-chloro-3-(trifluoromethyl)phenyl]-4-N-methylpyrimidine-2,4-diamine;
6-(2-chloro-3-fluorophenyl)-4-N-methylpyrimidine-2,4-diamine;
6-(2,3-difluorophenyl)-4-N-methylpyrimidine-2,4-diamine;
6-(3-chloro-2-methylphenyl)-4-N-methylpyrimidine-2,4-diamine;

6-(7-chloro-2H-1,3-benzodioxol-5-yl)-4-N-methylpyrimidine-2,4-diamine;
6-(2,3-dichloro-4-methoxyphenyl)-4-N-methylpyrimidine-2,4-diamine;
6-(2,3-dichloro-5-methoxyphenyl)-4-N-methylpyrimidine-2,4-diamine;
4-[2-amino-6-(methylamino)pyrimidin-4-yl]phenol;
{3-[2-amino-6-(methylamino)pyrimidin-4-yl]phenyl}methanol;
4-[2-amino-6-(methylamino)pyrimidin-4-yl]benzoic acid;
methyl 4-[2-amino-6-(methylamino)pyrimidin-4-yl]benzoate;
6-[3-chloro-4-(morpholine-4-carbonyl)phenyl]-4-N-methylpyrimidine-2,4-diamine;
4-[2-amino-6-(methylamino)pyrimidin-4-yl]-2,3-dichlorophenol;
methyl (2E)-3-{4-[2-amino-6-(methylamino)pyrimidin-4-yl]phenyl}prop-2-enoate;
methyl (2E)-3-{3-[2-amino-6-(methylamino)pyrimidin-4-yl]phenyl}prop-2-enoate;
4-[2-amino-6-(methylamino)pyrimidin-4-yl]benzaldehyde
1-(4-(2-amino-6-(methylamino)pyrimidin-4-yl)phenyl)ethanone;
4-[2-amino-6-(methylamino)pyrimidin-4-yl]-N-methylbenzamide;
6-(4-ethenylphenyl)-4-N-methylpyrimidine-2,4-diamine;
6-(2,3-dimethylphenyl)-4-N-[2-(piperidin-1-yl)ethyl]pyrimidine-2,4-diamine;
6-(2,3-dimethylphenyl)-4-N-[2-(morpholin-4-yl)ethyl]pyrimidine-2,4-diamine;
4-N-cyclopropyl-6-(2,3-dimethylphenyl)pyrimidine-2,4-diamine;
3-[2-amino-6-(methylamino)pyrimidin-4-yl]-N-(4-methylphenyl)benzamide;
6-(1H-indol-3-yl)-4-N-methylpyrimidine-2,4-diamine;
6-phenyl-4-N-(2-phenylethyl)pyrimidine-2,4-diamine;
6-(2,3-dimethylphenyl)-4-N-(2-phenylethyl)pyrimidine-2,4-diamine;
6-(3-chlorophenyl)-4-N-(2,2-difluoroethyl)pyrimidine-2,4-diamine;
6-(3-chloro-2-methoxypyridin-4-yl)-4-N-methylpyrimidine-2,4-diamine;
6-(3,5-difluorophenyl)-4-N-methylpyrimidine-2,4-diamine;
6-(2,3-dimethylphenyl)-4-N-[2-(4-methoxyphenyl)ethyl]pyrimidine-2,4-diamine;
6-(2,3-dimethylphenyl)-4-N-[2-(2-methoxyphenyl)ethyl]pyrimidine-2,4-diamine;
6-(2,3-dimethylphenyl)-4-N-[2-(4-methylphenyl)ethyl]pyrimidine-2,4-diamine;
4-N-[2-(4-chlorophenyl)ethyl]-6-(2,3-dimethylphenyl)pyrimidine-2,4-diamine;
6-(2,3-dimethylphenyl)-4-N-[2-(pyridin-2-yl)ethyl]pyrimidine-2,4-diamine;
6-(2,3-dimethylphenyl)-4-N-(2-phenylpropyl)pyrimidine-2,4-diamine;
6-(2,3-dimethylphenyl)-4-N-(3-phenylpropyl)pyrimidine-2,4-diamine;
6-(2,3-dimethylphenyl)-4-N-(2-phenoxyethyl)pyrimidine-2,4-diamine;
6-(2,3-dimethylphenyl)-4-N-[2-(phenylamino)ethyl]pyrimidine-2,4-diamine;
6-(2,3-dimethylphenyl)-4-N-[2-(1H-indol-3-yl)ethyl]pyrimidine-2,4-diamine;
6-(2,3-dimethylphenyl)-4-N-pentylpyrimidine-2,4-diamine;
1-(2-{[2-amino-6-(2,3-dimethylphenyl)pyrimidin-4-yl]amino}ethyl)imidazolidin-2-one;
1-(3-{[2-amino-6-(2,3-dimethylphenyl)pyrimidin-4-yl]amino}propyl)pyrrolidin-2-one;
4-[2-amino-6-(methylamino)pyrimidin-4-yl]-2,6-dimethylphenol;
4-[2-amino-6-(methylamino)pyrimidin-4-yl]-2-methoxyphenol;
4-[2-amino-6-(methylamino)pyrimidin-4-yl]-2-fluorophenol;
5-[2-amino-6-(methylamino)pyrimidin-4-yl]pyridin-2-ol;
{4-[2-amino-6-(methylamino)pyrimidin-4-yl]phenyl}methanol;
4-N-methyl-6-(2-methylphenyl)pyrimidine-2,4-diamine;
6-[1-(4-chlorobenzenesulfonyl)-1H-indol-3-yl]-4-N-methylpyrimidine-2,4-diamine;
4-N-methyl-6-(4-methyl-1H-indazol-5-yl)pyrimidine-2,4-diamine;
4-N-methyl-6-(6-methyl-1H-indazol-5-yl)pyrimidine-2,4-diamine;
4-N-methyl-6-(3-methylphenyl)pyrimidine-2,4-diamine;
6-(1H-indol-5-yl)-4-N-methylpyrimidine-2,4-diamine;
6-(3-chloropyridin-4-yl)-4-N-methylpyrimidine-2,4-diamine;
{5-[2-amino-6-(methylamino)pyrimidin-4-yl]pyridin-2-yl}methanol;
4-N-cyclobutyl-6-(2,3-dimethylphenyl)pyrimidine-2,4-diamine;
4-N-cyclobutyl-6-[1-(4-methylbenzenesulfonyl)-1H-indol-3-yl]pyrimidine-2,4-diamine;
4-N-cyclopentyl-6-(2,3-dimethylphenyl)pyrimidine-2,4-diamine;
4-N-cyclopentyl-6-[1-(4-methylbenzenesulfonyl)-1H-indol-3-yl]pyrimidine-2,4-diamine;
4-N-methyl-6-{1-[4-(trifluoromethyl)benzenesulfonyl]-1H-indol-3-yl}pyrimidine-2,4-diamine;
4-N-cyclohexyl-6-(2,3-dimethylphenyl)pyrimidine-2,4-diamine;
4-N-cyclohexyl-6-[1-(4-methylbenzenesulfonyl)-1H-indol-3-yl]pyrimidine-2,4-diamine;
6-(2,3-dimethylphenyl)-4-N-ethylpyrimidine-2,4-diamine;
4-N-ethyl-6-[1-(4-methylbenzenesulfonyl)-1H-indol-3-yl]pyrimidine-2,4-diamine;
4-N-tert-butyl-6-(2,3-dimethylphenyl)pyrimidine-2,4-diamine;
4-N-tert-butyl-6-[1-(4-methylbenzenesulfonyl)-1H-indol-3-yl]pyrimidine-2,4-diamine;
6-(2,3-dimethylphenyl)-4-N-(propan-2-yl)pyrimidine-2,4-diamine;
6-[1-(4-methylbenzenesulfonyl)-1H-indol-3-yl]-4-N-(propan-2-yl)pyrimidine-2,4-diamine;
4-N-(cyclopropylmethyl)-6-(2,3-dimethylphenyl)pyrimidine-2,4-diamine;
4-N-(cyclopropylmethyl)-6-[1-(4-methylbenzenesulfonyl)-1H-indol-3-yl]pyrimidine-2,4-diamine;
4-N-[(1R)-1-cyclopropylethyl]-6-(2,3-dimethylphenyl)pyrimidine-2,4-diamine;
4-N-[(1R)-1-cyclopropylethyl]-6-[1-(4-methylbenzenesulfonyl)-1H-indol-3-yl]pyrimidine-2,4-diamine;
4-N-[(1S)-1-cyclopropylethyl]-6-(2,3-dimethylphenyl)pyrimidine-2,4-diamine;
4-N-[(1S)-1-cyclopropylethyl]-6-[1-(4-methylbenzenesulfonyl)-1H-indol-3-yl]pyrimidine-2,4-diamine;

6-(1-benzofuran-3-yl)-4-N-methylpyrimidine-2,4-diamine;
6-(2-chloro-5-methylphenyl)-4-N-methylpyrimidine-2,4-diamine;
6-(1-benzothiophen-3-yl)-4-N-methylpyrimidine-2,4-diamine;
2-{4-[2-amino-6-(methylamino)pyrimidin-4-yl]phenyl}propan-2-ol;
6-(1H-indol-4-yl)-4-N-methylpyrimidine-2,4-diamine;
4-N-cyclohexyl-6-(2,3-dichlorophenyl)pyrimidine-2,4-diamine;
6-(2,3-dichlorophenyl)-4-N-(propan-2-yl)pyrimidine-2,4-diamine;
4-N-(cyclopropylmethyl)-6-(2,3-dichlorophenyl)pyrimidine-2,4-diamine;
4-N-[(1S)-1-cyclopropylethyl]-6-(2,3-dichlorophenyl)pyrimidine-2,4-diamine;
4-N-[(1R)-1-cyclopropylethyl]-6-(2,3-dichlorophenyl)pyrimidine-2,4-diamine;
6-(2,3-dichlorophenyl)-4-N-(2,2-dimethylpropyl)pyrimidine-2,4-diamine;
6-(2,3-dimethylphenyl)-4-N-(2,2-dimethylpropyl)pyrimidine-2,4-diamine;
4-N-(2,2-dimethylpropyl)-6-[1-(4-methylbenzenesulfonyl)-1H-indol-3-yl]pyrimidine-2,4-diamine;
6-(5-bromo-2-methoxyphenyl)-4-N-methylpyrimidine-2,4-diamine;
6-(2,5-dimethylphenyl)-4-N-methylpyrimidine-2,4-diamine;
4-N-methyl-6-[2-(trifluoromethyl)pyridin-3-yl]pyrimidine-2,4-diamine;
6-(3-chloro-2-methyl-phenyl)-N4-[2-(3-methylsulfonylanilino)ethyl]pyrimidine-2,4-diamine;
6-[4-(benzyloxy)-2-methylphenyl]-4-N-methylpyrimidine-2,4-diamine;
6-(4-methoxy-2,5-dimethylphenyl)-4-N-methylpyrimidine-2,4-diamine;
4-N-methyl-6-(2,4,5-trimethylphenyl)pyrimidine-2,4-diamine;
2-[2-amino-6-(methylamino)pyrimidin-4-yl]-4-chlorobenzonitrile;
6-(4,5-dichloro-2-methylphenyl)-4-N-methylpyrimidine-2,4-diamine;
6-(2,5-dichloro-4-methoxyphenyl)-4-N-methylpyrimidine-2,4-diamine;
6-(4-fluoro-2,5-dimethylphenyl)-4-N-methylpyrimidine-2,4-diamine;
4-N-methyl-6-[2-methyl-5-(trifluoromethyl)phenyl]pyrimidine-2,4-diamine;
6-[5-chloro-2-methyl-4-(trifluoromethyl)phenyl]-4-N-methylpyrimidine-2,4-diamine;
6-[2,5-bis(trifluoromethyl)phenyl]-4-N-methylpyrimidine-2,4-diamine;
6-(5-tert-butyl-2-methoxyphenyl)-4-N-methylpyrimidine-2,4-diamine;
6-[2-methoxy-5-(propan-2-yl)phenyl]-4-N-methylpyrimidine-2,4-diamine;
6-[2-chloro-5-(trifluoromethyl)phenyl]-4-N-methylpyrimidine-2,4-diamine;
6-(2-fluoro-5-methylphenyl)-4-N-methylpyrimidine-2,4-diamine;
6-(5-chloro-2-methoxyphenyl)-4-N-methylpyrimidine-2,4-diamine;
6-(5-fluoro-2-methylphenyl)-4-N-methylpyrimidine-2,4-diamine;
6-(2,5-dimethoxyphenyl)-4-N-methylpyrimidine-2,4-diamine;
6-(2-methoxy-5-methylphenyl)-4-N-methylpyrimidine-2,4-diamine;
6-(2-chloro-5-fluorophenyl)-4-N-methylpyrimidine-2,4-diamine;
3-[2-amino-6-(methylamino)pyrimidin-4-yl]-4-fluorobenzonitrile;
6-(2-chloro-5-methoxyphenyl)-4-N-methylpyrimidine-2,4-diamine;
6-[5-fluoro-2-(trifluoromethyl)phenyl]-4-N-methylpyrimidine-2,4-diamine;
6-(2,5-dichlorophenyl)-4-N-methylpyrimidine-2,4-diamine;
6-(5-chloro-2-fluorophenyl)-4-N-methylpyrimidine-2,4-diamine;
3-[2-amino-6-(methylamino)pyrimidin-4-yl]-4-methylbenzonitrile;
3-[2-amino-6-(methylamino)pyrimidin-4-yl]-4-methoxybenzonitrile;
6-(2-chloro-5-fluoro-4-methylphenyl)-4-N-methylpyrimidine-2,4-diamine;
6-(5-chloro-2-fluoro-4-methylphenyl)-4-N-methylpyrimidine-2,4-diamine;
6-(2-chloro-4-fluoro-5-methylphenyl)-4-N-methylpyrimidine-2,4-diamine;
4-N-cyclopropyl-6-(4-fluoro-2,5-dimethylphenyl)pyrimidine-2,4-diamine;
4-N-cyclopropyl-6-(4-methoxy-2,5-dimethylphenyl)pyrimidine-2,4-diamine;
4-N-cyclopropyl-6-(2,5-dimethylphenyl)pyrimidine-2,4-diamine;
6-(5-chloro-2-methylphenyl)-4-N-cyclopropylpyrimidine-2,4-diamine;
6-(5-chloro-2-methylphenyl)-4-N-cyclobutylpyrimidine-2,4-diamine;
6-(5-chloro-2-methylphenyl)-4-N-ethylpyrimidine-2,4-diamine;
6-(5-chloro-2-methylphenyl)-4-N-[2-(4-chlorophenyl)ethyl]pyrimidine-2,4-diamine;
4-N-[2-(4-chlorophenyl)ethyl]-6-(4-fluoro-2,5-dimethylphenyl)pyrimidine-2,4-diamine;
4-N-[2-(4-chlorophenyl)ethyl]-6-(2,5-dimethylphenyl)pyrimidine-2,4-diamine;
1-(3-{[2-amino-6-(quinolin-5-yl)pyrimidin-4-yl]amino}propyl)pyrrolidin-2-one;
6-(2-chloro-3-methylphenyl)-4-N-methylpyrimidine-2,4-diamine;
6-(2-chloro-3-methylphenyl)-4-N-cyclopropylpyrimidine-2,4-diamine;
6-(2-chloro-3-methylphenyl)-4-N-[2-(4-chlorophenyl)ethyl]pyrimidine-2,4-diamine;
1-(3-{[2-amino-6-(2-chloro-3-methylphenyl)pyrimidin-4-yl]amino}propyl)pyrrolidin-2-one;
4-N-cyclopropyl-6-(1H-indol-4-yl)pyrimidine-2,4-diamine;
4-N-[2-(4-chlorophenyl)ethyl]-6-(1H-indol-4-yl)pyrimidine-2,4-diamine;
4-N-cyclopropyl-6-(quinolin-5-yl)pyrimidine-2,4-diamine;
(2E)-3-{4-[2-amino-6-(methylamino)pyrimidin-4-yl]phenyl}prop-2-enoic acid;
tert-butyl 3-({[2-amino-6-(2,3-dimethylphenyl)pyrimidin-4-yl]amino}methyl)¬azetidine-1-carboxylate;
4-N-cyclopropyl-6-(1H-indol-5-yl)pyrimidine-2,4-diamine;
1-(3-{[2-amino-6-(1H-indol-5-yl)pyrimidin-4-yl]amino}propyl)pyrrolidin-2-one;

tert-butyl 4-((2-amino-6-(2,3-dimethylphenyl)pyrimidin-4-yl)amino)piperidine-1-carboxylate;
ethyl 4-((2-amino-6-(2,3-dimethylphenyl)pyrimidin-4-yl)amino)piperidine-1-carboxylate;
tert-butyl (3-((2-amino-6-(2,3-dimethylphenyl)pyrimidin-4-yl)amino)-2,2-dimethyl¬propyl)carbamate;
6-(5-chloro-4-methoxy-2-methylphenyl)-4-N-methylpyrimidine-2,4-diamine;
6-(3-chloro-2-methylphenyl)-4-N-[(1R)-1-phenylethyl]pyrimidine-2,4-diamine;
6-(3-chloro-2-methylphenyl)-4-N-(2-phenylpropan-2-yl)pyrimidine-2,4-diamine;
6-(3-chloro-2-methylphenyl)-4-N-[1-(1H-indol-3-yl)propan-2-yl]pyrimidine-2,4-diamine;
4-N-{bicyclo[221]heptan-2-yl}-6-(3-chloro-2-methylphenyl)pyrimidine-2,4-diamine;
6-(3-chloro-2-methylphenyl)-4-N-ethylpyrimidine-2,4-diamine;
6-(3-chloro-2-methylphenyl)-4-N-(propan-2-yl)pyrimidine-2,4-diamine;
4-N-[2-(2-chlorophenoxy)ethyl]-6-(2,3-dimethylphenyl)pyrimidine-2,4-diamine;
4-N-[2-(5-chloro-1H-1,3-benzodiazol-2-yl)ethyl]-6-(2,3-dimethylphenyl)pyrimidine-2,4-diamine;
4-N-[2-(2,5-dimethyl-1H-indol-3-yl)ethyl]-6-(2,3-dimethylphenyl)pyrimidine-2,4-diamine;
6-(2,3-dimethylphenyl)-4-N-[2-(pyridin-3-yloxy)propyl]pyrimidine-2,4-diamine;
6-(2,3-dimethylphenyl)-4-N-(1H-indazol-5-ylmethyl)pyrimidine-2,4-diamine;
6-(2,3-dimethylphenyl)-4-N-(1H-indazol-6-ylmethyl)pyrimidine-2,4-diamine;
6-(2,3-dimethylphenyl)-4-N-[(2-methoxypyridin-4-yl)methyl]pyrimidine-2,4-diamine;
4-N-[(5-chloropyrazin-2-yl)methyl]-6-(2,3-dimethylphenyl)pyrimidine-2,4-diamine;
6-(2,3-dimethylphenyl)-4-N-{imidazo[1,2-a]pyridin-2-ylmethyl}pyrimidine-2,4-diamine;
tert-butyl 4-{4-[2-amino-6-(methylamino)pyrimidin-4-yl]-2-(methoxymethyl)phenoxymethyl}piperidine-1-carboxylate;
6-[3-(methoxymethyl)-4-(piperidin-4-ylmethoxy)phenyl]-4-N-methylpyrimidine-2,4-diamine;
3-[2-amino-6-(methylamino)pyrimidin-4-yl]-2-methylbenzonitrile;
6-(4-methoxy-2,3-dimethylphenyl)-4-N-methylpyrimidine-2,4-diamine;
6-(4-fluoro-2,3-dimethylphenyl)-4-N-methylpyrimidine-2,4-diamine;
6-(2,3-dihydro-1-benzofuran-7-yl)-4-N-methylpyrimidine-2,4-diamine;
4-N-methyl-6-[2-methyl-5-(morpholine-4-sulfonyl)phenyl]pyrimidine-2,4-diamine;
4-N-[2-(4-chlorophenyl)ethyl]-6-(2,3-dichlorophenyl)pyrimidine-2,4-diamine;
4-N-[2-(4-chlorophenyl)ethyl]-6-(2-methylphenyl)pyrimidine-2,4-diamine;
4-N-[2-(4-chlorophenyl)ethyl]-6-[3-(trifluoromethyl)phenyl]pyrimidine-2,4-diamine;
4-N-[2-(4-chlorophenyl)ethyl]-6-(quinolin-5-yl)pyrimidine-2,4-diamine;
4-N-[2-(4-chlorophenyl)cyclopropyl]-6-(2,3-dimethylphenyl)pyrimidine-2,4-diamine;
6-(2,3-dimethylphenyl)-4-N-[2-(pyridin-3-yl)ethyl]pyrimidine-2,4-diamine;
3-(2-{[2-amino-6-(2,3-dimethylphenyl)pyrimidin-4-yl]amino}ethyl)phenol;
6-(2,3-dimethylphenyl)-4-N-[3-(morpholin-4-yl)propyl]pyrimidine-2,4-diamine;
tert-butyl N-(2-{[2-amino-6-(2,3-dimethylphenyl)pyrimidin-4-yl]amino}ethyl)¬carbamate;
N-(2-{[2-amino-6-(2,3-dimethylphenyl)pyrimidin-4-yl]amino}ethyl)acetamide;
benzyl N-(2-{[2-amino-6-(2,3-dimethylphenyl)pyrimidin-4-yl]amino}ethyl)¬carbamate;
tert-butyl N-(2-{[2-amino-6-(2,3-dimethylphenyl)pyrimidin-4-yl]amino}ethyl)-N-methylcarbamate;
tert-butyl N-(3-{[2-amino-6-(2,3-dimethylphenyl)pyrimidin-4-yl]amino}propyl)¬carbamate;
6-(2,3-dimethylphenyl)-4-N-[3-(5-methyl-1H-pyrazol-3-yl)propyl]pyrimidine-2,4-diamine;
3-{[2-amino-6-(2,3-dimethylphenyl)pyrimidin-4-yl]amino}-1-(morpholin-4-yl)propan-1-one;
4-N-[(4-benzylmorpholin-2-yl)methyl]-6-(2,3-dimethylphenyl)pyrimidine-2,4-diamine;
6-(2,3-dimethylphenyl)-4-N-[(4-methanesulfonylphenyl)methyl]pyrimidine-2,4-diamine;
6-(2,3-dimethylphenyl)-4-N-{[4-(4-methylpiperazin-1-yl)phenyl]methyl}pyrimidine-2,4-diamine;
4-N-[(3S)-1-azabicyclo[222]octan-3-yl]-6-(2,3-dimethylphenyl)pyrimidine-2,4-diamine;
tert-butyl 2-({[2-amino-6-(2,3-dimethylphenyl)pyrimidin-4-yl]amino}methyl)¬pyrrolidine-1-carboxylate;
tert-butyl 4-({[2-amino-6-(2,3-dimethylphenyl)pyrimidin-4-yl]amino}methyl)¬piperidine-1-carboxylate;
1-(3-{[2-amino-6-(2,3-dichlorophenyl)pyrimidin-4-yl]amino}propyl)pyrrolidin-2-one;
1-(3-{[2-amino-6-(3-chloro-2-methylphenyl)pyrimidin-4-yl]amino}propyl)pyrrolidin-2-one;
1-(3-{[2-amino-6-(4-fluoro-2,3-dimethylphenyl)pyrimidin-4-yl]amino}propyl)pyrrolidin-2-one;
1-(3-{[2-amino-6-(4-methoxy-2,3-dimethylphenyl)pyrimidin-4-yl]amino}propyl)pyrrolidin-2-one;
1-(3-{[2-amino-6-(4-methyl-1H-indazol-5-yl)pyrimidin-4-yl]amino}propyl)pyrrolidin-2-one;
1-[3-({2-amino-6-[2-methyl-5-(morpholine-4-sulfonyl)phenyl]pyrimidin-4-yl}amino)propyl]pyrrolidin-2-one;
1-(3-{[2-amino-6-(2,3-dihydro-1-benzofuran-7-yl)pyrimidin-4-yl]amino}propyl)pyrrolidin-2-one;
1-(3-{[2-amino-6-(2,5-dimethylphenyl)pyrimidin-4-yl]amino}propyl)pyrrolidin-2-one;
1-(3-{[2-amino-6-(5-chloro-2-methylphenyl)pyrimidin-4-yl]amino}propyl)pyrrolidin-2-one;
1-[3-({2-amino-6-[2-(trifluoromethyl)phenyl]pyrimidin-4-yl}amino)propyl]pyrrolidin-2-one;
1-(3-{[2-amino-6-(1H-indol-4-yl)pyrimidin-4-yl]amino}propyl)pyrrolidin-2-one;
4-N-{[1-(4-chlorophenyl)cyclopropyl]methyl}-6-(2,3-dimethylphenyl)pyrimidine-2,4-diamine;
4-(2-{[2-amino-6-(2,3-dichlorophenyl)pyrimidin-4-yl]amino}ethyl)benzene-1-sulfonamide;
4-(2-{[2-amino-6-(3-chloro-2-methylphenyl)pyrimidin-4-yl]amino}ethyl)benzene-1-sulfonamide;
4-N-(adamantan-1-yl)-6-(2,3-dichlorophenyl)pyrimidine-2,4-diamine;
6-(2,3-dichlorophenyl)-4-N-[(1R,2R,3R,5S)-2,6,6-trimethylbicyclo[311]heptan-3-yl]pyrimidine-2,4-diamine;
6-(2,3-dichlorophenyl)-4-N-({3-[(4-methylpiperidin-1-yl)methyl]phenyl}methyl)-pyrimidine-2,4-diamine;
4-(2-{[2-amino-6-(2,3-dichlorophenyl)pyrimidin-4-yl]amino}ethyl)phenol;
ethyl 4-{[2-amino-6-(2,3-dichlorophenyl)pyrimidin-4-yl]amino}piperidine-1-carboxylate;

N-(4-{[2-amino-6-(2,3-dichlorophenyl)pyrimidin-4-yl]amino}butyl)acetamide;
6-(2,3-dichlorophenyl)-4-N-{tricyclo[3310³,7]nonan-3-yl}pyrimidine-2,4-diamine;
6-(2,3-dichlorophenyl)-4-N-{[4-(1,2,3-thiadiazol-4-yl)phenyl]methyl}pyrimidine-2,4-diamine;
4-N-[2-(1-benzylpiperidin-4-yl)ethyl]-6-(2,3-dichlorophenyl)pyrimidine-2,4-diamine;
6-[2-[[2-amino-6-(2,3-dichlorophenyl)pyrimidin-4-yl]amino]ethylamino]-2,2-dimethyl-4H-1,4-benzoxazin-3-one;
N-{3-[2-amino-6-(methylamino)pyrimidin-4-yl]phenyl}-3-hydroxypyridine-2-carboxamide;
N-{3-[2-amino-6-(methylamino)pyrimidin-4-yl]phenyl}prop-2-enamide;
(2E)-N-{3-[2-amino-6-(methylamino)pyrimidin-4-yl]phenyl}-3-phenylprop-2-enamide;
N-{3-[2-amino-6-(methylamino)pyrimidin-4-yl]-2-methylphenyl}prop-2-enamide;
(2E)-N-{3-[2-amino-6-(methylamino)pyrimidin-4-yl]phenyl}-4-(dimethylamino)but-2-enamide;
N-{3-[2-amino-6-(methylamino)pyrimidin-4-yl]phenyl}ethene-1-sulfonamide;
N-{3-[2-amino-6-(methylamino)pyrimidin-4-yl]phenyl}prop-2-ynamide;
N-{3-[2-amino-6-(methylamino)pyrimidin-4-yl]phenyl}-2-oxopropanamide;
N-{3-[2-amino-6-(methylamino)pyrimidin-4-yl]phenyl}-2-oxo-2-phenylacetamide;
N-{4-[2-amino-6-(methylamino)pyrimidin-4-yl]phenyl}prop-2-enamide;
N-({4-[2-amino-6-(methylamino)pyrimidin-4-yl]phenyl}methyl)prop-2-enamide;
N-({3-[2-amino-6-(methylamino)pyrimidin-4-yl]phenyl}methyl)prop-2-enamide;
N-{3-[2-amino-6-(methylamino)pyrimidin-4-yl]-4-methylphenyl}prop-2-enamide;
N-{3-[2-amino-6-(methylamino)pyrimidin-4-yl]phenyl}-5-chloro-2-hydroxybenzamide;
N-{3-[2-amino-6-(methylamino)pyrimidin-4-yl]phenyl}-2-hydroxyacetamide;
N-{3-[2-amino-6-(methylamino)pyrimidin-4-yl]phenyl}-2-(4-chlorophenyl)-2-hydroxyacetamide;
N-{3-[2-amino-6-(methylamino)pyrimidin-4-yl]phenyl}-2-hydroxy-2-phenylacetamide;
N-{3-[2-amino-6-(methylamino)pyrimidin-4-yl]phenyl}-4-oxo-4-(pyrrolidin-1-yl)butanamide;
N-{3-[2-amino-6-(methylamino)pyrimidin-4-yl]phenyl}-2-hydroxybenzamide;
1-{4-[2-amino-6-(methylamino)pyrimidin-4-yl]phenyl}-2,2,2-trifluoroethan-1-one;
6-[3-(aminomethyl)phenyl]-4-N-methylpyrimidine-2,4-diamine;
6-[4-(aminomethyl)phenyl]-4-N-methylpyrimidine-2,4-diamine;
4-(2-{[2-amino-6-(2,3-dimethylphenyl)pyrimidin-4-yl]amino}ethyl)benzene-1-sulfonamide;
6-(2,3-dimethylphenyl)-4-N-[2-(4-methanesulfonylphenyl)ethyl]pyrimidine-2,4-diamine;
6-(2,3-dimethylphenyl)-4-N-[2-(5-methyl-1H-1,2,4-triazol-3-yl)ethyl]pyrimidine-2,4-diamine;
4-(2-{[2-amino-6-(2,3-dimethylphenyl)pyrimidin-4-yl]amino}ethyl)benzonitrile;
6-(2,3-dimethylphenyl)-4-N-[2-(pyridin-4-yl)ethyl]pyrimidine-2,4-diamine;
4-(2-{[2-amino-6-(2,3-dimethylphenyl)pyrimidin-4-yl]amino}ethoxy)benzonitrile;
4-({[2-amino-6-(2,3-dimethylphenyl)pyrimidin-4-yl]amino}methyl)benzene-1-sulfonamide;
1-(2-{[2-amino-6-(2,3-dimethylphenyl)pyrimidin-4-yl]amino}ethyl)-1,2-dihydropyridin-2-one;
3-({[2-amino-6-(2,3-dimethylphenyl)pyrimidin-4-yl]amino}methyl)-1,2-dihydropyridin-2-one;
6-(3-{[2-amino-6-(2,3-dimethylphenyl)pyrimidin-4-yl]amino}propyl)-5H,6H,7H-pyrrolo[3,4-b]pyridin-5-one;
6-({[2-amino-6-(2,3-dimethylphenyl)pyrimidin-4-yl]amino}methyl)pyridin-3-ol;
4-N-[2-(3-chlorophenyl)ethyl]-6-(2,3-dimethylphenyl)pyrimidine-2,4-diamine;
6-(2,3-dimethylphenyl)-4-N-[3-(1H-imidazol-1-yl)propyl]pyrimidine-2,4-diamine;
4-N-[2-(4-chlorophenyl)propyl]-6-(2,3-dimethylphenyl)pyrimidine-2,4-diamine;
6-(2,3-dimethylphenyl)-4-N-[2-(4-fluorophenyl)ethyl]pyrimidine-2,4-diamine;
6-(2,3-dimethylphenyl)-4-N-[2-(4-methoxyphenyl)-2-(pyrrolidin-1-yl)ethyl]pyrimidine-2,4-diamine;
4-N-{[4-(dimethylamino)phenyl]methyl}-6-(2,3-dimethylphenyl)pyrimidine-2,4-diamine;
4-N-[2-(benzenesulfonyl)ethyl]-6-(2,3-dimethylphenyl)pyrimidine-2,4-diamine;
6-(2,3-dimethylphenyl)-4-N-{[1-(4-fluorophenyl)-1H-pyrazol-4-yl]methyl}pyrimidine-2,4-diamine;
6-(2,3-dimethylphenyl)-4-N-{2-[5-(pyridin-4-yl)-1H-1,2,4-triazol-3-yl]ethyl}pyrimidine-2,4-diamine;
6-(2,3-dimethylphenyl)-4-N-{[1-(pyrimidin-2-yl)piperidin-3-yl]methyl}pyrimidine-2,4-diamine;
6-(2,3-dimethylphenyl)-4-N-[2-(6-methoxy-1H-1,3-benzodiazol-2-yl)ethyl]pyrimidine-2,4-diamine;
6-(2,3-dimethylphenyl)-4-N-[2-(4-methyl-1,3-thiazol-5-yl)ethyl]pyrimidine-2,4-diamine;
4-N-[(3-cyclopropyl-1H-pyrazol-5-yl)methyl]-6-(2,3-dimethylphenyl)pyrimidine-2,4-diamine;
4-N-[3-(3,5-dimethyl-1H-pyrazol-1-yl)propyl]-6-(2,3-dimethylphenyl)pyrimidine-2,4-diamine;
6-(2,3-dimethylphenyl)-4-N-{[1-(pyridin-2-yl)piperidin-3-yl]methyl}pyrimidine-2,4-diamine;
6-(2,3-dimethylphenyl)-4-N-[(2-phenyl-2H-1,2,3-triazol-4-yl)methyl]pyrimidine-2,4-diamine;
N-(3-{[2-amino-6-(2,3-dimethylphenyl)pyrimidin-4-yl]amino}propyl)-4-chlorobenzene-1-sulfonamide;
3-(3-{[2-amino-6-(2,3-dimethylphenyl)pyrimidin-4-yl]amino}propyl)-1-(4-chlorophenyl)urea;
N-(3-{[2-amino-6-(2,3-dimethylphenyl)pyrimidin-4-yl]amino}propyl)-3,5-dimethyl-1,2-oxazole-4-sulfonamide;
N-(3-{[2-amino-6-(2,3-dimethylphenyl)pyrimidin-4-yl]amino}propyl)-2-(dimethylamino)acetamide;
3-(3-{[2-amino-6-(2,3-dimethylphenyl)pyrimidin-4-yl]amino}propyl)-1-(2,6-dichloropyridin-4-yl)urea;
3-(3-{[2-amino-6-(2,3-dimethylphenyl)pyrimidin-4-yl]amino}propyl)-1-(3,4-difluorophenyl)urea;
N-[3-(3-{[2-amino-6-(2,3-dimethylphenyl)pyrimidin-4-yl]amino}propoxy)phenyl]acetamide;
6-(2,3-dimethylphenyl)-4-N-[(2-methyl-1H-indol-5-yl)methyl]pyrimidine-2,4-diamine;
4-N-[2-(3,5-dimethyl-1H-pyrazol-1-yl)ethyl]-6-(2,3-dimethylphenyl)pyrimidine-2,4-diamine;
6-(2,3-dimethylphenyl)-4-N-[4-(pyrrolidin-1-yl)butyl]pyrimidine-2,4-diamine;
N-(3-{[2-amino-6-(2,3-dimethylphenyl)pyrimidin-4-yl]amino}propyl)-3-bromobenzamide;

N-(3-{[2-amino-6-(2,3-dimethylphenyl)pyrimidin-4-yl]amino}propyl)benzamide;
1-(3-{[2-amino-6-(2,3-dimethylphenyl)pyrimidin-4-yl]amino}propyl)-3-(propan-2-yl)urea;
tert-butyl N-(4-{[2-amino-6-(2,3-dimethylphenyl)pyrimidin-4-yl]amino}butyl)-carbamate;
tert-butyl N-(5-{[2-amino-6-(2,3-dimethylphenyl)pyrimidin-4-yl]amino}pentyl)-carbamate;
tert-butyl N-(2-{[2-amino-6-(2,3-dimethylphenyl)pyrimidin-4-yl]amino}cyclohexyl)-carbamate;
tert-butyl N-(1-{[2-amino-6-(2,3-dimethylphenyl)pyrimidin-4-yl]amino}-2-methylpropan-2-yl)carbamate;
N-(3-{[2-amino-6-(2,3-dimethylphenyl)pyrimidin-4-yl]amino}propyl)-3-cyanobenzene-1-sulfonamide;
N-(3-{[2-amino-6-(2,3-dimethylphenyl)pyrimidin-4-yl]amino}propyl)-4-methanesulfonylbenzene-1-sulfonamide;
N-(3-{[2-amino-6-(2,3-dimethylphenyl)pyrimidin-4-yl]amino}propyl)benzenesulfonamide;
N-(3-{[2-amino-6-(2,3-dimethylphenyl)pyrimidin-4-yl]amino}-2,2-dimethylpropyl)-3-fluorobenzene-1-sulfonamide;
N-(3-{[2-amino-6-(2,3-dimethylphenyl)pyrimidin-4-yl]amino}-2,2-dimethylpropyl)-4-(morpholine-4-sulfonyl)benzene-1-sulfonamide;
6-(2,3-dimethylphenyl)-4-N-(prop-2-en-1-yl)pyrimidine-2,4-diamine;
1-(3-{[2-amino-6-(2,3-dimethylphenyl)pyrimidin-4-yl]amino}propyl)imidazolidin-2-one;
N-(3-{[2-amino-6-(2,3-dimethylphenyl)pyrimidin-4-yl]amino}propyl)-3-fluorobenzene-1-sulfonamide;
N-{4-[(3-{[2-amino-6-(2,3-dimethylphenyl)pyrimidin-4-yl]amino}propyl)sulfamoyl]-phenyl}acetamide;
N-(3-{[2-amino-6-(2,3-dimethylphenyl)pyrimidin-4-yl]amino}propyl)methanesulfonamide;
N-(2-{[2-amino-6-(2,3-dimethylphenyl)pyrimidin-4-yl]amino}ethyl)-3-fluorobenzene-1-sulfonamide;
N-(2-{[2-amino-6-(2,3-dimethylphenyl)pyrimidin-4-yl]amino}ethyl)-4-methoxybenzene-1-sulfonamide;
6-(2,3-dimethylphenyl)-4-N-(prop-2-yn-1-yl)pyrimidine-2,4-diamine;
2-{[2-amino-6-(2,3-dimethylphenyl)pyrimidin-4-yl]amino}acetamide;
N-(3-{[2-amino-6-(2,3-dimethylphenyl)pyrimidin-4-yl]amino}propyl)-4,5-dichlorothiophene-2-sulfonamide;
N-(3-{[2-amino-6-(2,3-dimethylphenyl)pyrimidin-4-yl]amino}propyl)-5-chloro-1,3-dimethyl-1H-pyrazole-4-sulfonamide;
2-{[2-amino-6-(2,3-dimethylphenyl)pyrimidin-4-yl]amino}acetonitrile;
N-(3-{[2-amino-6-(2,3-dimethylphenyl)pyrimidin-4-yl]amino}propyl)-1,2-dimethyl-1H-imidazole-4-sulfonamide;
N-(2-{[2-amino-6-(2,3-dimethylphenyl)pyrimidin-4-yl]amino}ethyl)-5-chloro-1,3-dimethyl-1H-pyrazole-4-sulfonamide;
4-N-{2-[(1,3-benzoxazol-2-yl)amino]ethyl}-6-(2,3-dimethylphenyl)pyrimidine-2,4-diamine;
6-(2,3-dimethylphenyl)-4-N-(4-phenylbutan-2-yl)pyrimidine-2,4-diamine;
4-N-(2,2-dimethyloxan-4-yl)-6-(2,3-dimethylphenyl)pyrimidine-2,4-diamine;
ethyl 2-{[2-amino-6-(2,3-dimethylphenyl)pyrimidin-4-yl]amino}acetate;
6-[(2-{[2-amino-6-(2,3-dimethylphenyl)pyrimidin-4-yl]amino}ethyl)amino]pyridine-3-carbonitrile;
4-N-{2-[(3-bromo-1,2,4-thiadiazol-5-yl)amino]ethyl}-6-(2,3-dimethylphenyl)pyrimidine-2,4-diamine;
6-(2,3-dimethylphenyl)-4-N-[(5-methyl-4H-1,2,4-triazol-3-yl)methyl]pyrimidine-2,4-diamine;
6-(2,3-dimethylphenyl)-4-N-{2-[5-(4-fluorophenyl)-1,3,4-oxadiazol-2-yl]ethyl}pyrimidine-2,4-diamine;
N-(2-{[2-amino-6-(2,3-dimethylphenyl)pyrimidin-4-yl]amino}ethyl)-4-methanesulfonylbenzene-1-sulfonamide;
N-(3-{[2-amino-6-(2,3-dimethylphenyl)pyrimidin-4-yl]amino}propyl)-3-methanesulfonylbenzene-1-sulfonamide;
N-(3-{[2-amino-6-(2,3-dimethylphenyl)pyrimidin-4-yl]amino}propyl)-2-methanesulfonylbenzene-1-sulfonamide;
6-(2,3-dimethylphenyl)-4-N-[2-(4-methanesulfonylphenyl)ethyl]pyrimidine-2,4-diamine;
6-(2,3-dichlorophenyl)-4-N-[2-(4-methyl-1,3-thiazol-5-yl)ethyl]pyrimidine-2,4-diamine;
6-(3-chloro-2-methylphenyl)-4-N-[2-(4-methyl-1,3-thiazol-5-yl)ethyl]pyrimidine-2,4-diamine;
4-N-{[2-(difluoromethyl)pyridin-4-yl]methyl}-6(2,3-dimethylphenyl)pyrimidine-2,4-diamine;
6-(2,3-dimethylphenyl)-4-N-[2-(1H-imidazol-4-yl)ethyl]pyrimidine-2,4-diamine;
4-N-[3-(1H-1,3-benzodiazol-2-yl)propyl]-6-(2,3-dimethylphenyl)pyrimidine-2,4-diamine;
6-(2,3-dimethylphenyl)-4-N-[(1-methyl-1H-1,3-benzodiazol-2-yl)methyl]pyrimidine-2,4-diamine;
6-(2,3-dimethylphenyl)-4-N-[(2-phenyl-1,3-thiazol-5-yl)methyl]pyrimidine-2,4-diamine;
6-(3-chloro-2-methylphenyl)-4-N-[2-(5-methyl-1H-1,2,4-triazol-3-yl)ethyl]pyrimidine-2,4-diamine;
6-(2,3-dichlorophenyl)-4-N-[2-(5-methyl-1H-1,2,4-triazol-3-yl)ethyl]pyrimidine-2,4-diamine;
4-(2-{[2-amino-6-(3-chloro-2-methylphenyl)pyrimidin-4-yl]amino}ethyl)-N,N-dimethylbenzene-1-sulfonamide;
4-(2-{[2-amino-6-(2,3-dichlorophenyl)pyrimidin-4-yl]amino}ethyl)-N,N-dimethylbenzene-1-sulfonamide;
4-(2-{[2-amino-6-(2,3-dimethylphenyl)pyrimidin-4-yl]amino}ethyl)-N,N-dimethylbenzene-1-sulfonamide;
4-N-{1-[(4-chlorophenyl)methyl]cyclopropyl}-6-(2,3-dimethylphenyl)pyrimidine-2,4-diamine;
4-N-cyclopropyl-6-(2,3,4-trichlorophenyl)pyrimidine-2,4-diamine;
4-N-[2-(4-chlorophenyl)ethyl]-6-(2,3,4-trichlorophenyl)pyrimidine-2,4-diamine;
6-(2,3-dimethylphenyl)-4-N-($^2$H3)methylpyrimidine-2,4-diamine;
6-(2,3-dichlorophenyl)-4-N-($^2$H$_3$)methylpyrimidine-2,4-diamine;
6-(2-chloro-3-methylphenyl)-4-N-($^2$H$_3$)methylpyrimidine-2,4-diamine;
4-N-[2-(4-chlorophenyl)ethyl]-6-(1H-pyrrol-2-yl)pyrimidine-2,4-diamine;
N-(4-{[2-amino-6-(2,3-dimethylphenyl)pyrimidin-4-yl]amino}butyl)-4-methanesulfonylbenzene-1-sulfonamide;
4-(2-{[2-amino-6-(4-fluoro-2,3-dimethylphenyl)pyrimidin-4-yl]amino}ethyl)benzene-1-sulfonamide;
4-(2-{[2-amino-6-(3-cyano-2-methylphenyl)pyrimidin-4-yl]amino}ethyl)benzene-1-sulfonamide;
4-(2-{[2-amino-6-(5-chloro-2-methylphenyl)pyrimidin-4-yl]amino}ethyl)benzene-1-sulfonamide;
4-(2-{[2-amino-6-(3,4-dichloro-2-methylphenyl)pyrimidin-4-yl]amino}ethyl)benzene-1-sulfonamide;

6-(3-chloro-2-methylphenyl)-4-N-(prop-2-yn-1-yl)pyrimidine-2,4-diamine;
6-(4-fluoro-2,3-dimethylphenyl)-4-N-[2-(4-methanesulfonylphenyl)ethyl]pyrimidine-2,4-diamine;
6-(3,4-dichloro-2-methylphenyl)-4-N-[2-(4-methanesulfonylphenyl)ethyl]pyrimidine-2,4-diamine;
4-(2-{[2-amino-6-(4-chloro-2-methylphenyl)pyrimidin-4-yl]amino}ethyl)benzene-1-sulfonamide;
4-(2-{[2-amino-6-(2-chloro-4-fluorophenyl)pyrimidin-4-yl]amino}ethyl)benzene-1-sulfonamide;
4-(2-{[2-amino-6-(2,3,4-trifluorophenyl)pyrimidin-4-yl]amino}ethyl)benzene-1-sulfonamide;
4-(2-{[2-amino-6-(4-fluoro-3-methylphenyl)pyrimidin-4-yl]amino}ethyl)benzene-1-sulfonamide;
4-N-cyclopropyl-6-(4-fluoro-2,3-dimethylphenyl)pyrimidine-2,4-diamine;
3-[2-amino-6-(cyclopropylamino)pyrimidin-4-yl]-2-methylbenzonitrile;
6-(2,3-dichlorophenyl)-4-N-(prop-2-yn-1-yl)pyrimidine-2,4-diamine;
4-(2-{[2-amino-6-(4-fluoro-2,5-dimethylphenyl)pyrimidin-4-yl]amino}ethyl)benzene-1-sulfonamide;
4-N-[2-(3,5-dimethyl-1H-pyrazol-4-yl)ethyl]-6-(2,3-dimethylphenyl)pyrimidine-2,4-diamine;
4-N-{2-[(6-chloropyridazin-3-yl)amino]ethyl}-6-(2,3-dimethylphenyl)pyrimidine-2,4-diamine;
2-[(2-{[2-amino-6-(2,3-dimethylphenyl)pyrimidin-4-yl]amino}ethyl)amino]pyridine-4-carbonitrile;
6-[(2-{[2-amino-6-(2,3-dimethylphenyl)pyrimidin-4-yl]amino}ethyl)amino]pyridine-3-sulfonamide;
1-N-(3-{[2-amino-6-(2,3-dimethylphenyl)pyrimidin-4-yl]amino}propyl)benzene-1,4-disulfonamide;
6-(2,3-dichlorophenyl)-4-N-[2-(4-methanesulfonylphenyl)ethyl]pyrimidine-2,4-diamine;
6-(2,3-dimethylphenyl)-4-N-[1-(1H-pyrazol-1-yl)propan-2-yl]pyrimidine-2,4-diamine;
6-(2,3-dimethylphenyl)-4-N-{2-[(3-methoxyphenyl)amino]ethyl}pyrimidine-2,4-diamine;
6-(2,3-dimethylphenyl)-4-N-{2-[(3-fluoro-4-methylphenyl)amino]ethyl}pyrimidine-2,4-diamine;
4-N-{2-[(3,4-dichlorophenyl)amino]ethyl}-6-(2,3-dimethylphenyl)pyrimidine-2,4-diamine;
4-N-{2-[(5-chloropyridin-2-yl)amino]ethyl}-6-(2,3-dimethylphenyl)pyrimidine-2,4-diamine;
4-N-{2-[(5-bromopyridin-2-yl)amino]ethyl}-6-(2,3-dimethylphenyl)pyrimidine-2,4-diamine;
4-[(2-{[2-amino-6-(2,3-dimethylphenyl)pyrimidin-4-yl]amino}ethyl)amino]benzene-1-sulfonamide;
4-N-[2-(4-chlorophenyl)ethyl]-6-(dimethyl-1,2-oxazol-4-yl)pyrimidine-2,4-diamine;
6-(2,3-dimethylphenyl)-4-N-{2-[(pyridin-3-yl)amino]ethyl}pyrimidine-2,4-diamine;
6-(3-chloro-2-methylphenyl)-4-N-[2-(4-methanesulfonylphenyl)ethyl]pyrimidine-2,4-diamine;
[4-[2-[[2-amino-6-(3-chloro-2-methyl-phenyl)pyrimidin-4-yl]amino]ethyl]phenyl]-morpholino-methanone;
6-[(3-{[2-amino-6-(2,3-dimethylphenyl)pyrimidin-4-yl]amino}propyl)amino]pyridine-3-sulfonamide;
6-[(2-{[2-amino-6-(2,3-dimethylphenyl)pyrimidin-4-yl]amino}ethyl)amino]-N-methylpyridine-3-sulfonamide;
6-(2,3-dichlorophenyl)-4-N-{2-[(pyridin-4-yl)amino]ethyl}pyrimidine-2,4-diamine;
4-(2-{[2-amino-6-(5-methylfuran-2-yl)pyrimidin-4-yl]amino}ethyl)benzene-1-sulfonamide;
6-(3-chloro-2-methylphenyl)-4-N-[2-(4-chlorophenyl)ethyl]pyrimidine-2,4-diamine;
6-[(2-{[2-amino-6-(2,3-dimethylphenyl)pyrimidin-4-yl]amino}ethyl)amino]pyridine-3-carboxamide;
4-N-methyl-6-(thiophen-3-yl)pyrimidine-2,4-diamine;
4-N-methyl-6-(4-methylthiophen-2-yl)pyrimidine-2,4-diamine;
4-N-methyl-6-(1-methyl-1H-pyrazol-5-yl)pyrimidine-2,4-diamine;
4-N-{2-[(5-bromopyridin-2-yl)amino]ethyl}-6-(2,3-dichlorophenyl)pyrimidine-2,4-diamine;
4-N-methyl-6-(3-methyl-1H-pyrazol-4-yl)pyrimidine-2,4-diamine;
4-N-methyl-6-(1H-pyrrol-3-yl)pyrimidine-2,4-diamine;
N-(4-{[2-amino-6-(2,3-dichlorophenyl)pyrimidin-4-yl]amino}butyl)-2-methoxyacetamide;
N-(4-{[2-amino-6-(2,3-dichlorophenyl)pyrimidin-4-yl]amino}butyl)-2,2,2-trifluoroacetamide;
N-(4-{[2-amino-6-(2,3-dichlorophenyl)pyrimidin-4-yl]amino}butyl)-4-methanesulfonylbenzamide;
N-(4-{[2-amino-6-(2,3-dichlorophenyl)pyrimidin-4-yl]amino}butyl)-1,2-oxazole-5-carboxamide;
N-(4-{[2-amino-6-(2,3-dichlorophenyl)pyrimidin-4-yl]amino}butyl)-3,4-dichlorobenzamide;
N-(4-{[2-amino-6-(2,3-dichlorophenyl)pyrimidin-4-yl]amino}butyl)-2,2-dimethylpropanamide;
N-(4-{[2-amino-6-(2,3-dichlorophenyl)pyrimidin-4-yl]amino}butyl)-4-methanesulfonylbenzene-1-sulfonamide;
3-(4-{[2-amino-6-(2,3-dichlorophenyl)pyrimidin-4-yl]amino}butyl)-1-[4-(methylsulfanyl)phenyl]urea;
3-(4-{[2-amino-6-(2,3-dichlorophenyl)pyrimidin-4-yl]amino}butyl)-1-(4-methanesulfinylphenyl)urea;
4-N-methyl-6-(2-methylfuran-3-yl)pyrimidine-2,4-diamine;
4-N-methyl-6-[5-(pyrrolidin-1-ylmethyl)thiophen-2-yl]pyrimidine-2,4-diamine;
6-(4-fluoro-2,5-dimethylphenyl)-4-N-{2-[(5-nitropyridin-2-yl)amino]ethyl}pyrimidine-2,4-diamine;
[2-(2-amino-6-{[2-(4-chlorophenyl)ethyl]amino}pyrimidin-4-yl)phenyl]methanol;
6-(3-chloro-2-methylphenyl)-4-N-cyclopropylpyrimidine-2,4-diamine;
6-(3-chloro-2-methylphenyl)-4-N-(2-fluoroethyl)pyrimidine-2,4-diamine;
6-(2,3-dimethylphenyl)-4-N-(2-fluoroethyl)pyrimidine-2,4-diamine;
4-(2-{[2-amino-6-(3-chloro-2-methylphenyl)pyrimidin-4-yl]amino}ethyl)benzoic acid;
4-(2-{[6-(2-acetylthiophen-3-yl)-2-aminopyrimidin-4-yl]amino}ethyl)benzene-1-sulfonamide;
3-{4-[2-amino-6-(methylamino)pyrimidin-4-yl]-1H-pyrazol-1-yl}propanamide;
N-{6-[(2-{[2-amino-6-(4-fluoro-2,5-dimethylphenyl)pyrimidin-4-yl]amino}ethyl)amino]pyridin-3-yl}acetamide;
N-{6-[(2-{[2-amino-6-(4-fluoro-2,5-dimethylphenyl)pyrimidin-4-yl]amino}ethyl)amino]pyridin-3-yl}methanesulfonamide;
6-(2,3-dimethylphenyl)-4-N-{2-[(6-methoxy-4-methylpyridin-3-yl)amino]ethyl}pyrimidine-2,4-diamine;
6-(2,3-dimethylphenyl)-4-N-{2-[(6-methanesulfonylpyridin-3-yl)amino]ethyl}pyrimidine-2,4-diamine;
5-[(2-{[2-amino-6-(2,3-dimethylphenyl)pyrimidin-4-yl]amino}ethyl)amino]pyridine-3-sulfonamide;
[4-[2-[[2-amino-6-(3,5-dichloro-2-methyl-phenyl)pyrimidin-4-yl]amino]ethyl]phenyl]-morpholino-methanone;

4-[(1R,2S)-2-{[2-amino-6-(3-chloro-2-methylphenyl)pyrimidin-4-yl]amino}cyclopropyl]benzene-1-sulfonamide;

2-[3-(2-amino-6-{[2-(4-chlorophenyl)ethyl]amino}pyrimidin-4-yl)phenoxy]acetamide;

2-[(2-{[2-amino-6-(2,3-dimethylphenyl)pyrimidin-4-yl]amino}ethyl)amino]pyrimidine-4-carboxamide;

6-(2,3-dimethylphenyl)-4-N-{2-[(pyrazin-2-yl)amino]ethyl}pyrimidine-2,4-diamine;

4-N-{2-[(6-chloropyrimidin-4-yl)amino]ethyl}-6-(2,3-dimethylphenyl)pyrimidine-2,4-diamine;

6-(3-chloro-2-methyl-phenyl)-N4-[3-(3-methylsulfonylanilino)propyl]pyrimidine-2,4-diamine;

4-[2-[[2-amino-6-(3-chloro-2-methyl-phenyl)pyrimidin-4-yl]amino]ethyl]benzenecarbothioamide;

4-(2-amino-6-{[2-(4-methanesulfonylphenyl)ethyl]amino}pyrimidin-4-yl)-N-tert-butylthiophene-2-sulfonamide;

tert-butyl N-{[5-(2-amino-6-{[2-(4-methanesulfonylphenyl)ethyl]amino}pyrimidin-4-yl)thiophen-2-yl]methyl}carbamate;

N-[4-(2-{[2-amino-6-(2,3-dimethylphenyl)pyrimidin-4-yl]amino}ethyl)phenyl]acetamide;

N-[4-(2-{[2-amino-6-(2,3-dimethylphenyl)pyrimidin-4-yl]amino}ethyl)phenyl]methanesulfonamide;

{2-[2-amino-6-(methylamino)pyrimidin-4-yl]phenyl}methanol;

4-[2-({2-amino-6-[2-(hydroxymethyl)phenyl]pyrimidin-4-yl}amino)ethyl]benzene-1-sulfonamide;

4-[(2-{[2-amino-6-(2,3-dimethylphenyl)pyrimidin-4-yl]amino}ethyl)amino]-N-methylbenzene-1-sulfonamide;

N-{4-[(2-{[2-amino-6-(2,3-dimethylphenyl)pyrimidin-4-yl]amino}ethyl)amino]-2-methylphenyl}acetamide;

6-[(2-{[2-amino-6-(2,3-dimethylphenyl)pyrimidin-4-yl]amino}ethyl)amino]-3,4-dihydro-2H-1,4-benzoxazin-3-one;

2-[(2-{[2-amino-6-(2,3-dimethylphenyl)pyrimidin-4-yl]amino}ethyl)amino]benzamide;

2-[(2-{[2-amino-6-(2,3-dimethylphenyl)pyrimidin-4-yl]amino}ethyl)amino]pyridine-4-carboxamide;

6-(2-{[2-amino-6-(2,3-dimethylphenyl)pyrimidin-4-yl]amino}ethoxy)pyridine-3-carboxamide;

N-[3-(2-amino-6-{[2-(4-methanesulfonylphenyl)ethyl]amino}pyrimidin-4-yl)-2-methylphenyl]-4-chloro-2-hydroxybenzamide;

3-(2-{[2-amino-6-(2,3-dimethylphenyl)pyrimidin-4-yl]amino}ethyl)-1H-indol-5-ol;

4-N-{2-[5-(benzyloxy)-1H-indol-3-yl]ethyl}-6-(2,3-dimethylphenyl)pyrimidine-2,4-diamine;

4-N-[2-(5-bromo-1H-indol-3-yl)ethyl]-6-(2,3-dimethylphenyl)pyrimidine-2,4-diamine;

6-(2,3-dimethylphenyl)-4-N-[2-(5-methoxy-1H-indol-3-yl)ethyl]pyrimidine-2,4-diamine;

6-(2,3-dimethylphenyl)-4-N-[2-(7-methyl-1H-indol-3-yl)ethyl]pyrimidine-2,4-diamine;

4-N-{2-[7-(benzyloxy)-1H-indol-3-yl]ethyl}-6-(2,3-dimethylphenyl)pyrimidine-2,4-diamine;

6-(2,3-dimethylphenyl)-4-N-[2-(6-methoxy-1H-indol-3-yl)ethyl]pyrimidine-2,4-diamine;

6-(2,3-dichlorophenyl)-4-N-(2-methylcyclopropyl)pyrimidine-2,4-diamine;

4-(2-{[2-amino-6-(3-hydroxyphenyl)pyrimidin-4-yl]amino}ethyl)benzene-1-sulfonamide;

ethyl 6-[(2-{[2-amino-6-(2,3-dimethylphenyl)pyrimidin-4-yl]amino}ethyl)amino]pyridine-3-carboxylate;

4-[(2-{[2-amino-6-(2,3-dimethylphenyl)pyrimidin-4-yl]amino}ethyl)amino]-2-(trifluoromethyl)benzene-1-sulfonamide;

4-[(2-{[2-amino-6-(2,3-dimethylphenyl)pyrimidin-4-yl]amino}ethyl)amino]benzamide;

ethyl N-[4-(2-{[2-amino-6-(2,3-dimethylphenyl)pyrimidin-4-yl]amino}ethyl)phenyl]carbamate;

5-[(2-{[2-amino-6-(2,3-dimethylphenyl)pyrimidin-4-yl]amino}ethyl)amino]-2-methoxybenzene-1-sulfonamide;

3-(2-amino-6-{[2-(4-sulfamoylphenyl)ethyl]amino}pyrimidin-4-yl)phenyl methanesulfonate;

3-(2-amino-6-{[2-(4-sulfamoylphenyl)ethyl]amino}pyrimidin-4-yl)phenyl trifluoromethanesulfonate;

4-(2-{[2-amino-6-(2,3-dimethylphenyl)pyrimidin-4-yl]amino}ethyl)benzoic acid;

6-[(2-{[2-amino-6-(3-chloro-2-methylphenyl)pyrimidin-4-yl]amino}ethyl)amino]-3,4-dihydro-2H-1,4-benzoxazin-3-one;

6-(2,3-dimethylphenyl)-4-N-{2-[(2-methyl-1,3-benzothiazol-6-yl)amino]ethyl}pyrimidine-2,4-diamine;

6-[(2-{[2-amino-6-(3-chlorophenyl)pyrimidin-4-yl]amino}ethyl)amino]-3,4-dihydro-2H-1,4-benzoxazin-3-one;

6-[(2-{[2-amino-6-(2,3-dichlorophenyl)pyrimidin-4-yl]amino}ethyl)amino]-3,4-dihydro-2H-1,4-benzoxazin-3-one;

6-(2,3-dichlorophenyl)-4-N-{2-[(2-methyl-1,3-benzothiazol-6-yl)amino]ethyl}pyrimidine-2,4-diamine;

6-(2,3-dimethylphenyl)-4-N-(2-{[4-(1H-1,2,3,4-tetrazol-5-yl)phenyl]amino}ethyl)pyrimidine-2,4-diamine;

6-(2,3-dimethylphenyl)-4-N-{2-[(3-methanesulfonylphenyl)amino]ethyl}pyrimidine-2,4-diamine;

5-[(2-{[2-amino-6-(2,3-dimethylphenyl)pyrimidin-4-yl]amino}ethyl)amino]-2-methoxybenzene-1-sulfonic acid;

4-[(2-{[2-amino-6-(2,3-dimethylphenyl)pyrimidin-4-yl]amino}ethyl)amino]-3-fluorobenzene-1-sulfonamide;

4-(2-{[2-amino-6-(3-chloro-2-methylphenyl)pyrimidin-4-yl]amino}ethyl)benzamide;

4-(2-{[2-amino-6-(2,3-dimethylphenyl)pyrimidin-4-yl]amino}ethyl)benzamide;

4-N-{2-[(2-amino-9H-purin-6-yl)amino]ethyl}-6-(2,3-dimethylphenyl)pyrimidine-2,4-diamine;

N-[3-(2-{[2-amino-6-(3-chloro-2-methylphenyl)pyrimidin-4-yl]amino}ethyl)phenyl]acetamide;

ethyl N-[3-(2-{[2-amino-6-(3-chloro-2-methylphenyl)pyrimidin-4-yl]amino}ethyl)phenyl]carbamate;

6-(2-{[2-amino-6-(3-chloro-2-methylphenyl)pyrimidin-4-yl]amino}ethyl)-3,4-dihydro-2H-1,4-benzoxazin-3-one;

4-N-(2-{[2-amino-6-(2,3-dimethylphenyl)pyrimidin-4-yl]amino}ethyl)-6-(2,3-dimethylphenyl)pyrimidine-2,4-diamine;

methyl 5-[(2-{[2-amino-6-(2,3-dimethylphenyl)pyrimidin-4-yl]amino}ethyl)amino]pyrazine-2-carboxylate;

methyl 2-[(2-{[2-amino-6-(2,3-dimethylphenyl)pyrimidin-4-yl]amino}ethyl)amino]-6-methylpyrimidine-4-carboxylate;

4-N-(2-{[2-amino-6-(2,3-dimethylphenyl)pyrimidin-4-yl]amino}ethyl)pyrimidine-2,4-diamine;

6-(2,3-dimethylphenyl)-4-N-{2-[(9H-purin-6-yl)amino]ethyl}pyrimidine-2,4-diamine;

1-[4-[2-[[2-amino-6-(3-chloro-2-methyl-phenyl)pyrimidin-4-yl]amino]ethyl]phenyl]-3-ethyl-urea;

6-(3-chloro-2-methylphenyl)-4-N-[2-(3-methanesulfonylphenyl)ethyl]pyrimidine-2,4-diamine;
5-N-(2-{[2-amino-6-(2,3-dimethylphenyl)pyrimidin-4-yl]amino}ethyl)pyridine-2,5-diamine;
1-N-(2-{[2-amino-6-(2,3-dimethylphenyl)pyrimidin-4-yl]amino}ethyl)-2-fluorobenzene-1,4-diamine;
1-[4-[2-[[2-amino-6-(3-chloro-2-methyl-phenyl)pyrimidin-4-yl]amino]ethyl]phenyl]-3-tert-butyl-urea;
1-allyl-3-[4-[2-[[2-amino-6-(3-chloro-2-methyl-phenyl)pyrimidin-4-yl]amino]ethyl]phenyl]urea;
ethyl N-[[4-[2-[[2-amino-6-(3-chloro-2-methyl-phenyl)pyrimidin-4-yl]amino]ethyl]phenyl]carbamoyl]carbamate;
1-[4-[2-[[2-amino-6-(3-chloro-2-methyl-phenyl)pyrimidin-4-yl]amino]ethyl]phenyl]-3-sec-butyl-urea;
1-[4-[2-[[2-amino-6-(3-chloro-2-methyl-phenyl)pyrimidin-4-yl]amino]ethyl]phenyl]-3-ethyl-thiourea;
N-[4-[2-[[2-amino-6-(3-chloro-2-methyl-phenyl)pyrimidin-4-yl]amino]ethyl]phenyl]morpholine-4-carboxamide;
isopropyl N-[4-[2-[[2-amino-6-(3-chloro-2-methyl-phenyl)pyrimidin-4-yl]amino]ethyl]phenyl]carbamate;
isobutyl N-[4-[2-[[2-amino-6-(3-chloro-2-methyl-phenyl)pyrimidin-4-yl]amino]ethyl]phenyl]carbamate;
2,2-dimethylpropyl N-[4-[2-[[2-amino-6-(3-chloro-2-methyl-phenyl)pyrimidin-4-yl]amino]ethyl]phenyl]carbamate;
2-methoxyethyl N-[4-[2-[[2-amino-6-(3-chloro-2-methyl-phenyl)pyrimidin-4-yl]amino]ethyl]phenyl]carbamate;
6-[2-[[2-amino-6-(3-chlorophenyl)pyrimidin-4-yl]amino]ethylamino]-2,2-dimethyl-4H-1,4-benzoxazin-3-one;
6-(3-chloro-2-methylphenyl)-4-N-(2-methylcyclopropyl)pyrimidine-2,4-diamine;
3-(2-{[2-amino-6-(3-chloro-2-methylphenyl)pyrimidin-4-yl]amino}ethyl)benzene-1-sulfonamide;
3-(2-{[2-amino-6-(2,3-dichlorophenyl)pyrimidin-4-yl]amino}ethyl)benzene-1-sulfonamide;
but-2-ynyl N-[4-[2-[[2-amino-6-(3-chloro-2-methyl-phenyl)pyrimidin-4-yl]amino]ethyl]phenyl]carbamate;
[4-[2-[[2-amino-6-(3-chloro-2-methyl-phenyl)pyrimidin-4-yl]amino]ethyl]phenyl]cyanamide;
6-(2-{[2-amino-6-(3-chloro-2-methylphenyl)pyrimidin-4-yl]amino}ethoxy)pyridine-3-carboxamide;
6-[(2-{[2-amino-6-(3-chloro-2-methylphenyl)pyrimidin-4-yl]amino}ethyl)amino]-2,2-dimethyl-3,4-dihydro-2H-1,4-benzoxazin-3-one;
4-[2-[[2-amino-6-(3-chloro-2-methyl-phenyl)pyrimidin-4-yl]amino]ethyl]benzamidine;
4-N-(azetidin-3-yl)-6-(2,3-dimethylphenyl)pyrimidine-2,4-diamine;
tert-butyl 3-{[2-amino-6-(2,3-dimethylphenyl)pyrimidin-4-yl]amino}azetidine-1-carboxylate;
2-(2-{[2-amino-6-(3-chloro-2-methylphenyl)pyrimidin-4-yl]amino}ethoxy)pyrimidine-4-carboxamide;
2-(2-{[2-amino-6-(3-chloro-2-methylphenyl)pyrimidin-4-yl]amino}ethoxy)pyrimidine-4-carboxylic acid;
N-[4-(2-{[2-amino-6-(3-chloro-2-methylphenyl)pyrimidin-4-yl]amino}ethyl)phenyl]-2,2-dimethylpropanamide;
N-[4-(2-{[2-amino-6-(3-chloro-2-methylphenyl)pyrimidin-4-yl]amino}ethyl)phenyl]-2,2,2-trifluoroethane-1-sulfonamide;
1-[4-(2-{[2-amino-6-(3-chloro-2-methylphenyl)pyrimidin-4-yl]amino}ethyl)phenyl]-3-(propan-2-yl)urea;
tert-butyl N-[4-(2-{[2-amino-6-(3-chloro-2-methylphenyl)pyrimidin-4-yl]amino}ethyl)phenyl]carbamate;
N-[4-(2-{[2-amino-6-(3-chloro-2-methylphenyl)pyrimidin-4-yl]amino}ethyl)phenyl]cyclopropanecarboxamide;
6-(2,3-dimethylphenyl)-4-N-[2-(thiophen-2-yl)ethyl]pyrimidine-2,4-diamine;
6-(3-chloro-2-methylphenyl)-4-N-[2-(3,4-dichlorophenyl)ethyl]pyrimidine-2,4-diamine;
6-(3-chloro-2-methylphenyl)-4-N-[2-(2,4-dichlorophenyl)ethyl]pyrimidine-2,4-diamine;
N-[4-(2-{[2-amino-6-(3-chloro-2-methylphenyl)pyrimidin-4-yl]amino}ethyl)phenyl]ethane-1-sulfonamide;
4-(2-{[2-amino-6-(2,4,5-trimethylphenyl)pyrimidin-4-yl]amino}ethyl)benzene-1-sulfonamide;
4-(2-{[2-amino-6-(4-methoxy-2,5-dimethylphenyl)pyrimidin-4-yl]amino}ethyl)benzene-1-sulfonamide;
4-(2-{[2-amino-6-(4,5-dichloro-2-methylphenyl)pyrimidin-4-yl]amino}ethyl)benzene-1-sulfonamide;
4-(2-{[2-amino-6-(5-chloro-4-methoxy-2-methylphenyl)pyrimidin-4-yl]amino}ethyl)benzene-1-sulfonamide;
4-(2-{[2-amino-6-(1H-indol-4-yl)pyrimidin-4-yl]amino}ethyl)benzene-1-sulfonamide;
4-(2-{[2-amino-6-(2,5-dimethylphenyl)pyrimidin-4-yl]amino}ethyl)benzene-1-sulfonamide;
4-(2-{[2-amino-6-(5-fluoro-2-methylphenyl)pyrimidin-4-yl]amino}ethyl)benzene-1-sulfonamide;
4-(2-{[2-amino-6-(3,4,5-trichloro-2-methylphenyl)pyrimidin-4-yl]amino}ethyl)benzene-1-sulfonamide;
4-(2-{[2-amino-6-(5-chloro-2-fluoro-3-methylphenyl)pyrimidin-4-yl]amino}ethyl)benzene-1-sulfonamide;
4-(2-{[2-amino-6-(3,5-dichloro-2-methylphenyl)pyrimidin-4-yl]amino}ethyl)benzene-1-sulfonamide;
4-(2-{[2-amino-6-(3,4,5-trichloro-2-methylphenyl)pyrimidin-4-yl]amino}ethyl)benzamide;
4-(2-{[2-amino-6-(3,5-dichloro-2-methylphenyl)pyrimidin-4-yl]amino}ethyl)benzamide;
4-(2-{[2-amino-6-(4-fluoro-2,3-dimethylphenyl)pyrimidin-4-yl]amino}ethyl)benzamide;
4-(2-{[2-amino-6-(3,4-dichloro-2-methylphenyl)pyrimidin-4-yl]amino}ethyl)benzamide;
4-(2-{[2-amino-6-(5-chloro-2-fluoro-3-methylphenyl)pyrimidin-4-yl]amino}ethyl)benzamide;
4-(2-{[2-amino-6-(3-chloro-2-fluorophenyl)pyrimidin-4-yl]amino}ethyl)benzamide;
N-[3-(2-{[2-amino-6-(3-chloro-2-methylphenyl)pyrimidin-4-yl]amino}ethyl)phenyl]-2,2-dimethylpropanamide;
1-[3-(2-{[2-amino-6-(3-chloro-2-methylphenyl)pyrimidin-4-yl]amino}ethyl)phenyl]-3-(propan-2-yl)urea;
tert-butyl N-[3-(2-{[2-amino-6-(3-chloro-2-methylphenyl)pyrimidin-4-yl]amino}ethyl)phenyl]carbamate;
N-[3-(2-{[2-amino-6-(3-chloro-2-methylphenyl)pyrimidin-4-yl]amino}ethyl)phenyl]cyclopropanecarboxamide;
N-[3-(2-{[2-amino-6-(3-chloro-2-methylphenyl)pyrimidin-4-yl]amino}ethyl)phenyl]-2-methylpropane-1-sulfonamide;
N-[4-(2-{[2-amino-6-(3-chloro-2-methylphenyl)pyrimidin-4-yl]amino}ethyl)phenyl]propane-2-sulfonamide;
N-[4-(2-{[2-amino-6-(3-chloro-2-methylphenyl)pyrimidin-4-yl]amino}ethyl)phenyl]-2-methylpropane-1-sulfonamide;
4-(2-{[2-amino-6-(3-chloro-2-methylphenyl)pyrimidin-4-yl]amino}ethyl)benzonitrile
3-[2-[[2-amino-6-(3-chloro-2-methyl-phenyl)pyrimidin-4-yl]amino]ethyl]benzamide;
4-[2-[[2-amino-6-(3-chloro-2-methyl-phenyl)pyrimidin-4-yl]amino]ethyl]-N-methyl-benzamide;

[4-[2-[[2-amino-6-(3-chloro-2-methyl-phenyl)pyrimidin-4-yl]amino]ethyl]phenyl]-pyrrolidin-1-yl-methanone;
7-[2-[[2-amino-6-(3-chloro-2-methyl-phenyl)pyrimidin-4-yl]amino]ethylamino]-4H-1,4-benzoxazin-3-one;
6-[2-[[2-amino-6-(3-chloro-2-methyl-phenyl)pyrimidin-4-yl]amino]ethylamino]-4-methyl-1,4-benzoxazin-3-one;
7-[2-[[2-amino-6-(3-chloro-2-methyl-phenyl)pyrimidin-4-yl]amino]ethylamino]-3H-quinazolin-4-one;
6-[2-[[2-amino-6-(2,3-dichlorophenyl)pyrimidin-4-yl]amino]ethylamino]-4-methyl-1,4-benzoxazin-3-one;
6-(3-chloro-2-methylphenyl)-4-N-[2-(3-nitrophenyl)ethyl]pyrimidine-2,4-diamine;
4-[2-[[2-amino-6-(2-chloro-3-methyl-phenyl)pyrimidin-4-yl]amino]ethyl]benzenesulfonamide;
4-[2-[[2-amino-6-(2,3,5-trichlorophenyl)pyrimidin-4-yl]amino]ethyl]benzenesulfonamide;
4-[2-[[2-amino-6-(2,3,4-trichlorophenyl)pyrimidin-4-yl]amino]ethyl]benzenesulfonamide;
4-[2-[[2-amino-6-(2,4-dichloro-3-methoxy-phenyl)pyrimidin-4-yl]amino]ethyl]benzenesulfonamide;
6-(3-chloro-2-methyl-phenyl)-N4-[2-(2-methyl-5-nitroimidazol-1-yl)ethyl]pyrimidine-2,4-diamine;
6-(3-chloro-2-methyl-phenyl)-N4-[2-[(2-methyl-1,3-benzothiazol-6-yl)amino]ethyl]pyrimidine-2,4-diamine;
4-[2-[[2-amino-6-(benzothiophen-3-yl)pyrimidin-4-yl]amino]ethyl]benzenesulfonamide;
N4-[2-(4-aminophenyl)ethyl]-6-(3-chloro-2-methyl-phenyl)pyrimidine-2,4-diamine;
4-[3-[[2-amino-6-(3-chloro-2-methyl-phenyl)pyrimidin-4-yl]amino]propylamino]benzamide;
4-[3-[[2-amino-6-(3-chloro-2-methyl-phenyl)pyrimidin-4-yl]amino]propylamino]-N-methyl-benzenesulfonamide;
6-(3-chloro-2-methyl-phenyl)-N4-[3-[(2-methyl-1,3-benzothiazol-6-yl)amino]propyl]pyrimidine-2,4-diamine;
2-[2-[[2-amino-6-(3-chloro-2-methyl-phenyl)pyrimidin-4-yl]amino]ethylamino]pyrimidine-4-carboxamide;
6-[2-[[2-amino-6-(3-chloro-2-methyl-phenyl)pyrimidin-4-yl]amino]ethylamino]pyridine-3-carboxamide;
1-[3-[2-[[2-amino-6-(3-chloro-2-methyl-phenyl)pyrimidin-4-yl]amino]ethyl]phenyl]-3-ethyl-urea;
1-[3-[2-[[2-amino-6-(3-chloro-2-methyl-phenyl)pyrimidin-4-yl]amino]ethyl]phenyl]-3-tert-butyl-urea;
N-[3-[2-[[2-amino-6-(3-chloro-2-methyl-phenyl)pyrimidin-4-yl]amino]ethyl]phenyl]morpholine-4-carboxamide;
3-[3-[2-[[2-amino-6-(3-chloro-2-methyl-phenyl)pyrimidin-4-yl]amino]ethyl]phenyl]-1,1-dimethyl-urea;
N-[3-[2-[[2-amino-6-(3-chloro-2-methyl-phenyl)pyrimidin-4-yl]amino]ethyl]phenyl]pyrrolidine-1-carboxamide;
isopropyl N-[3-[2-[[2-amino-6-(3-chloro-2-methyl-phenyl)pyrimidin-4-yl]amino]ethyl]phenyl]carbamate;
isobutyl N-[3-[2-[[2-amino-6-(3-chloro-2-methyl-phenyl)pyrimidin-4-yl]amino]ethyl]phenyl]carbamate;
2,2-dimethylpropyl N-[3-[2-[[2-amino-6-(3-chloro-2-methyl-phenyl)pyrimidin-4-yl]amino]ethyl]phenyl]carbamate;
1-[6-[2-[[2-amino-6-(3-chloro-2-methyl-phenyl)pyrimidin-4-yl]amino]ethylamino]-3-pyridyl]-3-tert-butyl-urea;
tert-butyl N-[6-[2-[[2-amino-6-(3-chloro-2-methyl-phenyl)pyrimidin-4-yl]amino]ethylamino]-3-pyridyl]carbamate;
N2-[2-[[2-amino-6-(3-chloro-2-methyl-phenyl)pyrimidin-4-yl]amino]ethyl]-1,3,5-triazine-2,4,6-triamine;
2-[2-[[2-amino-6-(3-chloro-2-methyl-phenyl)pyrimidin-4-yl]amino]ethylamino]-4-(trifluoromethyl)pyrimidine-5-carboxamide;
N-[2-[[2-amino-6-(3-chloro-2-methyl-phenyl)pyrimidin-4-yl]amino]ethyl]-3-fluoro-benzenesulfonamide;
2-(2-amino-6-(3-chloro-2-methylphenyl)pyrimidin-4-ylamino)-1-(4-(methylsulfonyl)phenyl)ethanol;
N-[2-[[2-amino-6-(3-chloro-2-methyl-phenyl)pyrimidin-4-yl]amino]ethyl]morpholine-4-carboxamide;
1-[2-[[2-amino-6-(3-chloro-2-methyl-phenyl)pyrimidin-4-yl]amino]ethyl]-3-(3-fluorophenyl)urea;
6-(3-chloro-2-methyl-phenyl)-N4-[2-(4-isopropylsulfonylanilino)ethyl]pyrimidine-2,4-diamine;
6-(3-chloro-2-methyl-phenyl)-N4-[2-(4-methylsulfonylanilino)ethyl]pyrimidine-2,4-diamine;
4-[2-[[2-amino-6-(3-chloro-2-methyl-phenyl)pyrimidin-4-yl]amino]ethyl]-3-fluoro-benzamide;
6-[3-[[2-amino-6-(3-chloro-2-methyl-phenyl)pyrimidin-4-yl]amino]azetidin-1-yl]phenyl-3-sulfonamide;
tert-butyl N-[3-[[2-amino-6-(3-chloro-2-methyl-phenyl)pyrimidin-4-yl]amino]propyl]carbamate;
4-[3-[[2-amino-6-(3-chloro-2-methyl-phenyl)pyrimidin-4-yl]amino]propylamino]benzenesulfonamide;
4-[[3-[[2-amino-6-(3-chloro-2-methyl-phenyl)pyrimidin-4-yl]amino]-2,2-dimethyl-propyl]amino]benzenesulfonamide;
6-(3-chloro-2-methyl-phenyl)-N4-[2,2-dimethyl-3-[(2-methyl-1,3-benzothiazol-6-yl)amino]propyl]pyrimidine-2,4-diamine;
6-(3-chloro-2-methyl-phenyl)-N4-[2-(3-isopropylsulfonylanilino)ethyl]pyrimidine-2,4-diamine;
6-[3-[[2-amino-6-(3-chloro-2-methyl-phenyl)pyrimidin-4-yl]amino]propylamino]pyridine-3-carboxamide;
2-[3-[[2-amino-6-(3-chloro-2-methyl-phenyl)pyrimidin-4-yl]amino]propylamino]pyrimidine-4-carboxamide;
6-(3-chloro-2-methyl-phenyl)-N4-[2-(4-isopropylsulfonylphenyl)ethyl]pyrimidine-2,4-diamine;
6-(3-chloro-2-methyl-phenyl)-N4-[2-(3-isopropylsulfonylphenyl)ethyl]pyrimidine-2,4-diamine;
4-[2-[[2-amino-6-(3-chloro-2-methyl-phenyl)pyrimidin-4-yl]amino]ethyl]-2-fluoro-benzamide;
6-(3-chloro-2-methyl-phenyl)-N4-[2-(3-fluoro-4-methylsulfonyl-phenyl)ethyl]pyrimidine-2,4-diamine;
5-[2-[[2-amino-6-(3-chloro-2-methyl-phenyl)pyrimidin-4-yl]amino]ethyl]-2-hydroxy-benzamide;
6-(3-chloro-2-methyl-phenyl)-N4-(4-phenylbutyl)pyrimidine-2,4-diamine;
6-(3-chloro-2-methyl-phenyl)-N4-[2-(cyclohexen-1-yl)ethyl]pyrimidine-2,4-diamine;
N4-but-3-enyl-6-(3-chloro-2-methyl-phenyl)pyrimidine-2,4-diamine;
5-[2-[[2-amino-6-(3-chloro-2-methyl-phenyl)pyrimidin-4-yl]amino]ethylamino]naphthalene-1-sulfonic acid;
6-(3-chloro-2-methyl-phenyl)-N4-[2-(cyclopropylmethoxy)ethyl]pyrimidine-2,4-diamine;
2-[2-[[2-amino-6-(3-chloro-2-methyl-phenyl)pyrimidin-4-yl]amino]ethylsulfanyl]pyrimidine-4-carboxamide;
6-(3-chloro-2-methyl-phenyl)-N4-(3,3-difluoroallyl)pyrimidine-2,4-diamine;
N4-(3-bromo-3,3-difluoro-propyl)-6-(3-chloro-2-methyl-phenyl)pyrimidine-2,4-diamine;
6-(3-chloro-2-methyl-phenyl)-N4-[2-[[5-[(dimethylamino)methyl]-2-furyl]methylsulfanylethyl]ethyl]pyrimidine-2,4-diamine;
6-(3-chloro-2-methyl-phenyl)-N4-[2-[(4-methylsulfonylphenyl)methylsulfanyl]ethyl]pyrimidine-2,4-diamine;

6-(3-chloro-2-methylphenyl)-N4-{2-[(2-phenylethyl)sulfanyl]ethyl}pyrimidine-2,4-diamine;
6-(3-chloro-2-methyl-phenyl)-N4-[2-[(4-methylsulfonylphenyl)methylsulfinyl]ethyl]pyrimidine-2,4-diamine;
6-(3-chloro-2-methyl-phenyl)-N4-[2-(2-phenylethylsulfinyl)ethyl]pyrimidine-2,4-diamine;
6-(3-chloro-2-methyl-phenyl)-N4-[2-[(4-methylsulfonylphenyl)methylsulfonyl]ethyl]pyrimidine-2,4-diamine;
6-(3-chloro-2-methyl-phenyl)-N4-[2-(2-phenylethylsulfonyl)ethyl]pyrimidine-2,4-diamine;
isopropyl 4-[2-[[2-amino-6-(3-chloro-2-methyl-phenyl)pyrimidin-4-yl]amino]ethyl]benzoate;
1-[3-[2-[[2-amino-6-(3-chloro-2-methyl-phenyl)pyrimidin-4-yl]amino]ethyl]phenyl]guanidine
4-(2-(2-amino-6-(3-chloro-2-methylphenyl)pyrimidin-4-ylamino)-1-hydroxyethyl)benzenesulfonamide;
6-[2-[[2-amino-6-(3-chloro-2-methyl-phenyl)pyrimidin-4-yl]amino]ethylsulfanyl]pyridine-3-sulfonamide;
methyl 4-[2-[[2-amino-6-(3-chloro-2-methyl-phenyl)pyrimidin-4-yl]amino]ethylsulfanylmethyl]benzoate;
6-(3-chloro-2-methyl-phenyl)-N4-[2-[(5-methylisoxazol-3-yl)methylsulfanyl]ethyl]pyrimidine-2,4-diamine;
6-(3-chloro-2-methyl-phenyl)-N4-[2-(3,5-dimethylisoxazol-4-yl)ethyl]pyrimidine-2,4-diamine;
6-(3-chloro-2-methyl-phenyl)-N4-propyl-pyrimidine-2,4-diamine;
N4-butyl-6-(3-chloro-2-methyl-phenyl)pyrimidine-2,4-diamine;
6-(3-chloro-2-methyl-phenyl)-N4-(2-methoxyethyl)pyrimidine-2,4-diamine;
6-(3-chloro-2-methyl-phenyl)-N4-(3-ethoxypropyl)pyrimidine-2,4-diamine;
6-(3-chloro-2-methyl-phenyl)-N4-(tetrahydropyran-4-ylmethyl)pyrimidine-2,4-diamine;
6-(3-chloro-2-methyl-phenyl)-N4-(tetrahydrofuran-2-ylmethyl)pyrimidine-2,4-diamine;
6-(3-chloro-2-methyl-phenyl)-N4-[(2E)-3,7-dimethylocta-2,6-dienyl]pyrimidine-2,4-diamine;
6-(3-chloro-2-methyl-phenyl)-N4-isobutyl-pyrimidine-2,4-diamine;
methyl 4-[2-[[2-amino-6-(3-chloro-2-methyl-phenyl)pyrimidin-4-yl]amino]ethyl]benzoate;
ethyl 4-[2-[[2-amino-6-(3-chloro-2-methyl-phenyl)pyrimidin-4-yl]amino]ethyl]benzoate;
propyl 4-[2-[[2-amino-6-(3-chloro-2-methyl-phenyl)pyrimidin-4-yl]amino]ethyl]benzoate;
6-(3-chloro-2-methyl-phenyl)-N4-(2-phenylethyl)pyrimidine-2,4-diamine;
6-(3-chloro-2-methyl-phenyl)-N4-[2-(4-pyridyl)ethyl]pyrimidine-2,4-diamine;
6-(3-chloro-2-methyl-phenyl)-N4-[2-(2-pyridyl)ethyl]pyrimidine-2,4-diamine;
2-hydroxyethyl 4-[2-[[2-amino-6-(3-chloro-2-methyl-phenyl)pyrimidin-4-yl]amino]ethyl]benzoate;
2-methylsulfonylethyl 4-[2-[[2-amino-6-(3-chloro-2-methyl-phenyl)pyrimidin-4-yl]amino]ethyl]benzoate;
2,3-dihydroxypropyl 4-[2-[[2-amino-6-(3-chloro-2-methyl-phenyl)pyrimidin-4-yl]amino]ethyl]benzoate;
6-(3-chloro-2-methyl-phenyl)-N4-[2-[(6-methylsulfonyl-3-pyridyl)amino]ethyl]pyrimidine-2,4-diamine;
N-[4-[2-[[2-amino-6-(3-chloro-2-methyl-phenyl)pyrimidin-4-yl]amino]ethylamino]-2-methyl-phenyl]acetamide;
6-(3-chloro-2-methyl-phenyl)-N4-[(2Z)-2-(fluoromethylene)-4-(4-fluorophenyl)butyl]pyrimidine-2,4-diamine;
6-(3-chloro-2-methylphenyl)-N4-(2-((5-(methylsulfonyl)pyridin-2-yl)oxy)ethyl)pyrimidine-2,4-diamine;
(2-(2-amino-6-(4-(methyl sulfonyl)phenethylamino)pyrimidin-4-yl)-6-chlorophenyl)methanol;
methyl 4-[2-[[2-amino-6-(3-chloro-2-methyl-phenyl)pyrimidin-4-yl]amino]ethylsulfinylmethyl]benzoate;
6-(3-chloro-2-methyl-phenyl)-N4-[2-[(5-methylisoxazol-3-yl)methylsulfinyl]ethyl]pyrimidine-2,4-diamine;
6-(3-chloro-2-methyl-phenyl)-N4-[2-(4-ethylphenyl)ethyl]pyrimidine-2,4-diamine;
4-[2-[[2-amino-6-(3-chloro-2-methyl-phenyl)pyrimidin-4-yl]amino]ethyl]benzene-1,2-diol
5-[2-[[2-amino-6-(3-chloro-2-methyl-phenyl)pyrimidin-4-yl]amino]ethyl]benzene-1,2,3-triol
6-(3-chloro-2-methyl-phenyl)-N4-(2-methylallyl)pyrimidine-2,4-diamine;
methyl 4-[2-[[2-amino-6-(3-chloro-2-methyl-phenyl)pyrimidin-4-yl]amino]ethyl sulfonylmethyl]benzoate;
methyl 4-[[[2-amino-6-(3-chloro-2-methyl-phenyl)pyrimidin-4-yl]amino]methyl]cyclohexanecarboxylate;
4-[4-[[2-amino-6-(3-chloro-2-methyl-phenyl)pyrimidin-4-yl]amino]but-2-ynylsulfanyl]benzoic acid;
6-(3-chloro-2-methyl-phenyl)-N4-[2-(3-pyridyl)ethyl]pyrimidine-2,4-diamine;
6-(3-chloro-2-methyl-phenyl)-N4-(2-pyrimidin-2-ylethyl)pyrimidine-2,4-diamine;
6-(3-chloro-2-methyl-phenyl)-N4-(2-pyrazin-2-ylethyl)pyrimidine-2,4-diamine;
N4-[2-(4-bromophenyl)ethyl]-6-(3-chloro-2-methylphenyl)pyrimidine-2,4-diamine;
4-(2-{[2-amino-6-(3-chloro-2-methylphenyl)pyrimidin-4-yl]amino}ethyl)-N-(1-hydroxypropan-2-yl)benzamide;
6-(3-chloro-2-methylphenyl)-4-N-{2-[4-(4-methylpiperazine-1-carbonyl)phenyl]ethyl}pyrimidine-2,4-diamine;
6-(3-chloro-2-methylphenyl)-N4-[2-(4-methanesulfinylphenyl)ethyl]pyrimidine-2,4-diamine;
4-[2-({2-amino-6-[2-methyl-3-(trifluoromethyl)phenyl]pyrimidin-4-yl}amino)ethyl]benzene-1-sulfonamide;
N4-[2-(4-methanesulfonylphenyl)ethyl]-6-[2-methyl-3-(trifluoromethyl)phenyl]pyrimidine-2,4-diamine;
6-(3-chloro-2-methylphenyl)-N4-(2-{[5-(trifluoromethyl)pyridin-2-yl]oxy}ethyl)pyrimidine-2,4-diamine;
6-(3-chloro-2-methylphenyl)-N4-(2-{furo[3,2-c]pyridin-4-yloxy}ethyl)pyrimidine-2,4-diamine;
6-(3-chloro-2-methylphenyl)-N4-{2-[(5-chloropyridin-2-yl)oxy]ethyl}pyrimidine-2,4-diamine;
4-(2-{[2-amino-6-(3-chloro-2-methylphenyl)pyrimidin-4-yl]amino}ethoxy)benzonitrile;
4-(2-{[2-amino-6-(3-chloro-2-methylphenyl)pyrimidin-4-yl]amino}ethoxy)benzamide;
6-(3-chloro-2-methylphenyl)-N4-{2-[4-(2H-1,2,3,4-tetrazol-5-yl)phenoxy]ethyl}pyrimidine-2,4-diamine;
4-(2-(2-amino-6-(3-chloro-2-(hydroxymethyl)phenyl)pyrimidin-4-ylamino)ethyl)-benzenesulfonamide;
(Z)-4-(2-{[2-amino-6-(3-chloro-2-methylphenyl)pyrimidin-4-yl]amino}ethoxy)-N'-hydroxybenzene-1-carboximidamide;
6-(3-chloro-2-methylphenyl)-N4-[3-(4-methanesulfonylphenoxy)propyl]pyrimidine-2,4-diamine;
2-(3-{[2-amino-6-(3-chloro-2-methylphenyl)pyrimidin-4-yl]amino}propoxy)pyrimidine-4-carboxamide;
6-(3-{[2-amino-6-(3-chloro-2-methylphenyl)pyrimidin-4-yl]amino}propoxy)pyridine-3-carboxamide;
6-(3-chloro-2-methylphenyl)-N4-{2-[4-(morpholine-4-sulfonyl)phenyl]ethyl}pyrimidine-2,4-diamine;

4-(2-{[2-amino-6-(3-chloro-2-methylphenyl)pyrimidin-4-yl]amino}ethyl)-N-(2-methoxyethyl)benzene-1-sulfonamide;

4-(2-{[2-amino-6-(3-chloro-2-methylphenyl)pyrimidin-4-yl]amino}ethyl)-N-(oxetan-3-yl)benzene-1-sulfonamide;

4-(2-{[2-amino-6-(3-chloro-2-methylphenyl)pyrimidin-4-yl]amino}ethyl)-N-(oxan-4-yl)benzene-1-sulfonamide;

4-(2-{[2-amino-6-(3-chloro-2-methylphenyl)pyrimidin-4-yl]amino}ethyl)-N-methyl-N-(prop-2-yn-1-yl)benzamide;

6-(3-chloro-2-methylphenyl)-N4-[2-(4-ethynylphenyl)ethyl]pyrimidine-2,4-diamine; and 6-(2-(2-amino-6-(3-chloro-2-methylphenyl)pyrimidin-4-ylamino)ethoxy)pyridine-3-sulfonamide.

19. The method as claimed in claim 1, wherein the condition is selected from rheumatoid arthritis, systemic lupus erythematosus, Crohn's disease, ulcerous colitis, multiple sclerosis, lymphoproliferative diseases, rejection after organ transplantation, Wegener' granulomatosus, psoriasis, Mb Bechterews, Behcets disease, Guillain Barre, dermatomyositis, myositis, polymyositis, primary biliary cirrhosis, anti-phospholipid syndrome, autoimmune hepatitis, autoimmune cardiomyopathy, alopecia areata, atherosclerosis, type 1 diabetes, autoimmune uveitis, Goodpasteure's syndrome, Graves' disease, Hashimotos disease, mixed connective tissue disease, myasthenia gravis, pemphigus vulgaris, pernicious anemia, Sjögren's syndrome, giant cell arteritis, ulcerative colitis, vasculitis, Churg-Strauss syndrome, post-polio syndrome, idiopathic thrombocytopenic purpura, Peyronie disease and Dupuytren's contracture.

20. The method as claimed in claim 19 wherein the condition is selected from the group consisting of rheumatoid arthritis, systemic lupus erythematosus, Crohn's disease, multiple sclerosis, rejection after organ transplantation and atherosclerosis.

21. The method as claimed in claim 19, wherein the condition is psoriasis.

22. A combination product comprising:
 (A) a compound of formula (I) as defined in claim 1, or a pharmaceutically acceptable salt thereof; and
 (B) one or more other therapeutic agent(s) that is/are useful in the treatment of a disease as defined in claim 1,
 wherein each one of components (A) and (B) is formulated in admixture with a pharmaceutically-acceptable adjuvant, diluent or carrier.

23. The combination product as claimed in claim 22, wherein component (B) is selected from the group consisting of glucocorticoids, TNF-alpha inhibitors, anti CD20, immunosupressants and antimetabolites.

* * * * *